US006682888B1

(12) United States Patent
Loring et al.

(10) Patent No.: US 6,682,888 B1
(45) **Date of Patent: *Jan. 27, 2004**

(54) GENES EXPRESSED IN ALZHEIMER'S DISEASE

(75) Inventors: Jeanne F. Loring, Foster City, CA (US); Debora W. Tingley, San Francisco, CA (US); Carla M. Edwards, Half Moon Bay, CA (US)

(73) Assignee: Incyte Corporation, Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/566,921

(22) Filed: May 5, 2000

(51) Int. Cl.[7] .......................... C12Q 1/70; G01N 33/53; C07H 21/04

(52) U.S. Cl. ...................... 435/6; 435/7.1; 435/DIG. 1; 435/DIG. 22; 435/DIG. 37; 435/DIG. 40; 530/23.1

(58) Field of Search ........................ 435/6, 7.1, DIG. 1, 435/DIG. 22, DIG. 37, DIG. 40; 536/23.1

*Primary Examiner*—Padmashri Ponnaluri
(74) *Attorney, Agent, or Firm*—Incyte Corporation

(57) ABSTRACT

The present invention relates to a composition comprising a plurality of cDNAs which are differentially expressed in disorders of the brain, particularly Alzheimer's disease and which may be used in their entirety or in part as to diagnose, to stage to treat or to monitor the treatment of a subject with a brain disorder.

16 Claims, 1 Drawing Sheet

SEQUENCE LISTING

```
<160> NUMBER OF SEQ ID NOS:  138

<210> SEQ ID NO 1
<211> LENGTH: 880
<212> TYPE: DNA
<213> ORGANISM: Homo sapiens
<220> FEATURE:
<221> NAME/KEY: misc_feature
<223> OTHER INFORMATION: Incyte ID No: 997264.12
```

-continued

<400> SEQUENCE: 1

```
cgttcgcagc gctacccttt tccgctccac ggtgacctcc gtgcggccgg gtgccgggcg     60
gagtcttcct cgatcccgtg gtgctccgcg gcgcggccgt tggctctctt ccggtcgcgg    120
ggacaccggg tgtagagggc ggtcgcggcg ggcagtggcg gcagaatgtt ggctaccagg    180
gtatttagcc tagttggcaa gcgagcaatt tccacctctg tgtgtgtacg agctcatgaa    240
agtgttgtga agagcgaaga cttttcgctc ccagcttata tggatcggcg tgaccacccc    300
ttgccggagg tggcccatgt caagcacctg tctgccagcc agaaggcact gaaggagaag    360
gagaaggcct cctggagcag cctctccatg gatgagaaag tcgagttgta tcgcattaag    420
ttcaaggaga gctttgctga gatgaacagg ggctcgaacg agtggaagac ggttgtgggc    480
ggtgccatgt tcttcatcgg tttcaccgcg ctcgttatca tgtggcagaa gcactatgtg    540
tacggccccc tcccgcaaag ctttgacaaa gagtgggtgg ccaagcagac caagaggatg    600
ctggacatga aggtgaaccc catccagggc ttagcctcca agtgggacta cgaaaagaac    660
gagtggaaga agtgagagat gctggcctgc gcctgcacct gcgcctggct ctgtcaccgc    720
catgcaactc catgcctatt tactggaaac ctgttatgcc aaacagttgt accactgcta    780
ataaatgacc agtttacctg aaaaaaaaaa ccaaaatggg gaagaaaaaa cttcggacaa    840
agaaggaagt gcgagaagaa gcccatgtgg agccgctcct                          880
```

<210> SEQ ID NO 2
<211> LENGTH: 1039
<212> TYPE: DNA
<213> ORGANISM: Homo sapiens
<220> FEATURE:
<221> NAME/KEY: misc_feature
<223> OTHER INFORMATION: Incyte ID No: 998433.2

<400> SEQUENCE: 2

```
cttagtcgcg ggctgactgg tgtttatccg tcactcgccg aggttccttg ggtcatggtg     60
ccagcctgac tgagaagagg acgctcccgg gagacgaatg aggaaccacc tcctcctact    120
gttcaagtac aggggcctgg tccgcaaagg gaagaaaagc aaaagacgaa aatggctaaa    180
ttcgtgatcc gcccagccac tgccgccgac tgcagtgaca tactgcggct gatcaaggag    240
ctggctaaat atgaatacat ggaagaacaa gtaatcttaa ctgaaaaaga tctgctagaa    300
gatggttttg gagagcaccc cttttaccac tgcctggttg cagaagtgcc gaaagagcac    360
tggactccgg aaggacacag cattgttggt tttgccatgt actattttac ctatgacccg    420
tggattggca agttattgta tcttgaggac ttcttcgtga tgagtgatta tagaggcttt    480
ggcataggat cagaaattct gaagaatcta agccaggttg caatgaggtg tcgctgcagc    540
agcatgcact tcttggtagc agaatggaat gaaccatcca tcaacttcta taaaagaaga    600
ggtgcttctg atctgtccag tgaagagggt tggagactgt tcaagatcga caaggagtac    660
ttgctaaaaa tggcaacaga ggagtgagga gtgctgctgt agatgacaac ctccattcta    720
ttttagaata aattcccaac ttctcttgct ttctatgctg tttgtagtga aataatagaa    780
tgagcaccca ttccaaagct ttattaccag tggcgttgtt gcatgtttga aatgaggtct    840
gtttaaagtg gcaatctcag atgcagtttg gagagtcaga tctttctcct tgaatatctt    900
tcgataaaca acaaggtggt gtgatcttaa tatatttgaa aaaaacttca ttctcgtgag    960
tcatttaaat gtgtacaatg tacacactgg tacttagagt ttctgtttga ttctttttta   1020
ataaactact ctttgattt                                                1039
```

<210> SEQ ID NO 3
<211> LENGTH: 2666
<212> TYPE: DNA
<213> ORGANISM: Homo sapiens
<220> FEATURE:
<221> NAME/KEY: misc_feature
<223> OTHER INFORMATION: Incyte ID No: 232838.13

<400> SEQUENCE: 3

| | | | | | |
|---|---|---|---|---|---|
| gccatctttc | cagcctcagt | cggacgggcg | cggagacgct | tctggaagga | acgccgcgat | 60 |
| ggctgcgcag | ggagagcccc | aggtccagtt | caaagtaggt | aaccctgcgg | ggcgggaggc | 120 |
| ggccgagccc | gaccgcgtgc | gactcgcggg | tccctcctcc | tggggccacg | atggctgtaa | 180 |
| tggggccccg | catccacatt | ctttgtttta | agtgagcctg | tggtggttaa | agttccgtga | 240 |
| ctctgggatc | ttgagaggtg | aagtgtttag | ggtttacttc | caaaatgtgt | ttttcaacag | 300 |
| cttgtattgg | ttggtgatgg | tggtactgga | aaaacgacct | tcgtgaaacg | tcatttgact | 360 |
| ggtgaatttg | agaagaagta | tgtagccacc | ttgggtgttg | aggttcatcc | cctagtgttc | 420 |
| cacaccaaca | gaggacctat | taagttcaat | gtatgggaca | cagccggcca | ggagaaattc | 480 |
| ggtggactga | gagatggcta | ttatatccaa | gcccagtgtg | ccatcataat | gtttgatgta | 540 |
| acatcgagag | ttacttacaa | gaatgtgcct | aactggcata | gagatctggt | acgagtgtgt | 600 |
| gaaaacatcc | ccattgtgtt | gtgtggcaac | aaagtggata | ttaaggacag | gaaagtgaag | 660 |
| gcgaaatcca | ttgtcttcca | ccgaaagaag | aatcttcagt | actacgacat | ttctgccaaa | 720 |
| agtaactaca | actttgaaaa | gcccttcctc | tggcttgcta | ggaagctcat | tggagaccct | 780 |
| aacttggaat | ttgttgccat | gcctgctctc | gccccaccag | aagttgtcat | ggacccagct | 840 |
| ttggcagcac | agtatgagca | cgacttagag | gttgctcaga | caactgctct | cccggatgag | 900 |
| gatgatgacc | tgtgagaatg | aagctggagc | ccagcgtcag | aagtctagtt | ttataggcag | 960 |
| ctgtcctgtg | atgtcagcgg | tgcagcgtgt | gtgccacctc | attattatct | agctaagcgg | 1020 |
| aacatgtgct | tcatctgtgg | gatgctgaag | gagatgagtg | ggcttcggag | tgaatgtggc | 1080 |
| agtttaaaaa | ataacttcat | tgtttggacc | tgcatattta | gctgttttgg | aacgcagttg | 1140 |
| attccttgag | tttcatatat | aagactgctg | cagtcacatc | acaatattca | gtggtgaaat | 1200 |
| cttgtttgtt | actgtcattc | ccattccttt | tcgtttagaa | tcagaataaa | gttgtatttc | 1260 |
| aaatatctaa | gcaagtgaac | tcatcccttg | tttataaata | gcatttggaa | accactaaag | 1320 |
| tagggaagtt | ttatgccatg | ttaatatttg | aattgccttg | cttttatcac | ttaatttgaa | 1380 |
| atctattggg | ttaatttctc | cctatgttta | tttttgtaca | tttgagccat | gtcacacaaa | 1440 |
| ctgatgatga | caggtcagca | gtattctatt | tggttagaag | ggttacatgg | tgtaaatatt | 1500 |
| agtgcagtta | agctaaagca | gtgtttgctc | caccttcata | ttggctaggt | agggtcacct | 1560 |
| agggaagcac | ttgctcaaaa | tctgtgacct | gtcagaataa | aaatgtggtt | tgtacatatc | 1620 |
| aaatagatat | tttaagggta | atattttctt | ttatggcaaa | agtaatcatg | ttttaatgta | 1680 |
| gaacctcaaa | caggatggaa | catcagtgga | tggcaggagg | ttgggaattc | ttgctgttaa | 1740 |
| aaataattac | aaattttgca | cttttttgtt | tgaatgttag | atgcttagtg | tgaagttgat | 1800 |
| acgcaaggaa | aatggtccat | gtttacccac | agttttcagg | tactcctaga | ctttaaagat | 1860 |
| gtcttgaaca | tttaagttct | tcagcagttc | acactacacc | gttttttttgt | tgttttttcc | 1920 |
| cccccgggag | ggttttttg | tagggcagca | cagcagagca | ggacatggat | gaaatactag | 1980 |
| gaatatgcac | agtggggcag | tgtgggggct | tctcagtaat | ggagaacagt | tggtgaaact | 2040 |

-continued

```
tttttttttt tttaactaag catttaattt atcttgcata ttttccacat ttaaaaatga   2100

attaggtcta ttaggataat taggagtttg atcccatcaa cactattctt gtagcagtta   2160

ggaatcttga gctatttttt tctcatacga ttactatagt ccagtttacc aaagttttct   2220

ttagatgtct gataatcttg agatgattgc ttaccttaaa aggtatagaa aggatcactt   2280

aaatatatgg aaaaatgaaa taagggtgaa gctgaataaa gttctactta ctgtattaac   2340

tggcaacagt tgagtttctt aagatctgaa ttgctgtgta tgttacgctg tattcagaac   2400

cagtttctaa ccagcctgtg agatgggaag ttttttcccc ataattggga tgaaaccttt   2460

cattcaggta ttttgaattg aaggtgtatg tgttgtttgt aaccttgtgg agattgcaag   2520

tggtgttgac attctggatc ttctatgtaa cagttgaaat ttggaagtga cgtcacttac   2580

ctgtctaacg tggtgtggga gagaatttac aagtccttta ttgaaagaat aattgttgca   2640

aaatatattg cttctacttt gcctgg                                        2666
```

```
<210> SEQ ID NO 4
<211> LENGTH: 4626
<212> TYPE: DNA
<213> ORGANISM: Homo sapiens
<220> FEATURE:
<221> NAME/KEY: misc_feature
<223> OTHER INFORMATION: Incyte ID No: 350407.1
<221> NAME/KEY: unsure
<222> LOCATION: 4607
<223> OTHER INFORMATION: a, t, c, g, or other

<400> SEQUENCE: 4
```

```
ggggggagcc ttagtcattt ccccgctcca gcctgctccc gcccgagcgc gcactcacgg     60

ccgctctccc tcctcgctcc gcagccgcgg cccatggagc ccgccggccc ggcccccggc    120

cgcctcgggc cgctgctctg cctgctgctc gccgcgtcct gcgcctggtc aggagtggcg    180

ggtgaggagg agctgcaggt gattcagcct gacaagtccg tgttggttgc agctggagag    240

acagccactc tgcgctgcac tgcgacctct ctgatccctg tggggcccat ccagtggttc    300

agaggagctg gaccaggccg ggaattaatc tacaatcaaa aagaaggcca cttccccccgg    360

gtaacaactg tttcagacct cacaaagaga aacaacatgg acttttccat ccgcatcggt    420

aacatcaccc cagcagatgc cggcacctac tactgtgtga agttccggaa agggagcccc    480

gatgacacgg agtttaagtc tggagcaggc actgagctgt ctgtgcgtgc caaaccctct    540

gcccccgtgg tatcgggccc tgcggcgagg gccacacctc agcacacagt gagcttcacc    600

tgcgagtccc acggcttctc acccagagac atcaccctga aatggttcaa aaatgggaat    660

gagctctcag acttccagac caacgtggac cccgtaggag agagcgtgtc ctacagcatc    720

cacagcacag ccaaggtggt gctgacccgc gaggacgttc actctcaagt catctgcgag    780

gtggcccacg tcaccttgca gggggaccct cttcgtggga ctgccaactt gtctgagacc    840

atccgagttc cacccacctt ggaggttact caacagcccg tgagggcaga gaaccaggtg    900

aatgtcacct gccaggtgag gaagttctac ccccagagac tacagctgac ctggttggag    960

aatggaaacg tgtcccggac agaaacggcc tcaaccgtta cagagaacaa ggatggtacc   1020

tacaactgga tgagctggct cctggtgaat gtatctgccc acagggatga tgtgaagctc   1080

acctgccagg tggagcatga cgggcagcca gcggtcagca aaagccatga cctgaaggtc   1140

tcagcccacc cgaaggagca gggctcaaat accgccgctg agaacactgg atctaatgaa   1200

cggaacatct atattgtggt gggtgtggtg tgcaccttgc tggtggccct actgatggcg   1260
```

-continued

```
gccctctacc tcgtccgaat cagacagaag aaagcccagg gctccacttc ttctacaagg   1320
ttgcatgagc ccgagaagaa tgccagagaa ataacacagg acacaaatga tatcacatat   1380
gcagacctga acctgcccaa ggggaagaag cctgctcccc aggctgcgga gcccaacaac   1440
cacacggagt atgccagcat tcagaccagc ccgcagcccg cgtcggagga caccctcacc   1500
tatgctgacc tggacatggt ccacctcaac cggacccccca agcagccggc cccaagcct   1560
gagccgtcct tctcagagta cgccagcgtc caggtcccga ggaagtgaat gggaccgtgg   1620
tttgctctag cacccatctc tacgcgcttt cttgtcccac agggagccgc cgtgatgagc   1680
acagccaacc cagttcccgg agggctgggg cggtgcaggc tctgggaccc aggggccagg   1740
gtggctcttc tctccccacc cctccttggc tctccagcac ttcctgggca gccacggccc   1800
cctcccccca cattgccaca tacctggagg ctgacgttgc caaaccagcc agggaaccaa   1860
cctgggaagt ggccagaact tcctggggtc caagaactct tgtgcctccg tccatcacca   1920
tgtgggtttt gaagaccctc gactgcctcc ccgatgctcc gaagcctgat cttccagggt   1980
ggggaggaga aaatcccacc tcccctgacc tccaccacct ccacacacac acaccacaca   2040
ccaccactac caccaccacc caactggggc tagagtgggg aagatttccc ctttagatca   2100
aactgcccct tccatggaaa agctggaaaa aaactctgga acccatatcc aggcttggtg   2160
aggttgctgc caacagtcct ggcctccccc atccctaggc taaagagcca tgagtcctgg   2220
aggaggagag gacccctccc aaaggactgg agacaaaacc ctctgcttcc ttgggtccct   2280
ccaagactcc ctggggccca actgtgttgc tccacccgga cccatctctc ccttctagac   2340
ctgagcttgc cctccagct agcactaagc aacatctcgc tgtggacgcc tgtaaattac   2400
tgagaaatgt gaaacgtgca atcttgaaac tgaggtgtta gaaaacttga tctgtggtgt   2460
tttgttttgt ttttttttctt aaaacaacag caacgtgatc ttggctgtct gtcatgtgtt   2520
gaagtccatg gttgggtctt gtgaagtctg aggtttaaca gtttgttgtc ctggagggat   2580
tttcttacag cgaagacttg agttcctcca agtcccagaa ccccaagaat gggcaagaag   2640
gatcaggtca gccactccct ggagacacag ccttctggct gggactgact tggccatgtt   2700
ctcagctgag ccacgcggct ggtagtgcag ccttctgtga ccccgctgtg gtaagtccag   2760
cctgcccagg gctgctgagg gctgcctctt gacagtgcag tcttatcgag acccaacgcc   2820
tcagtctgct catccgtaaa gtggggatag tgaagatgac acccctcccc accacctctc   2880
ataagcactt taggaacaca cagagggtag ggatagtggc cctggccgtc tatcctaccc   2940
ctttagtgac cgcccccatc ccggctttct gagctgatcc ttgaagaaga aatcttccat   3000
ttctgctctc aaaccctact gggatcaaac tggaataaat tgaagacagc caggggggatg   3060
gtgcagctgt gaagctcggg ctgattcccc ctctgtccca gaaggttggc cagagggtgt   3120
gacccagtta ccctttaacc cccacccttc cagtcgggtg tgagggcctg accgggccca   3180
gggcaagcag atgtcgcaag ccctatttat tcagtcttca ctataactct tagagttgag   3240
acgctaatgt tcatgactcc tggccttggg atgcccaagg gatttctggc tcaggctgta   3300
aaagtagctg agccatcctg cccattcctg gaggtcctac aggtgaaact gcaggagctc   3360
agcatagacc cagctctctg gggggatggtc acctggtgat ttcaatgatg gcatccagga   3420
attagctgag ccaacagacc atgtggacag ctttggccag agctcccgtg tggcatctgg   3480
gagccacagt gacccagcca cctggctcag gctagttcca aattccaaaa gattggcttg   3540
taaaccttcg tctccctctc ttttacccag agacagcaca tacgtgtgca cacgcatgca   3600
cacacacatt cagtatttta aaagaatgtt ttcttggtgc cattttcatt ttattttatt   3660
```

-continued

```
ttttaattct tggaggggga aataagggaa taaggccaag gaagatgtat agctttagct   3720
ttagcctggc aacctggaga atccacatac cttgtgtatt gaaccccagg aaaaggaaga   3780
ggtcgaacca accctgcgga aggagcatgg tttcaggagt ttattttaag actgctggga   3840
aggaaacagg ccccattttg tatatagttg caacttaaac tttttggctt gcaaaatatt   3900
tttgtaataa agatttctgg gtaataatga gtccttccgg tgttcagtat tcttgtcttt   3960
gtgagtgcgt cccggggccg cctcggggcc tgcctgccct cctgccaaag cctggaagag   4020
gattgaatgg accccagggt ttggaaacaa cctacagcat ttgagcccct cacgtaggtt   4080
ttagagacgt acaatttttg tttgccctgg ctcagaagga gccggtgtaa ggttgagata   4140
aaattccata tagacaactg agtttggatc tcggctctgc tgctttgtag ctgtgggagt   4200
tcaaacagca cctctttgag acttgggccc cgcgtcggca caatggggca ggaatagtcc   4260
ctgccagggt gactgtgtgg attcaaggag gttggaagca ctgagcccac gcttggcact   4320
gggtaggcca tcactgaggc ttgtgtcttt ccttcctgcc ctgaccctgc atagctgagt   4380
ctcgtggcct ctcaccactg atgggatctc ggacacccgg ctcaccctcc tcctggggcc   4440
tcactttcct tccccaccaa atgcagacat ctaatgcttg tcctgtaata tccttgccag   4500
atgactgatg tcaagtgctg gtttatagtg ggtgctcaat aaatgttagt ttcctttcta   4560
tccctccatt agatcattaa tgatattagt ggtaattatg taataangtt aaggcataaa   4620
tatgtc                                                              4626
```

<210> SEQ ID NO 5
<211> LENGTH: 3637
<212> TYPE: DNA
<213> ORGANISM: Homo sapiens
<220> FEATURE:
<221> NAME/KEY: misc_feature
<223> OTHER INFORMATION: Incyte ID No: 350454.2

<400> SEQUENCE: 5

```
cagcccctct ggcaggctcc cgccagcgtc gctgcggctc cggcccggga gcgagcgccc     60
ggagctcgga aagatgcggc gcccgcggcg gcctgggggt ctcgggggat ccgggggtct    120
ccggctgctc ctctgcctcc tgctgctgag cagccgcccg gggggctgca gcgccgttag    180
tgcccacggc tgtctatttg accgcaggct ctgctctcac ctggaagtct gtattcagga    240
tggcttgttt gggcagtgcc aggtgggagt ggggcaggcc cggccccttt tgcaagtcac    300
ctccccagtt ctccaacgct tacaaggtgt gctccgacaa ctcatgtccc aaggattgtc    360
ctggcacgat gacctcaccc agtatgtgat ctctcaggag atggagcgca tccccaggct    420
tcgcccccca gagccccgtc caagggacag gtctggcttg gcacccaaga gacctggtcc    480
tgctggagag ctgcttttac aggacatccc cactggctcc gcccctgctg cccagcatcg    540
gcttccacaa ccaccagtgg gcaaaggtgg agctggggcc agctcctctc tgtcccctct    600
gcaggctgag ctgctcccgc ctctcttgga gcacctgctg ctgcccccac agcctcccca    660
cccttcactg agttacgaac ctgccttgct gcagccctac ctgttccacc agtttggctc    720
ccgtgatggc tccagggtct cagagggctc cccagggatg gtcagtgtcg gcccccctgcc    780
caaggctgaa gcccctgccc tcttcagcag aactgcctcc aagggcatat ttggggacca    840
ccctggccac tcctacgggg accttccagg gccttcacct gcccagcttt ttcaagactc    900
tgggctgctc tatctggccc aggagttgcc agcacccagc agggccaggg tgccaaggct    960
gccagagcaa gggagcagca gccgggcaga ggactcccca gagggctatg agaaggaagg   1020
```

-continued

```
actaggggat cgtggagaga agcctgcttc cccagctgtg cagccagatg cggctctgca   1080
gaggctggcc gctgtgctgg cgggctatgg ggtagagctg cgtcagctga cccctgagca   1140
gctctccaca ctcctgaccc tgctgcagct actgcccaag ggtgcaggaa gaaatccggg   1200
aggggttgta aatgttggag ctgatatcaa gaaaacaatg gaggggccgg tggagggcag   1260
agacacagca gagcttccag cccgcacatc cccccatgcct ggacacccca ctgccagccc   1320
tacctccagt gaagtccagc aggtgccaag ccctgtctcc tctgagcctc ccaaagctgc   1380
cagacccccct gtgacacctg tcctgctaga gaagaaaagc ccactgggcc agagccagcc   1440
cacggtggca ggacagccct cagcccgccc agcagcagag gaatatggct acatcgtcac   1500
tgatcagaag cccctgagcc tggctgcagg agtgaagctg ctggagatcc tggctgagca   1560
tgtgcacatg tcctcaggca gcttcatcaa catcagtgtg gtgggaccag ccctcacctt   1620
ccgcatccgg cacaatgagc agaacctgtc tttggctgat gtgacccaac aagcagggct   1680
ggtgaagtct gaactggaag cacagacagg gctccaaatc ttgcagacag gagtgggaca   1740
gagggaggag gcagctgcag tccttcccca aactgcgcac agcacctcac ccatgcgctc   1800
agtgctgctc actctggtgg ccctggcagg tgtggctggg ctgctggtgg ctctggctgt   1860
ggctctgtgt gtgcggcagc atgcgcggca gcaagacaag gagcgcctgg cagccctggg   1920
gcctgagggg gcccatggtg acactacctt tgagtaccag gacctgtgcc gccagcacat   1980
ggccacgaag tccttgttca accgggcaga gggtccaccg gagccttcac gggtgagcag   2040
tgtgtcctcc cagttcagcg acgcagccca ggccagcccc agctcccaca gcagcacccc   2100
gtcctggtgc gaggagccgg cccaagccaa catggacatc tccacgggac acatgattct   2160
ggcatacatg gaggatcacc tgcggaaccg ggaccgcctt gccaaggagt ggcaggccct   2220
ctgtgcctac caagcagagc caaacacctg tgccaccgcg caggggggagg gcaacatcaa   2280
aaagaaccgg catcctgact tcctgcccta tgaccatgcc cgcataaaac tgaaggtgga   2340
gagcagccct tctcggagcg attacatcaa cgccagcccc attattgagc atgaccctcg   2400
gatgccagcc tacatagcca cgcagggccc gctgtcccat accatcgcag acttctggca   2460
gatggtgtgg gagagcggct gcaccgtcat cgtcatgctg accccgctgg tggaggatgg   2520
tgtcaagcag tgtgaccgct actggccaga tgagggtgcc tccctctacc acgtatatga   2580
ggtgaacctg gtgtcggagc acatctggtg cgaggacttt ctggtgcgga gcttctacct   2640
gaagaacgtg cagacccagg agacgcgcac gctcacgcag ttccacttcc tcagctggcc   2700
ggcagagggc acaccggcct ccacgcggcc cctgctggac ttccgcagga aggtgaacaa   2760
gtgctaccgg ggccgctcct gccccatcat cgtgcactgc agtgatggtg cggggaggac   2820
cggcacctac atcctcatcg acatggtcct gaaccgcatg gcaaaaggag tgaaggagat   2880
tgacatcgct gccaccctgg agcatgtccg tgaccagcgg cctggccttg tccgctctaa   2940
ggaccagttt gaatttgccc tgacagccgt ggcggaggaa gtgaatgcca tcctcaaggc   3000
cctgccccag tgagaccctg ggcccccttg gcgggcagcc cagcctctgt ccctctttgc   3060
ctgtgtgagc atctctgtgt acccactcct cactgcccca ccagccacct cttgggcatg   3120
ctcagccctt cctagaagag tcaggaaggg aaagccagaa ggggcacgcc tgcccagcct   3180
cgcatgccag agcctggggc atcccagagc ccagggcatc ccatggggggt gctgcagcca   3240
ggaggagagg aaaggacatg ggtagcaatt ctacccagag ccttctcctg cctacattcc   3300
ctggcctggc tctcctgtag ctctcctggg gttctgggag ttccctgaac atctgtgtgt   3360
```

-continued

```
gtccccctat gctccagtat ggaagaatgg ggtggagggt cgccacaccc ggctccccct   3420

gcttctcagc cccgggcctg cctctgactc acacttgggc gctctgccct ccctggcctc   3480

acgcccagcc tcctcccacc accctcccac catgcgctgc tcaacctctc tccttctggc   3540

gcaagagaac atttctagaa aaaactactt ttgtaccagt gtgaataaag ttagtgtgtt   3600

gtctgtgcag ctgcaaccca gaaaaaaaaa aaaaagg                            3637
```

<210> SEQ ID NO 6
<211> LENGTH: 2270
<212> TYPE: DNA
<213> ORGANISM: Homo sapiens
<220> FEATURE:
<221> NAME/KEY: misc_feature
<223> OTHER INFORMATION: Incyte ID No: 215696.7
<221> NAME/KEY: unsure
<222> LOCATION: 1487-1535
<223> OTHER INFORMATION: a, t, c, g, or other

<400> SEQUENCE: 6

```
ggggcagcgg gcggcggcag cagtggccgc acatctggat ggaagcgagc tttgtccaga     60

ccaccatggc tctggggctg tcctccaaga aagcgtcctc tcgcaacgtg gctgtggagc    120

gtaagaacct gatcaccgtg tgcaggttct ctgtgaaaac gctgctggag aagtacacag    180

cggagcccat cgatgactca tcggaggagt ttgtcaattt tgcagccatt ttagagcaga    240

tcctcagcca ccgcttcaaa gcctgtgccc cagcaggtcc agtgagctgg ttcagctcag    300

acgggcagcg gggcttttgg gactatatcc ggctggcctg cagcaaagtg cccaacaact    360

gtgtgagcag catcgagaac atggagaaca tcagcacagc ccgggccaag ggccgggcat    420

ggatccgggt ggcactgatg gagaagcgca tgtcagaata catcaccacg gctctgcgtg    480

acacccggac caccagacgg ttctatgact ctggagccat catgctgcgg gatgaagcca    540

ccatcctcac cggaatgctg atcggactga gcgccatcga cttcagcttc tgtctaaagg    600

gggaagtcct ggacgggaag acccccgtgg tcatcgatta cacgccctac ctaaagttca    660

cgcagagcta cgactacctg acggacgagg aggagcggca cagcgccgag agcagcacga    720

gcgaggacaa ctcgcccgag cacccgtacc tcccgctcgt caccgatgag gacagctggt    780

acagcaagtg gcacaagatg gagcagaagt tccgcatcgt ctacgcgcag aagggctacc    840

tggaggagct ggtgcgtctg cgcgagtcgc agctgaagga cctggaggcg gagaaccggc    900

ggcttcagct gcagctggag gaggcggcgg cgcagaacca gcgcgagaaa cgggagctgg    960

aaggcgtgat cctggagctg caggagcagc tgacaggtct gatccccagt gaccacgccc   1020

ctctggccca gggttccaag gagctcacta cacccctggt caatcaatgg ccctcactgg   1080

gaacgcttaa tggggccgag ggcgccagca actccaagct ctaccggaga cacagcttca   1140

tgagcacgga gccgctgtca gctgaagcca gtctgagctc ggactcccag cgcctgggag   1200

agggcacgcg ggacgaggag ccctggggtc ccatcggaag ctcagagcca aattagtggc   1260

tcccttcgag cgaatgccca ggacttcaac gcatgcactt tgtgttgacc tcatccctgg   1320

cttcaccttg gtttttccca tcctagttct ccctatgcct gaatatcctg tcttttcttt   1380

tttataagca accacactgt attggatgac cctagatctt ctttgagaca aggcaggctg   1440

tggccatgta gccccatcac actgtgtttg tgattgtctg tgtgtcnnnn nnnnnnnnnn   1500

nnnnnnnnnn nnnnnnnnnn nnnnnnnnnn nnnnngtccg ttctctgtat ccccagtgct   1560

tggaacagag cgagtgctca ctgtgtattt aataaatgga caaagagaga ggatgaccct   1620

cacggggaga cagagacatc aactgacgat tacaatacag tgtccccagc acggtgcctg   1680
```

-continued gcacaggcag gtgcttaacc aaagtttaac tgaaaatggc aaatgctgtg gaatatgcca 1740
aggtctcctg gggggtgact tgagggctgc cccttcactg cccacccctc taccaactcc 1800
cacacatgta gactggtcgc ttggcctcac ctgccctctc tccccaggga aggaccccac 1860
gccctccatg ctgggcctct gcggctccct ggcctccatt cccagctgca agtccctggc 1920
gagcttcaaa tccaacgagt gcctggtgag cgacagtccc gagggcagcc cagcactgag 1980
ccccagctga ggaacagcat gggcagtgcc agccccacct gccaggggcc atggacacct 2040
gccacctttc ttcaacaaga gtcccccaat ccaggctacc cttccagaga acgctaccca 2100
cccagccagg gttctctcgg ggaagatctc gtctgctcac cttagctttc tgccttggca 2160
gcacgggctg cggaagaaag cacgctgggc caggaggcag gggtgcccaa gccacaggga 2220
gcccctgggg aagcctgctc cattcttctg gtgaccttgg cgctccttca 2270

<210> SEQ ID NO 7
<211> LENGTH: 8137
<212> TYPE: DNA
<213> ORGANISM: Homo sapiens
<220> FEATURE:
<221> NAME/KEY: misc_feature
<223> OTHER INFORMATION: Incyte ID No: 411474.10
<221> NAME/KEY: unsure
<222> LOCATION: 3488-3788
<223> OTHER INFORMATION: a, t, c, g, or other

<400> SEQUENCE: 7
ccggcggcca ttttgggtgg aagcgatagc tgagtggcgg cggctgctga ttgtgttcta 60
ggggacggag taggggaaga cgtttgctct cccggaacag cctatgctca ttcctttctt 120
tcgattaccc gtggcgcgga gagtcagggc cggcggctgc ggcagcaagg gcggcggtgg 180
cggcggcggc agctgcagtg acatgtccag catgaatccc gaatatgatt atttattcaa 240
gttacttctg attggcgact caggggttgg aaagtcttgc cttcttctta ggtttgcaga 300
tgatacatat acagaaagct acatcagcac aattggtgtg gatttcaaaa taagaactat 360
agagttagac gggaaaacaa tcaagcttca aatatgggac acagcaggcc aggaaagatt 420
tcgaacaatc acctccagtt attacagagg agcccatggc atcatagttg tgtatgatgt 480
gacagatcag gagtccttca ataatgttaa acagtggctg caggaaatag atcgttatgc 540
cagtgaaaat gtcaacaaat tgttggtagg gaacaaatgt gatctgacca caaagaaagt 600
agtagactac acaacagcga aggaatttgc tgattccctt ggaattccgt ttttggaaac 660
cagtgctaag aatgcaacga atgtagaaca gtctttcatg acgatggcag ctgagattaa 720
aaagcgaatg ggtcccggag caacagctgg tggtgctgag aagtccaatg ttaaaattca 780
gagcactcca gtcaagcagt caggtggagg ttgctgctaa aatttgcctc catccttttc 840
tcacagcaat gaatttgcaa tctgaaccca agtgaaaaaa caaaattgcc tgaattgtac 900
tgtatgtagc tgcactacaa cagattctta ccgtctccac aaaggtcaga gattgtaaat 960
ggtcaatact gactttttttt ttattccctt gactcaagac agctaacttc attttcagaa 1020
ctgttttaaa cctttgtgtg ctggtttata aaataatgtg tgtaatcctt gttgctttcc 1080
tgataccaga ctgtttcccg tggttggtta gaatatattt tgttttgatg tttatattgg 1140
catgtttaga tgtcaggttt agtcttctga agatgaagtt cagccatttt gtatcaaaca 1200
gcacaagcag tgtctgtcac tttccatgca taaagtttag tgagatgtta tatgtaagat 1260
ctgatttgct agttcttcct tgtagagtta taaatggaaa gattacacta tctgattaat 1320

-continued

```
agtttcttca tactctgcat ataatttgtg gctgcagaat attgtaattt gttgcacact   1380

atgtaacaaa acaactgaag atatgtttaa taaatattgt acttattgga agtaatatca   1440

aactgtatgg tgataagtat tgttttgatt cttatggtta aagggaaata gagccttgca   1500

ttatattcaa cacagccatt tgtgtgtgca caatgcaaac taaggtattc tagacctatc   1560

ttagagcagc atccagtatt tgctttctag ataatatgcc caataacatg acctagaggg   1620

gcttctgtgc tgtgtaggga tttaaccaac ttcagtggtt cagggagctc aaactatatg   1680

taaaacaagt ttagaatgta tgctatctag cccgttatct ctgatccttc tctaaaacca   1740

tttgaaatag cttcattgat caacatttca taaatgcatc tgtggtagag gtagaaagca   1800

gcacctttcc taattggcaa atgatcagac taatgtgtgc taatgttttt cttccatgct   1860

ttcagtcaga ttcaactatt ttatcctcca cagttgctta acttggtgtt ggaggagggt   1920

ttaagcatta agataggaag caggaaattt gattgctcta aatttagaaa ttatatccct   1980

aaaaattaaa acatgaatac tgggtggtaa tgataattga ggcaaatgta tttattttgg   2040

tgacattttg catatatgaa gattttctga aataggacct tcaagatcct aggggggtttt   2100

gtttggtttt taattgtgag gaataaaaaa tcttctgccc acactggcat tttaaggtga   2160

ctgaggtcaa acgttgtttc cttaggttga aatagcagcc aaaacattct tcacgcaggg   2220

gcttgggata tggctgctgg caacacattt tgttgtgggc tccttaattt aatgataaaa   2280

tttaagctaa acacaagcca aaaatgaata ggttttttta atttttattt ttcactaaac   2340

aggcaattga aatacatggt acaaaaaataa gtggtaagat aattgtaaaa tgaaatggac   2400

agaatattca attttccatc tatgaaaatt tcacaataaa aatcatagtt tactttgtat   2460

tataggcgtg cttggtggat ctattcatcc tcacataagg caactgacaa attcctgaag   2520

ttaccaatag ttattttggt gaagatcttt aatgcttcag aagttttgtt tttgccttaa   2580

tacagtataa agggggaaag agttcagaaa ctattttcta aagtagctaa atgacacaaa   2640

acaaatgtca agatactgtg atgccatgcc gtgcacttca tttttacaca gtaaaagttg   2700

tttaaattgt cagcttattc ttggtgagtt agcggaaaca ttacatgaac ttaagatgag   2760

catatttaca gacttaagtt tggaaaattc cagcgttctt ttccccatgg cagtaaagat   2820

tgggatttac aacaaatttc agcatgcctt aagatttgct tctatgtata cgccaataaa   2880

tgtggttctg gaaaaaatat ataccccttt ataccccccat tttcaagtac aaacggttca   2940

aagctactac aggttttaat aatctgttca cttagtaaag ggaattacca cttgttctaa   3000

atataaggtg ctgccataaa ttagtttaca tagtgaagaa gagtgttctt aaatctaagc   3060

agctgcacac tctgtgaaat cctttcagaa tgatagtcat tgtggtctga gcagtaattt   3120

cctattcttc gaccttggat tgaatttccc ttagcctaca tcttgccttt ccagcatatc   3180

ttacctcaaa ccttctttgt gttccattcc cacctaagct tcaaaatagc cctgtgttga   3240

cgtcgtcttc catttgctga gcttacctat ggatctccaa gaacccagat cttgaaactg   3300

ctgatccagc tttgagtatc atcacttccc tgtggattta acttccatta attttaaggg   3360

actactaagt tattccagtg tggcatcaca gtgcagttag caagctcagc tacttgactc   3420

taatttggcc atgtttgctc atagaaatgc tgctggcagc atcttactag gctgaaacaa   3480

tttcagcnnn nnnnnnnnnn nnnnnnnnnn nnnnnnnnnn nnnnnnnnnn nnnnnnnnnn   3540

nnnnnnnnnn nnnnnnnnnn nnnnnnnnnn nnnnnnnnnn nnnnnnnnnn nnnnnnnnnn   3600

nnnnnnnnnn nnnnnnnnnn nnnnnnnnnn nnnnnnnnnn nnnnnnnnnn nnnnnnnnnn   3660

nnnnnnnnnn nnnnnnnnnn nnnnnnnnnn nnnnnnnnnn nnnnnnnnnn nnnnnnnnnn   3720
```

-continued

```
nnnnnnnnnn nnnnnnnnnn nnnnnnnnnn nnnnnnnnnn nnnnnnnnnn nnnnnnnnnn   3780
nnnnnnnntt cagcttgagt tttaaggtaa gtcttaaact taaagcacgg cggtataatt   3840
aacagttgtg ttgatactct tcagtagcat tcacagccag gtccagggag ttagcaccct   3900
ttagtctcac cttattcaga ggatgaacaa aaatatctta gatcatctct aggtaaggta   3960
gtactttctt gggaaacagg gtattgtgta acattctgtg caaattcctg tcagttgaag   4020
ctgattatta gttgaatggg aatagaatgc cacattctgc attcaattag tataatattg   4080
gccaatttgt ttctataggg ttttcatctc caacttttat gctaattaat acacttctat   4140
gcctgtcaaa tattagtaaa taaatgggtt taatttccta agggctattc agtaacatac   4200
tcagtggaag gacatgttcc tacttataaa tatacatcta agagaaggta aaatatatca   4260
atttaagaag aggccgtcag acatctctac ctttttaacc aactctaggt tttcaagaat   4320
gttttacata caggtttata attgacaatt atttgctaga gtggtttttc ccttttaaag   4380
tctcagtgtg tatggaacta agatgattaa tatggcaaac tcataagcca ttttaatttt   4440
gatcatgccc ttaagcatta tgataaagca taccacagca gcatcaggca cttgaaatac   4500
tgcattttat gtgtagctac tgttgaagag ctaatcttta aagaatttaa tggctatttt   4560
ccagtgacta taaagtctca gaaattctga agcagaaaag tcacattaat aataggactt   4620
tagtttccat tgttactgtg ctttcctcct tccaggttca ttcatggccc aacagaactt   4680
taaaagtgct tttctgtaga atctgcagtt accagcaata actgatcatc ttgctgcaaa   4740
aagctataga attgatgctt tgaatggttg atccatagtt tttttttttt tttaatcaaa   4800
gtacttatgt gtcaatgcca aagcaacgaa gaattcccct ttttccttca ctattgacag   4860
cttcagtttc tgtacttact gtgtcatcct atccattccc ttccctgagc ctggactgct   4920
cttccaaggg agactaggag tgaagggagg agtcctccca aagttaccct ttaagcttga   4980
taattagctc catagccatg ctaaagcatg actgtagatc cccaagtccc tgacacattt   5040
tcttctaaga aactggttag ccaagaaagt aaagacgtaa gccctgaaga tggcaaaagg   5100
tgtcataatc tcccaaagtc atctgtatag atgcttcatt taacccttttt tcttttgcag   5160
acaaagggtt aaaaatctct tctttctacc tatatcttta aagagggatt gacaagccca   5220
aatttccttt tatgaaaaga cccaaggttt ctggccaaca attcactttt ttcagtctct   5280
taggtcctct tgcatgcctg agaatattga gtattcggaa tctcctacca gcccttggta   5340
aatgacccta ccaggtggaa tagtttgagc tttatctgct cttttttaat gggatagagg   5400
ggaaggcaac acgtcttatt ttatcaaaaa ttgcaaagct acacgctctt tgtggagaag   5460
caccaaaagg aaaaccttag tttggaagga ttcattgtaa ataaaaatag taactcagcc   5520
ctccattcag ggaggagaaa ggcattttaa agctagtata ttgaaggttt ccccccttgac   5580
ttcagtgttg aatggctctt gcaaggactt cttgaaggat ttttttctca ctagccagtg   5640
tttggccgac aggttgcacc tctgcctgag aagatgccag gttaaacccc ttcacatggg   5700
tgctccattg ccgccatggg ctttttgtca gggataaggg tgcagccagc cagcatgtcc   5760
agagaggcca agatagagtc atacaggcga tctgcgtggc tctccagctc accagactgc   5820
tttgcgatcc tcccaaggac atcctctaaa actggggtgt tctccaacag gcactgaaga   5880
agaatctccc ccttctgtaa gacactctcc gtcagagact gatgttcatc tatatctttc   5940
ttaaattgcc ggtaaagctg cagagaagac ttgagacttg taagattgga cctggctgca   6000
gtcccgtggt cagtaacatc tgcaacatta tacagccagc agatcagctc ttccagctga   6060
```

-continued

```
cagcaaaatg tcttcacaca ttgcaccagt gattcttttc cctgttctcc tcctttcctg   6120

ggaagctgcc cttcaacatc tgggtctgag aatggccacc ggtccaacct agctggcaag   6180

gaggggcgtg ttttcagcag tccagaggag accccgaggg cctggctgct ccccagactg   6240

ccttcccctg cggagtcgtg ggcacggacg aaggagcgca ggaaacaggg attctggccc   6300

tcaggatccc cagatccttg gagggcagct ccagggggaa gctggctttg gctggagctt   6360

gaagggaagg aagctggccc atcactgtct gacacttcca aggggctctg ccctttgata   6420

tccccagtgg gcagggtaac caaggtagaa atggatccta gatacgaaac caggctagaa   6480

acctgtgtca gccgagcggg gagggcaaga tactcgtcat cactttccac ttcctcttct   6540

gatttccacc tagactctgt gcaggtaggg cgccgggcac tctggctggt cctcttctcc   6600

ctctctggcc tgggcgaggg ccaccctctg tcccgtgtcc ttagctgggg agagcccata   6660

tcaaggtgct tgcctatagt cagccggtcc ttcgcacccc tcagggctgg ctctctgcgc   6720

tcccaacgag catccctact gcctggggct ctgggggtag atgcaggttg gctccaagat   6780

gccaagccca tgccaccctg tttctggggt actctggagg gccactgctt aaggcttggc   6840

tctctgggcc cagaaaatgg cagggcagtg gcctctgctg gtgggcagtt gggggagaca   6900

ttagtaggtg atttgagggt gcttgctgga gagacagaga agctatccag gtctaccccg   6960

gagtcctgca ggacagggtc agctggcaca cggctatcaa ggtgctttgg gagctgaggc   7020

ccgggcctca gtgggtaagt atagtcaagc agatcttcat actctttatt tgggttccag   7080

agaggggagt ggcggtcggg tgatggaggc agggaatctg gcagcacaca ggcccagtac   7140

tcagcctgga aggagaggcg tctcctgcct agcccagaag catcaccccc agagaacaca   7200

ggctgtggtg accactgggg ccgaggtcct agccccacca cagaggaagg ttcctggggg   7260

acgaccggct ccagggagga ggagaccttg gccagagaac caccacgagg ctccgccctc   7320

tcctggtgac cctggagact gctgcctgtg gaggaagcag agatgctgca gctggaaggc   7380

tgagctgcgg aacctgggct cagcacggac ttccactgtg acaggcaaga gagacctgag   7440

ctgtgaggct gctggctgag gtccagtgcc tggggcaaat ctgctaggga tggatcatct   7500

tcggtatcag catcatgtcc tgagcaaata gttgttgttc tgggaaggct cagagtctga   7560

gggaactcct cggaggaaga aagcttggtc ttctccacct ggctttcccc ggagagcaga   7620

aggtctccag accccatggt ggcaggaggc aggccactga gtgcaggctc agacctctca   7680

gctacgggct ctctgttggc atcactggcc tgtggctggt gggctctaga ggggccgcca   7740

gggtcagtcc caatccagca agtaggggca ggtatccctt ctgcccccca tacaggggag   7800

atgagccctc cctcaggctt ccaggcgtgg gggctgctcc ccactcatgg gccctgggat   7860

gtccagctcc cgctccctgc agctccctct cccataggac tgggcctttg tgtcttcaga   7920

tgcttccgct tctgcctttt cttcacccag ggccattgag actccctacc taggtcaggg   7980

ttctgctgaa gacttcagct tccgcaccgc gaaaccttcg cacgtccgga gcggtctcag   8040

cagccccatg cgctggcccc gagctggcgg accctgactg caactgcggc cctccaaccg   8100

cagcccaaaa cgcgcagggc aggaccgagc gccaacc                            8137
```

<210> SEQ ID NO 8
<211> LENGTH: 4877
<212> TYPE: DNA
<213> ORGANISM: Homo sapiens
<220> FEATURE:
<221> NAME/KEY: misc_feature
<223> OTHER INFORMATION: Incyte ID No: 026470.4

-continued

<400> SEQUENCE: 8

```
gccgccaccg ccgcgccgcc gccacagccg ccagccgctt cgcgttcggc gggggaggag     60
ttggaggcgg agaagaaggc ggtggtggcg ggtggaggtt cgagcgctgt tctcgctccg    120
gagccgctgc acatttcgga atcttctgcg gcttgtccat agtgtgaata aaaactaaat    180
cacatctata attctactga actggtcaca cagacgctgc catatatgtc acagtacact    240
gaaaaggagc cagcagcaat ggaccaagaa tctggtaagg ctgtctggcc caaaccagca    300
ggagggtatc agacaattac aggcaggaga tatggaagaa gacatgctta tgtcagtttt    360
aaaccatgta tgaccagaca tgaaagaagc ttaggtcggg ctggtgatga ctatgaagtg    420
ttggaactag atgatgttcc aaaggaaaat tcctcaggtt ccagtccttt ggatcaagtt    480
gattcttctt tacccagtga acctatattt gaaaaaagtg aaacagaaat tcccacttgt    540
ggttcagcat tgaatcaaac cactgagagc agtcaatcct ttgttgcagt acatcacagt    600
gaggaaggca gggatacctt aggaagcagt acaaatcttc ataatcactc tgagggagag    660
tatattccag gagcttgtag tgcttcaagt gtccaaaatg gaattgcatt ggttcataca    720
gactcttatg atccagatgg caaacatgga gaagataatg accatcttca actttctgca    780
gaagtcgtgg aaggtagtag ataccaggaa tcattaggca atacagtatt tgagttggaa    840
aacagagagg cagaggcata cactggtctt tcaccaccag ttccctcatt taactgtgaa    900
gtaagagatg agtttgaaga gttagattct gtaccattag tgaaaagttc tgctggtgat    960
actgagtttg tccatcagaa tagccaggaa attcagaggt cttctcaaga tgaaatggtt   1020
agtacgaaac aacaaaataa tactagccag gaaagacaga cagaacattc acctgaagat   1080
gcagcctgtg gtccagggca tatttgtagt gaacgaaata ccaatgatag ggaaaagaac   1140
catggaagtt ctcctgaaca ggtagtgagg ccaaaagtta gaaaactgat aagttcaagc   1200
caggtggacc aagaaacagg ttttaatagg catgaggcga aacaaagaag tgttcaaaga   1260
tggagagagg ctttggaagt tgaggaaagt ggctcagatg acctcttaat aaaatgtgaa   1320
gaatatgatg gagagcatga ctgtatgttc ttggatccac catactcaag agttattaca   1380
caaagggaaa cagaaaataa ccaaatgaca tcagaaagtg gagccacagc gggaaggcaa   1440
gaagtggata acacctttg gaatggctgt ggagattatt accaactcta tgacaaagat   1500
gaagatagtt ctgaatgcag tgatggggaa tggtctgctt ctttgcctca tcgattttct   1560
ggtacagaaa aagatcaatc ctcaagtgat gaaagctggg agactctgcc aggaaaagat   1620
gagaatgaac ctgagctaca aagtgatagc agtggccctg aagaagaaaa ccaagaatta   1680
tctcttcagg aaggggaaca gacatccttg gaagagggag aaattccttg gttacagtac   1740
aatgaagtca atgaaagcag cagtgatgag ggaaatgaac ctgccaatga atttgcacag   1800
ccagctttca tgttggatgg taacaataac ctggaggatg actccagtgt gagtgaagac   1860
ttagatgtgg attggagcct atttgatggc tttgcagatg gactaggagt tgctgaagct   1920
atttcatatg tggatcctca gttccttacc tacatggcac tagaagaacg cttagcccag   1980
gctatggaga ctgctctggc ccatttagag tctcttgcag tggatgttga ggtggccaat   2040
ccaccagcta gtaaggaaag cattgatggt cttccagaga cccttgttct tgaagatcac   2100
actgctattg gtcaggaaca atgctgtcca atctgttgca gtgagtatat taaggatgat   2160
atagcaacag agttgccctg tcaccatttc tttcacaaac cttgtgtctc aatttggcta   2220
caaaagtcgg gaacatgccc tgtgtgccgc cgtcatttcc cacctgcggt tattgaagca   2280
tctgcagctc cttcctctga gcctgatcct gatgccccac cttcaaatga cagtattaca   2340
```

-continued

```
gaagcaccct aaaccttgac agttgaaatg agatcagtgt atcaaagtaa atctgcaaat   2400
tccttctaaa tttcatgtgc aaataattat atataaatat atttaaaaat gctatatata   2460
gtatatgcca tagtttagaa agaatattaa cctttctaaa ctaaatttag gtttgcagaa   2520
agtattaatc atttttaagc tgaatgttga gacagtgcat ccattttctt tagttgaata   2580
tgtttgtatt aattgtaaag ccaagcttat cagttgactc tctccagaat aaataatcat   2640
ctgtgtggca tacgttattg gctttgtctg taatactgcc actaagtgat tataattaag   2700
ctgtcctgtt tgcatcaaat gtaaagactg tgttcacaac cgtagtaaaa tttggtttca   2760
ttggaaatga aacaaattct aaagtatgct ttttcactag tccctttgat tttgctatat   2820
cataacctct tggttcatat gctgagaaat ttttcagaaa gtccattttt gtttaaaatt   2880
agaacttttc agaatgccaa atgaaggcta aaattttggc cagaacatta caaaagtttt   2940
aaatcgtaga cgtaactccc cctgaaataa agttaggtag taaaatcctt aatgaaacca   3000
gtggatgtgc ttaacgtaag gttagtaaag catacaaaga atctagtgtg ctcagggctt   3060
ggtacaatga gctgaattag atggccttat gaaactcttt ctaacctctt acccaacctg   3120
tttctccttg gttaaaatta tacttgaagg cccagaacac tcatggcaca tttgtttaat   3180
attgcttata gttagtttaa ggtaattttg cttctacagt attttggaag gtctgaaaac   3240
ttgcacaggg tcatctttgt aattatataa ccccaaacta agatgcacaa tgtctccttc   3300
aggtgatcac acacagtgga cgagtatgtg caaacatgga cataatagtt cacttacaaa   3360
tgtgatttga tgttaacact agagaatgat gactgtagaa catttgagca agtaaaatag   3420
taaagcacat agtgagtgta tgtccgtcta actggtacat tgataattta gtttgggcac   3480
ataaaaggaa tatttatatg gcttcccaaa tgcagagtta catcttattc gtgtatttct   3540
ctgagtattt atatcccgtc tcctttttc attcttaaaa ataaatgaat tttcactgtt   3600
ggcacatatg aggcttaaat ataaggaaca taacacttgc attctaattt ttgcatatat   3660
tgtaaatgtg tctggtattt acagcaaaat actgtgtatc cttttatggg taaaacaaaa   3720
gtgaacattg catgcatgta atgtgatgaa tttgtaattt aggagttctt tggggcttct   3780
gtgacttggg aaatgcttac attcaggcct taatgttgca ttagctagca tgttttccct   3840
ctgatgtata tagtcactgt tgtataaact aatctttgct tgttttctac tctgtgatct   3900
ttccatatca tatttcatta atgatcagtt agtgtcaagg agtcaaaaca gattaaaatt   3960
aatttcatgt gtatatggtg gaaatttgtg gctagtgtga tttttgtttg tttcctttta   4020
agtactgttg atcagttgtg acacttactg gttaaactta cgttgctaaa gatttctcta   4080
taataagcca cacattatat ttagactata ttaagggacc ttggttttct tctagatagc   4140
agctgtccca aagaaaatat ttcttctttg tctgttaaga tttagctatt atctgccagt   4200
tgttaagagg ttttggttcc aaactcaacc agcaatgttg agagctgaac ttaagatagc   4260
tgttgtactt tttgctttcc atctgttact gtccttcatt cttggctccc tactatctat   4320
aaacagctgc tgtgaagaag aaaagttgaa taagagttgg cttaaatttt aaaaaagaaa   4380
aagaaaattg aggttttagg attttcatgg taacaagctc tggtataagc taaggctggc   4440
aagttcagat actaaaatat tatttgatca tatcttggat ccttttgaaa aagttaagac   4500
tatatgaagg taaattagaa ataagtatga atattaataa aatagcattt atcttatttc   4560
tctattttat gttgtgactt aacctaattt tattttttta acattttctt atttcttata   4620
atatgaatgc tgatatttaa aggtagatct atgtggtatt ctttgtgttt cttaattgtt   4680
```

-continued

```
taactcttaa gattatttgt gatctggatt tatgtatttg ttagatacat acgaattgtt   4740

aaaatggaat gcaagttttt caaaagccca ggtctaaatg taatggttgg tttattgttc   4800

tataacccca gcccatcatt ttctgtgtaa atcataaaca ataaacagaa tatactcggt   4860

ggtcatttct aatattt                                                  4877


<210> SEQ ID NO 9
<211> LENGTH: 2680
<212> TYPE: DNA
<213> ORGANISM: Homo sapiens
<220> FEATURE:
<221> NAME/KEY: misc_feature
<223> OTHER INFORMATION: Incyte ID No: 331232.8
<221> NAME/KEY: unsure
<222> LOCATION: 1110
<223> OTHER INFORMATION: a, t, c, g, or other

<400> SEQUENCE: 9

cacgagaaga caggaggaag aaagggagag agggccaggc agtcgcactg tgaacagaac     60

aggagaaggc gaagcggggc aaagttccct gcccaccgac gccagcctgc ttggatgact    120

tgcctcgttt cataattcac ttactgtctg caccagccgg cctcagcctg gctggaccct    180

gctgcctgtg tggcccggag ccagaggccc ccacactccc agctgctctt ctacagatgc    240

catcaacgag caggactctg ggtggctcca ctgtctaagc ctggagagtc accgccgagg    300

gatgaggacg cgccacgccg ggggaacgcg ccagctgctt tcgcggcccc aagcgcgcag    360

tgcccagcag ccgcgccgag cctgacacgc tgtcctctcc cctcgcgcac agggctctgc    420

gagtgacccg gcgggcgagc tccgtgctgc atggaacggc tgcagaagca accacttacc    480

tcccccggga gcgtgagccc ctcccgagat tccagtgtgc ctggctctcc ctccagcatc    540

gtggccaaga tggacaatca ggtgctgggc tacaaggacc tggctgccat ccccaaggac    600

aaggccatcc tggacatcga gcggcccgac ctcatgatct acgagcctca cttcacttat    660

tccctcttgg aacacgtgga gctgcctcgc cagcgcgagc gctcgctgtc acccaaatcc    720

acatcccccc caccatcccc agaggtgtgg gcggacagcc ggtcgcctgg aatcatctct    780

caggcctcgg cccccagaac cactggaacc ccccggacca gcctgcccca tttccaccac    840

cctgagacct cccgcccaga ttccaacatc tacaagaagc ctcccatcta taagcagaga    900

gagtccgtgg gaggcagccc tcagaccaag cacctcatcg aggatctcat catcgagtca    960

tccaagtttc ctgcagccca gcccccagac cccaaccagc cagccaaaat cgaaaccgac   1020

tactggccat gcccccgtc tctggctgtt gtggagacag aatggaggaa gcggaaggcg   1080

tctcggaggg gagcagagga agaggaggan gaggaagatg acgactctgg agaggagatg   1140

aaggctctca gggagcgtca gagagaggaa ctcagtaagg ttacttccaa cttgggaaag   1200

atgatcttga aagaagagat ggaaaagtca ttgccgatcc gaaggaaaac ccgctctctg   1260

cctgaccgga cacccttcca tacctccttg caccagggaa cgtctaaatc ttcctctctc   1320

cccgcctatg gcaggaccac cctgagccgg ctacagtcca cagagttcag cccatcaggg   1380

agtgagactg gaagcccagg cctgcagatc tatccctatg aaatgctagt ggtgaccaac   1440

aaggggcgaa ccaagctgcc accgggggtg gatcggatgc ggcttgagag gcatctgtct   1500

gccgaggact tctcaagggt atttgccatg tcccctgaag agtttggcaa gctggctctg   1560

tggaagcgga atgagctcaa gaagaaggcc tctctcttct gatggccccc acctgctccg   1620

ggacggcccc cttaccccctg ctgcttcagg gtttttcccc ggcgggttgg gaggggcagg   1680

aggtggggtg gaaatagggt gggctccttt cctcaggtag agtgggggc caaaacctct    1740
```

-continued gcagtccccg gcagtgagct atggactttc ttcccctca caaggctggg ggcctcctgc 1800
tctcgtccct ggccctccct gcacagggca aagccagtct gggctctggc acacagagtt 1860
catgtttgcg ccctctccct gcccctcacc ccagagggtg aggaggaatg aggggcattg 1920
gtggttaggc cggttggctg tcttgaacag ctggagggaa gatgcagggg tgggaagcgg 1980
ccaggcagaa agagctccag gctcttgtgt cgcccaccca gccctcccat actcactcct 2040
gacagctttc ctgcactgca gcttcctgct cctctgactc tagtgggaac aggccccagc 2100
tcagcctccg gcagggaggt cacccctcca cttcagcttg ccctgacctc cgctcgcaaa 2160
ccccgagctt ccaagccttt tgctccagcc ctgcggcttc cccagaagcc tgggcttagg 2220
gtggagatgc cgcctacaca cgatcctggc cctccacctg cctccaggcc acgaaatggg 2280
aattccagca ctaagccagg caccgggcag aagctgggcc ttccgcctcc cttggatggg 2340
gtcaagaggc caggcctggc acattttgga gtgtcctggc taccagctct cacctacacc 2400
cacgcacccc cccacacact atgctctctc aagaatgtaa tttattgggg ccccccagc 2460 tgctttcctc acctgcccct gccctacctt acacccccag cttgacttct ttccagtcca 2520
cgtgtgtata taatgatatc tatatttttg cccaggtctg ggtattgctc ctgcccagac 2580
cctgacatcc ctttccactg tgtgtgtgac catgctgggg gagggggact ctgcttggaa 2640
ttaaaaggtt gcattgggtc cctaaaaaaa aaaaaaaagg 2680

<210> SEQ ID NO 10
<211> LENGTH: 1778
<212> TYPE: DNA
<213> ORGANISM: Homo sapiens
<220> FEATURE:
<221> NAME/KEY: misc_feature
<223> OTHER INFORMATION: Incyte ID No: 474508.2
<221> NAME/KEY: unsure
<222> LOCATION: 1636
<223> OTHER INFORMATION: a, t, c, g, or other

<400> SEQUENCE: 10
ttagggcgaa ttgggcctct agatgcatgc tctgagcgcg gccgccagtg tgctggaaag 60
ggagcatcgc agccggcccg ggcccccgcc agcctccctc ctcgcgtccc tcggtgtcct 120
ccgcgggccg gcgcgatgcg gctgggcccg aggaccgcgg cgttggggct gctgctgctg 180
tgcgccgccg cggccggcgc cggcaaggcc gaggagctgc actacccgct gggcgagcgc 240
cgcagcgact acgaccgcga ggcgctgctg ggcgtccagg aagatgtgga tgaatatgtt 300
aaactcggcc acgaagagca gcaaaaaaga ctgcaggcga tcataaagaa aatcgacttg 360
gactcagatg gctttctcac tgaaagtgaa actcagttca tggattcaga tgtcttttaa 420
gcattatgct atgcaagaag caaaacaaca gtttgttgaa tatgataaaa acagtgatga 480
tactgtgact tgggatgaat ataacattca gatgtatgat cgtgtgattg actttgatga 540
gaacactgct ctggatgatg cagaagagga gtcctttagg aagcttcact taaaggacaa 600
gaagcgattt gaaaaagcta accaggattc aggtcccggt ttgagtcttg aagaatttat 660
tgcttttgag catcctgaag aagttgatta tatgacggaa tttgtcattc aagaagcttt 720
agaagaacat gacaaaaatg gtgatggatt tgttagtttg gaagaatttc ttggtgatta 780
caggtgggat ccaactgcaa atgaagatcc agaatggata cttgttgaga aagacagatt 840
cgtgaatgat tatgacaaag ataacgatgg caggcttgat ccccaagagc tgttaccttg 900
ggtagtacct aataatcagg gcattgcaca agaggaggcg cttcatctaa ttgatgaaat 960

-continued

```
ggatttgaat ggtgacaaaa agctctctga agaagagatt ctggaaaacc cggacttgtt   1020

tctcaccagt gaagccacag attatggcag acagctccat gatgactatt tctatcatga   1080

tgagctttaa tctccgagcc tgtctcagta gagtactggc tccttttata atttgttacc   1140

agctttactt ttgtgataaa atattgatgt tgtattttac actcttaagt cttaaccaca   1200

gtcagaatta tcttaatgta gattataatt ttggtctttt aggaaaaaaa aacaaaaatc   1260

tgatatttat ttcaaaacgt attgaagcaa caaaatatta atattgtgcc atatgacaac   1320

aaagtctttc ctaaatactc catctgttta gtactgtatt gtggaatatt tgagttctat   1380

ttccatactt gaaaacatgg aggattttag agatgcctga acaatattat ttaagtagta   1440

tgtgaccgag ctataaattt ttgtttttgt tctaagtaga tttaatttgg gaactgacag   1500

gacaatgttt ttaggtttag cattttgttt aaaaaccttt aaagaaacct ttagaaggac   1560

ttagacctca catattaatg ttgagaagtt ctgcttaatt ttaaaatggt ttctataaag   1620

ggttttattg tatganatag aacttatatt tttgcatatg tatagatagt aattatattt   1680

aatgtataac tatagcatta tggtgagtgg aatttgacat tgtccaaacc tttttcattt   1740

ttgagtgatt aaaaatgaaa tgtcctttgt aaaaaaaa                             1778
```

<210> SEQ ID NO 11
<211> LENGTH: 532
<212> TYPE: DNA
<213> ORGANISM: Homo sapiens
<220> FEATURE:
<221> NAME/KEY: misc_feature
<223> OTHER INFORMATION: Incyte ID No: 1073954.1
<221> NAME/KEY: unsure
<222> LOCATION: 299, 304, 312, 347, 375-395, 401
<223> OTHER INFORMATION: a, t, c, g, or other

<400> SEQUENCE: 11

```
ccattcagac acatggatgt tgggtctctg tgcggacggt gacaatgttt acaagcacca     60

catttacaca tccacacacg cacacgggca ctcgcgaggc gacttctcaa gcttttgaat    120

gggtgagtgg tcgggtatct agtttttgca ctgtcttact attcaaggta agaggataca    180

aacaagagga ccacttgtct ctaatttatg aatggtgtcc atcctttccc catccctgcc    240

tcctgcccct gacgcccatt tcccccctta gagcagcgaa actgcccccct cctgcccgnc   300

cttncctgtc gntgaggcag gtttttactg tgaggtgaac gtggacntgt ttctgtttcc    360

agtctgtggt gatgnnnnnn nnnnnnnnnn nnnnngtggc ngcccctgga ccagtgatga    420

ctgatgaatc ttatgagctt ctgattgatc tcggggtcca tctgtgatat ttctttgtgc    480

caaaaagaaa aaaaaagagt ggatcagttt gctaaatgaa cattgaaatt ga            532
```

<210> SEQ ID NO 12
<211> LENGTH: 5735
<212> TYPE: DNA
<213> ORGANISM: Homo sapiens
<220> FEATURE:
<221> NAME/KEY: misc_feature
<223> OTHER INFORMATION: Incyte ID No: 474697.4
<221> NAME/KEY: unsure
<222> LOCATION: 3882-3908
<223> OTHER INFORMATION: a, t, c, g, or other

<400> SEQUENCE: 12

```
ttgcgggaaa gagccaaacc ctggcgttgg ggggcccggg cggggagccc ctcccgcggt     60

ccacagcgac gcctgcccag ccctcctccc cttccggctc cggcacgggg ccccgaggcg    120

ttcggaggcc aggcgggttt ctgtcaggcc cggggaggag gggcgggcgg ggcggccgct    180
```

-continued

```
gcctccccgg gacgggccgt accacgcgga cggggaggac ggggccaggg gactgcaggg    240
cggctgcacc gcccgggggc ggggtgcgga cgggccggcg ggctccccgg ggcggggcgg    300
gagggcgggg cgtggggcgg acggaaccac cggggcgggg tgggaggtaa cgggacgggc    360
gcgaccatgg cgcggtgagg gagcgggggt ggggatcggt ccgggggagg cctgaggccg    420
ctggcttgtg cgctgtctcc gccgcccctc tttcgccgcg ccgccgccgc ccgggcatgt    480
cgtccaactg caccagcacc acggcggtgg cggtggcgcc gctcagcgcc agcaagacca    540
agaccaagaa gaagcatttc gtgtgccaga aagtgaagct attccgggcc agcgagccga    600
tcctcagcgt cctgatgtgg ggggtgaacc acacgatcaa tgagctgagc aatgttcctg    660
ttcctgtcat gctaatgcca gatgacttca aagcctacag caagatcaag gtggacaatc    720
atctcttcaa taaggagaac ctgcccagcc gctttaagtt taaggagtat tgccccatgg    780
tgttccgaaa ccttcgggag aggtttggaa ttgatgatca ggattaccag aattcagtga    840
cgcgcagcgc ccccatcaac agtgacagcc agggtcggtg tggcacgcgt ttcctcacca    900
cctacgaccg gcgctttgtc atcaagactg tgtccagcga ggacgtggcg gagatgcaca    960
acatcttaaa gaaataccac caggtatgtt tatagtggag tgtcatggca acacgctttt   1020
gccacagttc ctgggcatgt accgcctgac cgtggatggt gtggaaacct acatggtggt   1080
taccaggaac gtgttcagcc atcggctcac tgtgcatcgc aagtatgacc tcaagggttc   1140
tacggttgcc agagaagcga gcgacaagga gaaggccaag gacttgccaa cattcaaaga   1200
caatgacttc ctcaatgaag ggcagaagct gcatgtggga gaggagagta aaaagaactt   1260
cctggagaaa ctgaagcggg acgttgagtt cttggcacag ctgaagatca tggactacag   1320
cctgctggtg ggcatccacg acgtggaccg ggcagagcag gaggagatgg aggtggagga   1380
gcgggcagag gacgaggagt gtgagaatga tggggtgggt ggcaacctac tctgctccta   1440
tggcacacct ccggacagcc ctggcaacct cctcagcttt cctcggttct ttggtcctgg   1500
ggaattcgac cctctgttgg acgtctatgc catgaaaagc catgaaagtt cccccaagaa   1560
ggaggtgtat ttcatggcca tcattgatat cctcacgcca tacgatacaa agaagaaagc   1620
tgcacatgct gccaaaacgg tgaaacacgg ggcaggggcc gagatctcga ctgtgaaccc   1680
tgagcagtac tccaaacgct tcaacgagtt tatgtccaac atcctgacgt agttctcttc   1740
taccttcagc cagagccaga gagctggata tggggtcggg gatcgggagt tagggagaag   1800
ggtgtatttg ggctagatgg gagggtggga gcagagtcgg gtttgggagg gctttagcaa   1860
tgagactgca gcctgtgaca ccgaaagaga ctttagctga agaggagggg gatgtgctgt   1920
gtgtgcacct gctcacagga tgtaacccca ccttctgctt acccttgatt ttttctcccc   1980
atttgacacc caggttaaaa aggggttccc tttttggtac cttgtaacct tttaagatac   2040
cttggggcta gagatgactt cgtgggttta tttgggtttt gtttctgaaa tttcattgct   2100
ccaggtttgc tatttataat catatttcat cagcctaccc accctcccca tctttgctga   2160
gctctcagtt cccttcaatt aaagagatac ccggtagacc cagcacaagg gtccttccag   2220
aaccaagtgc tatggatgcc agattggaga ggtcagacac ctcgccctgc tgcatttgct   2280
cttgtctgga ttaactttgt aatttatgga gtattgtgca caacttcctc cacctttccc   2340
ttggattcaa gtgaaaactg ttgcattatt cctccatcct gtctggaata caccaggtca   2400
acaccagaga tctcagatca gaatcagaga tctcagaggg gaataagttc atcctcatgg   2460
gatggtgagg ggcaggaaag cggctgggct cttggacacc tggttctcag agaaccctgt   2520
```

-continued

```
gatgatcacc caagccccag gctgtcttag cccctggagt tcagaagtcc tctctgtaaa   2580
gcctgcctcc cactaggtca agaggaacta gagtaccttt ggatttatca ggaccctcat   2640
gtttaaatgg ttatttccct ttgggaaaac ttcagaaact gatgtatcaa atgaggccct   2700
gtgccctcga tctatttcct tcttccttct gacctcctcc caggcactct tacttctagc   2760
cgaactctta gctctgggca gatctccaag cgcctggagt gctttttagc agagacacct   2820
cgttaagctc cgggatgacc ttgtaggaga tctgtctccc tgtgcctgga gagttacagc   2880
cagcaaggtg cccccatctt agagtgtggt gtccaaacgt gaggtggctt cctagttaca   2940
tgaggatgtg atccaggaaa tccagtttgg aggcttgatg tgggttttga cctggcctca   3000
gccttggggc tgtttttcct tgttgccccg ctctagactt ttagcagatc tgcagcccac   3060
aggctttttt tggaaggagt ggcttcctgc aggtgttcca cctgccttcg gagcctgcca   3120
cccaggccct cagaactgag ccacaggctg ctctggccag gagagaaaca gctctgttgt   3180
tctgcattgg gggaggtaca ttcctgcatc ttctcacccc ctcaaccagg aactggggat   3240
ttgggatgag atatggtcag acttgtagat aaccccaaag atgtgaagat cgcttgtgaa   3300
accattttga atgaatagat tggtttcctg tggctccctc caaacctggc caagcccagc   3360
ttccgaagca ggaaccagca ctgtctctgt gcctgactca cagcatatag gtcaggaaag   3420
aatggagacg gcattcttgg acttcactgg ggctgctgga ttggatggga aaccttctgg   3480
aagaggcaga tgggggtcaa accactgcct tggccccagg aaggggccat aggtaggtct   3540
gaacaactgc cgcaagacca ctacatgact tagggaactt gaaaccaact ggctcatgga   3600
gaaaacaaat ttgacttggg aaagggatta tgtaggaata atgtttggac ttgatttccc   3660
cacgtcataa tgaagaatgg aagtttggat ctgctcctcg tcaggcgcag catctctgaa   3720
gcttggaaag ctgtcttcca gcagcctccg tggcctcggg ttcctaccgg cttctctgca   3780
tttggtctgc tgatcatgtt gccataatgt gtatggaaag tgtaacacat tcttactggt   3840
taaagacgac taccaggtat ctaacttgtt taacattgag tnnnnnnnnn nnnnnnnnnn   3900
nnnnnnnntt tgtatattgt ttacattttg agaggtagca ttctgtttca aatgcttttt   3960
gtttttctga cagtattgtt gactgggtca taacattttg agctgtggtt tggtggattt   4020
tcaatttttt tttttaaagg tcattcgctg tgctatcttc aaaaccttga gtttggcccc   4080
caatttttgg cattcaaatg tttaaaagct atttatcttg gtttatacaa gtttcctttc   4140
tcttcttttt gtcatggtat tctatttggt ctgcagtttg aatgtagaga aagtggactg   4200
atcccccaag cgttgtctgc ccccactctt tcctccttgg gtcccgccat tcttttactg   4260
ggcagtcgag ggcattggag gggaagtgac tgccctcagc ctcactccct ggggccatga   4320
agaaaagcta aacagtctca tggcatctca gaataatgtt gggtctccca agaagaaagg   4380
tgtaagaata acgacatggc tgattaggcg aggccaggat agggctaagg ccaggattcc   4440
tggctggcat ccagtcaccc cttctcccat ccttcccccct cttcttccac aagtccgcag   4500
ccgagacact gtagtctccc agccactgtg atgagtgccc tggagactcc actgacctct   4560
agatgaaggc ccctggccct ggttcctgtt aattaacctc tgggtctttg agtcccccag   4620
cacaaacttc tttcctgtac cctgcggctt ggggtcacag ggcatgccgg gaagccacag   4680
ctgaggggcg cagactgaag cagtgctcca cctctccttc tttagctcag ggttgctgg   4740
tctgtggcag gcgccacgag tggcccctgt ggctgttctc agtggcagtc tcttaagttc   4800
ccaccacagg cagctcttta tcccctctcc ctacttgact ctttctcttg cctgtgcttt   4860
tggcctcaaa caggcctgct ggtagcgctc agggcgtgag gctacactcc tgccctgcct   4920
```

-continued ttcctgtctt catggtctgc cagggcatac cttggggagg tggaccaaag acccaggact 4980
ttttgcagta gccagtccta ccccccagtt gtctttttac caattcaggg tgggagagaa 5040
aactgcagca ccccagcatg tgagttactc aggtgttggg ggctagaagg gacagtgcgt 5100
ttaaacaaca ctcagagctc tggccttaaa cctgtggccc cccaagtcta ggagcctcat 5160
ctcttcctgg cagtcatgcg ggcaggaggt cctgaaaggg aaaacccatt cagacaactg 5220
ttccccaatc taccagccat ctgcaggggt cagtgaccgt ggccctctcc ctcctctaga 5280
atgtgccact tatgaagagt gccccatggg gaaaaggaga ctcagctgtc ccttggcagc 5340
ttgtgccagt atcccagggc agaagtttcc acaggagcct cttgcccttg cgcagagcca 5400
ctgtgagagg cggtgggagc caacaccctt gggggagggg gcagtactgc tcggcacatc 5460
ccagcatcag gtcagatcac tgaaattaaa aaatgtgaat taagttcata tccacctttt 5520
ggggaagcag gacaaaccac caccccacca agtgtgtgac ttctccatat cccactgcag 5580
tttccatttt ttaaatggga attttcaatc ccctgtgctt gtctaacgtc tgctttaaaa 5640
agtttgagac cctgttactg tttgaaaatg catgcatgtt acgatgaatc tccaacctga 5700
ggaaaaaaat aaaactcaaa aagctttgtg taaaa 5735

<210> SEQ ID NO 13
<211> LENGTH: 4481
<212> TYPE: DNA
<213> ORGANISM: Homo sapiens
<220> FEATURE:
<221> NAME/KEY: misc_feature
<223> OTHER INFORMATION: Incyte ID No: 242114.16

<400> SEQUENCE: 13
cgaccactgt gagcccgcgg cgtgacgcgt gggaggaagc gcggctgctg tcgcccagcg 60
ccgccccgtc gtcgtctgcc ttcgcttcac ggcgccgagc cgcggtccga gcagaactgg 120
ggctcccttg catcttccag ttacaaattc agtgccttct gcagtttccc cagagctcct 180
caagaataac ggaagggaga atatgacaga tacctagcat ctagcaaaat aatggcagct 240
gcttaccttg accccaactt gaatcacaca ccaaattcga gtactaagac tcacctgggt 300
actggtatgg aacgttctcc tggtgcaatg gagcgagtat taaaggtctt tcattatttt 360
gaaagcaata gtgagccaac cacctgggcc agtattatca ggcatggaga tgctactgat 420
gtcaggggca tcattcagaa gatagtggac agtcacaaag taaagcatgt ggcctgctat 480
ggattccgcc tcagtcacct gcggtcagag gaggttcact ggcttcacgt ggatatgggc 540
gtctccagtg tgagggagaa gtatgagctt gctcacccac cagaggagtg gaaatatgaa 600
ttgagaattc gttatttgcc aaaaggattt ctaaaccagt ttactgaaga taagccaact 660
ttgaatttct tctatcaaca ggtgaagagc gattatatgt tagagatagc tgatcaagtg 720
gaccaggaaa ttgctttgaa gttgggttgt ctagaaatac ggcgatcata ctgggagatg 780
cggggcaatg cactagaaaa gaagtctaac tatgaagtat tagaaaaaga tgttggttta 840
aagcgatttt ttcctaagag tttactggat tctgtcaagg ccaaaacact aagaaaactg 900
atccaacaaa catttagaca atttgccaac cttaatagag aagaaagtat tctgaaattc 960
tttgagatcc tgtctccagt ctacagattt gataaggaat gcttcaagtg tgctcttggt 1020
tcaagctgga ttatttcagt ggaactggca atcggcccag aagaaggaat cagttaccta 1080
acggacaagg gctgcaatcc cacacatctt gctgacttca ctcaagtgca aaccattcag 1140
tattcaaaca gtgaagacaa ggacagaaaa ggaatgctac aactaaaaat agcaggtgca 1200

-continued

```
cccgagcctc tgacagtgac ggcaccatcc ctaaccattg cggagaatat ggctgaccta   1260
atagatgggt actgccggct ggtgaatgga acctcgcagt catttatcat cagacctcag   1320
aaagaaggtg aacgggcttt gccatcaata ccaaagttgg ccaacagcga aaagcaaggc   1380
atgcggacac acgccgtctc tgtgtcagaa acagatgatt atgctgagat tatagatgaa   1440
gaagatactt acaccatgcc ctcaaaaagc tatggaatag atgaagccag ggattatgag   1500
attcaaagag aaagaataga acttggacga tgtattggag aaggccaatt tggagatgta   1560
catcaaggca tttatatgag tccagagaat ccagctttgg cggttgcaat taaaacatgt   1620
aaaaactgta cttcggacag cgtgagagag aaatttcttc aagaagcctt aacaatgcgt   1680
cagtttgacc atcctcatat tgtgaagctg attggagtca tcacagagaa tcctgtctgg   1740
ataatcatgg agctgtgcac acttggagag ctgaggtcat tttgcaagt aaggaaatac    1800
agtttggatc tagcatcttt gatcctgtat gcctatcagc ttagtacagc tcttgcatat   1860
ctagagagca aaagatttgt acacagggac attgctgctc ggaatgttct ggtgtcctca   1920
aatgattgtg taaaattagg agactttgga ttatcccgat atatggaaga tagtacttac   1980
tacaaagctt ccaaaggaaa attgcctatt aaatggatgg ctccagagtc aatcaatttt   2040
cgacgtttta cctcagctag tgacgtatgg atgtttggtg tgtgtatgtg ggagatactg   2100
atgcatggtg tgaagccttt tcaaggagtg aagaacaatg atgtaatcgg tcgaattgaa   2160
aatggggaaa gattaccaat gcctccaaat tgtcctccta ccctctacag ccttatgacg   2220
aaatgctggg cctatgaccc cagcaggcgg cccaggttta ctgaacttaa agctcagctc   2280
agcacaatcc tggaggaaga gaaggctcag caagaagagc gcatgaggat ggagtccaga   2340
agacaggcca cagtgtcctg ggactccgga gggtctgatg aagcaccgcc caagcccagc   2400
agaccgggtt atcccagtcc gaggtccagc gaaggatttt atcccagccc acagcacatg   2460
gtacaaacca atcattacca ggtttctggc taccctggtt cacatggaat cacagccatg   2520
gctggcagca tctatccagg tcaggcatct cttttggacc aaacagattc atggaatcat   2580
agacctcagg agatagcaat gtggcagccc aatgtggagg actctacagt attggacctg   2640
cgagggattg ggcaagtgtt gccaacccat ctgatggaag agcgtctaat ccgacagcaa   2700
caggaaatgg aagaagatca gcgctggctg gaaaaagagg aaagatttct gaaacctgat   2760
gtgagactct ctcgaggcag tattgacagg gaggatggaa gtcttcaggg tccgattgga   2820
aaccaacata tatatcagcc tgtgggtaaa ccagatcctg cagctccacc aaagaaaccg   2880
cctcgccctg gagctcccgg tcatctggga agccttgcca gcctcagcag ccctgctgac   2940
agctacaacg agggtgtcaa gccatggagg cttcagcccc aggaaatcag ccccccctcct  3000
actgccaacc tggaccggtc gaatgataag gtgtacgaga atgtgacggg cctggtgaaa   3060
gctgtcatcg agatgtccag taaaatccag ccagccccac cagaggagta tgtccctatg   3120
gtgaaggaag tcggcttggc cctgaggaca ttattggcca ctgtggatga gaccattccc   3180
ctcctaccag ccagcaccca ccgagagatt gagatggcac agaagctatt gaactctgac   3240
ctgggtgagc tcatcaacaa gatgaaactg gcccagcagt atgtcatgac cagcctccag   3300
caagagtaca aaaagcaaat gctgactgct gctcacgccc tggctgtgga tgccaaaaac   3360
ttactcgatg tcattgacca agcaagactg aaaatgcttg ggcagacgag accacactga   3420
gcctccccta ggagcacgtc ttgctaccct cttttgaaga tgttctctag ccttccacca   3480
gcagcgagga attaaccctg tgtcctcagt cgccagcact tacagctcca actttttga    3540
```

-continued

```
atgaccatct ggttgaaaaa tctttctcat ataagtttaa ccacactttg atttgggttc   3600

atttttttgtt ttgttttttt caatcatgat attcagaaaa atccaggatc caaaatgtgg   3660

cgtttttcta agaatgaaaa ttatatgtaa gcttttaagc atcatgaaga acaatttatg   3720

ttcacattaa gatacgttct aaagggggat ggccaagggg tgacatctta attcctaaac   3780

taccttagct gcatagtgga agaggagagc atgaagcaaa gaattccagg aaacccaaga   3840

ggctgagaat tcttttgtct accatagaat tattatccag actggaattt ttgtttgtta   3900

gaacaccctt cagttgcaat atgctaatcc cactttacaa agaatataaa agctatattt   3960

tgaagacttg agttatttca gaaaaaacta cagccctttt tgtcttacct gccttttact   4020

ttcgtgtgga tatgtgaagc attgggtcgg gaactagctg tagaacacaa ctaaaaactc   4080

atgtcttttt tcacagaata atgtgccagt tttttgtagc aatgatattt ctcttggaag   4140

cagaaatgct ttgtaccaga gcacctccaa actgcattga ggagaagttc cagaaccatc   4200

cccttttttcc atttttatat aatttataaa gaaagattaa agccatgttg actattttac   4260

agccactgga gttaactaac ccttccttgt atctgtcttc ccaggagaga atgaagcaaa   4320

acaggaattt ggttttcttt tgatgtccag ttacaccatc cattctgtta attttgaaaa   4380

aatataccct ccctttagtt tgttggggga tataaattat tctcaggaag aatataatga   4440

actgtacagt tactttgacc tattaaaaag gtgttaccag t                        4481
```

<210> SEQ ID NO 14
<211> LENGTH: 5032
<212> TYPE: DNA
<213> ORGANISM: Homo sapiens
<220> FEATURE:
<221> NAME/KEY: misc_feature
<223> OTHER INFORMATION: Incyte ID No: 445186.7
<221> NAME/KEY: unsure
<222> LOCATION: 5019
<223> OTHER INFORMATION: a, t, c, g, or other

<400> SEQUENCE: 14

```
gggcggggga atatacaaag tgaagccaca ttgccaaact tgcagcagcg attgcagcag     60

ttgctgccgc tgcgccgcgc ctgaagccgc gccgcgcggg ccgagggctc ctgcagctgc    120

tcgcgcgcag tcggaggcgg agaaggacga agactgagac tgacacttct gctcccggcc    180

gcccggcact tacgcggggg ccccccaacc cgccccagag caacgcgatt taaaaaaaaa    240

aaaaaagccg cccttagccc cctcctcccc tttcctgctt ctgcgagaac tccctccctc    300

cctccagctt ccgccagccc aggcgcccct tccctggaag ccgagcggct tcgctcgcat    360

ttcaccgccg ccgcctctcg caatattgca atataggggga aaagcagacc atggtgaatc   420

cgggcagcag ctcgcagccg cccccggtga cggccggctc cctctcctgg aagcggtgcg    480

caggctgcgg gggcaagatt gcggaccgct ttctgctcta tgccatggac agctattggc    540

acagccggtg cctcaagtgc tcctgctgcc aggcgcagct gggcgacatc ggcacgtcct    600

gttacaccaa aagtggcatg atcctttgca gaaatgacta cattaggtta tttggaaata    660

gcggtgcttg cagcgcttgc ggacagtcga ttcctgcgag tgaactcgtc atgagggcgc    720

aaggcaatgt gtatcatctt aagtgtttta catgctctac ctgccggaat cgcctggtcc    780

cgggagatcg gtttcactac atcaatggca gtttattttg tgaacatgat agacctacag    840

ctctcatcaa tggccatttg aattcacttc agagcaatcc actactgcca gaccagaagg    900

tctgctaaaa ggtcagagta atgcagaatg cgtgccttca tctcagattt gttcatcaca    960

ggtggatccc atgtgtcttc agtagacaag tcacctttgt agctagcacc agtgccagct   1020
```

-continued

```
ccatgccatt gcaccttctt tagtcttgat tgcccttccc gcatttattg gtgtattaaa   1080
atgactgaat atgaacatta aggactccat gaacctgggc taatgggaga ctgtagagaa   1140
aatgaaaaaa gatccaccag aggacatctt ggggaggggg agggagctgg gggggaggga   1200
aatgactaat gaagctaatt aaaagaagca ttcaaatctg ctttctaccc tcattaacaa   1260
ttagcagggc actggccaga gtttgtaccc tgtgttttac cttaacaaca ttctatttgc   1320
tctttgtata tttaagtgtt gtaaggaaac gtgtttcaat caaaactgac catgagataa   1380
aggaaagaga tgtggctttt gtgatattct atcacaaaca cttattgtat ctctgtaaaa   1440
tacaatgtat gtatgcatgt aagtgttttt gtcctaatgt tgctactccc atggcaaaga   1500
aaaaaaaaag aatgaaaaaa agaaaaaaat ttggaaaaaa aaatcaggct catagcagct   1560
actgtgtaga aaattccccc tacttctaat ttgctgaatg aagaaaaaaa aaaatctttt   1620
atttgtgata ttttcagaga catttgctct agtatggtgt atttaaataa taaaaactta   1680
aaagaaaaaa tatttaatgg tgtttgggtt taaacactgc tttttctctt ctgtattttg   1740
aagaaattta gtttttattg ttgttgaata acaagctcac tttaaatttg aaggagttga   1800
gggaggtgga gtgtatattt atttagctct gggccagtaa ggtattcttc aaattactta   1860
accacgccat tattggcagg ggtacaaagt agtttctaac agggtccttt ctataagtca   1920
agaatattct gttaacagca tttcgttaca cttctatatc acagtaagtc ttttgtgttt   1980
ataaatactt gagtgtccac tattttgttt attctttttc tcaatagcaa acaaagcctt   2040
gggtattgat gaaaagtatg tataaaaaaa aatacggcac aaccatcctg ttctcttatt   2100
gagtttatag cttttgaagg aagtcacaat ttctaagtca tacctgtaca tattttgaag   2160
ctcacttagt tgtagggacc cagagctctt tttttatggt gatctttgat tggtgaagta   2220
gccatttcct ggtgaccctt aggctcgtgt ggttggctgt aaggtgttta ttttgttttg   2280
ctcctacact tctttactga ctgcgtttcc gtatgtattt tgggggaaga ttctgacttc   2340
atttagtctt agtcttgaga tactgagttg ctggttgcag gcagcagagt gtccaccaca   2400
gtgcctgcac tgcccgcaga gctgccctcc ggaaagcatg cagtataaca gctagtgctg   2460
gaaggaggaa aaccaaatag gcctggaggc tgaggttgta ctgccagctt ccttagatgt   2520
gagcaaattt caactacaac ttccatcaca ggctaataaa accaggtgtg tgaacgctac   2580
tattttaaat tttctttttt aagatggcat tttattttgt tccagaaaag cgcctgatgt   2640
agaccctccc tctgagaata gccgtggagc catgtagaga ggtgtagctc agcacatctc   2700
aactaccagt cagcttccct ttgagaactt ctgtgctcac ttcctgtttt cagagattcc   2760
agggcagggg aaaaaaaaaa tcagttgaac ttcaaacctc ctagaggaga ttgtaaaggc   2820
atagagttga ggtgaatagt tttgttagaa ccttataaaa ataaaatgca agaaaataat   2880
atgaagaaat cacatatata tgtttgaatt agatgtctgt ttgaattaga tccttgggga   2940
atttcttcaa actagttctg gttcttatat ttgttttttt tcctttaagg aactttctga   3000
aggaagttag actgcgatgg taaaggggga aatgggttaa tgagattgca ggcattttct   3060
atattctttt tggcataagc acttatgtcc ctgatatgta caaattcaaa ggaggtggtt   3120
aataacttta gtaaataata tattgtcgca tttaatgatg tggagggcta aggtcattac   3180
ggactttaaa taaactatta tatggctggt tcctcaagca ctgctgcgta tttaataatg   3240
agcttctaaa agcatttctt aagttgcaga cctataagat tacaaatgtc actcatgtta   3300
gtataatcca catgcaagtg atgaagcctt ctctttgatg tgctaaattg gagaaggact   3360
```

-continued

```
aatggagcta tgaatataca atagaacata tttaagtagt agtcttgctt taggtaaaac   3420

actttcttga aaccagaggc atttcaaaca ataaaacccg gctctaatgg ggatgctctg   3480

tgtggataga aagctactaa aaacactcag gtttattctg atgtgagcag cgattgtgtg   3540

cagttcctcc cccaatctca acattgctta ggaaaaaaaa aaatctatga gtttattcca   3600

cctttcatcc attgcatttg tgatgttatt agttagcaag atggacactg ttctttagaa   3660

aggacttatt taatattaac cacgtcatag agcaagatgg cccccagtcc ctacaagcaa   3720

gtgcaattaa aaataaaagc aaatgttact gagccctgct gaactcctga taaaaaaaat   3780

tatgtttatg gtacatataa atgtctcaat catgcaaatt gtcactcttg ttaatgaaac   3840

aattttgtaa aaagatagtc ctctaaaagg gtttaatgtt ttttacctat ctaactgtct   3900

aattagattt acacatcccg caaggcaggg gagcctgaag gcttttccaa accaaatcgt   3960

ttgccactag aaactatttt cagctcttca tgatttatta ggaaatagtt taacccggac   4020

tgtagtgtct tataaaatac aaaacgagaa aactgacaca ccaaaatgaa gtctgtgaaa   4080

ttgtcatcct cttaatatta cctgtattta aattctttct tttgccctta ttaacactga   4140

tatttgaaac aactaatcat ctaaaaggaa gctcttaaag ggctttaaat gtcaatatag   4200

taagattcta atgtgcacta ctatttatat aaaatatttc ttagggccca taaatcatat   4260

aataaacagt gaacccaaga gctacatatg gagtctagtg aagagttccc atgtagccta   4320

actaattgta tttaaattga ggagatccaa aaaccccatc acccttcacc ccaaagaccc   4380

cttcaccctt caccagggaa ttctatcctg ggtgctgtcc cacctatgac cccttcaaga   4440

ggccattgga aaaaggccat ttacaagtta atgttactta tagctttgtt actaagactc   4500

acctattgtt agtgcagcca agtcacagaa gtgcttattg cagttaaata gcaatttgtt   4560

tccatgaaac tgcaattaaa gtattactga gcagccattt tagattggca gtgctctgaa   4620

cgcatgttaa acagccagct actcccactt gcagagtctg agatctgact agcagcaaag   4680

tgtagcacat tcgccgatgc tgggtaccta gttaaagagg catttgtagc cctctgctcc   4740

catcgtgaac atgctgagag caatgacaag tcagggctga tttttggaag gtgaacttgc   4800

aacttacctc aagtgaatac tgttttcagt tgtgcaagaa gtgctttatg ctagtagata   4860

tgtgcatgtt tcctagaggg aatgttttca agttcagatt gattctgctg agaatggacg   4920

gcaactcgga ggcctcaagc caataatgta ctacaggccc tgacatgtta cagctgtgta   4980

aacagggcca ttctatttcc taaatcacaa ctaataaanc agaggatgaa aa           5032
```

<210> SEQ ID NO 15
<211> LENGTH: 3339
<212> TYPE: DNA
<213> ORGANISM: Homo sapiens
<220> FEATURE:
<221> NAME/KEY: misc_feature
<223> OTHER INFORMATION: Incyte ID No: 247500.4

<400> SEQUENCE: 15

```
ctctgctgtg ctgcctcaaa cgcggagggc tgcgtgcagt gggagcgggc tccaggagcc     60

cgagcctcca gccgtcctca gagcaaggca gcaccgaggc ctggccacag caatatccat    120

ctggaagctc ttcccttcac tcccaactct gaggttgcct aactctttat taaaaattca    180

gaagggggaa tgccagcccc tagcatggac tgtgatgttt ccactctggt tgcctgtgtg    240

gtggatgtcg aggtctttac caatcaggag gttaaggaaa aatttgaggg actgtttcag    300

acttatgatg actgtgtgac gttccagcta tttaagagtt tcagacgtgt ccgtataaac    360
```

-continued

```
ttcagcaatc ctaaatctgc agcccgagct aggatagagc ttcatgaaac ccaattcaga    420
gggaaaaaat taaagctcta ctttgcacag gttcagactc cagagacaga tggagacaaa    480
ctgcacttgg ctccacccca gcctgccaaa cagtttctca tctcgccccc ttcctcccca    540
cctgttggct ggcagcccat caacgatgcc acgccagtcc tcaactatga cctcctctat    600
gctgtggcca aactaggacc aggagagaag tatgagctcc atgcagggac tgagtccacc    660
ccaagtgtcg tcgtgcacgt gtgcgacagt gacatagagg aagaagagga cccaaagact    720
tccccaaagc caaaaatcat ccaaactcgg cgtcctggcc tgccaccctc cgtgtccaac    780
tgagctgcct gctccttctc gataatagcc gtctcctctt tatcatgctt tttccccctg    840
ttgtttgtca aaaaaaattg cctttaaatt cctgggtgtt tggttgtttg agattccttc    900
cttgttatca agcctctcgg acaaaagggc taggaaaagg tgatatgtct cctgatcata    960
tcatacccat taagtataac ccattattta gaaggttcta gggaaaaaag tagtattttc   1020
ttattaaaca atcagcacag cctatatctt tgttctctca tgttgatcca agccagagac   1080
atcggtaaca aatagcacct gtgttgtttg tgaggtgttt cagtcccagt cctgatgtgt   1140
gtgcgttgtt ctctcctggc cacttaaata ggaccatatg taaacttgac tttgactgca   1200
tgagatatcc ctatctggtc tcactcagtc ctctgcatcc caacattccc aggacatgca   1260
tgatcaccag catttatttt cattatttga ggatatctta taactcacag attgtcagca   1320
tccagccatg tcctatctag attaggaaaa tgatcagaat attccagctc aacaagtctg   1380
ggtatactca ctattgtgag tcaatacacc atagctctgt tgaaattcct ggaggcaaaa   1440
ttgaccttgg ccccaaagat attcctcaat agatttcaaa caccactccc ctgtagaact   1500
ctcccagcct cgttggggag gcttgtccag ggtgatagag actgatttca gacaaaccta   1560
tttattacaa aagtttcatg gtgtctgaat gattgttttc tctctttgta tatttgtaca   1620
aatgtttcag ctgtgctttt aaaaaatctg gatgtttttt atttagtgat tgttcgacaa   1680
ttagctgctt caaaacataa tgtgcattgc ttatgaatgc cttcatatac taatacagat   1740
actctgataa tattacactc taataaggat aatgctgaat tttgaaagga cacaaaacat   1800
ctaatgccaa tatatacatg gttagccaac atctttgcta tcaagaccac ttgttttaaa   1860
taaagatgca agtgtcagtt gtagattatt gggatgaagc taaatcccca gaatgcagca   1920
gcagctgagc atgttaaaat ggggaaggat gatagctaca tgtatgccgg tcctactcac   1980
gcgacacccg tgtgctcaaa aaagttactt gtttttgtta cgtgtgattt tcctatttct   2040
ctagcccaaa gtgcattaca gaagatacac ctatagaacc attaccttct gctatgtgtg   2100
ccagggctca tctactcctg tacattaatg gattacttta gatgcaaatg cagattacaa   2160
tggagtgggg aagtactttc attacccaag cctcagaaaa acacacaaga acaataacac   2220
agcaaacaga ttgagggatt gttgtggttt ttgactaagg tgtatgttag tttcatcaga   2280
aacttaaaac atagactgat cactcagaaa ttaaagtccg ttttactgtg aatatagcaa   2340
tatagtactg gacacagtac tggtgaaact gaggagagca ttgcttgtaa aatcctgagt   2400
ttccataagg aaaatgaaaa ctccttttaa aaataaaatc tgaggagtgt acaataagca   2460
tatgctttga ctttcctttg ctgtggaggt ttttggtttt tcattgatga taaacgacta   2520
cagacttagt agtggagaaa tggtgtcctc tagtggaaga aatagtaggc tcagctattc   2580
agatgcagag cactgcagca tccagccttt caaagctgac tcttctcaat catctgtggg   2640
tcatttgact tgatttttta agctaccctg aatttccaga atgcaggttc taaagaaatc   2700
tagatgagag aaagtatttg aaaatgattt ttaaatgttt tttaaaagac acatctgaca   2760
```

-continued

```
tttttaacaa cttagtaaaa gttgaaatga ccattctgtg tagtcataaa agaaacacaa   2820

tgaagtgtat ggcctctgga gttagtctta gtaaaactta ttgctctgtg tcaatgttaa   2880

cctgtctcag atcaagtaat tctttcacta ggttgggttt ggggaggggg gaaaagaggg   2940

gcttttccta ggagaacgat aagaaatgga aagactcctt gaagtgttgc aagggaacct   3000

cctagcactg tgaaagtcag aatcgcctca gcatttccat gacgcacatt atgcaaatct   3060

ctttagcact attttaagtt tgaaaacttt aacaatgaag gggaagggga agatttccac   3120

caactgaatc atttgtgcac gtgtatagct caaagagctt agacttcaaa tatatctggt   3180

gaatgaatta cttgatctga gacaggttaa cattgacaca gagcaataag ttttactaag   3240

actaactcca gaggccatac acttcattgt gtttctttta tgactacaca gaatggtcat   3300

ttcaactttt actaagttgt taaaaatgtc agatgtgtc                          3339
```

```
<210> SEQ ID NO 16
<211> LENGTH: 3159
<212> TYPE: DNA
<213> ORGANISM: Homo sapiens
<220> FEATURE:
<221> NAME/KEY: misc_feature
<223> OTHER INFORMATION: Incyte ID No: 247500.5
<221> NAME/KEY: unsure
<222> LOCATION: 216, 3091, 3093, 3103
<223> OTHER INFORMATION: a, t, c, g, or other

<400> SEQUENCE: 16
```

```
ccagctatta gggagactcc agccccttgc caggcgagag agtggatggt caccctccat     60

ggaggaagtg tttcccaagg gtgtctgctg gggaaggaaa gcatgatgca gtgcagatta    120

atcagagaga agagccaacg tctcgtctac cttttttgt tgaaaacaaa caaaacgtga     180

ttgtatgtca actttggaaa aaaacaacgt agtgtnggga atgaggggag aatcatactt    240

catcggaatg aggagcccag ggcagcaggg acacgtccct gaagatggag gacttttctt    300

actgtgctgc atagacaggg actgggctgt cactcgttgt tttgcagaag aagcctttca    360

agcaatcact gacttcaatg acctccccaa ctcgttgttt gcgtgcaatg ttcaccagtc    420

agtgtttgaa ggagaagaga gcaaggaaaa atttgaggga ctgtttcgga cttatgatga    480

ctgtgtgacg ttccagctat ttaagagttt cagacgtgtc cgtataaact tcagcaatcc    540

taaatctgca gcccgagcta ggatagagct tcatgaaacc caattcagag ggaaaaaatt    600

aaagctctac tttgcacagg ttcagactcc agagacagat ggagacaaac tgcacttggc    660

tccaccccag cctgccaaac agtttctcat ctcgccccct tcctccccac ctgttggctg    720

gcagcccatc aacgatgcca cgccagtcct caactatgac ctcctctatg ctgtggccaa    780

actaggacca ggagagaagt atgagctcca tgcagggact gagtccaccc caagtgtcgt    840

cgtgcacgtg tgcgacagtg acatagagga agaagaggac ccaaagactt ccccaaagcc    900

aaaaatcatc caaactcggc gtcctggcct gccaccctcc gtgtccaact gagctgcctg    960

ctccttctcg ataatagccg tctcctcttt atcatgcttt ttccccctgt tgtttgtcaa   1020

aaaaaattgc ctttaaattc ctgggtgttt ggttgtttga gattccttcc ttgttatcaa   1080

gcctctcgga caaaagggct aggaaaaggt gatatgtctc ctgatcatat catacccatt   1140

aagtataacc cattatttag aaggttctag ggaaaaaagt agtattttct tattaaacaa   1200

tcagcacagc ctatatcttt gttctctcat gttgatccaa gccagagaca tcagtaacaa   1260

atagcacctg tgttgtttgt gagctgtttc agtcccagtc ctgatgtgtg tgcgttgttc   1320
```

-continued

```
tctcctggcc acttaaatag gaccatatgt aaacttgact ttgactgcat gagatatccc   1380
tatctggtct cactcagtcc tctgcatccc aacattccca ggacatgcat gatcaccagc   1440
atttattttc attatttgag gatatcttat aactcacaga ttgtcagcat ccagccatgt   1500
cctatctaga ttaggaaaat gatcagaata ttccagctca acaagtctgg gtatattcac   1560
tattgtgagt caatacacca tagctctgtt gaaattcctg gaggcaaaat tgaccttggc   1620
cccaaagata ttcctcaata gatttcaaac accactcccc tgtagaactc tcccagcctc   1680
gttggggagg cttgtccagg gtgatagaga ctgatttcag acaaacctat ttattacaaa   1740
agtttcatgg tgtctgaatg attgttttct ctctttgtat atttgtacaa atgtttcagc   1800
tgtgctttta aaaaatctgg atgtttttta tttagtgatt gttcgacaat tagctgcttc   1860
aaaacataat gtgcattgct tatgaatgcc ttcatatact aatacagata ctctgataat   1920
attacactct aataaggata atgctgaatt ttgaaaggac acaaaacatc taatgccaat   1980
atatacatga ttagccaaca tctttgctat caagaccact tgtttttaaa taaagatgca   2040
agtgtcagtt gtagattatt gggatgaagc taaatcccca gaatggcagc agcagctgag   2100
catgttaaaa tggggaagga tgatagctac atgtatgccg gtcctactca cgcgacaccc   2160
gtgtgctcaa aaaagttatt tgtttttgtt acgtgtgatt tttctatttc tctagcccaa   2220
agtgcattac agaagataca cctatagaac cattaccttc tgctatgtgt gccaggcctc   2280
atctactcct gtacattaat gaattacttt agatgcaaac gcagattaca atggagtggg   2340
gaagtacttt cattacccaa gcctcagaaa aacacacaag aacaataaca cagcaaacag   2400
attgagggat tgttgtggtt tttgactaag gtgtatgtta gtttcatcag aaacttaaaa   2460
catagactga tcactcagaa attaaagtcc gttttactgt gaatatagca atatagtact   2520
ggacacagta ctggtgaaac tgaggagagc attgcttgta aaatcctgag tttccataag   2580
gaaaatgaaa actcctttta aaaataaaat ctgaggagtg tacaataagc atatgctttg   2640
actttccttt gctgtggagg tttttggttt ttcattgatg ataaacgact acagacttag   2700
tagtggagaa atggtgtcct ctagtggaag aaatagtagg ctccgctatt cagatgcaga   2760
gcactgcagc atccagcctt tcaaagctga ctcttctcaa tcatctgtgg gtcatttgac   2820
ttgatttttt aagctaccct gaatttccag aatgcaggtt ctaaagaaat ctagatgaga   2880
gaaagtattt gaaaatgatt tttaaatgtt ttttaaaaga cacatctgac atttttaaca   2940
acttagtaaa agttgaaatg accattctgt gtagtcataa aagaaacaca atgaagtgta   3000
tggcctctgg agttagtctt agtaaaactt attgctctgt gtcaatgtta acctgtctca   3060
gatcaagtaa ttctttcact aggttgggtt ncngaggggg ganaagaggg gctttcctag   3120
gagaacgata agaaatggaa agactccttg aagtgttgc                          3159
```

<210> SEQ ID NO 17
<211> LENGTH: 2517
<212> TYPE: DNA
<213> ORGANISM: Homo sapiens
<220> FEATURE:
<221> NAME/KEY: misc_feature
<223> OTHER INFORMATION: Incyte ID No: 244622.1
<221> NAME/KEY: unsure
<222> LOCATION: 805, 810, 814
<223> OTHER INFORMATION: a, t, c, g, or other

<400> SEQUENCE: 17

```
cttccctggc tcgctcacgc ctgctctcag aagctccgat ccagacacac gcgaggcgct     60
gtcctttcag caccacaagc tcgggctgag gagggaggac tcctggccgt cctcctcctc    120
```

-continued ttcaaattgg cttgaatctg ctctgacccc ccacgagtgc agcacagtct gggaagaaag 180
gcgtaaggat ggtgaagctg aacagtaacc ccagcgagaa gggaaccaag ccgccttcag 240
ttgaggatgg cttccagacc gtccctctca tcactccctt ggaggttaat cacttacagc 300
tgcctgctcc agaaaaggtg attgtgaaga caagaacgga atatcagccg gaacagaaga 360
acaaagggaa gttccgggtg ccgaaaatcg ctgaatttac ggtcaccatc cttgtcagcc 420
tggccctagc tttccttgcg tgcatcgtgt tcctggtggt ttacaaagcc ttcacctatg 480
atcacagctg cccagaggga ttcgtctata agcacaaacg ctgtatccca gcctccctgg 540
atgcttacta ctcctcccag gaccccaatt ccagaagccg cttctacaca gtcatcagcc 600
actacagcgt ggccaagcag agcactgccc gggccatcgg gccgtggctg tcagcagccg 660
ctgtcatcca tgagcccaag ccgcccaaga cccagggcca ctagaggcct gccccagcca 720
gaatgggggg cggggtggag aggaggaccc ccattggcta agccaagctc cagttacaag 780
acaacactgt actcctggga tatgntggcn ggtncggggc agggcagggt gggggggaaga 840
acgcaccaaa aacgtggtgt gtgctggagt tgtctgaacc gatatttctt tttgttcctt 900
ggtattgttg attcgtcgcc gagtcaggct catgtacaaa ggcatgtttc gtgttgattg 960
ttcccatgta agatattttt aaagccactg cttattcttt gttaggaaaa tgtaacagca 1020
gaaaaggaaa gaaacaaaga acatgaacaa aaagcattaa actggctcca tcagaagacg 1080
ttgaagggca gtgaagagca cagactctgt gggcttctta gataagaaaa cgtagcttca 1140
gtgggggctc cagggttgca gagtatgagt gacacagacc gggactattc cattagcctg 1200
tggtctgcag ggtaggcccg caggaaatga ggaatggccg agctggagag aagagctgat 1260
tttggcatta ctaagcccag aacgcacata acccatagtg aaatgtgctg gcctctggtg 1320
cattttgcaa gatgagcaca aactttctgg gcctccatcc taggacctgg gcagacccac 1380
atggcctggg ctctgaatgc ccaccctgcg acggtgggtt ctgcatcagc aaacgctgag 1440
gagtgggcag attttctttg tcttttgctt gcattttcta gatccacacc tggatactgc 1500
ccatgttgac gagacagcag cagggggaga gggagggaag gaaggtgcgg ctgcaagaag 1560
gaaggcacgg gacaggcatg tgacactagg ccacaagcga taagcacagg cacctgactt 1620
ttaagttttt gtttgtttgt tgtttcccaa agtgctgata acaataacaa caacaatagg 1680
attccaacca ggagcctcaa gtgacagcca ggaagagacc tgaaggttgg ggccaccaca 1740
atgccaaatc gtttctaaag gaagctgaaa aatgggactg tcttttgccc acttcgttgt 1800
gttaaaaggg gacatttgtc caaactcccc aaccgagttc tagaagctcc tgacaaggag 1860
gcagcatcca gccttgacca ggcctcccag ttccctggaa ccgtatcagg cattcgcctg 1920
cctctcacaa atgtttcagg gaggccagtt ctgcagggtg tcagctccag gacccacagg 1980
gccagaacca gctgggagaa ttggttattt gagatgtggt actgcttcct cacaagtctc 2040
ccacaggcca tgtaaagggt atttttttgt ggcttgctgt gttgctgaga tcatcgtatg 2100
caacagctgg gtaataagac tagcatagct caaactatcc tgccaaacgc tctcatctga 2160
tttttcctcc cttctccccc aacctccaat caccctgagt cacctgtaaa ttcatttgtc 2220
attcaaagcg gaataacaag ttgtccctag caaaaccgct gagcgcttta taattttgtg 2280
gtgtattttt gtcagtaggt agcagagctt gggggagaag ggaggaaaaa taagactagc 2340
atagctcaaa ctatcctgcc aaacgctctc atctgatttt tcctcccttc tcccccaacc 2400
tccaatcacc ctgagtcacc tgtaaattca tttgtcattc aaagcggaat aacaagttgt 2460

-continued

```
ccctagcaaa accgctgagc gctttataat tttgtggtgt attttcctcc cttctcc      2517


<210> SEQ ID NO 18
<211> LENGTH: 391
<212> TYPE: DNA
<213> ORGANISM: Homo sapiens
<220> FEATURE:
<221> NAME/KEY: misc_feature
<223> OTHER INFORMATION: Incyte ID No: 1055005.1
<221> NAME/KEY: unsure
<222> LOCATION: 4, 18, 23, 35, 47, 56, 75, 79, 96, 209, 211-213,
      215-217, 223, 226,
<223> OTHER INFORMATION: a, t, c, g, or other

<400> SEQUENCE: 18

ctgnccagct taaggtcnta acnatgccgg agacntgtag ataccancct ttcaanccac     60

tctctattgg aggcntcanc attctgaagg ataccngtga agccattgag gagctggtgg    120

aacctgtggc agcacatggc ccaaaaatcg aggaggagga acaagagcca gaaccccccag   180

aaccatttga gtatattgat gattaaggnc nnnannntcg cantancttg gctgaagaag    240

attntccagn ctcatattgg gaatgcttat gaggaaattc atgccgagac ctgctattca    300

atgcatgtat cgttgcctct gcactnacct gaagaaccct gtctccaagt ctttggttga    360

agagaagata tatgactgtt gagtgtgctc t                                   391


<210> SEQ ID NO 19
<211> LENGTH: 1974
<212> TYPE: DNA
<213> ORGANISM: Homo sapiens
<220> FEATURE:
<221> NAME/KEY: misc_feature
<223> OTHER INFORMATION: Incyte ID No: 236240.3

<400> SEQUENCE: 19

gcaggttcca aagcgggtcc gagccgccgc cgcgcgcgcg ccgcgcactg cagccccagg     60

ccccggcccc cccacccacg tctgcgttgc tgccccgcct gggccgggcc ccaaaggcaa    120

ggacaaagca gctgtcaggg aacctccgcc ggagtcgaat ttacgtgcag ctgccggcaa    180

ccacaggttc caagatggtt tgcgggggct tcgcgtgttc caagaactgc ctgtgcgccc    240

tcaacctgct ttacaccttg gttagtctgc tgctaattgg aattgctgcg tggggcattg    300

gcttcgggct gatttccagt ctccgagtgg tcggcgtggt cattgcagtg ggcatcttct    360

tgttcctgat tgctttagtg ggtctgattg gagctgtaaa acatcatcag gtgttgctat    420

ttttttatat gattattctg ttacttgtat ttattgttca gttttctgta tcttgcgctt    480

gtttagccct gaaccaggag caacagggtc agcttctgga ggttggttgg aacaatacgg    540

caagtgctcg aaatgacatc cagagaaatc taaactgctg tgggttccga agtgttaacc    600

caaatgacac ctgtctggct agctgtgtta aaagtgacca ctcgtgctcg ccatgtgctc    660

caatcatagg agaatatgct ggagaggttt tgagatttgt tggtggcatt ggcctgttct    720

tcagttttac agagatcctg ggtgtttggc tgacctacag atacaggaac cagaaagacc    780

cccgcgcaaa tcctagtgca ttcctttgat gagaaaacaa ggaagatttc ctttcgtatt    840

atgatcttgt tcactttctg taattttctg ttaagctcca tttgccagtt taaggaagga    900

aacactatct ggaaaagtac cttattgata gtggaattat atatttttac tctatgtttc    960

tctacatgtt tttttctttc cgttgctgaa aaatatttga aacttgtggt ctctgaagct   1020

cggtggcacc tggaatttac tgtattcatt gtcgggcact gtccactgtg gcctttctta   1080

gcatttttac ctgcagaaaa actttgtatg gtaccactgt gttggttata tggtgaatct   1140
```

-continued gaacgtacat ctcactggta taattatatg tagcactgtg ctgtgtagat agttcctact 1200
ggaaaaagag tggaaattta ttaaaatcag aaagtatgag atcctgttat gttaagggaa 1260
atccaaattc ccaatttttt ttggtctttt taggaaagat gtgttgtggt aaaaagtgtt 1320
agtataaaaa tgataattta cttgtagtct tttatgatta caccaatgta ttctagaaat 1380
agttatgtct taggaaattg tggtttaatt tttgactttt acaggtaagt gcaaaggaga 1440
agtggtttca tgaaatgttc taatgtataa taacatttac cttcagcctc catcagaatg 1500
gaacgagttt tgagtaatca ggaagtatat ctatatgatc ttgatattgt tttataataa 1560
tttgaagtct aaaagactgc atttttaaac aagttagtat taatgcgttg gcccacgtag 1620
caaaaagata tttgattatc ttaaaaattg ttaaataccg ttttcatgaa atttctcagt 1680
attgtaacag caacttgtca aacctaagca tatttgaata tgatctccca taatttgaaa 1740
ttgaaatcgt attgtgtggc tctgtatatt ctgttaaaaa attaaaggac agaaaccttt 1800
ctttgtgtat gcatgtttga attaaaagaa agtaatggaa gaattgatcg atgaattaag 1860
tgaggtggaa ttcttttctt tctgctttag cttctctctg ttggacttag agctgggtat 1920
tgctatttta gtgtataatc aagctgtgga aataaatttc cagcattaat gtct 1974

<210> SEQ ID NO 20
<211> LENGTH: 2445
<212> TYPE: DNA
<213> ORGANISM: Homo sapiens
<220> FEATURE:
<221> NAME/KEY: misc_feature
<223> OTHER INFORMATION: Incyte ID No: 332162.5

<400> SEQUENCE: 20
gggggatggg gagagaagag ggatagggcc agcaaggcag ggatcgaacg agtgtctggc 60
agccgggagc ccagcgaaga gagcgagcaa gcttaggaaa acgagcgaag taaagggagt 120
aggggagact gagactgacc ggtagccagg caggcggacg gacgcacgcc cggacagact 180
gagcaggcgc cggagaacca ctcacaggtt ccccccgcct ttccctttga aagctaggat 240
tttgcctttc ccgtggcgcc cgagagagaa tgctggactc tgccgacttc agcgcaagct 300
aagatttctc agctagggac aaacgatcag cccaatcctg agaagggggg aaccaagcac 360
cccgtcccca tccccctccc ctcccccgac taaactcggg cgccaaaccc agcccttctc 420
taaccaccct acttcctcct ctcctttcta gcatggtggc tgtatggaca gtctgacaga 480
acagagactg acatctccca atctgccggc cccccacctg gaacactaca gtgttctgca 540
ttgcaccatg accctggatg tgcaaactgt agtcgttttt gccgtgattg tagtcctcct 600
gcttgtcaat gtcatactca tgtttttcct gggaacgcgc tgaatggagt ccagccacct 660
gagctgtcgc gaactctcgc tttgatttca tcccgagagc caccgagaaa aaaaaaaaat 720
ccacagacag agacagggaa agagagagaa agaacaagct ttcttactca gggggaaaa 780 cgttttgagc ttcaacatgg cctcgctgtg atatctgatc actggagatt ccatcgttag 840
tgctgaggca gtatgggatc acgtcaccat ggccaaccgg gagttggcat ttaaagctgg 900
cgacgtcatc aaagtcttgg atgcttccaa caaggattgg tggtggggcc agatcgacga 960
tgaggaggga tggtttcctg ccagctttgt gaggctctgg gtgaaccagg aggatgaggt 1020
ggaggagggg cccagcgatg tgcagaacgg acacctggac cccaattcag actgcctctg 1080
tctggggcgg ccactacaga accgggacca gatgcgggcc aatgtcatca atgagataat 1140
gagcactgag cgtcactaca tcaagcacct caaggatatt tgtgagggct atctgaagca 1200

-continued gtgccggaag agaagggaca tgttcagtga cgagcaactg aaggtaatct ttgggaacat 1260
tgaagatatc tacagatttc agatgggctt tgtgagagac ctggagaaac agtataacaa 1320
tgatgacccc cacctcagcg agataggacc ctgcttccta gagcaccaag atggattctg 1380
gatatactct gagtattgta acaaccacct ggatgcttgc atggagctct ccaaactgat 1440
gaaggacagc cgctaccagc acttctttga ggcctgtcgc ctcttgcagc agatgattga 1500
cattgctatc gatggtttcc ttttgactcc agtgcagaag atctgcaagt atcccttaca 1560
gttggctgag ctcctaaagt atactgccca agaccacagt gactacaggt atgtggcagc 1620
tgctttggct gtcatgagaa atgtgactca gcagatcaac gaacgcaagc gacgtttaga 1680
gaatattgac aagattgctc agtggcaggc ttctgtccta gactgggagg gcgaggacat 1740
cctagacagg agctcggagc tgatctacac tggggagatg gcctggatct accagcccta 1800
cggccgcaac cagcagcggg tcttcttcct gtttgaccac cagatggtcc tctgcaagaa 1860
ggacctaatc cggagagaca tcctgtacta caaaggccgc attgacatgg ataaatatga 1920
ggtagttgac attgaggatg gcagagatga tgacttcaat gtcagcatga agaatgcctt 1980
taagcttcac aacaaggaga ctgaggagat acatctgttc tttgccaaga agctggagga 2040
aaaaatacgc tggctcaggg ctttcagaga agagaggaaa atggtacagg aagatgaaaa 2100
aattggcttt gaaatttctg aaaaccagaa gaggcaggct gcaatgactg tgagaaaagt 2160
ccctaagcaa aaaggtgtca actctgcccg ctcagttcct ccttcctacc caccaccgca 2220
ggacccgtta aaccacggcc agtacctggt ccccgacggc atcgctcagt cgcaggtctt 2280
tgagttcacc gaacccaagc gcagccagtc accattctgg caaaacttca gcaggttaac 2340
ccccttcaaa aaatgatacc tacagggagg cagataattt taaaataaag taaataaaat 2400
tatatttatt aatacgactc actataggga gaatccaaat acaac 2445

<210> SEQ ID NO 21
<211> LENGTH: 5708
<212> TYPE: DNA
<213> ORGANISM: Homo sapiens
<220> FEATURE:
<221> NAME/KEY: misc_feature
<223> OTHER INFORMATION: Incyte ID No: 331744.3

<400> SEQUENCE: 21
gcacatccct gcactagtgg ccgcaaccga gacgccgcgc tccagcagct gctgccgccc 60
agcccggccc cgccgccgcc ccccagccct gcagccccgc agccccggcc gcgcccagcc 120
cggcgaggac agcaccagga ggcggccccc agcgcggcca caaagacccc cggcggcgtc 180
tctccgcgga ccggtcctac ttgaagtcca tcatgtcctt cggcagagac atggagctgg 240
agcacttcga cgagcgggat aaggcgcaga gatacagccg agggtcgcgg gtgaacggcc 300
tgccgagccc gacgcacagc gcccactgca gcttctaccg cacccgcacg ctgcagacgc 360
tcagctccga gaagaaggcc aagaaagttc gtttctatcg aaacggagat cgatacttca 420
aagggattgt gtatgccatc tccccagacc ggttccgatc ttttgaggcc ctgctggctg 480
atttgacccg aactctgtcg gataacgtga atttgcccca gggagtgaga acaatctaca 540
ccattgatgg gctcaagaag atttccagcc tggaccaact ggtggaagga gagagttatg 600
tatgtggctc catagagccc ttcaagaaac tggagtacac caagaatgtg aaccccaact 660
ggtcggtgaa cgtcaagacc acctcggctt ctcgggcagt gtcttcactg gccactgcca 720
aaggaagccc ttcagaggtg cgagagaata aggatttcat tcggcccaag ctggtcacca 780

-continued

```
tcatcagaag tggcgtgaag ccacggaaag ctgtcaggat tctgctgaac aagaaaacgg    840
ctcattcctt tgagcaggtc ctcaccgata tcaccgatgc catcaagctg gactcgggag    900
tggtgaaacg cctgtacacg ttggatggga aacaggtgat gtgccttcag gactttttg     960
gtgatgatga catttttatt gcatgtggac cggagaagtt ccgttaccag gatgatttct   1020
tgctagatga aagtgaatgt cgagtggtaa agtccacttc ttacaccaaa atagcttcat   1080
catcccgcag gagcaccacc aagagcccag gaccgtccag gcgtagcaag tcccctgcct   1140
ccaccagctc agttaatgga acccctggta gtcagctctc tactccgcgc tcaggcaagt   1200
cgccaagccc atcacccacc agcccaggaa gcctgcggaa gcagaggagc tctcagcatg   1260
gcggctcctc tacgtcactt gcgtccacca aagtctgcag ctcgatggat gagaacgatg   1320
gccctggaga agaagtgtcg gaggaaggct tccagattcc agctacaata acagaacgat   1380
ataaagtcgg aagaacaata ggagatggaa attttgctgt tgtcaaggaa tgtgtagaaa   1440
gatcgactgc tagagagtac gctctgaaaa ttatcaagaa aagcaaatgt cgaggcaaag   1500
agcacatgat ccagaatgaa gtgtctattt taagaagagt gaagcatccc aatatcgttc   1560
ttctgattga ggagatggat gtgccaactg aactgtatct tgtcatggaa ttagtaaagg   1620
ggggagacct tttgatgcc attacttcca ctaacaaata caccgagaga gacgccagtg    1680
ggatgctgta caacctagcc agcgccatca aatacctgca tagcctgaac atcgtccacc   1740
gtgatatcaa gccagagaac ctgctggtgt atgagcacca agatggcagc aaatcactga   1800
agctgggtga ctttggactg gccaccattg tagacggccc cctgtacaca gtctgtggca   1860
ccccaacata cgtggctcca gaaatcattg cagagactgg atacggcctc aaggtggaca   1920
tctgggcagc aggtgtaatc acttatatcc tgctgtgtgg tttccctcca ttccgtggaa   1980
gtggtgatga ccaggaggtg ctttttgatc agattttgat ggggcaggtg gactttcctt   2040
ctccatactg ggataatgtt tccgattctg caaaggagct cattaccatg atgctgttgg   2100
tcgatgtaga tcagcgattt tctgctgttc aagtacttga gcatccctgg gttaatgatg   2160
atggcctccc agaaaatgaa catcagctgt cagtagctgg aaagataaag aagcatttca   2220
acacaggccc caagccgaat agcacagcag ctggagtttc tgtcatagca ctggaccacg   2280
ggtttaccat caagagatca gggtctttgg actactacca gcaaccagga atgtattgga   2340
taagaccacc gctcttgata aggagaggca ggttttccga cgaagacgca accaggatgt   2400
gaggagccgg tacaaggcgc agccagctcc tcccgaactc aactcggaat cggaagacta   2460
ctccccaagc tcctccgaga ctgttcgctc ccctaactcg ccctttttaat aagacccttt   2520
tactcaaagt cctagcttaa ccctttgaga ctctgagatt tttttccccc aaatttgtgt   2580
aaaacagttt catctgatct atctagcgct caatgcttga atggcagaac tgaaagtgtt   2640
ttcaggtatc tttgtagcgg tttcccttta ctgaataaga tgacacgtgg tgattgtgaa   2700
gatggtaatt tgctgctaat agagtcctca aagggttaag gccaatttgc aatttttttt   2760
taaacttaga agcaatgaat gttttcatca gtcaagctag gatctgcagt atgtaatata   2820
gcacttgtta accctctgag tgcatagaat tttattgaga attcttgttt gggaattttt   2880
caggcctttg gatgtataca cacatgtttc ttgattttac tgcagatcaa ggggtgttgt   2940
tagatgctga aatgtccaga aaagaaggac atttagaatg atatcttgtt tgtccttttc   3000
tgtgggttta gaacgtggca ggtttataac ttcgacacac gcacggttct ttcttcttca   3060
caatcctatt cagaaacaga tttttttttt cattagagat atgactgtca gttgcagtga   3120
```

-continued

```
gttctgcatc ccaagtggag ggaattgggt ttgtggcaaa gagcttgacc caggaaatag   3180
atggtgcccc ccaaattgtc tccacatgaa gatgtactga tgacgcccca gaaatgctgc   3240
ttccatatca gctgctgcta gcgccagcgc agactctcag ggagtcacca cagcttgtct   3300
tgtgcttggt gagtgagggt ctctctactc agtgtcagac atctacagga aagaaacaac   3360
tggtggaaaa gagcaataaa ttgcccggtg ctctgcaggg ctggaatttc aaacagaaag   3420
agggaataag atcctgtgat ttttctcacc tgcttttcca cgcactgtgg tcatcactgt   3480
gcaatctaca tctagtatga aatccacaca taggagagct ggggcacaag ggactggag   3540
gcagttgctt tgcaagatgg ctgaggagaa agcacactgg gaacacaatc cagaatgttc   3600
taagcaataa gttttcagtg aataaaccac tggcaagaca attccatgtg cacctttagg   3660
ttacctatat agtctcctag gaagatcagg atgaaagacc tagatgatac ccctgaggat   3720
aaaacctcca tcccctaaaa tgattttttt taaataccac tgtctttagc tgtccaggag   3780
gtcagagtgt tttttctgtc tttgggccaa gtcctgtctg agacctgtat tttcactctt   3840
gttaccaaat ctatctccct agtgcagtgt ctccaggcct gagtttcttc tggaacagat   3900
tccattttag aatggggatt cacaggttct gtgcatcacc acagtgctca gagaggattc   3960
tcctggggtg tcttagaggc aggtgcccaa ctcaaatgta ttcccaaggt ttgctgggct   4020
ctgggatcca cgagacaacc agagagggat atctcatgaa atttgcatct ggtggctgaa   4080
cagtacctat gttctctgtt ttgaatatac tttaatacct gagagtctta aaatttgtga   4140
acaacgtttc tatagtcctt tattttcaaa tgcacattga tcttcacttg ctgcattttt   4200
actcttcaac cctgaaacta tggtctacat taatatggat ttttaaatca catgtcatta   4260
cttttgcaac accatcacca aaattttttg ctcttttaca tttaggttca tctctgtggt   4320
ctgtgttgtc ctgacatgta aaaagcatat cgtttattga ggttttttttc cccccctttt   4380
agagcatccg gaagtgataa cacgcaaaat cacaaagtag cataaatcag taaattagtt   4440
gagttgtttt tggggggggag gtgggggtag ggggcacaga acaccagaaa gagtgttggt   4500
gtgtaggtag attccatatt aatgaggaac actgaactag ttggaaatta ctgctttctc   4560
tagaaatata aagcaaagca ctattccaag gctatggagt agctctacag cctggcctca   4620
actctaaaag tgtgaagaat gcaatgggca gagacctacc tgcagtggac tgtcattttc   4680
ctttctttct ctgaattact gctttttctg tgggcattaa ctatattgct acagcatcta   4740
gtgtactgag cctgcggtgc atggctcagg cctttttccca tcgacgtcta gggggactct   4800
ggaccgtgtg aagctagggg gtgtttctca gcacactgca gaagggcagc tcagaagaat   4860
gcagggccca ttcagcatgg ggatcccagc acatcactgt agaatttgag tgatctatgc   4920
tgaataaaca gtggaatgtg accagtcaag tagaaatctt gagtaatcag gtggaatgca   4980
atctttctaa cattaagcta ccaagatcct gaatgtcaga gatgtactca gagggttaac   5040
agacaagcac aaggcatgct gactacattg gtgtatccag attgctttgc ttttagccag   5100
tgctttctaa tttttttctc gacattcttg ggatagttca agtttgaaat aattaagtgg   5160
tggtgttctt taaggaattt ctataaccaa attgatctta tttttgattt cacttatcat   5220
agaacaaata tgtatcatta tggcagtgta tctatgtaat tatcaattta atcatcacca   5280
ccggtgtttc catatttttt cccaagtatt taatatagct ctcttatggt ggtggcctgg   5340
tgatggggac cgtctttctt ttactgacac atgaccaatc atatggtatt ttcaagggaa   5400
ttttaagatt catcttttca gtttgatagt agactagtta aggaagaact ctttcattac   5460
ttgcatcgtg taaatcatct ctgtagacat gtgttcatat taatgaacac attttttctc   5520
```

-continued aacattgtag cagaaatcat tttattcgtc atgatcaatg aatatgtgat ttgctccaga 5580
tcgttagaag gaaaagtaag atttcagtca tcaaaaatgt ttttaccgta gccctcatct 5640
aacttacacg tggtgcatat taaaataagc agagaaaaaa aaatgtgaat aaactactga 5700
aaacactt 5708

<210> SEQ ID NO 22
<211> LENGTH: 9434
<212> TYPE: DNA
<213> ORGANISM: Homo sapiens
<220> FEATURE:
<221> NAME/KEY: misc_feature
<223> OTHER INFORMATION: Incyte ID No: 407676.3
<221> NAME/KEY: unsure
<222> LOCATION: 6500, 6506
<223> OTHER INFORMATION: a, t, c, g, or other

<400> SEQUENCE: 22
gggataatgc tcccgagaag gattctggca gcagttctca aaggctagac ttgagtggta 60
ttgctgcata tgcgctgatt cttcagcttg tctctaaccg aggaagcatt gattgggagc 120
tactcattca gaaaattaaa agaaagaagc cagaaaatat tatcaaccct ttgagaacac 180
gacacaacga actttatatt ttaccacttc cttgaatagt tgcaggagaa ataacaaggc 240
attgaagaat ggcagatgaa cggaaagatg aagcaaaggc acctcactgg acctcagcac 300
cgctaacaga ggcatctgca cactcacatc cacctgagat taaggatcaa ggcggagcag 360
gggaaggact tgtccgaagc gccaatggat tcccatacag ggaggatgaa gagggtgcct 420
ttggagagca tgggtcacag ggcacctatt caaataccaa agagaatggg atcaacggag 480
agctgacctc agctgacaga gaaacagcag aggaggtgtc tgcaaggata gttcaagtag 540
tcactgctga ggctgtagca gtcctgaaag gtgaacaaga gaaagaagct caacataaag 600
accagactgc agctctgcct ttagcagctg aagaaacagc taatctgcct ccttctccac 660
ccccatcacc tgcctcagaa cagactgtca cagtggagga agcctcgaag atggagttcc 720
acgatcaaca ggaattgact ccctctacag ctgagccttc agaccagaag gaaaaggagt 780
cagagaagca aagtaagcct ggtgaagacc ttaaacatgc tgccttagtt tctcagccag 840
agacaactaa aacttaccct gataaaaagg acatgcaagg cacggaagaa gaaaaagcac 900
ccctagcttt gtttgggcac actcttgttg ccagcctgga agacatgaaa cagaagacag 960
aaccaagcct tgtagtacct ggcattgacc tccctaaaga gcctccaact ccaaaagaac 1020
aaaaggactg gttcatcgaa atgccaacgg aagcaaaaaa ggatgagtgg ggtttagttg 1080
cccccatatc tcctggccct ctgactccca tgagggaaaa agatgtattt gatgatatcc 1140
caaaatggga agggaaacag tttgattctc ccatgccaag tccctttcaa gggggaagct 1200
tcactcttcc tttagatgtc atgaagaatg aaatagttac agaaacatcg ccctttgccc 1260
ctgccttttt acagccagat gacaaaaaat ctctgcaaca aaccagtggc ccagctactg 1320
ccaaagatag ttttaaaatt gaagagcccc atgaggctaa acctgacaaa atggcagaag 1380
caccaccctc agaggcaatg accttaccca aagatgctca cattccagtt gtagaagaac 1440
atgttatggg gaaagtttta gaggaagaaa aggaggccat aaatcaagag actgtgcagc 1500
aaagggatac tttcaccccc agtggacagg aacctatact tactgaaaag gaaactgagc 1560
tgaagcttga agaaaaaacc accatttctg acaaagaagc tgtgccaaaa gagagtaaac 1620
ccccaaaacc tgcagatgaa gaaataggca taattcagac ctccacagag cacactttct 1680

-continued

```
cagaacagaa agaccaagag cctaccacag atatgttgaa acaggactcg ttccctgtaa   1740
gtttggagca agcagttaca gattcagcca tgacctctaa aacactggag aaagccatga   1800
ccgaaccatc tgcattaatt gaaaagagct caattcagga actttttgaa atgagagttg   1860
atgacaaaga taagattgaa ggagttggag ctgcaacatc agctgagctt gatatgccat   1920
tttatgaaga taaatcagga atgtccaagt actttgaaac atctgccttg aaagaagaag   1980
caacaaaaag cattgagcca ggcagtgatt actatgaact gagtgacact agagaaagtg   2040
tccatgagtc tattgatacc atgtctccca tgcataaaaa tggtgacaag gagtttcaaa   2100
caggaaaaga atcccagccc agtcctccag cacaagaagc agggtacagc actctcgcac   2160
agagttatcc atcagattta cctgaagaac ccagttctcc tcaagaaaga atgttcacta   2220
ttgatccaaa agtgtatgga gagaaaaggg acctccacag taagaataag gatgatttga   2280
cccttagcag gagtttagga cttggtggta ggtctgcaat agaacaaaga agcatgtcaa   2340
tcaatttgcc gatgtcttgc ctagattcca tagcccttgg atttaacttt ggtcggggac   2400
atgatctttc tcctctggct tccgatattc taaccaacac tagtggaagt atggatgaag   2460
gggatgatta ccttccagcc accacacctg cactggagaa agccccttgc ttccctgtag   2520
aaagcaaaga ggaagaacag atagagaaag taaaagctac tggagaagaa agtactcaag   2580
cggagatatc atgtgagtct cctttcctag ccaaagattt ttacaaaaat ggtactgtca   2640
tggcacctga ccttcctgaa atgctagatc tggcaggcac aaggtcaaga ttggcttctg   2700
tgagtgcaga tgctgaggtt gccaggagga aatcagtccc atcagagact gtggttgagg   2760
atagtcgtac tggcttgccc ccggtaactg atgaaaacca tgtcattgta aaaacggaca   2820
gtcagctcga agacctgggc tactgtgtgt tcaataagta cacagtccca ttgccatcac   2880
ctgttcaaga cagtgagaat ttatcagggg agagtggtac cttttacgaa ggcactgatg   2940
ataaagttcg aagagatttg gccacagacc tttcactgat tgaagtgaaa ctggcagcag   3000
ccggaagagt caaagatgag ttcagtgttg acaaagaagc atccgcgcat atctctggtg   3060
acaaatcagg actgagtaag gagtttgacc aagagaagaa agctaatgat aggttggata   3120
ctgtactaga aaagagtgaa gaacatgctg attcaaaaga acatgccaag aaaactgaag   3180
aggctggtga tgaaatagaa acattcagat taggagtaac ctatgagcaa gctttggcca   3240
aagatttgtc aataccaaca gatgcatcct ctgagaaagc agagaagggt cttagttcag   3300
tgccagagat agctgaggta gaaccatcca aaaaggtgga acaaggtctg gattttgctg   3360
tccagggtca actagatgtt aaaattagtg actttggaca gatggcttca gggctaaaca   3420
tagatgatag aagggcaaca gagctaaaac ttgaggctac acaggacatg acccccctcat   3480
ccaaagcacc gcaggaggca gatgcattta tgggtgttga gtctggccac atgaaagaag   3540
gcactaaagt tagtgagaca gaagtcaaag agaaggtggc caagcctgac ttggtgcacc   3600
aggaggctgt agacaaggag gagtcctatg aatctagtgg tgagcatgaa agtctcacca   3660
tggagtcctt gaaagctgat gagggcaaga aggaaacatc tccagaatca tctctaattc   3720
aagatgagat tgccgtcaaa ttgtcagtgg aaataccttg cccacctgct gtttcagagg   3780
ctgatttagc cacagatgag agagctgatg tccagatgga atttattcag gggccaaaag   3840
aagaaagcaa agagaccccca gatatatcca tcacgccttc tgatgttgca gagccattgc   3900
atgaaacgat cgtatctgaa ccagcagaga ttcagagtga ggaagaagag atagaagccc   3960
agggagaata tgataaactg ctcttccgct cagacaccct tcagataact gacctgggtg   4020
tctcaggtgc cagggaggaa tttgtggaga cctgcccaag tgaacacaaa ggagtgattg   4080
```

-continued

```
agtctgttgt gaccatcgag gatgatttca tcactgtagt gcaaaccaca actgatgaag   4140
gggagtcagg gtcccacagc gtgcgttttg cagccctaga gcagcctgag gtggaaagga   4200
gaccatctcc tcatgatgaa gaagagtttg aagtagaaga ggcagctgaa gcccaggcag   4260
aacccaaaga tggttcccca gaggctccag cttcccctga gagagaagag gttgcacttt   4320
ctgaatataa gacagaaacc tatgacgatt acaaagatga gaccaccatt gacgactcca   4380
tcatggacgc tgacagcctc tgggtggaca ctcaagatga tgataggagc atcatgacag   4440
aacagttaga aactattcct aaagaggaga aagctgaaaa ggaagctcgg agatcatctc   4500
ttgagaaaca tagaaaagaa aagcctttta aaaccgggag aggcagaatt tccactcctg   4560
aaagaaaagt agctaaaaag gaacctagca cagtctccag agatgaagtg agaaggaaaa   4620
aagcagttta taagaaggct gaacttgcta aaaaaacaga agttcaggcc cactctccct   4680
ccaggaaatt cattttaaaa cctgctatca aatatactag accaactcat ctctcctgtg   4740
ttaagcggaa aaccacagca gcaggtgggg aatcagctct ggctcccagt gtatttaaac   4800
aggcaaagga caaagtctct gacggagtaa ccaagagccc agaaaagcgc tcttctctcc   4860
caagaccttc ctccattctc cctcctcggc gaggtgtgtc aggagacaga gatgagaatt   4920
ccttctctct caacagttct atctcttctt cagcacggcg gaccaccagg tcagagccaa   4980
ttcgcagagc agggaagagt ggtacctcaa cacccactac ccctgggtct actgccatca   5040
ctcctggcac cccaccaagt tattcttcac gcacaccagg cactcctgga acccctagct   5100
atcccaggac ccctcacaca ccaggaaccc ccaagtctgc catcttggtg ccgagtgaga   5160
agaaggtcgc catcatacgt actcctccaa aatctcctgc gactcccaag cagcttcggc   5220
ttattaacca accactgcca gacctgaaga atgtcaaatc caaaatcgga tcaacagaca   5280
acatcaaata ccagcctaaa ggggggcagg tacaaattgt taccaagaaa atagacctaa   5340
gccatgtgac atccaaatgt ggctctctga agaacatccg ccacaggcca ggtggcggac   5400
gtgtgaaaat tgagagtgta aaactagatt tcaaagaaaa ggcccaagct aaagttggtt   5460
ctcttgataa tgctcatcat gtacctggag gtggtaatgt caagattgac agccaaaagt   5520
tgaacttcag agagcatgct aaagcccgtg tggaccatgg ggctgagatc attacacagt   5580
ccccaggcag atccagcgtg gcatcacccc gacgactcag caatgtctcc tcgtctggaa   5640
gcatcaacct gctcgaatct cctcagcttg ccactttggc tgaggatgtc actgctgcac   5700
tcgctaagca gggcttgtga atatttctca tttagcattg aaataataat atttaggcat   5760
gagctcttgg caggagtggg ctctgagcag ttgttatatt cattctttat aaaccataaa   5820
ataaataatc tcatccccaa actgtagtaa ttgttacaat tttctattta aaaaatgaat   5880
agtacatgca gaaattgacc tgatttccat ttgcaacagg aagacactgg ctttacatgg   5940
gttcaattgg acaattattt ttgctctgct ctgttttgca tggagtatta ttattttaaa   6000
aattgcattt ttacctttca tgtgcctgaa ggctatccac tacattctga aggccttgtt   6060
aaaatccaag ctgctcattt cactattctg tttctgagtg agaagataaa aactgcccat   6120
tgtaacttat ttcaggttaa attaaaccaa ggagtctgat tgcaggaagg gaagagcatg   6180
taagaaataa gtttttttaa agtgttattt tgtataaatg ggaagaaaga ttcaattaag   6240
ttattaacat ttgggacctg gataattata tcagagtatg tcagtccaat aaattattta   6300
actaattaaa aaatagttgc aaagcatttg agctgtggtt gaggaagtgg tgtaaaagtg   6360
catccattag gaatgatgca ctttcattag gatggactcg tgtctgatta gaatgtcagt   6420
```

-continued tgatcagcta gatttgtgtc cacactacca gtttcacacc ccctttccat ctgtttgata 6480
cagtattata gatataaatn tatatntatt tctctgtggc catttgtgat acttcctcat 6540
atacttgaat attatacttc tttattcaca gtatctgtgt ctcctgcacc ctttggtgtt 6600
gcaattttag atatgtgaaa gtagatgtta gcagggttct ctccctattt aaaaaaaata 6660
cattaaaaaa gacaaaaaat tttagcatga agttgctttc tgtaacaact caaagccgta 6720
accctgtttt agtgccagat acaagtctct cccgtgatgc tagacaaaaa attatttttc 6780
tttgctttca ccaacatgga gtttgtgggg gtgggtccag ttatacatga aagggtttac 6840
agattgttgg tttaagatta tggatttatc tcatttttaa tcacaggata gtttggggtt 6900
tattcctatt attattcatg aaaccgactt aagatttttt ctttattttt cttttttttt 6960
ccatttgcta aagttgaaag ttgaaactaa ctataatagt ttgaaacatg ttttctcatt 7020
tttccaaata gtatctgttt attaaattct ctaatagaag atgtttgtct ttcttaccca 7080
aagtaaagat cccctgatca gaaagaaaaa atacaatact ttgggaagct atagctataa 7140
aacacttgag acacagatat ctaaatcagt ttttttccaa gactccaaca ttgcactctg 7200
taaagtaaca cactgtgatc tagtattatt tatcagtaga taatactgtt ctgactgtat 7260
atacagtcta gaactcacaa atcaattagt tcctctcaca aatcattcat cttagactta 7320
caaataagga atgaaatagt caatggcctg attaaggcaa agagctacca ggctagatgg 7380
acacttttta aaaattttat ctgttctttt tcttgctcag ggctggtagg ttggatctga 7440
accattaaaa tcaaatggtc cactaggcgt atgatctctt tgagccaaat cagttcctga 7500
atataaagga ggaaatgatg aggatgtact gaggcaacgg ggaagtatag aaacatccaa 7560
gacaaaagcc aagggatgca aaggcagaga cacaggtgct ttttggtgac ccagtggata 7620
tggcaaccag tgtaactgcc atacaagaaa ccctaggagc aaacccacac cactcattct 7680
cagctaagag attttacaca ggcaaacgtg tcttaaacca tctataaatc agttatttta 7740
tatgacagtc aaaaccttag aaaccttagg atcattatat ctattttctg cctattaatt 7800
gctgtgaggt ttgatttgac caatctgggc aatttattca tcagcttccc ttgaagtgca 7860
ccagaaaata gaagaaaggt gtgtggagac ttagggtatt ttattacatg ttttcatagt 7920
cttaaatagt gattaaattt ctctagaaag aagttaacag ctcattagaa aagttttaac 7980
ctgtgaaata agtatttttc tcaacattct ttaaagtttt tatataagtt aacactaggt 8040
aaacattctg catactagaa gtcagtttat tacaaataca tgtcaaaaat aaagattata 8100
caaggcacca aactactaga tttggcatta aaacaaatgt ttatttctaa tcacaacaaa 8160
attataatga ataaatgttc ttgctttgta tggaaataca attctttatt aaagttaaca 8220
gaaaggaact gatcgtttgt accagtaaaa gagagaaaca cacaggttaa atatcttctt 8280
gtggggttaa ggggtagaac ctatcttgcc ttcactctca agataacgac tcaaattaag 8340
ctttttgagc accactcttg tggggacaca catacgctga tctaggaatg aaatcttcgt 8400
ggtctcaatt ctagatctac tatgccagtt tctctctggc tttagccttt gagaacctgt 8460
ataagaatac gtaagtaatc cagagctgtg aagagtttaa aggccaactt ctccagtgaa 8520
ctcaacctct gggtcacttg caaccagaaa ttggatacct cataatgatg caggaaagac 8580
ccgagttcat gatgagtttc aaaggccacg ttcatttagg aaccaactct ctctggattt 8640
acctgctgag ttccagcagc gtgatgggct gacatcccac ctacaagtat gacacctgtg 8700
taacaccagc taggtacggc tggagaaggc tgaagagaga atgccattaa atggaagaat 8760
gtactgattg tagtgacctt ctccacacac acacacacca cccacacaca cacctacagt 8820

-continued

```
aatacagcaa gcgtggaata atcagccaat atataacatt ccatcagtat tttattaagg   8880

aaataacctg aatgtggttg attttgacat agctgcaatt acagttttct tctatttttc   8940

aagccacaat aaggaaaata aactactcat ggtctaaata ctagagataa agtagattca   9000

tggcttggta aggaaatttt aagcattcct tcaaagattg acgtgctaaa ataagcattg   9060

atgttttgag tttttttaca cctaggattt ttagcttggg tgtgtaggtg aaggccaaga   9120

ctctctgcag gaaaaagctt attttcaaac tcagaaaata aaatgtcaat cataaaaatc   9180

tacttcaact ttagcaaaaa gaaaaaaaaa tcaacaaaaa gtatactctg tatgctggga   9240

ttccgaggtt ccaacacact gttacaaatc tgtggggggt ttctttcttc tgataattct   9300

agagcctgtt accatagaaa ggcatttctt caatggctgg ttgtagttag ttcatgtttt   9360

tcaatcaaat ttgcaaatgt atttgttgct gtatagtgat tgttttgcaa aataaaattg   9420

cttgtcacct aaaa                                                      9434
```

<210> SEQ ID NO 23
<211> LENGTH: 3588
<212> TYPE: DNA
<213> ORGANISM: Homo sapiens
<220> FEATURE:
<221> NAME/KEY: misc_feature
<223> OTHER INFORMATION: Incyte ID No: 344676.11

<400> SEQUENCE: 23

```
cgggctccag cggcctcccg cgccgcaacc tcctcctcgg cgaagtctcc ctggccgccc     60

catgtcggcc gcccccgcct acagcgaaga caagggcggc tccgctggcc ccggggagcc    120

cgagtacggc cacgaccccg cgagcggcgg catcttctcc tccgactaca agcggcatga    180

tgacctgaag gagatgctgg acaccaacaa ggattctctc aagctggagg ccatgaagag    240

gattgtggcg atgattgccc gaggaaagaa tgcttcagac ctgtttcccg cggtggtgaa    300

gaacgtggcc tgtaagaaca tagaggtgaa gaagcttgtc tatgtgtacc tggtacgcta    360

cgctgaggag cagcaagacc tggccctgct gtccatctcc accttccaac gtggcctaaa    420

ggatcccaac cagctgattc gtgccagtgc cctccgtgtc ctctctagca tccgtgtgcc    480

catcatagtg cccatcatga tgctagctat caaggaagcc gcctcggaca tgtcacccta    540

tgtgcggaaa acagctgccc acgccatccc taaactctac agtttggact ctgaccagaa    600

ggatcagctg atagaagtca ttgagaagct tctggctgac aagaccacgc tggtggcggg    660

cagtgtggtg atggcctttg aggaggtctg cccggagcgc atcgacctga ttcacaaaaa    720

ctaccggaaa ctctgtaacc tgctgatcga cgtggaggag tggggccagg tggtcatcat    780

cagcatgctc acccgctacg cccgcacgca gttcctgagc ccccacccaga acgaatccct    840

actagaggag aacgcggaaa aagccttcta cggctcagag gaggacgagg ccaagggcgc    900

ggggtctgag gagacggccg ccgcggccgc cccctcccga aagccctatg tcatggaccc    960

cgaccaccgg ctgctgctgc gcaacaccaa acccctgctg cagagccgca gcgccgcggt   1020

ggtgatggcg gtggcgcagc tctacttcca cctggcgccc aaggcggaag tgggcgtcat   1080

cgccaaggcg ctggtgcgcc tgctgcgcag ccacagtgag gtgcagtacg ttgtgctcca   1140

gaacgtggcc accatgtcca tcaagcgccg gggtatgttt gagccctacc tgaagagctt   1200

ctacatcagg tccaccgacc ccacccagat taagatcctg aagctggaag tgctgaccaa   1260

cctggccaat gagaccaaca ttcctactgt cctacgggaa ttccagacct atattcgcag   1320

catggacaag gactttgtgg cagccacaat ccaggccatt ggacgctgtg caactaacat   1380
```

-continued

```
cggccgagtc cgtgacacct gcctcaatgg cctggtgcag ctgctgtcca accgtgatga   1440
gcttgtggtt gcagagtcag tggtcgtcat taagaaattg ctacagatgc agccagcaca   1500
acatggagag atcatcaaac acttggcaaa gcttacagac aacatccagg tgcccatggc   1560
ccgagccagc atcctgtggc tcatcggaga gtactgtgag catgtcccca ggattgcacc   1620
tgatgtctta agaaaaatgg ccaagtcatt cacagcagag gaggatattg tcaagctgca   1680
ggtcatcaac ctggcagcca agctctacct gaccaactct aaacagacca agctgctgac   1740
ccagtatgtg ctgagtctgg ccaaatatga ccagaactat gatattcgcg accgggcgcg   1800
cttcacccgg cagctcatcg tcccttccga gcagggtggg gccctcagcc gccatgccaa   1860
gaagctcttc ctggcaccca aaccagctcc agtcttggag tcatccttca aagaccggga   1920
ccacttccag ctgggctcac tgtcccacct gcttaatgcc aaggccacag gctaccagga   1980
gctcccagac tggccggagg aagccccaga cccatctgtg cgcaacgtgg aggtacctga   2040
atggaccaag tgctcaaatc gggagaagag aaaggagaag gaaaaaccct tctactcgga   2100
ctctgagggg gagtcaggcc ccacggagtc cgcagacagt gaccctgagt ctgagagtga   2160
atcggacagt aagagcagca gtgagagcgg ctctggggag tccagcagtg agtccgacaa   2220
tgaagaccag gatgaggatg aggagaaagg gagaggcagt gagagtgaac agagtgagga   2280
ggatggtaag aggaagacaa agaagaaggt gccagagaga aaaggagaag cgtcatcctc   2340
tgatgagggc agcgattcca gcagtagctc atcagagtcc gagatgacat cggagtccga   2400
ggaggagcag ttagaacctg cctcctggag caggaaaaca cctcccagca gcaaaagtgc   2460
tcctgcaacc aaggagatct ccctgcttga tctagaggat ttcacccctc ccagtgtcca   2520
gcctgtgtct cccccagcaa ttgtgtctac cagtctggct gctgacctgg agggcctgac   2580
actcacagac tccaccctgg taccgtcgct tctgagtcca gtatcgggtg ttgggcggca   2640
ggagctgctg caccgggtag ctggcgaggg gctggctgtg gactacacct tcagccgcca   2700
acctttctcc ggggatcccc acatggtgtc cgtgcacatc cacttctcca acagctctga   2760
taccccccatc aagggcctgc atgtgggcac tcccaaactg cctgctggca tcagcatcca   2820
agaatttccc gaaattgagt ccctggcacc tggagaatct gccactgctg taatgggcat   2880
taatttctgt gactcaaccc aggcagccaa cttccagctg tgcacccaga cccgacagtt   2940
ctacgtctcc attcagccac ctgttgggga gctgatggcc cctgtgttca tgagtgaaaa   3000
tgagtttaag aaggaacagg gaaagctgat gggcatgaat gagatcacag agaaactcat   3060
gctgccagac acctgtcgga gtgaccacat tgtggtgcag aaagtgactg ccactgccaa   3120
cctgggtcgt gttccttgtg ggacatctga tgagtacagg tttgcaggga ggacactgac   3180
tggtggaagc ctcgttctgc tgaccctgga tgcccggcca gctggagctg cccagctgac   3240
tgtcaacagc gagaaaatgg tgattggcac catgctggta aaggatgtga tacaggctct   3300
gacccagtga cttccaaatg ctgtgacctg tttggctccc atctatacct ccccatgaca   3360
cctaggctgt cagtctctct catctttctc tctctctctc atcatcctcc tcatgccaga   3420
tagcattcag ggtgtcctct ctccctctgg aggaccaagc cctcccctaa tgccctcccc   3480
atggattcct tagtgatctg tgcagagaga gatggcagcc actcccttca gtcctcccag   3540
atttctgtag ctatttatgt agcaggctca ataaaatgtc ttctctct               3588
```

<210> SEQ ID NO 24
<211> LENGTH: 1952
<212> TYPE: DNA

-continued

<213> ORGANISM: Homo sapiens
<220> FEATURE:
<221> NAME/KEY: misc_feature
<223> OTHER INFORMATION: Incyte ID No: 234735.15

<400> SEQUENCE: 24

```
aggctcggcc tccggcccag gcggcaccgg cggcggaaag gcatctgtcg gggccatggg     60
tgggggcgtc ggggcctcga gctccggggg tggacccggc ggcagcggcg gaggaggcag    120
cggaggcccc ggcgcaggca ctagcttccc gccgcccggg gtgaagctgg gccgtgacag    180
cgggaaggtg accacagtcg tagccactct aggccaaggc ccagagcgct cccaagaagt    240
ggcttacacg gacatcaaag tgattggcaa tggctcattt ggggtcgtgt accaggcacg    300
gctggcagag accagggaac tagtcgccat caagaaggtt ctccaggaca agaggttcaa    360
gaaccgagag ctgcagatca tgcgtaagct ggaccactgc aatattgtga ggctgagata    420
ctttttctac tccagtggcg agaagaaaga cgagctttac ctaaatctgg tgctggaata    480
tgtgcccgag acagtgtacc gggtggcccg ccacttcacc aaggccaagt tgaccatccc    540
tatcctctat gtcaaggtgt acatgtacca gctcttccgc agcttggcct acatccactc    600
ccagggcgtg tgtcaccgcg acatcaagcc ccagaacctg ctggtggacc ctgacactgc    660
tgtcctcaag ctctgcgatt ttggcagtgc aaagcagttg gtccgagggg agcccaatgt    720
ctcctacatc tgttctcgct actaccgggc cccagagctc atctttggag ccactgatta    780
cacctcatcc atcgatgttt ggtcagctgg ctgtgtactg gcagagctcc tcttgggcca    840
gcccatcttc cctggggaca gtggggtgga ccagctggtg gagatcatca aggtgctggg    900
aacaccaacc cgggaacaaa tccgagagat gaaccccaac tacacggagt tcaagttccc    960
tcagattaaa gctcacccct ggacaaaggt gttcaaatct cgaacgccgc cagaggccat   1020
cgcgctctgc tctagcctgc tggagtacac cccatcctca aggctctccc cactagaggc   1080
ctgtgcgcac agcttctttg atgaactgcg atgtctggga acccagctgc ctaacaaccg   1140
cccacttccc cctctcttca acttcagtgc tggtgaactc tccatccaac cgtctctcaa   1200
cgccattctc atccctcctc acttgaggtc cccagcgggc actaccaccc tcaccccgtc   1260
ctcacaagct ttaactgaga ctccgaccag ctcagactgg cagtcgaccg atgccacacc   1320
taccctcact aactcctcct gagggcccca ccaagcaccc ttccacttcc atctgggagc   1380
cccaagaggg gctgggaagg ggggccatag cccatcaagc tcctgccctg gctgggcccc   1440
tagactagag ggcagaggta aatgagtccc tgtccccacc tccagtccct ccctcaccag   1500
cctcacccct gtggtgggct ttttaagagg attttaactg gttgtgggga gggaagagaa   1560
ggacagggtg ttgggggat gaggacctcc tacccccttg gccccctccc ctcccccaga   1620
cctccacctc ctccagaccc cctcccctcc tgtgtccctt gtaaatagaa ccagcccagc   1680
ccgtctcctc ttcccttccc tggcccccgg gtgtaaatag attgttataa tttttttctt   1740
aaagaaaacg tcgattcgca ccgtccaacc tggccccgcc cctcctacag ctgtaactcc   1800
cctcctgtcc tctgccccca aggtctactc cctcctcacc ccaccctgga gggccagggg   1860
agtggagaga gctcctgatg tcttagtttc cacagtaagg tttgcctgtg tacaggacct   1920
ccgttcaata aattattggc atgaaaacct gc                                 1952
```

<210> SEQ ID NO 25
<211> LENGTH: 3821
<212> TYPE: DNA
<213> ORGANISM: Homo sapiens
<220> FEATURE:

-continued

```
<221> NAME/KEY: misc_feature
<223> OTHER INFORMATION: Incyte ID No: 197975.12
<221> NAME/KEY: unsure
<222> LOCATION: 550-578
<223> OTHER INFORMATION: a, t, c, g, or other

<400> SEQUENCE: 25

ctcaggaaat tccaggcgca catccgtgtc caaggggagg ctcagaaagt ggagcggctc     60

atagaggcgt tcagccagcg ctactgcaca ccacacaggg cacgcccggg ggtcgccagc    120

cgcacaccaa acccggggca cttctgttgc catctctccc ctctgcccct cacggcccaa    180

ccggagcccc aggagcccac ggggctggtg ttgtgtggaa caaaggccca gatttcattt    240

cttgttggca ccctgggctc tgctcacctc agtctgaggg atgggtgggc ctcagacacc    300

atcagccttg aaacggtgag ccagccaagt agtgttgaac tgcctccccc actccagctc    360

tcagctccct gtgccctaat gtacatgcat atgaaaaccc aacctagaaa acgaagaaat    420

gagatacaaa aacagacaaa acaaaccccca aaacttgctg cattattgct cttttattga    480

caatgggcaa aaaaataagt agacctgata tggttgatga aaatacgtaa gtaaacttta    540

tataaatatn nnnnnnnnnn nnnnnnnnnn nnnnnnnnct gtataggtag tacttgtgtg    600

tgaaaggcag gcgtttcagt ccacattagc aatacccacc ttacaaggag ctccacttac    660

ctaataggaa gacagtacct tagctgggtg tgtgagacaa tagaccaaac cctaaatgct    720

aggaacaaat tcagatactt catattttca tacaaagaag tccctctagg actggctaaa    780

atctttacac aatcattact aactgtgcca agtaacatag catctaactg tttaaaaagt    840

ccagtattgc tttgtataaa tccttatttt attaacagaa tactatcata aatagtatta    900

taatgctgtt atttcaggta agcaaatagc taaactgcag tacactctac agtagcaact    960

caggacagct ggttacaagc tggttgtctt aggacattgg ttacacggat tcttagacac   1020

tttaatggct gcgataactg tgactctcca tgatccatgt ttcttttatg cgcatatgat   1080

ttgacgcaca ctcattcaga gtcctccgag aggggcaccc atacacggca gaagtgttca   1140

tctccaacat gaaagtgacc agctctcatc ctcgtctccc caacaccata acgtcctcat   1200

cccgcctcca acccacacca ggccgaagcc ctcagagagt gttttcatca ggaaccactc   1260

tcgaacctga aggttgactt tagcgtttag caacccaggg cggtgtgtgt gtttcccgtt   1320

ttgttttctg agtggtagca gtgatcaccg taattccatg tagccatgtg ctagcagaac   1380

ccctgtgtcc tcaccgtggc ccgtgtgacc ccagccgacg agtgcccggc ggagccccccg   1440

ctgccttccc atggtccagt gagctgccag ggcatcacat gactctcagc tgtgctcttg   1500

tcgcttctgt gttgtggtga caccatgcgc tccccagggc cagacctgca cgcggcaggt   1560

ctgtgcccga gtcacccacg ggccatactt tgtagtttca gcctttcgag ccactgcagc   1620

cgtcagtgct gtgctcctaa gccatgggac ccgaggactg ccccccggcg cctgcccagg   1680

cggaggccct ttcagaaagg gcgaagctca cgcctgactc tgcgggccgc ggggccgcgt   1740

tcccagtgga cagcgtggtg agccgtggcc ggacggcagg aggagagggg agccccctct   1800

ggctgtgtgt caccttggct ggctggctgg ccagggtttt gccgatttcc ctcctcacat   1860

ccctcccacc ctcggtcata tcattgagat caccgtacca gcaaatctgc aaaccaagca   1920

ctttgttaat ctccagagag agcaaataca gcaatctaga gtttagcctt tttaaaaatg   1980

tgactttaac ccgcccacct gtgtcctccc attggcgtgg catttctttg gtgtctgctc   2040

agaaagaaac agcatgggac cgtgtgattg ggtccaggct gggctgtcag ggaagcgccc   2100

tggtgtctcc gactcatcaa ttctcgggtc tttttttaaa agccaggctc cccaaagcac   2160
```

-continued

```
tctttgtctc gcaattttga ggaggttgtt ccgacctgga agcgttaaac tgctgcatgt   2220
catctggcgt cagctgtgag gctgcgctct gcgtgttgtg cgtttgcaaa atgtattggc   2280
gtgactgtaa acacatcgtt gaagtaaagc gattacatat tgagtatgtc agcttttctc   2340
accctcttct gtgctgggag gagagtctaa ctgtaacctt taggttgttc cagaaaagat   2400
tcaggccgtt tggcacagaa ttgctctttc tgaagggtag cagtaatgaa taggaacaga   2460
cagaaaaccc ccaggagggg ctttcaggaa actctccctc tccatcgcca tcctgcaagc   2520
tccacagcct cgggctgcca gcctgtggca ctgtcctcgg tgtgtcctgg agctgtgctg   2580
ggcagcaggg cctcgcgtaa ggaactgctg gaacccactg agcccttccc ggggtttccc   2640
gccgcactca gtgtgttcct tcaggctagt gaggtttcat tctgttttat ttgcaagctt   2700
atcaaaagtt tgtggaagat acattgttgg gttccagagg ctggagtcat gctgcccaca   2760
tcttgtttgg gaaagcaaaa gctcccagtg agctggtgtc cccgtgtgtc tttcatggga   2820
ctgtcccctt tagagatccc acctgtcaga gccacagctt cggggtcctg tcatcacatc   2880
ccctgggagg ggaggcagga ggaggccgag ggccccagga tgtctgcctg gtcccttctc   2940
actgtgagga cgcccttggc acacctttct caagtcacac aaattattgc agttacatac   3000
agaattgctg acaggagcag gagacgctga gggaaacagc tggcaatgtg acaaaagtct   3060
tttctgggac aacaatcaaa tcatgtattt gtattttttt aagtttacca atgaattgta   3120
caacaatgta aaaataaagt tcatcctaat atgctgtgca catcttgctt aaaaatgtct   3180
tcagcaccca gtgcagtgat ctttccctca cacactgcat gcagcaggag cctcttgttt   3240
ttcttaatga gctgaaaaga cagcagatgt tcacagctga tgctgggtgt tgactcagcg   3300
ccacgggaag ctctgtgccc gcaggtaagc acgcacagtc ttacagttct ccttgtaaaa   3360
tatcatcacc cttcctgcct gagaaacgag tacatttgta ttttatgtaa caacaatagt   3420
caaggcagca ttgcaacact gagcagggtg aggtgggggt gctgagcaca ggacaagagg   3480
gaggaggcct gccctccatt cagatgcatc tgcatcgccc ttctgtgtgc agtcacatcg   3540
agactgcaca cagcatgcat ctcctcttgg aaaatatctt ttgcctccga gttgttttaa   3600
gcaattagaa tcaggtcctg aatccccaga ctgttcagag acttcaaggg acacctccct   3660
cacaagaagc ctggcacccc cactgtgtac ctttgagagg aaaggagtgc gtttgttttc   3720
atctgcattc tgtttgtcag tggcaacaga ctctatcaat gtaaaaccat ggttgtgatc   3780
atgtggggaa atcaaataaa tcctttgaaa ctctcggaaa a                       3821
```

<210> SEQ ID NO 26
<211> LENGTH: 1594
<212> TYPE: DNA
<213> ORGANISM: Homo sapiens
<220> FEATURE:
<221> NAME/KEY: misc_feature
<223> OTHER INFORMATION: Incyte ID No: 233896.7
<221> NAME/KEY: unsure
<222> LOCATION: 1569, 1580
<223> OTHER INFORMATION: a, t, c, g, or other

<400> SEQUENCE: 26

```
gacgtcactt ccgcccgggc ccggccgagg ttcggggctc cgttggccga ggggggcgta     60
cggaggtggc agctgtggga ggaggcggcg tggaaggccg aggagctcaa gcccggacca    120
atccccacgt tccgggccgc gaccctgacc ctgcagcgta ccgggaagcg aaaccggccg    180
gatgggccgc tgagcccgaa tcgggcactg tgtggagccc cctggagctg agatcaggat    240
```

-continued

```
gttccgcttc atgagggacg tggagcctga ggatcccatg ttcctgatgg atccctttgc    300

tattcaccgt cagcatatga gccgtatgtt gtcaggtggc tttggatata gccccttcct    360

cagcatcaca gatggcaaca tgccagggac caggcctgcc agccgccgga tgcagcaggc    420

tggagctgtc tcccccttg ggatgctggg aatgtcgggt ggtttcatgg acatgtttgg    480

gatgatgaat gacatgattg gaaacatgga acacatgaca gctggaggca attgccagac    540

cttctcatct tccactgtca tctcctactc caatacgggt gatggtgccc ccaaggtcta    600

ccaagagaca tcagagatgc gctcggcacc aggcgggatc cgggagacac ggaggactgt    660

tcgggattca gacagtggac tggagcagat gtccattggg catcacatcc gggacagggc    720

tcacatcctc cagcgctccc gaaaccatcg cacgggggac caggaggagc ggcaggacta    780

tatcaacctg gatgagagtg aggccgcagc gtttgatgac gagtggcggc gggagacctc    840

ccgattccgg gcagcagcgt cccctggagt ttcggcggct tgagtcctca ggggctgggg    900

gacgaagggc ggaggggcct ccccgcctgg ccatccaggg acctgaggac tccccttccc    960

gacagtcccg ccgctatgac tggtgagggc cccgggccct cagcctctct tgtacaggct   1020

gagaggctga gaaatcatcc cctgaataac tttttcctcc cgattcccat ccccaattta   1080

atattaaatt aacaggcaag ccggccccca cctctccctg ggggtctcag ggagaacctt   1140

tcacggcacc ctttccctac cttttccttc tttaatctcc tggtttacca ttgatgactt   1200

cgcctctgca tctactgact tgatttttca ttctgccact ccatcttcaa accccctcac   1260

ctttcccatc ctactcctgc catgcattga agggtcaatg cattttgggg tgagctctgg   1320

gtttaggggc cccctccatc cctcagctac cctggatctt tgcccacctc ttcctcagag   1380

cccccactga ggggccgtag ccctatctag ggctgtggaa ggagcagact ggttcctaac   1440

tctctccctc ctcctgccca cacacatcaa aagaatcttc cctacaccct tctctgcctt   1500

tattttttga tttgtgcaac ttgtaactag gtgtttatgg aataaaggag aatggaaaaa   1560

agaccaaana aaaaaaaaan aaaaaaaggg cggc                                 1594
```

```
<210> SEQ ID NO 27
<211> LENGTH: 519
<212> TYPE: DNA
<213> ORGANISM: Homo sapiens
<220> FEATURE:
<221> NAME/KEY: misc_feature
<223> OTHER INFORMATION: Incyte ID No: 197192.31
<221> NAME/KEY: unsure
<222> LOCATION: 34, 44, 53, 62, 65, 72, 85, 105, 132, 147
<223> OTHER INFORMATION: a, t, c, g, or other

<400> SEQUENCE: 27

atttctggct gccagggaag ccatggcgct cccntggtgt aatnctggtc cancgtgaca     60

tncgnccctc anttttaagc catgnctaga tgtggctgct gaggntcagt gtgattatct    120

tggcagagcc cnggccagta ttacttnaaa cccatgatga aggagttccg gtttgagcca    180

tcctcacaga tgatcgaggt gcaggaaggc cagaacctga agatcactct gctgaacaga    240

atttattttc tgagtcaaat ataatttatt attatttttg tcaaagaagt atttaagctg    300

tgctgtggtg tgagaatgtc attcttgatc ttcagccttc gtttgcaaga agagttccag    360

ttgacgtggt gtttggttcc atggcggggt accctaggga ttcatctgtt ttcttcactt    420

ccctttgcat ctgagatcct gctggaaacc acagcaacct gtatccacta ttaggaggta    480

aaaatcaata aaatggccca ttcatttgtg ttgtagctc                            519
```

-continued

<210> SEQ ID NO 28
<211> LENGTH: 2730
<212> TYPE: DNA
<213> ORGANISM: Homo sapiens
<220> FEATURE:
<221> NAME/KEY: misc_feature
<223> OTHER INFORMATION: Incyte ID No: 197402.2

<400> SEQUENCE: 28
ctctgtagct gtgaccctga taccgcgtgg tgtgctccga acacatggtg cccagaacga 60
aggcggcgtc cagaagccct aggtcccaga ggtccgctca gcggcaggcg cataaggcgg 120
ggccggcgcg ggcctttcct tccatcggaa ccgttctccc ggggctgagt ccctgcccgg 180
actccgaacg ccgaagacca ggggccggaa gcgcgcgccg ccactgccgc gccgtgtcag 240
tcgggaggga gggagcgagc aggcgaagcc gcggaggacg gggtgaagat ggcggccttc 300
tccgagatgg gtgtaatgcc tgagattgca caagctgtgg aagagatgga ttggctcctc 360
ccaactgata tccaggctga atctatccca ttgatcttag gaggaggtga tgtacttatg 420
gctgcagaaa caggaagtgg caaaactggt gcttttagta ttccagttat ccagatagtt 480
tatgaaactc tgaaagacca acaggaaggc aaaaaaggaa aaacaacaat taaaactggt 540
gcttcagtgc tgaacaaatg gcagatgaac ccatatgaca gaggatctgc ttttgcaatt 600
gggtcagatg gtctttgttg tcaaagcaga gaagtaaagg aatggcatgg gtgtagagct 660
actaaaggat taatgaaagg gaaacactac tatgaagtat cctgtcatga ccaagggtta 720
tgcagggtcg ggtggtctac catgcaggcc tctttggacc taggtactga caagtttgga 780
tttggctttg gtggaacagg aaagaaatcc cataacaaac aatttgataa ttatggagag 840
gaattcacta tgcatgatac cattggatgt tacctggata tagataaggg acatgtcaag 900
ttctccaaaa atggaaaaga tcttggtctg gcatttgaaa taccaccaca tatgaaaaac 960
caagccctct ttcctgcctg tgttttgaag aatgctgaac tgaaatttaa cttcggtgaa 1020
gaggaattta agtttccacc aaaagatggc tttgttgctc tttccaaggc accggatggt 1080
tacattgtca aatcacagca ctcaggtaat gcacaggtga cacaaacaaa gtttctcccc 1140
aatgctccga aagctctcat tgttgaacct tcccgggagt tagctgaaca aactttgaac 1200
aacatcaagc agtttaagaa atacattgat aatcctaaat taagggagct tctgataatt 1260
ggaggtgttg cagcccggga tcagctctct gttttggaaa atggagtaga tatagttgta 1320
ggtactccgg gaagactaga tgacttggtg tcaactggaa agctgaactt atctcaagtt 1380
agattcctgg tcctggatga agctgatggg cttctttctc aaggttattc tgattttata 1440
aataggatgc acaatcagat tcctcaggtt acctctgatg gaaaaagact tcaggtgatt 1500
gtttgctctg ccactttgca ttctttcgat gtaaagaaac tgtccgagaa gataatgcat 1560
tttcctacat gggttgactt aaaaggagaa gactctgttc cagatactgt acaccatgtt 1620
gttgtcccag taaatcccaa aactgacaga ctctgggaaa ggcttggaaa gagccacatt 1680
agaactgatg atgtacatgc aaaagataac acaagacctg gtgctaatag tccagagatg 1740
tggtctgaag ctattaaaat cctgaaaggg gagtatgctg tccgggcaat caaggaacat 1800
aagatggatc aagcaattat cttctgtaga accaaaattg actgtgataa cttggagcag 1860
tactttatac aacaaggagg aggacctgat aaaaaaggac accagttctc atgtgtttgt 1920
cttcatggtg acagaaagcc tcatgagaga aagcaaaact tggaaagatt taagaaagga 1980
gatgtaagat tcttgatttg cacagatgta gctgctagag gaattgatat ccacggtgtt 2040
ccttatgtta taaatgtcac tctgcccgat gaaaagcaaa actacgtaca tcgaattggc 2100

-continued

```
agagtaggaa gagctgaaag gatgggtctg gcaatttccc tggtggcaac agaaaaagaa   2160
aaggtttggt accatgtatg tagcagccgt ggaaaagggt gttataacac aagactcaag   2220
gaagatggag gctgtaccat atggtacaac gagatgcagt tactatctga gatagaagaa   2280
cacctgaact gtaccatttc tcaggttgag ccggatataa aggtaccagt ggatgaattt   2340
gatgggaaag ttacctacgg tcagaaaagg gctgctggtg gtggaagcta taaaggccat   2400
gtggatattt tggcacctac tgttcaagag ttggctgccc ttgaaaagga ggcgcagaca   2460
tctttcctgc atcttggcta ccttcctaac cagctgttca gaaccttctg atttttacat   2520
ttactgaata agatttgagt aatgaaagtc tgtagtctta aaactctaaa acagttgtac   2580
tgcttccaag cagcagtatt tatagtaacg taagctatta atgctaactc ttgcatgtca   2640
agaaacatta gtcttaggaa ttcttcaaaa aatggcatcc caatgaaaat aaatttgatg   2700
actataaaca aaagcaccaa ccccagggga                                    2730
```

<210> SEQ ID NO 29
<211> LENGTH: 3316
<212> TYPE: DNA
<213> ORGANISM: Homo sapiens
<220> FEATURE:
<221> NAME/KEY: misc_feature
<223> OTHER INFORMATION: Incyte ID No: 422524.4

<400> SEQUENCE: 29

```
ggccgtgcgg cccgccgggg ccatggcgaa gaagagcgcc gagaacggca tctatagcgt     60
gtccggcgac gagaagaagg gtcctctcat cgtgtccggg cccgatggtg ccccgtccaa    120
gggcgatggc cctgcgggcc tgggggcgcc cagcagccgc ctggccgtgc cgccgcgcga    180
gacctggacg cgccagatgg acttcatcat gtcgtgcgtg ggcttcgccg tgggcttggg    240
caacgtgtgg cgcttcccct acctgtgcta caagaacggc ggaggtgtgt tccttattcc    300
ctacgtcctg atcgccctgg ttggaggaat ccccattttc ttcttagaga tctcgctggg    360
ccagttcatg aaggccggca gcatcaatgt ctggaacatc tgtcccctgt tcaaaggcct    420
gggctacgcc tccatggtga tcgtcttcta ctgcaacacc tactacatca tggtgctggc    480
ctggggcttc tattacctgg tcaagtcctt taccaccacg ctgccctggg ccacatgtgg    540
ccacacctgg aacactcccg actgcgtgga gatcttccgc catgaagact gtgccaatgc    600
cagcctggcc aacctcacct gtgaccagct tgctgaccgc cggtcccctg tcatcgagtt    660
ctgggagaac aaagtcttga ggctgtctgg gggactggag gtgccagggg ccctcaactg    720
ggaggtgacc ctttgtctgc tggcctgctg ggtgctggtc tacttctgtg tctggaaggg    780
ggtcaaatcc acgggaaaga tcgtgtactt cactgctaca ttcccctacg tggtcctggt    840
cgtgctgctg gtgcgtggag tgctgctgcc tggcgccctg gatggcatca tttactatct    900
caagcctgac tggtcaaagc tggggtcccc tcaggtgtgg atagatgcgg ggacccagat    960
tttcttttct tacgccattg gcctgggggc cctcacagcc ctgggcagct acaaccgctt   1020
caacaacaac tgctacaagg acgccatcat cctggctctc atcaacagtg ggaccagctt   1080
ctttgctggc ttcgtggtct tctccatcct gggcttcatg gctgcagagc agggcgtgca   1140
catctccaag gtggcagagt cagggccggg cctggccttc atcgcctacc cgcgggctgt   1200
cacgctgatg ccagtggccc cactctgggc tgccctgttc ttcttcatgc tgttgctgct   1260
tggtctcgac agccagtttg taggtgtgga gggcttcatc accggcctcc tcgacctcct   1320
cccggcctcc tactacttcc gtttccaaag ggagatctct gtggccctct gttgtgccct   1380
```

-continued

```
ctgctttgtc atcgatctct ccatggtgac tgatggcggg atgtacgtct tccagctgtt   1440
tgactactac tcggccagcg gcaccaccct gctctggcag gccttttggg agtgcgtggt   1500
ggtggcctgg gtgtacggag ctgaccgctt catggacgac attgcctgta tgatcgggta   1560
ccgaccttgc ccctggatga aatggtgctg gtccttcttc accccgctgg tctgcatggg   1620
catcttcatc ttcaacgttg tgtactacga gccgctggtc tacaacaaca cctacgtgta   1680
cccgtggtgg ggtgaggcca tgggctgggc cttcgccctg tcctccatgc tgtgcgtgcc   1740
gctgcacctc ctgggctgcc tcctcagggc caagggcacc atggctgagc gctggcagca   1800
cctgacccag cccatctggg gcctccacca cttggagtac cgagctcagg acgcagatgt   1860
caggggcctg accaccctga ccccagtgtc cgagagcagc aaggtcgtcg tggtggagag   1920
tgtcatgtga caactcagct cacatcacca gctcacctct ggtagccata gcagcccctg   1980
cttcagcccc accgcacccc tccagggggc ctgcctttcc ctgacacttt tggggtctgc   2040
ctgggggagg aggggagaaa gcaccatgag tgctcactaa aacaactttt tccattttta   2100
ataaaacgcc aaaaatatca caacccacca aaaatagatg cctctccccc tccagcccta   2160
gccgagctgg tcctaggccc cgcctagtgc cccaccccca cccacagtgc tgcactcctc   2220
ctgcccctgc cacgcccacc ccctgcccac ctctccaggc tctgctctgc agcacacccg   2280
tgggtgaccc ctcaccccag aagcagcagt ggcagcttgg gaaatgtgag gaagggaagg   2340
agggagagac gggagggagg agagagagga gaagggaggc aggggagggg cagcagaacc   2400
aaggcaaata tttcagctgg gctatacccc tctccccatc cctgttatag aagcttagag   2460
agccagccag caatggaacc ttctggttcc tgcgccaatc gccaccagta tcaattgtgt   2520
gagcttgggt gcgagtgcac gcgtgcgtga gtacggagag tatatataga tctctatctc   2580
ttagcaaagg tgaatgccag atgtaaatgg cgcctctggg caaaggaggc ttgtattttg   2640
cacattttat aaaaacttga gagaatgaga tttctgcttg tatatttcta aaaagaggaa   2700
ggagcccaaa ccatcctctc cttaccactc ccatccctgt gagccctacc ttacccctct   2760
gcccctagcc aaggagtgtg aatttataga tctaactttc ataggcaaaa caaaagcttc   2820
gagctgttgc gtgtgtgagt ctgttgtgtg gatgtgcgtg tgtggtcccc agccccagac   2880
tggattggaa aagtgcatgg tgggggcctc ggggctgtcc ccacgctgtc cctttgccac   2940
aagtctgtgg ggcaagaggc tgcaatattc cgtcctgggt gtctgggctg ctaacctggc   3000
ctgctcaggc ttcccaccct gtgcggggca cacccccagg aagggaccct ggacacggct   3060
cccacgtcca ggcttaaggt ggatgcactt cccgcacctc cagtcttctg tgtagcagct   3120
ttaacccacg tttgtctgtc acgtccagtc ccgagacggc tgagtgaccc caagaaaggc   3180
ttccccgaca cccagacaga ggctgcaggg ctggggctgg gtgagggtgg cgggcctgcg   3240
gggacattct actgtgctaa aaagccactg cagacatagc aataaaaaca tgtcattttc   3300
caaagcaaaa aaaaaa                                                   3316
```

```
<210> SEQ ID NO 30
<211> LENGTH: 2097
<212> TYPE: DNA
<213> ORGANISM: Homo sapiens
<220> FEATURE:
<221> NAME/KEY: misc_feature
<223> OTHER INFORMATION: Incyte ID No: 350423.5

<400> SEQUENCE: 30

ggggcgtcgc cgtactaggc ctgccccctg tccggccagc ccctcgaagc acctactcca     60
```

-continued

```
caggtccagc cggccggtga gcgcctgggg accgcagagg tgagagtcgc gcccggggag    120
tccgccgcct gcgccaggat ggagttcgtg aaatgccttg ggccaccccg aagagttcta    180
caacctggtg cgcttccgga tcgggggcaa gcggaaggtg atgcccaaga tggaccagga    240
ctcgctcagc agcagcctga aaacttgcta caagtatctc aatcagacca gtcgcagttt    300
cgcagctgtt atccaggcgc tggatgggga aatgcgcaac gcagtgtggc atattttatc    360
tggttctccg agctctggac acactggaag atgacatgac catcagtgtg gaaaagaagg    420
tcccgctgtt acacaacttt cactctttcc tttaccaacc agactggcgg ttcatggaga    480
gcaaggagaa ggatcgccag gtgctggagg acttcccaac gatctccctt gagtttagaa    540
atctggctga gaaataccaa acagtgattg ccgacatttg ccggagaatg ggcattggga    600
tggcagagtt tttggataag catgtgacct ctgaacagga gtgggacaag tactgccact    660
atgttgctgg gctggtcgga attggccttt cccgtctttt ctcagcctca gagtttgaag    720
accccttagt tggtgaagat acagaacgtg ccaactctat gggcctgttt ctgcagaaaa    780
caaacatcat ccgtgactat ctggaagacc agcaaggagg aagagagttc tggcctcaag    840
aggtttggag caggtatgtt aagaagttag ggattttgc taagccggag aatattgact    900
tggccgtgca gtgcctgaat gaacttataa ccaatgcact gcaccacatc ccagatgtca    960
tcacctacct ttcgagactc agaaaccaga gtgtgtttaa cttctgtgct attccacagg   1020
tgatggccat tgccactttg gctgcctgtt ataataacca gcaggtgttc aaaggggcag   1080
tgaagattcg gaaagggcaa gcagtgaccc tcatgatgga tgccaccaat atgccagctg   1140
tcaaagccat catatatcag tatatggaag agatttatca tagaatcccc gactcagacc   1200
catcttctag caaaacaagg cagatcatct ccaccatccg gacgcagaat cttcccaact   1260
gtcagctgat ttcccgaagc cactactccc ccatctacct gtcgtttgtc atgcttttgg   1320
ctgccctgag ctggcagtac ctgaccactc tctcccaggt aacagaagac tatgttcaga   1380
ctggagaaca ctgatcccaa atttgtccat agctgaagtc caccataaag tggatttact   1440
tttttctttt aaggatggat gttgtgttct ctttattttt ttcctactac tttaatccct   1500
aaaagaacgc tgtgtggctg ggacctttag gaaagtgaaa tgcaggtgag aagaacctaa   1560
acatgaaagg aaagggtgcc tcatcccagc aacctgtcct tgtgggtgat gatcactgtg   1620
ctgcttgtgg ctcatggcag agcattcagt gccacggttt aggtgaagtc gctgcatatg   1680
tgactgtcat gagatcctac ttagtatgat cctggctaga atgataatta aaagtattta   1740
atttgaagca ccatttgaat gttcgtaata gtagaaaatg atgtgaattt tctttctgtt   1800
cggctcctat ttttctcatc attttgtttt ctttaattgg gttgaatgga gtagatagaa   1860
atatttatgg tttaggtaac agttagatgt ttcctaagaa tgcaaactgc cttttccaca   1920
caaaggctgg gaataaaatt ctgggtattc tcgtattctc atttaaagga gtttagcttt   1980
cagagagaaa cagcaggatt gcttttgacc ttttagaaga ttggtctcca gtaaaggtgg   2040
acatttttga gatttttata ataaagaatt taattgctct gcatttgtca agtaaaa      2097
```

<210> SEQ ID NO 31
<211> LENGTH: 4453
<212> TYPE: DNA
<213> ORGANISM: Homo sapiens
<220> FEATURE:
<221> NAME/KEY: misc_feature
<223> OTHER INFORMATION: Incyte ID No: 095888.2
<221> NAME/KEY: unsure
<222> LOCATION: 482, 502, 3907-4004

-continued

<223> OTHER INFORMATION: a, t, c, g, or other

<400> SEQUENCE: 31
gtttgcctga actgtttgta cctctgggcc atattgcaga accctgccct tctttgttga 60
ctgaggaaag ctcgctccct gcccaggttt ttcattgttg atcgaaatta acaccaggtg 120
gtgaatagag cccctcctaa ggttgctcag gataaatcat ttattaaata ggtctgctta 180
tcaggagggg cgtgaaggct cccaaaagga aatgctggca cctgggccca gaagccaggg 240
cctctaactc ctggggttga tttcttcagt gaagttgcac cctacaaagg gaatatggcc 300
aaagcggcac tcaactgaag gctgatatca ggcgattaga cagccatgca ttctgcgttt 360
gtctggaatg gattgtagag agatggactt atatgaggac taccagtccc cgtttgattt 420
tgatgcagga gtgaacaaaa gctatctcta cttgtctcct agtggaaatt catctccacc 480
cnggatcacc tactcttcag anatttggtc tgctgagaac agacccagtc cctgaggaag 540
gagaagatgt tgctgccacg atcagtgcca cagagaccct ctcggaagag gagcaggaag 600
agctaagaag agaacttgca aaggtagaag aagaaatcca gactctgtct caagtgttag 660
cagcaaaaga gaagcatcta gcagagatca agcggaaact tggaatcaat tctctacagg 720
aactaaaaca gaacattgcc aaagggtggc aagacgtgac agcaacatct gcttacaaga 780
agacatctga aaccttatcc caggctggac agaaggcctc agctgctttt tcgtctgttg 840
gctcagtcat caccaaaaag ctggaagatg taaatatacg ttccattcag cattcaatta 900
gcatgcctgc tatgagaaac tccccaactt ttaaatcatt tgaagaaaag gtcgaaaact 960
taaagtctaa agtaggggga accaagcctg ctggtggtga ttttggagaa gtcttgaatt 1020
cggctgcaaa tgctagtgcc accaccacgg agcctcttcc agaaaagaca caggagagcc 1080
tgtgagattc ctacctttgt tctgctaccc actgccagat gctgcaagcg aggtccaagc 1140
acatcttgtc aacatgcatt gccatgaatt tctaccagat gtgcttttat ttagctttac 1200
atattccttt gaccaaatag tttgtgggtt aaacaaaatg aaaatatctt cacctctatt 1260
cttgggaaac accctttagt gtacatttat gttcctttat ttaggaaaca ccattataaa 1320
aacacttata gtaaatgggg acattcacta taatgatcta agaagctaca gattgtcata 1380
gttgttttcc tgctttacaa aattgctcca gatctggaat gccagtttga cctttgtctt 1440
ctataatatt tccttttttt cccctctttg aatctctgta tatttgattc ttaactaaaa 1500
ttgttctctt aaatattctg aatcctggta attaaaagtt tgggtgtatt ttctttacct 1560
ccaaggaaag aactactagc tacaaaaaat attttggaat aagcattgtt ttggtataag 1620
gtacatattt tggttgaaga caccagactg aagtaaacag ctgtgcatcc aatttattat 1680
agttttgtaa gtaacaatat gtaatcaaac ttctaggtga cttgagagtg gaacctccta 1740
tatcattatt tagcaccgtt tgtgacagta accatttcag tgtattgttt attataccac 1800
ttatatcaac ttatttttca ccaggttaaa attttaattt ctacaaaata acattctgaa 1860
tcaagcacac tgtatgttca gtaggttgaa ctatgaacac tgtcatcaat gttcagttca 1920
aaagcctgaa agtttagatc tagaagctgg taaaaatgac aatatcaatc acattagggg 1980
aaccattgtt gtcttcactt aatccattta gcactattta aaataagcac accaagttat 2040
atgactaata taacttgaaa attttttata ctgaggggtt ggtgataact cttgaggatg 2100
taatgcatta ataaaaatca actcatcatt ttctacttgt tttcaatgtg ttggaaactg 2160
taaaatgata ctgtagaacc tgtctcctac tttgaaaact gaatgtcagg gctgagtgaa 2220
tcaaagtgtc tagacatatt tgcatagagg ccaaggtatt ctattctaat aactgcttac 2280

-continued

```
tcaacactac caccttttcc ttatactgta tatgattatg gcctacaatg ttgtatttgt   2340
tatttattaa attgtgattg ttttattatt gtttatgcca aatgttaact gccaagcttg   2400
gagtgaccta aagcattttt taaaagcatg gctagattta cttcagtata aattatctta   2460
tgaaaaccaa attttaaaag ccacaggtgt tgattgttat aaaataacat gctgccattc   2520
ttgattgcta gagtttttgt tagtactttg gatgcaatta aaactatgtg ctatcacatg   2580
tgaaaagctt aataaattcc atctatcagt agtataggtc tcaatattta ttatgagacc   2640
agtggtctgg aaacagcttg ttgtaccgaa tcaactggag tctatgctta aaaaaaaaaa   2700
attttttttt aaccatcctt aaattattgc ttaatggtat catattaaca tattctaaat   2760
aagggcttta aggcacaggc tgttgaagca ttttctcaga ggagtggatc tgtagaagtc   2820
tgtctttcta tagaaatatt gtgcttactc aagtgttaaa ttattttttc tatgaactag   2880
tctacttctt aaaattcaaa catattcttt tgatcacatt gtttcttgag catcctgccc   2940
tgctactaac ttttcaacaa ggcaaaatgg agtaaagtgg caatttcttt agatgagtga   3000
aataccctca agtctctttt ctgcccaaaa agggaaaagt gatagaaatg ggggtggcaa   3060
gtggggtgag tggatgaagg tgggtattgg gggtggctgt gaaagaaaat aatggagaat   3120
cacttttcta gacatctacc tatacttaat ctaagaaaca aagtaatcta ctgtaaagta   3180
ctctgcccct tgaaagaagt attaaaaaga gtgaggatgg atttagaaaa aaacatgaat   3240
ttagaaatat tcaaaatggt ttttgtggca gattcaatat tatgaattca cagatattta   3300
aagaatgaga aacatagtaa ttagtagaaa tgccagaaac agttcctggt tcctcttgtg   3360
tttgacacta agaaaatagc aagagtgtga aatctcagat acttatgaaa tctcacagat   3420
gtaaggactc aagtgtagaa gaaaatatcc ccttcttaca aaaagaaatg tcaatttatg   3480
gagtttgtgg gaaatagggc aagaattctt atgcttatga gagccaagta gtcagtggaa   3540
gagagtagag ctcaaaactg gattatcacc ttagcaactt agaatagttt gaaatagaaa   3600
aaaagtattt aatttggatc tggatctgtt aagatatgca cagtctattt tttgtatagt   3660
attggaaaat aaaaatgcta taatttgggt atgggttctt ttgtatacat tacctgccca   3720
ttgaggaaag gggcaagtcc attatgcaac ttctctccaa acccttcata ttctggatat   3780
gatacttaaa gagccatgag cagctacatt ctgcctatca gaaggcattt attaaatgac   3840
tgcttgctga agatttgtcc aaagagatcc tacattaagg tcatttgtca gaatgatgtt   3900
tgtgttnnnn nnnnnnnnnn nnnnnnnnnn nnnnnnnnnn nnnnnnnnnn nnnnnnnnnn   3960
nnnnnnnnnn nnnnnnnnnn nnnnnnnnnn nnnnnnnnnn nnnnttttat ttatagctct   4020
taaagcccag atgaagaaat cacatttttg cccatagtga agaaacattt ggccattgat   4080
tagtccttat tttcagtgac tgtcctgttt tcattagatt agagagaccc tgtgtgggcc   4140
acagttaata taaaccatta tcacttttaa gtaaacctgc acatcttaga tttcataatt   4200
tccttattgt tctgactcaa aatgaactaa gagcttttca ctttttgttt gtaagttctc   4260
agagagtcgg gtctgcaagt gcttttgcct gccaggattt tgtactcaaa taaatgctat   4320
ttggcaacta aaattcttgc cagctctcat gtaattttga tgttactgag gttggttggt   4380
agtttatttt attaattttg tggttcttct atcatataga aaaagccaaa tacagttttg   4440
tttgaatatt tgt                                                     4453
```

<210> SEQ ID NO 32
<211> LENGTH: 11917
<212> TYPE: DNA

-continued

<213> ORGANISM: Homo sapiens
<220> FEATURE:
<221> NAME/KEY: misc_feature
<223> OTHER INFORMATION: Incyte ID No: 475473.1
<221> NAME/KEY: unsure
<222> LOCATION: 9384, 10290-10321, 10325
<223> OTHER INFORMATION: a, t, c, g, or other

<400> SEQUENCE: 32

```
gccgcgcact ctccgcggcg ctgggagagg gcggaggggg aggcggcgcg cggcgccaga     60
ggaggggggga cgcagggggc ggagcggaga cagtaccttc ggagataatc ctttctcctg    120
ccgcagagga gaggagcggc cggagcgaga cacttcgccg aggcacagca gccggcagga    180
tggcgaccgt ggtggtggaa gccaccgagc cggagccgtc cggcagcatc gccaacccgg    240
cggcgtccac ctcgcctagc ctgtcgcacc gcttccttga cagcaagttc tacttgctgg    300
tggtcgtcgg cgagatcgtg accgaggagc acctgcggcg tgccatcggc aacatcgagc    360
tcggaatccg atcatgggac acaaacctga ttgaatgcaa cttggaccaa gaactcaaac    420
tttttgtatc tcgacactct gcaagattct ctcctgaagt cccaggacaa aagatccttc    480
atcaccgaag tgacgtttta gaaacagtgg tcctgatcaa cccttctgat gaagcagtca    540
gcaccgaggt gcgcttaatg atcactgatg ctgcccgaca caagctgctc gtgctgaccg    600
ggcagtgctt tgaaaatacc ggagagctca ttctccagtc cggctctttc tccttccaga    660
acttcataga gattttcacc gatcaagaga tcggggagtt actaagcacc acccatcctg    720
ccaacaaagc cagcttaacc ctgttctgtc ctgaagaagg ggactggaag aactccaatc    780
ttgacagaca caatctccaa gacttcatca atattaaact caattcagct tctatcttgc    840
cagaaatgga aggactttct gagtttaccg agtatctctc agaatcagtg gaagtcccat    900
ctccctttga catcttggaa cctcccacat cgggtggatt tctgaagctc tccaagccct    960
gctgttatat ttttccagga gggaggggcg attctgcctt gtttgcagtg aatggtttca   1020
atatgctcat caatggcgga tcagagagaa aatcctgctt ctggaagctc atccgacact   1080
tagaccgagt ggactccatc ctgctcaccc acattgggga tgacaatttg cctggaataa   1140
acagcatgtt acagcggaaa attgcagagc tcgaggaaga acagtcccag ggctccacc    1200
acaaatagtg actggatgaa aaacctcatc tcccctgact taggagttgt atttctcaat   1260
gtacctgaaa atctcaaaaa tccagagcca aacatcaaga tgaagagaag catagaagaa   1320
gcctgcttca ctctccagta cctaaacaaa ttgtccatga aaccagaacc tctgtttaga   1380
agtgtaggca atactattga tcctgtcatt cttttccaaa aaatgggagt aggtaaactt   1440
gagatgtatg tgcttaatcc agtcaagagc agcaaggaaa tgcagtattt tatgcagcag   1500
tggactggta ccaacaaaga caaggctgaa ttcattctgc ctaatggtca agaagtagat   1560
ctcccgattt cctacttaac ttcagtctca tctttgattg tgtggcatcc agcaaaccct   1620
gcggagaaaa tcatccgagt cctgtttcct gggaacagca cccagtacaa catcctggaa   1680
gggttggaaa agctcaaaca tctagacttt ctgaagcagc cactggccac ccaaaaggat   1740
ctcactggcc aggtgcccac tcctgtggtg aaacaaacaa aactgaaaca gagggctgat   1800
agccgagaaa gtctgaagcc agccgcaaaa ccacttccta gcaaatccgt gcgcaaggag   1860
tcaaaagaag aaacccctga ggtcacaaaa gtgaatcacg tggaaaagcc acccaaagtt   1920
gaaagcaaag aaaaggtaat ggtgaaaaaa gacaagccag taaaaacaga gaccaaacct   1980
tcagtgactg aaaaggaggt tcccagcaaa gaagagccat ctccagtgaa agccgaggtg   2040
gctgagaagc aagccacaga tgtcaaaccc aaagctgcca aggagaagac ggtgaaaaag   2100
```

-continued

```
gaaacaaagg taaagcctga agacaagaaa gaggagaaag aaaagccaaa gaaagaagtg   2160
gctaaaaagg aggacaaaac acctatcaag aaggaggaaa aaccaaaaaa ggaagaggtg   2220
aaaaaagaag tcaaaaaaga gatcaagaaa gaagagaaaa aagaacccaa gaaagaggtt   2280
aagaaagaaa caccgccaaa ggaagtcaag aaggaagtta agaaggaaga gaagaaggaa   2340
gtgaaaaagg aagaaaagga acccaaaaaa gaaattaaga agctccctaa agacgcaaag   2400
aaatcatcta ctcctctgtc tgaagcaaaa aaaccagctg ctttaaaacc aaaagtaccc   2460
aagaaggaag agtctgtcaa gaaagattct gttgctgccg gaaagccaaa ggagaagggg   2520
aaaataaaag tcattaagaa ggaaggcaag gccgcagagg ctgtcgctgc agctgtcggc   2580
actggagcca ccacagcagc tgtcatggcg gcagctggaa tagcagccat tggccctgcc   2640
aaagaactcg aagctgagag gtcccttatg tcatctcctg aggatctaac caaggacttt   2700
gaagagttaa aggctgaaga ggtcgatgta acaaaggaca tcaagcctca gctggagcta   2760
atcgaagacg aagagaaact gaaggaaact gagccagtcg aagcctacgt catccagaag   2820
gagagagaag tcaccaaagg tcctgccgag tcccctgatg agggaatcac taccactgaa   2880
ggggagggcg aatgtgaaca gacacctgag gagctggagc ccgtcgagaa gcagggagta   2940
gacgacattg aaaaatttga agatgaagga gccggttttg aagaatcttc agagactgga   3000
gactatgaag agaaggcaga aactgaggag gctgaggagc cagaagagga tggggaggaa   3060
cacgtatgtg tgagcgcctc caagcacagc cccactgagg atgaggaaag tgccaaggcg   3120
gaggctgatg catacatcag ggagaagagg gagtctgtgg ccagtgggga tgaccgagcc   3180
gaagaagaca tggatgaggc cattgagaaa ggagaggctg aacaatctga agaggaggct   3240
gatgaggagg acaaagctga agatgccaga gaggaggaat atgagccgga aaaaatggaa   3300
gctgaagact atgtgatggc tgtggtcgac aaggctgcag aggctggtgg tgccgaggag   3360
cagtatggat tcctcaccac accaaccaag caactaggag cccagtctcc tggccgagaa   3420
cctgcatctt caattcatga tgagacttta cctggaggct cagagagcga ggccaccgct   3480
tctgatgagg agaatcgaga agaccagcct gaggaattca ctgccacctc tggctacact   3540
cagtctacta ttgagatatc cagtgagccc acccccatgg atgagatgtc tacccctcga   3600
gacgtgatga gtgatgagac caacaatgaa gagacggagt ccccttctca ggaattcgta   3660
aatatcacca aatatgaatc ttcattgtat tctcaggaat actctaaacc tgctgatgtt   3720
acaccgctca acggattttc tgaaggatca aaaacagatg ccactgatgg caaggattac   3780
aatgcttcag cctctaccat atcaccaccc tcttccatgg aggaagacaa attcagcaga   3840
tctgctttac gtgatgctta ctgctctgaa gtgaaagcca gcaccacttt ggacatcaaa   3900
gatagcatct cagctgtttc aagtgaaaag gtcagcccat cgaagagccc gtccctgagt   3960
ccatctccac catcaccctt agaaaagacc cccctgggtg aacgtagtgt gaacttctct   4020
ctgacgccca atgagattaa agtctctgca gaggcagaag tagccccggt gtctcctgag   4080
gtgacccaag aagtagttga agaacattgt gctagtcctg aggacaagac tctggaagtg   4140
gtgtcaccat ctcagtccgt gactggcagt gctggtcaca caccttacta tcaatctcct   4200
actgacgaga aatccagtca tctccctaca gaagtcattg aaaaaccacc agcagttcca   4260
gtgagttttg aattcagtga tgccaaagat gagaatgaaa gggcttcagt aagccccatg   4320
gatgagcccg tgcctgactc agagtctcct attgaaaaag ttttgtctcc tttacgcagc   4380
ccgcccctca ttggatccga gtctgcttat gaaagttttc taagtgctga tgacaaggct   4440
```

-continued

```
tctggcagag gtgccgaaag tccttttgaa gaaaagagtg gaaaacaagg ctctccagac   4500
caagtaagtc cagtttctga aatgacttct actagtcttt accaagacaa acaggaaggg   4560
aaaagcacag actttgcacc aataaaagaa gactttggcc aagaaaagaa aactgatgat   4620
gttgaagcca tgagttctca accagcactg gctctggatg aaaggaaatt aggagatgtt   4680
tctcccacac aaatagatgt cagtcagttt ggatctttta aagaagacac taagatgtcc   4740
atttctgaag gtactgtctc agacaagtca gctactcctg ttgatgaggg cgtagcagaa   4800
gacacgtact ctcatatgga gggtgtggcc tcagtgtcca cagcctcagt ggctacgagc   4860
tcatttccag agccaacaac agatgatgtg tctccatctc tgcatgctga ggttggctcc   4920
ccacattcca cagaagtaga tgactccctt tcagtgtctg ttgtgcaaac acctaccaca   4980
ttccaggaaa cagaaatgtc tccatctaaa gaagaatgcc caagaccgat gtcaatttct   5040
ccaccagatt tctcccctaa aactgcaaag tccaggacac ccgttcaaga tcacagatct   5100
gaacagtcct caatgtctat tgaatttggc caagaatctc ctgagcaatc ccttgctatg   5160
gacttcagtc gacagtctcc agatcaccct acagtgggtg caggcgtgct tcacatcact   5220
gaaaatgggc caactgaagt ggactacagt ccttctgaca tgcaggactc cagtttatca   5280
cataagatac cacctatgga ggagccgtcc tacacccaag ataatgatct ttctgagctc   5340
atctcagtat ctcaggtaga ggcctccccg tccacctctt ctgctcatac cccttctcag   5400
atcgcttctc ctctccaaga agatactcta tccgatgttg ctcctcccag agatatgtcc   5460
ttatatgcct cactcacctc tgaaaaagtg caaagtctgg aaggagagaa gctctctcca   5520
aaatctgata tctctccact caccccacga gagtcctctc ctttatattc acctactttt   5580
tcagattcta cctctgcagt caaagagaaa acagcaactt gccacagttc ctcttctcca   5640
ccaatagatg cagcatccgc agagccctat ggcttccgtg cctcagtgtt attcgataca   5700
atgcaacacc atctagcctt gaatagagat ttgtccacac ctggcctgga gaaggacagt   5760
ggagggaaga cacctggtga ctttagctat gcctatcaaa agcctgagga aacaaccagg   5820
tccccagatg aagaagatta tgactatgag tcttatgaga agaccacccg gacctcagat   5880
gtgggtggct attactatga gaagatagag agaaccacaa aatctccaag tgacagtggc   5940
tactcctatg agaccattgg gaaaactacc aagacccctg aagatggtga ctattcctat   6000
gaaattattg agaagaccac acggacccct gaagagggtg ggtactcata tgacataagt   6060
gaaaagacca ccagcccccc cgaagtgagt ggttacagct atgaaaagac tgagaggtct   6120
agaaggcttc tggatgacat cagcaatggc tatgatgact ctgaggatgg tggccacaca   6180
cttggggacc ccagctactc ttatgaaacc actgagaaaa ttaccagttt ccctgagtct   6240
gaaggttatt cctatgagac atctacaaag acaacacgaa cccctgatac ttccacatac   6300
tgttacgaga ctgcagagaa aatcactaga acccctcagg catccacata ttcctacgag   6360
acttcagacc tatgctacac tgcagaaaag aagtccccct cagaagcccg tcaggatgtc   6420
gatttatgcc tcgtgtcctc ttgtgaatac aagcacccca agacagagct ttcaccctct   6480
ttcattaatc ccaatcctct tgagtggttt gccagtgaag aacccactga agaatctgaa   6540
aagcccctca ctcaatcagg gggagcccca ccgcctccag gaggaaagca acagggccga   6600
cagtgtgatg aaacccctcc cacctcagtc agcgagtcag ccccatccca gaccgactct   6660
gatgttcccc cggagactga agagtgcccc tccatcacgg ccgatgccaa tatcgactct   6720
gaagacgagt cggaaaccat ccccacagac aaaactgtca cgtacaaaca catggaccca   6780
cctccagctc ccgtgcaaga ccgcagccct tcgccacgcc accctgatgt gtccatggtg   6840
```

-continued

```
gacccagagg ccttggccat tgagcagaac ctgggcaaag ctctaaagaa agatctgaaa   6900
gagaagacca aaaccaaaaa gccaggtaca aagaccaagt catcttcacc tgtcaaaaag   6960
agtgatggga agtctaagcc cttggcagct tcaccaaaac cagcgggctt gaaagaatcc   7020
tcggataaag tgtccagggt ggcttctcct aagaagaaag aatctgtgga aaaggcagca   7080
aaacccacca ccactcctga ggtcaaagct gcacgtgggg aagagaaaga caaggagacc   7140
aagaatgctg ccaatgcctc tgcatccaag tcggccaaga ccgccactgc aggaccagga   7200
actaccaaga cgaccaagtc atctgctgtg cccccaggcc tccctgtgta tttggacctg   7260
tgctacattc ctaaccacag caatagtaag aatgttgatg tggaattttt caagagagtg   7320
cggtcttcct actacgtggt gagtgggaat gaccctgctg ctgaggagcc cagccgggct   7380
gtcctggacg ctttgttgga aggaaaggct cagtggggca gcaacatgca ggtgacactg   7440
atcccaactc atgactcaga agtgatgagg gaatggtacc aggagaccca tgagaaacag   7500
caagatctca acatcatggt tttagcaagc agcagcacag tggttatgca agatgaatcc   7560
ttccctgcat gcaagattga actgtaaaaa ccaaggccag ccacaccaca ggatctgaac   7620
tttgtttcca gaaattcttc aatttgaaat cacctttttct aaaaagtcaa ttcatctagt   7680
taagtcgctg aacaattacc tgccaaatgc tatactgtgt catggtgatg caagtcacta   7740
aatttctcag tttttgctga ttgctaaggg aaataacagt atttccacaa tagggttcaa   7800
attcctgcaa aattacctac cccagttcat ctctgctgaa catttggaaa ccatgcacta   7860
gccaacccaa ctgacttctg ctaggtagag gcatttgtct tagagagaga gagagcgcgg   7920
gagagagtga gagagagtga gagcacaaag ataacgcagg tgagagagag agaaagtatg   7980
aggaaagaaa aggaatgcaa gagaaggaga tgtaatgaca gagagttctg gtgagatacc   8040
cagagagaaa aagagagagc agggtggggt aaggaggaga aaataaacca acaattaggt   8100
ctgcattttc tcaggcagta ggcattcttt agtctacata ggcaaagttt tccatttttg   8160
tcagtctgag tcatcaaaaa gagtcttaat tttctaaaac aagttggcta gaagaaagta   8220
aaaagaacaa cacttgttat gagggcatgt gatattttca catcttaatt aagctccttc   8280
agtttgaagg ctgcacactg acataatgta gtgagtgtag actggccatg caagtggttt   8340
gggccccatt cagaactctc agactctaaa cacacaagta gattgatcta aggcatgctc   8400
ccagcatttg tccacccact tagtccactc tgagtcgatt aacctgcatg cagcaacacc   8460
caagtccacc ccaattaact gaagcaaata ccaaagcagt tgggagtaca tatggtagac   8520
aatttgcctt aggaagtgac ttgaatgtac aaagatactt gatgcactta ttttttaatg   8580
tgagacagca agtttataaa acatccatat aggattatag atacttaaag gaacacgtgg   8640
gtgagcgtgt gtgggggtac tagaagctga tctgattggt ccaacagttt gatgctgagt   8700
catgcgtgtt gaatcccact tcagtgcacc tgtggcctct cagtcaaaca agttgtgcct   8760
ttcacagctt ctttactact gcaagttcaa gactgaaatg gcttctatga tcagaactgg   8820
gaaaacagtg aatcttatgg tggaagaggt tctcagcaag tgtacagtat ttaccttcct   8880
ttgtcttaca ttggcttttt aaattttcca ttaatttcaa cataattatg ggaacaagtg   8940
tacagaagaa tttttttttt aagatatgtg agaacttttc atagatgaac tttttaacaa   9000
atgttttcat ttacaggaaa ttgcaaagaa aattctcaag tgatagtctt ttttttttaag  9060
tgtttcgtaa gacaaaaatt gaataatgtt ttttgaagtt ctggcaagat tgaagtctga   9120
tattgcagta atgatattta ttaaaaaccc ataactacca ggaataatga tacctcccac   9180
```

-continued

```
ccccttgattc ccataacata aaagtgctac ttgagagtgg gggagaatgg catggtaggc   9240
tacttttcag ggccttgaca agtacatcac ccagtggtat cctacatact tctttcaaga   9300
tcttcaacca tgaggtaaaa gagccaagtt caaagaaccc tagcacaaat ttgctttggg   9360
atttcttttt ctggaaaaaa aaantaaaag aaatagtaca ttgaaaacaa atgaattctc   9420
aactcctacg gttcatgtag agtttagaga aaatttccat cattgtcatc attgaactgt   9480
gaacctggga agccagatca tgattaacac tgacattcaa gtttcaagtt gcagatcaat   9540
gcacccagtg ttcagatgag gcaaacttct ccgtgacaac tgtgctgtgc tctgtcacat   9600
tacatttcct gcagactcta agatctacgg agtagagaac aatgacctca ttttattttc   9660
tatgttagtt atttatttca aaattaacat tttagttgat ttttgtctga taagtctatg   9720
ttttgcactg ctaactatga tgagggttta aaaaaatgct tcttcagggt cctttcactg   9780
aggacctatg cagtctactt aatgctgtga attacatttt tcaaatgttt aattttttaa   9840
agaaaattaa tattctattt ttgttaggct tctctagaaa tgcagctttt atttattacc   9900
ccatttcttt caagtccttg gaaaataaca tattaagggt acaagaaatt aacacatgat   9960
ggaaaagtca ttgtgacgcc aatgaatttc attgagtata aactcatcta cttcaaattt  10020
attttataac acaacctaag atactcaaga taattattta atggttagct cttaagttga  10080
attggtctac ataatgcgtg ggaagaaaac cagattttta gccttcttgc caaatccaga  10140
cctctggttg atttttcttt gacagaagat gcaagttatt ttccaatttc acaattaaat  10200
gtatttaaca tgaacattat tttgctttaa aaactataaa cattgtagga gaattatagc  10260
cagtcttcag ttataaccac tccaccctcn nnnnnnnnnn nnnnnnnnnn nnnnnnnnnn  10320
ntgcnatggg atttaatggg aaaaatatgt aaaaactgtc actagtcagc tggctctttt  10380
tcctatgaaa tctatcagta cctttctcca tccgttgttc tcaataatga ccacagagcc  10440
tgagtatacc aagaaaacca atattcgcat tacaggttgc tcctgtcctt ccagacacct  10500
ttcctgcctg tgtgactaac ctaattttgc tagttccata aatacacgat tagtttagta  10560
acagccatca caatgtacca tgtacattca tggtgagagc taaagatcga cacagacttc  10620
taggagcttt gttcatactg attacttaat ccaattgtat agattgaata tttgagtgga  10680
aggaatttac actctgttta aatgatggga ttctatcgag atagcactca tgatcatgac  10740
ctttttggta gtattcttaa acaaaattct acagagacta aatgttagcg atgatcctcc  10800
attttcaatt ttaaccaatt ctgtcccctt tctcaaaacc ctgagccctg tgcatgcttt  10860
ctcagtcttg tggtgggact ggatacaatg actaacttcc cctcctcccc tctttaaaca  10920
ccatttttcca tggagttcaa aaaaattttt tttcttaacg ttacatatca tagtgaatgg  10980
tttccccagt gtatatgaat gttttaagtg tctccaatag cttatgcagt ctaggagctt  11040
tccaatactc atttaattaa gatttaatca tttgctaatg gaaatcttac cacctttcat  11100
tttccctctg ttaccaaatt tcagctctta ggagctgctc tacaattctg aatttgcttt  11160
tcttgcctct ctttagtcac ctgtcacagg aggttcctgc tcagtaatga tattgtgagt  11220
taggataata acttttttttt tttgtgcttc agatttagaa gaaaagatcc tgtttccatt  11280
tgaaaggaac tgtaagcttt tatcttttaa ccaactgaac aatacaccaa aagcagccta  11340
gggatgagca tttctttgaa agcaattagg ttattcacct ggtattaaaa ctatttactg  11400
ttaaaaaatc tgtgacttca tgaagttgat ttttaaaggc agcatcaaaa actgaaaagg  11460
aagggaaaaa ataggcagct tctctgcact tgtttggagc tccccaaaac aggagccatg  11520
gagaagtggc atcaagaccg ggctgccctt tcgagaacac cctgtggcag ttcagagaca  11580
```

-continued

```
cgcttttcct acactgcatg cagcccctct ttccagcact ggaaagaagt ggtcttgagc  11640

ccagctgaga agcacttcac actcctctct cttgttctga atggtgtttg tgtcagtctg  11700

cagctgtgta tggtattatg tcttataatc ctgcatcact tctatcctat ccagtcatat  11760

ctaatgtaga aaattagttt ccagtgaaag taatatgtag tgcttttatg atatttgtgt  11820

gcaatatccc ctcttccatt gaggatattt gatgtaaagg aaaaaaaaaa actcagttcc  11880

acaataaaat acaaaagtgg caaaaaaaaa aaaaagg                           11917
```

<210> SEQ ID NO 33
<211> LENGTH: 2982
<212> TYPE: DNA
<213> ORGANISM: Homo sapiens
<220> FEATURE:
<221> NAME/KEY: misc_feature
<223> OTHER INFORMATION: Incyte ID No: 413797.7
<221> NAME/KEY: unsure
<222> LOCATION: 1770-1816
<223> OTHER INFORMATION: a, t, c, g, or other

<400> SEQUENCE: 33

```
cgtagattac aacgtcgtga cgtgcgaaaa attgggtttc ttggaaatca cctgtccatc     60

gttaatttta aacaatctcc atatctccaa agaatctctt ccatgttagt ctggaatgtg    120

gttaatgaaa aacaagtagg gaggatttct ggggcaaaca ctgccggatc aggatcgtag    180

ttctcaggca cggaatggct agtgtgagaa acaccaacag caggcccatc tcagatcttc    240

actatggcaa cttatgcaag aaactgttga attagacccg tttcctatag atgagaaacc    300

atacaagctg tggtatttat gagcctccat ttcttatact actgcagtga accaacattg    360

gatgtgaaaa ttgccttttg tcagggattc gataaacaag tggatgtgtc atatattgcc    420

aaacattaca acatgagcaa aagcaaagtt gacaaccagt tctacagtgt ggaagtggga    480

gactcaacct tcacagttct caagcgctac cagaatctaa agcctattgg ctctggggct    540

cagggcatag tttgtgccgc gtatgatgct gtccttgaca gaaatgtggc cattaagaag    600

ctcagcagac cctttcagaa ccaaacacat gccaagagag cgtaccggga gctggtcctc    660

atgaagtgtg tgaaccataa aaacattatt agtttattaa atgtcttcac accccagaaa    720

acgctggagg agttccaaga tgtttactta gtaatggaac tgatggatgc caacttatgt    780

caagtgattc agatggaatt agaccatgag cgaatgtctt acctgctgta ccaaatgttg    840

tgtggcatta agcacctcca ttctgctgga attattcaca gggatttaaa accaagtaac    900

attgtagtca agtctgattg cacattgaaa atcctggact ttggactggc caggacagca    960

ggcacaagct tcatgatgac tccatatgtg gtgacacgtt attacagagc ccctgaggtc   1020

atcctgggga tgggctacaa ggagaacgtg gatatatggt ctgtgggatg cattatggga   1080

gaaatggttc gccacaaaat cctctttcca ggaagggact atattgacca gtggaataag   1140

gtaattgaac aactaggaac accatgtcca gaattcatga agaaattgca acccacagta   1200

agaaactatg tggagaatcg gcccaagtat gcgggactca ccttccccaa actcttccca   1260

gattccctct tcccagcgga ctccgagcac aataaactca aagccagcca agccagggac   1320

ttgttgtcaa agatgctagt gattgaccca gcaaaaagaa tatcagtgga cgacgcctta   1380

cagcatccct acatcaacgt ctggtatgac ccagccgaag tggaggcgcc tccacctcag   1440

atatatgaca agcagttgga tgaaagagaa cacacaattg aagaatggaa agaacttatc   1500

tacaaggaag taatgaattc agaagaaaag actaaaaatg gtgtagtaaa aggacagcct   1560
```

-continued

```
tctccttcag cacaggtgca gcagtgaaca gcagtgagag tctccctcca tcctcgtctg   1620

tcaatgacat ctcctccatg tccaccgacc agaccctggc atctgacact gacagcagcc   1680

tggaagcctc ggcaggaccc ctgggttgtt gcaggtgact agccgcctgc ctgcgaaacc   1740

cagcgttctt caggagatga tgtgatggan nnnnnnnnnn nnnnnnnnnn nnnnnnnnnn   1800

nnnnnnnnnn nnnnnnacat caagaaaaca gcaagggaga gaatccaagc ctaaaattaa   1860

ataaatcttt cagcctgctt cttccccagg gttctgtatt gcagctaagc tcaaatgtat   1920

atttaacttc tagttgctct tgctttggtc ttcttccaat gatgcttact acagaaagca   1980

aatcagacac aattagagaa gccttttcca taaagtgtaa ttttaatggc tgcaaaaccg   2040

gcaacctgta actgcccttt taaatggcat gacaaggtgt gcagtggccc catccagcat   2100

gtgtgtgtct ctatcttgca tctacctgct ccttggccta gtcagatgga tgtagataca   2160

gatccgcatg tgtctgtatt catacagcac tacttactta gagatgctac tgtcagtgtc   2220

ctcagggctc taccaagaca taatgcactg ggtaccacca tggtccattt catgtgatct   2280

attactctga cataaaccca tctgtaatat attgccagta tataagctgt ttagtttgtt   2340

aattgattaa actgtatgtc ttataagaaa acatgtaaag ggggaatata tgggggggagt   2400

gagctctctc agacccttga agatgtagct tccaaatttg aatggattaa atggcacctg   2460

tataccaatt tgtagaaaga acatatgtga tacttatgta aagtgtgggg ggagtgggta   2520

acagttttca ggcacaaaat ggtttggcct tcagaaggca ggtgtgaata aaagctgaga   2580

gtcttttctg tgacagtaaa gagtaggaga gactggaggg tagtgtgtgg tgtggactaa   2640

gactgaaagg aggttattac ccagatacta ggagacactg gtgtccctgt tttagagatt   2700

tggctctata cccatttgtc atttctcaat tactggtcac aacaagaggc cactggagaa   2760

agtggcaggt ggtgaagcaa ggttattgtg tgtgcttttg atgataagaa tctctctctg   2820

gaactgagca gaattgcctc catgtgaatt ccttcaacaa aaaaatgagc ctgcctagac   2880

tactttcaga ttgtggattg tgttttccat gtgtgggctg cttccctgat tcatactctg   2940

ccaaagtttt attttgagaa ataatattac tttcctcttc tg                       2982


<210> SEQ ID NO 34
<211> LENGTH: 2677
<212> TYPE: DNA
<213> ORGANISM: Homo sapiens
<220> FEATURE:
<221> NAME/KEY: misc_feature
<223> OTHER INFORMATION: Incyte ID No: 413797.5
<221> NAME/KEY: unsure
<222> LOCATION: 2024
<223> OTHER INFORMATION: a, t, c, g, or other

<400> SEQUENCE: 34

ctcgagggca gcatcacgct gcacaatggt ttccaggcag tgaaagaggg tgattcagca     60

agccactctt cttctatttt ctttaacctc cccttcactt tttattttta tgggggtggg    120

tggtgcttgc tatatgctta cctttttctt ttctttttc atttttacaa atttcctttt    180

ttgtcctcac ccctcaattc ctaggggctt gagtgagttt aagattgggt tttcttggaa    240

atcacctgtc catcgttaat tttaaacaat ctccatatct ccaaagaatc tcttccatgt    300

tagtctggaa tgtggttaat gaaaaacaag tagggaggat ttctggggca aacactgccg    360

gatcaggatc gtagttctca ggcacggaat ggctagtgtg agaaacacca acagcaggcc    420

catctcagat cttcactatg gcaacttatg caagaaactg ttgaattaga cccgtttcct    480

atagatgaga aaccatacaa gctgtggtat ttatgagcct ccatttctta tactactgca    540
```

-continued

```
gtgaaccaac attggatgtg aaaattgcct tttgtcaggt gtgtgttcct tacaggtaaa    600
acaagggatt cgataaacaa gtggatgtgt catatattgc caaacattac aacatgagca    660
aaagcaaagt tgacaaccag ttctacagtg tggaagtggg agactcaacc ttcacagttc    720
tcaagcgcta ccagaatcta aagcctattg gctctggggc tcagggcata gtttgtgccg    780
cgtatgatgc tgtccttgac agaaatgtgg ccattaagaa gctcagcaga ccctttcaga    840
accaaacaca tgccaagaga gcgtaccggg agctggtcct catgaagtgt gtgaaccata    900
aaaacattat tagtttatta aatgtcttca caccccagaa aacgctggag gagttccaag    960
atgtttactt agtaatggaa ctgatggatg ccaacttatg tcaagtgatt cagatggaat   1020
tagaccatga gcgaatgtct tacctgctgt accaaatgtt gtgtggcatt aagcacctcc   1080
attctgctgg aattattcac agggatttaa aaccaagtaa cattgtagtc aagtctgatt   1140
gcacattgaa aatcctggac tttggactgg ccaggacagc aggcacaagc ttcatgatga   1200
ctccatatgt ggtgacacgt tattacagag cccctgaggt catcctgggg atgggctaca   1260
aggagaacgt ggatatatgg tctgtgggat gcattatggg agaaatggtt cgccacaaaa   1320
tcctctttcc aggaagggac tatattgacc agtggaataa ggtaattgaa caactaggaa   1380
caccatgtcc agaattcatg aagaaattgc aacccacagt aagaaactat gtggagaatc   1440
ggcccaagta tgcgggactc accttcccca aactcttccc agattccctc ttcccagcgg   1500
actccgagca caataaactc aaagccagcc aagccaggga cttgttgtca aagatgctag   1560
tgattgaccc agcaaaaaga atatcagtgg acgacgcctt acagcatccc tacatcaacg   1620
tctggtatga cccagccgaa gtggaggcgc ctccacctca gatatatgac aagcagttgg   1680
atgaaagaga acacacaatt gaagaatgga aagaacttat ctacaaggaa gtaatgaatt   1740
cagaagaaaa gactaaaaat ggtgtagtaa aaggacagcc ttctccttca ggtgcagcag   1800
tgaacagcag tgagagtctc cctccatcct cgtctgtcaa tgacatctcc tccatgtcca   1860
ccgaccagac cctggcatct gacactgaca gcagcctgga agcctcggca ggacccctgg   1920
gttgttgcag gtgactagcc gcctgcctgc gaaacccagc gttcttcagg agatgatgtg   1980
atggaacaca cacacacgca gacacacaca cacaccacaa attnaggaca cacaacatca   2040
agaaaacagc aagggagaga atccaagcct aaaattaaat aaatctttca gcctgcttct   2100
tccccagggt tctgtattgc agctaagctc aaatgtatat ttaacttcta gttgctcttg   2160
ctttggtctt cttccaatga tgcttactac agaaagcaaa tcagacacaa ttagagaagc   2220
cttttccata aagtgtaatt ttaatggctg caaaaccggg aacctgtaac tgccctttta   2280
aatggcatga caaggtgtgc agtggcccca atcagcatgt gtgtgtctct atcctgcatc   2340
tacctgctcc ttggcctagt cagatggatg tagatacaga tccgcatgtg tctgtattca   2400
tacagcacta cttacttaga gatgctactg tcagtgtcct cagggctcta ccaagacata   2460
atgcactggg gtaccacatg gtccatttca tgtgatctat tactctgaca taaacccatc   2520
tgtaatatat tgccagtata taagctgttt agtttgttaa ttgattaaac tgtatgtctt   2580
ataagaaaac atgtaaaggg ggaatatatg gggggagtga gctctctcag acccttgaag   2640
atgtagcttc caaatttgaa tggattaaat ggcacct                            2677
```

<210> SEQ ID NO 35
<211> LENGTH: 4898
<212> TYPE: DNA
<213> ORGANISM: Homo sapiens
<220> FEATURE:

-continued

<221> NAME/KEY: misc_feature
<223> OTHER INFORMATION: Incyte ID No: 347118.5

<400> SEQUENCE: 35

```
ccggcggagc cctgctctcg caactcaaga tggcggacga gagtgagaca gcagtgaagc     60
cgccggcacc tccgctgccg cagatgatgg aagggaacgg gaacggccat gagcactgca    120
gcgattgcga gaatgaggag gacaacagct acaaccgggg tggtttgagt ccagccaatg    180
acactggagc caaaaagaag aaaaagaaac aaaaaaagaa gaaagaaaaa ggcagtgaga    240
cagattcagc ccaggatcag cctgtgaaga tgaactcttt gccagcagag aggatccagg    300
aaatacagaa ggccattgag ctgttctcag tgggtcaggg acctgccaaa accatggagg    360
aggctagcaa gcgaagctac cagttctggg atacgcagcc cgtccccaag ctgggcgaag    420
tggtgaacac ccatggcccc gtggagcctg acaaggacaa tatccgccag gagccctaca    480
ccctgcccca gggcttcacc tgggatgctt tggacctggg cgatcgtggt gtgctaaaag    540
aactgtacac cctcctgaat gagaactatg tggaagatga tgacaacatg ttccgatttg    600
attattcccc ggagtttctt ttgtgggctc tccggccacc cggctggctc ccccagtggc    660
actgtggggt tcgagtggtc tcaagtcgga aattggttgg gttcattagc gccatcccag    720
caaacatcca tatctatgac acagagaaga agatggtaga gatcaacttc ctgtgtgtcc    780
acaagaagct gcgttccaag agggttgctc cagttctgat ccgagagatc accaggcggg    840
ttcacctgga gggcatcttc caagcagttt acactgccgg ggtggtacta ccaaagcccg    900
ttggcacctg caggtattgg catcggtccc taaacccacg gaagctgatt gaagtgaagt    960
tctcccacct gagcagaaat atgaccatgc agcgcaccat gaagctctac cgactgccag   1020
agactcccaa gacagctggg ctgcgaccaa tggaaacaaa ggacattcca gtagtgcacc   1080
agctcctcac caggtacttg aagcaatttc accttacgcc cgtcatgagc caggaggagg   1140
tggagcactg gttctacccc caggagaata tcatcgacac tttcgtggtg gagaacgcaa   1200
acggagaggt gacagatttc ctgagctttt atacgctgcc ctccaccatc atgaaccatc   1260
caacccacaa gagtctcaaa gctgcttatt ctttctacaa cgttcacacc cagacccctc   1320
ttctagacct catgagcgac gcccttgtcc tcgccaaaat gaaagggttt gatgtgttca   1380
atgcactgga tctcatggag aacaaaacct tcctggagaa gctcaagttt ggcatagggg   1440
acggcaacct gcagtattac ctttacaatt ggaaatgccc cagcatgggg gcagagaagg   1500
ttggactggt gctacaataa ccagtcacca gtgcgattct ggataaagcc actgaaaatt   1560
cgaaccagga aatggaaccc caccactgtt ggtccaattt tcacacacgt gagaatccct   1620
ggcaaaggga gcagaactga accggcttta ccaaaccgcc agcgaacttg acaattgtat   1680
tgcgatggcg tgggctgcgt gacgtcacct ccggtcgtgt ctctggtctc cgtgttttcc   1740
agttaattac atcctcatgc agccgtgatc aagggaatgt aactgctgaa aactagctcg   1800
tgattggcat ataatggagt taacgggtga ataataaaag tatatatata tattatatat   1860
atataaatat tttaaatatc tttcatgttc caaatgtaca aggatgtttg gtctttaatg   1920
aaaagctgaa tctagatcat tcctcagaat gaggacccga ggacagtggc agacagacgc   1980
gttggcacag ttcatggttt cctccagagg agacattggc ttatcatggg gaaaaagagg   2040
atctggagaa cctcatccag ctccccttct gaatcagctg ggatgactgg ctttgagaag   2100
gaagggaaga tggaacaggc tcagatctca tgggatagca cgtggagctc ttggctgggg   2160
ctgaccctgg gcagggactt tcctgcaggg ccagacctgc ctgcattctg agacaaagca   2220
```

-continued

```
atggacggtc cgcagaagca gacctcattg attgagtcct ttcttccatc cccttggcct   2280
gctccctgta ggaagtcatc ctgccaactg atttaaaagg gctctttagc cagttgttgc   2340
caaccttata gggatgagtc ccctgtgaga ttttgctttt ccactgcctg ggatgatgca   2400
gtttgaagag gcccttggac ctccttgtaa catcagggac ctttggagac cattatcagt   2460
gtaagccctg cttagctcat cttagagcaa agagccagca ccctgatgtc cctggggtgg   2520
ctaggcagga gtggcgtggg gccaataccc agaccccttc agccaccagc ccctggcctg   2580
tgccttccaa cccattagcc atttcttgtt gtgccccttt ccaagataca gcctgcaagt   2640
ggtagcaaga agtgattaga ggcagatctg gacttggcaa cagaagtggt ttcccatctc   2700
cattgtctga gtctgatttt cgctgatgct gttttgtgga tttttgtggt agtgatggtt   2760
gtcagtgctg ccagtttccc aaaacgtaat caagcctctg gtcacatggc tgtcgatgta   2820
ggcattctgg agtggtgttc agccaagtga ccgggcaaaa ttgggctgtg aaattgtact   2880
tccaggcttg gatgtaattt ttgctctaga gagaagcaag tggtgggaag gaggtagcat   2940
gacgtgtggt gtgcgggttt ccttgctgcc gtcacctctc cgctcataca ggaatgaagc   3000
cttagccagg aggccaggct cagccctgtg ccactcaccg aagccacttt ctacaggcca   3060
gcaggggctt gttgcaggct gtgggttttg gtgtggtttg tcagaggcta attctgcaga   3120
gtttccaaaa ccagaagaca tcgtatgctt gggatggggg ccgtgccacc cgtgggaatg   3180
ctgcccgctc tgcagactgc tgctagagcc agcaactcca ctaaggtgga ttttcatcag   3240
gggcctgcag ggccctccct tttcccattg ttcctgcgct gcaaattgca ggccccagca   3300
atcgtgactg acgtttgctc cttgactcca agaaactgag accaaagaag ctgctgttct   3360
tagcaagatg cgcactgcat tccacaggtg ggaggagtcg gagaggcagg ggcttgcttt   3420
gcagccccac agacaacagt tgcacagtgc ctcaagcccc agagtggctc accctgtcca   3480
gacctttgag gatatcaaag gacaaagtgc ccaagtcttt cctaccttgg gggaacctgg   3540
aacttggaaa ggctccctgt cctagtcttg atctgttctg ggccaggtcc cagcttgagc   3600
tgcctctgag atttgggctg tgcggatctc tggagtgagc tctgtttcgg ttgacccagg   3660
tcatggaatg gaaacggtga ggccccagtg gctgttctgg aagaaacaga tctcctggca   3720
aaggccccag catctccctc actgaaacca ggtggccggc tcctcggact ctgctttatg   3780
ttgcggtgag aactctgccc aggtgtgcag ggtttggctt gtgggctgct tgctgctcat   3840
ctgatttttg tcccagtagt ccctgcgttc ttcattcaac cccttctggg acttcagctc   3900
agagagcacc atcccggggg tcagggcctc cccacaggag ccctgcagtg tggtagcgcc   3960
atggctgtct caaaccaagc aaaggaagga ccctgaggcc ttcacgctaa ccgtcctcga   4020
gcaactgctg ttggaaggcc tccctgggcc tggcccccac cctctgccac ccagtcctcc   4080
cagctgccat gtttcaaaga cgacctttac ctcctgcctt tggattgact ctgcatttga   4140
ccacggactc cagtctgtgt gtagggagag agctgagtag gaggcctcca ctccggatcg   4200
aggcctgtat agggctcgtt tccccacaca tgcctatttc tgaagaggct tctgtcttat   4260
ttgaaggcca gcccacaccc agctacttta acaccaggtt tatggaaaat gtcaggcctt   4320
ccccacaact cccgtctaac tgctgtcgcc cccctacttg ctggctctca gaagcctagg   4380
ggagtccctg tggtcctgaa ttctttcccc aaagacgacc agcatttaac caacctaagg   4440
gcccaaaggc cttggacaac tgcatggagc tgcactctag gagaaggagg ggaaccagat   4500
gttagatcag gggagggagc aggagtgtcc ctcccgtcag tgcctaccca cctgtgaggc   4560
agccttctga tggcctggcc caccttcccc agaaccaggg gaggcctgag gcttcagttt   4620
```

-continued

```
tactctgctg caaaatgaag gcgggcctgc aagccgacta cacctacgga ggctgttgag   4680

gacaatttca ttccattaaa ttaaaaaata ctgactggct ggcaggcagg tgccatgtct   4740

gggaacaggg acgggggagc ttcacctttt tgtcttggct tttctttggg ctgtgggggg   4800

gcatccattt ccagggtcgg ggaggaaata ccaaatgcat tgttgttctg ctcaatacat   4860

ctcacttgtt tctaataaag aaagcagctg aacaaaaa                           4898
```

<210> SEQ ID NO 36
<211> LENGTH: 3430
<212> TYPE: DNA
<213> ORGANISM: Homo sapiens
<220> FEATURE:
<221> NAME/KEY: misc_feature
<223> OTHER INFORMATION: Incyte ID No: 234069.2

<400> SEQUENCE: 36

```
aaagcagcag ccagcagcgc gccggtggcg tgcggctcga aaggccggga ggacgtcatc     60

gacgcgctgt cgagcctcca gcccgcccgg gtttccttcg cagtcgcgca ccgacgctca    120

aacgcgcgct ccaacccgca gcctcctcct gcctcaccgc ccgaagatgg cggctctcaa    180

actcctctcc tccgggcttc ggctctgcgc ctctgcccgc ggatctgggg caacctggta    240

caagggatgt gtttgttcct tttccaccag tgctcatcgc cataccaagt tttatacaga    300

tccagtagaa gctgtaaaag acatccctga tggtgccacg gttttggttg gtggttttgg    360

gctatgtgga attccagaga atcttataga tgctttactg aaaactggag taaaaggact    420

aactgcagtc agcaacaatg caggggttga caattttggt ttggggcttt tgcttcggtc    480

caagcagata aaacgcatgg tctcttcata tgtgggagaa aatgcagaat ttgaacgaca    540

gtacttatct ggtgaattag aagtggagct gacaccacag ggcacacttg cagagaggat    600

ccgtgcaggc ggggctggag ttcctgcatt ttacacccca acagggtatg ggaccctggt    660

acaagaagga ggatcgccca tcaaatacaa caaagatggc agtgttgcca ttgccagtaa    720

gccaagagag gtgagggagt tcaatggtca gcactttatt ttggaggaag caattacagg    780

ggattttgct ttggtgaaag cctggaaggc ggaccgagca ggaaacgtga ttttcaggaa    840

aagtgcaagg aatttcaact tgccaatgtg caaagctgca gaaaccacag tggtagaggt    900

tgaagaaatt gtggatattg gagcatttgc tccagaagac atccatattc ctcagattta    960

tgtacatcgc cttataaagg gagaaaaata tgagaaaaga attgagcgtt tatcaatccg   1020

gaaagaggga gatggggaag ccaaatctgc taaacctgga gatgacgtaa gggaacgaat   1080

catcaagagg gccgctcttg agtttgagga tggcatgtat gctaatttgg gcataggaat   1140

ccctctcctg gccagcaatt ttatcagccc aaatataact gttcatcttc aaagtgaaaa   1200

tggagttctg ggtttgggtc catatccacg acaacatgaa gctgatgcag atctcatcaa   1260

tgcaggcaag gaaacagtta ctattcttcc aggagcctct tttttctcca gcgatgaatc   1320

atttgcaatg attagaggtg gacacgtcga tctgacaatg ctaggagcga tgcaggtttc   1380

caaatatggt gacctggcta actggatgat acctgggaag atggtgaaag gaatgggagg   1440

tgctatggat ttagtgtcca gtgcgaaaac caaagtggtg gtcaccatgg agcattctgc   1500

aaagggaaat gcacataaaa tcatggagaa atgtacatta ccattgactg gaaagcaatg   1560

tgtcaaccgc attattactg aaaaggctgt gtttgatgtg gacaagaaga aagggttgac   1620

tctgattgag ctctgggaag gcctgacagt ggatgacgta cagaagagta ctgggtgtga   1680

ttttgcagtt tcaccaaaac tcatgccaat gcagcagatc gcaaattgaa atatggatat   1740
```

-continued

```
ttgtaccagg ctgcgtgttt ttcattttaa acacacaaga tttaattgaa aggacatcaa   1800
taatcataat tgtgtattta acaggtggtt ttttattagt tttcttgtgt ttcagacttt   1860
atgcagccat ataaactgtt ctctaggcat gctgtgacat tttaataaaa agcaaaagga   1920
gcatttataa ttatctcatt tgttaaggct gagaaggttg tttttataat aggtaattat   1980
attgaatgca ttttcactga atatggtatg tatgctaaat tatatgaacc tttccccaag   2040
aagggcccta gaaattgatg tggctttcct cttaaatatt aattattagt cctgaaagaa   2100
agataacata tgtgattttt gtggttagga gagttgctgt catgattgtt ttttcttcag   2160
cctcctctga cttttctttt ggggcttcag attttatgat tacatcttgt ccccctagaa   2220
catccccctt cctcccatac tgcttttaaa cagatgccca agaaggcaag caggaatgcc   2280
tcttgtgggg gagggcaggg agaaataact agttcaaacc aactatctat ctatgctttg   2340
caaagactaa ggcgtattat aggaagaggg ctagaaacct aactgattct tctcagtttt   2400
ctcattttaa aacagcccag tattcctttg tatcctcaag ggtccttgag aatacttctg   2460
ttattgagac cctgtgggct acttgtactg tacctcctct caagccaaga agggctgtgg   2520
gataatttac catgaatcct tagtagcaat gacagcagag ttaaaaaata aaaggtgttt   2580
tactttcagg ctcttgtttt ggttcagagg agattttaaa tattgaatga cacttctaca   2640
gaacaacggt ttttcttctg ccaaggctac ttcctttaac gaagtgcctt taattcagcc   2700
ttatccaact agggaaaata atgttggaca agtctaggat ttgaagagtc agtgaacttt   2760
tagtgtcagg gaataaacat ggtgggtaga ttaggtttga aaaaaacttc cttagaggta   2820
tttattctca atacctgaca ggggcccatg ggaatgactt cagaagcatc ccggataata   2880
gatgggtaaa aagtctaggc accctgaaga acaggtgaga cagctggcct ctggacagag   2940
gtaggcatag tacagtacga tatatcattc ctctggtcct aaatatacaa acttattcat   3000
gtttttaggt gatgatggtc attgaaactc acttcttttc aggtgtagct acaattgtgt   3060
aatgtacaat attagagaaa ggacaggctt tttatgagta acacacacca tatataaaac   3120
agcctttctg gctgaccaca tggttaaatg catacettcc cagtactggg gggaaaaaat   3180
gacccttctt agaatgtgca agttccatga gagtaatata ttgatatgat tttgaaaaga   3240
attgttgata gttacatctt caaacttatc attccagtat gcatctttaa gataatgtga   3300
ttctaagtag atgactttat attcttgatt aaagagtgct atacatgtta agaaatgcat   3360
taaggaatac aataaatatt ctaaagtgat gtaaaaaaaa aaaaaagggc ggacgccgac   3420
tagttgagct                                                          3430
```

<210> SEQ ID NO 37
<211> LENGTH: 1630
<212> TYPE: DNA
<213> ORGANISM: Homo sapiens
<220> FEATURE:
<221> NAME/KEY: misc_feature
<223> OTHER INFORMATION: Incyte ID No: 246531.2

<400> SEQUENCE: 37

```
agctgagctg cgggctgaat gtcaggtgat gcgtcctgac ctcttcctga gcacctagtg     60
tgtgccctgt gctgggccca ggaggcatgc tgggggcaat gtgggcctca aggaggaggt    120
cgggtgatga ggggccaacc caggggcatg gtctagtggc ccagtcagga cgcggaaaca    180
ctccctggag gttctgaccc gctccctctc agcctccgcc tggtctctgg tgtagtcgcc    240
gccgccagcc gccatgggca aacagaacag caagctgcgg cccgaggtgc tgcaggacct    300
```

-continued gcgggagaac acggagttca ccgaccacga gctgcaggag tggtacaagg gcttcctcaa 360
ggactgcccc accggccacc tgaccgtgga cgagttcaag aagatctacg ccaacttctt 420
cccctacggc gacgcttcca agttcgccga gcacgtcttc cgcaccttcg acaccaacgg 480
cgacggcacc atcgacttcc gggagttcat cattgcgctg agcgtgacct cgcggggcaa 540
gctggagcag aagctcaagt gggccttcag catgtacgac ctggacggca acggctacat 600
cagccgcagc gagatgctgg agatcgtgca ggccatctac aagatggtgt cgtctgtgat 660
gaagatgccg gaggatgagt ccaccccgga gaagcgcaca gacaagatct tcaggcagat 720
ggacaccaac aatgacggca aactgtcctt ggaagaattc atcagaggtg ccaagagcga 780
cccctccatc gtccgcctgc tgcagtgcga ccccagcagt gccagtcagt tctgagcgag 840
cggcccctgg acagttgcag agaaacacag gcttgtcgtg ccgtttaagc tttgcttgca 900
agagtggatg ccccgcaatc gttcctgctc tcccgggccc cgggcctggg gcatgcgttg 960
cacctgcccg gcccggtggc tgcgcctccc tcctccacct gaccaacgcg acattcctcc 1020
cctcacgcct ggcccggtcc cttccagggc aactcccagg gatgtggtga catgcagggt 1080
tcaagtgttc ttggttccag gcacctcccg gctcacgggg agctcagagg tccatgccga 1140
ggagaccagg caggacctcc cgaggctgcg ccccggccgg cccatgcgtt ttgtgatccc 1200
aagtgactct gtgggaaggg tggggacgag gcgtcgggag ggtatacagg gagcccctcc 1260
cgtgcatggc tgcccccccg ttcattttct ccaccacagc cgcttgcacg tatagatact 1320
gtggtcccct ttcttttaat atataaatta tgtatggtga agtggagtgt attgtgtagg 1380
tcccgtattt aatgcctctg actgcctttg aagcgcagcc ctctgtggcc cgcagccccc 1440
tgagcctggc tgttgtgtgg tatttatgct ctctttgtct gcctgtttct aaggaaatgc 1500
atgtgtgccc tgagccgtga tgatcctccc atccgtgttg tgagcacagg catttgtgtc 1560
tggtctgtcc tccctgttga ttggtctggc atttccggta ttaaaatgat aaaataaatg 1620
gcattttctg 1630

<210> SEQ ID NO 38
<211> LENGTH: 1884
<212> TYPE: DNA
<213> ORGANISM: Homo sapiens
<220> FEATURE:
<221> NAME/KEY: misc_feature
<223> OTHER INFORMATION: Incyte ID No: 255816.9
<221> NAME/KEY: unsure
<222> LOCATION: 29
<223> OTHER INFORMATION: a, t, c, g, or other

<400> SEQUENCE: 38
caggccccct ccccagcctt gcagggctna ggttacccct ggcctttcct aaaggtcact 60
cattcctctt gacgtttgca aaaggggaat gtaatcctgg ggtgggggga gacccctcat 120
ctgtagcccc tcccttgctc ctcccaaagg gtggaattag aacagggact gttattggga 180
gacagaaagt gggggatagt agttgacctt tggtaagggg gcaggtgccc agggccagag 240
gcttctgctt caggctgtag tgggcacttg gctgccagcc cagtgtgaag gggggaggat 300
ggagagaaag agaggcgggg ctggctgggg accgagtggc tcagggataa atgcgcagcc 360
tgagaggggg tgagctgaca ctgtcccagc tgccacctag actcggagct ccatccaaac 420
ctccagcgaa gacatcccag gttgggtgaa tcttccagcc ctgggggtgg aggtagtaaa 480
ggccatggcc atgcagaaaa tctttgcccg ggaaatcttg gactccaggg gcaaccccac 540

-continued

```
ggtggaggtg gacctgcaca cggccaaggg ccgattccga gcagctgtgc ccagtggggc    600

ttccacgggt atctatgagg ctctggaact aagagacgga gacaaaggcc gctacctggg    660

gaaaggagtc ctgaaggctg tggagaacat caacagtact ctgggccctg ctctgctgca    720

aaagaaacta agcgttgcgg atcaagaaaa agttgacaaa tttatgattg agctagatgg    780

gaccgagaat aagtccaagt ttggggccaa tgccatcctg ggcgtgtcct tggccgtgtg    840

taaggcggga gcagctgaga agggggtccc cctgtaccgc cacatcgcag atctcgctgg    900

gaaccctgac ctcatactcc cagtgccagc cttcaatgtg atcaacgggg gctcccatgc    960

tggaaacaag ctggccatgc aggagttcat gattctgcct gtgggagcca gctccttcaa   1020

ggaagccatg cgcattggcg ccgaggtcta ccaccacctc aagggggtca tcaaggccaa   1080

gtatgggaag gatgccacca atgtgggtga tgaaggtggc ttcgcaccca acatcctgga   1140

gaacaatgag gccctggagc tgctgaagac ggccatccag gcggctggtt acccagacaa   1200

ggtggtgatc ggcatggatg tggcagcatc tgagttctat cgcaatggga agtacgatct   1260

tgacttcaag tcgcctgatg atcccgcacg gcacatcact ggggagaagc tcggagagct   1320

gtataagagc tttatcaaga actatcctgt ggtctccatc gaagacccct ttgaccagga   1380

tgactgggcc acttggacct ccttcctctc ggggggtgaac atccagattg tgggggatga   1440

cttgacagtc accaacccca agaggattgc ccaggccgtt gagaagaagg cctgcaactg   1500

tctgctgctg aaggtcaacc agatcggctc ggtgaccgaa tcgatccagg cgtgcaaact   1560

ggctcagtct aatggctggg gggtgatggt gagccaccgc tctggggaga ctgaggacac   1620

attcattgct gaccttgtgg tggggctctg cacaggacag atcaagactg gcgccccctg   1680

ccgctcggag cgtctggcca aatacaacca actcatgagg atcgaggagg ctcttgggga   1740

caaggcaatc tttgctggac gcaagttccg taacccgaag gccaagtgag aagctggagg   1800

ctccaggact ccactggaca gacccaggtc ttccagacct gcttcctgaa ataaacactg   1860

gtgccaacca aaaaaaaaaa aaaa                                          1884
```

```
<210> SEQ ID NO 39
<211> LENGTH: 5766
<212> TYPE: DNA
<213> ORGANISM: Homo sapiens
<220> FEATURE:
<221> NAME/KEY: misc_feature
<223> OTHER INFORMATION: Incyte ID No: 253109.2
<221> NAME/KEY: unsure
<222> LOCATION: 4790
<223> OTHER INFORMATION: a, t, c, g, or other

<400> SEQUENCE: 39
```

```
cggagggata ccggcgacga ggggaccatg taccgggacc cggaggcggc cagcccaggg     60

gcgccctcgc gcgacgtcct gctggtctct gccatcatca ccgtcagcct tagcgtcact    120

gtcgtcctct gcggcctctg ccactggtgt cagcgcaaac tgggcaaacg ctacaagaat    180

tccttggaga cggtgggcac gccagactca gggcgtgggc gcagtgagaa gaaggctatc    240

aagttgcctg caggagggaa ggcggtgaac acagcccccg tgccaggcca gacaccccac    300

gatgagtccg accgccggac cgagccacgt tcctccgtct cagacctcgt caactccctc    360

accagcgaga tgctcatgct ctccccaggc tccgaggagg atgaggccca cgagggttgc    420

agccgagaga acctgggccg gatccagttc agtgtcggct acaacttcca ggagtccacg    480

ctcaccgtga agatcatgaa ggcccaggag ctgccggcca aggacttcag cggcaccagc    540

gaccccttcg tcaagatcta cctgctgccc gacaagaagc acaagctgga gaccaaggtg    600
```

-continued

```
aagcggaaga acctgaaccc ccactggaac gagaccttcc tctttgaagg ttttccctat    660
gagaaggtgg tgcagaggat cctctacctc caagtcctgg actatgaccg cttcagccgc    720
aacgacccca ttggggaggt gtccatcccc cttaacaagg tggacctgac ccagatgcag    780
accttctgga aggatctgaa gccatgcagc gatgggagtg taaggcccca tgggggagcc    840
gaggggagct gctcttgtct ctctgctaca accccctctgc caactccatc atcgtgaaca    900
tcatgcaaag cccggaacct caaagccatg gacatcgggg gcacatcaga cccctacgtg    960
aaggtatggc tgatgtacaa ggacaagcgg gtggagaaga agaagacggt gacgatgaag   1020
aggaacctga accccatctt caatgagtcc ttcgccttcg atatccccac ggagaagctg   1080
agggagacga ccatcatcat cactgtcatg gacaaggaca agctcagccg caatgacgtc   1140
atcggcaaga tctacctgtc ctggaagagc gggccagggg aggtgaagca ctggaaggac   1200
atgattgccc gtccccggca gcccgtggcc cagtggcacc agctgaaggc ctgagtgggg   1260
ccaagggagg cccagggggc cgagggccca ggtccccatc atgccctcac cactttatgc   1320
acaacgcccg gcctgagccc cctgccatag ggaggggagg accctgaggg ctcagccagg   1380
gaggggtccc aggactcaac tgggccccgt ttctaggaag taccagcccc atcccccaca   1440
gtccagctcc ggggaagggg ctctgggagg cattttcctg ctttgcccct tttcttcctg   1500
acttactaat actaaagaag ttgggggagc tcgagagcca gacggccaga caggcagacc   1560
cctccagagg cccgccaggt gggcatggtc ccccatttc tttaaggcag cacctggagt   1620
ggagagaggc cactccctct ccagccccg atgtggaccc ggggagggga ggctgaggcg   1680
tttggccccg gcctggccag gagaggccca tccccagggc agtttcaggt gccggctggg   1740
ccctgaatgt cgaggatagt atatagcccg ctcctgggtc ctggagctgt ggccctttgt   1800
actcgtgttg tgtccattgt gtgtgtgcgt ggggacagag gcctggaaat gcggaggact   1860
atacagagaa ggcaggtttt gtgaaggcca ggcagggttg gaggccgggg gtgtgagagg   1920
agaggcccat agggctgagt ggggtcgggt gaggcagagg tcagaaacag aagagctgca   1980
gttgctggag ctgggctgag aactgggctg cctcctgcca tccccccgtc tcctcccctt   2040
ctccccttgg tgccccccctc tgctcagaat ctgaagtagt tccctcctca gcaatttcat   2100
ctcttgaaca ctgactcaca ccttttaggc acctactgtg tgcatagcat tccaccagga   2160
ctcatctccc ttccttctca gggggtcccg agccccgact agctttgccc taactccttc   2220
atcaaaagac cccccgccag cttcccacac ctcatacgca gccacatctg ccctattctc   2280
catgctttcc agcttgcctg cccttcctca tctctccctg cctgtgcaga cctccaccct   2340
tctttcctcc acccctccat cccccaatgc ttgtagacct tccattcatt ccgtctcatc   2400
gtgcgtggtc tctgatcgtc catcacctga ccttctccag gactgtcttc tcacccttcc   2460
ccactccctg gtccccggga gcagctcctt ctgcccgact cactcacagt gcagggaaag   2520
gaggcaggga aaagaccagg attctgtgag ttctgaggtt gccacacaca aagaagctgt   2580
ggtttctctg cctcggccac tgatgagact aaaactggct tccccttgga gacggcagat   2640
ttcaggctga tccctgctta agccctctca tccccacgct ggtcctggta ttgatacaag   2700
acccagctgg tgacaaagcc tccaatcctg ggggtccacg agcctgggcc tgacattccc   2760
agaactaccg ccaggtggcg ccaggccccc acagtctgtg gccgtggtct tagcccccag   2820
ttccactctg gatgggcctg tgacacccca aagagaagaa ggggactctg gatagggtcc   2880
ccacatccag ggcgtgggga gaccattggc atttgggaac cattttcctt cgaacggctt   2940
```

-continued

```
ccccttgagc tgagcattct gcttgctgca gtagacgggt cgccttttgc ccataccgaa   3000
attttctgaa attaaatcgc acaccccac catttcctct ccctgggatc tggaggaaca   3060
tcatacatag taggtgaatc gttttgtaga gtgaagaatg ctaatgtaaa gcaaatagtc   3120
acccacgttc cttgtaaatc caaatgtttc tatattgtag ctttgcttaa aatggggtcg   3180
gccccaactg catcctcctc tttggcgggc tggggagcgg cccccagccg ggacgggagg   3240
gcagcgaccc cgaggcctcg tggacgtggg agagagtgtg gtgggaagtc ttgagcggag   3300
gaggggatct gcccttctcc actcctctct tggatccgcc tcggtttcct gtccccccac   3360
cacccgcctg ccccgcggaa gaccgcccag tgagccagcc cccaccttcc aggcgccttc   3420
gccctgggga tccaaccaac ttgtatcgag tgggcggggc aacggctccc catttttccc   3480
gagccccgcc cacagagctc ttagccaatc ctatgcagag agcatctcct ggcaggggtc   3540
tcttcccaac cagaccccac ccaggcacat tagcgaccag gcttgggctt ccccagcgcc   3600
ccaccaccac cacgtgcagg tggagctctg ggatgctatg ttggggcggc aagcggtggg   3660
ccgagggccg ggtaggctag cacgggaggt aagggtggta tgggatgggg cgggggcggt   3720
ctagggcaat aggagagcag agaatggggg aacttgaggg tggggggagg gcaccggagc   3780
cttgccacca tcccaggact ttgggcaagt cacccgcact ccctgggcct cggtttcccc   3840
atctgtaaaa tgatggtaat aatacttcac ctacctcata ggggaggttg tgaggccacc   3900
atcacctgac ctggggggtca aggcaggagg actccgaagg tgctacccgt gagcaaagtg   3960
taattaccga atcctgactg caaggcccac ctgcccctcc cccacagagc ctccagagct   4020
agctgaggcc aacgcaggcc catccgtctc ttcactctgt cgcaggccct ttcatgggct   4080
tcgtctgcca tctttgtggg tgccctagac ttagtcctta tcttgtcctg gtttcctttc   4140
ttgtgaccat ctccccatga aagtgctgta caaattccac ccgccccagg acccccgcac   4200
ctgccctctg gcaccagatg ccagggaagg gacagaggaa aacagccaca aacaagccag   4260
gggggctccc cggagcccca ggggtgggga ttggtggcca ctgtttgtat gttcttgagt   4320
gcaagtgttt tataaaaaat aaaacaaaaa cccaccatca caaaaaaaaa aattttgcag   4380
cgaagagaaa tgaagaaaaa ctgaagaaaa aaaaaacaca ggaaaaaaag aaccatacaa   4440
aatttttcca ccacacatac cctctaagcc agcaagattt cctctttgca aaatcatatt   4500
tttgtgggaa tgggccctgc tttttgtggc aaggcctgtt ctgattaata aaggatcgtg   4560
aaaaagtagg gccttggctg ttttcctccg tgggtcccag ccctccctca cctccctggg   4620
ggcagaggca gtggggtgaa ggggatgggg gccccggggc tgagcctccc ctcagtgtgt   4680
cacctttggg atttgacttc actggtgacc aggcccttcc cgagtgtcca gccatcctca   4740
gatctctata gaatatgatc ccactggctt cccagaaagc agagaggcan tacatctccc   4800
agatcaggcc tgacacaagg ctttttggga gtagagtcct ctctaggcct caggggtgcc   4860
ctccagggtc acccagcctg acgtcccctc cctcagttcc cagaggacac ttgccatcct   4920
ccaaggcagc tcagacaaac caaaggggga cgctccagct ttcccaccac catccatggg   4980
gccactgtag tttcaggcca gcgcctcctt cctggtccct gaggtgggaa aaggaaagac   5040
aatgagctct gtgtctgttg gctggacctg cggcttctct cagccctctt ctagtttcat   5100
tctttaggat tagaaaagtc tcttccactc aatagaacag gttccagcct gaggtgtggg   5160
aagctgggtt gtaatccctt ctgcagcctc tgtggccctg ggcaagctct ttccttccac   5220
ctgtttcttc tggccacaac aaagcaataa ccatccccat cccctgccct ttcttcccca   5280
cccagcccag gggaagctga gcccccgcag ctctcagggt acttcagaag gaaggtgcta   5340
```

-continued catctggttc agacacaggc acaaaaggaa cgagcacatc cccattgtca tgtgtccacc 5400
tgctggcccc tgcccccacc aggagtgaag cgggccatcc catccgccct ctgctcccag 5460
cacttggggc cagcagctgc ctcccggagc tgcactaagt accccatcca aagctgtctg 5520
tccctcattt cccacaacct ggtttagata tcacttctga tctctgttcc agagatcaga 5580
ggaagccccg gggtcaggta agtagcctca ggggctccct tggccagagc ttctgttcag 5640
gcgctctcca tgaaagcagc cctggaaaac tgagcctgaa gtcagagaca gctcaggccc 5700
agcacagggg gcagtccctt gccactggct cgggcccctt ccctggactt tttgcttcct 5760
ccattt 5766

<210> SEQ ID NO 40
<211> LENGTH: 3237
<212> TYPE: DNA
<213> ORGANISM: Homo sapiens
<220> FEATURE:
<221> NAME/KEY: misc_feature
<223> OTHER INFORMATION: Incyte ID No: 279800.2

<400> SEQUENCE: 40
cgcacctctc ctttcttctg tagctcgcgt tgaagccgca cgtccggccc cgatcccggc 60
accatgagct tcggctcgga gcactacctg tgctcctcct cctcctaccg caaggtgttc 120
ggggatggct ctcgcctgtc cgcccgcctc tctggggccg gcggcgcggg cggcttccgc 180
tcgcagtcgc tgtcccgcag caatgtggcc tcctcggccg cctgctcctc ggcctcgtcg 240
ctcggcctcg gcctggccta tgcccggccg ccggcgtccg acgggctgga cctgagccag 300
gcggcggcgc gcaccaacga gtacaagatc atccgctcca acgagaagga gcagctgcag 360
ggcctcaacg accgcttcgc cgtgttcatc gagaaggtgc atcagctgga gacgcagaac 420
cgcgcgttgg aggccgagct ggcgcgctgc gacacccacg ctgagccgtc gcgcgtcggg 480
cagctcttcc agcgcgagcc tcgccacctg ccgcagctgg aggaggccag ctcggctcgc 540
tcgcaggccc tgctggagcg cgacgggctg gcggaggagg tgcagcggct gcgggcgcgc 600
tgcgaggagg agagccgcgg acgcgaaggc gccgagcgcg ccctgaaggc gcagcagcgc 660
gacgtggacg gcgccacgct ggcccgcctg gacctggaga agaaggtgga gtcgctgctg 720
gacgagctgg ccttcgtacg ccaggtgcac gacgaggagg tagccgagct gctggccacg 780
ctgcagcggt cgtcgcaggc cgcggccgag gtggacgtga ctgtggctaa accagacctg 840
acctcggctc tgagggagat ccgcgcccag tatgagtccc tggccgctaa gaacctgcag 900
tccgcggaag aatggtacaa gtccaagttt gccaacctga acgagcaggc ggcgcgcacg 960
accgaggcca tccgggccag ccgcgaggag atccacgagt atcggcgcca gctgcaggcg 1020
cgcaccatcg agatcgaggg cctgcgcggg gccaacgagt ccttggagag gcagatcctg 1080
gagctggagg agcggcacag tgccgaggta gctggctacc aggatagcat tgggcagctg 1140
gagaatgatc tgaggaacac caagagtgag atggcacgcc accttcggga ataccaggac 1200
ttgctcaatg tcaaaatggc tcttgacatt gagatagcag cttacaggaa actgctggaa 1260
ggcgaggaga cacgttttag caccagtggg ttaagcattt cggggctgaa tccacttccc 1320
aatccaagtt acctgctccc acctagaatc ctcagtgcta caacctccaa agtctcatcc 1380
actgggctat cacttaagag agaggaggag gaggaggagg catctaaggt agcctctaag 1440
aaaacctccc agatagggga aagttttgaa gaaatattag aggagacagt aatatctact 1500
aagaaaaccg agaaatcaaa tatagaagaa accaccattt caagccaaaa aatataattc 1560

-continued

```
cattgctttg aaaaagttaa tgcttaagag ggaatgatat gcatttgact tgttaaacag   1620
cctattcctg aactataaca cctgccacca ctataaaatg tcttcaaggc ttcagtctca   1680
tatttagtat tgaatactta cattctctaa taagaaaacc accccttaga ttgaagtaaa   1740
ctgcagtcct ggagcaatca cagatgagtt atctaagaat acagctttct gaccttcagc   1800
tcacgcttca cagtgatcga tgattcaggt gcagaggaag tacaaactaa ggtgctaaat   1860
ctgcgatcat cgtcatttgc tgtgaactga aattaaaact attcatgcta cccagccatt   1920
acccagctaa ataatcttac tctagatacc taaaacataa gatcactgcc agagataaac   1980
taatggtcca cacccaattc cactctgata gaattatttc acaaataata ggtgtttgtt   2040
taatggacac ttttcacctc cttcaattcc atatatcctt ttcttctatg taggaaaaaa   2100
atagtctagt gtagtattct tcccttttaa acacattttg gttcttctca aaagaactta   2160
cccccattcg cgctctgctc agtgggtaaa attagatgca tgttgaccat gtctatgatt   2220
cgtgtaatta cttatccctg cccatttcat attctttcaa ttctgtaggt taaaaaaatg   2280
gcagtgatga attttaaggg tttcccccaa catataaaat aatgcaaaga atccctagac   2340
tttaggcttt cagcttacac aaatctattt aattaggaaa aaaactatta aggatgtagc   2400
ttttcacctt tactttagaa gcacagtaaa tatcccaaac tgtgatgaag ccgaccttag   2460
atttagtagt gtaagctaga agaagtgagt gtttctatga gtggaaaaag ccaaggtgtc   2520
atttatgtgt cagttcattt gtggtgatat agaattagct ttttcatccc cttaccctta   2580
gaatccacgt attccccttc ccactagcct aggtcataaa gaggcgttgc tttcactctc   2640
ctatgccttt tacgagtgct aagtgtagga tattttgtca ccagaacaca atgctaccgc   2700
cccaaagtaa aagaaaccac ttctggtcaa tcaacactac cagcgtatat ataagaaaga   2760
catctttctc ttttctaaaa gacttcccta acacttaccc catggctgca cagttggtgg   2820
ggtcctgccg gagaggaaga gacactcaga ccagagaagg ggtgtgcatg cgcctactcg   2880
cttgctagaa gtagattctg gacagtcagc tcttcatctg cccaactgtg tagcatctgc   2940
attgcccagt ctttcatgtg tgccaaggct gatgcaggat ttgttctctg tccagcagtc   3000
acttcggcca gagctgaaga gttgccccgt ctctgttcca tgtctccttt aagagctctg   3060
gtgataagga catgatgctt ttactgaact ttcttatcct agcacatgct tcaatagttc   3120
aaggaacttg aaaaatactt ttccttacct ttaccccatc cctgtcttta ctcctcacac   3180
ttactgtaag acattagtaa cataataaat taaaagtcac acgaatctca ccaacat      3237
```

<210> SEQ ID NO 41
<211> LENGTH: 1936
<212> TYPE: DNA
<213> ORGANISM: Homo sapiens
<220> FEATURE:
<221> NAME/KEY: misc_feature
<223> OTHER INFORMATION: Incyte ID No: 247570.1
<221> NAME/KEY: unsure
<222> LOCATION: 18, 31, 1931-1933
<223> OTHER INFORMATION: a, t, c, g, or other

<400> SEQUENCE: 41

```
gagggggtgc ctggagangc ggaggctcgc ncgcctgcgc atccagctcc agggacccta     60
ggttttctat gggattccca atctgcagca gagatttacc cgagcgtgtt gcggcagcgg    120
ctgggcttgc aaggcgcgat ccaagaggga tttaagcagc ccagagctcc agagaaaaag    180
agagcgagag agaaccacac acagagacgg cttaagcgtt tacccgaatt aaatatatat    240
```

-continued

```
ttttaaaaag aactgttgag ttttatcatt ttcgttaagt gaccgtgcgc agcgctgtaa    300

ctgcaggatg gggaagcaga atagcaaact ggcccctgaa gtgatggagg acctggtgaa    360

gagcacagag tttaatgagc atgaactcaa gcagtggtac aaaggatttc tcaaggactg    420

tccaagtggg aggctaaatc tcgaggaatt tcagcagctc tatgtgaagt tctttcctta    480

tggagacgcc tccaagtttg cccagcatgc cttccgaacc ttcgacaaga atggggacgg    540

caccattgac ttccgagagt tcatctgcgc tctgtccatc acctccaggg gcagctttga    600

gcagaagctg aactgggcct tcaatatgta tgacctggat ggtgatggca agatcacccg    660

agtggagatg ctggagatca tcgaggctat ctacaaaatg gtaggcactg tgatcatgat    720

gaaaatgaat gaggatggcc tgacgcctga gcagcgagta gacaagattt tcagcaagat    780

ggataagaac aaagatgacc agattacact ggatgaattc aaagaagctg caaagagcga    840

cccttccatt gtattacttc tgcagtgcga catccagaaa tgagctgatg tcaatgctat    900

ggactgcaca aaagtctcaa tgttccattc agtctgcagc tattcacaca cacacacaca    960

cacacacaca cacatacaca cacacacaca aatattgctt ggactaccta taaatggact   1020

tgcttcttgt gtttgaaaca ctcgtgtgca tgagaatgtc atttgctaat gaattttaaa   1080

agcatatata aaacaaaaca aacaacctgc cacaatgtga tatgtgtaat atcatttcat   1140

aaaaatccct cttcctccaa agcctgggca gaaatgtgct gcaaagagtt atatgacttc   1200

ttgttcatgt tttgctaatg ctcgtatctc cttgattaca taatgttagt agcactgaga   1260

cccccatggt aatgtaactt aattataagc tatgtcacta ccctcctgta aaatactatt   1320

ggacagacac agagggaccc ttggctcctg tgtctggtcc acacaccaca gaagcttgta   1380

ttatcagtga atataaatgt actacatttg catgcctttt gggtttgcct taattcttac   1440

ctcatttgca tcctatcgat ctggaaagag ctgttttgga tgaatgcagt ataaaatgta   1500

aaaaccctgc taaatgactt attgattaag tatatctatc tatatataca tatacacaaa   1560

gatattattt atcgaaagta aaaaagatgg aagtgtattg gtttctgttt gaattttcaa   1620

aggcttccaa tgtggtggca ataaatgtcc caaataaatt tataacaatt gattttcccc   1680

ctaattctta ttttataatt ttaaaattgc agcagttgct agcaacaact tactaaatct   1740

actcttaaat atacaacttt ggaatttgaa gaattaatga caacaaaagg gaaaaaagca   1800

actttccaac ttttcatcca ggctcccaaa agagggacaa cgaacatggc atgtgaaaag   1860

taaaacagat ttgttcattc cgaaaaaaaa atgttcattc tatgacaata aattttatct   1920

cagtgtgaaa nnnaaa                                                   1936
```

<210> SEQ ID NO 42
<211> LENGTH: 6856
<212> TYPE: DNA
<213> ORGANISM: Homo sapiens
<220> FEATURE:
<221> NAME/KEY: misc_feature
<223> OTHER INFORMATION: Incyte ID No: 401746.2

<400> SEQUENCE: 42

```
aatacacccc gggcaggtgg agcgctcgcg gctgctcgcg gcgagcccgg gagtgatggc     60

gaggcccctg cgggcggcca gcgcctgagg cgccccgccc cgccccgccc cgcgcggccc    120

tccccgcccg gccctgccct gccctgctcc ctgccggcgg ctgcgggcgc ttcctagtcc    180

gctcgggcgg ccgcccaggc gaggtgcggc ctccgcacag gccggggggc gtaggcgcgc    240

ggggcccgcc atggctgcgt cggagctcta cacaaagttt gccagggttt ggatacctga    300
```

-continued

```
tccagaggaa gtctggaagt cagcagagct gctcaaagat tataagccag gagataaagt    360
cctcctgctt cacctcgagg aaggaaagga tttggaatac catctagatc caaagaccaa    420
ggagctgcct cacttacgaa atcctgacat acttgttggt gaaaatgacc tcacagccct    480
cagctatctt catgagcctg ctgtgctcca taatctcaga gtccgcttta ttgattccaa    540
acttatttat acgtattgtg gtatagtcct agtagctata aatccctatg aacagctgcc    600
tatttatgga gaagatatta ttaatgcata cagtggtcag aacatgggtg atatggatcc    660
acatatcttt gcagtagctg aagaagctta caagcaaatg gccagagatg aacgaaatca    720
gtccatcatc gtaagtggag agtctggggc aggaaaaaca gtctcagcta agtatgccat    780
gcgatacttt gcaactgtga gtggttctgc cagtgaggcc aatgtggagg aaaaggtctt    840
ggcctccaac cccatcatgg agtccattgg aaatgctaaa acaaccagga atgataatag    900
cagccgtttt gggaagtata ttgagattgg ttttgataag agatatcgaa tcattggtgc    960
caatatgaga acttatcttt tagagaaatc cagagtggta ttccaggcag aagaggagag   1020
aaactatcat atcttctatc agctttgtgc ctcagcaaag ttacctgaat ttaaaatgct   1080
acgattagga aatgcagata actttaatta cacaaaacaa ggaggcagtc ctgtgattga   1140
aggagtggat gatgcaaagg agatggcaca tactaggcag gcctgcactt tgctaggaat   1200
tagtgaatct catcaaatgg gaattttccg aatacttgct ggcatccttc acttaggcaa   1260
tgttggattt acatcccgag atgcagacag ctgcacaata cctcccaagc atgaacctct   1320
ctgcatcttc tgtgacctca tgggtgtgga ctatgaggag atgtgtcact ggctctgcca   1380
tcggaaactg gctactgcca cagagacata catcaagccc atctccaagc tgcaggccac   1440
gaatgcccgc gatgctttgg ccaaacacat ctatgccaag ctctttaact ggattgtaga   1500
taatgtcaat caggctctcc attctgctgt caaacagcac tcttttattg gtgtgctaga   1560
catttacgga tttgaaacat ttgagataaa tagttttgaa cagttttgca taaattatgc   1620
aaatgaaaaa ctacagcaac aattcaatat gcatgtcttc aaattggagc aagaagaata   1680
tatgaaggaa caaattccat ggacactcat agatttttat gataatcagc cttgtattaa   1740
tcttatagaa tcaaaactag gcattctaga tttactggat gaggaatgca agatgcctaa   1800
aggcacagat gacaactggg cccaaaaatt gtacaacaca catttgaaca aatgtgcact   1860
ctttgaaaag cctcgtctat caaacaaagc tttcatcatc caacattttg ctgacaaagt   1920
ggaataccag tgtgaaggat ttctcgaaaa gaataaagac accgtttttg aagaacaaat   1980
taaagttctt aaatcaagca agtttaagat gctaccagaa ctatttcaag atgatgagaa   2040
ggccatcagt ccaacttcag ccacctcctc agggcgcaca cccctcacac gaactcctgc   2100
aaagcccacc aaaggcagac caggccaaat ggccaaagag cacaagaaaa cagtggggca   2160
tcagttcaga aactccctgc acctgcttat ggagacactc aatgccacta cccctcacta   2220
tgtgcgctgt atcaagccta atgacttcaa gttcccattc acgtttgatg agaagagggc   2280
agtgcagcag ctgagagcat gtggtgtcct ggaaaccatc cgaatcagtg cggccggttt   2340
cccctcacgg tggacttacc aagaattttt cagccgctac cgtgtcctaa tgaagcagaa   2400
agatgtgctg agtgacagaa agcaaacatg caagaatgtg ttagagaaac tgatactgga   2460
caaggacaaa taccagtttg gtaagacaaa gatctttttc cgtgccggtc aagtggccta   2520
tctagaaaaa ttgagagctg acaaactgag agctgcctgc atccggatcc agaagaccat   2580
ccgagggtgg ctgctgagaa agaagtacct acgcatgcgg aaggcagcca tcaccatgca   2640
gagatacgtg cggggctacc aggcccgatg ctatgctaag tttctgcgca gaaccaaggc   2700
```

-continued

```
agcaaccatc attcaaaagt actggcgcat gtatgtggtc cgcaggaggt acaagattag   2760
acgagctgcc actattgttc ttcagtctta cttgcgaggc ttcttggcca gaaataggta   2820
tcgcaagata ctccgtgggc acaaagcagt catcattcag aagcgagtcc ggggctggct   2880
ggcccgcaca cactacaaga ggagcatgca tgccatcatc taccttcagt gctgcttcag   2940
gcggatgatg gccaagcgtg agctaaagaa gctcaaaatc gaggctcgct cagtggagcg   3000
ctataagaag ctgcgcatcg gcatggagaa caagatcatg cagctgcagc gcaaagttga   3060
tgagcagaac aaagactaca aatgccttgt ggagaaacta accaatctgg aaggaatata   3120
caactctgag actgagaaac tacgaagtga cttagaacgt cttcaactaa gtgaagagga   3180
agcgaaagtt gccactgggc gggtccttag tctgcaggaa gaaattgcca agctccggaa   3240
agacctggag caaactcgtt cagagaaaaa atgcattgag gaacatgcag atcgatacaa   3300
acaagaaaca gagcagctgg tatcaaatct gaaggaagaa aatactttgc tgaagcaaga   3360
aaaagaagcc ctcaatcacc gcatcgtgca gcaggctaag gagatgacag aaactatgga   3420
gaagaagtta gtagaagaaa cgaaacaact ggaactcgac cttaatgatg aaaggctgag   3480
atatcagaac cttctgaatg agttcagtcg cctggaagaa agatatgatg acctcaagga   3540
agagatgacc cttatggtgc atgtgcctaa gcctggacac aagagaacag actccaccca   3600
cagcagcaac gagtctgaat atatctttag ctctgaaatt gcagaaatgg aagacattcc   3660
atcaaggaca gaggaaccaa gtgagaagaa ggtacctctg gacatgtcat tgttccttaa   3720
gctccagaag cgggtcacag agctggagca ggagaagcag gtgatgcagg atgagctgga   3780
ccgcaaggag gagcaggtgc tccgcagcaa ggccaaggaa gaagaaagac cacaaattag   3840
aggtgcagaa ctggaatatg agtcactcaa gcgtcaagaa ctagaatcag aaaacaaaaa   3900
actgaagaat gagctaaatg agttgcgcaa ggccctcagt gagaaaagtg ccccagaggt   3960
gaccgcccca ggtgcacctg cctactgtgt cctcatggag cagctgacct ctgtgagcga   4020
ggagcttgat gtccgcaagg aggaagtcct catcttaagg tctcaactgg tgagccagaa   4080
agaggccatc caacccaagg atgacaagaa tacaatgaca gattccacaa tacttttgga   4140
agatgtacaa aaaatgaaag ataaaggtga aatagcacaa gcatacattg gtttgaaaga   4200
aacaaataga tcatctgctc tggattacca tgagttgaat gaggatggag agctgtggct   4260
ggtttatgaa gggttaaaac aagccaatag gctcctggaa tcccagctgc agtcacagaa   4320
gaggagccat gagaatgagg ccgaggccct ccgtggggag atccagagcc tgaaggagga   4380
gaacaaccga cagcagcagc tgctggccca gaacctgcag ctgcccccag aggcccgcat   4440
tgaggccagc ctgcagcacg agatcacccg gctgaccaac gaaaacttgg atttgatgga   4500
acaacttgaa aaacaggata agacggtccg taaactgaaa aaacaactga aagtatttgc   4560
caaaaaaatt ggcgaactag aagtgggcca gatggagaac atatccccag gacagatcat   4620
tgatgaaccc atccgaccag tcaacattcc caggaaagaa aaggatttcc aagggatgct   4680
ggaatacaag aaggaggatg agcaaaaact tgttaagaac ctgattctgg aactgaagcc   4740
acgtggtgta gcagtcaatt tgattccagg attaccggca tatatcctgt tcatgtgtgt   4800
tcgacatgct gactacctga atgatgatca gaaagtaagg tcgttgctaa catcaacaat   4860
taacagcatc aaaaaagtat tgaagaaaag aggtgatgat tttgaaaccg tctccttctg   4920
gctctctaac acatgccgat tttgcactg cttgaaacag tacagtggag aagagggctt   4980
tatgaagcac aacacatctc gccagaatga acactgcctc accaattttg acctggctga   5040
```

-continued

```
gtatcggcag gtgctgagtg acttggccat tcagatctac cagcagctcg tgcgggtgtt   5100

agagaacatc cttcagccaa tgattgtctc aggcatgctg gaacatgaaa cgattcaggg   5160

cgtgtctggg gtgaagccca cagggttgag aaagcgaacc tccagtatcg ccgacgaggg   5220

cacctacaca ctggactcca tcctccggca gctcaactcc ttccactcgg tcatgtgtca   5280

gcatggcatg gaccctgaac tgatcaagca ggtggtcaag cagatgttct acatcatagg   5340

ggccatcacc ctgaacaacc ttctcctgcg gaaggacatg tgctcctgga gtaaaggcat   5400

gcagatcagg tacaatgtca gtcaactgga agaatggctg cgtgacaaga atctgatgaa   5460

tagtggggct aaagaaaccc tggaacctct cattcaggct gctcaacttt tgcaagtgaa   5520

aaagaaaaca gatgatgatg cagaagccat ttgttctatg tgcaatgctt taactactgc   5580

ccagattgtg aaagtgttga atttgtatac tccagttaat gagtttgaag aaagagtctc   5640

tgtgtcgttc attcgtacta tacagatgcg tttacgagac aggaaagact ctccccagct   5700

gctcatggat gctaaacaca tctttcctgt cacctttcct ttcaacccat cttccctcgc   5760

actagaaacc atccagattc cagccagcct cggcctgggc ttcatttcac gggtctgaaa   5820

gtgatgtcca ggcaaaaatt gacaatacat ttcttgcccg aaataagaac ccattatttc   5880

cagtgagtta ctgaaaatac atttttaaag agaaagtact gattatctcc caaatgagaa   5940

gtcattaact ggaaatctcc ctagaatact ttcatcactt tggaaacaaa gataggctct   6000

ttcgtgctgt gttatcttta tagcaacact catccttaac caactaggta ccgtgagttt   6060

acatacagga gaatgatgga aggaagggag gaaggaaagg aggagaaaaa tgtgtcttca   6120

gctggcagca tttattttaa atccttagca ctgagtttga atggtataaa aagtataact   6180

tccatagatg agctgttgtt aggaaggcac caaagaacct cctctgcact aaacaggaga   6240

atggaaagaa aagtctccat tgagtacata tcatgtcagt ttagtaatca attatgttga   6300

tattgttaaa ctggttcaaa gaaataaact ggcaatatgt aaagtaattc ctcatttgtg   6360

tcactatgat atagagatat taaaggaatg ttggtttgct aaatagtata gatgtccatt   6420

tgtactatag tttactgagc attttaaatt gctgctacat actgtcttct taaaatgtaa   6480

gtgatattag gcactacaat aagtttctct tgtcaattct gtttacaatt caatcagatc   6540

acagttttaa ctggattata tgcaaatacc tacagattca cctgcacaag tagcagacac   6600

tggaaagtca tgtagtaata tgacaaaatg cttgacattt aggggtagga ttagacaaag   6660

tggctattgt tgatgtcatt atttattcag gatgtattac attgatgtgc tcattaattt   6720

tccctgggtg gaaattgcgt cagggtacag tgttctgtga agtgacttat ttttaactac   6780

cagatctgat tccttcagtg catattttca accttgacag gttttctctc ttcttaattt   6840

attaagaatt aatctc                                                   6856
```

<210> SEQ ID NO 43
<211> LENGTH: 2834
<212> TYPE: DNA
<213> ORGANISM: Homo sapiens
<220> FEATURE:
<221> NAME/KEY: misc_feature
<223> OTHER INFORMATION: Incyte ID No: 001697.5

<400> SEQUENCE: 43

```
cacacaggac agaggtcagc tgacaatcct gggacctcag gatccatgct ctcccagagg     60

acgcctctca cacacatggg tcggcagtca tgttacactc ccaggggcat tctcaccccg    120

cggacagtgg aagcccctca gggggtgcag aacagagtgc tgcaggagag agagggcgct    180
```

-continued

```
ggctggtgcg aagccgtccg aggtgcagca cagcccacaa ggcccgccag tgtctttccc    240
gaggacacgc gaatcctggg gggctcactc cggcaaagag gacgagacac tgcaccaagg    300
acagggcctg acctctctgg ccgccttccc cggggcctca gtttccccg atggtgagag     360
tggagccgac catgcgccct gctgtggact cacccggcgc cctggcgtcg agtggcggcg    420
gagacctgac agacagcgtg ggaaaaatca agatgtctgc agatttcgag agatggggtg    480
cggtggcggg cgctggcggc ggcggaggag agggagcagc gtcacgggcg cccggcccgt    540
taaaacgctg ctggctggag ccacctccct ccctgcagcc cgcaacggga atggagtaaa    600
gggagacccg tcgacctggc cacggggatc agcgatggaa ttaaagcaat ctttgtccac    660
ccatctggaa gccgagaagc ctctgaggcg ctatggggcg gtggaggaga cggcttggaa    720
aacggagaga ctggggagaa atcagctgga catcatctcc atggcggaga caaccatgat    780
gccagaggag attgagctgg agatggcaaa aattcagcgt ctccgggaag tcttggtccg    840
ccgggagtct gagctcaggt tcatgatgga tgacatccag ctctgcaagg acatcatgga    900
cttgaagcag gagctgcaga acttggtcgc catcccagaa aaagaaaaaa ccaaactgca    960
gaagcagaga gaggatgagc taatccagaa gatccacaaa ctggtgcaga agagagactt   1020
cctggtggac gatgcggagg tcgagcggtt aagggagcaa gaagaagaca aggaaatggc   1080
tgatttcctg agaatcaagt taaaacctct agacaaagta accaaatctc cagccagctc   1140
ccgggcagag aagaaagcag agcccccacc tagcaagccc acggtggcca agacggggct   1200
ggcattgatc aaggattgtt gcggggccac ccagtgcaac atcatgtagc cccacgtgg    1260
ggtgccctgg gccatgggga cccccccca ccctcttgtc tttatagccc ccatttcacc    1320
ggggcccaag agctctccaa ggcagaaggg gttgaaggca agcccgtgac tgtcaccaga   1380
ggccatgggc acggcaggcg ggcctggcca ccctgtacag agtgtagcag tagggagtct   1440
ctcaccgtcg catggtcctc cccagagcat gccgaaccca ggagtctgtc tcactgttta   1500
tccaaacacc aggaaaggtc ctccctcaaa aaagcatatc tccacttctc tctagctgta   1560
tctaacccac cgtgtgaatg aactgggaga ggggcatgct ccccagctgt gtgtagtcgt   1620
gacttctcaa caatctagca ccatgtcgga cacgttcccc atccaccctc ctagctctgc   1680
tctcagagct aggcacatgg gcacaggtcc cctcccgtct gtcctctccc agcaactgtg   1740
ccctggaggg ctccacatgg cccccgtgtc tctcgggcac cacccatata gcagtcccag   1800
agggcccatc tgtaaagatc gagcttgtgt gtggtgtcgt ggtcacatct cccgcttccc   1860
cccatcctgt gtctgggcac agttcacatc aggacagcgt ccattgtgct ctcagtctgc   1920
ctcaggtgtg tgcctggagg gggcctggac tggcatggat ccagtgtgca gaagagccag   1980
cagggaaccg gaagctctga tgtcaaggcc agagcagttg agaatgggac ccagagtaga   2040
tgctgacctg ggcactccac cattccgggg ccaccacaga gatgccagca ggatgccact   2100
ttgccagccc gacacacgga cctttgtaaa gaacagcaac aggcaggaga ggcagcgtgt   2160
gaccagattg tgtcccgtca ttgggtggca tatgttaact agctgccaaa caacttcaac   2220
ccgtgtaatt catgtacatt tgcaacagcc agcccggtac agcctgtgtg acttctctgt   2280
atgtgtgtgt gtgtcgtgac cagcctaagt agttagcata actcaagatg ctgatgtgca   2340
gtcacccatc agagaaaata aaaatggaaa ccacgttcac agcattttaa aagtttttac   2400
tttttttctt gattatggaa gtaatccatg tacatagtaa atcattttaa aagtacaaaa   2460
agtatgaaga agtttgtctt aaaaaaaaaa aaattattcc tccaactaga gaccactctg   2520
atgtttcgac gttttaaaaa agtctttttt tgtgcatttt ttcatcgttg acatcatatt   2580
```

-continued gtgatatcat ttataaccag ttttttccta cttattatac caccatcttc cacatcatta 2640
aaagctcttt gtaaacatta aacactcttc ataaatcatg ccaatgtctg tttagtaatc 2700
catcttgtgg atgtactgta attcatctaa tcatttcctc actattggat gtgtagactg 2760
gttctaggtt ttcttataaa tagtgtcttg gattagccag gcatggtaat gggtgcctgt 2820
aatcccagct actt 2834

<210> SEQ ID NO 44
<211> LENGTH: 8050
<212> TYPE: DNA
<213> ORGANISM: Homo sapiens
<220> FEATURE:
<221> NAME/KEY: misc_feature
<223> OTHER INFORMATION: Incyte ID No: 979567.11
<221> NAME/KEY: unsure
<222> LOCATION: 3498, 5122, 8041, 8043
<223> OTHER INFORMATION: a, t, c, g, or other

<400> SEQUENCE: 44
ggagtacgtg tcggagatcc gctcgcgcgc cgaaggttat gagaagacag atgatgtttc 60
agagaagacc tcactggctg accaggagga agtaaggact attttcatca accagcccca 120
gctgacaaaa ttctgcaata accatgtcag cactgcaaaa tacaacataa tcacattcct 180
tccaagattt ctctactctc agttcagaag agctgctaat tcattttttc tctttattgc 240
actgctgcag caaatacctg atgtgtcacc aacaggtcgt tatacaacac tggttcctct 300
cttatttatt ttagctgtgg cagctatcaa agagataata gaagatatta aacgacataa 360
agctgataat gcagtgaaca agaaacaaac gcaagttttg agaaatggtg cttgggaaat 420
tgtccactgg gaaaaggtgg cagtagggga gatagtgaaa gtgaccaatg gggaacatct 480
cccagcagat ctcatcagtc tgtcctcaag tgagccccaa gccatgtgct acattgaaac 540
atccaactta gatggtgaaa caaacttgaa aattagacag ggcttaccag caacatcaga 600
tatcaaagac gttgacagtc tgatgaggat ctctggcaga attgagtgtg aaagtccaaa 660
cagacatctt ctacgatttt gttggaaaca taaggcttga tggacatggc accgttccac 720
tgggagcaga tcagattctt cttcgaggag ctcagttgag aaatacacag tgggttcatg 780
gaatagttgt ctacactgga catgacacca agctgatgca gaattcaaca agtccaccac 840
ttaagctctc aaatgtggaa cggattacaa atgtacaaat tttgatttta ttttgtatct 900
taattgccat gtctcttgtc tgttctgtgg gctcagccat ttggaatcga aggcattctg 960
gaaaagactg gtatctcaat ctaaactatg gtggcgctag taattttgga ctgaatttct 1020
tgaccttcat catccttttc aacaatctca ttcctatcag cttattggtt acattagaag 1080
ttgtgaaatt tacccaggca tacttcataa attgggatct tgacatgcac tatgaaccca 1140
cagacactgc tgctatggct cgaacatcta atctgaatga ggaacttggc caggttaaat 1200
acatattttc tgacaaaact ggtactctga catgcaatgt aatgcagttt aagaagtgca 1260
ccatagcggg agttgcttat ggccatgtcc ctgaacctga ggattatggc tgctctcctg 1320
atgaatggca gaactcacag tttggagatg aaaaaacatt tagtgattca tcattgctgg 1380
aaaatctcca aaataatcat ccaactgcac ctataatatg tgaatttctt acaatgatgg 1440
cagtctgtca cacagcagtg ccagagcgag aaggtgacaa gattatttat caagcagcat 1500
ctccagatga gggagcattg gtcagagcag ccaagcaatt gaattttgtt ttcactggaa 1560
gaacacccga ctcggtgatt atagattcac tggggcagga agaaagatat gaattgctca 1620

-continued

```
atgtcttgga gtttaccagt gctaggaaaa gaatgtcagt gattgttcgc actccatctg   1680
gaaagttacg actctactgc aaaggagctg acactgtaat ttatgatcga ctggcagaga   1740
cgtcaaaata caaagaaatt accctaaaac atttagagca gtttgctaca gaagggttaa   1800
gaactttatg ttttgctgtg gctgagattt cagagagcga ctttcaggag tggcgagcag   1860
tctatcagcg agcatctaca tctgtgcaga acaggctact caaactcgaa gagagttatg   1920
agttgattga aaagaatctt cagctacttg gagcaacagc cattgaggat aaattacaag   1980
atcaagtgcc tgaaaccata gaaacgctaa tgaaagcaga catcaaaatc tggatcctta   2040
caggggacaa gcaagaaact gccattaaca tcggacactc ctgcaaactg ttgaagaaga   2100
acatgggaat gattgttata aatgaaggct ctcttgatgg aacaagggaa actctcagtc   2160
gtcactgtac taccettggt gatgctctcc ggaaagagaa tgattttgct cttataattg   2220
atgggaaaac cctcaaatat gccttaacct ttggagtacg acagtatttc ctggacttag   2280
ctttgtcatg caaagctgtc atttgctgtc gggtttctcc tcttcaaaaa tctgaagtgt   2340
tgagatggtt aagaaacaag tcaaagtcgt aacgcttgca atcggtgatg gagcaaatga   2400
tgtcagcatg atacagacag cgcacgttgg tgttggtatc agtggcaatg aaggcctgca   2460
ggcagctaat tcctctgact actccatagc tcagttcaaa tatttgaaga atttactgat   2520
gattcatggt gcctggaact ataacagagt ctccaagtgc atcttatact gcttctacaa   2580
gaatatagtg ctctatatta tcgagatctg gtttgccttt gttaatggct tttctggaca   2640
gatcctcttt gaaagatggt gtataggtct ctataacgtg atgtttacag caatgcctcc   2700
tttaactctt ggaatatttg agagatcatg cagaaaagag aacatgttga agtaccctga   2760
attatacaaa acatctcaga atgccctgga cttcaacacc aaggttttct gggttcattg   2820
tttaaatggc ctcttccact cagttattct gttttggttt ccactaaaag cccttcagta   2880
tggtactgca tttggaaatg ggaaaacctc ggattatctg ctactgggaa actttgtgta   2940
cacttttgtg gtgataactg tgtgtttgaa agctggattg gagacatcat attggacatg   3000
gttcagccac atagcgatat gggggagcat cgcactctgg gtggtgtttt ttggaatcta   3060
ctcatctctg tggcctgcca ttccgatggc cctgatatg tcaggagagg cagccatgtt   3120
gttcagttct ggagtctttt ggatgggctt gttattcatc cctgtggcat ctctgctcct   3180
tgatgtggtg tacaaggtta tcaagaggac tgcttttaaa acattggtcg atgaagttca   3240
ggagctggag gcaaaatctc aagacccagg agcagttgta cttggaaaaa gcctgaccga   3300
gagggcgcaa ctgctcaaga acgtctttaa gaagaaccac gtgaacttgt accgctctga   3360
atccttgcaa caaaatctgc tccatgggta tgcgttctct caagatgaaa atggaatcgt   3420
ttcacagtct gaagtgataa gagcatatga taccacgaaa cagaggcccg acgaatggtg   3480
atggggagat cctgaaangc aggctctgtt acctctctaa ggagagctac caggttgtca   3540
ccgcagtctg ctaaccaatt ccagtctggt ccatgaagag gaaaggtaga tctgagctca   3600
tctcgctgat ggacattcag attcatgtat attatagaca taagcactgt gcaactgtac   3660
tgtaacacca tctcttttgg attttttaa ggtatttgct aagtctttgt aaacggaaat   3720
tgaaaatgac ctggtatctt gccagagggc tttcttaaac ggagaataag tcagtattct   3780
tatgccatta ctgtggggct gtaactgact gtcagtttat tggctgtacc acaaggtaac   3840
caaccattaa aaaactctaa agtgataatt tagttaaagg gactcttggt atccagactt   3900
agatttcagg atatgctgaa acaaaccagc attcttaagg aactgactca cctttcctgg   3960
accaaaattt ctaaacaagc atttgtgtcc aaaattgtct tgataaatgt ttgccaaaga   4020
```

-continued ggttcagtaa gtgtttttct agttcagtag tcatatgccc agaaatgtaa gagaaagttt 4080
acttccagtt ccgctgtaag atctgcatgc ctgactttcc aaatgtaaga gtgatttaca 4140
aaaatgaata tttcaaggca tttgctacta aaatcggtga tgttgcacct ttggccttac 4200
aaatgcttct ttgttgtttg tcgtgtttat ttgttagagg acacacgtgt taatgtgact 4260
ctgttgttat gacactgatt tttcaaacta tgtatgtttc aggtatttct gatgaagttt 4320
catcatcatt tagatttttc taaaaatctg gctaatgcag tagattgagt gatgtcattt 4380
tgtcttaaag tttttcctct taagaaacat atgctacgta tttacgtggg atttccaaag 4440
cttctgttgc aatatttgga ataacatgtc agataaatgc atgggctttt gtcctgtgtt 4500
ccagttccca ctagagatgc ctgtgtcttg tgtagcacac ccagtgttat ggtgactgcc 4560
ccctatactg aagactgaaa attatttcac agttcactca tcaaatagtt cccaaaattc 4620
gtcacatgct gcttattggg acaaataggt agtacatttt ccccatttaa aaaatgcgga 4680
ttttactcag gccggtaact ttacagtcag aggacacgtt catcatgagt agcttttgtt 4740
agtatgtttt aaaatgtatc ttcagttcaa ttattttcag catttacaag acatctgaaa 4800
atggctattt tgctaccaac agtaaatgaa ggggctgttt aaaaaccaca accagttttc 4860
tacactattt tttaaataat actttcattt gaaaaaaagg aattagtttt cagatacact 4920
tcagagattg aagcaaacta tttgcctttt actcaaaagc ctgcttgcct ttacatggac 4980
ttaccagcaa aataggtaga actttctctt ttaaaaaaag tcaactagaa ttgagaagag 5040
gtgatttttt ttcagatcgc ttctcgagtt taatattttc acattctttt caccctttt 5100
ctcaatctag atttaaaatt anggatatat gtcatttcct tgtctgtatt tgtagctcct 5160
tagttaccag tatgcctctc cattttctac aaataagagg ttataacaca tatacataat 5220
tctaacctta agggaacaca cgtttacata ctttacttcc caagcccttc ctgtttgggg 5280
tacagattga gagagtcatg aatcaacaca tctagcaaga ccacaggtgt aagagtctaa 5340
gatcgtcttc aaaattctga agtcccagtc tttacctgtc cagtgaatga atattcagag 5400
cagcttttcc tggggcttcc cagtggtgat agctgaggtc aaaccacaaa aaataagaaa 5460
gcaagagtga aatgcacccc tccagagaaa cactttgtag tgtttaattc tgttaataga 5520
gaagagctgc ttctgtttgc gctcacttca tcagtggcac ccttctgcag aattttaata 5580
taaaaacatt atggatataa tagaactgga ttttctgact taaaaatgta agttttattt 5640
taatcttgaa acgtggattg tttctgtgga gctcttaaac atgagaagaa tacttacggt 5700
tgataatgtg taacatgatc tgaaatgtga ctcatttgag cctctttgtc ccatcgtcct 5760
gtttttgaat tattgacatt gtcagtctct ttgcttcctg ggtgagactt ggggtttgag 5820
ggacagggaa tgaccttctt ggtgaaactt aaaatataac attgcaattg cagtgacttt 5880
acagtgttaa attagagaaa atagtctgat tttttaaacc ttccttaact ggaaaaaagt 5940
cacatggttt taccaggatt gaaataaaca gtcaatgtga cttttaacat gtgttttttt 6000
gaaataaagg gcacgtactc ttcaattaaa aagttcctta tagggactct ggcaaatgct 6060
aacacagttg ctttacaatg tttacaattc agacaatacg acttataata gaaaatcctc 6120
attcatttag cattgaaaag ctggaagttg cttctttaat gttgaatagt atacagtggt 6180
attgagcatg gactttctaa atgttttata tatacatata aaaatatatt ggtgtctcac 6240
acccagaaag atgttatatt gtagatatta ttaggaaaaa acagtgtttc tcaggaacgt 6300
tgtaaatttt aaatgatata tgtacttccc gtcctcccac ctccactctg tgctctaatg 6360

-continued

```
tgagactgct tcagcagtgt tgctaagtta atggaaaact ttttctaatc aagtcaggtg   6420

aatgtgtatt ctgctaaata atgttagcca tttacatgaa ttgtatggtc attaaatgga   6480

atcagtgatt cctctttaat ttccagaggg gaaatgaatt atggaaatca gtcagcattc   6540

tgatcattaa attttatact ttaattttgc cgttcagcat tctaaatatc caatgtgaaa   6600

gtcacatgat aatttgtttt gcattgcgtg cactgtacaa cacttacaac ttgtcattta   6660

aaatgttttc tcgggaaatg aatgctagtc agaaagtaat agattgtatt attcatagtt   6720

ttaaaattat gacaatgtca taattactac aaagctaaat aatcgtgttt atttttgtgc   6780

agttgccctt tgatagttcc tggttttaaa acctattaag tgtataatct tacaaatagt   6840

catctacaaa atttatggag aaagtgccca gcccattcac atcacatgga ccaggaattc   6900

ttttgtaaat gacttaaggt aacatcatgc agttcagtgc ctaataaatg ctttttaatg   6960

atgagcattt ctataatgac tcgtaagata ccatagtctg atttttctca cattaaaata   7020

actgaagtca cttgtgtaac gtagttatac tttgctgcat tttaattaac cttcaacagc   7080

tattaaagtg gaatgtaagt taaattttga aggaaaggaa ataaatgttt tccatatttc   7140

gtcttgattt actttctgta tgagaacagc tgtgtttttg ataggtttat ggtttgcatg   7200

agttcatatt taaagtgatc caggccaatg catggctatt gctgtaaatc ttgatgttta   7260

tttctgcctt gtaaagttct atcacggcct acctggaatt taaaattcag tagacaaatt   7320

aattggtcct ctgcacaact tttttaataa gtagattatt ttacaaagaa atttgaacaa   7380

atttaattga atcttttgtt tagcttgcct ctaagaactt ttcttaataa agctcccaaa   7440

acttctcagc aaataaatct cccttaagta ggaaaactag atttcatatt tgcttacttt   7500

gaattaacag caactttcca caggtaaatc tgttcttgca aagatgtgag cagaatagtt   7560

aaaaataata tttttatgtt tcatggttct aaatggaagc cataaatgca gtaaatacta   7620

tctgttgttt aactacttta atcgtcattt tttacatttt caagtttatt aggttaagaa   7680

aaacagggca gccttggaag gcagctacta cagaaaactg cagttttgcg ttaaagataa   7740

agtagtattt tcagctccct gaaaaaccat tcctgctgaa actgctgtag aaattgtgaa   7800

gctgcatgag tggagagtat tgaatctgtg gttatagtag ttttctcagg tttgtttatc   7860

ttgatgtttg atgcactgtg ttttatagtt attaaaattg agtaatatta tttctatgca   7920

gtgttatgtg tcattggcct tttgtgaatg tgcatgtttt aaactgcaaa ttttaaacat   7980

tttgtcctct aattgttatt aaaaatgaaa taaactttac cattactcaa aaaaaaaaaa   8040

nangggcggc                                                          8050
```

```
<210> SEQ ID NO 45
<211> LENGTH: 9610
<212> TYPE: DNA
<213> ORGANISM: Homo sapiens
<220> FEATURE:
<221> NAME/KEY: misc_feature
<223> OTHER INFORMATION: Incyte ID No: 996794.11

<400> SEQUENCE: 45

gaaagcgcac gccgagagga ggtgtgggtg ttccgcttcc atcctaacgg aacgagctcc     60

ctcttcgcgg acatgggatt acccagcggc tgctaacccc tctcctcgcc ctgctccccc    120

aaaccggcgt ggctccccgg gcaccaagga gctgactaca gaggagcagg atttgcaccc    180

ctcgctgggc ttgctttggc aacagagtgc ctgacccagg tcaggatttt caagaaagac    240

atgtctgaca aaatgtctag cttcctacat attggagaca tttgttctct gtacgcggag    300
```

-continued

```
ggatcgacaa atggatttat tagcaccttg ggcctggttg atgatcgttg tgttgtacag    360

ccagaaaccg gggaccttaa caatccacct aagaaattca gagactgcct ctttaagcta    420

tgtcccatga accgctactc tgcccaaaag cagttctgga aagccgctaa gcctggggcc    480

aacagcacca cagacgcagt gctactcaac aaactgcacc acgctgcaga cttggaaaag    540

aagcagaatg agacagaaaa caggaaattg ctggggaccg taatccagta tggcaatgtg    600

atccagctcc tgcatttgaa aagtaataaa tacctaacag tgaataagag gcttcctgct    660

ctgttggaga agaatgccat gagagtcaca ttggacgagg ctggaaatga agggtcctgg    720

ttttatattc agccattcta caagctgcga tccattggag acagcgtggt cataggtgac    780

aaggtggttc tgaaccccgt caatgctggt cagcccctac atgctagcag ccatcaactg    840

gtagataacc caggctgcaa tgaggtcaat tccgtcaact gcaatacaag ctggaaaata    900

gtccttttca tgaaatggag tgataacaaa gacgacatat taaagggggg tgacgtggtg    960

aggctgtttc atgctgagca ggagaagttt ctcacctgtg acgaacacag gaagaagcag   1020

cacgtcttcc tgagaaccac gggccggcag tcggccacat ctgccaccag ttcaaaagcc   1080

ctgtgggagg tggaggtggt ccagcatgac ccatgtcggg gcggagcagg gtattggaac   1140

agccttttcc gtttcaagca tctggccacg gggcattact tggcagcaga ggtggaccct   1200

gatcaggacg cctctcgaag taggttgcgg aatgcccaag aaaagatggt atactccctg   1260

gtctctgtgc ctgaaggcaa tgacatctcc tccattttcg agctagatcc caccactctg   1320

cgtggaggtg acagccttgt cccaaggaac tcttatgttc ggctcagaca cctatgtact   1380

aatacctggg ttcacagcac aaatattcct attgacaagg aagaagaaaa gcccgtgatg   1440

ctgaaaattg gcacctctcc tgtgaaggag gataaggaag catttgccat agttccggtt   1500

tctcctgctg aagttcggga cctggacttt gccaatgatg ccagcaaggt gctgggctcc   1560

attgctggga agctagagaa gggcaccatc acccagaatg aaaggaggtc tgtaaccaag   1620

ctgctagaag atttggttta cttcgtcact ggtggaacta attctggtca agatgttctc   1680

gaagttgtct tctccaagcc caacagagaa cggcagaaac tgatgagaga acagaatatt   1740

ctcaagcaga tcttcaagtt gttacaagcc ccattcacag actgcggtga tggcccaatg   1800

cttcggctgg aagagctcgg ggaccagcgg cacgctcctt tcagacacat ctgccggctc   1860

tgctacaggg tgctgagaca ctcgcagcaa gactacagga agaaccagga gtatatagcc   1920

aagcagtttg gcttcatgca gaagcagatt ggctatgatg tgttggctga agacactatc   1980

actgccctgc tccacaataa tcggaaactc ctggaaaaac acattaccgc ggcagagatt   2040

gacacatttg tcagcctggt gcgaaagaac agggagccca gattcttaga ttacctctcc   2100

gacctctgtg tctccatgaa caaatcaatt ccagtgaccc aggaactgat atgtaaagct   2160

gtgctgaacc ccaccaacgc tgacatcctg attgagacca agttggttct ttctcgtttt   2220

gaatttgaag gtgtctcttc cactggagag aatgctctgg aggcaggaga agacgaggaa   2280

gaggtgtggc tgttttggag ggacagcaac aaagagattc gcagcaagag tgtgagggaa   2340

ttggctcagg atgctaaaga agggcagaag gaggaccgag acgttctcag ctactacaga   2400

tatcagctga acctctttgc gaggatgtgt ctggaccgcc aatacctggc catcaacgaa   2460

atctcaggcc agctggatgt cgatctcatt ctccgctgca tgtctgacga gaacctgccc   2520

tatgacctca gggcgtcctt ctgccgcctc atgcttcaca tgcatgtgga ccgagatccc   2580

caggaacaag tcacccccgt gaaatatgcc cgcctctggt cggagattcc ctcggagatc   2640

gccattgacg actatgatag tagtggagct tccaaagatg aaattaagga gagatttgct   2700
```

-continued

```
cagaccatgg agtttgtgga ggagtattta agagatgtgg tttgtcagag gttccctttc   2760
tctgataaag agaagaataa gcttacgttt gaggttgtaa atttagctag gaatctcata   2820
tactttggtt tctacaactt ctctgacctt ctccgattaa ctaagatcct tctggccata   2880
ttggactgtg tacatgtgac aacaatcttc cccattagca agatggcgaa aggagaagag   2940
aataaaggca gtaacgtgat gagatctatt catggcgtgg gagagctgat gacccaggtg   3000
gtgctccggg gaggaggctt tttgcccatg actcccatgg ctgctgcccc tgaaggcaat   3060
gtgaagcagg cagagcctga gaaggaggac atcatggtca tggacaccaa gctgaagatc   3120
attgagatac tccagtttat tttgaatgtg aggttggatt ataggatctc ctgcctcctg   3180
tgtatattta agcgagagtt tgatgaaagc aattcccaga cttcagaaac atcctccgga   3240
aacagcagcc aagaagggcc aagtaatgta ccaggtgctc ttgactttga acacattgaa   3300
gaacaagcag aaggcatctt tggaggaagt gaggagaaca ccccactgga cttggatgac   3360
cacggcggca gaacctttct ccgtgtcctg ctccacttga cgatgcatga ctacccaccc   3420
ctggtgtcag gggccctgca gctcctcttc cggcacttca gccagaggca ggaggtgctc   3480
caggccttca aacaggttca actgctggtt accagccaag atgtggacaa ctacaaacag   3540
atcaaacaag acttggatca actgaggtcc atcgtggaaa agtcagagct ttgggtgtac   3600
aaagggcagg gccccgatga gactatggat ggtgcatctg gagaaaatga acataagaaa   3660
acggaggagg gaaataacaa gccacaaaag catgaaagca ccagcagcta caactacaga   3720
gtggtcaaag agattttgat tcggcttagc aaactctgtg ttcaagagag tgcctcagtg   3780
agaaagagca ggaagcagca acagcgtctg ctccggaaca tgggcgcgca cgccgtggtg   3840
ctggagctgc tgcagattcc ctatgagaag gccgaagata ccaagatgca agagataatg   3900
aggttggctc atgaattttt gcagaatttc tgcgcaggca accagcagaa tcaagctttg   3960
ctacataaac acataaacct gtttctcaac ccagggatcc tggaggcagt aaccatgcag   4020
cacatcttca tgaacaattt ccagctttgc agtgagatca acgagagagt tgttcagcac   4080
ttcgttcact gcatagagac tcacggtcgg aatgtccagt atataaagtt cttacagaca   4140
attgtcaagg cagaagggaa atttattaaa aaatgccaag acatggttat ggccgagctg   4200
gtcaattcgg gagaggatgt cctcgtgttc tacaacgaca gagcctcttt ccagactctg   4260
atccagatga tgcggtcaga acgggatcgg atggatgaga acagccctct catgtaccac   4320
atccacttgg tcgagctcct ggctgtgtgc acggagggta agaatgtcta cacagagatc   4380
aagtgcaact ccctgctccc gctggatgac atcgttcgcg tggtgaccca cgaggactgc   4440
atccctgagg ttaaaattgc atacattaac ttcctgaatc actgctatgt ggatacagag   4500
gtggaaatga aggagattta taccagcaat cacatgtgga aattgtttga gaatttcctt   4560
gtagacatct gcagggcctg taacaacact agtgacagga aacatgcaga ctcgattttg   4620
gagaagtatg tcaccgaaat cgtcatgagt attgttacta ctttcttcag ctctcccttc   4680
tcagaccaga gtacgacttt gcagactcgc cagcctgtct ttgtgcaact gctgcaaggc   4740
gtgttcaggg tttaccactg caactggtta atgccaagcc aaaaagcctc cgtggagagc   4800
tgtattcggg tgctgtctga tgtagccaag agccgggcca ttgccattcc cgtggacctg   4860
gacagccaag tcaacaacct ctttctcaag tcccacagca ttgtgcagaa aacagccatg   4920
aactggcggc tctcagcccg caatgccgca cgcagggact ctgttctggc agcttccaga   4980
gactaccgga atatcattga gagattgcag gacatcgtct ccgcgctgga ggaccgtctc   5040
```

-continued

```
aggcccctgg tgcaggcaga gttatctgtg ctcgtggatg ttctccacag acccgagctg   5100
cttttcccag agaacacaga cgccagaagg aaatgtgaaa gtggcggttt catttgcaag   5160
ttaataaagc atacaaaaca gctgctagaa gaaaatgaag agaagctctg cattaaggtc   5220
ctacagaccc tgagggaaat gatgaccaaa gatagaggct atggagaaaa gggtgaggcg   5280
ctcaggcaag ttctggtcaa ccgttactat ggaaacgtca gaccttcggg acgaagagag   5340
agccttacca gctttggcaa tggcccactg tcagcaggag gacccggcaa gcccggggga   5400
ggagggggag gttccggatc cagctctatg agcaggggtg agatgagtct ggccgaggtt   5460
cagtgtcacc ttgacaagga gggggcttcc aatctagtta tcgacctcat catgaacgca   5520
tccagtgacc gagtgttcca tgaaagcatt ctcctggcca ttgcccttct ggaaggaggc   5580
aacaccacca tccagcactc ctttttctgt cgcttgacag aagataagaa gtcagagaaa   5640
ttctttaagg tgttttatga ccggatgaag gtggcccagc aagaaatcaa agcaacagtg   5700
acagtgaaca ccagtgactt gggaaataaa aagaaagacg atgaggtaga cagggatgcc   5760
ccatcacgga aaaaagctaa agagcccaca acacagataa cagaagaggt ccgggatcag   5820
ctcctggagg cctccgctgc caccaggaaa gccttcacca ctttcaggag ggaggctgat   5880
cccgacgacc actaccagcc tggagagggc acccaggcca ctgccgacaa ggccaaggac   5940
gacctggaga tgagcgcggt catcaccatc atgcagccca tcctccgctt ccttcagctc   6000
ctgtgtgaaa accacaaccg agacctgcag aacttcctcc gttgccaaaa taacaagacc   6060
aactacaatt tggtatgtga gaccctgcag tttctggact gtatttgtgg aagcacaact   6120
ggaggccttg gtcttctggg cttgtatata aatgaaaaga acgtagcgct tatcaaccaa   6180
accctggaaa gtctgaccga atactgtcaa ggaccttgcc atgagaacca gaactgcata   6240
gccacccatg aatccaatgg cattgacatc atcacagccc tgatcctcaa tgatatcaat   6300
cctttgggaa agaagaggat ggaccttgtg ttagaactga agaacaatgc ctcgaagttg   6360
ctcctggcca tcatggaaag caggcacgac agtgaaaacg cagagaggat actttataac   6420
atgaggccca aggaactggt ggaagtgatc aagaaagcct acatgcaagg tgaagtggaa   6480
tttgaggatg gagaaaacgg tgaggatggg gcggcgtccc ccaggaacgt ggggcacaac   6540
atctacatat tagcccatca gttggctcgg cataacaaag aacttcagag catgctgaaa   6600
cctggtggcc aagtggacgg agatgaagcc ctggagtttt atgccaagca cacggcgcag   6660
atagagattg tcagattaga ccgaacaatg gaacagatag tctttcccgt gcccagcata   6720
tgtgaattcc taaccaagga gtcaaaacta cgaatttact atactacaga gagagacgaa   6780
caaggcagca aaatcaatga tttctttctg cggtctgaag acctcttcaa tgaaatgaat   6840
tggcagaaga aactgagagc ccagcccgtg ttgtactggt gtgcccgcaa catgtctttc   6900
tggagcagca tttcgtttaa cctggccgtc ctgatgaacc tgctggtggc gtttttctac   6960
ccgtttaagg gagtccgagg aggaaccctg gagccccact ggtcgggact cctgtggaca   7020
gccatgctca tctctctggc catcgtcatt gccctcccca agccccatgg catccgggcc   7080
ttaattgcct ccacaattct acgactgata ttttcagtcg ggttacaacc cacgttgttt   7140
cttctgggcg ctttcaatgt atgcaataaa atcatctttc taatgagctt tgtgggcaac   7200
tgtgggacat tcacaagagg ctaccgagcc atggttctgg atgttgagtt cctctatcat   7260
ttgttgtatc tggtgatctg tgccatgggg ctctttgtcc atgaattctt ctacagtctg   7320
ctgctttttg atttagtgta cagagaagag actttgctta atgtcattaa aagtgtcact   7380
cgcaatggac ggtccatcat cctgacagca gttctggctc tgatcctcgt ttacctgttc   7440
```

-continued

```
tcaatagtgg gctatctttt cttcaaggat gactttatct tggaagtaga taggctgccc   7500
aatgaaacag ctgttccaga aaccggcgag agtttggcaa gcgagttcct gttctccgat   7560
gtgtgtaggg tggagagtgg ggagaactgc tcctctcctg cacccagaga agagctggtc   7620
cctgcagaag agacggaaca ggataaagag cacacatgtg agacgctgct gatgtgcatt   7680
gtcactgtgc tgagtcacgg gctgcggagc gggggtggag taggagatgt actcaggaag   7740
ccgtccaaag aggaacccct gtttgctgct agagttattt atgacctctt gttcttcttc   7800
atggtcatca tcattgttct taacctgatt tttggggtta tcattgacac ttttgctgac   7860
ctgaggagtg agaagcagaa gaaggaagag atcttgaaga ccacgtgctt tatctgtggc   7920
ttggaaagag acaagtttga caacaagact gtcacctttg aagagcacat caaggaagaa   7980
cacaacatgt ggcactatct gtgcttcatc gtcctggtga aagtaaagga ctccaccgaa   8040
tatactgggc ctgagagtta cgtggcagaa atgatcaagg aaagaaacct tgactggttc   8100
cccaggatga gagccatgtc attggtcagc agtgattctg aaggagaaca gaatgagctg   8160
agaaacctgc aggagaagct ggagtccacc atgaaacttg tcacgaacct ttctggccag   8220
ctgtcggaat taaaggatca gatgacagaa caaaggaagc agaaacaaag aattggtctt   8280
ctaggacatc ctcctcacat gaatgtcaac ccacaacaac cagcataagc aaatgaaaga   8340
aaggaattgt atttaccttt tataattatt attagtgtgg gtatggctaa tgagttctga   8400
ttcacccacg aaggttacat ttatgctgaa tacatttgta aatactcagt tttatactgt   8460
atgtatatga ttgctactct aaaggtttgg atatatgtat tgtaattaga attgttggca   8520
tgatgacatt tcatttgtgc caaaaatatt aaaaatgcct tttttggaag gactaacaga   8580
aagcacctga tttgcacttg aaccagatta tagatttaaa agtatatgac atgtattttg   8640
tatttaaaac tagaatagcc agtatttatg tttttttataa aactgtgcaa tacgaattat   8700
gcaatcacaa tacatttgta gctcccgagt gtcctaaagg gagtgcactt ctttgaagct   8760
ggtgtgttaa tactatgtaa taaatggtta actttcaaat gatgctgctg ccaaaattat   8820
attaatagtg agtttcaggc ccctgggcat tttgtaccat gtaattatcc tctggtgatg   8880
ctgtttctcg ttagtggcag tagtgcctcc gtctcctagt gataatgctc caagtctatg   8940
aactgttaaa tcagcattca ttttaagaaa agcaacttta gtttcaaaga tacttttaag   9000
cttctaaatt gatcatttaa actatttctt taaataagag agccaaatta gaggctcata   9060
ctttagcttg tgaagaagat aatgaatttt ttaaagggaa ctttctatgc aatgttcagg   9120
ataaatgcat actgctggcc aatcagtgtc atctcctggg taaattttga tgtcgcatta   9180
taaagacatg cataattgat ggtttctaga ttatctagtc caaacaatag agtttatttt   9240
ttcttcatct gaaccaacat gctacagtag ctaagaagta ttaaaactat atacatccat   9300
ataaagatga aatatgaact atctcattag aagtcatagt tgaccacaga catgttattc   9360
ttctgaaaga gccacatttt ggttttattt cttgtcacat gatttctttt cttgatggat   9420
gaaaaatatg aaaggaaact tttatatctg ttgcctagtt ttgtacatgg atctcatttt   9480
acaagagaat ctctctgcaa aaaaaaaaaa aaaacagttt aaaaatgcat tgaaagcaga   9540
gttctgaaat gagtaaagtt tgtaaatgca tatataaaaa tatttaataa atgatgcaga   9600
atatacagtg                                                          9610
```

<210> SEQ ID NO 46
<211> LENGTH: 1882
<212> TYPE: DNA

-continued

<213> ORGANISM: Homo sapiens
<220> FEATURE:
<221> NAME/KEY: misc_feature
<223> OTHER INFORMATION: Incyte ID No: 237723.1
<221> NAME/KEY: unsure
<222> LOCATION: 1241-1275
<223> OTHER INFORMATION: a, t, c, g, or other

<400> SEQUENCE: 46

```
ttggaggact ctgggactta cgagtgcagg gccagcaacg accccaagag gaatgacttg     60

aggcaaaacc cctccataac atggattcga gcccaggcca ccataagcgt ccttcagaag    120

ccaaggattg tcaccagtga agaggtcatt attcgagaca gccctgttct ccctgtcacc    180

ctgcagtgta acctcacctc cagctctcac acccttacat acagctactg gacaaagaat    240

ggggtggaac tgagtgccac tcgtaagaat gccagcaaca tggagtacag gatcaataag    300

ccgagagctg aggattcagg cgaataccac tgcgtatatc actttgtcag cgctcctaaa    360

gcaaacgcca ccattgaagt gaaagccgct cctgacatca ctggccataa acggagtgag    420

aacaagaatg aagggcagga tgccactatg tattgcaagt cagttggcta cccccaccca    480

gactggatat ggcgcaagaa ggagaacggg atgcccatgg acattgtcaa tacctctggc    540

cgcttcttca tcatcaacaa ggaaaattac actgagttga acattgtgaa cctgcagatc    600

acggaagacc ctggcgagta tgaatgtaat gccacctggc cccactctgg cctttcttgg    660

gaattctggc tgaaattatc atccttgtgg tgatcattgt tgtgtatgag aagaggaaga    720

ggccagatga ggttcctgac gatgatgaac cagctggacc aatgaaaacc aactctacca    780

acaatcacaa agataaaaac ttgcgccaga gaaacacaaa ttaagtactg cttacaatat    840

ctttaggttc ctgaaactgg tggcaacatg acctgctaaa attttctgct tggacctctt    900

tggttctctc ccctttcaag tgagcaacac cacaatgact gtctaaagca tgccttattt    960

agcctctcct gtaagggtga tctagccagg tacattttaa acaatgcttc agtgtagaag   1020

gtgtaaacta ttttgggctt gatgtgctgt gaatgttgct tttttttttt cctttgttaa   1080

aatatttaaa tagaagtgaa aaggtcctct gaggatcaga tcatgcatgc gccatttttt   1140

tacttaatgc agctgttaaa ttggcaaagc tctaaaatgc actgctgcca tctagtgata   1200

cacttttgta aagtacagca aaacctacag atatatacag nnnnnnnnnn nnnnnnnnnn   1260

nnnnnnnnnn nnnnngggggg tgggagaaat ccaaaataaa gtaaatgctt gtttcatttt   1320

taagctgctg atattcattc cttattgtat gttgtcagat gaggaaattg tgcagttctg   1380

gtacataaag atgagtaata taaactgaaa tctataattt taagggctta acctgtgact   1440

ttaataagct ggaacagtcc actgaatggg tataatgaat tgcagtatat acgtatgatt   1500

gctttttaag tgattatctt ttcttctgtt aagtcatgta aattcataaa tccttttgca   1560

ctgatgtgtt gaaccttatt cttgtacatt cattcaatca aggcaaactt ttataatttt   1620

tcttttgttt ccaatgacct tgaaatgtta tagcatggta atattctatg caactatagt   1680

tatacttttt ggtttgacac tgtatttttt cacattgatt tactggttga tgatagattt   1740

tataacctaa cggttctcat gcggtgcgta attgtagatg catgtacttg tgtgttttgt   1800

gtaattattg aagtgcaatg atgtataaaa aagtggattc acctgttttt aaaaataaaa   1860

cattgataaa aggtgtttgg at                                            1882
```

<210> SEQ ID NO 47
<211> LENGTH: 1921
<212> TYPE: DNA
<213> ORGANISM: Homo sapiens -continued
<220> FEATURE:
<221> NAME/KEY: misc_feature
<223> OTHER INFORMATION: Incyte ID No: 233764.5

<400> SEQUENCE: 47
gccgccgccg aaccccgcgc gccactcgct cgctcagagg gaggagaaag tggcgagttc 60
cggatccctg gcctagcggc ggccccaacc tttactccag agatcatggc tgccgaggat 120
gtggtggcga ctggcgccga cccaagcgat ctggagagcg gcgggctgct gcatgagatt 180
ttcacgtcgc cgctcaacct gctgctgctt ggcctctgca tcttcctgct ctacaagatc 240
gtgcgcgggg accagccggc ggccagcggc gacagcgacg acgacgagcc gccccctctg 300
ccccgcctca agcggcgcga cttcaccccc gccgagctgc ggcgcttcga cggcgtccag 360
gacccgcgca tactcatggc catcaacggc aaggtgttcg atgtgaccaa aggccgcaaa 420
ttctacgggc ccgaggggcc gtatggggtc tttgctggaa gagatgcatc caggggcctt 480
gccacatttt gcctggataa ggaagcactg aaggatgagt acgatgacct ttctgacctc 540
actgctgccc agcaggagac tgctgagtga ctgggagtct cagttcactt tcaagtatca 600
tcacgtgggc aaactgctga aggaggggga ggagcccact gtgtactcag atgaggaaga 660
accaaaagat gagagtgccc ggaaaaatga ttaaagcatt cagtggaagt atatctattt 720
ttgtattttg caaaatcatt tgtaacagtc cactctgtct ttaaaacata gtgattacaa 780
tatttagaaa gttttgagca cttgctataa gtttttaat taacatcact agtgacacta 840
ataaaattaa cttcttagaa tgcatgatgt gtttgtgtgt cacaaatcca gaaagtgaac 900
tgcagtgctg taatacacat gttaatactg tttttcttct atctgtagtt agtacaggat 960
gaatttaaat gtgtttttcc tgagagacaa ggaagacttg ggtatttccc aaaacaggta 1020
aaaatcttaa atgtgcacca agagcaaagg atcaactttt agtcatgatg ttctgtaaag 1080
acaacaaatc cctttttttt tctcaattga cttaactgca tgatttctgt tttatctacc 1140
tctaaagcaa atctgcagtg ttccaaagac tttggtatgg attaagcgct gtccagtaac 1200
aaaatgaaat ctcaaaacag agctcagctg caaaaaagca tattttctgt gtttctggac 1260
tgcactgttg tccttgccct cacatagaca ctcagacacc ctcacaaaca cagtagtcta 1320
tagttaggat taaaatagga tctgaacatt caaaagaaag ctttggaaaa aaagagctgg 1380
ctggcctaaa aacctaaata tatgatgaag attgtaggac tgtcttccca agccccatgt 1440
tcatggtggg gcaatggtta tttggttatt ttactcaatt ggttactctc atttgaaatg 1500
agggagggac atacagaata ggaacaggtg tttgctctcc taagagcctt catgcacacc 1560
cctgaaccac gaggaaacag tacagtcgct agtcaagtgg tttttaaagt aaagtatatt 1620
cataaggtaa cagttattct gttgttataa aactataccc actgcaaaag tagtagtcaa 1680
gtgtctaggt ctttgatatt gctcttttgg ttaacactaa gcttaagtag actatacagt 1740
tgtatgaatt tgtaaaagta tatgaacacc tagtgagatt tcaaacttgt aattgtggtt 1800
aaatagtcat tgtattttct tgtgaactgt gttttatgat tttacctcaa atcagaaaac 1860
aaaatgatgt gctttggtca gttaataaaa atggttttac ccactaaaaa aaaaaaaaag 1920
g 1921

<210> SEQ ID NO 48
<211> LENGTH: 2246
<212> TYPE: DNA
<213> ORGANISM: Homo sapiens
<220> FEATURE:
<221> NAME/KEY: misc_feature -continued
<223> OTHER INFORMATION: Incyte ID No: 474194.5

<400> SEQUENCE: 48

```
gccgcgtgca gaggtgctca agcctcctgc gcggtccgca gtcagtgccg ccgcgcccgg      60
cctcccgcac gccccgcagg tagcgccccc gcccgcggcc cagagtgcgc tcgcgccggc     120
accagctccc ggataaacgg cgcgccgcgc ggagatgaca gccgaggaga tgaaggcgac     180
cgagagcggg gcgcagtcgg cgccgctgcc catggaggga gtggacatca gccccaaaca     240
ggacgaaggc gtgctgaagg tcatcaagag agagggcaca ggtacagaga tgcccatgat     300
tggggaccga gtctttatcc actacactgg ctgggctatt agatggcaca aagtttgact     360
ccagtctgga tcgcaaggac aaattctcct ttgacctggg aaaaggggag gtcatcaagg     420
cttgggacat tgccatagcc accatgaagg tgggggaggt gtgccacatc acctgcaaac     480
cagaatatgc ctacggttca gcaggcagtc ctccaaagat tcccccaat gccacgcttg      540
tatttgaggt ggagttgttt gagtttaagg gagaagatct gacggaagag gaagatggcg     600
gaatcattcg cagaatacag actcgcggtg aaggctatgc taagcccaat gagggtgcta     660
tcgtggaggt tgcactggaa gggtactaca aggacaagct ctttgaccag cgggagctcc     720
gctttgagat tggcgagggg gagaacctgg atctgcctta tggtctggag agggccattc     780
agcgcatgga gaaaggagaa cattccatcg tgtacctcaa gcccagctat gcttttggca     840
gtgttgggaa ggaaaagttc caaatcccac caaatgctga gctgaaatat gaattacacc     900
tcaagagttt tgaaaaggcc aaggagtctt gggagatgaa ttcagaagag aagctggaac     960
agagcaccat agtgaaagag cggggcactg tgtacttcaa ggaaggtaaa tacaagcaag    1020
ctttactaca gtataagaag atcgtgtctt ggctggaata tgagtctagt tttccaatg     1080
aggaagcaca gaaagcacag gcccttcgac tggcctctca cctcaacctg gccatgtgtc    1140
atctgaaact acaggccttc tctgctgcca ttgaaagctg taacaaggcc ctagaactgg    1200
acagcaacaa cgagaagggc ctcttccgcc ggggagaggc ccacctggcc gtgaatgact    1260
ttgaactggc acgggctgat ttccagaagg tcctgcagct ctaccccaac aacaaagccg    1320
ccaagaccca gctggctgtg tgccagcagc ggatccgaag gcagcttgcc cgggagaaga    1380
agctctatgc caatatgttt gagaggctgg ctgaggagga gaacaaggcc aaggcagagg    1440
cttcctcagg agaccatccc actgacacag agatgaagga ggagcagaag agcaacacgg    1500
cagggagcca gtctcaggtg gagacagaag catagcccct ctccaccagc cctactcctg    1560
cggctgcctg ccccccagtc tccccactcc accctgttag ttttgtaaaa actgaagaat    1620
tttgagtgaa ttagaccttt atttttctat ctggttggat ggtggcttta ggggaagggg    1680
gaaaggtgta ggctggggga ttgaggtggg gaatcatttt agctggtgtc agcccctctt    1740
cccttcctcc attgcacatg aacatatgtc catccatata tattcatcag aatgttaatt    1800
tattttgctc cctctgttag gtccattttc taagggtaga agaggcaagt ggtagggatg    1860
aggtctgata agaacccagg gtggagaggg agactcctgg gcagccgttt tcctcatcct    1920
ttccctctcc cagtccattt ccaaatgtgg cctccatgtg ggtgctaggg acatgggaaa    1980
aaccactgct atgccatttc ttctctctgt tcccttcctc acccccgacg gtgtggctga    2040
tgatgtcttc tggtgtcatg gtgaccaccc cctgttccct gttctggtat ttcccctgtc    2100
agtttcccct ctcggccagg ttgtgtccca aaatcccctc agcctcttct ctgcacgttg    2160
ctgaaggtcc aggcttgcct caagttccat gcttgagcaa taaagtggaa acaataaaac    2220
ctgggtgtca gacaaccctt tctgtt                                         2246
```

-continued

<210> SEQ ID NO 49
<211> LENGTH: 1094
<212> TYPE: DNA
<213> ORGANISM: Homo sapiens
<220> FEATURE:
<221> NAME/KEY: misc_feature
<223> OTHER INFORMATION: Incyte ID No: 1098468.1
<221> NAME/KEY: unsure
<222> LOCATION: 315
<223> OTHER INFORMATION: a, t, c, g, or other

<400> SEQUENCE: 49

```
agctggttac acctttgggc aagatatttc tgagacattt aatcatgcca atggcctcac     60

gttggtgtct agagctcacc agctagtgat ggagggatat aactggtgcc atgaccggaa    120

tgtagtaacg attttcagtg ctccaaacta ttgttatcgt tgtggtaacc aagctgcaat    180

catggaactt gacgatactc taaaatactc tttcttgcag tttgacccag cacctcgtag    240

ggcgacgtcc acatgttact cgtcgtaccc cagactactt cctgtaatga aattttaaac    300

ttgtacagta ttgancatga accatatatc gacctaatgg aaatgggaag agcaacagta    360

actccaaagt gtcagaaaat agttaacatt caaaaaactt gttttcacat ggaccaaaag    420

atgtgccata taaaaataca aagcctcttg tcatcaacag ccgtgaccac tttagaatga    480

accagttcat tgcatgctga agcgacattg ttggtcaaga aaccagtttc tggcatagcg    540

ctatttgtag ttacttttgc tttctctgag agactgcaga taataagatg taaacattaa    600

cacctcgtga atacaattta acttccattt agctatagct ttactcagca tgactgtaga    660

taaggatagc agcaaacaat cattggagct taatgaacat ttttaaaaat aattaccaag    720

gcctcccttc tacttgtgag ttttgaaatt gttcttttta ttttcaggga taccgtttaa    780

tttaattata tgatttgtct gcactcagtt tattccctac tcaaatctca gccccatgtt    840

gttctttgtt attgtcagaa cctggtgagt tgttttgaac agaactgttt tttccccttc    900

ctgtaagacg atgtgactgc acaagagcac tgcagtgttt ttcataataa acttgtgaac    960

taagaactga gaaggtcaaa ttttaattgt atcaatgggc aagactggtg ctgtttatta   1020

aaaaagttaa atcaattgag taaattttag aatttgtaga cttgtaggta aaataaaaat   1080

caagggcact acat                                                     1094
```

<210> SEQ ID NO 50
<211> LENGTH: 3768
<212> TYPE: DNA
<213> ORGANISM: Homo sapiens
<220> FEATURE:
<221> NAME/KEY: misc_feature
<223> OTHER INFORMATION: Incyte ID No: 298463.3
<221> NAME/KEY: unsure
<222> LOCATION: 3749, 3765
<223> OTHER INFORMATION: a, t, c, g, or other

<400> SEQUENCE: 50

```
ccttccgatg attcggctct tctcggctca gtctcagcga agcgtctgcg accgtcgttt     60

gagtcgtcgc tgccgctgcc gctgccactg ccactgccac ctcgcggatc aggagccagc    120

gttgttcgcc cgacgcctcg ctgccggtgg gaggaagcga gagggaagcc gcttgcgggt    180

ttgtcgccgc tgctcgccca ccgcctggaa gagccgagcc ccggcccagt cggtcgcttg    240

ccaccgctcg tagccgttac ccgcgggccg ccacagccgc cggccgggag aggcgcgcgc    300

catggcttct ggagccgatt caaaaggtga tgacctatca acagccattc tcaaacagaa    360
```

-continued

```
gaaccgtccc aatcggttaa ttgttgatga agccatcaat gaggacaaca gtgtggtgtc    420
cttgtcccag cccaagatgg atgaattgca gttgttccga ggtgacacag tgttgctgaa    480
aggaaagaag agacgagaag ctgtttgcat cgtcctttct gatgatactt gttctgatga    540
gaagattcgg atgaatagag ttgttcggaa taaccttcgt gtacgcctag ggatgtcat     600
cagcatccag ccatgccctg atgtgaagta cggcaaacgt atccatgtgc tgcccattga    660
tgacacagtg gaaggcatta ctggtaatct cttcgaggta taccttaagc cgtacttcct    720
ggaagcgtat cgacccatcc ggaaaggaga catttttctt gtccgtggtg ggatgcgtgc    780
tgtggagttc aaagtggtgg aaacagatcc tagcccttat tgcattgttg ctccagacac    840
agtgatccac tgcgaagggg agcctatcaa acgagaggat gaggaagagt ccttgaatga    900
agtagggtat gatgacattg gtggctgcag gaagcagcta gctcagataa aggagatggt    960
ggaactgccc ctgagacatc ctgccctctt taaggcaatt ggtgtgaagc ctcctagagg   1020
aatcctgctt tacggacctc ctggaacagg aaagaccctg attgctcgag ctgtagcaaa   1080
tgagactgga gccttcttct tcttgatcaa tggtcctgag atcatgagca aattggctgg   1140
tgagtctgag agcaaccttc gtaaagcctt tgaggaggct gagaagaatg ctcctgccat   1200
catcttcatt gatgagctag atgccatcgc tcccaaaaga gagaaaactc atggcgaggt   1260
ggagcggcgc attgtatcac agttgttgac cctcatggat ggcctaaagc agagggcaca   1320
tgtgattgtt atggcagcaa ccaacagacc caacagcatt gacccagctc tacggcgatt   1380
tggtcgcttt gacagggagg tagatattgg aattcctgat gctacaggac gcttagagat   1440
tcttcagatc cataccaaga acatgaagct ggcagatgat gtggacctgg aacaggtagc   1500
caatgagact cacgggcatg tgggtgctga cttagcagcc ctgtgctcag aggctgctct   1560
gcaagccatc cgcaagaaga tggatctcat tgacctagag gatgagacca ttgatgccga   1620
ggtcatgaac tctctagcag ttactatgga tgacttccgg tgggccttga gccagagtaa   1680
cccatcagca ctgcgggaaa ccgtggtaga ggtgccacag gtaacctggg gaagacatcg   1740
ggggcctaga ggatgtcaaa cgtgagctac aggagctggt ccagtatcct gtggagcacc   1800
cagacaaatt cctgaagttt ggcatgacac cttccaaggg agttctgttc tatggacctc   1860
ctggctgtgg gaaaactttg ttggccaaag ccattgctaa tgaatgccag gccaacttca   1920
tctccatcaa gggtcctgag ctgctcacca tgtggtttgg ggagtctgag gccaatgtca   1980
gagaaatctt tgacaaggcc cgccaagctg cccccctgtgt gctattcttt gatgagctgg   2040
attcgattgc caaggctcgt ggaggtaaca ttggagatgg tggtggggct gctgaccgag   2100
tcatcaacca gatcctgaca gaaatggatg gcatgtccac aaaaaaaaat gtgttcatca   2160
ttggcgctac caaccggcct gacatcattg atcctgccat cctcagacct ggccgtcttg   2220
atcagctcat ctacatccca cttcctgatg agaagtcccg tgttgccatc ctcaaggcta   2280
acctgcgcaa gtccccagtt gccaaggatg tggacttgga gttcctggct aaaatgacta   2340
atggcttctc tggagctgac ctgacagaga tttgccagcg tgcttgcaag ctggccatcc   2400
gtgaatccat cgagagtgag attaggcgag aacgagagag gcagacaaac ccatcagcca   2460
tggaggtaga agaggatgat ccagtgcctg agatccgtcg agatcacttt gaagaagcca   2520
tgcgctttgc gcgccgttct gtcagtgaca atgacattcg gaagtatgag atgtttgccc   2580
agacccttca gcagagtcgg ggctttggca gcttcagatt cccttcaggg aaccagggtg   2640
gagctggccc cagtcagggc agtggaggcg gcacaggtgg cagtgtatac acagaagaca   2700
atgatgatga cctgtatggc taagtggtgg tggccagcgt gcagtgagct ggcctgcctg   2760
```

-continued

```
gaccttgttc cctgggggtg ggggcgcttg cccaggagag ggaccagggg tgcgcccaca   2820

gcctgctcca ttctccagtc tgaacagttc agctacagtc tgactctgga caggggggttt   2880

ctgttgcaaa aatacaaaac aaaagcgata aaataaaagc gattttcatt tggtaggcgg   2940

agagtgaatt accaacaggg aattgggcct tgggcctatg ccatttctgt tgtagtttgg   3000

ggcagtgcag gggacctgtg tggggtgtga accaaggcac tactgccacc tgccacagta   3060

aagcatctgc acttgactca atgctgcccg agccctccct tccccctatc caacctgggt   3120

aggtgggtag gggccacagt tgctggatgt ttatatagag agtaggttga tttattttac   3180

atgcttttga gttaatgttg gaaaactaat cacaagcagt ttctaaacca aaaaatgaca   3240

tgttgtaaaa ggacaataaa cgttgggtca aaatggagcc tgagtcctgg gccctgtgcc   3300

tgcttctttt cctgggaaca gccttgggct acccaccact cccaaggcat tcttccaaat   3360

gtgaaatcct ggaagtaaga ttgcaccttc ttcctctcct gatcaacatc ggtatgatgt   3420

ctcctgttgc ctcacccttt gtctgcagta tcactggata ggactggtgg aaagggagca   3480

gcctgacaga gctccaaatg tggagaatat ggcatccctc cacctatatt tgatgtggac   3540

ggtaaggcta ggcctgcagg atcccttatc ctgaccaaag actgtgttgg ggtgccattt   3600

gaaaatcgca gggttgcaaa agaatacaat cttacttgca ggtggatatt ctctatactc   3660

tcttttaatg catctaaaaa tcccaaacat cccctggttg gtgatcactt acagttgtgt   3720

ccacctttat tttatgtact ttgattaana aaaaaaaaac ttttngtt                3768
```

<210> SEQ ID NO 51
<211> LENGTH: 2333
<212> TYPE: DNA
<213> ORGANISM: Homo sapiens
<220> FEATURE:
<221> NAME/KEY: misc_feature
<223> OTHER INFORMATION: Incyte ID No: 369950.68

<400> SEQUENCE: 51

```
cctttgccgc cgccttagcc cgggacccga acccagcctc tcccctaccc gaacaccggc     60

cccggctcca ccgaggcccg ggtcccccag cccgtctcgc cgccgccatg gcggacccta    120

aatacgccga ccttcccggc attgccagga atgagccaga tgtttatgaa actagcgacc    180

tacctgagga tgatcaagcg gagttcgatg cgtttgcaca agagctggag gagctgacaa    240

gcacaagtgt ggaacacatc attgtcaatc ctaatgctgc ctatgacaag ttcaaggaca    300

agagagtggg gacaaaggga cttgatttct cagatcgtat tggaaaaacc aagaggacag    360

gatatgaatc tggagaatat gagatgcttg gagagggtct gggagtgaag gagacacccc    420

agcaaaagta ccagcgccta ctgcatgagg tccaagagct gacaactgaa gttgaaaaaa    480

tcaagacgac agtgaaggag tcagccacag aggagaagct gacccctgtg ttgctggcta    540

aacagctggc agccctgaag cagcagctgg ttgcttccca cctggagaag ctgctgggac    600

cagatgctgc aatcaacctt accgaccccg atggcgccct ggctaagcgc ctactactgc    660

agctggaagc aacaaagaac agcaaagggg gatcaggggg aaaaaccact gggacccccc    720

cagatagcag ccttgtcact tatgaactac attctcggcc tgagcaggac aagttctctc    780

aagctgccaa agtcgcagaa cttgaaaagc gcctgacaga gctggagaca gctgtacgtt    840

gtgatcagga tgctcagaat cccctttctg caggtctaca gggagcctgt ctcatggaga    900

ctgtagagct gttgcaagca aaggtgagcg ccctagacct tgcagttttg gatcaagtgg    960

aggctcggct acagagtgtc ctgggaaagg tgaacgagat tgccaagcat aaagcctctg   1020
```

-continued

```
tagaagatgc agatacacaa agcaaggtgc accagctata tgaaactata cagcgctgga   1080
gccccattgc ctccaccctc cctgagctgg tgcagagact tgtcaccatc aagcagctgc   1140
acgagcaagc catgcagttt ggtcagctcc tgacacactt ggataccacc cagcagatga   1200
ttgctaattc cttgaaggac aataccaccc tcttgaccca ggtgcagaca accatgcgtg   1260
aaaacctggc cacagttgag gggaactttg ccagcattga tgaacggatg aagaagctgg   1320
gaaagtgagc acatttggga gctggagaac aggggttatc cctacccctg tgaactctgt   1380
taacagctta catagggttt cccctttact ataactctag catccccatc ccatttgaca   1440
ctgggggcaa gggttcttct tgcatgtggg gtttataccc ctcccctgat gaatacagag   1500
tggtagctag ggttggtta tcatcagaag gtggtctccc ctcaggcctg gggataagg   1560
acgtgggccc agccacatgc caactcatgt ccaatactgc tttgcctggt gtggggaagg   1620
attgggtctt gtcccccaac acagcttctg tggctgactg taatactgta caactgtttc   1680
tgaccattaa atgctgttgt actctgtgtg gcctctgctg tgtttcctgg ggaggaagca   1740
gcactaggac atagatattc attcgtcata acaggcaatc taagccactc tatactacaa   1800
gagatggatt taaattgtaa cctgttctta ccaaagaact aaataaaaaa tgagtacaga   1860
gccagagcca gagtttcaaa atattctcat ctgttaaatt aagagtgtct cccatagaaa   1920
agcagtggag gccccacagg gcaagtacaa aacagaatta aaactcccaa gggtcttgtc   1980
tttacaaaag aaaaggcagg aggcagcccc tggacagctg gtcatgctgg ccgctccggt   2040
tggaccacgt tgcataatcc tcagtcgcat catcacaacg tctctttcac tgggaaggag   2100
ggcagcagcc aacagtagct cacaggtttg taaactgagc ctgttggcca ctgtccacag   2160
gtgcaggtgg ctggcagggg ctcccaaggc tcagcactca gctctcccca atcagggtca   2220
gatccagctc caggtatggc tgctatgggg ccagtttcct cctcttgttt ttggcaggac   2280
ggccagggcg ggcccgggga ggcagaggga cagctgctcg ggctgtaggg ctg          2333
```

<210> SEQ ID NO 52
<211> LENGTH: 2201
<212> TYPE: DNA
<213> ORGANISM: Homo sapiens
<220> FEATURE:
<221> NAME/KEY: misc_feature
<223> OTHER INFORMATION: Incyte ID No: 223035.8

<400> SEQUENCE: 52

```
gaaagtttca tttatctaat caatgatttg gttaggcggt aatcattttt taatttgatt     60
caaatatgcc ccacgggtaa cagatgccca tgtcccctct ggccccaggg gacatcttca    120
tcaccagcgt ggacgccgcc acgaccttcg aggagctctg tgaggaagtg agagacatgt    180
gtcgtctgca ccagcagcac ccgctcaccc tcaagtgggt ggacagcgaa ggtgaccctt    240
gcacggtgtc ctcccagatg gagctggaag aggctttccg cctggcccgt cagtgcaggg    300
atgaaggcct catcattcat gttttcccga gcacccctga gcagcctggc ctgccatgtc    360
cgggagaaga caaatctatc taccgccggg gagccagaag atggaggaag ctgtaccgtg    420
ccaacggcca cctcttccaa gccaagcgct ttaacaggag agcgtactgc ggtcagtgca    480
gcgagaggat atggggcctc gcgaggcaag gctacaggtg catcaactgc aaactgctgg    540
tccataagcg ctgccacggc ctcgtcccgc tgacctgcag gaagcatatg gattctgtca    600
tgccttcccg agagcctcca gtagacgaca agaacgagga cgccgacctt ccttccgagg    660
agacagatgg aattgcttac atttcctcat cccggaagca tgacagcatt aaagacgact    720
```

-continued

```
cggaggacct taagccagtt atcgatggga tggatggaat caaaatctct caggggcttg    780
ggctgcagga ctttgaccta atcagagtca tcgggcgcgg gagctacgcc aaggttctcc    840
tggtgcggtt gaagaagaat gaccaaattt acgccatgaa agtggtgaag aaagagctgg    900
tgcatgatga cgaggatatt gactgggtac agacagagaa gcacgtgttt gagcaggcat    960
ccagcaaccc cttcctggtc ggattacact cctgcttcca gacgacaagt cggttgttcc   1020
tggtcattga gtacgtcaac ggcggggacc tgatgttcca catgcagagg cagaggaagc   1080
tccctgagga gcacgccagg ttctacgcgg ccgagatctg catcgccctc aacttcctgc   1140
acgagagggg gatcatctac agggacctga agctggacaa cgtcctcctg gatgcggacg   1200
ggcacatcaa gctcacagac tacggcatgt gcaaggaagg cctgggccct ggtgacacaa   1260
cgagcacttt ctgcggaacc ccgaattaca tcgcccccga aatcctgcgg ggagaggagt   1320
acgggttcag cgtggactgg tgggcgctgg gagtcctcat gtttgagatg atggccgggc   1380
gctccccgtt cgacatcatc accgacaacc cggacatgaa cacagaggac taccttttcc   1440
aagtgatcct ggagaagccc atccggatcc cccggttcct gtccgtcaaa gcctcccatg   1500
ttttaaaagg atttttaaat aaggacccca aagagaggct cggctgccgg ccacagactg   1560
gattttctga catcaagtcc cacgcgttct tccgcagcat agactgggac ttgctggaga   1620
agaagcaggc gctccctcca ttccagccac agatcacaga cgactacggt ctggacaact   1680
ttgacacaca gttcaccagc gagcccgtgc agctgacccc agacgatgag gatgccataa   1740
agaggatcga ccagtcagag ttcgaaggct ttgagtatat caacccatta ttgctgtcca   1800
ccgaggagtc ggtgtgaggc cgcgtgcgtc tctgtcgtgg acacgcgtga ttgacccttt   1860
aactgtatcc ttaaccaccg catatgcatg ccaggctggg cacggctccg agggcggcca   1920
gggacagacg cttgcgccga gaccgcagag ggaagcgtca gcgggcgctg ctgggagcag   1980
aacagtccct cacacctggg cccgggcagg ccagcttcgt gctggaggaa cttgctgctg   2040
tgcctgcgtc gcggcggatc cgcggggacc ctgccgaggg ggctgtcatg cggtttccaa   2100
ggtgcacatt ttccacggaa acagaactcg atgcactgac ctgctccgcc aggaaagtga   2160
gcgtgtagcg tcctgaggaa taaaatgttc cgatgatgtg g                       2201
```

<210> SEQ ID NO 53
<211> LENGTH: 3770
<212> TYPE: DNA
<213> ORGANISM: Homo sapiens
<220> FEATURE:
<221> NAME/KEY: misc_feature
<223> OTHER INFORMATION: Incyte ID No: 232956.2

<400> SEQUENCE: 53

```
gtcggtccct agcgcggctg cggggcggag agctgcggct ggcccagcgc gcccacctga     60
ggaggcggcg gggtccgcag gcgtcgcggg acgaggagat cggagccggg agactcgcgc    120
aggccatggc ccccattggc ctcaaagctg ttgtcggaga gaagattatg catgatgtga    180
taaagaaggt caagaagaag ggggaatgga aggtgctggt ggtggatcag ttaagcatga    240
ggatgctgtc ctcctgctgc aagatgacag acatcatgac cgagggcata acgattgtgg    300
aagatatcaa taagcgcaga gagccgctcc ccagcctggg aggctgtgta tctcatcact    360
ccatccgaga agtccgtcca ctctctcatc agtgacttta aggacccgcc gactgctaaa    420
taccgggctg cacacgtctt cttcactgac tcttgtccag atgccctgtt taatgaactg    480
gtaaaatccc gagcagccaa agtcatcaaa actctgacgg aaatcaatat tgcatttctc    540
```

-continued

```
ccgtatgaat cccaggtcta ttccttggac tctgctgact ctttccaaag cttctacagt    600
ccccacaagg ctcagatgaa gaatcctata ctggagcgcc tggcagagca gatcgcgacc    660
ctttgtgcca ccctgaagga gtacccggct gtgcggtatc ggggggaata caaggacaat    720
gccctgctgg ctcagctaat ccaggacaag ctcgatgcct ataaagctga tgatccaaca    780
atgggggagg gcccagacaa ggcacgctcc cagctcctga tcctggatcg aggctttgac    840
cccagctccc ctgtgctcca tgaattgact tttcaggcta tgagttatga tctgctgcct    900
atcgaaaatg atgtatacaa gtatgagacc agcggcatcg gggaggcacg ggtgaaggag    960
gtgctcctgg acgaggacga cgacctgtgg atagcactgc gccacaagca catcgcagag   1020
gtgtcccagg aagtcacccg gtctctgaaa gatttttctt ctagcaagag aatgaatact   1080
ggagagaaga ccaccatgcg ggacctgtcc cagatgctga agaagatgcc tcagtaccag   1140
aaagagctca gcaagtactc cacccacctg caccttgctg aggactgtat gaagcattac   1200
caaggcaccg tagacaaact ctgccgagtg gagcaggacc tggccatggg cacagatgct   1260
gagggagaga agatcaagga ccctatgcga gccatcgtcc ccattctgct ggatgccaat   1320
gtcagcactt atgacaaaat ccgcatcatc cttctctaca tctttttgaa gaatggcatc   1380
acggaggaaa acctgaacaa actgatccag cacgcccaga tacccccgga ggatagtgag   1440
atcatcacca acatggctca cctcggcgtg cccatcgtca ccgattccac gctgcgtcgc   1500
cggagcaagc cggagcggaa ggaacgcatc agcgagcaga cctaccagct ctcacggtgg   1560
actccgatta tcaaggacat catggaggac actattgagg acaaacttga caccaaacac   1620
taccctttata tctctacccg ttcctctgcc tccttcagca ccaccgccgt cagcgcccgc   1680
tatgggcact ggcataagaa caaggcccca ggcgagtacc gcagtggccc ccgcctcatc   1740
attttcatcc ttggggggtgt gagcctgaat gagatgcgct gcgcctacga ggtgacccag   1800
gccaacggaa agtgggaggt gctgatagga tccacacaca tcctcacccc acagaaactg   1860
ctggacacac tgaagaaact gaataaaaca gatgaagaaa taagcagtta aaaaaataag   1920
tcgcccctcc aaaacacgcc cccatcccac agcgctccgc agcttcccac caccgcccgc   1980
ctcagttcct ttgcgtctgt tgcctcccca gccctgcacg ccctggctgg cactgttgcc   2040
gctgcattct cgtgttcagt gatgccctct tcttgtttga aacaaaagaa aataatgcat   2100
tgtgtttttt aaaaagagta tcttatacat gtatcctaaa aagagaagct catgtgcaat   2160
tggtgcacag caggagaaat ttctggactg ttaggatgaa tggacgcctt ctccccgtta   2220
tttaagattt gtgaccttgt acataaccct gggtgacgtg cacattgctt gggtatggaa   2280
cggtagaaat ttgggtgttt ttaaaacctt gtttggggtt gttcctgtcc ttgttgagaa   2340
tcatagagat gtctgtgttc ttggagtatt tcacactgag gactaatctg ctatcttcat   2400
tccagtccct accccctcagt gcctgctctc atccaaataa cctgggaggt gacaatcagg   2460
atatctcagg aggtccaagg tggaacagac ctctttgcct ttcccagcgt ctcatacccc   2520
cggtagtgca gctgtgggtg gaggctgggg tgtctgcacg aagtcaggcc agcgtcctcc   2580
tccacagcct gtcactgccc cctccccagc ctgtgtccac agtgctgtga tcccgaggga   2640
agtcctccag tctaagtcac agtgccctga caggtgagaa gcaaactccc gctggaagcc   2700
tccatctctt tggaaaaaca gttagtctgg agcctgtggc ccaggccctt ctgtccccag   2760
gcatcatccc aacagctcat tttccctagt ccgccttcgt tcaagggtca ggaatggacc   2820
agaacagatg ggttctggag gcccctgaac agagggctat ggctgtggag aaggttcttg   2880
```

-continued

```
gcccgttgga ctcacacaga ccctgtaccc tctcggcaag catcttcagt cagattatcc   2940

tcagtttcag atacttcata ataccttgtg ttgtgtgggg tcatacatca tcgtgtttgt   3000

aagagaagat ggtcatttta ttctctgtat aaaacttagc tctaaagcag aaactaaagc   3060

agcaaatgca ggaaggctgt ctcgccatcc tcaagactca gcagctctca ttctccagtg   3120

gtgagcacac catttgtgct gctgctgttg tcgtgaaata taataacagt ggaagtcaca   3180

aaaatgtccc ctgcccagcc ccctcgccgc ccttgacctc ctgcaggcca tgtgtgtatt   3240

acttgtctag tgatgtcctc tcaaagtgct gtacgcgagc tcggcgccac ctccgcctcc   3300

ctttcagagc ctgctccccg ccctctctgc tcgctgcatt gtggtgttct cttctcaagg   3360

ctttgaaatc tccccttgca ctgagattag tcgtcagatc tctccccgtc tccctcccaa   3420

cttatacgac ctgatttcct taggacggaa ccgcaggcac ctgcgccggg cgtcttactc   3480

ccgctgcttg ttctgtcccc tccctcggac caaacagtgc tcatgcttca ggaccttgtt   3540

tgtcgaagat gttggtttcc ctttctctgt tatttatata aaaataattt atcaaaagga   3600

tattttaaaa aagctagtct gtcttgaaac ttgtttacct taaaattatc agaatctcag   3660

tgtttgaaag tactgaagca caaacatata tcatctctgt accattctgt actaaagcac   3720

ttgagtctaa taaataaaga aatcagcacc ccttcccggt gtccaggggg              3770


<210> SEQ ID NO 54
<211> LENGTH: 5722
<212> TYPE: DNA
<213> ORGANISM: Homo sapiens
<220> FEATURE:
<221> NAME/KEY: misc_feature
<223> OTHER INFORMATION: Incyte ID No: 331485.3

<400> SEQUENCE: 54

ggcggctcag acacggcccg agcgccgccg gggacgcgga cagagacccg cacgggcacg     60

ggcgctgcgc tggaggctcc cctcgcggtc cggggctgcg cgaccatggc ggacaaggag    120

gccggcggca gcgacgggcc ccgagaaacg gctcccacat ctgcatattc atctccagcc    180

cggagtcttg gggacacagg aataacgcct ctgtccccct cccatattgt gaacgacact    240

gactccaacg tctcagaaca gcagtcattt ctcgtggtgg tggccgtcga ctttgggacc    300

acatccagtg gctatgccta cagcttcacc aaggagccgg aatgcatcca tgtgatgagg    360

cgatgggagg gaggtgaccc tggtgtgtcc aatcagaaga ctccaaccac catcttgctg    420

actcccgaga ggaagttcca cagcttcggg tatgccgcca gggactttta ccatgacctg    480

gatcccaatg aggccaagca gtggctgtac ctggagaagt tcaagatgaa gctgcacacc    540

actggggacc tcaccatgga tacagacctg acggcagcaa atggcaagaa agtcaaagcc    600

cttgaaatct ttgcttatgc cctgcagtac tttaaggagc aggcgctgaa ggagctgagt    660

gaccaggcgg gttcggagtt cgagaactct gatgtcagat gggtcatcac ggtgcctgcc    720

atctggaagc agccggccaa gcagttcatg agacaagctg cctaccaggc aggcctggcc    780

tcccccgaga actcggagca gctcatcatt gccttggagc ctgaggcagc ctctatctac    840

tgccgaaagc tgcggctaca ccagatgatt gagctgagca gcaaggcagc cgtcaatggg    900

tacagcggca gtgacacagt aggagctggg tttacacagg ctaaggaaca catacggcgt    960

aatcggcaga gtcggacctt tttggtggag aatgtcatag gagaaatctg gtccgagctg   1020

gaggaaggtg ataagtatgt ggttgtggac agtggcggtg gcaccgtaga cctgacagtc   1080

catcagatcc ggttaccgga gggacacctt aaggaactgt ataaagcaac aggcggaccc   1140
```

-continued

```
tatggatctt tagagagtag attatgagtt cgaaaaactt ctgtataaaa tatttggaga   1200
ggattttatt gaacaattca aaatcaaacg ccctgcagcc tgggttgact taatgattgc   1260
gtttgagtct cgcaaaaggg cggctgcccc agacagaact aacccgctga acatcaccct   1320
gcccttctcc ttcattgact actacaagaa gttccgcggg cacagtgtgg agcacgcctt   1380
gcggaaaagc aatgtggatt tggtgaagtg gtcctcgcag gggatgctgc ggatgagtcc   1440
agatgccatg aacgcccttt ttaagccgac catcgatagc atcattgagc atctccggga   1500
cctgtttcag aagcccgagg tgtccaccgt caagttcctc tttctggtgg gcggctttgc   1560
cgaggcgccc ctgctgcagc aggcggtgca ggctgctttt ggggaccagt gccggatcat   1620
catcccccag gacgtgggcc tcaccatcct caagggtgcc gtcctctttg gcctggaccc   1680
cgcggtcatc aaggtgcgcc ggtcgccgct cacctacggg gtaggcgtgc tgaaccgcta   1740
cgtggagggc aagcacccgc ctgagaagct gctggtgaag gatggcactc ggtggtgcac   1800
cgacgtcttt gacaagttca tctctgccga ccagtctgtg gctctgggtg agctggtcaa   1860
gcgtagctac accccggcca agccctccca gctggtcatt gtcatcaaca tctacagctc   1920
tgagcacgac aacgtcagct tcatcactga tcccggggtg aagaagtgtg gcacgctccg   1980
cctggatctc acagggacca gtggcactgc ggtgcccgcc cggagggaga tccagaccct   2040
tatgcagttc ggggacaccg agatcaaagc cacagccatt gatatagcca cttcgaagag   2100
tgtcaaagtt gggatcgact tcttaaatta ctaaccctcc cgccccgctg cctgtcccct   2160
tggactcaac ttatctgcat ctgctgacct caaccttgac tgttctttcc ctaaccttga   2220
ccctcaccat tgcccatgtg aatttcagca gggaagatga gaacaatcag ggctagaaat   2280
aattagtgac ttttgagggc acactggagt cagaaaaaca gaaattaaga ttaaggttta   2340
ggcatagaaa attaaaggat cctggaggag cagctagttt tcataggtac aaaagtggtg   2400
aaatggccac ggagaaggga atcagtacat ttctgcagca gtggttgcgc tgctttgaac   2460
agatctccgt tatgtagaat ttaggatgcc ctattgctgt ctttctagat ttaaaatgag   2520
atctttgaac caggaggaga tcttcatctg agacttgtct ttctaaattt tttggatggc   2580
catcaatata aaatgccacc catctgcagt taatttcttt tcctcatcat gtgattaaaa   2640
gtggtgattc agtgggaact gggaatgttt ttagctggtg gtagaaggct gcctacactg   2700
ggcactgttt tagattctca tatcatttaa acagcaagga ggttcaggga agaataaccg   2760
tagccttggg taatccacta gggcttttgt gagtaggaga gctgatacct cacattctta   2820
gcaggtgaaa acttgccatg atggaaacag atagtgaaga gttactgacg tatcccaaat   2880
tatatgctgt gacataaatt cccagcatgc ccagccctga tttctgagtt cataagtaat   2940
tctagtgaac cttagtagga attctgggta agaaaatgag gttgccattg gtcttgtttg   3000
catcaccaag accagacatc cagaagagcc cctcaccttg aaaagcagac agattttaaa   3060
ttaacccccct ccttcccact caccttcatc tccctaagag ttttggccat ttaattccac   3120
attttgaaag gaatacattg gtgaaatttg ggaagagaat ctgtgctatg caatgtttca   3180
ttaaaatctt cagtttttca agtctctcta aaaataattt gtagatctat acttgatgta   3240
ttaagtcagt ttttttttcac agcgggcctg tggctcgcct gcatcagaat tgcctgggtg   3300
cgtgttcaga acaggttcct ggatctgagc ccttttttaac tgaggccgac tcttggagag   3360
gggcaccaga atctgcattt gtagtgtata ccacatcgtg gttcaactga aattggagaa   3420
atactaacct gagattttgt tgaagttcac acacagatca cagcccgccc tctgcaggtg   3480
tccccctttgg gctcctttag gaagagggtt ccatgagaag gtgaccccat accttgccct   3540
```

-continued

```
cttggtcaat gggattgggg ctccacctgg cttggagatg gcccttttaa ccctcacagg   3600
aagggccagg ggaggaaaaa aattgcaaga aagcgacacc aagaacggag ctgactgagg   3660
aaccaactgg agggtcttca ctctctcctt ccccagtgta caaaaccagt tttctgcaac   3720
attcaggagc caaatgagga aaaagaatca agaatctgac tcacagccca tctgatctgt   3780
tcaaagctgt cttttccacc tgctgaaatt cattaaatca ctggaggcat gcataatgaa   3840
tggagaatga gtgaacttcc aatgcaactt ggattcacaa acccattatc atagccaata   3900
tgcagatttt aaacagcatt tcacatttca tttgaccatg tcttcttttt cggcatcgcc   3960
tgctgcagaa ttccctacta gaatgtgaaa caacgaacaa accacagaac ttagagtgtg   4020
ctggttagtc acataactta gtagcaggat tgtgtatcca ggcacaaagg tgtctttgct   4080
aatgttctct tgctacctgc cctgcttcaa acgctaaatg gtatgggtct ttctttgttg   4140
ccagccatat tctacaaata agacttttca atatagttat gagtaatata attttatgta   4200
catataatgt tagaatattg tacagaatct tggtttctac gatgcgcttt tcttgtttca   4260
aaaagaggaa aatgcttgat ttttgttgat gatacttttg ttactgtcct taattttcca   4320
tagtttggtt tcttaattgt gctcactaag catcgatctg tgctgatgcc aagctatgga   4380
ctatgtacgc aagaccgagc aatagacaga ggtgcctagg gtccaaacac actgaacgca   4440
cgtggaccgc ctggatcagg agcctcatca gacccttctc catgcacatc cttcccaaac   4500
agtcacagat tccattgaaa ggagcagatt ctatcagttc ttctgtgcag actttaagag   4560
ctgaacgttc tggttctgga agccatgtga ctgcgcagaa caacctaaga aaccctttgt   4620
gtcctgaggg gtcgttgacc tctccttccg ggtcggagca gtcactctga gggcaaagcg   4680
tggtccactg tgtgtgatgt tttcaggatg ctagggtcaa agaaagaaac caagtggtac   4740
ataagcccag cttttctgct gggctaagtg taagtgtgag taacatggtc aagcccctct   4800
tttttgggct aatgtaaagc ctttcctgcc ttgcattaat gctatctccc tgtgtactgt   4860
ttctcttaaa tgagcagata gaaatctgca gtgttggcag ataggtgatg gagaggatga   4920
taattttatc ttctggccac agagctgcag ccccagttgt cagagtcctt aaatgaaacc   4980
cccaaatcca tccctccttc cctacccccca ctggaatatt ctagaataag agcactggat   5040
aagtacactt gaacacattt ttctaacctt agaaaatacc tacaaggcct gttgtcttga   5100
cccattactc aattgtccct ggcatattat ctgatcttca cgtttcttgg aagcagaatc   5160
atcaaggctt tcctttgtaa ctgccctttc cgtacacagc aggcatgaat aaatgctgag   5220
taacagacaa gttacagaca ggaggggaaa gaggaggaac catacaactg tttttgcaaa   5280
atgatggctg agtccagatt atagaggttg ccttaccctt agaatgttat ttagaccaag   5340
tttagctttt agagtccagg tctggttaat tgccagggta gcaaagaatc gcatgcacca   5400
atgtaaacag gagtcagaat gcattattag tcaaagatcg aatttcacat tgtagagatg   5460
tatagctgtg attaagctgc atatgtatgc tgggaaacgg cttgagtgga tggctaatat   5520
aaaagttgtt ggccataatg ccacacctct catctgcttg aaatatggac cagtattcta   5580
aaatatcagc tactggggtc tcattcacta caagataaat tcaaacttca cagaactttg   5640
cagcagttca ccaccagacg ggactgtgtc tgcaaactct cttgtcttca cagacgccta   5700
ataaagcaaa actctgaatc tc                                           5722
```

<210> SEQ ID NO 55
<211> LENGTH: 4494
<212> TYPE: DNA

-continued

<213> ORGANISM: Homo sapiens
<220> FEATURE:
<221> NAME/KEY: misc_feature
<223> OTHER INFORMATION: Incyte ID No: 024844.5

<400> SEQUENCE: 55
gacaagtcta gagcagcact agcgcagagt gagactcatc agctggcaag caggattctg 60
tgtctctggg ttcaggaatc ctcaggcagc agaggggact tgctcctcag cccccatcac 120
tgcccccacc cctacccgtg taggccaccg agtgaggccc atggactggg gagggctgtg 180
cctgacgact cctgtgtccc tctatgaggg cccagcgccc tgaccctcct gcctaggttt 240
ctaccttttc tctctgtctt tggccagctg ggggaggggg tagaggccgg gtgagcaaca 300
tggcacagag caagatgcac gtgtacagcc ggacgcccag cggcagcagg atgagtgcgg 360
aggcaagcgc ccggcctctg cgggtgggct cccgtgtaga ggtgattgga aaaggccacc 420
gaggcactgt ggcctatgtt ggagccacac tgtttgccac tggcaaatgg gtaggcgtga 480
ttctggatga agcaaagggc aaaaatgatg gaactgttca aggcaggaag tacttcactt 540
gtgatgaagg gcatggcatc tttgtgcgcc agtcccagat ccaggtattt gaagatggag 600
cagatactac ttccccagag acacctgatt cttctgcttc aaaagtcctc aaaagagagg 660
gaactgatac aactgcaaag actagcaaac tgcggggact gaagcctaag aaggcaccga 720
cagcccgaaa gaccacaact cggcgaccca agcccacgcg cccagccagt actggggtgg 780
ctggggccag tagctccctg ggcccctctg gctcagcgtc agcaggtgag ctgagcagca 840
gtgagcccag caccccggct cagactccgc tggcagcacc catcatcccc acgccggtcc 900
tcacctctcc tggagcagtc cccccgcttc cttccccatc caaggaggag gagggactaa 960
gggctcaggt gcgggacctg gaggagaaac tagagaccct gagactgaaa cgggcagaag 1020
acaaagcaaa gctaaaagag ctggagaaac acaaaatcca gctggagcag gtgcaggaat 1080
ggaagagcaa aatgcaggag cagcaggccg acctgcagcg gcgcctcaag gaggcgagaa 1140
aggaagccaa ggaggcgctg gaggcaaagg aacgctatat ggaggagatg gctgatactg 1200
ctgatgccat tgagatggcc actttggaca aggagatggc tgaagagcgg gctgagtccc 1260
tgcagcagga ggtggaggca ctgaaggagc gggtggacga gctcactact gacttagaga 1320
tcctcaaggc tgagattgaa gagaagggct cagatggcgc tgcatccagt tatcagctca 1380
agcagcttga ggagcagaat gcccgcctga aggatgccct ggtgaggatg cgggatcttt 1440
cttcctcaga gaagcaggag catgtgaagc tccagaagct catggaaaag aagaaccaag 1500
agctggaagt tgtgaggcaa cagcgggagc gtctgcagga ggagctaagc caggcagaga 1560
gcaccattga tgagctcaag gagcaggtgg atgctgctct gggtgctgag gagatggtgg 1620
agatgctgac agatcggaac ctgaatctgg aagagaaagt gcgcgagttg agggagactg 1680
tgggagactt ggaagcgatg aatgagatga acgatgagct gcaggagaat gcacgtgaga 1740
cagaactgga gctgcgggag cagctggaca tggcaggcgc gcgggttcgt gaggcccaga 1800
agcgtgtgga ggcagcccag gagacggttg cagactacca gcagaccatc aagaagtacc 1860
gccagctgac cgcccatcta caggatgtga atcgggaact gacaaaccag caggaagcat 1920
ctgtggagag gcaacagcag ccacctccag agacctttga cttcaaaatc aagtttgctg 1980
agactaaggc ccatgccaag gcaattgaga tggaattgag gcagatggag gtggcccagg 2040
ccaatcgaca catgtccctg ctgacagcct tcatgcctga cagcttcctt cggccaggtg 2100
gggaccatga ctgcgttctg gtgctgttgc tcatgcctcg tctcatttgc aaggcagagc 2160

-continued

```
tgatccggaa gcaggcccag gagaagtttg aactaagtga gaactgttca gagcggcctg   2220
ggctgcgagg agctgctggg gagcaactca gctttgctgc tggactggtg tactcgctga   2280
gcctgctgca ggccacgcta caccgctatg agcatgccct ctctcagtgc agtgtggatg   2340
tgtataagaa agtgggcagc ctgtaccctg agatgagtgc ccatgagcgc tccttggatt   2400
tcctcattga actgctgcac aaggatcagc tggatgagac tgtcaatgtg gagcctctca   2460
ccaaggccat caagtactat cagcatctgt acagcatcca ccttgccgaa cagcctgagg   2520
actgtactat gcagctggct gaccacatta agttcacgca gagtgctctg gactgcatga   2580
gtgtggaggt aggacggctg cgtgccttct tgcagggtgg gcaggaggct acagatattg   2640
ccctcctgct ccgggatctg gaaacttcat gcagtgacat ccgccagttc tgcaagaaga   2700
tccgaaggcg aatgccaggg acagatgctc ctgggatccc agctgcactg gcctttggac   2760
cacaggtatc tgacacgctc ctagactgca ggaaacactt gacgtgggtc gtggctgtgc   2820
tgcaggaggt ggcagctgct gctgcccagc tcattgcccc actggcagag aatgaggggc   2880
tacttgtggc tgctctggag gaactggctt tcaaagcaag cgagcagatc tatgggaccc   2940
cctccagcag cccctatgag tgtctgcgcc agtcatgcaa catcctcatc agtaccatga   3000
acaagctggc cacagccatg caggaggggg agtatgatgc agagcggccc cccagcaagc   3060
ctccaccggt tgaactgcgg gctgctgccc ttcgtgcaga gatcacagat gctgaaggcc   3120
tgggtttgaa gctcgaagat cgagagacag ttattaagga gttgaagaag tcactcaaga   3180
ttaagggaga ggagctaagt gaggccaatg tgcggctgag cctcctggag aagaagttgg   3240
acagtgctgc caaggatgca gatgagcgca tcgagaaagt ccagactcgg ctggaggaga   3300
cccaggcact gctgcgaaag aaggagaaag agtttgagga gacaatggat gcactccagg   3360
ctgacatcga ccagctggag gcagagaagg cagaactaaa gcagcgtctg aacagccagt   3420
ccaaacgcac gattgaggga ctccggggcc ctcctccttc aggcattgct actctggtct   3480
ctggcattgc tggtgaagaa cagcagcgag gagccatccc tgggcaggct ccagggtctg   3540
tgccaggccc agggctggtg aaggactcac cactgctgct tcagcagatc tctgccatga   3600
ggctgcacat ctcccagctc cagcatgaga acagcatcct caagggagcc cagatgaagg   3660
catccttggc atccctgccc cctctgcatg ttgcaaagct atcccatgag ggccctggca   3720
gtgagttacc agctggagcg ctgtatcgta agaccagcca gctgctggag acattgaatc   3780
aattgagcac acacacgcac gtagtagaca tcactcgcac cagccctgct gccaagagcc   3840
cgtcggccca acttatggag caagtggctc agcttaagtc cctgagtgac accgtcgaga   3900
agctcaagga tgaggtcctc aaggagacag tatctcagcg ccctggagcc acagtaccca   3960
ctgactttgc caccttccct tcatcagcct tcctcagggc caaggaggag cagcaggatg   4020
acacagtcta catgggcaaa gtgaccttct catgtgcggc tggttttgga cagcgacacc   4080
ggctggtgct gacccaggag cagctgcacc agcttcacag tcgcctcatc tcctaagcac   4140
tcctttcccc tgctgtcccc ttcgaccctc agccctctgg tgccgctctg cccgatgcac   4200
agcccacctc agccagcccc caggtagaaa cgtgggttaa gctcttcctg ccccgttcag   4260
cttcactccc accctttcag cgtcctgccc cttcaccttg acccgggttc ccccactccc   4320
attccctggc ctctgccata atttgttgtt caactgctcc ctccttcctg aggggcctca   4380
gggcttgtgg ggggtaggct gagaccccac caccaaaggt taagtgaggt ccccttgatt   4440
gaggacttca ccccttgatt aaagcaactt ctgcttcaaa aaaaaaaaaa aggg         4494
```

-continued

<210> SEQ ID NO 56
<211> LENGTH: 2056
<212> TYPE: DNA
<213> ORGANISM: Homo sapiens
<220> FEATURE:
<221> NAME/KEY: misc_feature
<223> OTHER INFORMATION: Incyte ID No: 481594.7

<400> SEQUENCE: 56

```
gaggccgcgg gcccgccccc gccggctagg tgaaggtgag tgtctcctcc agtcgcaacg     60
gccagacctg acctgccagc tccgggcgtg gggtgaaatc tcttgattcc tagtctctcg    120
atatggcacc tccgtcagtc tttgccgagg ttccgcaggc ccagcctgtc ctggtcttca    180
agctcactgc cgacttcagg gaggatccgg acccccgcaa ggtcaacctg ggagtgggag    240
catatcgcac ggatgactgc catccctggg ttttgccagt agtgaagaaa gtggagcaga    300
agattgctaa tgacaatagc ctaaatcacg agtatctgcc aatcctgggc ctggctgagt    360
tccggagctg tgcttctcgt cttgcccttg ggatgacag cccagcactc aaggagaagc    420
gggtaggagg tgtgcaatct ttggggggaa caggtgcact tcgaattgga gctgatttct    480
tagcgcgttg gtacaatgga acaaacaaca agaacacacc tgtctatgtg tcctcaccaa    540
cctgggagaa tcacaatgct gtgttttccg ctgctggttt tagagacatt cggtcctatc    600
gctactggga tgcagagaag agaggattgg acctccaggg cttcctgaat gatctggaga    660
atgctcctga gttctccatt gttgtcctcc acgcctgtgc acacaaccca actgggattg    720
acccaactcc ggagcagtgg aagcagattg cttctgtcat gaagcaccgg tttctgttcc    780
ccttctttga ctcagcctat cagggcttcg catctggaaa cctggagaga gatgcctggg    840
ccattcgcta ttttgtgtct gaaggcttcg agttcttctg tgcccagtcc ttctccaaga    900
acttcgggct ctacaatgag agagtcggga atctgactgt ggttggaaaa gaacctgaga    960
gcatcctgca agtcctttcc cagatggaga agatcgtgcg gattacttgg tccaatcccc   1020
ccgcccaggg agcacgaatt gtggccagca ccctctctaa ccctgagctc tttgaggaat   1080
ggacaggtaa tgtgaagaca atggctgacc ggattctgac catgagatct gaactcaggg   1140
cacgactaga agccctcaaa acccctggga cctggaacca catcactgat caaattggca   1200
tgttcagctt cactgggttg aaccccaagc aggttgagta tctggtcaat gaaaagcaca   1260
tctacctgct gccaagtggt cgaatcaacg tgagtggctt aaccaccaaa aatctagatt   1320
acgtggccac ctccatccat gaagcagtca ccaaaatcca gtgaagaaac accacccgtc   1380
cagtaccacc aaagtagttc tctgtcatgt gtgttccctg cctgcacaaa cctacatgta   1440
cataccatgg attagagaca cttgcaggac tgaaaggctg ctctggtgag gcagcctctg   1500
tttaaaccgg ccccacatga agagaacatc ccttgagacg aatttggaga ctgggattag   1560
agcctttgga ggtcaaagca aattaagatt tttatttaag aataaaagag tactttgatc   1620
atgagacata ggtatcttgt ccctctcact aaaaaggagt gttgtgtgtg gcggccacgt   1680
gcttctatgt ggtgtttgac tctgtacaaa ttctagtccc aaagatcaag ttgtctgaag   1740
gagccaaagt gtgaatgtgg gtgtcggctg cggcattaaa ttcatcatct caacccagag   1800
tgtctggtct ccctgctctt tctgcatggt tgtgtcccta gtcctaagct ttggttcttt   1860
agggtgactg tggtaagaag gatatttaat catgacatgc acggacacgt acatatttaa   1920
ctgaaacaag ttttaccaaa cagtatttac tcgtgatgtg cgtagtgcat tctgatattt   1980
ttgagccatt ctattgtgtt ctacttcacc taaaaaaata aaataaaaat gttgatcaag   2040
aaaaaaaaaa aaaagg                                                   2056
```

-continued

<210> SEQ ID NO 57
<211> LENGTH: 6268
<212> TYPE: DNA
<213> ORGANISM: Homo sapiens
<220> FEATURE:
<221> NAME/KEY: misc_feature
<223> OTHER INFORMATION: Incyte ID No: 453592.3
<221> NAME/KEY: unsure
<222> LOCATION: 2956, 4230-4252, 4825-4887
<223> OTHER INFORMATION: a, t, c, g, or other

<400> SEQUENCE: 57
catcagcggg cgggggtgtc gccgaacagg ctgctccgca gagcccgccg cgaccccgcg 60
ccgccccgcc ccgcggcctg cctgccagag gagccgaggg ggccgcccct cgcccaacct 120
gcccgacatg gggaaccccg ggcccaggcg tgctggtcac catgacaaca gagacaggcc 180
ccgactctga ggtgaagaaa gctcaggagg aggccccgca gcagcccgag gctgctgccg 240
ctgtgaccac ccctgtgacc cctgcaggcc acggccaccc agaggccaac tccaatgaga 300
agcatccatc ccagcaggac acgcggcctg ctgaacagag cctagacatg gaggagaagg 360
actacagtga ggccgatggc ctttcggaga ggaccacgcc cagcaaggcc cagaaatcgc 420
cccagaagat tgccaagaaa tacaagagtg ccatctgccg ggtcactctg cttgatgcct 480
cggagtatga gtgtgaggtg gagaaacatg gccggggcca ggtgctgttt gacctggtct 540
gtgaacacct caacctccta gagaaggact acttcggcct gaccttctgt gatgctgaca 600
gccagaagaa ctggctggac cctccaaggg agatcaagaa gcagatccgg agtagcccct 660
ggaattttgc cttcacagtc aagttctacc cgcctgatcc tgcccagctg acagaagaca 720
tcacaagata ctacctgtgc ctgcagctgc gggcagacat catcacgggc cggctgccat 780
gctcctttgt cacgcatgcc ctactgggct cctacgctgt gcaggctgag ctgggtgact 840
atgatgctga ggagcatgtg ggcaactatg tcagcgagct ccgcttcgcc cctaaccaga 900
cccgggagct ggaggagagg atcatggagc tgcataagac atatagggg atgaccccgg 960 gagaagcaga aatccacttc ttagagaatg ccaagaagct ttccatgtac ggagtagacc 1020
tgcaccatgc caaggactct gagggcatcg acatcatgtt aggcgtttgt gccaatggcc 1080
tgctcatcta ccgggaccgg ctgagaatca accgctttgc ctggcccaag atcctcaaga 1140
tctcctacaa gaggagtaac ttctatatca agatccggcc tggggagtat gagcaatttg 1200
agagcacaat tggctttaag ctcccaaacc accggtcagc caagagactg tggaaggtct 1260
gcatcgagca tcatacattc ttccggctgg tgtcccctga gcccccaccc aagggcttcc 1320
tggtgatggg ctccaagttc cggtacagtg ggaggaccca ggcacagact cgccaggcca 1380
gcgccctcat tgaccggcct gcacccttct ttgagcgttc ttccagcaaa cggtacacca 1440
tgtcccgcag ccttgatgga gcagagttct cccgcccagc ctcggtcagc gagaaccatg 1500
atgcagggcc tgacggtgac aagcgggatg aggatggcga gtctgggggg caacggtcag 1560
aggctgagga gggagaggtc aggactccaa ccaagatcaa ggagctaaag ccggagcagg 1620
aaaccacgcc gagacacaag caggagttct tagacaagcc agaagatgtc ttgctgaagc 1680
accaggccag catcaatgag ctcaaaagga ccctgaagga gcccaacagc aaactcatcc 1740
accgggatcg agactgggaa cgggagcgca ggctgccctc ctcccccgcc tccccctccc 1800
ccaagggcac ccctgagaaa gccaatgaga gagcagggct gagggagggc tccgaggaga 1860
aagtcaaacc accacgtccc cgggccccag agagtgacac aggcgatgag gaccaggacc 1920

-continued

```
aggagaggga cacggtgttc ctgaaggaca accacctggc cattgagcgc aagtgctcca   1980
gcatcacggt cagctctacg tctagcctgg aggctgaggt ggacttcacg gtcattggtg   2040
actaccatgg cagcgccttc gaagacttct cccgcagcct gcctgagctc gaccgggaca   2100
aaagcgactc ggacactgag ggcctgctgt tctcccggga tctcaacaag ggggccccca   2160
gccaggatga tgagtctggg ggcattgagg acagcccgga tcgaggggcc tgctccaccc   2220
cggatatgcc ccagtttgag cccgtgaaaa cagaaaccat gactgtcagc agtctggcca   2280
ttagaaagaa gattgagccg gaggccgtac tgcagaccag agtctccgct atggataaca   2340
cccagcaggt tgatgggagt gcctcagtgg ggagggagtt catagcaacc actccctcca   2400
tcaccacgga gaccatatcg accaccatgg agaacagtct caagtccggg aagggggcag   2460
ctgccatgat cccaggccca cagacggtgg ccacggaaat ccgttctctt tctccgatca   2520
tcgggaaaga tgtcctcacc agcacctacg gcgccactgc ggaaaccctc tcaacctcca   2580
ccaccaccca tgtcaccaaa actgtgaaag gagggttttc tgagacaagg atcgagaagc   2640
gaatcatcat tactggggat gaagatgtcg atcaagacca ggccctggct ttggccatca   2700
aggaggccaa actgcagcat cctgatatgc tggtaaccaa agctgtcgta tacagagaaa   2760
cagacccatc cccagaggag agggacaaga agccacagga atcctgacct ctgtgaagag   2820
atcctggcat ttctggtcca acccaagcca gagaaccatt aagaaggggc cttcattctg   2880
gattctccga cgcaacactg acgtcccagc tgcgacgtac tgtcactgat gagagactgg   2940
gaagggaaaa gcatanatat atagatatat agagatatag atatatatac aggaaacacc   3000
gcatccttgc actgctgctg gggctggcag agcagttggc tgacagcaac aaccgacatc   3060
tgaacaccta catttccttt gcagacaaat tgaagaactg gtgggatttt tttcaagaaa   3120
aaaaattata taataactat aatcccttgc tcacccettt cccccgccaa ataagaaacg   3180
caagccagac cacgatgatt gtagaagtcc ctcccgccct ggttctgcac gttacagtta   3240
gcagacgagc aattccattt gttcttctcc agcatctcta aggcccactt gaatgcaaag   3300
gaaaacactt gcacagcaaa gcaagagaag tcacagcagc aagacacgca cagtcaacca   3360
ttttccgaga aaaaaagaaa attccccact tggaaagaaa gaggaggaac actggattct   3420
tactttctgg atcttgacac tgggctgcaa aacctacctt cctctctccc gcctcccctc   3480
accctcaact ctcaatgtct tgctgtcatt ttctgtctcg gctccctcct ccccccttccc   3540
ccttccccca ccccacaccc ttcaccctct gtgtcctggt ccttctgagg gccactgcag   3600
atgactctcc tttgaaatga gaaaaagaaa agaaagcaag aacagaaaac gaagccacag   3660
gaagggaagt agacattgta tgcttatggt ttctcattat gaaggtgcag cttgtaggag   3720
gtttgtacgg atgtgctttg aagttatgta tattacatat aacaggaaaa aatattaaaa   3780
taaacagtgc tggtaagtat gaagctgaca ttctaaaatt ataattatct gactgtgatt   3840
gatgtatcct gaggttccta gatctcactg aactggccca gctaaggaga cctggactct   3900
gggtgtgggt tggctcacag taggggctga cgggttcagt gtagtaatac tgtgtgtggt   3960
gtttgtaatt ggttgattgg tggggagggg tggggggccc taatggagag gtgtgggttt   4020
ggcaagaaag aagcaacaca gatgtcgtcc ccaaaatgcc agttcaagac accttctccc   4080
tgcccccctg gtagtaacag tcagggcctg gtctgtgctc aggtactggg tcccagtctg   4140
ggactctgct gctgaagttg ccacagtaga ggtccctggc ttagtcctta tctccctacg   4200
gggcttgcct tggttttcag tcttctctcn nnnnnnnnnn nnnnnnnnnn nngccacatt   4260
ctgcccttcc ctgaccccat tgtaataacc aactccatat ccaaagggag gtggtgctct   4320
```

-continued

```
cagccattgt agaagatggt ggctttaacc tgactgtcta aaaattccca gctaagcctt   4380
ttcctctact ctcttccttg ttctgaatca tttcttcttc tcaggccaaa gtagccatgg   4440
taaggaggct tcatggggca gaccctgaaa gatcaaaact gcatttgcaa agccctcccc   4500
tgtcccagga caaagctgag actgacgggt gatgttgctc ataggctcca gctctgcata   4560
agaccttggc ttggagacct ccctctcagt caacagctga actctgagct tgtgcccaga   4620
aattacccca agaccacagg aacccttcaa gaagctccca tcacaagctt ggcattgctc   4680
tctgccacac gtgggcttcc tcaggcttgt ctgccacaag ctacttctct gagctcagaa   4740
agtgcccctt gatgagggaa aatgtcccac tgcactgcga atttctcagt tccattttac   4800
ctcccagtcc tccttctaaa ccagnnnnnn nnnnnnnnnn nnnnnnnnnn nnnnnnnnnn   4860
nnnnnnnnnn nnnnnnnnnn nnnnnnntga agaaggtggg aggggagggc ggaacctgag   4920
gagccacctg agccagcttt atatttcaac catggctggc ccatctgaga gcatctcccc   4980
actctcgcca acctatcggg gcatagccca gggatgcccc caggcggccc aggttagatg   5040
cgtccctttg gcttgtcagt gatgacatac accttagctg cttagctggt gctggcctga   5100
ggcagggcag gaaatcagaa tagcatttgc ttctctgggc aaatgggaag ttcagcgggg   5160
cagcagaatc agtggcattc cccctggtgc aggccggtgg gtccactcca actccccctg   5220
agtgtagcag cacactttcc atacaccagg ttctttctac aatcctggtg gaaaagccac   5280
agaaccttct tcctgccctt cttgagagtt ccccctcttt ctgggtcaag agctggagtg   5340
gtggctccat cctctctggg ccacttcggt ctaggaactc atctttgcag gaaccaggag   5400
tcctgagcac actgaacaca cctcagaggg aggatccttg ttgtggattt tgcacctggc   5460
tttggggcag gggtgaagtg accaggctta gcttgtggag tttatgggcc accagggttt   5520
ggggaaatca ccatcccgcg gatgctgtga cctcccttct acggagatgc aggcagtgcc   5580
acgagggagg aggggacctg caaagctaga atctagggca ctgtttcctc cccatccttc   5640
tctttgtaga gaatagagac gtttgtcttg tctgtcttca acctactttt cctttctctt   5700
tttttgtttc tcatcctctc tgtgccacct ctccacccag gaggccatgt agcatagtgg   5760
aaaaagtccc tgagggcggt taggagttct gggtgaccat cctggctcag ctcctaactc   5820
accatgtgac atcaggctat ccccattccc cctcttgggc ctcagtttcc cgacttgcaa   5880
aataagcaga aagaaccaga tgctctccag ggtctttttc tactttgcta tctcatgggt   5940
cttcattttc tcttattttg ttttctctgg atcttttcca tctgagggta caggaagtac   6000
caggacctgt ttcagttttt gaatcctgca agcacattcc aagactggcc tgaaactgca   6060
tgagcaacat cactcgaaat aatttttttt ttcaaaagca ccttaacaac caattgcgat   6120
gctgtcctgt tcctttttac tcacaccctt ctctcctttc tcgtccccat gctcccccac   6180
ctcagtgctc cgtgctgtat gcgtgtgctc tctgttcttg tatactcaat ataagtgaaa   6240
taaatgtgtt tgatgctgaa ccataaaa                                      6268
```

<210> SEQ ID NO 58
<211> LENGTH: 2637
<212> TYPE: DNA
<213> ORGANISM: Homo sapiens
<220> FEATURE:
<221> NAME/KEY: misc_feature
<223> OTHER INFORMATION: Incyte ID No: 127112.18

<400> SEQUENCE: 58

```
ggaggctacg aaacttgggg gagtgcacag aagaacttcg ggagcgcacg cgggaccagg     60
```

-continued

```
gaccaggctg agactcgggg cgccagtccg ggcaggggca gcgggagccg gccgggtagg    120
gtgcagcctg aggcttgttc agcagaacag gtgcaagcca cattgttgcc aagacctgcc    180
tgaagccgga ttctccccac tgcctccttc aaccccgcct cttcctcctc ctgtgggact    240
gctccccct cctgtgaggc tagatagatg ccctgtatcc aagcccaata tgggacacca    300
gcaccgagtc cgggaccccg tgaccacctg gcaagcgacc ccctgacccc tgagttcatc    360
aagcccacca tggacctggc cagccccgag gcagcccccg ctgcccccac tgccctgccc    420
agcttcagca ccttcatgga cggctacaca ggagagtttg acaccttcct ctaccagctg    480
ccaggaacag tccagccatg ctcctcagcc tcctcctcgg cctcctccac atcctcgtcc    540
tcagccacct cccctgcctc tgcttccttc aagttcgagg acttccaggt gtacggctgc    600
taccccggcc ccctgagcgg cccagtggat gaggccctgt cctccagtgg ctctgactac    660
tatggcagcc cctgctcggc cccgtcgccc tccacgccca gcttccagcc gccccagctc    720
tctccctggg atggctcctt cggccacttc tcgcccagcc agacttacga aggcctgcgg    780
gcatggacag agcagctgcc caaagcctct gggcccccac agcctccagc cttcttttcc    840
ttcagtcctc ccaccggccc cagccccagc ctggcccaga gcccccctgaa gttgttcccc    900
tgcacaggcc acccaccagc tgggggaggg agagagctat tccatgccta cggccttccc    960
aggtttggca cccacttctc cacaccttga gggctcgggg atactggata cacccgtgac   1020
ctcaaccaag gcccggagcg gggccccagg tggaagtgaa ggccgctgtg ctgtgtgtgg   1080
ggacaacgct tcatgccagc attatggtgt ccgcacatgt gagggctgca agggcttctt   1140
caagcgcaca gtgcagaaaa acgccaagta catctgcctg gctaacaagg actgccctgt   1200
ggacaagagg cggcgaaacc gctgccagtt ctgccgcttc cagaagtgcc tggcggtggg   1260
catggtgaag gaagttgtcc gaacagacag cctgaagggg cggcggggcc ggctaccttc   1320
aaaacccaag cagcccccag atgcctcccc tgccaatctc ctcacttccc tggtccgtgc   1380
aacacctgga ctcaggggcc cagcactgcc aaactggact actccaagtt ccaggagctg   1440
gtgctgcccc actttgggaa ggaagatgct ggggatgtac agcagttcta cgacctgctc   1500
tccggttctc tggaggtcat ccgcaagtgg gcggagaaga tccctggctt tgctgagctg   1560
tcaccggctg accaggacct gttgctggag tcggccttcc tggagctctt catcctccgc   1620
ctggcgtaca aggtctaagc caggcgaggg caagctcatc ttctgctcag gcctggtgct   1680
acaccgggct gcagtgtgcc cgtggcttcg gggactggat tgacagtatc ctggccttct   1740
caaggtccct gcacagcttg cttgtccgat gtccctgcct tcgcctgcct ctctgccctt   1800
gtcctcatca ccgaccggca tgggctgcag gagccgcggc gggtggagga gctgcagaac   1860
cgcatcgcca gctgcctgaa ggagcacgtg ggcagctgtg gcgggcgagc cccagccagc   1920
cagctgcctg tcacgtctgt tgggcaaact gcccgagctg cggaccctgt gcacccaggg   1980
cctgcagcgc atcttctacc tcaagctgga ggacttggtg ccccctccac ccatcattga   2040
caagatcttc atggacacgc tgcccttctg acccctgcct gggaacacgt gtgcacatgc   2100
gcactctcat atgccacccc atgtgccttt agtccacgga cccccagagc acccccaagc   2160
ctgggcttga gctgcagaat gactccacct tctcacctgc tccaggaggt ttgcagggag   2220
ctcaagccct tggggagggg gatgccttca tgggggtgac cccacgattt gtcttatccc   2280
ccccagcctg gccccggcct ttatgttttt tgtaagataa accgttttta acacatagcg   2340
ccgtgctgta aataagccca gtgctgctgt aaatacagga agaaagagct tgaggtggga   2400
```

-continued

```
gcggggctgg gaggaaggga tgggccccgc cttcctgggc agcctttcca gcctcctgct   2460

ggctctctct tcctaccctc cttccacatg tacataaact gtcactctag gaagaagaca   2520

aatgacagat tctgacattt atatttgtgt attttcctgg atttatagta tgtgactttt   2580

ctgattaata tatttaatat attgaataaa aaatagacat gtagttggaa ctgaaaa      2637
```

<210> SEQ ID NO 59
<211> LENGTH: 1408
<212> TYPE: DNA
<213> ORGANISM: Homo sapiens
<220> FEATURE:
<221> NAME/KEY: misc_feature
<223> OTHER INFORMATION: Incyte ID No: 127112.16
<221> NAME/KEY: unsure
<222> LOCATION: 112-252, 1365
<223> OTHER INFORMATION: a, t, c, g, or other

<400> SEQUENCE: 59

```
accgcactta cccaaccagc gccttggtca agaaagagca cataactgcc ccccagaacc     60

cattattgtg ccccttcca gtcatttgcc ctccccaagg gtaaccacta cnnnnnnnnn    120

nnnnnnnnnn nnnnnnnnnn nnnnnnnnnn nnnnnnnnnn nnnnnnnnnn nnnnnnnnnn    180

nnnnnnnnnn nnnnnnnnnn nnnnnnnnnn nnnnnnnnnn nnnnnnnnnn nnnnnnnnnn    240

nnnnnnnnnn nncttcactg tgacttctga cagtgcagat cagattggtt gtgcctgttt    300

tggactttat gtaaatgtag ttctgcagga tggaatctgg tgttgaatgc agaggttttc    360

agatttctct gtttttaaa ggaaagaatc caccctcgtt catttttca cttaaattgc    420

acaggggacc caacgatata gaacacaatc agaggtactc tgggctgagg gagtgctgag    480

ttctgaggct gggtttctca gaacagtcta gattttaaaa acccaatgat ctagccagaa    540

aacgtaggtt aggattttat ttcctgtttg tgaccctggg caagtcatta gcctcctggg    600

cctcgggttc tcacttggag tatgaggata atgagggtta ctgcttctca gacttgtgac    660

gatgcttact aatggccaac atgtgaatgc gcttttgtga aatgccagca gagcatgagg    720

ggtggtcagg ggcagcagtt ttaggggcct gggggaggct ggggctttgg gggcctggtt    780

ctcagatgta cagctaatcc tgtacccttc ccgcagaccg gcatggggct gcaggagccg    840

cggcgggtgg aggagctgca gaaccgcatc gccagctgcc tgaaggagca cgtggcagct    900

gtggcggggc gagccccagc caggccagct gcctgtcacg tctgttgggg caaactgccc    960

gagctgcgga ccctgtgcac ccagggcctg cagcgcatct tctacctcaa gctggaggac   1020

ttggtgcccc ctccacccat cattgacaag atcttcatgg acacgctgcc cttctgaccc   1080

ctgcctggga acacgtgtgc acatgcgcac tctcatatgc caccccatgt gcctttagtc   1140

cacggacccc cagagcaccc ccaagcctgg ggcttgagct gcagaatgac tccaccttct   1200

cacctgctcc aggaggtttg gcagggagct caagcccttg gggaggggga tgccttcatg   1260

ggggtgaccc cacgatttgt cttatccccc ccagcctggc ccccggcctt tatgtttttt   1320

gtaagataaa ccgtttttaa cacatagcgc cgtgctgtaa ataancccag tgctgctgta   1380

aatacaggaa gaaagagctt gaggtgga                                      1408
```

<210> SEQ ID NO 60
<211> LENGTH: 1756
<212> TYPE: DNA
<213> ORGANISM: Homo sapiens
<220> FEATURE:
<221> NAME/KEY: misc_feature
<223> OTHER INFORMATION: Incyte ID No: 347786.12

-continued

<400> SEQUENCE: 60
cacgaagggg acgtgggaaa gtgttagcgg ggaacgctgg gaaactcccg gcctccgcca 60
ccatcttgct ttcctttaat ccggcagtga ccgtgtgtca gaacaatctt gaatcatgaa 120
gctactaacc agagccggct ctttctcgag attttattcc ctcaaagttg cccccaaagt 180
taaagccaca gctgcgcctg caggagcacc gccacaacct caggaccttg agtttaccaa 240
gttaccaaat ggcttggtga ttgcttcttt ggaaaactat tctcctgtat caagaattgg 300
tttgttcatt aaagcaggca gtagatatga ggacttcagc aatttaggaa ccacccattt 360
gctgcgtctt acatccagtc tgacgacaaa aggagcttca tctttcaaga taacccgtgg 420
aattgaagca gttggtggca aattaagtgt gaccgcaaca agggaaaaca tggcttatac 480
tgtggaatgc ctgcggggtg atgttgatat tctaatggag ttcctgctca atgtcaccac 540
agcaccagaa tttcgtcgtt gggaagtagc tgaccttcag cctcagctaa agattgacaa 600
agctgtggcc tttcagaatc cgcagactca tgtcattgaa aatttgcatg cagcagctta 660
ccggaatgcc ttggctaatc ccttgtattg tcctgactat aggattggaa aagtgacatc 720
agaggagtta cattacttcg ttcagaacca tttcacaagt gcaagaatgg ctttgattgg 780
acttggtgtg agtcatcctg ttctaaagca agttgctgaa cagtttctca acatgagggg 840
tgggcttggt ttatctggtg caaaggccaa ctaccgtgga ggtgaaatcc gagaacagaa 900
tggagacagt cttgtccatg ctgcttttgt agcagaaagt gctgtcgcgg gaagtgcaga 960
ggcaaatgca tttagtgttc ttcagcatgt cctcggtgct gggccacatg tcaagagggg 1020
cagcaacacc accagccatc tgcaccaggc tgttgccaag gcaactcagc agccatttga 1080
tgtttctgca tttaatgcca gttactcaga ttctggactc tttgggattt atactatctc 1140
ccaggccaca gctgctggag atgttatcaa ggctgcctat aatcaagtaa aaacaatagc 1200
tcaaggaaac ctttccaaca cagatgtcca agctgccaag aacaagctga aagctggata 1260
cctaatgtca gtggagtctt ctgagtgttt cctggaagaa gtcgggtccc aggctctagt 1320
tgctggttct tacatgccac catccacagt ccttcagcag attgattcag tggctaatgc 1380
tgatatcata aatgcggcaa agaagtttgt ttctggccag aagtcaatgg cagcaagtgg 1440
aaatttggga catacacctt ttgttgatga gttgtaatac tgatgcacac attacaggag 1500
agagctgaac gttctctcag cccagagcag caaacacatg aaagtcagaa gtctctaata 1560
tatcatttgt ctttttttcca gtgaggtaaa ataaggcata aatgcaggta attattccca 1620
gctgacctaa agtcaataaa acattctgtt taagtgtttt tcttacgttt ttctcaatga 1680
gttaatcaca acgtatttat tatgtgctga tatctttgtt ttagatcttt aaagctttcc 1740
agcacactgc gccgta 1756

<210> SEQ ID NO 61
<211> LENGTH: 3911
<212> TYPE: DNA
<213> ORGANISM: Homo sapiens
<220> FEATURE:
<221> NAME/KEY: misc_feature
<223> OTHER INFORMATION: Incyte ID No: 166400.9

<400> SEQUENCE: 61
gaggcgtcca cggaagacct ccatgagaag gtgaccttgg cataaagagg caaacgtggg 60
agcatgctca ggcagaccac ggtggtcaga agttgaattc aggccggagg aggaggagtg 120
catgaagccc ccagaatttt cccactgtaa aaaaccgagc aagtctggat aagtgaggct 180

-continued

```
ggctccatgt atccagaatc aacgacgggc tccccggctc ggctctcgct gcggcagacg    240
ggctcccccg ggatgatcta cagtactcgg tatgggagtc ccaaaagaca gctccagttt    300
tacaggaacc tgggcaagtc tggcctgcgg gtctcctgcc tgggacttgg aacatgggtg    360
accttcggag gccagatcac cgatgagatg gcagagcagc tcatgacctt ggcctatgat    420
aatggcatca acctcttcga tacagcagaa gtctacgcag ccggcaaggc tgaagtggta    480
ctgggaaaca tcattaagaa gaaaggatgg aggcggtcca gcctcgtcat caccaccaag    540
atcttctggg gcggaaaggc ggagacggag cggggcctgt ccaggaagca cataatcgaa    600
ggtctgaaag cttccctgga gcgactgcag ctggagtacg tggatgtggt gtttgccaac    660
cgcccggacc ccaacacccc gatggaagag accgtccgcg ccatgaccca cgtcatcaac    720
caggggatgg ccatgtactg gggcacgtca cgctggagct ccatggagat catggaggcc    780
tactccgtgg cccggcagtt caacctgacc ccgcccatct gcgagcaggc tgagtaccac    840
atgttccagc gtgagaaagt ggaggtgcag ctgccggagc tgttccacaa gataggagtg    900
ggcgccatga cctggtcccc tctggcctgt ggcattgttt ctggcaagta cgacagtggc    960
atcccaccct actcaagagc ctccttgaag ggctaccagt ggctgaagga caagatcctc   1020
agtgaggagg gccggcgcca gcaagccaag ctgaaggagc tgcaggccat cgccgagcgc   1080
ctgggctgca ccctgcccca gctggccata gcctggtgcc tgaggaatga gggagtcagc   1140
tccgtgctcc tgggggcctc caatgcggac cagctcatgg agaacattgg ggcaatacag   1200
gtccttccga aactgtcgtc ttccattatc cacgagattg atagtatttt gggcaataaa   1260
ccctacagca aaaaggacta cagatcctaa gccgcccccg cccgcctgct cggacagttt   1320
ccgttccctc ctagtctctg ttcgctcgct taagctgttt tgaagccaag tgaagagtgt   1380
ggtttgcatc caagagaaaa caccacactg tgatgtcatc gggaaatgat ctcccaagtc   1440
gctgccagac accacccact gcttcgccgg acaatgtcga agtccagtct gtgccgggga   1500
aggcactggt taggaaggat gttcaaacgg tcccacccaa gcctgtcacc tctgctcatc   1560
ctccaagacc acccagcttt ctcccagcca cagccaagat tcccaaagtc aaggcccaaa   1620
gatttccaag gttcccaaag tcaaggccag gccaaggcct ggttgggtcc ttggggcggg   1680
cagggccagc ctctcctctg ctgagaatcc ccacttggtg taggggggaga ggggaaaggg   1740
gtctggccca tcgaggggcc ccttctgcca gggccttggt tgctggggca gggcctcccc   1800
actgggggtc ttcctccacc tcccactttc caagggctcc aggaatctgg ggcctgacca   1860
cagattcctc tcccatcctt ttctgctcca acctgcccca ctgggtcccg gcaggggcca   1920
tgcctaccaa gctcgagctg gcccttgacc cccacccacc cccacccttg ctggcagggg   1980
cagggacccc aggggggattg actctgcagt ttgggagcca caaaaagcgt agcggtgtga   2040
tttctagctc agcctcccac cgtcttcctc ctacacacca atgatgagcc tcatgccagt   2100
gaggcccgga gcgcttggga ggggtcccag tggggcaggc ccctctgtct ggccacccct   2160
ctgtcctggc cccggaaggc cctgtggtca tgtgctccta gctgcacggt ggctgctggc   2220
cacaccacgg caagtggcag caggggccgg ccctgtgcac aaggatgcac tcctctcggc   2280
ccctgtagac tttctctaaa gccgcccgcc agcccaggcc gctgctctgc accgagctgg   2340
tgggcttggg ttttgtggag cgcatgcttg gaccctttca gtaaggaagg gtctttgggg   2400
ttttctgtgc ccatgacttg ggggctgcac ccccacagca cccccacaat gtaggaaaag   2460
acctcaggga acctctccct ggaaagacgg gcagggctgg ttagcccctc ccactgcctg   2520
acacctggga caggctgggc agaggggaga gagggcagga caggccagag tgacgccccc   2580
```

-continued

```
gtgcagcttg ggccggaggg caagggatgc cagtaagtct gcaggtgcgg ggtgccacct   2640
acaggcccag gcctgtgtcc caagcagtac ccaggctttg cagaccacgc ggggcagggc   2700
tccactgaag ccaccccac ccctcgccag ctagctccat agggaagcct gtgtctcctg   2760
cccccagggc gcaccctcag tgcaggcacc tctgttcccg ctttgcccct ggaggagcca   2820
ctattccaga aggctccacc ctgccgtcct gcgggagcct gctgtccagt cctgggccgg   2880
gccaaggcct gggaaactgt gaaagtcaga aaggccagcg gggagaggct ggggcgaggg   2940
gaggaggggg atcagcttct gctattaccg accccccttc atgctgcccc tggcgcctag   3000
aacccttgcc cctcctcata gaccaagtcc cgggggtctc cactcagtcc tgctgcctgc   3060
ttcaccagaa gcagccctgt gagtgtgggg tggggaagtc ccttcccaac ggaggtccca   3120
gcctatggcc ctgggcccag gtgggggtcg cctgcttcct tcccggacag ggtcctgcag   3180
tggccaatgg tgccagaggg caggtggccc accctcgccg tcagggaggg tggctggccc   3240
catccccact gccacccagc cccacccact gttggaagag ggaccagcgc gaggtggtgc   3300
ccagggtggg cactgctgct taatgcgagg cacacctggg gcagctgagc cccccgaagg   3360
ctgcgggttt gccaaacaca gagaggccag gccccagtgt caggatgcag tcagcctctg   3420
gcgcagctct ttccacgacc tggttcctgg atgtcctgct tgctccacac ccatctacag   3480
ggaggatgtg agggggctct gcctcctagg gccaggtccc ccctctcggg agggggtatt   3540
gggtaggacc atccaagaaa gggcagaaga ccaagggcag tcggggtcta gaaaggaggg   3600
cgctggccct gctgggcgct tcggagcccc cactgtttcc cactcagctt tgtgctcaga   3660
tcccaggtcc caaggagtga caggggcttc ctcccacctt ctgtccttgt ccagtcatgt   3720
aaataatgtg ctatttctct ccccgagtct tttttttaa aacctaccgt ggttcctcag   3780
ctaactgcat tccctaccca ggcagagact gtcctatgcc tcgagcttcc aaacgagact   3840
cagaccgcga cacagccacc gtatttatgg aatgacaaaa taaataaagc ccaaacccat   3900
cggtctctgt g                                                        3911
```

<210> SEQ ID NO 62
<211> LENGTH: 2421
<212> TYPE: DNA
<213> ORGANISM: Homo sapiens
<220> FEATURE:
<221> NAME/KEY: misc_feature
<223> OTHER INFORMATION: Incyte ID No: 413497.15

<400> SEQUENCE: 62

```
ctgcctcttt ttccttcccg ccgtgccccg cggccgggcc ggggcagccg ggaagcgggt     60
ggggtggtgt gttacccagt agctcctggg acatcgctcg ggtacgctcc acgccgtcgc    120
agccactgct gtggtcgccg gtcggccgag gggccgcgat actggttgcc cgcggtgtaa    180
gcagaattcg acgtgtatcg ctgccgtcaa gatggagggg cctttgtccg tgttcggtga    240
ccgcagcact ggggaaacga tccgctccca aaacgttatg gctgcagctt cgattgccaa    300
tattgtaaaa agttctcttg gtccagttgg cttggataaa atgttggtgg atgatattgg    360
tgatgtaacc attactaacg atggtgcaac catcctgaag ttactggagg tagaacatcc    420
tgcagctaaa gttctttgtg agctggctga tctgcaagac aaagaagttg gagatggaac    480
tacttcagtg gttattattg cagcagaact cctaaaaaat gcagatgaat tagtcaaaca    540
gaaaattcat cccacatcag ttattagtgg ctatcgactt gcttgcaagg aagcagtgcg    600
ttatatcaat gaaaacctaa ttgttaacac agatgaactg ggaagagatt gcctgattaa    660
```

-continued

```
tgctgctaag acatccatgt cttccaaaat cattggaata aatggtgatt tctttgctaa    720
catggtagta gatgctgtac ttgctattaa atacacagac ataagaggcc agccacgcta    780
tccagtcaac tctgttaata ttttgaaagc ccatgggaga agtcaaatgg agagtatgct    840
catcagtggc tatgcactca actgtgtggt gggatcccag ggcatgccca agagaatcgt    900
aaatgcaaaa attgcttgcc ttgacttcag cctgcaaaaa acaaaaatga agcttggtgt    960
acaggtggtc attacagacc ctgaaaaact ggaccaaatt agacagagag aatcagatat   1020
caccaaggag agaattcaga agatcctggc aactggtgcc aatgttattc taaccactgg   1080
tggaattgat gatatgtgtc tgaagtattt tgtggaggct ggtgctatgg cagttagaag   1140
agttttaaaa agggacctta aacgcattgc caaagcttct ggagcaacta ttctgtcaac   1200
cctggccaat ttggaaggtg aagaaacttt tgaagctgca atgttgggac aggcagaaga   1260
agtggtacag gagagaattt gtgatgatga gctgatctta atcaaaaata ctaaggctcg   1320
tacgtctgca tcgattatct tacgtggggc aaatgatttc atgtgtgatg agatggagcg   1380
ctctttacat gatgcacttt gtgtagtgaa gagagttttg gagtcaaaat ctgtggttcc   1440
cggtgggggt gctgtagaag cagccctttc catatacctt gaaaactatg caaccagcat   1500
ggggtctcgg gaacagcttg cgattgcaga gtttgcaaga tcacttcttg ttattcccaa   1560
tacactagca gttaatgctg cccaggactc cacagatctg gttgcaaaat taagagcttt   1620
tcataatgag gcccaggtta acccagaacg taaaaatcta aaatggattg gtcttgattt   1680
gagcaatggt aaacctcgag acaacaaaca agcaggggtg tttgaaccaa ccatagttaa   1740
agttaagagt ttgaaatttg caacagaagc tgcaatcacc attcttcgaa ttgatgatct   1800
tattaaatta catccagaaa gtaaagatga taaacatgga agttatgaag atgctgttca   1860
ctctggagcc cttaatgatt gatctgatgt tccttttatt tataacaatg ttaaatgcaa   1920
ttgtcttgta ccttgagttg agtattacac attaaagtaa agtacaagct gtaaacttgg   1980
gtttttgtga tgtaggaaat ggtttccatc tgtactttgg tcctctgatt tcacatattg   2040
caacctagta ctttattagt ttaaaaagaa attgaggttg ttcaaagttt aagcaattca   2100
ttctctctga acacacattg ctattcccat cccaccccca atgcacaggg ctgcaacacc   2160
acgacttctg cccattctct ccagtgtgtg taacagggtc acaagaattc gacagccaga   2220
tgctccaaga gggtggccca aggctatagc ccctccttca atattgacct agcgggggag   2280
aaaagattta gattgtttat tcttctgtgg acacagttta aaatcttaaa cttgtctttt   2340
tcctcttaat gtatcagcat gctacccttt caaactcaaa ttttcatttt aactgcttag   2400
gaataaattt acacctttgt g                                             2421
```

<210> SEQ ID NO 63
<211> LENGTH: 3505
<212> TYPE: DNA
<213> ORGANISM: Homo sapiens
<220> FEATURE:
<221> NAME/KEY: misc_feature
<223> OTHER INFORMATION: Incyte ID No: 263336.12

<400> SEQUENCE: 63

```
ggtaggtcgt ggtctgaggc cggtacagct gcgcgtctgc gggaataggt gcagcgggcc     60
cttggcgggg gactctgagg gaggagctgg ggacggcgac cctaggagag ttctttgggg    120
tgactttcaa gatggactct actctaacag caagtgaaat ccggcagcga tttatagatt    180
tcttcaagag gaacgagcat acgtatgttc actcgtctgc caccatccca ttggatgacc    240
```

-continued

```
ccactttgct ctttgccaat gcaggcatga accagtttaa acccattttc ctgaacacaa    300
ttgacccatc tcaccccatg gcaaagctga gcagagctgc caatacccag aagtgcatcc    360
gggctggggg caaacataat gacctggacg atgtgggcaa ggatgtctat catcacacct    420
tcttcgagat gctgggctct tggtcttttg gagattactt taaggaattg gcatgtaaga    480
tggctctgga actcctcacc caagagtttg gcattcccat tgaaagactt tatgttactt    540
actttggcgg ggatgaagca gctggcttag aagcagatct ggaatgcaaa cagatctggc    600
aaaatttggg gctggatgac accaaaatcc tcccaggcaa catgaaggat aacttctggg    660
agatgggtga cacgggcccc tgtggtcctt gcagtgagat ccactacgac cggattggtg    720
gtcgggacgc cgcacatctt gtcaaccagg acgaccctaa tgtgctggag atctggaacc    780
ttgtgttcat ccagtataac agggaagctg atggcattct gaaacctctt cccaagaaaa    840
gcattgacac agggatgggc ctggaacgac tggtatctgt gctgcagaat aagatgtcca    900
actatgacac tgaccttttt gtcccttact ttgaagccat tcagaagggc acaggtgccc    960
gaccatacac tgggaaagtt ggtgctgagg atgccgatgg gattgacatg gcctaccggg   1020
tgctggctga ccatgctcgg accatcactg tggcactggc tgatggtggc cggcctgaca   1080
acacagggcg tggatatgtg ttgagacgga ttctccgccg agctgtccga tacgcccatg   1140
aaaagctcaa tgccagcagg ggcttctttg ctacgttagt ggatgttgtc gtccagtccc   1200
tgggagatgc atttcctgag ctgaagaagg acccagacat ggtgaaggac atcattaatg   1260
aagaagaggt gcagtttctc aagactctca gcagagggcg tcgcatcctg gacaggaaaa   1320
ttcagagcct gggagacagc aagaccattc ccggagacac tgcttggctc ctctatgaca   1380
cctatgggtt tccagtggat ctgactggac tgattgctga agagaagggc ctggtggtag   1440
acatggatgg ctttgaagag gagaggaaac tggcccagct gaaatcacag ggcaagggag   1500
ctggtgggga agacctcatt atgctggaca tttacgctat cgaagagctc cgggcacggg   1560
gtctggaggt cacagatgat tccccaaagt acaattacca tttggactcc agtggtagct   1620
atgtatttga gaacacagtg gctacggtga tggctctgcg cagggagaag atgttcgtgg   1680
aagaggtgtc cacaggccag gagtgtggag tggtgctgga caagacctgt ttctatgctg   1740
agcaaggagg ccagatctat gacgaaggct acctggtgaa ggtggatgac agcagtgaag   1800
ataaaacaga gtttacagtg aagaatgctc aggtccgagg agggtatgtg ctacacattg   1860
gaaccatcta cggtgacctg aaagtggggg atcaggtctg gctgtttatt gatgagcccc   1920
gacgaagacc catcatgagc aaccacacag ctacgcacat tctgaacttc gccctgcgct   1980
cagtgcttgg ggaagctgac cagaaaggct cattggttgc tcctgaccgc ctcagatttg   2040
actttactgc caagggagcc atgtccaccc aacagatcaa gaaggctgaa gagattgcta   2100
atgagatgat tgaggcagcc aaggccgtct atacccagga ttgcccccctg gcagcagcga   2160
aagccatcca gggcctacgg gctgtgtttg atgagaccta tcctgaccct gtgcgagtcg   2220
tctccattgg ggtcccggtg tccgagttgc tggatgaccc ctctgggcct gctggctccc   2280
tgacttctgt tgagttctgt gggggaacgc acctgcggaa ctcgagtcat gcaggagctt   2340
ttgtgatcgt gacggaagaa gccattgcca agggtatccg gaggattgtg gctgtcacag   2400
gtgccgaggc ccagaaggcc ctcaggaaag cagagagctt gaagaaatgt ctctctgtca   2460
tggaagccaa agtgaaggct cagactgctc caaacaagga tgtgcagagg gagatcgctg   2520
accttggaga ggccctggcc actgcagtca tcccccagtg gcagaaggat gaattgcggg   2580
```

-continued

```
agactctcaa atccctaaag aaggtcatgg atgacttgga ccgagccagc aaagccgatg   2640

tccagaaacg agtgttagag aagacgaagc agttcatcga cagcaacccc aaccagcctc   2700

ttgtcatcct ggagatggag agcggcgcct cagccaaggc cctgaatgaa gccttgaagc   2760

tcttcaagat gcactcccct cagacttctg ccatgctctt cacggtggac aatgaggctg   2820

gcaagatcac gtgcctgtgt caagtccccc agaatgcagc caatcggggc ttaaaagcca   2880

gcgagtgggt gcagcaggtg tcaggcttga tggacggtaa aggtggtggc aaggatgtgt   2940

ctgcacaggc cacaggcaag aacgttggct gcctgcagga ggcgctgcag ctggccactt   3000

ccttcgccca gctgcgcctc ggggatgtaa agaactgagt ggggaaggag gaggctccca   3060

ctggatccat ccgtccagcc aagagctctt catctgctac aagaacattt gaatcttggg   3120

acctttaaag agcccctcct aacccagcag taactggaac acacttggga gcagtcctat   3180

gtctcagtgc cccttaaatt tctgccctga gccctccacg tcagtgccat cggtctagaa   3240

ccactaaccc cgcattgctg ttgatcgtca cgctcgcatc tatagataac ggctctccag   3300

acctgagctt tccgcgtcag caagtaggaa tcgtttttgc tgcagagaat aaaaggacca   3360

cgtgcaatac ttaatgccgc atgatctcta tccctcttcc caataggggc tggctctttt   3420

gacagccttt ggcgtctgta gaataaatgc tgtggctcct gaaaaacagg aaaccagggg   3480

aacccggggg ggggtccaaa gggcg                                          3505
```

<210> SEQ ID NO 64
<211> LENGTH: 872
<212> TYPE: DNA
<213> ORGANISM: Homo sapiens
<220> FEATURE:
<221> NAME/KEY: misc_feature
<223> OTHER INFORMATION: Incyte ID No: 234202.24
<221> NAME/KEY: unsure
<222> LOCATION: 732, 745, 758, 800, 821, 826, 830, 850-851, 854-855
<223> OTHER INFORMATION: a, t, c, g, or other

<400> SEQUENCE: 64

```
cgcggccaca gtccctgcat tgcgcgcgac ccggcggcgg gacaggcttg ctgcttcctc     60

ctcctcggcc tcaccattcc agaccaaaat tgaaaaaatg gttgacctca cccaggtaat    120

gggatgatga agtattcatg gcttttgcat cctatgcaac aattattctt tcaaaaatga    180

tgcttatgag tactgcaact gcattctata gattgacaag aaaggttttg ccaatccaga    240

agactgtgta gcatttggca aaggagaaaa tgccaagaag tatcttcgaa cagatgacag    300

agtagaacgt gtacgcagag cccacctgaa tgaccttgaa aatattattc catttcttgg    360

aattggcctc ctgtattcct tgagtggtcc cgacccctct acagccatcc tgcacttcag    420

actatttgtc ggagcacgga tctaccacac cattgcatat ttgacacccc ttccccagcc    480

aaatagagct ttgagttttt ttgttggata tggagttact ctttccatgg cttacaggtt    540

gctgaaaagt aaattgtacc tgtaaagaaa atcatacaac tcagcatcca gttggctttt    600

taagaattct gtacttccaa tttataatga atactttctt agattttagg taggagggga    660

gcagaggaat tatgaactgg ggtaaaccca tttgaatatt agcatgccaa tatcctgtat    720

tcttgtttta cntttggatt agaantttaa catagtantt cttaagtctt tgtctgattt    780

ttaaagtact ttcttataan ttggatcagt tatgattgta ncatcncacn acacccactt    840

tgaactatan nagnntgacg atgagaacct ta                                  872
```

<210> SEQ ID NO 65
<211> LENGTH: 2145

-continued

<212> TYPE: DNA
<213> ORGANISM: Homo sapiens
<220> FEATURE:
<221> NAME/KEY: misc_feature
<223> OTHER INFORMATION: Incyte ID No: 405309.8

<400> SEQUENCE: 65
gtagtgtata ccatttaaag gtgtgcggcg ggtctctgtt cacatggctc aactggaaac 60
ctgtttcatg aacaagctta ctcaggaacc atctggtggt attccagcac attgttcttc 120
agggggacga ctctaagtcg ctttgtggtg gcagcagctt agaatcagta tttgtggttg 180
ggaaagatgg acttacggga gcttggtaat gcaggtggtg aaggagcagg ttatgagagc 240
acttacaacc aagcctagct ccctggacca gttcaagagc aaactgcaga acctgagcta 300
cactgagatc ctgaaaatcc gccagtccga gaggatgaac caggaagatt tccagtcccg 360
cccgattttg gaactaaagg agaagattca gccagaaatc ttagagctga tcaaacagca 420
acgcctgaac cgccttgtgg aagggacctg ctttaggaaa ctcaatgccc ggcggaggca 480
agacaagttt tggtattgtc ggctttcgcc aaatcacaaa gtcctgcatt acggagactt 540
agaagagagt cctcagggag aagtgcccca cgattccttg caggacaaac tgccggtggc 600
agatatcaaa gccgtggtga cgggaaagga ctgccctcat atgaaagaga aaggtgccct 660
taaacaaaac aaggaggtgc ttgaactcgc tttctccatc ttgtatgact caaactgcca 720
actgaacttc atcgctcctg acaagcatga gtactgtatc tggacggatg gactgaatgc 780
gctactcggg aaggacatga tgagcgacct gacgcggaat gacctggaca ccctgctcag 840
catggaaatc aagctccgcc tcctggacct ggaaaacatc cagatccctg acgcacctcc 900
gccgattccc aaggagccca gcaactatga cttcgtctat gactgtaact gaagtggccg 960
ggcccagaca tgccccttcc aaaactggaa cacctagcta acaggagaga ggaatgaaaa 1020
cacacccacg ccttggaacc gtcctttggt aaagggaagc tgtgggtcca cattcccttc 1080
agcatcacct ctagccctgg caactttcag cccctagctg gcatcttgct caccgccctg 1140
attctgttcc tcggctccac tgcttcaggt cacttcccat ggctgcagtc cactggtggg 1200
acaagagcaa agcccactgc cagtaagaag gccaaagggc ccttccatcc tagccctctg 1260
caggcatgcc cttccttccc ttgggcagga aagccagcag ccccagactg cccaaaaact 1320
tgcccaccag accaagggca gtgccccaag gcccctgtct ggaggaaatg gcctagctat 1380
ttgatgagaa gaccaaaccc cacatcctcc tttcccctct ctctagaatc atctcgcacc 1440
accagttaca cttgaattaa gatctgcgct caaatctcct cccacctctc tccctgcttt 1500
tgccttgctc tgttcctctt tggtcccaag agcagcagcc gcagcctcct cgtgatcctc 1560
cctagcataa atttcccaaa cagtccacag gtcccatgcc cactttgcgt ctgcactgtg 1620
atcgtgacaa atcttccctc ctcaccagct agtctggggt ttcctctccc tgccccaggc 1680
cagaactgcc ttcttcattt ccacccacgc tcccagcctc ttagctgaaa gcacaaatgg 1740
tgaaatcagt agtctcgctc catctctaat agactaaacc taaatgcctc taggacggac 1800
tgttgctatc caagcgtttg gtgttacctt ctcctgggag gtcctgctgc aactcaagtt 1860
ccacaggatg gtcaagctgt cagacatcca agtttacatc attgtaatta ttactggtat 1920
ttacaatttg caagagtttt gggttagttt tttttttttt ttgctttgtt tttgtacaaa 1980
agagtctaac attttttgcc aaacagatat atatttaatg aaaagaagag atacataaat 2040
gtgtgaattt ccagtttttt tttaattatt ttaatcccaa acatcttcct gaaaataaca 2100
ttcccttaaa catgctgtgg aataaaatgg attgtgatga tttgg 2145

-continued

<210> SEQ ID NO 66
<211> LENGTH: 1747
<212> TYPE: DNA
<213> ORGANISM: Homo sapiens
<220> FEATURE:
<221> NAME/KEY: misc_feature
<223> OTHER INFORMATION: Incyte ID No: 244561.6

<400> SEQUENCE: 66

```
gctgcgggcc aggcggcggc ccctagcgtc gcgcagggtc ggggactgcg cggcggtgcc     60

caggccgggc gtgggcgaga gcacgaacgg gctgcctgcg ggctgagagc gtcgagctgt    120

ccaccatggg tgatcacgct tggagcttcc taaaggactt cctggccggg ggcgtcgccg    180

ctgccgtctc caagaccgcg gtcgccccca tcgagagggt caaactgctg ctgcaggtcc    240

agcatgccag caaacagatc agtgctgaga agcagtacaa agggatcatt gattgtgtgg    300

tgagaatccc taaggagcag ggcttcctct ccttctggag gggtaacctg gccaacgtga    360

tccgttactt ccccacccaa gctctcaact tcgccttcaa ggacaagtac aagcagctct    420

tcttaggggg tgtggatcgg cataagcagt tctggcgcta ctttgctggt aacctggcgt    480

ccggtggggc cgctggggcc acctcccttt gctttgtcta cccgctggac tttgctagga    540

ccaggttggc tgctgatgtg ggcaagggcg ccgcccagcg tgagttccat ggtctgggcg    600

actgtatcat caagatcttc aagtctgatg gcctgagggg gctctaccag ggtttcaacg    660

tctctgtcca aggcatcatt atctatagag ctgcctactt cggagtctat gatactgcca    720

aggggatgct gcctgacccc aagaacgtgc acatttttgt gagctggatg attgcccaga    780

gtgtgacggc agtcgcaggg ctggtgtcct accccctttga cactgttcgt cgtagaatga    840

tgatgcagtc cggccggaaa ggggccgata ttatgtacac ggggacagtt gactgctgga    900

ggaagattgc aaaagacgaa ggagccaagg ccttcttcaa aggtgcctgg tccaatgtgc    960

tgagaggcat gggcggtgct tttgtattgg tgttgtatga tgagatcaaa aaatatgtct   1020

aatgtaatta aaacacaagt tcacagattt acagtgaact tgatctacaa gttcacagat   1080

ccattgtgtg gtttaataga ctattcctag gggaagtaaa aagatctggg ataaaaccag   1140

actgaaagga atacctcaga agagatgctt cattgagtgt tcattaaacc acacatgtat   1200

tttgtattta ttttacattt aaattcccac agcaaataga aaataattta tcatacttgt   1260

acaattaact gaagaattga taataactga atgtgaaaca tcaataaaga ccacttaatg   1320

cacgctttct attttattga actcttatta actgtaaaat gcatttttaa aagatcaaaa   1380

atgcatattt tctagcatga ttcatgtatc agtcagcagc caagcttcta aatgccagat   1440

attatattga gaatgtatta tatgagaacg tacaatgctt aaagttccgg ttttcaaact   1500

taggcaggtc atattctatc tatcttatcc agcgttactg taggctagaa agtgataatg   1560

gctttcataa tcctgccttg tcttaggcac tttcctgcag tctttagaaa ttctaagatt   1620

ctgctaaaag ttttaaatca caatctggag aattttctat gattaggaag tgctctgttt   1680

tcatcccttt agataactgt gacacctaga attttatgtt aagtagagag tattcattga   1740

aaatcaa                                                              1747
```

<210> SEQ ID NO 67
<211> LENGTH: 558
<212> TYPE: DNA
<213> ORGANISM: Homo sapiens
<220> FEATURE:
<221> NAME/KEY: misc_feature -continued
<223> OTHER INFORMATION: Incyte ID No: 255712.1

<400> SEQUENCE: 67
gacttctcat atcttgccta ggaactccag gcttgtcttg gctccaaatg gatcccaact 60
gctcctgcac cacaggtggc tcctgtgcct gcgccggctc ctgcaagtgc aaagagtgca 120
aatgtacctc ctgcaagaag tgctgctgct cttgctgccc cgtgggctgt gccaagtgtg 180
cccagggctg tgtctgcaaa ggctcatcag agaagtgccg ctgctgtgcc tgatgttggg 240
agagccctgc tcccagacat aaatagagca accagtacta acctggattt tttttttaac 300
taccctgacc ggtttgctac attctttttt ctattcaata tgtgaaagac aataaaacac 360
gtttgacttg aaaaaaggca taacattacc tggaagggat ttcccaaaaa tatgaaaacc 420
tcgggggcgg accccccctag tctattcagc ccaccggata tttactccgc cgatgaaaac 480
cgggccaaaa aactttctca aaactagggc ccggagagac cttgccgtct atcttggccg 540
aatgcttggc atccagcc 558

<210> SEQ ID NO 68
<211> LENGTH: 2336
<212> TYPE: DNA
<213> ORGANISM: Homo sapiens
<220> FEATURE:
<221> NAME/KEY: misc_feature
<223> OTHER INFORMATION: Incyte ID No: 034137.5

<400> SEQUENCE: 68
ggagggggcc aggtcggagg gaagcccgcc cgtgcccgag cccgcgcccg agcagggact 60
acatttcccg aggggcctcg gcggcggctg cggcgacggg cgcggcaacg tcccccggaa 120
gtggagcccg ggacttccac tcgtgcgtga ggcgagagga gccggagacg agaccagagg 180
ccgaactcgg gttctgacaa gatggccggg ctgccccgca ggatgcatca aggaaaccca 240
gcgtttgctg gcagaaccag ttcctggcat caaagccgaa ccagatgaga gcaacgcccg 300
ttattttcat gtggtcattg ctggccctca ggattccccc tttgagggag ggacttttaa 360
acttgaacta ttccttccag aagaataccc aatggcagcc cctaaagtac gtttcatgac 420
caaaatttat catcctaatg tagacaagtt gggaagaata tgtttagata ttttgaaaga 480
taagtggtcc ccagcactgc agatccgcac agttctgcta tcgatccagg ccttgttaag 540
tgctcccaat ccagatgatc cattagcaaa tgatgtagcg gagcagtgga agaccaacga 600
agcccaagcc atagaaacag ctagagcatg gactaggcta tatgccatga ataatattta 660
aattgatacg atcatcaagt gtgcatcact tctcctgttc tgccaagact tcctcctctt 720
tgtttgcatt taatggacac agtcttagaa acattacaga ataaaaaagc ccagacatct 780
tcagtccttt ggtgattaaa tgcacattag caaatctatg tcttgtcctg attcactgtc 840
ataaagcatg agcagaggct agaagtatca tctggattgt tgtgaaacgt ttaaaagcag 900
tggcccctcc ctgcttttat tcatttcccc catcctggtt taagtataaa gcactgtgaa 960
tgaaggtagt tgtcaggtta gctgcagggg tgtgggtgtt tttattttat tttaatttta 1020
ttttattttt gagggggggag gtagtttaat tttatgggct cctttccccc ttttttggtg 1080
atctaattgc attggttaaa agcagctaac caggtcttta gaatatgctc tagccaagtc 1140
taactttatt tagacgctgt agatggacaa gcttgattgt tggaaccaaa atgggaacat 1200
taaacaaaca tcacagccct cactaataac attgctgtca agtgtagatt cccccccttca 1260 aaaaaagctt gtgaccattt tgtatggctt gtctggaaac ttctgtaaat cttatgtttt 1320

-continued

```
agtaaaatat tttttgttat tctactttgc ctttgtacag tttattttac tgtgtttatt   1380

tcattttccc aatttgacaa tcgtatttta aaattgaaac tgatggaaca ttctttcttg   1440

gtcttcacca tctgacaaat tgaatggcaa gaggtggatt ttgccagttt cttttcactg   1500

atgcagattt gtgttaagat agtactgaat ggagtattta taaactggcc ctgagcatgc   1560

ataaagcatc agtatctgac cttttttttaa ccttctagga atttgaaata aatgtgtttg   1620

tgttgtctga ttagatgatc attggtgtct tgccacaatg tttaaaaatt actgtacagg   1680

aaagtcacag caaagatagc agttgtgact gacatgtagg actttcacag ttgtgccaca   1740

tttttgccta aaatttgggt tatgacattt ttcttggttc ttatctgaaa atttcatctg   1800

taacctttca tgtgtgttaa gaaacactga tctgatcatt tgggatttgc tgaggcattt   1860

gtgagtcttc cttataaacc tgatgagcag atctcaacta tctagcttgt gtgtcatcag   1920

aaaggtttat ccctttgaga gtatcaagtc ctcagttaat gattcttgct ttcatccctc   1980

cagtatttgc tgtgggagct cgttttattc tttaatttgg aattcagtaa tttttcttct   2040

ttattgacga attcctcccc tcacaaaact gttctttccc acctctctcc atatctaatt   2100

cctgattctt gttattttta agtcataaat gtagccagtc ataaatacat aaatgttaac   2160

cttcgggttg caaccttgtc tcttgcagtt taaggtaatg gatattgtag cccatttgaa   2220

ttttcttcac tcttattctc gtaattctgg agtttcttca gattgtggtg tattttattg   2280

tgctcctatg taagatgaag aattaactat taaaattaca ttttcaacat acaaaa       2336
```

```
<210> SEQ ID NO 69
<211> LENGTH: 2468
<212> TYPE: DNA
<213> ORGANISM: Homo sapiens
<220> FEATURE:
<221> NAME/KEY: misc_feature
<223> OTHER INFORMATION: Incyte ID No: 374578.5
<221> NAME/KEY: unsure
<222> LOCATION: 1521, 1528, 1531, 1536
<223> OTHER INFORMATION: a, t, c, g, or other

<400> SEQUENCE: 69
```

```
gagagactgc cagagaggaa gagaaaagaa aggaagaaac attagaaaga aaaaggaagg     60

aaaacggtat aaagagagat caattaccca cccttaaata gctagattgg ggggggaggg    120

gggtggaaaa gaaagctgtg gaggtgtgcc ccagcacggc tgctttgaaa ggtttatcat    180

ctatccgttt ggtttatgga gaaaaagaaa atggtaactc agggtaacca ggagccgaca    240

acaactcctg acgcaatggt tcagcctttt actaccatcc catttccacc acctccgcag    300

aatggaattc ccacagagta tggggtgcca cacactcaag actatgccgg ccagaccggt    360

gagcataacc tgacactcta cggaagtacg caagcccacg gggagcagag cagcaactca    420

cccagcacac aaaatggatc tcttacgcag acagaaggtg gagcacagac agacggccag    480

cagtcacaga cacaaagtag tgaaaattca gagagtaaat ctaccccgaa acggctgcat    540

gtctctaata ttcctttccg cttccgggac cctgacctcc ggcagatgtt tgggcagttt    600

ggcaaaatcc tagatgtaga aataatcttt aatgaacgtg gctctaaggg attcgggttc    660

gtaactttcg agaatagtgc tgatgcagac agggccaggg agaaattaca cggcaccgtg    720

gtagagggcc gtaaaatcga ggtgaataat gctacagcac gtgtaatgac caataagaag    780

atggtcacac catatgcaaa tggttggaaa ttaagcccag tagttggagc tgtatatggt    840

ccggagttat atgcagcatc cagctttcaa gcagatgtgt ccctaggcaa tgatgcagca    900

gtgcccctat caggaagagg gggtatcaac acttacattc ctttaatcat tcctggcttc    960
```

-continued

```
ccttacccta ctgcagccac cacggcagcc cgctttcaga ggagcccatt tgaggggcag   1020

agggcggaca gtatatggtg cagtccgagc ggtacctcca acagccatcc ccgcctatcc   1080

aggggtggat atgcagccta cagatatgca cagcctgcta ctgcaaccgc agccaccgct   1140

gctgcagccg ctgcagccgc ttacagtgac ggttatggca gggtgtacac agccgacccc   1200

taccatgccc ttgcccctgc cgctagctat ggagttggcg ctgtggcgag tttataccga   1260

ggtggctaca gccgatttgc cccctactga agtgacgtga gacccctgca aatgggacag   1320

ccccccagtt catgaggcct ggctattgca atatttacta gtagaggaac tctatagcaa   1380

gatgaagagg aaaaacaaac aaacaaacaa acaaaaacac aaaaaaagaa agaatacttt   1440

tttatacctc actatgttct ttgaatatgt atttttcctt taaatttctg cctttaattc   1500

ttttgttcca aagattgtgc nttttttnct ntgtgntttt aaactgtggt aaaaaaaaaa   1560

aaaaataatg catttccatg tctgtatgtc cgtgcttagc ttattctatc aatcacggaa   1620

gaggcagtca aggaggaagg agagacatta ggagccgata aatgcatctg atcagaaatc   1680

agcagacaga attaccaaag tgtatctggt gctgaatgac tgggggacaa gcagaagtgg   1740

aagagatctt tctgcaacag gatattcttc tagtcttctg agtttctggt ctttgacagg   1800

caattctggt tggctgtggc tggaatccac atgctgatag ataggaattt gtgcttacaa   1860

agcaggagaa ttaaaaagac gctttcctct cctcttccct cctgtcttct ccgttctttt   1920

tacaatcatc ttacacgcac agcctgagac agctggcata gtttttggaa ttatagtatt   1980

gatatttcca aacgtgctct cagacagtgg ataataaaca cctcattagg aaaccgatct   2040

cagaatgaac tctggagtat gaaaaagatc atttcttttt gttcctgtaa cctagcattc   2100

cttctaggct tcttctcctt taattgaacc acagcttagc tcatgtattc ttttattaac   2160

accctgctct catgtccata agattcagga atttaggacc cagggacaga aaagtgaata   2220

agccagtgac cagatttccc ccagatgtct tgaggattag aagtacaaat tgttgacagc   2280

cattaaagag ggtgaggaag ggaaaaggaa tattagaaga tctggtattt cttacttttt   2340

tcttgcctca gaaagtacaa agtttaaaaa atagaataaa gaatctgctg gggaaagata   2400

gagtaccagg tcctaggtca gtagtccctg gaagttttgg tgatgaggac atggaagggc   2460

aggcagag                                                            2468
```

```
<210> SEQ ID NO 70
<211> LENGTH: 1876
<212> TYPE: DNA
<213> ORGANISM: Homo sapiens
<220> FEATURE:
<221> NAME/KEY: misc_feature
<223> OTHER INFORMATION: Incyte ID No: 234151.1
<221> NAME/KEY: unsure
<222> LOCATION: 1360, 1362-1391, 1864
<223> OTHER INFORMATION: a, t, c, g, or other

<400> SEQUENCE: 70
```

```
gggctcgcag ggacgtttcc tccctcccgg ctcgcggccc cgcccggccc ggcccccgcc     60

cagagcccca gcgcgccgag gatgtgagtc ctgctcgcct ctggcggagc agcagccact    120

cgcgcgcgga gccggagcgc agcgcagcgc agccgcgggc gctctccggg ccgctcgcgc    180

gagtgccgcg ctcttgccct agcggcgtcc cccggcctct cgccggcgcc accgccgcag    240

cagcccgcgg gccgtccccg gccggccgcc cccggcccca gcgccgctga ccctgtccgc    300

cgcgggcggg gacgcgggcg gaggaggcgc cgcggcggag ccccggacgc gaccatgtcg    360
```

-continued

```
gaggtgctgc cctacggcga cgagaagctg agcccctacg gcgacggcgg cgacgtgggc    420

cagatcttct cctgccgcct gcaggacacc aacaacttct tcggcgccgg gcagaacaag    480

cggccgccca agctgggcca gatcggccgg agcaagcggg ttgttattga agatgatagg    540

attgatgacg tgctgaaaaa tatgaccgac aaggcacctc ctggtgtcta actcccccaa    600

agacaatgag ttaagggaga gaataagaac ggcggtaaca gttattggca aaaagcatga    660

aaagagaaag cactttgaaa tttattacta gcttgctacc cacgatgaaa tcaacaacct    720

gtatctggta tcaggccggg agacagatga ggcgagagga ggagggggag gaggagaagg    780

ctctgggctc ctctgcaaaa ataaaaataa aaaaaataaa taaaatttta aaaataataa    840

aaattcacta tatacacata taaagaaata aaaagaagtc tcagttgcag ctatttgtca    900

aaattaatat ccatttcttt ttatatacgg tgaatattgc gcaattatag atctggattt    960

tgaaccactt aatgaagcgg caacaccagg tgttttgagg tgttggcatt cttcgctgat   1020

ttggctgttc ccaatgttta cattatttaa tcttgcaaaa atggttctgt gcacttggat   1080

gtgaaatgct gtccagtttt atttttttta tgttgttatc cttggatgta caaaaaattc   1140

agaaaatgat ctctgtagat attctgtttt attttggtca tctttagaag ttatcaggaa   1200

tgtgtttaaa acaagaagag aacttttcta aggaatgata catagaaaag attttatttt   1260

aaaatgagtt gtaaagcttg tgtttctttg ttgctgcaag ctatctgccc aagttaatgc   1320

aaatggacac attttttatg tcagaaaaac acacacacan gnnnnnnnnn nnnnnnnnnn   1380

nnnnnnnnnn ngaaaaacaa agaaaaaaat gcttgagctt tttctaactt ccccttgcag   1440

tctgttgtgt gagcagcctg tttatttctc taatattatg tcagtttatt ctctttaatg   1500

gactgtaaaa aaatgtaatc acaagagtgc caaatatctt gaaatgccaa aaggcatttt   1560

agtttctttt ctctgtgctc tgagtccacg tacaggaatg cttggagtgt cttttctgtt   1620

atttataggg attctcttaa ggcacaccag ctgcctgttt tgcatggtat ttgcaaaaat   1680

gcctcttgcg tgaggaaatc ttttaccatt ttttgtttgc aactttggac ctcaagaggt   1740

ttcccttccc ttccccgttc cctcttttct taattcaata ttctgtatgt tgcaccttga   1800

accagcacac agggctattt ctccaatgta caataaaaga attgttcctg tgtcaaaaaa   1860

aaanaccacc gttccg                                                    1876
```

<210> SEQ ID NO 71
<211> LENGTH: 1811
<212> TYPE: DNA
<213> ORGANISM: Homo sapiens
<220> FEATURE:
<221> NAME/KEY: misc_feature
<223> OTHER INFORMATION: Incyte ID No: 198145.6

<400> SEQUENCE: 71

```
cgggcgcgac gcctgtaggg acagtctggg gtttggctgt ccggacggtg cagcggcgag     60

gccggccgcg aagatgccag tggcggtgat ggcggaaagc gcctttagtt tcaaaaagtt    120

gctggatcag tgcgagaacc aggagctcga ggcccctgga ggaattgcta cacccccagt    180

gtatggtcag cttctagctt tatatttgct ccataatgac atgaataatg caagatatct    240

ttggaaaaga ataccacctg ctataaaatc tgcaaattct gaacttgggg gaatttggtc    300

agtaggacaa agaatctggc agagagattt ccctgggatc tatacaacca tcaacgctca    360

ccagtggtct gagacggtcc agccaattat ggaagcactt agagatgcaa caaggagacg    420

cgcctttgcc ctggtctctc aagcgtatac ttcaatcatc gccgatgatt ttgcagcctt    480
```

-continued tgttggactt cctgtagaag aggctgtgaa aggcatatta gaacaaggat ggcaagctga 540
ttccaccaca agaatggttc tgcccagaaa gccagttgca ggggccctgg atgtttcctt 600
taacaagttt attcccttat cagagcctgc tccagttccc ccaataccca atgaacagca 660
gttagccaga ctgacggatt atgtggcttt ccttgaaaac tgatttatca ctctgagttc 720
aagattcatc ttcagaatcc tgtatactga caaacgtaga aatgtaaagt ttgtattttc 780
aatttattgg atggcttaag cacctcagca ttccttacta tgtgataaaa tacatataga 840
atataagata tactatatac attttgtcca taaacgttat gctgaatagt tgttgaaaca 900
gttctcattt tgtagtattt aataatctgg atggagcctg tcagtattac agttagtttt 960
ctagtgactc ataaaataag atttcctgtt tcatgtagaa tagtgtttgt caactgtctt 1020
ttctctgtcc cagcacatgc cgtactctta tatgtaccat tggttgataa ttataatgat 1080
tcatttggac ttgaagaaag attgtcccca ggcacagtat ctgaatcact ggggattatg 1140
attcaccctc tttggagaac atgctctctt ttcacccccc acctcctgag agccactaat 1200
gtaagataca gaaacatagc tgaggaacaa atagaccatt tccatactaa accagtttgt 1260
taactttaga ttttttccaa tagtgtgagt atatccattg ctggcagtgg agggcttgcc 1320
atgaaaatgc aacttattta agacatttat gagacatatt aacttgtgct gtcgcctttt 1380
agaaggagaa acttaagtgt ggaatgcatt atatgggcaa agaagctatg aagatacatg 1440
atacactttg tacaactatc ctgcagccca ttggttgctt atatttatcg cttggctcaa 1500
gttctgccct ttggagaaat actgagcaag tctttcattc tctgtgtgac agccctctga 1560
atatttgaag ttgtttgttg taacttaagg ttataacagc ccttagttca tttactctgc 1620
atttgttcaa taaatattta actgaattct tcaattattt catctaagat agtttctgga 1680
aatttcactc tcgatctttc tgtggacaca atctattttg tcattgtgtc tatatgaatc 1740
tcttaagtag aaatgagttg tatggtgaat ctgtgtagtg ataattatat aatttattta 1800
ttttgaatgc a 1811

<210> SEQ ID NO 72
<211> LENGTH: 2962
<212> TYPE: DNA
<213> ORGANISM: Homo sapiens
<220> FEATURE:
<221> NAME/KEY: misc_feature
<223> OTHER INFORMATION: Incyte ID No: 349676.8

<400> SEQUENCE: 72
aaagacctgc agtattgtct cttaaagctc actatctctg gccattcact aaggaaccag 60
gcaccgtctt aaatcgcggt ttggaaaata ttttgttcaa gataaaactg ttttaagata 120
tacgtgtata tatcttatat atctgtattc gcatggtaac atatcttcgg ccttcctgag 180
ccgctgggct ctcagcggcc ctccaaggca gcccgcaggc ccctgtgtgc ctcagggatc 240
cgacctccca cagccccggg gagaccttgc ctctaaagtt gctgcttttg cagcctctgc 300
cacaaccgcg cgtcctcaga gccagcccgg aggagctaga accttccccg catttctttc 360
agcagcctga gtcagaggcg ggctggcctg gcgtagccgc ccagcctcgc ggctcatgcc 420
ccgatctgcc cgaaccttct cccggggtca gcgccgcgcc gcgccacccg gctgagtcag 480
cccgggcggg cgagaggctc tcaactgggc gggaaggtgc gggaaggtgc ggaaaggttc 540
gcgaaagttc gcggcggcgg gggtcgggtg aggcgcacaa ggataaaaag cccgtggaag 600
cggcgctgag cagatccgag ccgggctggc tgcagagaaa ccgcagggag agcctcactg 660

-continued

```
ctgagcgccc cttcgacggc ggagcggcag caggcctgcc gtggcctcca gcatccgaca    720
agaagcttca gccatgcagg ccccacggga gctcgcggtg ggcatcgacc tgggcaccac    780
ctactcgtgc gtgggcgtgt ttcagcaggg ccgcgtggag atcctggcca acgaccaggg    840
caaccgcacc acgcccagct acgtggcctt caccgacacc gagcggctgg tcggggacgc    900
ggccaagagc caggcggccc tgaaccccca caacaccgtg ttcgatgcca agcggctgat    960
cgggcgcaag ttcgcggaca ccacggtgca gtcggacatg aagcactggc ccttccgggt   1020
ggtgagcgag ggcggcaagc ccaaggtgcg cgtatgctac cgcggggagg acaagacgtt   1080
ctaccccgag gagatctcgt ccatggtgct gagcaagatg aaggagacgg ccgaggcgta   1140
cctgggccag cccgtgaagc acgcagtgat caccgtgccc gcctatttca atgactcgca   1200
gcgccaggcc accaaggacg cgggggccat cgcggggctc aacgtgttgc ggatcatcaa   1260
tgagcccacg gcagctgcca tcgcctatgg gctggaccgg cggggcgcgg gagagcgcaa   1320
cgtgctcatt tttgacctgg gtgggggcac cttcgatgtg tcggttctct ccattgacgc   1380
tggtgtcttt gaggtgaaag ccactgctgg agatacccac ctgggaggag aggacttcga   1440
caaccggctc gtgaaccact tcatggaaga attccggcgg aagcatggga aggacctgag   1500
cgggaacaag cgtgccctgc gcaggctgcg cacagcctgt gagcgcgcca agcgcaccct   1560
gtcctccagc acccaggcca ccctggagat agactccctg ttcgagggcg tggacttcta   1620
cacgtccatc actcgtgccc gctttgagga actgtgctca gacctcttcc gcagcaccct   1680
ggagccggtg gagaaggccc tgcgggatgc caagctggac aaggcccaga ttcatgacgt   1740
cgtcctggtg gggggctcca cacgcatccc caaggtgcag aagttgctgc aggacttctt   1800
caacgggcaa ggagctgaac aagagcatca accctgatga ggctgtggcc tatggggctg   1860
ctgtgcaggc ggccgtgttg atgggggaca aatgtgagaa agtgcaggat ctcctggctg   1920
ctggatgtgg ctcccctgtc tctggggctg gagacagcag gtggggtgat gaccacgctg   1980
atccagagga acgccactat ccccaccaag cagacccaga ctttcaccac ctactcggac   2040
aaccagcctg ggtcttcat ccaggtgtat gagggtgaga gggccatgac caaggacaac   2100
aacctgctgg ggcgttttga actcagtggc atccctcctg ccccacgtgg agtcccccag   2160
atagaggtga cctttgacat tgatgctaat ggcatcctga gcgtgacagc cactgacagg   2220
agcacaggta aggctaacaa gatcaccatc accaatgaca agggccggct gagcaaggag   2280
gaggtggaga ggatggttca tgaagccgag cagtacaagg ctgaggatga ggcccagagg   2340
gacagagtgg ctgccaaaaa ctcgctggag gcccatgtct tccatgtgaa aggttctttg   2400
caagaggaaa gccttaggga caagattccc gaagaggaca ggcgcaaaat gcaagacaag   2460
tgtcgggaag tccttgcctg gctggagcac aaccagctgg cagagaagga ggagtatgag   2520
catcagaaga gggagctgga gcaaatctgt cgccccatct tctccaggct ctatgggggg   2580
cctggtgtcc ctgggggcag cagttgtggc actcaagccc gccaggggga ccccagcacc   2640
ggccccatca ttgaggaggt tgattgaatg gcccttcgtg ataagtcagc tgtgactgtc   2700
agggctatgc tatgggcctt ctagactgtc ttctatgatc ctgcccttca gagatgaact   2760
ttccctccaa agctagaact ttcttcccag gataactgaa gtcttttgac tttttgcggg   2820
gagggcggtt catcctcttc tgcttcaaat aaaaagtcat taatttatta aaacttgtgt   2880
ggcactttaa cattgctttc acctatattt tgtgtacttt gttacttgca tgtatgaatt   2940
ttgttatgta aaatatagtt at                                            2962
```

-continued

```
<210> SEQ ID NO 73
<211> LENGTH: 3772
<212> TYPE: DNA
<213> ORGANISM: Homo sapiens
<220> FEATURE:
<221> NAME/KEY: misc_feature
<223> OTHER INFORMATION: Incyte ID No: 078171.3
<221> NAME/KEY: unsure
<222> LOCATION: 1746-1768
<223> OTHER INFORMATION: a, t, c, g, or other

<400> SEQUENCE: 73

cgcgcctagg agcagtggac gctgagagca gcaaggccag agttgaaaac ttacagagtc     60

ctgaggcttt cagactgaaa aaggctttct tctgtcactg acaatcgcca ccatgatcca    120

tagtcttttc ttgatcaact cctctggaga cattttcctg gagaaacatt ggaaaagtgt    180

ggtcagccgt tctgtttgtg attacttttt tgaggcgcaa gagagagcta ctgaggcaga    240

aaatgtgcct ccggttatcc ctacccctca ccactatctc ttaagtgttt accgccacaa    300

gatctttttt gtggccgtga tccagacgga ggtcccccct ctgtttgtca ttgagtttct    360

tcaccgagtg gtggacacat ttcaggatta ttttggagtc tgttcagagc cagtgatcaa    420

agacaatgta gttgtggttt atgaggtatt ggaagagatg cttgacaatg gttttccatt    480

ggctaccgag tcgaacattc ttaaagaact cataaagcct cctaccatcc ttcgaacggt    540

tgtcaacacc atcacaggaa gcacgaatgt gggtgaccag cttcccactg ggcagctgtc    600

agtggtgcct tggcgacgga ctggggtgaa atataccaac aatgaggcct attttgatgt    660

gattgaagag attgatgcaa ttattgataa atcaggctcc acaattactg ctgagatcca    720

gggggtgatt gatgcctgtg tcaagctgac tggcatgcca gaccttacac tttccttcat    780

gaaccctagg ttgttggatg atgtcagctt ccatccttgt gttcgtttca aacgctggga    840

atctgagcgc atcctctcct tcatccctcc tgatggaaac ttccgcctgc tgtcttacca    900

tgtcagtgca cagaatctgg ttgcaatccc agtgtatgtc aaacataaca tcagtttccg    960

ggacagtagt tcccttggac gctttgaaat aacggtggga cccaagcaga cgatggggaa   1020

gaccattgag ggagtgactg tcaccagcca gatgcccaag ggggtcctga acatgagcct   1080

tactccatca caggggacac acacattcga cccagtcaca aagatgctgt cttgggatgt   1140

aggaaaaata aatccacaaa agctaccaag tttgaagggg accatgagtc ttcaggctgg   1200

agcttccaaa ccagatgaaa accccacaat taacctgcag tttaagatcc agcagctggc   1260

catttctgga ctcaaggtga atcgtctgga tatgtatgga gaaaagtaca aaccctttaa   1320

gggcataaaa tacatgacca aagctgggaa gttccaagtt cgaacctgaa gggagcattt   1380

gctgagggaa tagtcttgca catttttttca tttcttactt gtctaaaagt aaaaaaaaat   1440

atcagcctgt ctcctaggtc agtcccctcc tggacccacc cgctcccttt tttccttagc   1500

cttcagtgcc atggaactaa tcaagggagg aaaaggtcac cagggagaac tggacagaac   1560

tgaaacacag caacaccagt tctcaaggac aaggtgtgtg atgggggtag gaagcttggt   1620

gcttatgtaa ccattttaaa cgtggtttct ataggaaaga ccaacatttg tttagcttgc   1680

ttggctttaa ttatctaaag ccaatgaaag acttctttgt tgattttttta agatagaaag   1740

attaannnnn nnnnnnnnnn nnnnnnnnat gaatgtcagt caaggaaagg ccacttaagg   1800

atctgctcta tgaaggagaa gaaagaggaa aaagaagtaa aggagttagg aggagacact   1860

taaatgaaag attggcaaga aaagcagtcg gactctacct taaggaggga tgggaaggaa   1920

agagttgagt tggtttcttt ctgattcctc tactcatgta gaaaacactt gtacttctgg   1980
```

-continued

```
aaatggactg gagacttttt aaatttgagt ccactattga catggaaacc ccagtggaat   2040

cagattttcc ctcaaagacc atgatggtat cggactagtt ttcagacact gcctgttgct   2100

gtccatcagc acttggtctc ttatcttcag tgagaaggtg acccgccttc ttcccatggt   2160

ggctgcctaa agtgcttctt ttctaaccca aaacagttct actcacttcc ttttacagaa   2220

ttcaccggcc attttcctgt tacctgatcc ttctacagga tttttaaaaa gtaagagagt   2280

ttcagagaag ccgatcccat aatccccagt gcagccaggg tttgtgtgtc atcgtactgg   2340

agtagagggc cgactcttcc catgaaggtg agcacagctg tgagtgagtg agctcatatc   2400

tccatttgtc agtgctggac tggtaccaga tcgtaacctt cccgttggtc ggaaactttt   2460

ccatctgtcg ccctagaaaa agagaaagct taccatcgag ggtgtggttg atccttgaag   2520

ctgcttggta aagttatcat ttcctcagtc ttttcttttg tactcctatc atgtattcat   2580

taatatctac cagtcccttt tcattctaag acaaaacatt tctcctaaat ctctgaataa   2640

aatcagtgct gtaggaagat ggactgtgtt gatcatgggt gtaagcaacc cagtttaaga   2700

aacatggcaa ctaaagggat acctcaggct ttctttccca gtgggtcatt tttgtcctag   2760

ttcagtgtgt ctgttactat ttaaatattt atacaaaagg gtttttgttt atagcttaag   2820

gaatgatact gtgctctgct tggtgcatgg agaaaaagga agacccatac tctccacacc   2880

ctagagcttt tctctaaata ttgtgcaaag tttttgctag ttttatcttc tgactttggg   2940

actagttttt gctgcagagt tgtgttgctt tgtgattttc ctctgggata gtgtactgta   3000

cacaaccaga tgtgttccac actccgtgac tccgcagttt gtcctggagt gacatacaca   3060

tccaccatgg aaagggaagc atctctgcct gtggattctc aagtacttgg aagcacctct   3120

cctgaggaac ctacaggatt ctaaggtttc ctaggtcact gaacaactaa tcttggtccc   3180

tgaatatttc taggtttgta agtgcagcag ttttatttcc tctagaactc atcctgtttc   3240

aagggaagta cctaagaaga tatagagtgt ttctagggta agggacctgc aggtgtaagc   3300

atagatgaaa taactgtcct gtcacatgtg cagcaggcca tggagtgtag cgggcatcgc   3360

tgccgccatt cctgcagcat caccataagc agtgcagggt gtctccatcg agctgtttgg   3420

ttccatgtgt gtttaacatg tgcagaagta gcttctctgt ttaagtttaa taaagttgag   3480

tttcaccagt cttctatgtc ctaagtggtt tgttaccaga actaacaaca gtgctatgcc   3540

actcaaacct cagtagaagc agtgagtaag gaattcatcg actcaggagg atcttactgc   3600

ttctgtcctg tctagccagc agacctaaag catgtgtttt gatcgattct ttggtcacat   3660

ctggaagata gcagatgctg atattaatgt catttttagg gtggtgagca taaggtccag   3720

atccacctag ttatttttca ccagagttct aaaagacgaa atcgttgaag ct           3772
```

<210> SEQ ID NO 74
<211> LENGTH: 9262
<212> TYPE: DNA
<213> ORGANISM: Homo sapiens
<220> FEATURE:
<221> NAME/KEY: misc_feature
<223> OTHER INFORMATION: Incyte ID No: 246655.92
<221> NAME/KEY: unsure
<222> LOCATION: 1941-1942, 1952-1953, 1956, 1958, 1963, 6600-6601
<223> OTHER INFORMATION: a, t, c, g, or other

<400> SEQUENCE: 74

```
atcagttgca ctttccttgg tcccacccat tatacatgaa cccctctact tcctttcgca     60

ttgcttctga gtatgctgac tacccaaagc cccttctgtg ttattaataa acacagtact    120

gattgtccca tttttcagcc catcagtcca agatctccct accactttgg tgtgttggtg    180
```

-continued

```
cagtgttgac tatgaaaagc aggcctgaac taggtggata agccttcact cattttcttt    240
catttattaa tgatcctagt ttcaattatt gtcagattct ggggacaaga accattcttg    300
cccacctgtg ttactgcttt actgtgcaaa atactgaagg caagtcagac ccagggagct    360
ggattgccat cctttatttt gtgtttccag tgtacactat aaaattgtct ccccaggaag    420
gaaggttggc actttctctg cattcttctt tccagagcag attgcctggt taagaatctc    480
ttgttgtccc ctttgtatat tgttattgta aagtgccaaa tgccaggata cagccagaaa    540
aattgcttat tattattaaa aaaatttttt taagaaagac atctggattg tagggtggac    600
tcgataacct ggtcattatt tttttgaagc caaaatatcc atttatacta tgtacctggt    660
gaccagtgtc tctcatttta actgagggtg gtgggtctgt ggatagaaca ctgactcttg    720
ctattttaat atcaaagata ttctagagtg gaactcttaa gaccagtatc tttgtgtggg    780
ctttaccagc attcactttt agaaaaacta cctaaatttt ataatccttt aatttcttca    840
tctggagcac ctgcccctac ttatttcaag aagattgcag taaaacgatt aaatgaggga    900
acatatgcag aggtgctttt aaaaagcata tgccaccttt tttattaatt attatataaa    960
atgaagcatt taattatagt aataatttga agtagtttga agtaccacac tgaggtgagg   1020
acttaaaaat gataagacga gttccctatt ttataagaaa aataagccaa aattaaatat   1080
tcttttggat ataaatttca acagtgagat agctgcctag tggaaatgaa taatatccca   1140
gccactagtg tacagggtgt tttgtggcac aggattatgt aatatggaac tgctcaagca   1200
aataactagt catcacaaca gcagttcttt gtaataactg aaaaagaata ttgtttctcg   1260
gagaaggatg tcaaaagatc ggcccagctc agggagcagt ttgccctact agctcctcgg   1320
acagctgtaa agaagagtct ctggctcttt agaatactga tcccattgaa gataccacgc   1380
tgcatgtgtc cttagtagtc atgtctcctt aggctcctct tggacattct gagcatgtga   1440
gacctgagga ctgcaaacag ctataagagg ctccaaatta atcatatctt tccctttgag   1500
aatctggcca agctccagct aatctacttg gatgggttgc cagctatctg gagaaaaaga   1560
tcttcctcag aagaataggc ttgttgtttt acagtgttag tgatccattc cctttgacga   1620
tccctaggtg gagatggggc atgaggatcc tccaggggaa aagctcacta ccactgggca   1680
acaaccctag gtcaggaggt tctgtcaaga tactttcctg gtcccagata ggaagataaa   1740
gtctcaaaaa caaccaccac acgtcaagct cttcattgtt cctatctgcc aaatcattat   1800
acttcctaca agcagtgcag agagctgagt cttcagcagg tccaagaaat ttgaacacac   1860
tgaaggaagt cagccttccc acctgaagat caacatgcct ggcactctag cacttgagga   1920
tagctgaatg aatgtgtatt nntttgtctc tnnctntntt gtntttgctc tttgttctct   1980
atctaaagtg tgtcttaccc atttccatgt ttctcttgct aatttctttc gtgtgtgcct   2040
ttgcctcatt ttctcttttt gttcacaaga gtggtctgtg tcttgtctta gacatatctc   2100
tcatttttca ttttgttgct atttctcttt gctctcctag atgtggctct tctttcacgc   2160
tttatttcat gtctcctttt tgggtcacat gctgtgtgct ttttgtcctt ttcttgttct   2220
gtctacctct cctttctctg cctacctctc ttttctcttt gtgaactgtg attatttgtt   2280
acccccttccc cttctcgttc gttttaaatt tcaccttttt tctgagtctg gcctcctttc   2340
tgctgtttct actttttatc tcacatttct catttctgca tttcctttct gcctctcttg   2400
ggctattctc tctctcctcc cctgcgtgcc tcagcatctc ttgctgtttg tgattttcta   2460
tttcagtatt aatctctgtt ggcttgtatt tgttctctgc ttcttccctt tctactcacc   2520
```

-continued

```
tttgagtatt tcagcctctt catgaatcta tctccctctc tttgatttca tgtaatctct   2580
ccttaaatat ttctttgcat atgtgggcaa gtgtacgtgt gtgtgtgtca tgtgtggcag   2640
aggggcttcc taacccctgc ctgataggtg cagaacgtcg gctatcagag caagcattgt   2700
ggagcggttc cttatgccag gctgccatgt gagatgatcc aagaccaaaa caaggcccta   2760
gactgcagta aaacccagaa ctcaagtagg gcagaaggtg gaaggctcat atggatagaa   2820
ggcccaaagt ataagacaga tggtttgaga cttgagaccc gaggactaag atggaaagcc   2880
catgttccaa gatagataga agcctcaggc ctgaaaccaa caaaagcctc aagagccaag   2940
aaaacagagg gtggcctgaa ttggaccgaa ggcctgagtt ggatggaagt ctcaaggctt   3000
gagttagaag tcttaagacc tgggacagga cacatggaag gcctaagaac tgagacttgt   3060
gacacaaggc caacgaccta agattagccc agggttgtag ctggaagacc tacaacccaa   3120
ggatggaagg cccctgtcac aaagcctacc tagatggata gaggacccaa gcgaaaaagg   3180
tatctcaaga ctaacggccg gaatctggag gcccatgacc cagaacccag gaaggataga   3240
agcttgaaga cctggggaaa tcccaagatg agaaccctaa accctacctc ttttctattg   3300
tttacacttc ttactcttag atatttccag ttctcctgtt tatctttaag cctgattctt   3360
ttgagatgta ctttttgatg ttgccggtta cctttagatt gacagtatta tgcctgggcc   3420
agtcttgagc cagctttaaa tcacagcttt tacctatttg ttaggctata gtgttttgta   3480
aacttctgtt tctattcaca tcttctccac ttgagagaga caccaaaatc cagtcagtat   3540
ctaatctggc ttttgttaac ttccctcagg agcagacatt catataggtg atactgtatt   3600
tcagtccttt cttttgaccc cagaagccct agactgagaa gataaaatgg tcaggttgtt   3660
ggggaaaaaa aagtgccagg ctctctagag aaaaatgtga agagatgctc caggccaatg   3720
agaagaatta gacaagaaat acacagatgt gccagacttc tgagaagcac ctgccagcaa   3780
cagcttcctt ctttgagctt aggtgagcag gattctgggg tttgggattt ctagtgatgg   3840
ttatggaaag ggtgactgtg cctgggacaa agcgaggtcc caaggggaca gcctgaactc   3900
cctgctcata gtagtggcca aataatttgg tggactgtgc caacgctact cctgggttta   3960
atacccatct ctaggcttaa agatgagaga acctgggact gttgagcatg tttaatactt   4020
tccttgattt ttttcttcct gtttatgtgg gaagttgatt taaatgactg ataatgtgta   4080
tgaaagcact gtaaaacata agagaaaaac caattagtgt attggcaatc atgcagttaa   4140
catttgaaag tgcagtgtaa attgtgaagc attatgtaaa tcaggggtcc acagtttttc   4200
tgtaaggggt caaatcataa atactttaga ctgtgggcca tatggtttct gttacatatt   4260
tgttttttaa acaacgtttt tataaggtca aaatcattct tagtttttga gccaattgga   4320
tttggcctgc tgttcatagc ttaccacccc ctgatgtatt atttgttatt cagagaaaat   4380
ttctgaatac tactagtttc cttttctgtg cctgtccctg tgctaggcac taaaaatgca   4440
atgattattg atatctaggt gacctgaaaa aaaatagtga atgtgctttg taaactgtaa   4500
agcacttgta ttctactgtg ataagcgttg tggatacaaa gaaaggagca agcataaaaa   4560
agtgctcttt caaaaggata tagtactatg cagacacaag gaattgtttg ataaatgaat   4620
aaattatatg tatatttgag gccaatttgt gtttgctgct ctggtaattt tgagtaaaaa   4680
tgcagtattc caggtatcag aaacgaaaac acatggaaac tgcttttaaa ctttaaaata   4740
tactgaaaac ataagggact aagcttgttg tggtcaccta taatgtgcca gataccatgc   4800
tgggtgctag agctaccaaa gggggaaaag tattctcata gaacaaaaaa tttcagaaag   4860
gtgcatatta aagtgctttg taaactaaag catgatacaa atgtcaatgg gctacatatt   4920
```

-continued

```
tatgaatgaa tgaatggatg aatgaatatt aagtgcctct tacataccag ctattttggg   4980
tactgtaaaa tacaagatta attctcctat gtaataagag gaaagtttat cctctatact   5040
attcagatgt aaggaatgat atattgctta attttaaaca atcaagactt tactggtgag   5100
gttaagttaa attattactg atacattttt ccaggtaacc aggaaagagc tagtatgagg   5160
aaatgaagta atagatgtga gatccagacc gaaagtcact taattcagct tgcgaatgtg   5220
ctttctaaat tataaagcac ttgtaaatga aaaatttgat gctttctgta tgaataaaac   5280
tttctgtaag ctaggtattg tctctacaaa attctcattg tatagttaaa ccacagtgag   5340
aagggttcta taagtagtta tacaaaccaa gggtttaaat acctgttaaa tagatcaatt   5400
ttgattgcct actatgtgaa ctcactgtta aaggcactga aaatttatca tatttcattt   5460
agccacagcc aaaaataagg caatacctat gttagcattt tgtgaactct aaggcaccat   5520
ataaatgtaa ctgttgattt tctcacttgg tgctgggtac taggtttata aaattgtatg   5580
atagttatta tattgtgcaa ataaagtagg aaaatttgaa taacaatgat tatcttttga   5640
atacgcatac gcaagggatt ggttgtctga agaatgccac tatagtagtt atctattgtg   5700
tgccaatctc attgctaggc attggggatg caaagataaa ccatctttat tgtgtcttgg   5760
gtagcagaag aaaatatgtg taaaatcaat ttataatttg taaactgcca cccatatata   5820
agctatatct gctgaatgat cattgattac tcttatcctt agagataaca actgggggca   5880
caaacattta ttatcattat tgaacctaca acagagatct atgtgtagat ttacaaagcc   5940
tacagttcta tacagatagg aatgaactat tggcttactg aatggtgatt actttctgtg   6000
gggctcggaa ctacatgccc taggatataa aaatgatgtt atcattatag agtgctcaca   6060
gaaggaaatg aagtaatata ggtgtgagat ccagaccaaa agtcatttaa caagtttatt   6120
cagtgatgaa aacatgggac aaatggacta atataaggca gtgtactaag ctgagtagag   6180
agataaagtc ctgtccagaa gatacatgct tcctggcctg attgaggaga tggaaaattt   6240
ttgcaaaaaa caaggtgttg tggtcttcca tccagtttct taagtgctga tgataaaagt   6300
gaattagacc caccttgacc tggcctacag aagtaaagga gtaaaaataa atgcctcagg   6360
cgtgcttttt gattcatttg ataaacaaag catcttttat gtggaatata ccattctggg   6420
tcctgaggat aagagagatg agggcattag atcactgaca gctgaagata gaagaacatc   6480
tttggtttga ttgtttaaat aatatttcaa tgcctattct ctgcaaggta ctatgtttcg   6540
taaattaaat aggtctggcc cagaagaccc actcaattgc ctttgagatt aaaaaaaaan   6600
naaaaaagaa agaaaaatgc aagtttcttt caaaataaag agacattttt cctagtttca   6660
ggaatccccc aaatcacttc ctcattggct tagtttaaag ccaggagact gataaaaggg   6720
ctcagggttt gttctttaat tcattaacta aacattctgc ttttattaca gttaaatggt   6780
tcaagatgta acaactagtt ttaaaggtat ttgctcattg gtctggctta gagacaggaa   6840
gacatatgag caataaaaaa aagattcttt tgcatttacc aatttagtaa aaatttatta   6900
aaactgaata aagtgctgtt cttaagtgct tgaaagacgt aaaccaaagt gcactttatc   6960
tcatttatct tatggtggaa acacaggaac aaattctcta agagactgtg tttctttagt   7020
tgagaagaaa cttcattgag tagctgtgat atgttcgata ctaaggaaaa actaaacaga   7080
tcacctttga catgcgttgt agagtgggaa taagagaggg ctttttattt tttcgttcat   7140
acgagtattg atgaagatga tactaaatgc taaatgaaat atatctgctc caaaaggcat   7200
ttattctgac ttggagatgc aacaaaaaca caaaaatgga atgaagtgat actcttcatc   7260
```

-continued

```
aaacagaagt gactgttatc tcaaccattt tgttaaatcc taaacagaaa acaaaaaaaa   7320
tcatgacgaa aagacacttg cttattaatt ggcttggaaa gtagaatata ggagaaaggt   7380
tactgtttat ttttttcat gtattcattc attctacaaa tatattcggg tgccagtagg   7440
tacttggtat aaggtttttg gccccagaga catgggaaaa aaatgcatgc cttcccagag   7500
aatgcctaat actttccttt tggcttgttt tcttgttagg ggcatggctt agtccctaaa   7560
taacattgtg tggtttaatt cctactccgt atctcttcta ccactctggc cactacgata   7620
agcaggtagc tgggttttgt agtgagcttg ctccttaagt tacaggaact ctccttataa   7680
tagacacttc attttcctag tccatccctc atgaaaaatg actgaccact gctgggcagc   7740
aggagggatg atgaccaact aattcccaaa ccccagtctc attggtacca gccttgggga   7800
accacctaca cttgagccac aattggtttt gaagtgcatt tacaaggttt gtctattttc   7860
agttctttac tttttacatg ctgacacata catacactgc ctaaatagat ctctttcaga   7920
aacaatcctc agataacgca tagcaaaatg gagatggaga catgatttct catgcaacag   7980
cttctctaat tataccttag aaatgttctc ctttttatca tcaaatctgc tcaagaaggg   8040
ctttttatag tagaataata tcagtggatg aaaacagctt aacattttac catgcttaag   8100
ttttaagaat aaaataaaaa ttggaaataa ttggccaaaa ttgaaaggaa aaattttttt   8160
aaaatttctc taaatgtagg cctggctggg ctttgacctt ttccgttttt aaatcactca   8220
cagagggtgg gacaggagga agagtgaagg aaaaggtcaa acctgtttta agggcaacct   8280
gcctttgttc tgaattggtc ttaagaacat taccagctcc aggtttaaat tgttcagttt   8340
catgcagttc caatagctga tcattgttga gatgaggaca aaatcctttg tcctcactag   8400
tttgctttac atttttgaaa agtattattt ttgtccaagt gcttatcaac taaaccttgt   8460
gttaggtaag aatggaattt attaagtgaa tcagtgtgac ccttcttgtc ataagattat   8520
cttaaagctg aagccaaaat atgcttcaaa agaagaggac tttattgttc attgtagttc   8580
atacattcaa agcatctgaa ctgtagtttc tatagcaagc caattacatc cataagtgga   8640
gaaggaaata gataaatgtc aaagtatgat tggtggaggg agcaaggttg aagataatct   8700
ggggttgaaa ttttctagtt ttcattctgt acatttttag ttagacatca gatttgaaat   8760
attaatgttt acctttcaat gtgtggtatc agctggactc agtaacaccc ctttcttcag   8820
ctggggatgg ggaatggatt attggaaaat ggaaagaaga aagtaactaa aagccttcct   8880
ttcacagttt ctggcatcac taccactact gattaaacaa gaataagaga acattttatc   8940
atcatctgct ttattcacat aaatgaagtt gtgatgaata aatctgcttt tatgcagaca   9000
caaggaatta agtggcttcg tcattgtcct tctacctcaa agataattta ttccaaaagc   9060
taagataaat ggaagactct tgaacttgtg aactgatgtg aaatgcagaa tctcttttga   9120
gtctttgctg tttggaagat tgaaaaatat tgttcagcat gggtgaccac cagaaagtaa   9180
tcttaagcca tctagatgtc acaattgaaa caaactgggg agttggttgc tattgtaaaa   9240
taaaatatac tgttttgaaa ac                                           9262
```

```
<210> SEQ ID NO 75
<211> LENGTH: 7647
<212> TYPE: DNA
<213> ORGANISM: Homo sapiens
<220> FEATURE:
<221> NAME/KEY: misc_feature
<223> OTHER INFORMATION: Incyte ID No: 334247.2
<221> NAME/KEY: unsure
<222> LOCATION: 4641
<223> OTHER INFORMATION: a, t, c, g, or other
```

-continued

<400> SEQUENCE: 75

```
cggaccctgc gcgcccccgt cccggctccc ggccggctcg ggggagaagg cgcccgaggg     60
gaggcgccgg acagatcgct tttcggaggc ggcgcaggtg ctgtaaactg caaaccataa    120
tcctgtctta atactgcaaa caaatcatag tggaactaag ggaacttaa tttactgttt     180
ccaggttaac taaggtctca gctgtaaacc aaaagtgaga ggagacatta agattttcat    240
tcttaccggg ttgtcttctt cctgaagagc aatggagccg cttttacttg gaagaggact    300
aatcgtatat ctaatgttcc tcctgttaaa attctcaaaa gcaattgaaa taccatcttc    360
agttcaacag gttccaacaa tcataaaaca gtcaaaagtc caagttgcct ttcccttcga    420
tgagtatttt caaattgaat gtgaagctaa aggaaatcca gaaccaacat tttcgtggac    480
taaggatggc aacccttttt atttcactga ccatcggata attccatcga acaattcagg    540
aacattcagg atcccaaacg aggggcacat atctcacttt caagggaaat accgctgctt    600
tgcttcaaat aaactgggaa tcgctatgtc agaagaaata gaatttatag ttccaagtgt    660
tccaaaattc ccaaaagaaa aaattgaccc tcttgaagtg gaggagggag atccaattgt    720
cctcccatgc aatcctccca aaggcctccc acctttacac atttattgga tgaatattga    780
attagaacac atcgaacaag atgaaagagt atacatgagc caaaagggag atctatactt    840
cgcaaacgtg gaagaaaagg acagtcgcaa tgactactgt tgctttgctg catttccaag    900
attaaggact attgtacaga aaatgccaat gaaactaaca gttaacagtt caaagcatgc    960
taatgactca agttcatcca cagaaattgg ttccaaggca aattccatca agcaaagaaa   1020
acccaaactg ctgttgcctc ccactgagag tggcagtgag tcttcaatta ccatcctcaa   1080
aggggaaatc ttgctgcttg agtgttttgc tgaaggcttg ccaactccac aggttgattg   1140
gaacaaaatt ggtggtgact taccaaaggg gagagaagca aaagaaaatt atggcaagac   1200
tttgaagata gagaatgtct cctaccagga caaaggaaat tatcgctgca cagccagcaa   1260
tttcttggga acagccactc acgattttca cgttatagta gaagagcctc ctcgctggac   1320
aaagaagcct cagagtgctg tgtatagcac cggaagcaat ggcatcttgt tatgtgaggc   1380
tgaaggagaa cctcaaccca caatcaagtg gagagtcaat ggctccccag ttgacaatca   1440
tccatttgct ggtgatgttg tcttccccag ggaaatcagt tttaccaacc ttcaaccaaa   1500
tcatactgct gtgtaccagt gtgaagcctc aaatgtccat ggaactatcc ttgccaatgc   1560
caatattgat gttgtggatg tccgtccatt gatacaaacc aaagatggag aaaattacgc   1620
tacagtggtt gggtacagtg ctttcttaca ttgcgagttc tttgcttcac ctgaggcagt   1680
cgtgtcctgg cagaaggtgg aagaagtgaa acccctggag ggcaggcggt atcatatcta   1740
tgaaaatggc acattgcaga tcaacagaac caccgaagaa gatgctgggt cttactcatg   1800
ttgggtagaa aatgctatag gaaaaactgc agtcacagcc aatttggata ttagaaatgc   1860
tacaaaactt agagtttctc ctaagaatcc tcgtatcccc aaattgcata tgcttgaatt   1920
acattgtgaa agcaaatgtg actcacattt gaaacacagt ttgaagttgt cctggagtaa   1980
agatggagaa gcctttgaaa ttaatggcac agaagatggc aggataatta ttgatggagc   2040
taatttgacc atatctaatg taactttaga ggaccaaggt atttactgct gttcagctca   2100
tactgctcta gacagtgctg ccgatataac tcaagtaact gttcttgatg ttccggatcc   2160
accagaaaac cttcacttgt ctgaaagaca gaacaggagt gttcggctga cctgggaagc   2220
tggagctgac cacaacagca atattagcga gtatattgtt gaatttgaag gaaacaaaga   2280
```

-continued

```
agagcctgga aggtgggagg aactgaccag agtccaagga aagaaaacca cagttatctt   2340
acctttggct ccatttgtga gataccagtt cagggtcata gccgtgaacg aagtagggag   2400
aagtcagcct agccagccgt cagaccatca tgaaacacca ccagcagctc cagataggaa   2460
tccacaaaac ataagggttc aagcctctca acccaaggaa atgattataa agtgggagcc   2520
tttgaaatcc atggagcaga atggaccagg cctagagtac agagtgacct ggaagccaca   2580
gggagcccca gtggagtggg aagaagaaac agtcacaaac cacacattgc gggtgatgac   2640
gcctgctgtc tatgcccctt atgatgtcaa ggtccaggct atcaatcaac taggatctgg   2700
gcctgaccct cagtcagtga ctctctattc tggagaagac tatcctgata cagctccagt   2760
gatccatggg gtggacgtta taaacagtac attagttaaa gttacctggt caacagttcc   2820
aaaggacaga gtacatggac gtctgaaagg ctatcagata aattggtgga aaacaaaaag   2880
tctgttggat ggaagaacac atcccaaaga agtgaacatt ctaagatttt caggacaaag   2940
aaactctgga atggttcctt ccttagatgc ctttagtgaa tttcatttaa cagtcttagc   3000
ctataactct aaaggagctg gtcctgaaag tgagccttat atatttcaaa caccagaagg   3060
agtacctgaa cagccaactt ttctaaaggt catcaaagtt gataaagaca ctgccacttt   3120
atcttgggga ctacctaaga aattaaatgg aaacttaact ggctatcttt tgcaatatca   3180
gataataaat gacacctacg agattggaga attaaatgat attaacatta caactccatc   3240
aaagcccagc tggcacctct caaacctgaa tgcaactacc aagtacaaat tctacttgag   3300
ggcttgcact tcacagggct gtggaaaacc gatcacggag gaaagctcca ccttaggaga   3360
agggagtaaa ggtatcggga agatatcagg agtaaatctt actcaaaaga ctcacccagt   3420
agaggtattt gagccgggag ctgaacatat agttcgccta atgactaaga attggggcga   3480
taacgatagc atttttcaag atgtaattga gacaagaggg agagaatatg ctggtttata   3540
tgatgacatc tccactcaag gctggtttat tggactgatg tgtgcgattg ctcttctcac   3600
actactatta ttaactgttt gctttgtgaa gaggaataga ggtggaaagt actcagttaa   3660
agaaaaggaa gatttgcatc cagacccaga aattcagtca gtaaaagatg aaacctttgg   3720
tgaatacagt gacagtgatg aaaagcctct caaaggaagc cttcggtccc ttaataggga   3780
tatgcagcct actgaaagtg ctgacagctt agtcgaatac ggagagggag accatggtct   3840
cttcagtgaa gatggatcat ttattggtgc ctacgctgga tctaaggaga agggatctgt   3900
tgaaagcaat ggaagttcta cagcaacttt tccccttcgg gcataaacac aacatatgta   3960
agcaacgcta ctggttcacc ccaaccttcc atatttatct gttcaaagga gcaagaactt   4020
tcatatagga atagaaacat gctggccgaa gatttcatcc agaagtcaac atcctgcaat   4080
tatgttgaaa agagtagtac tttcttcaaa atataaaatg ccaagcactt caggcctatg   4140
ttttgcttat attgttttca ggtgctcaaa atgcaaaaca caaaacaaat cctgcattta   4200
gatacacctc aactaaatcc aaagtcccca ttcagtatat tccatatttg cctgatttta   4260
ctattcggtg tgtttgcata gatgttgcta cttggtgggt tttctccgt atgcacattg   4320
gtatacagtc tctgagaact ggcttggtga ctttgcttca ctacaggtta aaagaccata   4380
agcaaactgg ttatttaaaa tgtaaaaagg aatatgaaag tcttattaaa acacttcatt   4440
gaaaatatac agtctaaatt tattatttaa attttactag caaaagtctt aggtgaacaa   4500
tcaactagta tttgttgagc tcctatttgc ccagagatgg tcatatttaa acagaagtat   4560
acgtttttca gtttcaacat gaattttttt atttctgtca gttatgacat ccacgagcat   4620
cactttttgt gtctgttttt nttttttttct tggactaaat tcaactgcat ggaagcggtg   4680
```

-continued gtcagaaggt tgttttatac gagaacaggc agaaagtgcc cattgttcag gattctaata 4740
gctacatcta cttaatatct tcatttctaa attgactgct tttacctttt tctcatgttt 4800
atataatggt atgcttgcat atatttcatg aatacattgt acatattatg ttaatattta 4860
cacaatttaa aatatagatg tgttttattt tgaagtgaga aaatgaacat taacaggcat 4920
gtttgtacag ctagaatata ttagtaagat actgtttttc gtcattccag agctacaact 4980
aataacacga ggttccaaag ctgaagactt tgtataaagt atttgggttt tgttcttgta 5040
ttgctttctt tcaacagttt caaaataaaa tatcatacaa atattgaggg aaatgttttc 5100
atatttttca aaataggttt ttattgttga atgtacatct accccagccc ctcaaaagaa 5160
aaactgttta catagaaatt cctacacata cgtttgcgta tatgttattt taaacatctt 5220
tgtggtgaga attttttccc cgatattctc cttctgtcaa agtcagaaca aattcaggga 5280
atttattttc tggcagttgt gctccagtcc ttttaaaatt gtacatgaac atgttttaga 5340
aacaatatgg aggatgatgc atacatgtcg gtcaagttca gcgctcgaca ttttatggaa 5400
agattttttt aaccttacca cgaaatactt aactactgtt taagtgaatt gacttatttc 5460
actttagttt ttgaactgtg attattggta tactgttata tcctcaactt ggatttatgg 5520
taacccettt tagttcatgg agaccaaaat ttggggtatt tataatagtc agcgcaggaa 5580
tgcacatgga atatctactt gtccttttga acctcacgag tcatccagaa tgtatagaca 5640
ggaaaagcat gtcttattta aaactgtaat ttatgggctc aggatctgac cgcagtcccg 5700
ggagtaagca tttcaaaggg ggaaggcagt gtggtcccta ccctgtgtga atgtgaggat 5760
gtagacatcc atcagtgcaa ctgcgagctc catcctcctc cgatttctaa ggttccagtt 5820
ttctggaggg acagtcatca tgttttgatt tatctgggag aaaactgtgg tgcacagctt 5880
gtgaggaggg caaggttgtg acgttcgagc ttagttctgg tgttattctg tctcctcttc 5940
tttgtcatca gccaaaacgt ggtttttaaa gagagtcatg caggttagaa ataatgtcaa 6000
aaatatttag gaatttaata acctttaagt cagaaactaa aacaaatact gaaatattag 6060
ctcttcctac acttcgtgtt cccctttagc tgcctgaaaa tcaagattgc tcctactcag 6120
atcttctgag tggctaaaac ttatggatat gaaaaatgag attgaatgat gactatgctt 6180
tgctatcatt gttacctttc ctcaatacta tttggcaact actgggactc ttcagcacaa 6240
aaggaataga tctatgattg accctgattt taattgtgaa attatatgat tcatatattt 6300
tatgaatcag aataaccttc aaataaaata aatctaagtc ggttaaaatg gatttcatga 6360
ttttccctca gaaaatgagt aacggagtcc acggcgtgca atggtaatta taaattggtg 6420
atgcttgttt gcaaattgcc cactcgtgat aagtcaacag ccaatattta aaactttgtt 6480
cgttactggc tttaccctaa ctttctctag tctactgtca atatcatttt aatgtaattg 6540
attgtatata gtctcaagaa tggttggtgg gcatgagttc ctagagaact gtccaagggt 6600
tggaaaaatc caaattctct tcctggctcc agcactgatt ttgtacataa acattaggca 6660
ggttgcttaa cctttttatt tcaaactctc tcaactctaa agtgctaata ataatctcag 6720
ttaccttatc tttgtcacag ggtgttcttt tttatgaaga aaaatttgaa aatgataaaa 6780
gctaagatgc cttctaactt cataagcaaa cctttaacta attatgtatc tgaaagtcac 6840
ccccacatac caactcaact tttttcctgt gaacacataa atatattttt atagaaaaac 6900
aaatctacat aaaataaatc tactgtttag tgagcagtat gacttgtaca tgccattgaa 6960
aattattaat cagaagaaaa ttaagcaggg tctttgctat acaaaagtgt tttccactaa 7020

-continued

```
ttttgcatgc gtatttataa gaaaaatgtg aatttggtgg ttttattcta tcggtataaa   7080

ggcatcgata ttttagatgc acccgtgttt gtaaaaatgt agagcacaat ggaattatgc   7140

tggaagtctc aaataatatt tttttcctat tttatactca tggaagagat aagctaaaga   7200

ggggacaata atgagaaatg ttggtgtgct tttctaagca tttaaaacat aattgccaat   7260

tgaaacccta aatatgttta cataccatta agatatgatt catgtaacaa tgttaaatta   7320

attataatgg gattgggttt gttatctgtg gtagtatata tcctagtgtt cctatagtga   7380

aataagtagg gttcagccaa agctttcttt gttttgtacc ttaaattgtt cgattacgtc   7440

atcaaaagag atgaaaggta tgtagaacag gttcacgtga ttaccttttt cttttggctt   7500

ggattaatat tcatagtaga actttataaa acgtgtttgt attgtaggtg gtgtttgtat   7560

tatgcttatg actatgtatg gtttgaaaat attttcatta tacatgaaat tcaactttcc   7620

aaataaaagt tctacttcat gtaatcc                                       7647
```

<210> SEQ ID NO 76
<211> LENGTH: 1738
<212> TYPE: DNA
<213> ORGANISM: Homo sapiens
<220> FEATURE:
<221> NAME/KEY: misc_feature
<223> OTHER INFORMATION: Incyte ID No: 233456.8

<400> SEQUENCE: 76

```
ccagctgctg cagccgcaga ggcagccgga ggcagagggg cggcgggcag gaccagacag     60

ggctgggcag ggggctggcc gagcgccgtg cgccgcttgg gagaaggccg gaagcttacc    120

agccgagaag gaattcctag ctagcttcag agccggtgcc tccggagcca gcgtggtggc    180

catagacaac aagatcgaac aggccatgga tctggtgaag aatcatctga tgtatgctgt    240

gagagaggag gtggagatcc tgaaggagca gatccgagag ctggtggaga agaactccca    300

gctagagcgt gagaacaccc tgttgaagac cctgggcaag cccagagcag ctggagaagt    360

tccagtcctg tctgagccct gaagagccag ctcccgaatc cccacaagtg cccgaggccc    420

ctggtggttc tgcggtgtaa gtggctctgt cctcagggtg ggcagagcca ctaaacttgt    480

tttacctagt tctttccagt ttgtttttgg ctccccaagc atcatctcac gaggagaact    540

ttacacctag cacagctggt gccaagagat gtcctaagga catggccacc tgggtccact    600

ccagcgacag acccctgaca agagcaggtc tctggaggct gagttgcatg gggcctagta    660

acaccaagcc agtgagcctc taatgctact gcgccctggg ggctcccagg gcctgggcaa    720

cttagctgca actggcaaag gagaagggta gtttgaggtg tgacaccagt ttgctccaga    780

aagtttaagg ggtctgtttc tcatctccat ggacatcttc aacagcttca cctgacaacg    840

actgttccta tgaagaagcc acttgtgttt taagcagagg caacctctct cttctcctct    900

gtttcgtgaa ggcaggggac acagatggga gagattgagc caagtcagcc ttctgttggt    960

taatatggta taatgcatgg ctttgtgcac agcccagtgt gggattacag ctttgggatg   1020

accgcttaca aagttctgtt tggttagtat tggcatagtt tttctatata gccataaatg   1080

cgtatatata cccatagggc tagatctgta tcttagtgta gcgatgtata catatacaca   1140

tccacctaca tgttgaaggg cctaaccagc cttgggagta ttgactggtc ccttacctct   1200

tatggctaag tctttgactg tgttcattta ccaagttgac ccagtttgtc ttttaggtta   1260

agtaagactc gagagtaaag gcaaggaggg gggccagcct ctgaatgcgg ccacggatgc   1320

cttgctgctg caaccctttc cccagctgtc cactgaaacg tgaagtcctg ttttgaatgc   1380
```

-continued

```
caaacccacc attcactggt gctgactaca tagaatgggg ttgagagaag atcagtttgg   1440

gcttcacagt gtcatttgaa aacgtttttt gttttgtttt gtaattattg tggaaaactt   1500

tcaagtgaac agaaggatgg tgtcctactg tggatgaggg atgaacaagg ggatggcttt   1560

gatccaatgg agcctgggag gtgtgcccag aaagcttgtc tgtagcgggt tttgtgagag   1620

tgaacacttt ccactttttg acaccttatc ctgatgtatg gttccaggat ttggattttg   1680

attttccaaa tgtagcttga aatttcaata aactttgctc tgtttttcta aaaaaaa      1738
```

<210> SEQ ID NO 77
<211> LENGTH: 2823
<212> TYPE: DNA
<213> ORGANISM: Homo sapiens
<220> FEATURE:
<221> NAME/KEY: misc_feature
<223> OTHER INFORMATION: Incyte ID No: 408334.3

<400> SEQUENCE: 77

```
cgcccacctc tcgtaaccaa tggaaccgcg gcgctcggcc gattctcgca ggcgccctca     60

gatctacgct ctctgatgca acgccggaat cgcggaaacc gccggtgcac gttggagtca    120

taagacggcg tcggtgttgc agtctgtgtc cttggaggtg accagggcca ctgcaggcat    180

ggtgctagca gagctgtacg tctctgaccg agagggaagc gatgccacgg gagatggaac    240

caaggagaaa ccatttaaaa caggtctaaa ggctttgatg acagtaggga aagaaccatt    300

tcctaccatt tacgtagatt cacaaaaaga aaatgagagg tggaatgtta tttctaaatc    360

acagttgaag aacattaaaa agatgtggca tagggaacaa atgaagagtg aatcccggga    420

aaagaaagag gcagaagata gtttacgaag agaaaagaac ctggaagaag caaagaagat    480

taccattaaa aatgatccaa gtctcccaga gccaaaatgt gtgaagattg gtgcgttaga    540

aggatataga ggccaaagag taaaggtgtt tggctgggtc cacaggctgc gcaggcaagg    600

aaagaattta atgtttctgg tgttgcgaga tggtacaggt tatcttcagt gtgtcttggc    660

ggatgagttg tgtcagtgct acaatggagt tctcttgtcc acggagagca gtgttgcagt    720

gtatggaatg ctaaatctta ccccaaaggg caagcaggct ccaggtggcc atgagctgag    780

ttgtgacttc tgggaactaa ttgggttggc cctgctggag gagctgaca acctgatcaa     840

tgaggagtct gacgttgatg tccagctcaa caacagacac atgatgatcc gaggagaaaa    900

catgtccaaa atcctaaaag cacgatccat ggtcaccagg tgctttagag atcacttctt    960

tgataggggg tactatgaag ttactcctcc aacattagtg caaacacaag tagaaggtgg   1020

tgccacactc ttcaagcttg actattttgg ggaagaggca tttttgactc aatcctctca   1080

gttgtacttg gagacctgcc tcccagccct gggagatgtt ttttgtattg ctcagtcata   1140

ccgggcagag cagtccagaa cacgaaggca cctggctgag tacactcacg tggaagctga   1200

gtgtcctttc ctgacttttg acgacctcct gaaccggttg gaggacttgg tttgtgatgt   1260

ggtagatcga atattgaagt cacctgcagg gagcatagtg catgagctca acccgaactt   1320

tcagcccccc aaacggcctt tcaaacggat gaactattca gatgctatcg tttggctaaa   1380

agaacatgat gtaaagaaag aagatggaac tttctatgaa tttggagaag atatcccaga   1440

agctcctgag agactgatga cagacaccat taatgaacca atcttgctgt gtcgatttcc   1500

tgtggagatc aagtccttct acatgcagcg atgtcctgag gattcccgtc ttactgaatc   1560

tgtcgacgtg ttgatgccca atgttggtga gattgtggga ggctcaatgc gtatctttga   1620

tagtgaagaa atactggcag gttataaaag ggaagggatt gaccccactc cctattactg   1680
```

-continued

```
gtatacggat cagagaaaat acggtacatg tccccatgga ggatatggct tgggcttgga   1740

acgattctta acgtggattc tgaataggta tcacatccga gacgtgtgct tataccctcg   1800

atttgtccag cgttgcacgc cataaccatt ttctccagaa gcgtggagga aagattatga   1860

aaggaacagg ctctttaaaa aagaaaacaa aaagccagaa tcttcctttt tttgtttcat   1920

tggggtttct ctttctgttt ttctttctac taccataaaa actatctcaa atcacctgaa   1980

catcaagtga tattaaggtt gtcatcttaa gaaaaaatat ccattttttt cttaagttcg   2040

ggaaacaaag ttcggggaaa atacctggca tgaaactgta gttagggata catttcagca   2100

ttttactcac tttatccaag ttattcattt tattcaagtt atatgtatgt ataattcaac   2160

aattttagat tatggtgtaa gatactccag taacttatct ttctgtcctt ttaagtgtac   2220

cttgaattct ttgatttatt ttattgcatc aatgaattaa aacaaaaatc ttgggggaag   2280

aaattggcaa tatcgtataa aaatctgctc atattagaac acagtataat tcagcagtaa   2340

acactagaat caaatgaata gccttttgta tcagttatta atcttttcta actctgctta   2400

gctgctaata atcctgaggc atagaaattg aagaatttgt aaaaatagaa ttgccttaaa   2460

ggatttgaag taagaacata attttgggga gagtttttta gtgattcaca gtatccctct   2520

tagcattaat ttaaggtaaa gaggcagatt gattttccct ctttcctggt aattcctaag   2580

taattaagaa taaataagtt ccaaaagaaa ttgtagctgg aatcttaata acaattgtga   2640

gtggctgttt gagttgcccc caccatgtcc ttagatctaa tctgtgctac cttattaact   2700

cacagcaggc ttactgaatg gcttcatttc agatttagtt gatttctcca ccaaatgcat   2760

gtcatgtatt ctcaataggc tgtattccca gcagtcaata aatgaacacc cgtaaaaact   2820

ctt                                                                 2823
```

```
<210> SEQ ID NO 78
<211> LENGTH: 546
<212> TYPE: DNA
<213> ORGANISM: Homo sapiens
<220> FEATURE:
<221> NAME/KEY: misc_feature
<223> OTHER INFORMATION: Incyte ID No: 986408.2

<400> SEQUENCE: 78

tgaggtcatc ctttacggca ggcgtccgcg tcgctagcta gtcgttctga agcggcggcc     60

agagaagagt caagggcacg agcatcggcc atgcctttct tggacatcca gaaaaggttc    120

ggccttaaca tagatcgatg gttgacaatc cagagtggtg aacagcccta caagatggct    180

ggtcgatgcc atgcttttga aaaagaatgg atagaatgtg cacatggaat cggttatact    240

cgggcagaga aagagtgcaa gatagaatat gatgatttcg tagagtgttt gcttcggcag    300

aaaacgatga gacgtgcagg taccatcagg aagcagcggg ataagctgat aaaggaagga    360

aagtacaccc ctccacctca ccacattggc aagggggagc ctcggccctg aacagagcag    420

ctgctgatgt ctggaggctg attttcctgt tctctgttct ccactggaaa ggttgtttac    480

gacaaacctc cttgtcaaag tgtgtaaaaa taaaggattg ctccatccta aaaaaaaaaa    540

aaaagc                                                              546
```

```
<210> SEQ ID NO 79
<211> LENGTH: 2015
<212> TYPE: DNA
<213> ORGANISM: Homo sapiens
<220> FEATURE:
<221> NAME/KEY: misc_feature
<223> OTHER INFORMATION: Incyte ID No: 251918.2
```

-continued

<400> SEQUENCE: 79

```
gcgtcaatgc gcccgccgtg tccatggaga gaagctgagg cggccgacct tcggcccgag      60
gcaccggggc gccgggacgg cgaagatgtc ggcttcctta gtccgggcaa ctgtccgggc     120
tgtgagcaag aggaagctgc agcccacccg ggcagccctc accctgacac cttcagcagt     180
aaacaagata aaacaacttc ttaaagataa gcctgagcat gtaggtgtaa aagttggtgt     240
ccgaaccagg ggctgtaatg gcctttctta tactctagaa tatacaaaga caaaaggaga     300
ttctgatgaa gaagttattc aagatggagt cagagtattc atcgaaaaga aagcacagct     360
aacactttta ggaacagaaa tggactatgt tgaagacaaa ttatccagtg agtttgtgtt     420
caataaccca aacatcaaag ggacttgtgg ctgtggagaa agctttaata tttgaaatct     480
caggactctt ctggccgtag gttccaggaa agctcgtgga agctttgggg ctcactgcag     540
aaatcatgtg actgtcacgt gctggaaaat aaagtgatac atcttgaaaa tgaatccagt     600
gtgttggatt ccagaagaaa tgatatttat attctctata ggggacagaa aatgagaagc     660
catcactctt tttggatcat ttaggtctct tgtatccttt gttttagaac cagtttcatt     720
aaagttgcct tcctgggcac ctgtttatcc atttcctgaa ctgtgtgcac tccttagatc     780
gctattgatg gcttgatcat ccctcagcat ttctcccaac cagatcggtg actcctaaaa     840
tctgagacag gacatcgtga ctgctggtag taatatggtg gtgcattgtt ttttccaccc     900
aaacttaaca tagccttttt atacattttt atgaaaaatt tcattgtcag ctgcctcact     960
gcatactctt taatagtacc aggcaaagat tttcttcaac tatagtacag attagttctg    1020
agtgatggta tcaaaaggtg agaaagacgt catccgcctt tttttaatcc atttcttttg    1080
ccaccctata tgtctgttca gagatgggct ctcaagctga ctttgattct tttagttgag    1140
aagtctctta aagccatcta gcccacctcc atcaattccc tatgtgagga agcaaaaccc    1200
cagggaagcc aaagggctcc tgtccaccct gacaccacag gccgggggag agtagggact    1260
ctacccccct ctccccttgt aggtgacaca tgctctgccc tctgaggcag tcagcgaagg    1320
caaatggtct gacttcttta tgtggtcaac attttgatag aatttcttta taatttgata    1380
gagattatat tatttttatt ttattttgag tgggaagaat tttaaaacct ttttatgtca    1440
attaccatct tgtttctttc acctttgaaa caatggtttg tagcagagat gacattgtag    1500
caacccagaa ttatgctttt ggaatgtggt cctcactgta caggagaatg tgtaatcttt    1560
tgttaaaatt cccagtgtgc atacattttc tggttcctcg gtccagttgc taaagttctt    1620
agtattttag cctaacatat ttatcaccaa cttttcttta aaagtgttcc ttttgtcact    1680
tagttactga ttttcctggg tttgacataa gtattctatg agatgatata tatgcttttt    1740
ttgaaagctg attctcatga attcaagtag ctgagttcct ttatgtttcg tttattcact    1800
aaagtagctg acacaaaaca caccaaaacc tagagcggta gttttatgta aatgctcatg    1860
agtttgtatc aataatataa ttgttgatcc acttataatt cgtgcaacac tgtatgtatg    1920
tagagattga gttgtcaatt aaaaaaaatg tggcctcttt gtgatcataa aattgccttt    1980
tattattgag gggagagggt ttgggacagc agctg                               2015
```

<210> SEQ ID NO 80
<211> LENGTH: 2628
<212> TYPE: DNA
<213> ORGANISM: Homo sapiens
<220> FEATURE:
<221> NAME/KEY: misc_feature
<223> OTHER INFORMATION: Incyte ID No: 474401.5

-continued

<400> SEQUENCE: 80

```
gggcgcgcg actgctccgg gcggcgatgg cggcggacgg ggactggcag gatttctatg     60
agttccagga gccggcccgg agcctcctgg accaggagaa ctgtaacgcg agccccgagc    120
ctggggcgga ggcgggggcc ggggcgggtg ggggcgccga cggtttcccg gccctggcct    180
gcagcttgga ggagaagctg agcctgtgct tccgcccctc ggatccgggg cgccgagccc    240
ccgaggacgg ccgtgcggcc catcacggag cgcacctcct gcagggggac gagatttgga    300
atgccctgac agataattat gggaatgtga tgcctgtaga ctggaagtca tcgcatacta    360
ggaccttggc acttgcttac tctgaacctc tcagaaaaag gggtaagtga cagtttgctc    420
tttgatacat cagatgatga agagctgaga gaacagctgg atatgcactc aatcatcgtc    480
tcctgtgtta atgatgaacc cctcttcacg gcagaccagg ttattgaaga aattgaagaa    540
atgatgcagg aatcaccgga cccagaagat gatgaaaccc ctacacagtc agatcggctt    600
tcaatgcttt cccaggaaat tcaaactctc aagaggtcta gtaccggcag ttatgaagag    660
agagtgaaaa ggctctcagt gtctgagtta aatgaaatcc tggaagaaat tgagactgcc    720
attaaggagt actctgagga gctggtgcag cagttggctt tacgagatga actggagttt    780
gaaaaggaag tgaaaaacag ctttatttct gttcttattg aagtgcaaaa caaacagaaa    840
gagcacaaag aaacagcaaa aaagaaaaag aaactaaaaa atggcagctc tcagaatggg    900
aagaatgaga gaagtcatat gcccggcaca tatttgacta cagtcattcc ttatgagaaa    960
aaaaacggac caccgtctgt tgaagatctt caaatattaa caaaaattct tcgtgccatg   1020
aaggaggaca gtgaaaaagt tccgagcttg ttaactgatt atattctgaa agttctgtgt   1080
cctacataga gcagcaactt tatctgcggt gggctccaag ctagatttcc gacagcatta   1140
ttctgagagc tggctaccat taccettctt gctattggaa actcagcaca tttgaacttg   1200
ggtttgattc agtattaaca gatcttgact acactaattc tttatattat agaaccaacg   1260
gaaatatggg cactattttg aattctagag atggtttttg ttaaatctac taataaactg   1320
ttctcttagt agattaagag agagtaatat taattgtgca tgtgcagttg tatttctcat   1380
taactgacag tatgcccatt tgtttttatg gctttcttat ctaaactgca ctgatgaact   1440
agattaaagc cttgggagat ttatactata aattcagtga tggcaagaac caacactgtt   1500
tttttgtgag aattgtcagt gtaactatta cctaccagta ttgttcagag agattgaaac   1560
agaataaacg ggctgttctt gaagaagcaa aaccagaata tgcattactt tggtttaata   1620
cttagtgcta acattgaaac tgttggtggt gatggatttt gtagcttgct gcttcaagaa   1680
cagcccgttt attctgtttc aatctctctg aacaatactg gtaggtaata gttacactga   1740
caattctcac aaaaaaacag tgttggttct tgccatcact gaatttatag tataaatctc   1800
ccaaggcttt aatctagttc atcagtgcag tttagataag aaagccataa aaacaaatgg   1860
gcatactgtc agttaatgag aaatacaact gcccatgcac aattaatatt actctctctt   1920
aatctactaa gagaacagtt tattagtaga tttaacaaaa accatctcta gaattcaaaa   1980
tagtgcccat atttccgttg gttctataat ataaagaatt agtgtagtca agatctgtta   2040
atactgaatc aaacccaagt tcaaatgtgc tgagtttcca atagcaagaa gggtaatggt   2100
agccagctct cagaataatg ctgtcggaaa tctagcttgg agcccaccgc agataaagtt   2160
gctgctctat gtaggacaca gaactagaag aaaaagagaa ctttcagaat ataatcagtt   2220
aacaagctcg gaactttttc actgtcctcc ttcatggcac gaagaatttt tgttaatatt   2280
```

-continued

```
tgaagatctt caacagacgg tggtccgttt tttttctcat aaggaatgac tgtagtcaaa   2340

tactgtttct ctccacctga atttccaaag gtgtggcgga ggccattctg aatgacattt   2400

gagatccctt ccatgctgaa gcgtgtgccg ggcatatgac ttctctcatt cttcccattc   2460

tgagagctgc catttttttag tttctttttc ttttttgctg tttctttgtg ctctttctgt   2520

ttgttttgca cttcaataag aacagaaata aagctgtttt tcacttcctt ttcaaactcc   2580

agttcatctc gtaaagccaa ctgctgcacc agctcctcag agtactcc                2628
```

<210> SEQ ID NO 81
<211> LENGTH: 4438
<212> TYPE: DNA
<213> ORGANISM: Homo sapiens
<220> FEATURE:
<221> NAME/KEY: misc_feature
<223> OTHER INFORMATION: Incyte ID No: 350230.2

<400> SEQUENCE: 81

```
aaggagttcg ctggagccct ttcctcagac ccggcccggt cttcgcgccc ggactcctgg     60

cgccagcgct aggcgcactc accgctctga cgggtgcaga cgcgggagtt gtcccagact    120

gtggagtggc gggcacggcc ccagcccccc ttcccttccc tgaccccttc ttgccatcgc    180

cccagacatg gggaacgcgg cgaccgccaa gaaaggcagc gaggtggaga gcgtgaaaga    240

gtttctagcc aaagccaaag aagacttttt gaaaaaatgg gagaatccaa ctcagaataa    300

tgccggactt gaagattttg aaaggaaaaa aacccttgga acaggttcat ttggaagagt    360

catgttggta aaacacaaag ccactgaaca gtattatgcc atgaagatct tagataagca    420

gaaggttgtt aaactgaagc aaatagagca tactttgaat gagaaaagaa tattacaggc    480

agtgaatttt cctttccttg ttcgactgga gtatgctttt aaggataatt ctaatttata    540

catggttatg gaatatgtcc ctgggggtga aatgttttca catctaagaa gaattggaag    600

gttcagtgag ccccatgcac ggttctatgc agctcagata gtgctaacat tcgagtacct    660

ccattcacta gacctcatct acagagatct aaaacctgaa aatctcttaa ttgaccatca    720

aggctatatc caggtcacag actttgggtt tgccaaaaga gttaaaggca gaacttggac    780

attatgtgga actccagagt atttggctcc agaaataatt ctcagcaagg gctacaataa    840

ggcagtggat tggtgggcat taggagtgct aatctatgaa atggcagctg gctatccccc    900

attctttgca gaccaaccaa ttcagattta tgaaaagatt gtttctggaa aggtccgatt    960

cccatcccac ttcagttcag atctcaagga ccttctacgg aacctgctgc aggtggattt   1020

gaccaagaga tttggaaatc taaagaatgg tgtcagtgat ataaaaactc acaagtggtt   1080

tgccacgaca gattggattg ctatttacca gaggaaggtt gaagctccat tcataccaaa   1140

gtttagaggc tctggagata ccagcaactt tgatgactat gaagaagaag atatccgtgt   1200

ctctataaca gaaaaatgtg caaaagaatt tggtgaattt taaagaggaa caagatgaca   1260

tctgagctca cactcagtgt ttgcactctg ttgagagata aggtagagct gagaccgtcc   1320

ttgttgaagc agttacctag ttccttcatt ccaacgactg agtgaggtct ttattgccat   1380

catcccgtgt gcgcactctg catccaccta tgtaacaagg caccgctaag caagcattgt   1440

ctgtgccata acacagtact agaccacttt cttacttctc tttgggttgt ctttctcctc   1500

tcctacatcc atttcttcct tttccaattt cattggtttt ctctaaacag tgctccattt   1560

tattttgttg gtgtttcaga tgggcagtgt tatggctacg tgatatttga agggaaggat   1620

aagtgttgct ttcagtagtt attgccaata ttgttgttgg tcaatggctt gaagataaac   1680
```

-continued

```
tttctaataa ttattatttc tttgagtagc tcagacttgg ttttgccaaa actcttggta   1740
atttttgaag atagactgtc ttatcaccaa ggaaatttat acaaattaag actaactttc   1800
ttggaattca ctattctggc aataaatttt ggtagactaa tacagtacag ctagacccag   1860
aaatttggaa ggctgtagat cagaggttct agttcccttt ccctcctttt atatcctcct   1920
ctccttgagt aatgaagtga ccagcctgtg tagtgtgaca aacgtgtctc attcagcagg   1980
aaaaactaat gatatggatc atcacccaga ttctctcact tggtaccagc atttctgtag   2040
gtattagaga agagttctaa gttttctaaa ccttaactgt tccttaagga ttttagccag   2100
tattttaata gaacatgatt aatgaaagtg acaaatttta aattttctct aatagtcctc   2160
atcataaact ttttaaagga aaataagcaa actaaaaaga acattggttt agataaatac   2220
ttatactttg caaagtcaaa aatggcttga tttttggaaa caatatagag gtattcatat   2280
ttaaatgagg gtttacattt gttttgtttt gtaaccgtta aaaagaagtt gtttccagct   2340
aattattgtg gtgtactata tttgtgagcc tagggtaggg gcactgctgc aacttctgct   2400
ttcatcccat gcctcatcaa tgaggaaagg gaacaaagtg tataaaactg ccacaattgt   2460
atttttaattt tgaggtatga tattttcaga tatttcataa tttctaacct ctgttctctc   2520
agtaaacaga atgtctgatc gatcatgcag atacaatgtt ggtatttgag aggttagttt   2580
ttttcctaca cttttttttg ccaactgact taacaacatt gctgtcaggt ggaaatttca   2640
agcacttttg cacatttagt tcagtgtttg ttgagaatcc atggcttaac ccacttgttt   2700
tgctattttt ttctttgctt ttaattttcc ccatctgatt ttatctctgc gtttcagtga   2760
cctaccttaa aacaacacac gagaagagtt aaactgggtt cattttaatg atcaatttac   2820
ctgcatataa aatttatttt taatcaagct gatcttaatg tatataatca ttctatttgc   2880
tttattatcg gtgcaggtag gtcattaaca ccacttcttt tcatctgtac cacaccctgg   2940
tgaaaccttt gaagacataa aaaaaacctg tctgagatgt tctttctacc aatctatatg   3000
tctttcggtt atcaagtgtt tctgcatggt aatgtcatgt aaatgctgat attgatttca   3060
ctggtccatc tatatttaaa acgtgcaaga aaaaaataaa atactctgct ctagcaagtt   3120
ttgtgtaaca aaggcatatc gtcatgttaa taaatttaaa acatcattcg tataaaatat   3180
tttaattttc ttgtatttca tttagaccca agaacatgct gaccaatgtg ttctatatgt   3240
aaactacaaa ttctatggta gctttgttgt atattattgt aaaattattt taataagtca   3300
tggggatgac aatttgatta ttacaattta gttttcagta atcaaaaaga tttctatgaa   3360
ttctaaaaaa tatttttttc tatgaaatta ctagtgccca gctgtagaat ctaccttagg   3420
tagatgatcc ctagacatac gttggttttg agggctattc agccattcca ttttactctc   3480
tatttaaagg ccgtgagcaa gcttgtcatg agcaaatatg tcaagggagt caatttctga   3540
ccaatcaagt acactaaatt agaatatttt taaagtatgt aacattccca gtttcagcca   3600
caatttagcc aagaataaga taaaaacttg aataagaagt aagtagcata aatcagtatt   3660
taacctaaaa ttacatattt gaaacagaag atattatgtt atgctcagta aataattaag   3720
agatggcatt gtgtaagaag gagccctaga ctgaaagtca agacatctga atttcaggct   3780
ggaaaactat cagtatgatc tcagcctcag ttctcttgtc tgtaaaatgg aagaactgga   3840
ttaggcagtt tgtaagattc ctcctaactt tcacagtcga tgacaagatt gtctttttat   3900
ctgatatttt gaagggtata ttgctttgaa gtaagtctca ataaggcaat atattttagg   3960
gcatctttct tcttatctct gacagtgttc ttaaaattat ttgaatatca taagagcctt   4020
ggtgtctgtc ctaattcctt tctcactcac cgatgctgaa tacccagttg aatcaaactg   4080
```

-continued

```
tcaacctacc aaaaacgata ttgtggctta tgggtattgc tgtctcattc ttggtatatt   4140
cttgtgttaa ctgcccattg gcctgaaaat actcattgta agcctgaaaa aaaaaatctt   4200
tcccactgtt ttttctgctt gttgtaagaa tcaaatgaaa taatgtatgt gaaagcacct   4260
tgtaaactgt aacctatcaa tgtaaaatgt taaggtgtgt tgttatttca ttaattactt   4320
ctttgtttag aatggaattt cctatgcact actgtagcta ggaaatgctg aaaacaactg   4380
tgtttttaa ttaatcaata actgcaaaat taaagtacct tcaatggata agacaaaa     4438
```

```
<210> SEQ ID NO 82
<211> LENGTH: 1781
<212> TYPE: DNA
<213> ORGANISM: Homo sapiens
<220> FEATURE:
<221> NAME/KEY: misc_feature
<223> OTHER INFORMATION: Incyte ID No: 221712.2

<400> SEQUENCE: 82

tggcagagca gctgcagaag tgcagggatc ggaaaggtac cagggcagct gctttccgct     60
gcctccggtc cgggcagctg cagaaacagc agggggagga gcaacagctg ccaaattcgc    120
caactagagg agggagaggc ggagcttggg tccctgtaga agccagaggc gcagtctgga    180
ctgtagtttc ccgggagaga cgaaagcagg aacgagagcg gagcggagca cagtccgccg    240
agcacaagct ccagcatccc gtcaggggtt gcaggtgtgt gggaggcttg aaactgttac    300
aatatggctt tccttggact cttctctttg ctggttctgc aaagtatggc tacaggggcc    360
actttccctg aggaagccat tgctgacttg tcagtgaata tgtataatcg tcttagagcc    420
actggtgaag atgaaaatat tctcttctct ccattgagta ttgctcttgc aatgggaatg    480
atggaacttg ggcccaagg atctacccag aaagaaatcc gccactcaat gggatatgac    540
agcctaaaaa atggtgaaga attttctttc ttgaaggagt tttcaaacat ggtaactgct    600
aaagagagcc aatatgtgat gaaaattgcc aattccttgt ttgtgcaaaa tggatttcat    660
gtcaatgagg agtttttgca aatgatgaaa aaatatttta atgcagcagt aaatcatgtg    720
gacttcagtc aaaatgtagc cgtggccaac tacatcaata agtgggtgga gaataacaca    780
aacaatctgg tgaaagattt ggtatcccca agggattttg atgctgccac ttatctggcc    840
ctcattaatg ctgtctattt caaggggaac tggaagtcgc agtttaggcc tgaaaatact    900
agaacctttt ctttcactaa agatgatgaa agtgaagtcc aaattccaat gatgtatcag    960
caaggagaat tttattatgg ggaatttagt gatggctcca atgaagctgg tggtatctac   1020
caagtcctag aaataccata tgaaggagat gaaataagca tgatgctggt gctgtccaga   1080
caggaagttc ctcttgctac tctggagcca ttagtcaaag cacagctggt tgaagaatgg   1140
gcaaactctg tgaagaagca aaaagtagaa gtatacctgc ccaggttcac agtggaacag   1200
gaaattgatt taaaagatgt tttgaaggct cttggaataa ctgaaatttt catcaaagat   1260
gcaaatttga caggcctctc tgataataag gagatttttc tttccaaagc aattcacaag   1320
tccttcctag aggttaatga agaaggctca gaagctgctg ctgtctcagg aatgattgca   1380
attagtagga tggctgtgct gtatcctcaa gttattgtcg accatccatt tttctttctt   1440
atcagaaaca ggagaactgg tacaattcta ttcatgggac gagtcatgca tcctgaaaca   1500
atgaacacaa gtggacatga tttcgaagaa ctttaagtta ctttatttga ataacaagga   1560
aaacagtaac taagcacatt atgtttgcaa ctggtatata tttaggattt gtgttttaca   1620
gtatatctta agataatatt taaaatagtt ccagataaaa acaatatatg taaattataa   1680
```

-continued gtaacttgtc aaggaatgtt atcagtatta agctaatggt cctgttatgt cattgtgttt 1740
gtgtgctgtt gtttaaaata aaagtaccta ttgaacatgt g 1781

<210> SEQ ID NO 83
<211> LENGTH: 4132
<212> TYPE: DNA
<213> ORGANISM: Homo sapiens
<220> FEATURE:
<221> NAME/KEY: misc_feature
<223> OTHER INFORMATION: Incyte ID No: 251826.7

<400> SEQUENCE: 83
cgggcggcgc aggggcgggg ctttacggac gcaagcacgt cgaagcgctg ctcctggagc 60
cgcggagggt gcgggtttgg ctgcggtggt ttctgtggcg gttgctgtgg cggagtttgg 120
aggttggaga gaaatccagg tactcactag actggtacct tctgccacca tgggggagct 180
tttccggagt gaagaaatga cactggccca gctttttcta cagtcagagg ctgcttattg 240
ttgtgtcagt gaattaggag aacttggaaa ggttcagttt cgtgacttaa atccagatgt 300
gaatgttttc caacggaaat ttgtgaatga agttagaaga tgtgaagaaa tggatcgaaa 360
gcttcgattt gttgagaaag agataagaaa agctaacatt ccgattatgg acaccggtga 420
aaacccagag gttcccttcc cccgggacat gattgactta gaggccaatt ttgagaagat 480
tgaaaatgaa ctgaaggaaa tcaacacaaa ccaggaagct ctgaagagaa acttcctgga 540
actgaccgaa ttaaaattta tacttcgcaa aactcagcaa ttttttgatg agatggcgga 600
tccagacttg ttggaagagt cctcatccct cttggagcca agtgagatgg gaagaggcac 660
tcctttaaga cttggcttcg tggctggtgt cattaaccgg gagcgcatcc ctacttttga 720
gcgcatgctt tggcgggtat gccggggaaa tgtgttcctg cgacaggctg aaatcgagaa 780
ccccctggag gatcctgtga ctggcgacta cgtgcacaag tctgtgttta tcattttctt 840
ccaaggcgat cagctgaaaa acagagtcaa gaaaatctgt gaagggttcc gagcctcact 900
ccatccctgt cctgagacac cacaggagag gaaggaaatg gcttctggag tgaataccag 960
gattgatgat ctccaaatgg ttctgaatca aacggaggat caccgccaga gggttctgca 1020
ggcagctgct aagaacatcc gtgtctggtt catcaaagtg cggaagatga aggccatcta 1080
tcacaccctg aacctgtgca acatagatgt gactcagaaa tgcttgattg cagaggtctg 1140
gtgccctgtc accgaccttg actccatcca gtttgcactc agaaggggca cggaacacag 1200
tggttccact gtaccttcca ttttgaacag gatgcagaca aaccagactc cccaacccta 1260
taacaaaacc aacaagttta cctatggctt tcagaacata gtagatgctt atggaattgg 1320
aacttaccga gagataaatc cagctccgta tactattatc acgttccctt ttctatttgc 1380
tgtgatgttt ggagacttcg gtcatggcat tttaatgacc ctttttgctg tgtggatggt 1440
actgagggag agccggatcc tttcccagaa gaatgagaat gagatgttta gcactgtgtt 1500
cagtggtcga tacattattt tattgatggg tgtgttctcc atgtacactg gcctcatcta 1560
caatgattgc ttttccaagt ctcttaatat ctttgggtca tcctggagtg tacggccgat 1620
gtttacttat aattggactg aagagacgct tcgggggaac cctgttctac agctgaaccc 1680
agccctccct ggagtgtttg gtggaccata ccctttttggc attgatccaa tttggaacat 1740
tgctaccaat aaactgacgt tcttgaactc ctttaagatg aagatgtctg ttatccttgg 1800
tatcatccat atgctgtttg gagtcagcct gagtctgttc aaccatatct atttcaagaa 1860
gcccctgaat atctactttg gatttattcc tgaaataatc ttcatgacct ctttgtttgg 1920

-continued

```
ctatttggtt atccttattt tttacaagtg gacggcctat gatgctcata cctctgagaa   1980
tgcaccaagc cttctgatcc atttcataaa catgttcctc ttttcctacc cagagtctgg   2040
ttattcaatg ttgtattctg gacagaaagg aattcagtgt ttcctggtag tggttgcact   2100
actgtgtgta ccttggatgc tgctgtttaa accattggtc cttcgccgtc agtatttgag   2160
gagaaagcat ttgggaactc tcaactttgg tgggatcagg gtgggcaacg gaccgacaga   2220
ggaggatgct gagattattc agcatgacca gctctccacc cactcagagg acgcagacga   2280
gtttgacttt ggggacacca tggtccacca ggccatccac accatcgagt actgcctggg   2340
ctgcatctcc aacactgcct cctacttgcg gctctgggcc ctcagcctcg ctcatgcgca   2400
gctgtctgag gtgctttgga ccatggtgat ccacatcggc ctgagcgtga agagcttggc   2460
gggaggtttg gtgctgttct tcttcttcac tgcctttgcc accctgaccg tggccatcct   2520
cctgatcatg gagggcctct cggcctttct ccacgcactg cgcttacact gggttgagtt   2580
ccagaataaa ttctacagcg ggaccggttt caagttctta cccttctcct tcgagcatat   2640
tcgggaaggg aagtttgaag agtgagtccc tgtgagggcc gtgtgcccca tgctaccctc   2700
cccgcctccc tccacagtga tcagctgtgc ctctctgcct gttggttgtg atctgtgggc   2760
accagctcat tcgtgtcacc ctgtctgtga gtcatttaga tagaatagtc ctccttgggt   2820
ctcccaccac ccctagcttt gtgtgtagtg tagtgatttt ctggctgtca ctcatactca   2880
ctgggcacca gccttgccct cttagcctcc atccatccag acagcccttc ccacctcctg   2940
gtggtgagcc agtctgcatt cccacgccat cccaaagccc tttcatcttc cccgtgcatt   3000
gtagatggaa ggagcaccca tgccattcac atctagactt tgagttccct gcatctgcca   3060
ccgtagtttc tagcaggagt agtgggggga gtaatacaga ttcttcccta gaaggggaca   3120
ctggtaacat gtcccactct tggattagca ggggtgggtc caggaagatg atatttgcgt   3180
cttttgccca cccccctggg cattcagctg gacccaacta ggccatcatg agtggcttct   3240
ccctgtcacc cccaggggtc ataggatatc tacaccgcct ttctgacccc accctgcact   3300
cccatccttt cctctctccc cgttcatgcc ctgcactaca tagcacagcc gggatgcttg   3360
gaacagaggc cttgggctgc tccgcagtgc acagggcttc cctctctcgg ggttggcttc   3420
ttcccaggcc ttgcatgggc cctgcccaca agcacaccct caggccgagg gtgcagactg   3480
atgctcttcc ctgatggaga ccctgagatc ttccccaccc ccaatcatga tgtcttcagt   3540
gtgggactgg ggtcctcttg gttctgcctg cagcctgcct ggctccgccc ctagtgcccc   3600
ctcctcacca cactggcccc aggtctcagg aggggtgtcc tgggcaggga aggtcagtgt   3660
cactgatggt ttgctgtttg gaagccattg gcagggctgc cgtgcatgtg gctgtgaggg   3720
ctgcacagtc ctgccaaggg gcttcctcct tgtcaccccg aaccttgtaa tcgtgtgctg   3780
gcgtggcagc cctggctaag ttaatcccca ccgctttcag tggtagaaag aattccctga   3840
gtgggccagg ctggtgccct cctcctaccc tggcttttct gagtgagctg cctggagccc   3900
tcatcccctc tcccaggctg ggctggccct gggcggggcc actgtgtgct ggcccactgt   3960
gacctgaccc gaccttgtgc agccccccctg ccctggtgtc ctgggttttc gtgatgatct   4020
ttgctctgtt tccagtgggg tttgaagcag agttcaggga accctgccca aggtcctcct   4080
gttcagacat tcctatgttg aataaagtat gtttgacttc cccggaaaaa aa           4132
```

<210> SEQ ID NO 84
<211> LENGTH: 2931
<212> TYPE: DNA

-continued

<213> ORGANISM: Homo sapiens
<220> FEATURE:
<221> NAME/KEY: misc_feature
<223> OTHER INFORMATION: Incyte ID No: 246704.2

<400> SEQUENCE: 84
cggctctctg cgcgcgaacg cgagtcccgg gcgggtgggg cgggggtcca ctgagaccgc 60
taccggcccc tcggcgctga cgggaccgcg cggggcgcac ccgctgaagg cagccccggg 120
gcccgcggcc cggacttggt cctgcgcacg ggcgcggggc agcgcacgct gaggaagcga 180
gaggtgctgc cctccccccg gagttggaag cgcgttaccc gggtccaaaa tgcccaagaa 240
gaagccgacg cccatccagc tgaacccggc ccccgacggc tctgcagtta acgggaccag 300
ctctgcggag accaacttgg aggccttgca gaagaagctg gaggagctag agcttgatga 360
gcagcagcga aagcgccttg aggcctttct tacccagaag cagaaggtgg gagaactgaa 420
ggatgacgac tttgagaaga tcagtgagct gggggctggc aatggcggtg tggtgttcaa 480
ggtctcccac aagccttctg gcctggtcat ggccagaaag ctaattcatc tggagatcaa 540
acccgcaatc cggaaccaga tcataaggga gctgcaggtt ctgcatgagt gcaactctcc 600
gtacatcgtg ggcttctatg gtgcgttcta cagcgatggc gagatcagta tctgcatgga 660
gcacatggat ggaggttctc tggatcaagt cctgaagaaa gctggaagaa ttcctgaaca 720
aattttagga aaagttagca ttgctgtaat aaaaggcctg acatatctga gggagaagca 780
caagatcatg cacagagatg tcaagccctc caacatccta gtcaactccc gtggggagat 840
caagctctgt gactttgggg tcagcgggca gctcatcgac tccatgggcc aactccttcg 900
tgggcacaag gtcctacatg tcgccagaaa gactccaggg gactcattac tctgtgcagt 960
cagacatctg gagcatggga ctgtctctgg tagagatggc ggttgggagg tatcccatcc 1020
ctcctccaga tgccaaggag ctggagctga tgtttgggtg ccaggtggaa ggagatgcgg 1080
ctgagacccc acccaggcca aggacccccg ggaggcccct tagctcatac ggaatggaca 1140
gccgacctcc catggcaatt tttgagttgt tggattacat agtcaacgag cctcctccaa 1200
aactgcccag tggagtgttc agtctggaat ttcaagattt tgtgaataaa tgcttaataa 1260
aaaaccccgc agagagagca gatttgaagc aactcatggt tcatgctttt atcaagagat 1320
ctgatgctga ggaagtggat tttgcaggtt ggctctgctc caccatcggc cttaaccagc 1380
ccagcacacc aacccatgct gctggcgtct aagtgtttgg gaagcaacaa agagcgagtc 1440
ccctgcccgg tggtttgcca tgtcgctttt gggcctcctt cccatgcctg tctctgttca 1500
gatgtgcatt tcacctgtga caaaggatga agaacacagc atgtgccaag attctactct 1560
tgtcattttt aatattactg tctttattct tattactatt attgttcccc taagtggatt 1620
ggctttgtgc ttggggctat ttgtgtgtat gctgatgatc aaaacctgtg ccaggctgaa 1680
ttacagtgaa attttggtga atgtgggtag tcattcttaa aattgcactg ctgttcctgc 1740
tccatgactg gctgtctgcc tgtattttcg ggattctttg acgacatttg gtggtacttt 1800
attcttgctg ggcatacttt ctctctagga gggagccttg tgagatcctt cacaggcagt 1860
gcatgtgaag catgctttgc tgctatgaaa atgagcatca gagagtgtac atcatgttat 1920
tttattatta ttatttgctt ttcatgtaga actcagcagt tgacatccaa atctagccag 1980
agcccttcac tgccatgata gctggggctt caccagtctg tctactgtgg tgatctgtag 2040
acttctggtt gtatttctat atttattttc aatatactgt gtgggatact tagtggtatg 2100
tctctttaag ttttgattaa tgtttcttaa atggaattat tttgaatgtc acaaattgat 2160

-continued

```
caagatatta aaatgtcgga tttatctttc cccatatcca agtaccaatg ctgttgtaaa   2220

caacgtgtat agtgcctaaa attgtatgaa aatcctttta accattttaa cctagatgtt   2280

taacaaatct aatctcttat tctaataaat atactatgaa ataaaaaaaa aaggatgaaa   2340

gctacttttg cttttgtggt aagcttttca gtttctttag tacacaagaa atactggttt   2400

agccaagcaa cactggtgag ggggaaaggt gaagatgagg aggaggctgg aaggcagaaa   2460

caggacaccg agttcagtgc tttggactaa tggggcttcc tgtaatttca atctctggac   2520

tcagtccagc tcttctcacc caacaccctt atctgtgact cttccaacca ccttccttgt   2580

gggacctgtg aatagatcct gtatattcct ttgatctctt ttatacaagg gaaaagcagc   2640

tgatggggga ctgggagcaa atctgagaaa aatgacaaaa catttcttat ctcacagaac   2700

atttctcatt ttccatatac caatagttga gctgagggcc tgcctgcact tttaggctgt   2760

catgctcata ggagggcctt gctggtggcc aacttgccta cctggtgtgg gagctttctg   2820

cacaacatag gacagtctgt ctcctttgcg acattaagca atggtttccc ttctttcacc   2880

acttacactt aaccacacct tcctagaaag gaggaatgtg cctggcgctg g            2931
```

<210> SEQ ID NO 85
<211> LENGTH: 1544
<212> TYPE: DNA
<213> ORGANISM: Homo sapiens
<220> FEATURE:
<221> NAME/KEY: misc_feature
<223> OTHER INFORMATION: Incyte ID No: 411180.6

<400> SEQUENCE: 85

```
ttggaaagac ggtgaatgga aaggggatgg ctggtggtct tgggtgtgat gtgtgttatt     60

ggtttgtaga ggagaagcag gagaaacaag gtattctgcc tgagagagct gaagaggcaa    120

agctaaaggc caaataccca agcctaggac aaaagcctgg aggctccgac ttcctcatga    180

agagactcca gaaagggcaa aagtactttg actcaggaga ctacaacatg gccaaagcca    240

agatgaagaa taagcagctg ccaagtgcag gaccagacaa gaacctggtg actggtgatc    300

acatccccac cccacaggat ctgccccaga gaaagtcctc gctcgtcacc agcaagcttg    360

cgggtggcca agttgaatga tgctgcccgg ggctctgcca gatcctgaga cgcttcccct    420

ccctgcccca cccgggtcct gtgctggctc ctgccccttc ctgcttttgc agccaggggt    480

caggaggtgg ctcgggtgtg ggctggagag gcagaagccc tttcctgttg gtgtcccagc    540

acatggagcc ccttgggctg agcaccaaga ccttgaacct tttttgtttt accttttttc    600

caaataacag ttgggagaaa tatcaatgaa attctggggg tgggggtggg gttgaaaggg    660

tggggtggga gatatggagg agtatgaatt agggcttgga gttggtaaaa acattcctga    720

ctatccttct taaccacgtg gctgatgtgg ggtaggtatg aggggaagga agtggagtag    780

cctaatgaaa aggggttcta gttgagctct gtagataaat gccttgtttc agtgtggttg    840

gagacctggt gtcagataaa agaaactcca tccgcacaga cagatgcaaa cagctcctct    900

agttctgcag agctagttga gaactcaaca ttaatcattt taaaaagtac tgtccttgaa    960

atagatttgc tgtgggaaga agggcagtga gtgtgggaga aaggagccgt gagcgtgggg   1020

aaccccacag agcccaaagg actttttcag tattcgaaat aaacaaaaca aaaacccatg   1080

aaaaaaccca acccagaaat attctgaagc agttggtgtg ttttattggg gtttgggagg   1140

gggaagaaaa caatactgaa gacattgtta atgtgagatg cggctgagtt ccccaatacc   1200

atcacttagg aaagggagca ggaatgttgg cataaacctt gcccatccct ttgtttctgt   1260
```

-continued

```
aaccaatgta gaaggtgcat caacctcagt ttgtggctca caaaatgagg catttaagat   1320

atttgatcta aatggtttct tgacacctaa gcctagtcca ggtttagcag aaaaggaggc   1380

ccagtctcct tttccctctg tcttccattc cttttcaagt tcccatgttt gtgagggaga   1440

aatgtgacaa accaaaagaa atatattatt tctttgtaat aagccaaaag aaactcaagt   1500

ctttctgctg gtggccagca ggaggcagag tgatttcttt cctc                     1544


<210> SEQ ID NO 86
<211> LENGTH: 887
<212> TYPE: DNA
<213> ORGANISM: Homo sapiens
<220> FEATURE:
<221> NAME/KEY: misc_feature
<223> OTHER INFORMATION: Incyte ID No: 233576.23
<221> NAME/KEY: unsure
<222> LOCATION: 610
<223> OTHER INFORMATION: a, t, c, g, or other

<400> SEQUENCE: 86

cacagtcggc gctccttccc gctcccttca cacaccggcc tcaggcccgc accggcagta     60

gaagatggtg aaactttttg agacacccta tggccttctt gtcaaaacct tcactggagc    120

tcaagaaaag catttctgtt gtgttatttg cagtgcagat gatgtctgtg taacaacata    180

atggttattc acctttttt gattttgatt tttgctgtgt tatcaaaaac ttgaatactg    240

tgagaagaag tgaattttca gttgacgaat cagcatcttg ttcccatggt gataacacta    300

attgaatata tctatgaggg catgtattag ttaatggaaa aaaaaataca acactaacaa    360

tacatagctg caatgtgtac aatggctgat ttaattaaat aaaatgtaca agtgttaaat    420

gtggcaacgg tgatttgttc ttctttatca tgaatctgtg atttcaggag aataagaggt    480

tttaaaaagt tgagctagac ttgaaaccaa cagaaagaca caaattgctt tttttcttat    540

ggtttttatt tagtcgctga atatgctata tgcctggcac tggattaagc actgggataa    600

atagattttn cctctgccct caagaaattc ttattgttct tgttatgcaa aagaagaaaa    660

tgaggatttt tgttttggat cactactaaa tgaaagaaaa taggaatttg gggacttgca    720

ggggatgaga aagggtaagt gggattggca gcacagcaag actggtttgg ttctctccca    780

tgaggccatg gctgtcacta aatactttct gtctttggga acagcagttg gctctggagt    840

tttctttctg tcttagagcc tgagaattta aaattaaatg gatatat                  887


<210> SEQ ID NO 87
<211> LENGTH: 1562
<212> TYPE: DNA
<213> ORGANISM: Homo sapiens
<220> FEATURE:
<221> NAME/KEY: misc_feature
<223> OTHER INFORMATION: Incyte ID No: 1098781.3

<400> SEQUENCE: 87

cgccggcgtc cgcgtccccg cgccgagctg ctcgggctcc ctgagccccc agatctgacc     60

ccttcccttc ggcaacctga acgactcccg ccttccacgg aagggaccga gcccgtgcca    120

aacaggctga gcgatttggg agtgaggagc catcctaccg ctttccccaa cctggaaaca    180

gcaaagcgca aggcctctga gtcagttagg tctctgccac ccacgggcaa aggatgctct    240

cctccatcct ccttcctccc tccaccgaaa tcggagagcc gcgggcctga tccaaagagg    300

catccccttc tcgttcattc cccagaggcc tcaatacaaa ccccaggagt tggcccctct    360

tcttttgcta caaattcttg ccttgcaaag gggagaggtg gtttgtgctc cccctactgc    420
```

-continued

```
ctatatcgac ttcgcccggc agaagctaga tcccaagatt gctgtggctg cgcagaactg    480

ctacaaagtg actaatgggg cttttactgg ggagatcagc cctggcatga tcaaagactg    540

cggagccacg tgggtggtcc tggggcactc agagagaagg catgtctttg gggagtcaga    600

tgagctgatt gggcagaaag tggcccatgc tctggcagag ggactcggag taatcgcctg    660

cattggggag aagctagatg aaagggaagc tgggcatcac tgagaaggtt gttttcgagc    720

agacaaaggt catcgcagat aacgtgaagg actggagcaa ggtcgtcctg ggcctatgag    780

cctgtgtggg ccattggtac tggcaagact gcaacacccc aacaggccca ggaagtacac    840

gagaagctcc gaggatggct gaagtccaac gtctctgatg cggtggctca gagcacccgt    900

atcatttatg gaggctctgt gactggggca acctgcaagg agctggccag ccagcctgat    960

gtggatggct tccttgtggg tggtgcttcc ctcaagcccg aattcgtgga catcatcaat   1020

gccaaacaat gagccccatc catcttccct acccttcctg ccaagccagg gactaagcag   1080

cccagaagcc cagtaactgc cctttccctg catatgcttc tgatggtgtc atctgctcct   1140

tcctgtggcc tcatccaaac tgtatcttcc tttactgttt atatcttcac cctgtaatgg   1200

ttgggaccag gccaatccct tctccactta ctataatggt tggaactaaa cgtcaccaag   1260

gtggcttctc cttggctgag agatggaagg cgtggtggga tttgctcctg ggttccctag   1320

gccctagtga gggcagaaga gaaaccatcc tctcccttct tacaccgtga ggccaagatc   1380

ccctcagaag gcaggagtgc tgccctctcc catggtgccc gtgcctctgt gctgtgtatg   1440

tgaaccaccc atgtgaggga ataaacctgg cactaggtct tgtggtttgt ctgccttcac   1500

tggacttgcc cagataatct tcctttttga ggcagctata taaatgatca tttgtgcaag   1560

aa                                                                  1562
```

<210> SEQ ID NO 88
<211> LENGTH: 2475
<212> TYPE: DNA
<213> ORGANISM: Homo sapiens
<220> FEATURE:
<221> NAME/KEY: misc_feature
<223> OTHER INFORMATION: Incyte ID No: 255828.26
<221> NAME/KEY: unsure
<222> LOCATION: 1001, 1011
<223> OTHER INFORMATION: a, t, c, g, or other

<400> SEQUENCE: 88

```
atcacctgca tcctcgagga cagaccttgt gaagtcagag ctgctacaca ttgaatctca     60

agtcgagctt ctgagattcg atgattcagg aagaaaggat tctgaggttt tgaagcaaaa    120

tgcagtgaac agcaaccaat ccaatgttgt aattgaagac tttgagtcct cacggatctc    180

ttcgtctttg cagcgtagcc cgagtcggtc agcgccggag gacctcagca gccatgtcga    240

agccccatag tgaagccggg actgccttca ttcagaccca gcagctgcac gcagccatgg    300

ctgacacatt cctggagcac atgtgccgcc tggacattga ttcaccaccc atcacagccc    360

ggaacactgg catcatctgt accattgggc ccagcttccc gatcagtgga gacgttgaag    420

gagatgataa gtctggaatg aatgtggctc gtctgaattc tctcatggac tcatgagtac    480

catgcggaga ccatcaagaa tgtgcgcaca gccacggaaa gctttgcttc tgaccccatc    540

ctctaccggc ccgttgctgt ggctctagac actaaaggac ctgagatccg aactgggctc    600

atcaagggca gcggcactgc agaggtggag ctgaagaagg gagccactct caaaatcacg    660

ctggataacg cctacatgga aaagtgtgac gagaacatcc tgtggctgga ctacaagaac    720

atctgcaagg tggtggaagt gggcagcaag atctacgtgg atgatgggct tatttctctc    780
```

-continued

```
caggtgaagc agaaaggtgc cgacttcctg gtgacggagg tggaaaatgg tggctccttg    840

ggcagcaaga agggtgtgaa ccttcctggg gctgctgtgg acttgcctgc tgtgtcggag    900

aaggacatcc caggatctga aagtttgggg gtcgagcagg atgttgatat ggtgtttggc    960

gtcattccat cccgcaaagg catctggatg tcccatggaa ngtttaggaa nggtcctggg   1020

gagagaaggg aaaagaaaca tccaagatta tccagcaaaa tcgagaatca tgaggggggtt  1080

cggaggtttg atgaaatcct ggaggccagt gatgggatca tggtggctcg tggtgatcta   1140

ggcattgaga ttcctgcaga gaaggtcttc ttgctcagaa gatgatgatt ggacggtgca   1200

acccgagact gggaagcctg tcatctgtgc tactccagat gctggagagc atcgatcaag   1260

aagccccgcc ccactcgggc tgaaggcagt gatgtggcca atgcagtcct ggatggagcc   1320

gactgcatca tgctgtctgg agaaacagcc aaaggggact atcctctgga ggctgtgcgc   1380

atgcagcacc tgattgcccg tgaggcagag gctgccatct accacttgca attatttgag   1440

gaactccgcc gcctggcgcc cattaccagc gaccccacag aagccaccgc cgtgggtgcc   1500

gtggaggcct ccttcaagtg ctgcagtggg gccataatcg tcctcaccaa gtctggcagg   1560

tctgctcacc aggtggccag ataccgccca cgtgccccca tcattgctgt gacccggaat   1620

ccccagacag ctcgtcaggc ccacctgtac cgtggcatct tccctgtgct gtgcaaggac   1680

ccagtccagg aggcctgggc tgaggacgtg gacctccggg tgaactttgc catgaatgtt   1740

ggcaaggccc gaggcttctt caagaaggga gatgtggtca ttgtgctgac cggatggcgc   1800

cctggctccg gcttcaccaa caccatgcgt gttgttcctg tgccgtgatg gaccccagag   1860

cccctcctcc agcccctgtc ccaccccctt cccccagccc atccattagg ccagcaacgc   1920

ttgtagaact cactctgggc tgtaacgtgg cactggtagg ttgggacacc agggaagaag   1980

atcaacgcct cactgaaaca tggctgtgtt tgcagcctgc tctagtggga cagcccagag   2040

cctggctgcc catcatgtgg ccccacccaa tcaagggaag aaggaggaat gctggactgg   2100

aggcccctgg agccagatgg caagagggtg acagcttcct ttcctgtgtg tactctgtcc   2160

agttccttta gaaaaaatgg atgcccagag gactcccaac cctggcttgg ggtcaagaaa   2220

cagccagcaa gagttagggg ccttagggca ctgggctgtt gttccattga agccgactct   2280

ggccctggcc cttacttgct tctctagctc tctaggcctc tccagtttgc acctgtcccc   2340

accctccact cagctgtcct gcagcaaaca ctccaccctc caccttccat tttcccccac   2400

tactgcagca cctccaggcc tgttgctata gagcctacct gtatgtcaat aaacaacagc   2460

tgaagcacca aaaaa                                                    2475
```

<210> SEQ ID NO 89
<211> LENGTH: 2550
<212> TYPE: DNA
<213> ORGANISM: Homo sapiens
<220> FEATURE:
<221> NAME/KEY: misc_feature
<223> OTHER INFORMATION: Incyte ID No: 233643.1
<221> NAME/KEY: unsure
<222> LOCATION: 16, 19, 40, 45, 50, 56, 70, 507-546
<223> OTHER INFORMATION: a, t, c, g, or other

<400> SEQUENCE: 89

```
gaggctgttt gaaganagna gccaggggcc ggctgcctgn gggantcgtn aggacnccgc     60

tgtcccaggn gaacaaggtc tgggaccagt cttcagtata aatctcagcc agaaaaacca    120

actcctcatc ttgatctgca ggaaaacacc aaacacacta tggaactctg ctgatgggga    180
```

-continued

```
cccaagcgcc cacgtgctca gccaccctct ggctcagcgg ggcccagacc cacctcggca    240
cggacacccc tgtctccagg aggggcaggt ggctgaggct cttcggagct gtcagcgccc    300
ggtgcctgcc ctgggcacct ccctgcagtc atctctttgc actttgttac tctttcaaag    360
cattcacaaa cttttgtacc tagctctagc ctgtaccagt tagttcatca aaggaaacca    420
accgggatgc taactacaac atggttagaa tcctaattag ctactttaag atcctaggat    480
tggttggttt ttcttttttt tttctcnnnn nnnnnnnnnn nnnnnnnnnn nnnnnnnnnn    540
nnnnnnttct taatagattt gaatagcgac gtatttcctg ttgtagtcat ttttagctcg    600
accacatcat caggtctttg ccaccgaggc atagtgtaga acagtcccgg tcagttggcc    660
aacctcccgc agccaagtag gttcatcctt gttcctgttc attctcatag atggccctgc    720
tttccccagg gtgacatcgt agccaaatgt ttactgtttt cattgccttt tatggccttg    780
acgacttccc ctcccaccag ctgagaatgt atggaggtca tcggggcctc agctcggagg    840
cagtgacttg gggccaaggg acctcgagac gctttccttc cccacccccc agcgtcatct    900
ccccagcctg ctgttcccgc tttccatata gctttggcca ggaaagcatg caatagactt    960
gctcggagcc cagcactcct gggtctcggg gtcggggagg ggacgggggc acccacttcc   1020
ttgtctgtga cggcgtgttg ttccccactc tgggatgggg aagaggcccg tcgggagttc   1080
tgcatggcag ttcactgcat gtgctgcccc cttgggttgc tctgccaatg tattaatacc   1140
atcccatagc tcctgccaaa tcgagaccct ctgacgactt gccgactaac tggccaccac   1200
aagctgcagt ctgtagcact gaacaaacaa aaaacaaaac gctcaagcct tacgaccaga   1260
gaaggatttc agcaaaccac cacctcccac tcagtgtccc ctccaaactt cacacttccc   1320
tgcctgcaga ggatgactct gttcacaccc aatccagcgc ggttctaccc cacgaaactg   1380
tgactttcca aatgagcctt tccctagggc tagacctaag accaggaagt ttgagaaagc   1440
agccgcagct caactcttcc agctccgcca gggttgggaa gtccttaggt gcagtgcggc   1500
tcccactggg tccgcggacc ctcctattag agtacgaaat tcctggcaac tggtacagaa   1560
ccaacctaga ggctttgcag ttggcaagct aactcgcggc cttatttctg cctttaatct   1620
cccacaaggc atctgttgct ttgggtcctc cacgactctt aggcccgcct caacaaccca   1680
ggcacctcct aggtaggctc aaaggtagac ccgtttccac cgcagcaggt gaacatgacc   1740
gtgttttcaa ctgtgtccac agttcagatc cctttccaga ttgcaacctg gcctgcatcc   1800
cagctccttc ctgctcgtgt cttaacctaa gtgctttctt gtttgaaacg cctacaaacc   1860
tccatgtggt agctcctttg gcaaatgtcc tgctgtggcg ttttatgtgt tgcttggagt   1920
ctgtggggtc gtactccctc ccctcccgtc cccagggcag atttgattga atgtttgctg   1980
aagttttgtc tcttggtcca cagtatttgg aaaggtcact gaaaatgggt ctttcagtct   2040
tggcatttca tttaggatct ccatgagaaa tgggcttctt gagccctgaa aatgtatatt   2100
gtgtgtctca tctgtgaact gctttctgct atatagaact agctcaaaag actgtacata   2160
tttacaagaa actttatatt cgtaaaaaaa aaaagaggaa attgaattgg tttctacttt   2220
tttattgtaa aaggtgcatt tttcaacact tacttttggt ttcaatggtg gtagttgtgg   2280
acagccatct tcactggagg gtggggagct ccgtgtgacc accaagatgc cagcaggata   2340
taccgtaaca cgaaattgct gtcaaaagct tattagcatc aatcaagatt ctaggtctcc   2400
aaaagtacag gctttttctt cattaccttt tttattcaga acgaggaaga gaacacaagg   2460
aatgattcaa gatccacctt gagaggaatg aactttgttg ttgaacaatt agtgaaataa   2520
agcaatgatc taaactaaaa aaaaaaaaaa                                    2550
```

<210> SEQ ID NO 90
<211> LENGTH: 543
<212> TYPE: DNA
<213> ORGANISM: Homo sapiens
<220> FEATURE:
<221> NAME/KEY: misc_feature
<223> OTHER INFORMATION: Incyte ID No: 1094632.1
<221> NAME/KEY: unsure
<222> LOCATION: 535
<223> OTHER INFORMATION: a, t, c, g, or other

<400> SEQUENCE: 90

```
ctttcctctg aagataagga gaccatggaa aaagctgtag aagaaaagat tgaatgcctg      60

gaaagccacc aagatgctga cattgaagac ttcaaagcta agaagaagga actggaagaa     120

attgttcaac caattatcag caaactctat ggaagtgcag gccctccccc aactggtgaa     180

gaggatacag cagaaaaaga tgagttgtag acactgatct gctagtgctg taatattgta     240

aatactggac tcaggaactt ttgttaggaa aaaattgaaa gaacttaagt ctcgaatgta     300

attggaatct tcacctcaga gtggagttga aactgctata gcctaagcgg ctgtttactg     360

cttttcatta gcagttgctc acatgtcttt gggtgggggg gagaagaaga attggccatc     420

ttaaaaagcg ggtaaaaaac ctgggttagg gtgtgtgttc accttcaaaa tgttctattt     480

aacaactggg tcatgtgcat ctggtgtagg aagttttttc taccataagc acacnaataa     540

atg                                                                   543
```

<210> SEQ ID NO 91
<211> LENGTH: 3268
<212> TYPE: DNA
<213> ORGANISM: Homo sapiens
<220> FEATURE:
<221> NAME/KEY: misc_feature
<223> OTHER INFORMATION: Incyte ID No: 412068.12
<221> NAME/KEY: unsure
<222> LOCATION: 62, 115-180
<223> OTHER INFORMATION: a, t, c, g, or other

<400> SEQUENCE: 91

```
gcccctcccg tggggccgtg gcaaccccgt gcctcgcttg cccaatgaga acacggtttg      60

gngcggggcg cggccaggta ccggagcgga agtggcgatc ggagcggaag tggannnnnn     120

nnnnnnnnnn nnnnnnnnnn nnnnnnnnnn nnnnnnnnnn nnnnnnnnnn nnnnnnnnnn     180

actgcaggca ccgctgccgc cgcctgagta gtgggcttag gaaggaagag gtcatctcgc     240

tcggagcttc gctcggaagg gtctttgttc cctgcagccc tcccacggca gagtctccag     300

agatttgggc cgctacaaaa agtgcatttt gcccattcgg ctgtggatag agaagcagga     360

agagcactgg acttggagtc agggaatgac aatggataaa agtgagctgg tacagaaagc     420

caaactcgct gagcaggctg agcgctatga tgatatggct gcagccatga aggcagtcac     480

agaacagggg catgaactct ccaacgaaga gagaaatctg ctctctgttg cctacaagaa     540

tgtggtaggc gcccgccgct cttcctggcg tgtcatctcc agcattgagc agaaaacaga     600

gaggaatgag aagaagcagc agatgggcaa agagtaccgt gagaagatag aggcagaact     660

gcaggacatc tgcaatgatg ttctggagct gttggacaaa tatcttattc ccaatgctac     720

acaaccagaa agtaaggtgt tctacttgaa aatgaaagga gattatttta ggtatctttc     780

tgaagtggca tctggagaca acaaacaaac cactgtgtcg aactcccagc aggcttacca     840

ggaagcattt gaaattagta agaaagaaat gcagcctaca cacccaattc gtcttggtct     900
```

-continued

```
ggcactaaat ttctcagtct tttactatga gattctaaac tctcctgaaa aggcctgtag    960
cctggcaaaa acggcatttg atgaagcaat tgctgaattg gatacgctga atgaagagtc   1020
ttataaagac agcactctga tcatgcagtt acttagggac aatctcactc tgtggacatc   1080
ggaaaaccag ggagacgaag gagacgctgg ggagggagag aactaatgtt tctcgtgctt   1140
tgtgatctgt tcagtgtcac tctgtaccct caacatatat cccttgtgcg ataaaaaaaa   1200
aaaaaaaaaa aaaaagagaa tcgtacgtcg actttcgatt tttcacagcc tcagcctagg   1260
aaaaatggtt catgggataa acagctggta tttgtatcta aaactcagat tggtcacata   1320
aatgccacgg cattccgaag ttttgatttt gattaacatt gacaggatta ctgtgtgttt   1380
aattttttaa aaactgaaca ctgtgattat ggggttttgt aatttagcag aactcttact   1440
ggtagaaaaa atagacctga attatgtgta actttttgga aggtttaatc tgatatcaaa   1500
ataatcattg aaatacaatt ccattgtaaa gttgtacaga aagttataga gattatattg   1560
tgatgctgga acttggagtg agacacacat catttggcat ttgagttgaa tggtaattca   1620
cagtaatgct gccgttgttc gggacttaaa gacacttgac ctgtttgggc tgttgccact   1680
taaaagttca tgaccacaaa tgtccacagt gtcttcctct gaggaaactc gaatcctgaa   1740
atggaaattc tttgtggcag ataactggct tatgacacct tgaaaagttc aagtgctcat   1800
ataacacacc acactgaacc ccctttccta cagcaatatg ttcactatgt taccaatttg   1860
caacttgtgc ttcaatagtg gaatctactt tcattgttaa cactgagcta aagaaaaaaa   1920
gccgtgtgtt ttatgaatga ccttatctgt ttcctggata atacctttaa gaataatgtc   1980
ctgagtcagg cgtggtggtg cgtgcatcta gtcccaacta tttggggagg ctgaggcagg   2040
aggatcgctt gagcccaggg agtttaaagc tgcagtgccc tgtgggttgc acctgtgaat   2100
aacttgcact ccagcctggg gcaaacatag cgagacctca tctccaaaaa agaaaacaaa   2160
aaacaaaaaa aggaatgatg ttctgtagag atggcctttc acttgaggag tactcagttt   2220
tcaggttctt cctagctcgg ggcttttaaa ttttgaaatc taaacattct ttcccaccat   2280
cctttttgac tgttgacctt ggttttctct tctaagtttc tgtccctctg cttccttact   2340
ttttttcctt tttgaattct atctttatct gtcttttgtt cactttttaa tgctatatat   2400
gggcaggggt gagagacatt actgagcacc ttggtgagca agcctggctt taaagattgg   2460
agaagagctt ctggcaccag aaccctgtct tcctccagtt ctcaacatgg tgttgctctt   2520
cagtcatacc ggaatctgaa tcaaaaaagt atttttaaat atccatgatt tctccctgta   2580
ttgaggctag ccctgatcat gctttttgtg cctgtcacca ggtctcccaa gtgcactcat   2640
ccaggtcagt gctcagatgt gtttaaggag accctatatt cagggaagtt gcgtgaacac   2700
tgcagtgggg agaattgaga atagtcaggc ctatcagtct cacagaatca cccctctacc   2760
tttgatattc cacttagctg tagagtccat ctgtttgtcc atctgctgaa atgagaaaag   2820
aaaaatttat gcactgattt aaaacaaacc aaaaaaaaag aaaaaaacca aaaaaaaaat   2880
tccctccttt ctagctgaac aaaaatgtgc agttaataca gacaggcttg gttccacatt   2940
cactactgca ttttcaagcg ccaagtatta actgcagtag tgaatgtgga accaagcctg   3000
tctgtatatc tggtagctct tttctggctt ggttttttct taccagtatt ctgcctaacg   3060
ttggcttctg tgatggttat attgcctagc aagcacaccc gtggttgtga aaatagtata   3120
gcaaaaaaga aaaatccccg gttattgatg tactagattt gtgtatgtct tttaaacagt   3180
tctagtttca ccttacacag aataatcagg aaaagtgtaa aaattcaaaa gtgaaataaa   3240
aattttatca gttagttgcc tgtgaaaa                                      3268
```

-continued

<210> SEQ ID NO 92
<211> LENGTH: 2418
<212> TYPE: DNA
<213> ORGANISM: Homo sapiens
<220> FEATURE:
<221> NAME/KEY: misc_feature
<223> OTHER INFORMATION: Incyte ID No: 885713.5
<221> NAME/KEY: unsure
<222> LOCATION: 77
<223> OTHER INFORMATION: a, t, c, g, or other

<400> SEQUENCE: 92
gcagattgca gggcccgggc tgacgggaag tgggtgggag ctgcctgcac acgcggtgcc 60
gcggggcggg agtagangcg gagggagggg acacggggct cattgcggct gtgcgccctg 120
cactctgtcc ctcactcgcc gccgacgacc tgtctcgccc gagcgcacgc ccttgccgcc 180
gccccgcaga aatgctttcg gttacccaca gtctttcgcc agatgagacc ggtgtccagg 240
gtactggctc ctcatctcac tcggggctta tgccaaagat gtaaaatttg gtgcagatgc 300
cccgagcctt aatgcttcaa ggtgtagacc ttttagccga tgctgtggcc gttacaatgg 360
ggccaaaggg aagaacagtg attattgagc agagttgggg aagtcccaaa gtaacaaaag 420
atggtgtgac tgttgcaaag tcaattgact taaaagataa atacaaaaac attggagcta 480
aacttgttca agatgttgcc aataacacaa atgaagaagc tggggatggc actaccactg 540
ctactgtact ggcacgctct atagccaagg aaggcttcga gaagattagc aaaggtgcta 600
atccagtgga aatcaggaga ggtgtgatgt tagctgttga tgctgtaatt gctgaactta 660
aaaagcagtc taaacctgtg accacccctg aagaaattgc acaggttgct acgatttctg 720
caaacggaga caaagaaatt ggcaatatca tctctgatgc aatgaaaaaa gttggaagaa 780
agggtgtcat cacagtaaag gatggaaaaa cactgaatga tgaattagaa attattgaag 840
gcatgaagtt tgatcgaggc tatatttctc catactttat taatacatca aaaggtcaga 900
aatgtgaatt ccaggatgcc tatgttctgt tgagtgaaaa gaaaatttct agtatccagt 960
ccattgtacc tgctcttgaa attgccaatg ctcaccgtaa gcctttggtc ataatcgctg 1020
aagatgttga tggagaagct ctaagtacac tcgtcttgaa taggctaaag gttggtcttc 1080
aggttgtggc agtcaaggct ccagggtttg gtgacaatag aaagaaccag cttaaagata 1140
tggctattgc tactggtggt gcagtgtttg gagaagaggg attgaccctg aatcttgaag 1200
acgttcagcc tcatgactta ggaaaagttg gagaggtcat tgtgacccaa agacgatgcc 1260
atgctcttaa aaggaaaagg tgacaaggct caaattgaaa aacgtattca agaaatcatt 1320
gagcagttag atgtcacaac tagtgaatat gaaaaggaaa aactgaatga acggcttgca 1380
aaactttcag atggagtggc tgtgctgaag gttggtggga caagtgatgt tgaagtgaat 1440
gaaaagaaag acagagttac agatgccctt aatgctacaa gagctgctgt tgaagaaggc 1500
attgttttgg gagggggttg tgccctcctt cgatgcattc cagccttgga ctcattgact 1560
ccagctaatg aagatcaaaa aattggtata gaaattatta aaagaacact caaaattcca 1620
gcaatgacca ttgctaagaa tgcaggtgtt gaaggatctt tgatagttga gaaaattatg 1680
caaagttcct cagaagttgg ttatgatgct atggctggag attttgtgaa tatggtggaa 1740
aaaggaatca ttgacccaac aaaggttgtg agaactgctt tattggatgc tgctggtgtg 1800
gcctctctgt taactacagc agaagttgta gtcacagaaa ttcctaaaga agagaaggac 1860
cctggaatgg gtgcaatggg tggaatggga ggtggtatgg gaggtggcat gttctaactc 1920

-continued

```
ctagactagt gctttacctt tattaatgaa ctgtgacagg aagcccaagg cagtgttcct   1980

caccaataac ttcagagaag tcagttggag aaaatgaaga aaaaggctgg ctgaaaatca   2040

ctataaccat cagttactgg tttcagttga caaaatatat aatggtttac tgctgtcatt   2100

gtccatgcct acagataatt tattttgtat ttttgaataa aaaacatttg tacattcctg   2160

atactgggta caagagccat gtaccagtgt actgctttca acttaaatca ctgaggcatt   2220

tttactacta ttctgttaaa atcaggattt tagtgcttgc caccaccaga tgagaagtta   2280

agcagccttt ctgtggagag tgagaataat tgtgtacaaa gtagagaagt atccaattat   2340

gtgacaacct ttgtgtacaa agtagagaag tatccaatta tgtgacaacc tttgtgtaat   2400

aaaaatttgt ttaaagtt                                                 2418
```

<210> SEQ ID NO 93
<211> LENGTH: 1482
<212> TYPE: DNA
<213> ORGANISM: Homo sapiens
<220> FEATURE:
<221> NAME/KEY: misc_feature
<223> OTHER INFORMATION: Incyte ID No: 885713.13

<400> SEQUENCE: 93

```
ggcgcgaata agagccggac cgcgcttgcg cattgagtcc cactccttcg acctctgctg     60

cagcccgtgc cgccgccgcc tcctgggaag cctcttttcc tccgcagaga ggaagcggga    120

gaggagccca cgtcgcctgt cacccaatat ctccagccgc gcagtcccga agagtgtaag    180

atgttcgcct gcgccaagct cgcctgcacc ccctctctga tccgagctgg atccagagtt    240

gcatacagac caatttctgc atcagtgtta tctcgaccag aggctagtag gactggagag    300

ggctctacgg tatttaatgg ggcccagaat ggtgtgtctc agctaatcca aagggagttt    360

cagaccagtg caatcagcag agacattgat actgctgcca aatttattgg tgcaggtgct    420

gcaacagtag gagtggctgg ttctggtgct ggtattggaa cagtctttgg cagccttatc    480

attggttatg ccagaaaccc ttcgctgaag cagcagctgt tctcatatgc tatcctggga    540

tttgccttgt ctgaagctat gggtctcttt tgtttgatgg ttgctttctt gattttgttt    600

gccatgtaac aaattactgc ttgacatgtt ggcattcata ttaattacgg atgtaattct    660

gtgtatctta ctgtgactcc gaaaactgta gtattggtgt catgggaatg tacgttattt    720

ccaaagtcat ttcattaaag atgaaaactt taatttcttc tgtgatttgt acttacacta    780

agtttagatt atcacaaaga agaacgtgca ttcaggcaga tgctgtccca ttcagaggaa    840

gctacagcag ttgctccact gatgaaaaat attccaatgt aatttttatg ggaattcttt    900

tatatagtgt tctgcatatt gtaattcata gggcttttgt ttattcatat aaaggataaa    960

tatttgggtg ttttgagctt ctataaaata tgattaatta aaggtagtta atactcaaga   1020

tggtcttgag tttttaaggt ctaacatcag ttagaatact tcaaatcaga atcaccttcc   1080

aagactgact tgacaggtgg ttctaaaaat aaatcacgtc agctttttag gaaatgaagc   1140

cttaagctag ggggtaatgt gacttttgtt tttcagtaag tctcacatta agcaattgtg   1200

tgcctctaat gaatcttcca tgtcttttca gaacagaaac tagcagctag tttcttactt   1260

gaacaagact attaaaaacc aaatatcaaa aaactgaatt ggctagattt ttacagccaa   1320

aaattgctgt aaggcagtgt gtatcactgt tgctaacatg tttatagtgg gagtcttggg   1380

gatgatagct ggttcaacag tattttgctg ctaatacttt atgttgcttc ttggtcaaac   1440

ttttcccatt caaaggaaga agatggtgct actatagaca gt                      1482
```

-continued

<210> SEQ ID NO 94
<211> LENGTH: 2403
<212> TYPE: DNA
<213> ORGANISM: Homo sapiens
<220> FEATURE:
<221> NAME/KEY: misc_feature
<223> OTHER INFORMATION: Incyte ID No: 481039.8
<221> NAME/KEY: unsure
<222> LOCATION: 594, 596, 598, 602, 604, 606, 608, 610, 614, 616, 618-662
<223> OTHER INFORMATION: a, t, c, g, or other

<400> SEQUENCE: 94
ctgtgccggg gcaagccttc gcgcccatcc cgcggagccc gttgcccgcc ggtccttcgt 60
cctgcaccag tccccggagc ccgctgcccg cgcctcccag gcccttcctc taccgccgct 120
cgcccacgga ctccgacgtg tccctcgact ccgaggactc cggggctaag tctccaggca 180
tcctgggcta caatatctgt ccccgcgggt ggaatggcag ccttcggctc aagcgtggca 240
gcctccccgc cgaggcctcc tgcaccacct agagccccac ccccgacccc accccgggag 300
ggcagagcca gaagaaggct cattagacct gggggaccca aagggtctgg cctctttggg 360
cagccccaga gatgaggggt cagcagagga gagctctggg gttggggatg ggttagggac 420
gcaagcttga gttctagccc ttgctctcat tcagctgttg tgtgaccctg ggtaagaccc 480
ttccttgttt gaccctcagc tttcccatct gtttaatggt ggctttggcc aaggcaatcc 540
acaaacgtca aaattcccct tcccatcagt acacacaccg atgcacacac actntntntt 600
tntntntntn tctntntnnn nnnnnnnnnn nnnnnnnnnn nnnnnnnnnn nnnnnnnnnn 660
nntagttagt gccttggatg aggcggggca gtgtgtatat ggacccctgg acttgctacc 720
ttcagggttc catactcgtc cctcccctcc tggctctgct gtctggagtc tggcaagcgg 780
ggtgtgttca gaaggtccta ggcctgtgtc gcatgtccag gcactggcct gaccatccgg 840
ctccctggca ccaagtccca gggcaggagc agctgttttc catcccttcc cagacaagct 900
ctatttttat cacaatgacc tttagagagg tcctcccagg ccagctcaag gtgtcccact 960
atcccctctg gagggaagag gcaggaaaat tctccccggg tccctgtcat gctactttct 1020
ccatcccagt tcagactgtc caggacatct tatctgcagc cataagagaa ttataaggca 1080
gtgatttccc ttaggcccag gacttgggcc tccagctcat ctgttccttc tgggcccatt 1140
catggcaggt tctgggctca aagctgaact ggggagagaa gagatacaga gctaccatgt 1200
gactttacct gattgccctc agtttggggt tgcttattgg gaaagagaga gacaaagagt 1260
tacttgttac gggaaatatg aaaagcatgg ccaggatgca tagaggagat tctagcaggg 1320
gacaggattg gctcagatga cccctgaggg ctcttccagt cttgaaatgc attccatgat 1380
attaggaagt cgggggtggg tggtggtggt gggctagttg ggtttgaatt taggggccga 1440
tgagcttggg tacgtgagca gggtgttaag ttagggtctg cctgtatttc tggtcccctt 1500
ggaaatgtcc ccttcttcag tgtcagacct cagtcccagt gtccatatcg tgcccagaaa 1560
agtagacatt atcctgcccc atcccttccc cagtgcactc tgacctagct agtgcctggt 1620
gcccagtgac ctgggggagc ctggctgcag gccctcactg gttccctaaa ccttggtggc 1680
tgtgattcag gtccccaggg gggactcagg gaggaatatg gctgagttct gtagtttcca 1740
gagttgggct ggtagagcct tctagaggtt cagaatatta gcttcaggat cagctggggg 1800
tatggaattg gctgaggatc aaacgtatgt aggtgaaagg ataccaggat gttgctaaag 1860
gtgagggaca gtttgggttt gggacttacc ggggtgatgt tagatctgga acccccaagt 1920

-continued

```
gaggctggag ggagttaagg tcagtatgga agatagggtt gggacagggt gctttggaat   1980

gaaagagtga ccttagaggg ctccttgggc ctcaggaatg ctcctgctgc tgtgaagatg   2040

agaaggtgct cttactcagt taatgatgag tgactatatt taccaaagcc cctacctgct   2100

gctgggtccc ttgtagcaca ggagactggg gctaagggcc cctcccaggg aagggacacc   2160

atcaggcctc tggctgaggc agtagcatag aggatccatt tctacctgca tttcccagag   2220

gactagcagg aggcagcctt gagaaaccgg cagttcccaa gccagcgcct ggctgttctc   2280

tcattgtcac tgccctctcc ccaacctctc ctctaaccca ctagagattg cctgtgtcct   2340

gcctcttgcc tcttgtagaa tgcagctctg gccctcaata aatgcttcct gcattcttct   2400

gcc                                                                 2403
```

<210> SEQ ID NO 95
<211> LENGTH: 7390
<212> TYPE: DNA
<213> ORGANISM: Homo sapiens
<220> FEATURE:
<221> NAME/KEY: misc_feature
<223> OTHER INFORMATION: Incyte ID No: 337896.11
<221> NAME/KEY: unsure
<222> LOCATION: 5097-5416
<223> OTHER INFORMATION: a, t, c, g, or other

<400> SEQUENCE: 95

```
ccagcttgat cttgaacctc ctgtgtgtgg gcagagagac atggccctgc tactgcttga     60

acggcttccg gagacagtga cttgtttcct ttttccctct gaactatgcc gtagggccag    120

gtgagctgct gtgaaggact cattcttggt agccggcagt tactggcaac ttgtgagctt    180

ggtgggctcc tactaacgca cctgggacac caggctgctg ggctcccctc taggcagcct    240

cccctccagg cagcctcacc agcagctccc ctgagccatg gagaccccag aggtccccgt    300

gggctcgcta atcgactttg ggcctgaggc acccacctct tctcccctgg aggcaccacc    360

ccctgtgctg caggacggcg atggctccct gggggacggt gcatcagaga gtgagaccac    420

tgagtctgcg gacagtgaga atgacatggg cgagtcgccc tcgcacccgt cctgggacca    480

agaccgccgt tcctcctcca acgagtcctt ctcctccaac cagagcaccg agtctaccca    540

ggatgaagag accctggcac tcagggactt catgcgtggc tacgtggaga agatcttctc    600

tggaggggag gacttggatc aggaggagaa agccaagttt ggagagtact gcagcagtga    660

aaatggaaaa ggccgggagt ggtttgctcg atacgtgagt gcccagcgct gcaactccaa    720

gtgtgtctca gaggcaacct tctaccgcct ggtgcagtct tttgcagtgg tgctgttcga    780

gtgtcatcag atggatgact ttgggcctgc caagaacctc atgaccatgt gcttcaccta    840

ctaccacatc ggaaaaccac agctgctgcc cccggagtcc cgggagaagc ccgcgggcag    900

catcgactcc tacctgaaat ccgcaaacag ctggctggcc gaaaagaagg acatcgccga    960

gcggctgctg aagaacacct cggccaggac tgagaatgtc aagggcttct tcgggggct    1020

ggagaccaag ctgaaggggc ccctggccag gaggaacgag gaagacgaga acaaacccca   1080

ggagaagcgg cccagggctg tgaccgcgta cagccccgag gacgaaaaga agggggagaa   1140

gatctacctg tacacgcacc tgaagcaaca gcccatctgg cacactctga ggttctggaa   1200

tgcagccttt tttgacgctg tccattgtga gaggacaaag cgatctccca ctaccaggga   1260

gaagtggtgc cacatgaccc aggaggagcg cgacgacagc ctccggttca acgagaacat   1320

caccttcggg cagctgggca cattcacgca caacatgctg gcctttggac tgaacaagaa   1380

gctgtgcaat gacttcctga agaagcaggc tgtgattggc aacctggatg aagagcaata   1440
```

-continued

```
caagctgctt agtgaccaca ttgagcaaat ggccactgag taggccccag aggtcgcact   1500
ccgcaggagg actgaggcca tgtgccattc tcccgggccc agcgcccggc cgtcacccca   1560
cccgatgacc tgcatgaagc cagcagcacc cagagccact cctgctgccc tagaactagc   1620
ggttagaaga atccgctgtt cctccctcat ctcctctgcc tgtgtctgcg acccccatcc   1680
atgtgccaaa gtgtcccttg ggtcacacag ctaaagccga ggtgaccagt tgtaccccga   1740
gtgccaggct tgtgagatga gaccaagagg gaggagggga aggactccat gggccatcgt   1800
gggccaaggg ctggcgaggg tgggggcggg caagggatgc aggcaggaca gccatgaggt   1860
ggggctgcag ccggcacacc cagtggtgga gggccggcgc tgccactcac ggtgggtggc   1920
cgtgggccac cttccctgca atgggtgcac acgcggctcc catccagccc tctcagcgtg   1980
gggctgtggc tggtcctcac tattccccag tctcccgctg tggggcagga acaggaagtg   2040
acgggaacct tgaggaggaa acgcctgtgt tagggagaga gtgggtgcgg tgtagaggat   2100
gctcttggcc ggctggagca agacctggct cccaccagag ggacgtgtgt gtgcctgcag   2160
acggcccggg agctgtgtgt ctccgccaga gtcacagcag tgccgaggtg tccgcggcag   2220
accacacaga ccgtctgaaa tgcgcccgcc tggcggacag ctcccttctg aagcagagaa   2280
gcctccatgg tcacgaagca gcgttgtgct gtgtgtccct cgcaagaagc acaggaaaga   2340
gaagtttctt tagtagccac tagacaacca ccctttctga aagcaaacag tgctgctctt   2400
tattccagac aaggcaggaa agtctgagtt gggagtgaca gtggctggag agaagcagat   2460
ctgtgcaacg tgcagggcaa gccagtggcg tggcctctgc ctctaagcgc tgagcattgg   2520
gccccttccc caccagacct ttgtagctcc tccagcctct gcagagactc ccttcacctc   2580
gcacttactg cctgggaacc acggcccttc tcttctgtgg gtctgtacca ggtactccag   2640
gccagcccat gggcccgggg cctgacccca acacctgcat gctgggtcca gagccttctg   2700
tttcaccgtg cgtggacact gctaggccgc ctggggtccc ctgcctcctg cctgtcgctg   2760
ccgtggtccc tgactgcgaa ataggcccgc ggggctctcc ctcctcctgc catcctcccc   2820
tcccgccctt cctggctacc tcctctgaca tgcggtcaga taagtcccgt cttgtttgtg   2880
agtaccacag aaacgcctga gagtcactta cccggccact gcttggaagg tttccctccg   2940
gggaatgcct ccctggaatg ttccagagac ggaacattct ctagagacaa cagtctgtgc   3000
tgcagattgg ttggatcaca gaatgtgtgt ctggggcatt atctgaaacg tggtgtcatc   3060
tgatgcattt ggaccatatg ctgccagact gcagaacggg ggagccgggg ctcagggccc   3120
ctgactgcat ggtgcatgag tgatctcagc ctagcgatgc cgctggccag accgtgacca   3180
tgctgccagt gtgctcgcca tgagctgggt cagggctggg gagttgtgca ggctggggtg   3240
acccttcccc catcattggg ccccaacggg catgtctcca ccgaatccat ttagagaaat   3300
gtcagagcga gggttgtgtg gacacccctc gctctgatgc caactgcaga taatacacac   3360
ctcctgcagc gtccagccac ggctccaggg cactgctctc ctccttgcac cggtgaaact   3420
caggccacac tcaagggctg actgtccagg cgctcccttc agccgcctcg tcgtcagcgt   3480
tcttagtcat gcattattcg tgttagctga aatgcattca gactttgttc tgcggtgccc   3540
acaggactta cccctgtatg tacaggattt ttgtatgaaa gttttgtttg attctgagac   3600
tctcttggga acgctggaga gcttgtgcac agcctctgga aggaaaggca gcgctgactt   3660
cgttgggctt ttttccaagc actttaactt cagaaatggt cttgacactt ttttctccac   3720
atagactctt gaaatagcca tttcagggga ggaaagggtt ggggttttct ttgttcgtct   3780
```

-continued

```
gtttgtttcc ccctttacta cctgttcttg tagatctagc tcctcagagt tggaggaagg   3840
ctgacagaga aggtctcctc tgtgctccat ccacacagga tgccggagag acagcccctt   3900
gtgctgtgag cagagcaggc agtggctctg gaggctgcct gtggtctcct tccggctgtg   3960
gctgacagtg gctctggcca gggttgcttg gagaaggctc agtgtgcctg ggacagggct   4020
taccacctgc caccaaggtt tcctctcttc ccccaggacc tgggcagagc aggcatgagc   4080
tgggctgtgg tgcagagcaa gcagacccag ccacactgct caaaggtccc tgcgtgggga   4140
ggtgtcacac caggggcaca cccagggcca cctgggtgta ggagagctct ggtggcccct   4200
ccgtaaactc aggaagtgtc aggtgatttc ctagggagag gttcccagtc ccagcaggca   4260
gaatgcccaa aaccaggagc acgaaggcct gtcatccatg ggccattgc aggcactctg   4320
ccgcccgacc ttgagggctg tgccaatcct agtgaaccaa aatgcaaaca actcacacaa   4380
gtgaaaagct ccctgctttg aaaacaggac atgttgacag gcagcatggt atgtttttag   4440
cctttgttac agttttagca acattgatgt ctaagagggg ccgtggtaat agattgcatc   4500
tgccctgtgc atgcgcatgt ttaaccacag gccagagaac tcaattctga tgtcgtaagt   4560
tctctgtaag tgaaatgggg tagactgtat gattttccta ttgccaaaag aaagaaaggg   4620
ggccaaacag ctctgaaatt tccaaaaaat ggctagaggg agagtccagt ttctgagctc   4680
tgtacccaaa ttaaaatcct gatgttcagg ttaatccaag caacacgcat tgggtttaaa   4740
accagcaccg aggcccagtg gggaatcac agacatcacc aagtctcgtc ttctttcctt   4800
cctgtgagtt gaaaccaaac aggcctctcg ctcactcctc ccagcccagt aatgctgagg   4860
agttcagttg tgaggaaaga aggctggagc tgtgagattc gcttttccct aggctgttcc   4920
gcgtgggtta ccttatcacc ctggagcact tggtattcca gacccctgac atgaggaatg   4980
caggttcaca ctgtaaagag tttgtgaaag gtttcagtct aactggggtt ccttagctgg   5040
aagccagggc tggaagctac aggcctgacc ttcctgggtc ccactatctg ttggcannnn   5100
nnnnnnnnnn nnnnnnnnnn nnnnnnnnnn nnnnnnnnnn nnnnnnnnnn nnnnnnnnnn   5160
nnnnnnnnnn nnnnnnnnnn nnnnnnnnnn nnnnnnnnnn nnnnnnnnnn nnnnnnnnnn   5220
nnnnnnnnnn nnnnnnnnnn nnnnnnnnnn nnnnnnnnnn nnnnnnnnnn nnnnnnnnnn   5280
nnnnnnnnnn nnnnnnnnnn nnnnnnnnnn nnnnnnnnnn nnnnnnnnnn nnnnnnnnnn   5340
nnnnnnnnnn nnnnnnnnnn nnnnnnnnnn nnnnnnnnnn nnnnnnnnnn nnnnnnnnnn   5400
nnnnnnnnnn nnnnnngaag gatccagcta ggcccgtgtg gttagatcag ctttgttact   5460
gaattaccta aaaccagacc acagcacagc cagggagccc agtagtgttt ccaagaacag   5520
tgtggagctt gagaaagaga actttaaaaa ttagagggtc cctttctgca gaggaaggga   5580
tgctcgcagg gtggcagtgg cccagcccca gcctcaggga cggggaggga gagccccctc   5640
tgggcccagc aggcaggtgt tctgaggctg gtccctcctc agtttccgca gccacaaggc   5700
gaaacggcca gattctcact caaggtcgtt ctcactcctt ttcctgtccc gtttccagtc   5760
ccactgagcc attcacttct gctgaaccat ttttcttagg atgcagccgt ctcactccct   5820
tgtcctgtaa atcgtgtatt catgttgatg attcttggag ataggtttca ctttttccca   5880
gctgcgtcca caggaaaggg gagtcggatg ccagctgcac cccgcctggc tcgcacaggc   5940
taagaccaca gacagagcag ggcttcccgg agccacacag gccacgcacc ccaggaaccc   6000
ttgctgctgc gggccaggaa caggaatgtg ttggtgcctg agacaccaaa tggaagaagc   6060
acatcaagac tgttctcctg cggccaacac tggcccggaa gccgccctcc atacaggccc   6120
tcaggggcc tgccttctgc gcctcagtcc cccgtgcatc cctgggcctg ggtatcacat   6180
```

-continued gctctccagg aaagggacgg aatcaatcgt gtgaccgatg ggctcgcaag gatgggtgcc 6240
gccgtgggag ccctgcctct ggtgctggca agggattggg tttgtgtggg tgtctctagc 6300
ctgcagagtg cagtgagtga gagtccttgg gagcgcggcg ctgcctgtag ctgcgcctgg 6360
ggatgcacgt ggccacggga tttcagtggg acagcgctcc cacaggggct gggggtgggg 6420
gtggggtttc ttagttactg ttggaaaggg aaaaattcac catatccaag gggagagacg 6480
atgggctggg tttgtttact ccaacttccc ttctacaccc ctcctgcagg acagtacgat 6540
ttggggagaa cccagctccc cactttatct gcagactctg ggacctgaca aaacagtcag 6600
agcctgagtg cactgcagcc tgaactccct tgagcagcgc tataagggac tttgcacttt 6660
aaaaagggga tgcctgtcag taaatcccct gtgcattgac tagaactggg gggctgcgcc 6720
cgctccctcc ttaatcctag atgatttgct catgaaatag aggtggggga cgaccgcatg 6780
cactctggga ggtgcagccc taaggggtgg actccagatc tccctgcaag agacagcttg 6840
gcttggcttt ggctgttggg gaggagtccc tgccatcccg gtgagcctgg ggctgttgct 6900
tagggtcttc tgggtggaca cgtggagaaa gagaaggcaa acgttggaac actaggaaaa 6960
gctagaaatt cagacaacac acatggatcc ccttaaaaca tgtaaatgtg tcagaacacg 7020
gttgacctgc cgccttcttg aacctggtgg cccccgttgg aactatcagt ggcgtctccc 7080
atgcacacgc cctctgcttt ctctttccta gactcgcggt gctcacatcc agacattacc 7140
ttgttggtag cccccaagtg gcgtgcagtg acaccagtat cttctctgtt gcatttttgc 7200
aatcttgtgt cccgctcggt gatgttctac aaactctgtt ttaaggttga gaaagtttca 7260
agggtgaaga tctcaaaaca gtgctaaaat caaaggtgtt tgctgtgaag aaaaacatgt 7320
gtatatattg caccttgagt tgtcagaagg tagaaactga aataaactaa ctttaaaaaa 7380
aaaaaaaagg 7390

<210> SEQ ID NO 96
<211> LENGTH: 1272
<212> TYPE: DNA
<213> ORGANISM: Homo sapiens
<220> FEATURE:
<221> NAME/KEY: misc_feature
<223> OTHER INFORMATION: Incyte ID No: 951830.16

<400> SEQUENCE: 96
tttttcatag acagaggcta acaaatcctg cctcaggttt atttgtacaa atagcacagg 60
aggaccccca gcccccatgc aaaatggtaa ccccaggggc ggggggtggg gggtcgcacc 120
agtccttctg tcctccatgt tggcagagaa tacctactct gaagcctttg taggggccct 180
gggctacgtt ttgggagcct gagctgggaa ctgaagctgg ggctgcagcc tggggccttg 240
gtttgatcct tggccttggc ctggccttgg ccttggcctt ggccttggcc tttggccggc 300
acagcctgag ccccttgggc aatacggggc acgaagcacg cttcccaagc ttggggcggg 360
caatgtaggc aaagtcgatc gagcttgcgg cttgacaccc ttttgggatc ttgggcttaa 420
ccttccttgg gctttacaag ggccttgata agcctcggca cgtgcactca tggccttggc 480
atcgttggcc tgcatcttct ttaggccctt tttgtctgtg cttcttggca aagcgcatgt 540
tcctcaggaa cttggggtcc acccccttaa gagattcgta tctttgtgat cggggtttct 600
tgataccatt tctgtgccat tttcgggagc cgcggcttat ggtgcagaca tggccaagtc 660
caagaaccac accacacaca accagtcccg aaaatggcac agaaatggta tcaagaaacc 720
ccgatcacaa agatacgaat ctcttaaggg ggtggacccc aagttcctga ggaacatgcg 780

-continued

```
ctttgccaag aagcacaaca aaaagggcct aaagaagatg caggccaaca atgccaaggc    840

catgagtgca cgtgccgagg ctatcaaggc cctcgtaaag cccaaggagg ttaagcccaa    900

gatcccaaag ggtgtcagcc gcaagctcga tcgacttgcc tacattgccc accccaagct    960

tgggaagcgt gctcgtgccc gtattgccaa ggggctcagg ctgtgccggc caaaggccaa   1020

ggccaaggcc aaggccaagg atcaaaccaa ggcccaggct gcagccccag cttcagttcc   1080

agctcaggct cccaaacgta cccaggcccc tacaaaggct tcagagtaga tatctctgcc   1140

aacatgagga cagaaggact ggtgcgaccc cccacccccg cccctgggct accatctgca   1200

tggggctggg gtcctcctgt gctatttgta caaataaacc tgaggcagga tttgtcaaaa   1260

aaaaaaaaaa gg                                                       1272
```

<210> SEQ ID NO 97
<211> LENGTH: 4675
<212> TYPE: DNA
<213> ORGANISM: Homo sapiens
<220> FEATURE:
<221> NAME/KEY: misc_feature
<223> OTHER INFORMATION: Incyte ID No: 234630.26

<400> SEQUENCE: 97

```
agcggacccc agcctctgcc aggttcggtc cgccatcctc gtcccgtcct ccgccggccc     60

ctgccccgcg cccagggatc ctccagctcc tttcgcccgc gccctccgtt cgctccggac    120

accatggaca agttttggtg gcacgcagcc tggggactct gcctcgtgcc gctgagcctg    180

gcgcagatcg atttgaatat aacctgccgc tttgcaggtg tattccacgt ggagaaaaat    240

ggtcgctaca gcatctctcg gacggaggcc gctgacctct gcaaggcttt caatagcacc    300

ttgcccacaa tggcccagat ggagaaagct ctgagcatcg gatttgagac ctgcaggtat    360

gggttcatag aagggcatgt ggtgattccc cggatccacc ccaactccat ctgtgcagca    420

aacaacacag ggggtgtacat cctcacatcc aacacctccc agtatgacac atattgcttc    480

aatgcttcag ctccacctga agaagattgt acatcagtca cagacctgcc caatgccttt    540

gatggaccaa ttaccataac tattgttaac cgtgatggca cccgctatgt ccagaaagga    600

gaatacagaa cgaatcctga agacatctac cccagcaacc ctactgatga tgacgtgagc    660

agcggctcct ccagtgaaag gagcagcact tcaggaggtt acatctttta caccttttct    720

actgtacacc ccatcccaga cgaagacagt ccctggatca ccgacagcac agacagaatc    780

cctgctacca atatggactc cagtcatagt acaacgcttc agcctactgc aaatccaaac    840

acaggtttgg tggaagattt ggacaggaca ggacctcttt caatgacaac gcagcagagt    900

aattctcaga gcttctctac atcacatgaa ggcttggaag aagataaaga ccatccaaca    960

acttctactc tgacatcaag caataggaat gatgtcacag gtggaagaag agacccaaat   1020

cattctgaag gctcaactac tttactggaa ggttatacct ctcattaccc acacacgaag   1080

gaaagcagga ccttcatccc agtgacctca gctaagactg ggtcctttgg agttactgca   1140

gttactgttg gagattccaa ctctaatgtc aatcgttcct tatcaggaga ccaagacaca   1200

ttccacccca gtggggggtc ccataccact catggatctg aatcagatgg acactcacat   1260

gggagtcaag aaggtggagc aaacacaacc tctggtccta taaggacacc ccaaattcca   1320

gaatggctga tcatcttggc atccctcttg gccttggctt tgattcttgc agtttgcatt   1380

gcagtcaaca gtcgaagaag gtgtgggcag aagaaaaagc tagtgatcaa cagtggcaat   1440

ggagctgtgg aggacagaaa gccaagtgga ctcaacggag aggccagcaa gtctcaggaa   1500
```

-continued

```
atggtgcatt tggtgaacaa ggagtcgtca gaaactccag accagtttat gacagctgat   1560
gagacaagga acctgcagaa tgtggacatg aagattgggg tgtaacacct acaccattat   1620
cttggaaaga aacaaccgtt ggaaacataa ccattacagg gagctgggac acttaacaga   1680
tgcaatgtgc tactgattgt ttcattgcga atctttttta gcataaaatt ttctactctt   1740
tttgtttttt gtgttttgtt ctttaaagtc aggtccaatt tgtaaaaaca gcattgcttt   1800
ctgaaattag ggcccaatta ataatcagca agaatttgat cgttccagtt cccacttgga   1860
ggcctttcat ccctcgggtg tgctatggat ggcttctaac aaaaactaca catatgtatt   1920
cctgatcgcc aacctttccc ccaccagcta aggacatttc ccagggttaa tagggcctgg   1980
tccctgggag gaaatttgaa tgggtccatt ttgcccttcc atagcctaat ccctgggcat   2040
tgctttccac tgaggttggg ggttggggtg tactagttac acatcttcaa cagacccccct  2100
ctagaaattt ttcagatgct tctgggagac acccaaaggg tgaagctatt tatctgtagt   2160
aaactattta tctgtgtttt tgaaatatta aaccctggat cagtcctttg atcagtataa   2220
ttttttaaag ttactttgtc agaggcacaa aagggtttaa actgattcat aataaatatc   2280
tgtacttctt cgatcttcac cttttgtgct gtgattcttc agtttctaaa ccagcactgt   2340
ctgggtccct acaatgtatc aggaagagct gagaatggta aggagactct tctaagtctt   2400
catctcagag accctgagtt cccactcaga cccactcagc caaatctcat ggaagaccaa   2460
ggagggcagc actgtttttg ttttttgttt tttgtttttt ttttttttgac actgtccaaa   2520
ggttttccat cctgtcctgg aatcagagtt ggaagctgag gagcttcagc ctcttttatg   2580
gtttaatggc cacctgttct ctcctgtgaa aggctttgca aagtcacatt aagtttgcat   2640
gacctgttat ccctggggcc ctatttcata gaggctggcc ctattagtga tttccaaaaa   2700
caatatggaa gtgccttttg atgtcttaca ataagagaag aagccaatgg aaatgaaaga   2760
gattggcaaa ggggaaggat gatgccatgt agatcctgtt tgacattttt atggctgtat   2820
ttgtaaactt aaacacacca gtgtctgttc ttgatgcagt tgctatttag gatgagttaa   2880
gtgcctgggg agtccctcaa aaggttaaag ggattcccat cattggaatc ttatcaccag   2940
ataggcaagt ttatgaccaa acaagagagt actggcttta tcctctaacc tcatattttc   3000
tcccacttgg caagtccttt gtggcattta ttcatcagtc agggtgtccg attggtccta   3060
gaacttccaa aggctgcttg tcatagaagc cattgcatct ataaagcaac ggctcctgtt   3120
aaatggtatc tcctttctga ggctcctact aaaagtcatt tgttacctaa acttatgtgc   3180
ttaacaggca atgcttctca gaccacaaag cagaaagaag aagaaaagct cctgactaaa   3240
tcagggctgg gcttagacag agttgatctg tagaatatct ttaaaggaga gatgtcaact   3300
ttctgcacta ttcccagcct ctgctcctcc ctgtctaccc tctcccctcc ctctctccct   3360
ccacttcacc ccacaatctt gaaaaacttc ctttctcttc tgtgaacatc attggccaga   3420
tccattttca gtggtctgga tttcttttta ttttcttttc aacttgaaag aaactggaca   3480
ttaggccact atgtgttgtt actgccacta gtgttcaagt gcctcttgtt ttcccagaga   3540
tttcctgggt ctgccagagg cccagacagg ctcactcaag ctctttaact gaaaagcaac   3600
aagccactcc aggacaaggt tcaaaatggt tacaacagcc tctacctgtc gccccaggga   3660
gaaaggggta gtgatacaag tctcatagcc agagatggtt ttccactcct tctagatatt   3720
cccaaaaaga ggctgagaca ggaggttatt ttcaatttta ttttggaatt aaatactttt   3780
ttccctttat tactgttgta gtccctcact tggatatacc tctgttttca cgatagaaat   3840
```

-continued

```
aagggaggtc tagagcttct attccttggc cattgtcaac ggagagctgg ccaagtcttc   3900

acaaaccctt gcaacattgc ctgaagttta tggaataaga tgtattctca ctcccttgat   3960

ctcaagggcg taactctgga agcacagctt gactacacgt catttttacc aatgattttc   4020

aggtgacctg ggctaagtca tttaaactgg gtctttataa aagtaaaagg ccaacattta   4080

attattttgc aaagcaacct aagagctaaa gatgtaattt ttcttgcaat tgtaaatctt   4140

ttgtgtctcc tgaagacttc ccttaaaatt agctctgagt gaaaaatcaa aagagacaaa   4200

agacatcttc gaatccatat ttcaagcctg gtagaattgg cttttctagc agaacctttc   4260

caaaagtttt atattgagat tcataacaac accaagaatt gattttgtag ccaacattca   4320

ttcaatactg ttatatcaga ggagtaggag agaggaaaca tttgacttat ctggaaaagc   4380

aaaatgtact taagaataag aataacatgg tccattcacc tttatgttat agatatgtct   4440

ttgtgtaaat catttgtttt gagttttcaa agaatagccc attgttcatt cttgtgctgt   4500

acaatgacca ctgttattgt tactttgact tttcagagca caccccttcct ctggtttttg   4560

tatatttatt gatggatcaa taataatgag gaaagcatga tatgtatatt gctgagttga   4620

aagcacttat tggaaaatat taaaaggcta acattaaaag actaaaggaa acaga        4675
```

<210> SEQ ID NO 98
<211> LENGTH: 2063
<212> TYPE: DNA
<213> ORGANISM: Homo sapiens
<220> FEATURE:
<221> NAME/KEY: misc_feature
<223> OTHER INFORMATION: Incyte ID No: 444820.3

<400> SEQUENCE: 98

```
tctggggagg aggatggaca caacatccca tctttgtgtt tcgatacaga ctaagctttt     60

aggccaaccc tcctgactgg atgggggcgg cgggcgtggc atgcatgaaa agtaaacatc    120

agagacctga agaagcttat aaaatagctt gggagaggcc agtcaccaag acaggcatct    180

caaatcggct gattctgcat ctggaaactg ccttcatctt gaaagaaaag ctccaggtcc    240

cttctccagc cacccagccc caagatggtg atggctggct tgctgctgct gctgctttcc    300

gcactgggct gggcctcttc ggtgcggcag agggacaagc atttcatctt ggggaagtgc    360

cccaatcctc cggtgcagga gaattttgac gtgaataagt atctcggaag atggtacgaa    420

attgagaaga tcccaacaac ctttgagaat ggacgctgca tccaggccaa ctactcacta    480

atggaaaacg gaaagatcaa agtgttaaac caggagttga gagctgatgg aactgtgaat    540

caaatcgaag gtgaagccac cccagttaac ctcacagagc ctgccaagct ggaagttaag    600

ttttcctggt ttatgccatc ggcaccgtac tggatcctgg ccaccgacta tgagaactat    660

gccctcgtgt attcctgtac ctgcatcatc caactttttc acgtggattt tgcttggatc    720

ttggcaagaa accctaatct ccctccagaa acagtggact ctctaaaaaa tatcctgact    780

tctaataaca ttgatgtcaa gaaaatgacg gtcacagacc aggtgaactg ccccaagctc    840

tcgtaaccag gttctacagg gaggctgcac ccactccatg ttacttctgc ttcgctttcc    900

cctaccccac ccccccccat aaagacaaac caatcaacca cgacaaagga agttgaccta    960

aacatgtaac catgccctac cctgttacct tgctagctgc aaaataaact tgttgctgac   1020

ctgctgtgct cgcaaggtaa cagggtaggg catggttaca tgtttaggtc aacttccttt   1080

gtcgtggttg attggtttgt ctttatggcg gggggtgggg taggggaaag cgaacgagaa   1140

gtaacatgga gtgggtgcag cctccctgta gaacctggtt acgagagctt ggggcagttc   1200
```

-continued

```
acctggtctg tgaccgtcat tttcttgaca tcaatgttat tagaagtcag gatatttttt   1260

agagagtcca ctgtttctgg agggagatta gggtttcttg ccaagatcca agcaaaatcc   1320

accgttgaaa aagtttggat gatgcaggta caggaataca cgagggcata gttctcatag   1380

tcggtggccc aggatccagt acggtccgat ggcataaacc aggaaaactt aacttccagc   1440

ttggcaggct ctgtgaaggt ttaactgggt tggcttcacc ttccgatttg attcacagtt   1500

cccatcagct ctcaactccc tggtttaaca ctttgatctt tccgttttcc attagtgagt   1560

agttggcctg gatgcagcgt ccattctcaa aggttgttgg gatcttctca atttcgtacc   1620

atcttccgag atacttattc acgtcaaaat tctcctgcac cggaggattg gggcacttcc   1680

caagatgaaa tgcttgtccc tctgccgcac cgaagaggcc agccagtgcg gaaagcagca   1740

gcagcagcat caccatcttg gggctgggtg gctggagaag ggacctggag cttttctttc   1800

aagatgaagg cagtttccag atgcagaatc agccgatttg agatgcctgt cttggtgact   1860

ggcctctccc aagctatttt ataagcttct tcaggtctct gatgtttact tttcatgcat   1920

gccacgcccg ccgcccccat ccagtcagga gggttggcct aaaagcttag tctgtatcga   1980

aacacaaaga tgggatgttg tgtccatcct cctcccccga tttccttcac agctgctccc   2040

tgaagaagaa atgagatatt gtt                                           2063
```

<210> SEQ ID NO 99
<211> LENGTH: 759
<212> TYPE: DNA
<213> ORGANISM: Homo sapiens
<220> FEATURE:
<221> NAME/KEY: misc_feature
<223> OTHER INFORMATION: Incyte ID No: 230012.44
<221> NAME/KEY: unsure
<222> LOCATION: 245
<223> OTHER INFORMATION: a, t, c, g, or other

<400> SEQUENCE: 99

```
ttttttttgca tttcatattt attatcagtg cttcaatata gaatgttttg taatgattag     60

caacattgta aacaccacca ggtttttcca acactaactg ctagtctttt ccagtaaata    120

ttttttcccc agagaattcg attcgaattc atggttcgct attcacttga cccggagaac    180

cccacgaaat catgcaaatc aagaggttcc aatcttcgtg ttcactttaa gaacactcgt    240

gaaantgctc aggcccatca agggtatgca tatacgaaaa gccacgaagt atctgaaaga    300

tgtcacttta cagaaacagt gtgtaccatt ccgacgttac aatggtggag ttggcaggtg    360

tgcgcaggcc aagcaatggg gctggacaca aggtcggtgg cccaaaaaga gtgctgaatt    420

tttgctgcac atgcttaaaa acgcagagag taatgctgaa cttaagggtt tagatttaga    480

ttctctggtc attgagcata tccaagtgaa caaagcacct aagatgcgcc gccggaccta    540

cagagctcat ggtcggatta acccatacat gagctctccc tgccacattg agatgatcct    600

tacggaaaag gaacagattg ttcctaaacc agaagaggag gttgcccaga agaaaaagat    660

atcccagaag aaactgaaga aacaaaaact tatggcacgg gagtaaattc agcattaaaa    720

taaatgtaat taaaaggaaa agaatgttgg ttgtcttta                           759
```

<210> SEQ ID NO 100
<211> LENGTH: 1203
<212> TYPE: DNA
<213> ORGANISM: Homo sapiens
<220> FEATURE:
<221> NAME/KEY: misc_feature
<223> OTHER INFORMATION: Incyte ID No: 233653.9

-continued

<400> SEQUENCE: 100
attacggcgc agtgtgctgg caagcgccct tgctcgccgc cgcgcgccgc ctcgcggcct 60
ggccccgccg cgcccggcgc gcccgccgcc cggggggatg tcttacaaac cgaacttggc 120
cgcgcacatg cccgccgccg ccctcaacgc cgctgggagt gtccactcgc cttccaccag 180
catggcaacg tcttcacagt accgccagct gctcagtgac tacgggccac cgtccctagg 240
ctacacccag ggaactggga acagccaggt gccccaaagc aaatacgcgg agctgctggc 300
catcattgaa gagctgggga aggagatcag acccacgtac gcagggagca agagtgccat 360
ggagaggctg aagcgcggca tcattcacgc tagaggactg gttcgggagt gcttggcaga 420
aacggaacgg aatgccagat cctagctgcc ttgttggttt tgaaggattt ccatcttttt 480
acaagatgag aagttacagt tcatctcccc tgttcagatg aaacccttgt tttcaaaatg 540
gttacagttt cgtttttcct cccatggttc acttggctct gaacctacag tctcaaagat 600
tgagaaaaga ttttgcagtt aattaggatt tgcattttaa gtagttagga actgcccagg 660 tttttttgt tttttaagca ttgatttaaa agatgcacgg aaagttatct tacagcaaac 720
tgtagtttgc ctccaagaca ccattgtctc cctttaatct tctcttttgt atacatttgt 780
tacccatggt gttctttgtt ccttttcata agctaatacc actgtaggga ttttgttttg 840
aacgcatatt gacagcacgc tttacttagt agccggttcc catttgccat acaatgtagg 900
ttctgcttaa tgtaacttct tttttgctta agcatttgca tgactattag tgcttcaaag 960
tcaattttta aaaatgcaca agttataaat acagaagaaa gagcaaccca ccaaacctaa 1020
caaggacccc cgaacacttt catactaaga ctgtaagtag atctcagttc tgcgtttatt 1080
gtaagttgat aaaaacatct ggaagaaaat gactaaaact gtttgcatct ttgtatgtat 1140
ttattacttg atgtaataaa gcttattttc attaacaatt tgtattaaaa tgtgggttcc 1200
ttg 1203

<210> SEQ ID NO 101
<211> LENGTH: 660
<212> TYPE: DNA
<213> ORGANISM: Homo sapiens
<220> FEATURE:
<221> NAME/KEY: misc_feature
<223> OTHER INFORMATION: Incyte ID No: 255844.48

<400> SEQUENCE: 101
gcaggtggtg gaaaagcaga accttagcaa agaggagctg atagcggagt gcaggtgacc 60
gctgatgtca tcaacgcagc tgagaaactc caggtggtgg gcagggctgg cacaggtgtg 120
gacaatgtgg atctggaggc cgcaacaagg aagggcatct tggttatgaa cacccccaat 180
gggaacagcc tcagtgccgc agaactcact tgtggaatga tcatgtgcct ggccaggcag 240
attccccagg cgacggcttc gatgaaggac ggcaaatggg agcggaagaa gttcatggga 300
acagagctga atggaaagac cctgggaatt cttggcctgg gcaggattgg gagagaggta 360
gctacccgga tgcagtcctt tgggatgaag actataggt atgaccccat catttcccca 420
gaggtctcgg cctcctttgg tgttcagcag ctgcccctgg aggagatctg gcctctctgt 480
gatttcatca ctgtgcacac tcctctcctg ccctccacga caggcttgct gaatgacaac 540
acctttgccc agtgcaagaa gggggtgcgt gtggtgaact gtgcccgtgg agggatcgtg 600
gacgaaggcg ccctgctccg ggccctgcag tctggccatg tgcggggctg cactggacgt 660

<210> SEQ ID NO 102

-continued

<211> LENGTH: 1395
<212> TYPE: DNA
<213> ORGANISM: Homo sapiens
<220> FEATURE:
<221> NAME/KEY: misc_feature
<223> OTHER INFORMATION: Incyte ID No: 1000124.9

<400> SEQUENCE: 102

```
ggcggagtgg ccttctgtgg acgaatcaga ttcctctcca gcaccgactt taagaggcga     60

gccggggggt cagggtccca gatgcacagg aggagaagca ggagctgtcg ggaagatcag    120

aagccagtca tggatgacca gcgcgacctt atctccaaca atgagcaact gcccatgctg    180

ggccggcgcc ctggggcccc ggagagcaag tgcagccgcg gagccctgta cacaggcttt    240

tccatcctgg tgactctgct cctcgctggc caggccacca ccgcctactt cctgtaccag    300

cagcagggcc ggctggacaa actgacagtc acctcccaga acctgcagct ggagaacctg    360

cgcatgaagc ttcccaagcc tcccaagcct gtgagcaaga tgcgcatggc caccccgctg    420

ctgatgcagg cgctgcccat gggagccctg ccccaggggc ccatgcagaa tgccaccaag    480

tatggcaaca tgacagagga ccatgtgatg cacctgctcc agaatgctga ccccctgaag    540

gtgtacccgc cactgaaggg gagcttcccg gagaacctga gacaccttaa gaacaccatg    600

gagaccatag actggaaggt ctttgagagc tggatgcacc attggctcct gtttgaaatg    660

agcaggcact ccttggagca aaagcccact gacgctccac cgaaagagtc actggaactg    720

gaggacccgt cttctgggct gggtgtgacc aagcaggatc tgggcccagt ccccatgtga    780

gagcagcaga ggcggtcttc aacatcctgc cagccccaca cagctacagc tttcttgctc    840

ccttcagccc ccagcccctc ccccatctcc caccctgtac ctcatcccat gagaccctgg    900

tgcctggctc tttcgtcacc cttggacaag acaaaccaag tcggaacagc agataacaat    960

gcagcaaggc cctgctgccc aatctccatc tgtcaacagg ggcgtgaggt cccaggaagt   1020

ggccaaaagc tagacagatc cccgttcctg acatcacagc agcctccaac acaaggctcc   1080

aagacctagg ctcatggacg agatgggaag gcacagggag aagggataac cctacaccca   1140

gaccccaggc tggacatgct gactgtcctc tcccctccag cctttggcct tggcttttct   1200

agcctattta cctgcaggct gagccactct cttccctttc cccagcatca ctccccaagg   1260

aagagccaat gttttccacc cataatcctt tctgccgacc cctagttccc tctgctcagc   1320

caagcttgtt atcagctttc agggccatgg ttcacattag aataaaaggt agtaattaga   1380

aaaaaaaaaa aaagg                                                      1395
```

<210> SEQ ID NO 103
<211> LENGTH: 1181
<212> TYPE: DNA
<213> ORGANISM: Homo sapiens
<220> FEATURE:
<221> NAME/KEY: misc_feature
<223> OTHER INFORMATION: Incyte ID No: 998375.1
<221> NAME/KEY: unsure
<222> LOCATION: 775-796
<223> OTHER INFORMATION: a, t, c, g, or other

<400> SEQUENCE: 103

```
ctagaattga agaaccaggg agaaccagat gggctgggca gatcaagcac aaacctgaga     60

tccaactgtc cctcttatgc gcctgggttt cttcactgga caccagtatg agtcaacttt    120

cctgtaaagc agaacaagca cgagattgga ccatgttaga ggaggaatgg tgtcatctcc    180

acttctggag agatccctgt ccccgtgttt gggggaagga ccaagcctca ctcccatgca    240
```

-continued

```
gagaagaggc tctgactgta actgcacctg tggagagatg gcgccgaaag cgaagacagg    300

aagctcctgc ccctcctaaa gctgaagcca aagcgaaggc tttaaaggcc aagaaggcag    360

tgttgaaagg tgtccacagc cacaaaaaga agaagatccg cacgtcaccc accttccggc    420

ggccgaagac actgcgactc cggagacagc ccaaatatcc tcggaagagc gctcccagga    480

gaaacaagct tgaccactat gctatcatca agtttccgct gaccactgag tctgccatga    540

agaagataga agacaacaac acacttgtgt tcattgtgga tgttaaagcc aacaagcacc    600

agattaaaca ggctgtgaag aagctgtatg acattgatgt ggccaaggtc aacaccctga    660

ttcggcctga tggagagaag aaggcatatg ttcgactggc tcctgattac gatgctttgg    720

atgttgccaa caaaattggg atcatctaaa ctgagtccag ctgcctaatt ctgannnnnn    780

nnnnnnnnnn nnnnnntcac catatacatg cctgtctgtc aatttctggt tgggctggga    840

ggccacacac acacactgac atgacagggc ttgggcaaga ctcctgttct acttatcctt    900

ttgaaatacc tcaccctgcc actccaccat gtatgatcat tccagagatc tttgtgacta    960

gagttagtgt cctaggaaaa ccagaactca gaacttgcct ccatggttga gtaacaagct   1020

gtacaagaac cccttttatc cctggaagag gctgtgtatg aaaccaatgc ccagggtttg   1080

aagggtgtta gcatccattt caggggagtg tggattggct ggctctctgg tagcattttg   1140

tcctcacaca cccatctact atgtccaacc ggtctgtctg c                       1181


<210> SEQ ID NO 104
<211> LENGTH: 550
<212> TYPE: DNA
<213> ORGANISM: Homo sapiens
<220> FEATURE:
<221> NAME/KEY: misc_feature
<223> OTHER INFORMATION: Incyte ID No: 243794.6

<400> SEQUENCE: 104

ctatggagat aaaaagatta aaaacagaaa caaaaaccga acagtgtgaa cagtgcaccc     60

tgaggtctcc ctggggtccc ttgtacccct caggagcctg tggatgaccc tgtgcaaaca    120

gttgggtgga agactgtgtc ttcctgtgtg tttggatgag taccagaact ttctgcgtct    180

gtttttcacc ctacccaatg cagtgcttac ctaaaaaatg cgttgaatag agcttcttcc    240

ttttacctcg ttgcactgct gagagcaaga tgggtcacca gcagctgtac tggagccacc    300

cgcgaaaatt cggccagggt tctcgctctt gtcgtgtctg ttcaaaccgg cacggtctga    360

tccggaaata tggcctcaat atgtgccgcc agtgtttccg tcagtacgcg aaggatatcg    420

gtttcattaa gttggactaa atgctcttcc ttcagaggat tatccggggc atctactcaa    480

tgaaaaacca tgataattct ttgtatataa aataaacatt tgaaaaaacc cttcaaaaaa    540

aaaaaaaagg                                                           550


<210> SEQ ID NO 105
<211> LENGTH: 2970
<212> TYPE: DNA
<213> ORGANISM: Homo sapiens
<220> FEATURE:
<221> NAME/KEY: misc_feature
<223> OTHER INFORMATION: Incyte ID No: 902288.16
<221> NAME/KEY: unsure
<222> LOCATION: 2113-2202
<223> OTHER INFORMATION: a, t, c, g, or other

<400> SEQUENCE: 105

attcctcaca ataaccagat agcctctgct ttctttttcc tttcttcgga atgagagact     60
```

-continued

```
caaccataat agaaagaatg gagaactatt aaccaccatt cttcagtggg ctgtgatttt    120
cagaggggaa tactaagaaa tggttttcca tactggaacc caaaggtaaa gacactcaag    180
gacagacatt tttggcagag catagatgaa aatggcaagt tccctggctt tccttctgct    240
caactttcat gtctcactct tcttggtcca gctgctcact ccttgctcag ctcagttttc    300
tgtgcttgga ccctctgggc ccatcctggc catggtgggt gaagacgctg atctgccctg    360
tcacctgttc ccgaccatga gtgcagagac catggagctg aggtgggtga gttccagcct    420
aaggcaggtg gtgaacgtgt atgcagatgg aaaggaagtg gaagacaggc agagtgcacc    480
gtatcgaggg agaacttcga ttctgcggga tggcatcact gcagggaagg ctgctctccg    540
aatacacaac gtcacagcct ctgacagtgg aaagtacttg tgttatttcc aagatggtga    600
cttctacgaa aaagccctgg tggagctgaa ggttgcagca ttgggttctg atcttcacat    660
tgaagtgaag ggttatgagg atggagggat ccatctggag tgcaggtcca ctggctggta    720
cccccaaccc caaataaagt ggagcgacac caagggagag aacatcccgg ctgtggaagc    780
acctgtggtt gcagatggag tgggcctgta tgcagtagca gcatctgtga tcatgagagg    840
cagctctggt gggggtgtat cctgcatcat cagaaattcc ctcctcggcc tggaaaagac    900
agccagcata tccatcgcag accccttctt caggagcgcc cagccctgga tcgcggccct    960
ggcagggacc ctgcctatct cgttgctgct tctcgcagga gccagttact tcttgtggag   1020
acaacagaag gaaaaaattg ctctgtccag ggagacagaa agagagcgag agatgaaaga   1080
aatgggatac gctgcaacag agcaagaaat aagcctaaga gagaagctcc aggaggaact   1140
caagtggagg aaaatccagt acatggctcg tggagagaag tctttggcct atcatgaatg   1200
gaaaatggcc ctcttcaaac ctgcggatgt gattctggat ccagacacgg caaacgccat   1260
cctccttgtt tctgaggacc agaggagtgt gcagcgtgct gaagagccgc gggatctgcc   1320
agacaaccct gagagatttg aatggcgtta ctgtgtcctt ggctgtgaaa acttcacatc   1380
agggagacat tactgggagg tggaagtggg ggacagaaaa gagtggcata ttggggtatg   1440
tagtaagaac gtggagagga aaaaaggttg ggtcaaaatg acaccggaga acggatactg   1500
gactatgggc ctgactgatg ggaataagta tcgggctctc actgagccca gaaccaacct   1560
gaaacttcct gagcctccta ggaaagtggg gatcttcctg gactatgaga ctggagagat   1620
ctcgttctat aatgccacag atggatctca tatctacacc tttccgcacg cctctttctc   1680
tgagcctcta tatcctgttt tcagaatttt gaccttggag cccactgccc tgaccatttg   1740
cccaatacca aaagaagtag agagttcccc cgatcctgac ctagtgcctg atcattccct   1800
ggagacacca ctgaccccgg gcttagctaa tgaaagtggg gagcctcagg ctgaagtaac   1860
atctctgctt ctccctgccc accctggagc tgaggtctcc ccttctgcaa caaccaatca   1920
gaaccataag ctacaggcac gcactgaagc actttactga tattcattcc attattccat   1980
atgacagttg ttttgagttt cgtaccacct tattgtcccc ttatacagat aaggaaactg   2040
gggtgcagaa aggtgaatta actttacaaa gtagacatga caagtgaaca gcagagctgg   2100
gatctaaaca gcnnnnnnnn nnnnnnnnnn nnnnnnnnnn nnnnnnnnnn nnnnnnnnnn   2160
nnnnnnnnnn nnnnnnnnnn nnnnnnnnnn nnnnnnnnnn nntgtcgggt agtcatattt   2220
tgcaagtatg gaagctgagg cagggcaaca tgaagtaact tacataactc atacagtaat   2280
ttgtgcagtt gggagatgtt cagccttagt ccctggctaa ttgcctgttc ttttccagcc   2340
tgattttttt tcccacagga agagcccaca tgtagccctg aggtttcctt cccaggacag   2400
ctgcagggta gagatcattt taagtgcttg tggagttgac atccctattg actctttccc   2460
```

-continued

```
agctgatatc agagacttag acccagcact ccttggatta gctctgcaga gtgtcttggt   2520

tgagagaata acctcatagt accaacatga catgtgactt ggaaagagac tagaggccac   2580

acttgataaa tcatggggca cagatatgtt cccacccaac aaatgtgata agtgattgtg   2640

cagccagagc cagccttcct tcaatcaagg tttccaggca gagcaaatac cctagagatt   2700

ctctgtgata taggaaattt ggatcaagga agctaaaaga attacaggga tgtttttaat   2760

cccactatgg actcagtctc ctggaaatag gtctgtccac tcctggtcat tggtggatgt   2820

taaacccata ttcctttcaa ctgctgcctg ctagggaaaa ctgctcctca ttatcatcac   2880

tattattgct caccactgta tcccctctac ttggcaagtg gttgtcaagt tctagttgtt   2940

caataaatgt gttaataatg cttactcctc                                    2970
```

```
<210> SEQ ID NO 106
<211> LENGTH: 5621
<212> TYPE: DNA
<213> ORGANISM: Homo sapiens
<220> FEATURE:
<221> NAME/KEY: misc_feature
<223> OTHER INFORMATION: Incyte ID No: 243902.5

<400> SEQUENCE: 106

tttcaggggc agagattgtt ttatttttta tttattttag aggtttacag taatcatagg     60

cctcatgggg tgcctcagat cacacgatgg aggcagctag acatgctgcc tgcatgtgag    120

cccaattctc tctccatttc aatttccttg tctctaaatc caagtgataa aacttgcact    180

tccttctacc accccagggt catgaaaaag ttaggaaacc aaacgtatta cattttataa    240

ggtttgtttt ccactgcaag aagtgtggat gctatctata taaagtgaga ctcctcacat    300

ttggaggggc aatttctctc ttgggaaact tgtgagaaga gctcttaggt tggctcctta    360

cactgatgaa acctctaatg aggtgtcaaa accacaaaca aaactataac acatgatggc    420

caaaacaaac ttattaaatg ctgataaaat cgttaagatg agtaggttga attggatcag    480

aggtttttga ccatattgtg ctaacacact ggtgagtcac aatcccatgt gccatatatg    540

ttataagtac ttgctcacta ataattgtcc aaatttttta tttactatag ggaacatctg    600

ttggttttgc ccactctgct tccattctcc cattttctag taacgcccct cagtcttcct    660

ttggggaata ctcccatagc cctcttagt ccatgtggtt caaatgaggc cgatgccacc    720

tccatcccca cttccatcct gagaatggtg aagtgacttg ctcagccaca gagcatggga    780

aactcaagtt tgcttcctaa ccagctccct ttcttcctcc tgatgcacaa aactgttgtc    840

cccagcaagc ttgtaggtga tctccatggg caacatgtgg gagggggttc tggaagacag    900

gcaggcagca ggattctgct catgggttca tccagacaag ggacataacc tgtgcccagt    960

atccaactga agacagctct cccagctgaa gacagctccc ctccatgtga tgattcagaa   1020

acccaggctc cttccgactc ctggctgcac tgttccttag ggtcttgggc ctcatgatta   1080

tctgtattca actagcagga agggaatgag agccaggaga ggacacactg gcttcttggc   1140

ctgtaaatag ggatactttg gagatatagt cagagaaggc tgttgctgcc cttgaaatcc   1200

ctgcacttag gtagccattt ttcttcacat gatgaatcct tctgaaggac cccttcacaa   1260

tgacagttac tcagcattga gagaagctgc tgctgctaat gctgctgctg ctgctgccgc   1320

cgccgccgct gctgctgctg ctgttggtct gaggctgcag taggtttctg tgcagcattg   1380

cagaatccac acctagagaa cagaagacac agacacgtac gtctactacc cttgttagaa   1440

ggaagctttg gatcttcggt ggataacaag agtaatccac agacttaaaa catgagctca   1500
```

-continued

```
gatgccagcc aaggcgtgat taccactcct cctcctccca gcatgcctca caaagagaga   1560
tattttgacc gcatcaatga aaatgaccca gaatacatta gggagaggaa catgtctcct   1620
gatctacgac aagacttcaa catgatggag cagaggaaac gagttactca gatcctgcaa   1680
agtcctggcc agtggtattc tatttccaaa tgagtacatt tcttaatgga gaaattctaa   1740
gcctttcggg aagacttgga atgccttatt caagaacaga tgaagaaagg ccacaaccca   1800
actggattac tagcattaca gcagattgca gattacatca tggccaattc tttctcgggt   1860
ttttcttcac ctcctctcag tcttggcatg gtcacaccta tcaatgacct tcctggtgca   1920
gatacatcct catatgtgaa gggagaaaaa cttactcgct gtaaacttgc cagcctgtac   1980
agacttgtag acttgtttgg atgggcacac ctggcaaata cctatatctc agtaagaata   2040
agtaaggagc aagaccacat tataataatt cccagaggcc tatctttttc tgaagctaca   2100
gcctccaatt tggtgaaagt caatataata ggagaagtgg ttgaccaggg aagtaccaat   2160
ttgaaaattg accatacagg attcagtccc catgctgcaa tctattcaac acgtcctgat   2220
gttaagtgtg tgatacacat ccatacctt gcaacagcag ctgtatcctc catgaaatgt   2280
gggatccttc caatttctca agagtctctt cttctgggag atgttgccta ttatgactac   2340
caagggtcac ttgaagaaca ggaggagaga attcaactgc agaaggttct gggaccaagt   2400
tgtaaggtgc tggtactcag gaatcatggt gtggttgcac ttggagaaac attagaggag   2460
gcttttcatt atatttttaa tgtgcaacta gcctgtgaga ttcaggtgca ggccctagca   2520
ggtgcaggtg gagtagacaa tctccatgta ctggactttc agaagtataa agctttcact   2580
tacactgtag cagcgtctgg tggaggaggt gtgaatatgg gttcccatca aaaatggaag   2640
gttggcgaaa ttgagtttga agggcttatg aggactctgg acaacttggg gtatagaaca   2700
ggctatgctt acaggcatcc tctcattcga gagaagccta gggcacaaga gtgatgtgga   2760
aatcccagca actgtgactg ctttttcctt tgaagacgat acagtgccac tctctcctct   2820
caaatacatg gcacagaggg caacagcgtg aaaaaacaag atggctgaac tcaccaaata   2880
cttacatgaa agtgaatgtg cctgaggagt ctcggaacgg agaaaccagt ccccgaacca   2940
aaatcacgtg gatgaaagca gaagactcat ctaaagttag tggtggaaca cctatcaaaa   3000
ttgaagatcc aaatcagttt gttcctttaa acacaaaccc gaatgaggta ctagaaaaga   3060
gaaataagat tcgggaacaa aatcgatatg acttgaaaac agcaggacca caatctcagt   3120
tgcttgctgg aattgttgtg gataagccac cttctactat gcaatttgaa gatgatgatc   3180
atggcccacc agctcctcct aacccattta gtcatctcac agaaggagaa cttgaagagt   3240
ataagaggac aatcgaacgt aaacaacaag gcctagaaga aaaccatgag ctgttttcca   3300
agagcttcat ctccatggaa gtgcctgtca tggtagtaaa tggcaaggat gatatgcatg   3360
atgttgaaga tgagcttgct aagcgagtga gtaggttaag cacaagtaca accatagaaa   3420
acatcgagat tactattaag tctccagaga aaatcgaaga agtcctgtca cctgaaggct   3480
ccccttcaaa atcgccatcc aagaaaaaga agaaattccg cactccttct tttctgaaaa   3540
agaacaaaaa aaaggagaaa gttgaggcct aaataaagtc tttttataat tattattata   3600
acaatgtgac attgcacatc taaataccac atttaagttg atcattaata tgcaatggta   3660
gatcagattg gggatgtag caaactggac tttaagaact ggaaagaggt tttacaaaag   3720
aaaaactttc agattcatct ctcattttat atgtccagaa atggctttga attttaagca   3780
attactagtt ttaattagct ctgccctcat gaagtattat tataattcac cataaacagc   3840
```

-continued

```
tatctgtctg aattacttca ggccttctcc ataatatctg ttagaaagaa attgccagtg   3900

agcaagtgag aatttttatt tctcaatacc tgcttcactt gataatcata ttataatttt   3960

ttatcatgat tattgactat atttttggag tcccattgtt tcagtgggca ttaacagaat   4020

gctttaaaaa cttctaagac aagaatctat agcattagta tacactggca cataattttt   4080

taaaaagttt taagaaaaga ttcatttgga attttattca cagtataaaa tttcctcacc   4140

tgaagtaact ttgtttgcca aaaaagttgt tttaataaac tataattttt gaaaacttcc   4200

ttttttatta gtttagaaag ccccttattt ttcaacaaag gggattttgt acacataaca   4260

tgggttattt agtttaactc tggcaaaaaa aaaaaaaaat tttgtatgtt gatgtttgta   4320

taccgttcag tataaaagtg tcctaagcat attagccaat cttttcacag tagagcatac   4380

ttaaggctgc ttggtactga gtatacttaa atataactcc agaatccagg gacttggtgt   4440

taaaacagga ttagagcatg taaaggtaca tctagattca tatttgaatc ttaaactgta   4500

tttttctctt agtattgcta atgagtaaag aaaagtctca taaggtagcc aaatgaaaaa   4560

gaatgaaagg gaaagtgaaa aattaagggg acaaaagatg ggatgtgaaa agaagaattc   4620

tagtttgatg gtgactcata ttcacgatag gatacaaagt gtgatttgtt ggaaacatgt   4680

cccaaatttc taaaattctg cttctctgcc aaaagcaatg tctttcttgg ttgatatttg   4740

agttttaaaa gggtcaaatc tttctaattt tttgtatctt tagagggcag cactagaaga   4800

aatcagcagg tctaatccca ccagtaagaa aactaccact tcttgatttt tacagattta   4860

aaaaaatctt ttcagtgacc tttcttttta atgtaaatac aaatttaaac ctaggcttaa   4920

tataggcgtt tccccttca cccaagtgat gtcacagttc gatgcaaaat caatgatcca    4980

gaatgatcgt gggtaaaaat aactcaaagt gtttcttaag ggtgagttgg catgcaaaaa   5040

attacattga ttacagtgtg ttttggagct ggctctgttt gtgtgcatat gataatgcag   5100

agttgagcca gagcctggaa atgtcattct agatctcact aactactgga atcagtgttt   5160

taatctcttg gtggaaactt tcagttgctt aactctctat tggaagattt ttttaatgtt   5220

ctacatcatt tatgttgtat tacaatgtat gtagaaatag taacctgtga actatgcttt   5280

tccataactt tttaaaaata tatatatcta aatgaatgca atgtgcataa atattttta    5340

aacataacag tgaactattg caccttttgc taatgcctct atttacttgc tttggcataa   5400

agaatgagcc aatgaacctc tgtgtcctgt ggaaaaatgt ataaatgtta tctgatattg   5460

ctcttagatg taatgctaat taatgttaaa tcacaaataa acagtatttt aaatatacgg   5520

acttgtatca tgaggtttcc attcacaggt ggttacttag cctattcatg gtctgttgag   5580

ttttatactt cagtgaaact tggtaagtta ttgatgcttc t                       5621
```

```
<210> SEQ ID NO 107
<211> LENGTH: 5129
<212> TYPE: DNA
<213> ORGANISM: Homo sapiens
<220> FEATURE:
<221> NAME/KEY: misc_feature
<223> OTHER INFORMATION: Incyte ID No: 1000186.8

<400> SEQUENCE: 107

agcaacccct taacactcct ccccatcctc tccctctgtc cctctgtccc tctgaccctg     60

cactgtccca gcaccatggg acccacctca ggtcccagcc tgctgctcct gctactaacc    120

cacctccccc tggctctggg gagtcccatg tactctatca tcacccccaa catcttgcgg    180

ctggagagcg aggagaccat ggtgctggag gcccacgacg cgcaagggga tgttccagtc    240
```

-continued

```
actgttactg tccacgactt cccaggcaaa aaactagtgc tgtccagtga gaagactgtg    300
ctgacccctg ccaccaacca catgggcaac gtcaccttca cgatcccagc caacagggag    360
ttcaagtcag aaaaggggcg caacaagttc gtgaccgtgc aggccacctt cgggacccaa    420
gtggtggaga aggtggtgct ggtcagcctg cagagcgggt acctcttcat ccagacagac    480
aagaccatct acacccctgg ctccacagtt ctctatcgga tcttcaccgt caaccacaag    540
ctgctacccg tgggccggac ggtcatggtc aacattgaga acccggaagg catcccggtc    600
aagcaggact ccttgtcttc tcagaaccag cttggcgtct tgcccttgtc ttgggacatt    660
ccggaactcg tcaacatggg ccagtggaag atccgagcct actatgaaaa ctcaccacag    720
caggtcttct ccactgagtt tgaggtgaag gagtacgtgc tgcccagttt cgaggtcata    780
gtggagccta cagagaaatt ctactacatc tataacgaga agggcctgga ggtcaccatc    840
accgccaggt tcctctacgg gaagaaagtg gagggaactg cctttgtcat cttcgggatc    900
caggatggcg aacagaggat ttccctgcct gaatccctca agcgcattcc gattgaggat    960
ggctcggggg aggttgtgct gagccggaag gtactgctgg acggggtgca gaacccccga   1020
gcagaagacc tggtggggaa gtctttgtac gtgtctgcca ccgtcatctt gcactcaggc   1080
agtgacatgg tgcaggcaga gcgcagcggg atccccatcg tgacctctcc ctaccagatc   1140
cacttcacca agacacccaa gtacttcaaa ccaggaatgc cctttgacct catggtgttc   1200
gtgacgaacc ctgatggctc tccagcctac cgagtccccg tggcagtcca gggcgaggac   1260
actgtgcagt ctctaaccca gggagatggc gtggccaaac tcagcatcaa cacacacccc   1320
agccagaagc ccttgagcat cacggtgcgc acgaagaagc aggagctctc ggaggcagag   1380
caggctacca ggaccatgca ggctctgccc tacagcaccg tgggcaactc caacaattac   1440
ctgcatctct cagtgctacg tacagagctc agacccgggg agaccctcaa cgtcaacttc   1500
ctcctgcgaa tggaccgcgc ccacgaggcc aagatccgct actacaccta cctgatcatg   1560
aacaagggca ggctgttgaa ggcgggacgc caggtgcgag agcccggcca ggacctggtg   1620
gtgctgcccc tgtccatcac caccgacttc atcccttcct tccgcctggt ggcgtactac   1680
acgctgatcg gtgccagcgg ccagagggag gtggtggccg actccgtgtg ggtggacgtc   1740
aaggactcct gcgtgggctc gctggtggta aaaagcggcc agtcagaaga ccggcagcct   1800
gtacctgggc agcagatgac cctgaagata gagggtgacc acggggcccg ggtggtactg   1860
gtggccgtgg acaagggcgt gttcgtgctg aataagaaga acaaactgac acagagtaag   1920
atctgggacg tggtggagaa ggcagacatc ggctgcaccc cgggcagtgg gaaggattac   1980
gccggtgtct tctccgacgc agggctgacc ttcacgagca gcagtggcca gcagaccgcc   2040
cagagggcag aacttcagtg cccgcagcca gccgcccgcc gacgccgttc cgtgcagctc   2100
acggagaagc gaatggacaa agtcggcaag taccccaagg agctgcgcaa gtgctgcgag   2160
gacggcatgc gggagaaccc catgaggttc tcgtgccagc gccggacccg tttcatctcc   2220
ctgggcgagg cgtgcaagaa ggtcttcctg gactgctgca actacatcac agagctgcgg   2280
cggcagcacg cgcgggccag ccacctgggc ctggccagga gtaacctgga tgaggacatc   2340
attgcagaag agaacatcgt ttcccgaagt gagttcccag agagctggct gtggaacgtt   2400
gaggacttga aagagccacc gaaaaatgga atctctacga agctcatgaa tatatttttg   2460
aaagactcca tcaccacgtg ggagattctg gctgtcagca tgtcggacaa gaaagggatc   2520
tgtgtggcag accccttcga ggtcacagta atgcaggact tcttcatcga cctgcggcta   2580
ccctactctg ttgttcgaaa cgagcaggtg gaaatccgag ccgttctcta caattaccgg   2640
```

-continued

```
cagaaccaag agctcaaggt gagggtggaa ctactccaca atccagcctt ctgcagcctg   2700
gccaccacca agaggcgtca ccagcagacc gtaaccatcc cccccaagtc ctcgttgtcc   2760
gttccatatg tcatcgtgcc gctaaagacc ggcctgcagg aagtggaagt caaggctgcc   2820
gtctaccatc atttcatcag tgacggtgtc aggaagtccc tgaaggtcgt gccggaagga   2880
atcagaatga acaaaactgt ggctgttcgc accctggatc cagaacgcct gggccgtgaa   2940
ggagtgcaga aagaggacat cccacctgca gacctcagtg accaagtccc ggacaccgag   3000
tctgagacca gaattctcct gcaagggacc ccagtggccc agatgacaga ggatgccgtc   3060
gacgcggaac ggctgaagca cctcattgtg accccctcgg gctgcgggga acagaacatg   3120
atcggcatga cgcccacggt catcgctgtg cattacctgg atgaaacgga gcagtgggag   3180
aagttcggcc tagagaagcg gcagggggcc ttggagctca tcaagaaggg gtacacccag   3240
cagctggcct tcagacaacc cagctctgcc tttgcggcct tcgtgaaacg ggcacccagc   3300
acctggctga ccgcctacgt ggtcaaggtc ttctctctgg ctgtcaacct catcgccatc   3360
gactcccaag tcctctgcgg ggctgttaaa tggctgatcc tggagaagca gaagcccgac   3420
ggggtcttcc aggaggatgc gcccgtgata caccaagaaa tgattggtgg attacggaac   3480
aacaacgaga aagacatggc cctcacggcc tttgttctca tctcgctgca ggaggctaaa   3540
gatatttgcg aggagcaggt caacagcctg ccaggcagca tcactaaagc aggagacttc   3600
cttgaagcca actacatgaa cctacagaga tcctacactg tggccattgc tggctatgct   3660
ctggcccaga tgggcaggct gaaggggcct cttcttaaca aatttctgac cacagccaaa   3720
gataagaacc gctgggagga ccctggtaag cagctctaca acgtggaggc cacatcctat   3780
gccctcttgg ccctactgca gctaaaagac tttgactttg tgcctcccgt cgtgcgttgg   3840
ctcaatgaac agagatacta cggtggtggc tatggctcta cccaggccac cttcatggtg   3900
ttccaagcct tggctcaata ccaaaaggac gcccctgacc accaggaact gaaccttgat   3960
gtgtccctcc aactgcccag ccgcagctcc aagatcaccc accgtatcca ctgggaatct   4020
gccagcctcc tgcgatcaga agagaccaag gaaaatgagg gtttcacagt cacagctgaa   4080
ggaaaaggcc aaggcacctt gtcggtggtg acaatgtacc atgctaaggc caaagatcaa   4140
ctcacctgta ataaattcga cctcaaggtc accataaaac cagcaccgga aacagaaaag   4200
aggcctcagg atgccaagaa cactatgatc cttgagatct gtaccaggta ccggggagac   4260
caggatgcca ctatgtctat attggacata tccatgatga ctggctttgc tccagacaca   4320
gatgacctga agcagctggc caatggtgtt gacagataca tctccaagta tgagctggac   4380
aaagccttct ccgataggaa caccctcatc atctacctgg acaaggtctc acactctgag   4440
gatgactgtc tagctttcaa agttcaccaa tactttaatg tagagcttat ccagcctgga   4500
gcagtcaagg tctacgccta ttacaacctg gaggaaagct gtacccggtt ctaccatccg   4560
gaaaaggagg atggaaagct gaacaagctc tgccgtgatg aactgtgccg ctgtgctgag   4620
gagaattgct tcatacaaaa gtcggatgac aaggtcaccc tggaagaacg gctggacaag   4680
gcctgtgagc caggagtgga ctatgtgtac aagacccgac tggtcaaggt tcagctgtcc   4740
aatgactttg acgagtacat catggccatt gagcagacca tcaagtcagg ctcggatgag   4800
gtgcaggttg gacagcagcg cacgttcatc agccccatca agtgcagaga agccctgaag   4860
ctggaggaga agaaacacta cctcatgtgg ggtctctcct ccgatttctg ggggagagaag   4920
cccaacctca gctacatcat cgggaaggac acttgggtgg agcactggcc tgaggaggac   4980
```

-continued

```
gaatgccaag acgaagagaa ccagaaacaa tgccaggacc tcggcgcctt caccgagagc   5040

atggttgtct ttgggtgccc caactgacca cacccccatt cccccactcc agataaagct   5100

tcagttatat ctcaaaaaaa aaaaaaaagg                                    5129
```

<210> SEQ ID NO 108
<211> LENGTH: 2681
<212> TYPE: DNA
<213> ORGANISM: Homo sapiens
<220> FEATURE:
<221> NAME/KEY: misc_feature
<223> OTHER INFORMATION: Incyte ID No: 986123.32

<400> SEQUENCE: 108

```
acgcagccgt tcccaccacc cacacccacc gcgcccttcg ttcgcctctt ctccgggagc     60

cagtccgcgc caccgccgcc gcccaggcca tcgccaccct ccgcagccat gtccaccagg    120

tccgtgtcct cgtcctccta ccgcaggatg ttcggcggcc cgggcaccgc gagccggccg    180

agctccagcc ggagctacgt gactacgtcc acccgcacct acagcctggg cagcgcgctg    240

cgccccagca ccagccgcag cctctacgcc tcgtccccgg ggcggcgtgt atgccacgcg    300

ctcctctgcc gtgcgcctgc ggagagcgtg cccggggtgc ggctcctgca ggactcggtg    360

gacttctcgc tggccgacgc catcaacacc gagttcaaga acacccgcac caacgagaag    420

gtggagctgc aggagctgaa tgaccgcttc gccaactaca tcgacaaggt gcgcttcctg    480

gagcagcaga ataagatcct gctggccgag ctcgagcagc tcaagggcca aggcaagtcg    540

cgcctggggg acctctacga ggaggagatg cgggagtgcg ccggcaggtg gaccagctaa    600

ccaacgacaa agcccgcgtc gaggtggagc gcgacaacct ggccgaggac atcatgcgcc    660

tccgggagaa attgcaggag gagatgttca gagagaggaa gccgaaaaca ccctgcaatc    720

tttcagacag gatgttgaca atgcgtctct ggcacgtctt gaccttgaac gcaaagtgga    780

atctttggca agaagagatt gcctttttga agaaactcca cgaagaggaa atccaggagc    840

tgcaggctca gattcaggaa cagcatgtcc aaatcgatgt ggatgtttcc aagcctgacc    900

tcacggctgc cctgcgtgac atacgtcagc aatatgaaag tgtgggctgc caagaacctg    960

caggagggca gaagaatggt acaaatccaa gtttgctgac ctctctgagg gctgccaacc   1020

ggaacaatga cgccctgcgc cagggcaaag caggagtcca ctgagtaccg gagacaggtg   1080

cagtccctca cctgtgaagt ggatgccctt aaaggaacca atgagtccct ggaacgccag   1140

atgcgtgaaa tggaagagaa ctttgccgtt gaagctgcta actaccaaga cactattggc   1200

cgcctgcagg atgagattca gaatatgaag gaggaaatgg ctcgtcacct tcgtgaatac   1260

caagacctgc tcaatgttaa gatggccctt gacattgaga ttgccaccta caggaagctg   1320

ctggaaggcg aggagagcag gatttctctg cctcttccaa acttttcctc cctgaacctg   1380

agggaaacta atctggattc actccctctg gttgataccc actcaaaaag gacacttctg   1440

attaagacgg ttgaaactag agatggacag gttatcaacg aaacttctca gcatcacgat   1500

gaccttgaat aaaaattgca cacactcagt gcagcaatat attaccagca agaataaaaa   1560

agaaatccat atcttaaaga aacagctttc aagtgccttt ctgcagtttt tcaggagcgc   1620

aagatagatt tggaatagga ataagctcta gttcttaaca accgacactc ctacaagatt   1680

tagaaaaaag tttacaacat aatctagttt acagaaaaat cttgtgctag aatacctttt   1740

aaaaagtatt ctagcacaag atttttctgt aaactagatt atgttgtaaa cttttttcta   1800

aatcttgtag gagtgtcggt tgttaagaac tagagcttat tcctattcca aatctatctt   1860
```

-continued

```
gcgctcctga aaaactgcag aaaggcactt gaaagctgtt tctttaagat atgaatttct   1920

tttttattct tgctggtaat atattgctgc actgagtgtg tgcaattttt attcaaggtc   1980

atcgtgatgc tgagaagttt cgttgataac ctgtccatct ctagtttcaa ccgtcttaat   2040

cagaagtgtc ctttttgagt gggtatcaac cagagggagt gaatccagat tagtttccct   2100

caggttcagg gaggaaaagt ttggaagagg cagagaaatc ctgctctcct cgccttccag   2160

cagcttcctg taggtggcaa tctcaatgtc aagggccatc ttaacattga gcaggtcttg   2220

gtattcacga aggtgacgag ccatttcctc cttcatattc tgaatctcat cctgcaggcg   2280

gccaatagtg tccttggtag ttagcagctt caaacggcaa agttctcttc ccatttcaac   2340

gcatctggcg ttcccaggga cctcaattgg gttcccttta tagggcatcc acttcacaag   2400

gtgagggact gcacctgtct ccggtactca gtggactcct gctttgcccg gcgcagggcg   2460

tcattgttcc ggttggcagc ctcagagagg tcaggcttgg aaacatccac atcgaatttg   2520

gaacatgctg ttcctgaatc tgagcctgca gctcctggat ttcctcttcg tggagtttct   2580

tcaaaaaggc aatctcttct tgcaaagatt ccactttgcg ttcaaggtca agacgtgcca   2640

gagacgcatt gtcaacatcc tgtctgaaag attgcagggt g                        2681
```

<210> SEQ ID NO 109
<211> LENGTH: 4792
<212> TYPE: DNA
<213> ORGANISM: Homo sapiens
<220> FEATURE:
<221> NAME/KEY: misc_feature
<223> OTHER INFORMATION: Incyte ID No: 369213.15

<400> SEQUENCE: 109

```
agggattcta tttagcccgc caggaattaa ccttgactat aaataggcca tcaatgacct     60

ttccagagaa tgttcagaga cctcaacttt gtttagagat cttgtgtggg tggaacttcc    120

tgtttgcaca cagagcagca taaagcccag ttgctttggg aagtgtttgg gaccagatgg    180

attgtaggga gtagggtaca atacagtctg ttctcctcca gctccttctt tctgcaacat    240

ggggaagaac aaactccttc atccaagtct ggttcttctc ctcttggtcc tcctgcccac    300

agacgcctca gtctctggaa aaccgcagta tatggttctg gtcccctccc tgctccacac    360

tgagaccact gagaagggct gtgtccttct gagctacctg aatgagacag tgactgtaag    420

tgcttccttg gagtctgtca ggggaaacag gagcctcttc actgacctgg aggcggagaa    480

tgacgtactc cactgtgtcg ccttcgctgt cccaaagtct tcatccaatg aggaagtaat    540

gttcctcact gtccaagtga aaggaccaac ccaagaattt aagaagcgga ccacagtgat    600

ggttaagaac gaggacagtc tggtctttgt ccagacagac aaatcaatct acaaaccagg    660

gcagacagtg aaatttcgtg ttgtctccat ggatgaaaac tttcaccccc tgaatgagtt    720

gattccacta gtatacattc aggatcccaa aggaaatcgc atcgcacaat ggcagagttt    780

ccagttagag ggtggcctca agcaattttc ttttcccctc tcatcagagc cccttccagg    840

gctcctacaa ggtggtggta cagaagaaat caggtggaag gacagagcac cctttcaccg    900

tggaggaatt tgttcttccc aagtttgaag tacaagtaac agtgccaaag ataatcacca    960

tcttggaaga agagatgaat gtatcagtgt gtggcctata cacatatggg aagcctgtcc   1020

ctggacatgt gactgtgagc atttgcagaa agtatagtga cgcttccgac tgccacggtg   1080

aagattcaca ggctttctgt gagaaattca gtggacagct aaacagccat ggctgcttct   1140

atcagcaagt aaaaaccaag gtcttccagc tgaagaggaa ggagtatgaa atgaaacttc   1200
```

-continued

```
acactgaggc ccagatccaa gaagaaggaa cagtggtgga attgactgga aggcagtcca   1260
gtgaaatcac aagaaccata accaaactct catttgtgaa agtggactca cactttcgac   1320
agggaattcc cttctttggg caggtgcgcc tagtagatgg gaaaggcgtc cctataccaa   1380
ataaagtcat attcatcaga ggaaatgaag caaactatta ctccaatgct accacggatg   1440
agcatggcct tgtacagttc tctatcaaca ccaccaatgt tatgggtacc tctcttactg   1500
ttagggtcaa ttacaaggat cgtagtccct gttacggcta ccagtgggtg tcagaagaac   1560
acgaagaggc acatcacact gcttatcttg tgttctcccc aagcaagagc tttgtccacc   1620
ttgagcccat gtctcatgaa ctaccctgtg gccatactca gacagtccag gcacattata   1680
ttctgaatgg aggcaccctg ctggggctga agaagctctc cttctattat ctgataatgg   1740
caaagggagg cattgtccga actgggactc atggactgct tgtgaagcag gaagacatga   1800
agggccattt ttccatctca atccctgtga agtcagacat tgctcctgtc gctcggttgc   1860
tcatctatgc tgttttacct accggggacg tgattgggga ttctgcaaaa tatgatgttg   1920
aaaattgtct ggccaacaag gtggatttga gcttcagccc atcacaaagt ctcccagcct   1980
cacacgccca cctgcgagtc acagcggctc ctcagtccgt ctgcgccctc cgtgctgtgg   2040
accaaagcgt gctgctcatg aagcctgatg ctgagctctc ggcgtcctcg gtttacaacc   2100
tgctaccaga aaaggacctc actggcttcc ctgggccttt gaatgaccag gacgatgaag   2160
actgcatcaa tcgtcataat gtctatatta atggaatcac atatactcca gtatcaagta   2220
caaatgaaaa ggatatgtac agcttcctag aggacatggg cttaaaggca ttcaccaact   2280
caaagattcg taaacccaaa atgtgtccac agcttcaaca gtatgaaatg catggacctg   2340
aaggtctacg tgtaggtttt tatgagtcag atgtaatggg aagaggccat gcacgcctgg   2400
tgcatgttga agagcctcac acggagaccg tacgaaagta cttccctgag acatggatct   2460
gggatttggt ggtggtaaac tcagcaggtg tggctgaggt aggagtaaca gtccctgaca   2520
ccatcaccga gtggaaggca ggggccttct gcctgtctga agatgctgga cttggtatct   2580
cttccactgc ctctctccga gccttccagc ccttctttgt ggagctcaca atgccttact   2640
ctgtgattcg tggagaggcc ttcacactca aggccacggt cctaaactac cttcccaaat   2700
gcatccgggt cagtgtgcag ctggaagcct ctcccgcctt cctagctgtc ccagtggaga   2760
aggaacaagc gcctcactgc atctgtgcaa acgggcggca aactgtgtcc tgggcagtaa   2820
ccccaaagtc attaggaaat gtgaatttca ctgtgagcgc agaggcacta gagtctcaag   2880
agctgtgtgg gactgaggtg ccttcagttc ctgaacacgg aaggaaagac acagtcatca   2940
agcctctgtt ggttgaacct gaaggactag agaaggaaac aacattcaac tccctacttt   3000
gtccatcagg tggtgaggtt tctgaagaat tatccctgaa actgccacca aatgtggtag   3060
aagaatctgc ccgagcttct gtctcagttt tgggagacat attaggctct gccatgcaaa   3120
acacacaaaa tcttctccag atgccctatg gctgtggaga gcagaatatg gtcctctttg   3180
ctcctaacat ctatgtactg gattatctaa atgaaacaca gcagcttcct ccagagatca   3240
agtccaaggc cattggctat ctcaacactg gttaccagag acagttgaac tacaaacact   3300
atgatggctc ctacagcacc tttggggagc gatatggcag gaaccagggc aacacctggc   3360
tcacagcctt tgttctgaag acttttgccc aagctcgagc ctacatcttc atcgatgaag   3420
cacacattac ccaagccctc atatggctct cccagaggca gaaggacaat ggctgtttca   3480
ggagctctgg gtcactgctc aacaatgcca taaagggagg agtagaagat gaagtgaccc   3540
tctccgccta tatcaccatc gcccttctgg agattcctct cacagtcact caccctgttg   3600
```

-continued

```
tccgcaatgc cctgttttgc ctggagtcag cctggaagac agcacaagaa ggggaccatg   3660

gcagccatgt atataccaaa gcactgctgg cctatgcttt tgccctgggc aggtaaccag   3720

gacaagagga aggaagtact caagtcactt aatgaggaag ctgtgaagaa agacaactct   3780

gtccattggg agcgccctca gaaacccaag gcaccagtgg ggcatttttta cgaaccccag  3840

gctccctctg ctgaggtgga gatgacatcc tatgtgctcc tcgcttatct cacggcccag   3900

ccagccccaa cctcggagga cctgacctct gcaaccaaca tcgtgaagtg gatcacgaag   3960

cagcagaatg cccagggcgg tttctcctcc acccaggaca cagtggtggc tctccatgct   4020

ctgtccaaat atggagcagc cacatttacc aggactggga aggctgcaca ggtgactatc   4080

cagtcttcag ggacattttc cagcaaattc caagtggaca acaacaaccg cctgttactg   4140

cagcaggtct cattgccaga gctgcctggg gaatacagca tgaaagtgac aggagaagga   4200

tgtgtctacc tccagacatc cttgaaatac aatattctcc cagaaaagga agagttcccc   4260

tttgctttag gagtgcagac tctgcctcaa acttgtgatg aacccaaagc ccacaccagc   4320

ttccaaatct ccctaagtgt cagttacaca gggagccgct ctgcctccaa catggcgatc   4380

gttgatgtga agatggtctc tggcttcatt cccctgaagc caacagtgaa aatgcttgaa   4440

agatctaacc atgtgagccg gacagaagtc agcagcaacc atgtcttgat ttaccttgat   4500

aaggtgtcaa atcagacact gagcttgttc ttcacggttc tgcaagatgt cccagtaaga   4560

gatctgaaac cagccatagt gaaagtctat gattactacg agacggatga gtttgcaatt   4620

gctgagtaca atgctccttg cagcaaagat cttggaaatg cttgaagacc acaaggctga   4680

aaagtgcttt gctggagtcc tgttctcaga gctccacaga agacacgtgt ttttgtatct   4740

ttaaagactt gatgaataaa cactttttct ggtcaaaaaa aaagaaaaaa ag           4792


<210> SEQ ID NO 110
<211> LENGTH: 2041
<212> TYPE: DNA
<213> ORGANISM: Homo sapiens
<220> FEATURE:
<221> NAME/KEY: misc_feature
<223> OTHER INFORMATION: Incyte ID No: 216189.2
<221> NAME/KEY: unsure
<222> LOCATION: 109-141
<223> OTHER INFORMATION: a, t, c, g, or other

<400> SEQUENCE: 110

agccaatcag gcgtcgttgc tacctgaaca agatcactca aggtgaagga taatctacta     60

ataccagcac tttgaatgaa aatttgtttc tctgccacaa actgaacann nnnnnnnnnn    120

nnnnnnnnnn nnnnnnnnnn nggtggggga gttgaaacct aattttgtgg cgtacagcta    180

tgcagcttga aatccaagta gcactaaatt ttattatttc gtatttgtac aataagcttc    240

ccaggagacg tgtcaacatt tttggtgaag aacttgaaag acttcttaag aagaaatatg    300

aagggcactg gtatcctgaa aagccataca aaggatcggg gtttagatgt atacacatag    360

gggagaaagt ggacccagtg attgaacaag catccaaaga gagtggtttg gacattgatg    420

atgttcgtgg caatctgcca caggatctta gtgtttggat cgacccattt gaggtttctt    480

accaaattgg tgaaaaggga ccagtgaagg tgctttacgt ggatgataat aatgaaaatg    540

gatgtgagtt ggataaggag atcaaaaaca gctttaaccc agaggcccag gtttttatgc    600

ccataagtga cccagcctca tcagtgtcca gctctccatc gcctcctttt ggtcactctg    660

ctgctgtaag ccctaccttc atgccccggt ccactcagcc tttaaccttt accactgcca    720
```

-continued

```
cttttgctgc caccaagttc ggctctacca aaatgaagaa tagtggccgt agcaacaagg    780

ttgcacgtac ttctcccatc aacctcggct tgaatgtgaa tgacctcttg aagcagaaag    840

ccatctcttc ctcaatgcac tctctgtatg ggcttggctt gggtagccag cagcagccac    900

agcaacagca gcagccagcc cagccgccac cccccccacc acaaacacag cagcaacaac    960

agcagaaaac ctctgctctt tctcctaatg ccaaggaatt tatttttcct aatatgcagg   1020

gtcaaggtag tagtaccaat ggaatgttcc caggtgacag ccccccttaac ctcagtcctc   1080

tccagtacag taatgccttt gatgtgtttg cagcctatgg aggcctcaat gagaagtctt   1140

ttgtagatgg cttgaatttt agcttaaata acatgcagta ttctaaccag caattccagc   1200

ctgttatggc taactaaaaa aaagaaaatg tatcgtacaa gttaaaatgc acggggccca   1260

agggggattt tttttttcac ctccttgaga attttttttt taaagcttat agtaaggata   1320

cattcaagct tggttaaaaa aataataata aaacatgcat catttttcat ttgccaacca   1380

agcacaaagt tattttatac tgactgtata ttttaaagta tactctcaga tatggcctct   1440

tacagtattt aagatatagc aaggacatgg ctgatttttt tttataaaaa ttggcactaa   1500

taagtgggtt tattggtctt ttctaattgt ataatttaat ttagtacaaa gtttgtaaaa   1560

tatcagagga tatatatata ttgtttctac gacatggtat tgcatttata tctttttact   1620

acagtgatct gtgacagcag cagcttcatg ttgtattttt tttactgaaa ttgtaaaata   1680

tccatcttaa agacatcaac tattctaaaa attgtgtaca ggatattcct ttagtggtgg   1740

aattaaaatg tacgaatact tgctttttca aaaaaatgta ttttctgtta aaagtttaaa   1800

gatttttgct atatattatg gaagaaaaat gtaatcgtaa atattaattt tgtacctata   1860

ttgtgcaata cttgaaaaaa acggtataaa agtattttga gtcagtgtct tacatgttaa   1920

gagggactga aatagtttat attaagtttg tattaaaatt ctttaaaatt aaaaatgcct   1980

attgtctttg tttttaagtg ttttctgaag atcgacctct ggagttatta tgttgtaaat   2040

g                                                                   2041


<210> SEQ ID NO 111
<211> LENGTH: 3208
<212> TYPE: DNA
<213> ORGANISM: Homo sapiens
<220> FEATURE:
<221> NAME/KEY: misc_feature
<223> OTHER INFORMATION: Incyte ID No: 900146.4

<400> SEQUENCE: 111

tggctggaag agcaacagag ggctgggaaa gagcttctat atatacctca ggaggaaagg     60

catcccagac agttttgaag ttttcaaaga ctgggctctg ctgttaagaa gttgtactta    120

aagcggagga gctaagccac ctgccaaaat gtgcaaagga cttgcagctt tgccccactc    180

atgcctggaa agggccaagg agattaagat caagttggga attctcctcc agaagccaga    240

ctcagttggt gaccttgtca ttccgtacaa tgagaagcca gagaaaccag ccaagaccca    300

gaaaacctcg ctggacgagg gccctgcagt ggcgtgattc cctggacaaa ctcctgcaga    360

acaactatgg acttgccagt ttcaaaagtt tcctgaagtc tgaattcagt gaggaaaacc    420

ttgagttctg gattgcctgt gaggattaca agaagatcaa gtcccctgcc aagatggctg    480

agaaggcaaa gcaaatttat gaagaattca ttcaaacgga ggctcctaaa gaggtgaata    540

ttgaccactt cactaaggac atcacaatga agaacctggt ggaaccttcc ctgagcagct    600

ttgacatggc ccagaaaaga atccatgccc tgatggaaaa ggattctctg cctcgctttg    660
```

-continued

```
tgcgctctga gttttatcag gagttaatca agtagtaatt tagccaggct atgaaatcat    720
cctgtgagtt atttcctcca taataaccct gcatttccca ttaatctaca tatcttccca    780
cagcagcttt gctcagtgat acccacatgg gaaaaatccc aggggatgtt gcttactctt    840
tttgcccaca ctgctttgga tacttatcta ctgtccgaag gccttctttc cccactcaat    900
tcttcctgcc ctgttattaa ttaagatatc ttcagcttgt agtcagacac aatcagaatc    960
acagaaaaat cctgcctaag gcaaagaaat ataagacaag actatgatat caatgaatgt   1020
gggttaagta atagatttcc agctaaattg gtctaaaaaa gaatattaag tgtggacaga   1080
cctatttcaa aggagcttaa ttgatctcac ttgttttagt tctgatccag ggagatcacc   1140
cctctaatta tttctgaact tggttaataa aagtttataa gatttttatg aagcagccac   1200
tgtatgatat tttaagcaaa tatgttattt aaaatattga tccttccctt ggaccacctt   1260
catgttagtt gggtattata aataagagat acaaccatga atatattatg tttatacaaa   1320
atcaatctga acacaattca taaagatttc tcttttatac cttcctcact ggcccccctcc   1380
acctgcccat agtcaccaaa ttctgtttta aatcaatgac ctaagatcaa caatgaagta   1440
ttttataaat gtatttatgc tgctagactg tgggtcaaat gtttccattt tcaaattatt   1500
tagaattctt atgagtttaa aatttgtaaa tttctaaatc caatcatgta aaatgaaact   1560
gttgctccat tggagtagtc tcccacctaa atatcaagat ggctatatgc taaaaagaga   1620
aaatatggtc aagtctaaaa tggctaattg tcctatgatg ctattatcat agactaatga   1680
catttatctt caaaacacca aattgtcttt agaaaaatta atgtgattac aggtagaggc   1740
cttctaggtg agacactttt aaggtacact gcattttgca gaaaaaaaaa aaaaaaagta   1800
atcttttagc aaccccagta ttccttcact atttcgcttc ctgcattagc aaattttact   1860
tacagtcaaa agtgcagatt tatactcctg acgtgtctca ttcacagcta aataataggc   1920
cataggactt ttggtaggtt taaactttta attctgtatt tcatgattat aagtcttgct   1980
agaatttttt ctaatcttta gtagatttga ttaaataatg attcacagaa tttagtaaca   2040
gaatcaaact aagccatgta tgagggtaat cgagatgagg atattaactc aaaagaaata   2100
gggtgatttt taaaggatta ataaaattct gaaatgttaa gtagaagatt acattgtcta   2160
gtcttgtatt tcctccttct gttgctctct ttcattcaca cactctcagt ttctcatatt   2220
tgtagctcat ttatttggtt atttcctaag aatattgaaa gtgaagcaac tatgtgactg   2280
tattcttcag gtaaacactg actgcgcttg ttggattttc cctatttttg tgacttcaag   2340
aataatatgc cctgctgaat acatgccatt tcacattctg aaactgggta gagtggttgg   2400
gtgttctgcc aacaattgct agtggtgtga attcattcat atttgccagt attgctcact   2460
tcaaagaaac tccttcatca agcagtccag agctaggcca gatcaacgct acaatcatga   2520
agttctcatt gcatgcaatt gtgtaggatt gacaaggaac tcagataaaa atttccaggg   2580
tgcacttcca gaaccagctt caacatatgt ctacattgcc cccaagttaa taaagtgcca   2640
accctttact ctctcataca gccagaaatg ttagaaatcc aaaatcttgg tgcattattt   2700
tttcataaac gctaaaacat ttgaagaaac aatttaatta tttaaaattc aagtatttta   2760
ttcacattat ttgcaatatc caaatgttta aaaattccca gataattaac tagctattac   2820
agatctcacc tagagggttg atgttatgaa gactccagtg gactgtactc acaaattgac   2880
tggacaccct atgaaagtgg gtagacctct cagcggaaaa taagaagggc ttttacctac   2940
agggcaggac agggtcccat gagagcagtt ctgtggagat ataaaaagaa tggaagaagg   3000
aatgccttat agtgatattg tgacattata tctatatatc tacatatatc tatctatcta   3060
```

-continued

```
tatctacatc tatataatct tacatttaaa attgtattcc tacacatatt agaaactctt   3120

ctaataaatg aagtaaaaaa attaaaaaga tacaaatatt ccagccccaa atgagaatca   3180

aactattaaa ttgttcagaa tttctttg                                       3208
```

<210> SEQ ID NO 112
<211> LENGTH: 5773
<212> TYPE: DNA
<213> ORGANISM: Homo sapiens
<220> FEATURE:
<221> NAME/KEY: misc_feature
<223> OTHER INFORMATION: Incyte ID No: 109082.18

<400> SEQUENCE: 112

```
gctgcgatgc agagtctgta cgcgtttgat gaggaggaga cggagatgag gaaccaagtc     60

gtggaagacc tgaagacagc cctccggaca cagcctatga ggtttgtgac ccgcttcatt    120

gagctggagg gcttgacctg tctgctaaat ttcctccgga gcatggacca cgccacctgt    180

gagagccgca tccacacctc actcattggc tgcatcaaag cattgatgaa caactcccag    240

gggcgggcac atgtgctggc acagcctgag gccattagta ccatagccca gagcctacgc    300

acagagaaca gcaagaccaa ggtggctgtg ctggagatcc tgggtgctgt gtgcctcgtg    360

cctggtggcc acaagaaggt gctgcaggcc atgctgcact accaggtgta tgcagcagag    420

cgaacccgct tccagaccct gctgaacgag ctagaccgaa gtctgggccg gtaccgggat    480

gaagtgaatc tgaaaacagc catcatgtcc ttcatcaatg ctgtcctcaa tgctggagct    540

ggagaggata atctggagtt ccgcctacat ctacggtatg aattcctgat gctgggtata    600

cagcctgtga ttgacaagct ccggcaacat gaaaatgcca tcctggacaa acatttagac    660

ttcttcgaga tggtgcggaa tgaggatgac ctggagctag ccaggaggtt tgacatggtc    720

cacatcgaca ccaagagtgc ttcccagatg tttgagttga tccacaagaa gctgaagtac    780

acggaggcct acccctgcct gctctctgtg ctgcaccact gcctgcagat gccctacaaa    840

cggaacggtg gctacttcca gcagtggcag ctcctggacc gcatcctcca gcagattgtc    900

ctccaggatg agcggggtgt ggaccctgac ctggctccct tggagaactt caatgtcaag    960

aacatcgtca acatgctcat caacgagaat gaagtgaaac agtggcgaga ccaggcagag   1020

aagttccgga aagaacacat ggagcttgtg agccgtctgg agaggaagga gcgggaatgc   1080

gagacaaaga cattggagaa ggaagagatg atgcggacgc tgaacaaaat gaaggacaag   1140

ctggcccggg agtcccagga gctgcgccag gctcggggac aagtggcaga gctggtagcc   1200

cagctcagtg aactctcaac aggccctgta tcttccccac cacccccTgg gggcccactc   1260

accttgtctt cctcaatgac aaccaatgac ctgcctccac cccctcctcc tctgcccttt   1320

gcctgttgtc cccctccccc accaccaccc cttcctcccg ggggaccccc gactccccca   1380

ggtgccccac cttgcctcgg catgggcctg cccctccctc aggacccccta ccccagcagt  1440

gacgtcccac tcaggaaaaa gcgtgtcccc cagccttctc acccactgaa gtccttcaac   1500

tgggtgaagc tgaatgagga gcgtgtccct ggcaccgtat ggaatgagat tgatgacatg   1560

caggtatttc ggatcctgga cctagaggat tttgaaaaaa tgttttcagc ctaccagagg   1620

caccaggagc tgataactaa tccttctcag cagaaagagc tgggctccac tgaagacata   1680

tacctggctt cccgcaaggt caaagagctg tcggtcattg atggccggag ggcccaaaac   1740

tgcatcatcc ttctttccaa gttgaagctt tctaacgagg agatccggca ggccatcttg   1800

aagatggatg agcaggagga ccttgctaag gacatgctgg agcagctcct caagttcatc   1860
```

-continued ccagagaaga gtgacattga cctcctggag gagcacaagc atgaaattga gcggatggcc 1920
cgtgctgacc gcttcctcta tgaaatgagc aggattgacc actaccagca gcgactgcaa 1980
gccctcttct tcaagaagaa attccaggag cggctggctg aggcaaagcc caaagtggaa 2040
gccatcctgt tggcctcccg ggagctggtc cgcagcaagc gtcttagaca gatgctagag 2100
gtcatcctag ccataggcaa cttcatgaac aaagggcagc gtgggggcgc ctacgggttc 2160
cgggtggcca gcctcaacaa gattgctgac accaagtcca gcatcgacag aaacatctct 2220
ctgctccatt acctgatcat gatcctggag aagcattttc ctgatattct aaacatgcct 2280
tcagagctgc aacatcttcc agaagccgcc aaagtcaacc tagcagaact ggagaaggag 2340
gtgggcaacc tcaggagggg cctgagagcg gtggaggtgg agctggagta tcagaggcgc 2400
caggtacggg agcccagtga caagtttgtc cctgtcatga gcgacttcat cacggtgtcc 2460
agcttcagct tctccgagct ggaggaccag ctaaatgagg ccagggacaa gttcgccaag 2520
gccttgatgc acttcgggga gcatgacagc aagatgcagc cagacgaatt ctttggcatc 2580
tttgatacct tcttgcaggc cttctcagag gcccggcagg atctagaggc catgaggagg 2640
aggaaggagg aggaggagcg gcgggcgcgc atggaagcca tgctgaagga gcagagggaa 2700
cgtgagcggt ggcagcggca gcggaaggtc ctggctgcag gcagctcgct ggaggaggga 2760
ggagagttcg atgacctggt gtcggccctg cgctctgggg aggtcttcga caaggactta 2820
tgcaagctca agcgcagccg caagcgatca gggagccagg ccctggaagt tacccgggag 2880
cgggcaataa accggctaaa ttattgacct ggggaactag ccacacagga ggccgggaga 2940
cagggactgg tgagaatggg gctgagtgga ggaggtggtg atatttaaac catttggtgc 3000
ttggtttaga gccttgggct gggtcctggg atggggggct gtgtgaggct ggaccaggtg 3060
tctccccacg cttaccttaa ggggctcctc ttatctcccc ttcacacgat tccttctgtg 3120
ccctggcccc aggtattatt ctgaggctgc cttggatggc ctcaggccag gtaaccccag 3180
gctgaagggg ccctgctccc catcccctac catgggcacc catgtgctgg cacagaacag 3240
ttccagatct agactggaga ggtccacagc cttgtccaga gttcctgtgt agcacgggga 3300
gcaatgatgg agggagcccc tgagagggaa tctggtgagg gaatccagac tcccttctct 3360
caaggggagg ctcaacagaa cattgacctg ggggcaaact ttcctcttga atgggaacag 3420
aggaggcatt atatattcta gttagatcag ctctggtagg ttccagagaa cagtcaatgt 3480
tggaaggatg atgcagggac caaagccatc aggacagagt agcagtgtct gtttcccatg 3540
tcacaagtcc tctggcctct ccctgcatgt cttaagtatc tttcccttcc ttctctaccc 3600
tcacctccat cctgtctact aatccacagt cctagaagac tcaccttggg tttccacagc 3660
tatggctcac taccaggtgc ttgatgaatc tggcgagggg ctcaagacag acctcatgca 3720
tcaccacacc tcatgccttt tgggcatctc ccatgtcccc atctcctgga cacctggcca 3780
ttgttgtgaa gccagacagt gacctcaaat gttgccttgg agtcccctac agcccctcag 3840
cagagggcag cacttgaatg cttagctcca tcccatagtt ctctacttca tataaattgc 3900
tcaggccctc ccaccccttc tctaacacta gcttcaaggc agaagccaca gcagcctctg 3960
tccagcctgc aggtggccac ttggaaccat gtgtccactg gcgttgggga gttggttcct 4020
gagaggtctg agggccagag ctgccctcta cattaacatg ctgtctctaa gggtggcccc 4080
tcctctcagg cgttcagatg gtgcgaacag cagagcaggc aagggaaact ggggagatgg 4140
ggatggagga ggaaggctga tatcctctgg ggagcacatc acctgaaggt gccaaggagg 4200

-continued

```
aaggctgaga gggggccac cccatttctg gtacccaatt tggttcttca gcccaacttg   4260

caaggggttc cttctggtcc tcccatccac tgccaccttc cattttgtcc atctcatgct   4320

ggccttggtg gatgggatgg ctgtatctag acaaaatttt tctaaaactc catcaaggct   4380

cttattcaat accacgttcc gagttggcct ttcatcttct ttgagactgg ccctgcctaa   4440

cctctaccat caatgagctc ttggcccttc tgcccttccc tgtgtttctc actttccaac   4500

ctaatccctg gctcagggtt attgccagtg gagactggtg agctgggcct actctcagct   4560

gcctatcttc tgcctttcac ttgcatccaa ctcctggggc tgggaccgta gtagctgcgg   4620

gggggaagaa acacagggtc ggtgagccca gcatgtgcgt tggtttgagg gggcgggcgg   4680

tgtgtgtgtg ttctggtggg agggatctga gcaagtgcaa gcctggctga cacaggtgtg   4740

aagaggccat cctggaaccc aggtgagggc aagatgaagg cttccaggca gaacagctgc   4800

agagagtttg gctatatgca tctgcagccc caagagctcc cactgcaaga caagtgttgg   4860

ggaagatggg aggttgtggg tgaggcctct aaaggtcctc tcccaaactg accaggctga   4920

tgtcaaccta accccctcag gggcagggaa caggggaggg ctccacaagc gtgtctggca   4980

ttcccaccca ccatggaaga ctggatacgc acctggaaac aaaaggacta tggaagctgt   5040

tcaagataca tttgatcttc agaaaagcag aatttggttc aactgttgac agaggacaca   5100

aatacgttgt tccagagctc agccttctca ctctaaaaga aagatatttt tctatttatt   5160

ttctacatct ggccagtggc tctggtgcta gatgccactg tagccagatc tccaacagtg   5220

ccttggacca tggactcata ctcaactgag taagaagggg ctggtgccca gtcggggtgg   5280

ctgagctggt ccttaatagg ttgtttcttg gtcttgcttt cttcatgccc tccccactgc   5340

tcctgccacc tttagataag tttctctagc taattttgtg gccaatgtaa aattcgtcat   5400

caacctaaca aacacaacct tctcagcagc atttctcccc tgtgatggaa ataaataaag   5460

tgtttagggc agtgggagga gaaaattctc caggtgaatg gggaagggtc tgttccagcc   5520

tctccctact cccatcccat ttccaccaac tggggaactg tgactatcta tctcccccga   5580

cttctaccag ggatgccttc acgccaaggc tgttctcacc agctgcctca gatgacaaat   5640

gaggctaatg gacataatct acagtgtcct ttttcacttg caccttttttt ataagaatat   5700

attgtaatac taaaaaatat taaattcata ccatccctta aaaaaaacaa aaaggggggcc   5760

gctctagact cga                                                      5773
```

<210> SEQ ID NO 113
<211> LENGTH: 422
<212> TYPE: DNA
<213> ORGANISM: Homo sapiens
<220> FEATURE:
<221> NAME/KEY: misc_feature
<223> OTHER INFORMATION: Incyte ID No: 1000189.1
<221> NAME/KEY: unsure
<222> LOCATION: 84
<223> OTHER INFORMATION: a, t, c, g, or other

<400> SEQUENCE: 113

```
gtcaacttcc cgctggtgtt cggcctgcta ggctggcgcg gctatatggga ctccggtgga    60

gattgcattg cgctgccgcg cggntcccgg ccgaccagga caggtttatt tgtatctacc   120

ccgcttattt aaattaatta gagagagacc atagctgagc gggaggcgga tccccattaa   180

taaggctgta gaaaacccac ggtactgaga tcaggatgta tgtcagcagt tggactgaat   240

gcgtttctgg agaaaaacaa aatgtactcc agagaatgga atcgtgatgt tcagtataga   300

ggcagagttc gggtacagct caaacaggaa gatggcagcc tctgtcttgt acagttccca   360
```

-continued

```
tcacgtaagt cggtgatgct gtacgtagca gaaatgatac ccaagctaaa aacaaggact    420

ca                                                                   422
```

<210> SEQ ID NO 114
<211> LENGTH: 5444
<212> TYPE: DNA
<213> ORGANISM: Homo sapiens
<220> FEATURE:
<221> NAME/KEY: misc_feature
<223> OTHER INFORMATION: Incyte ID No: 087469.9
<221> NAME/KEY: unsure
<222> LOCATION: 4458-4769
<223> OTHER INFORMATION: a, t, c, g, or other

<400> SEQUENCE: 114

```
ggggaggaag aaaggcgaag gcaaggcgaa ggggtggaga gtgatatgaa gagcgagaga     60

aaagagagga cagcggacga gcagatccgg tatctggaat cccggcgcct agaacgtgtt    120

tttcgggaga gcaaaggctg tgtctacggc aggctgggga tatagcctct ccttccgatg    180

aaaagagaaa ggaagaatgg actacagcca ccaaacgtcc ctagtcccat gtggacaaga    240

taaatacatt tccaaaaatg aacttctctt gcatctgaag acctacaact tgtactatga    300

aggccagaat ttacagctcc ggcaccggga ggaagaagac gagttcattg tggaggggct    360

cctgaacatc tcctggggcc tgcgccggcc cattcgcctg cagatgcagg atgacaacga    420

acgcattcga ccccctccat cctcctcctc ctggcactct ggctgtaacc tgggggctca    480

gggaaccact ctgaagcccc tgactgtgcc caaagttcag atctcagagg tggatgcccc    540

gccggagggt gaccagatgc caagctccac agactccagg ggcctgaagc ccctgcagga    600

ggacacccca cagctgatgc gcacacgcag tgatgttggg gtgcgtcgcc gtggcaatgt    660

gaggacgcct agtgaccagc ggcgaatcag acgccaccgc ttctccatca acggccattt    720

ctacaaccat aagacatccg tgttcacacc agcctatggc tctgtcacca acgtccgcat    780

caacagcacc atgaccaccc cacaggtcct gaagctgctg ctcaacaaat ttaagattga    840

gaattcagca gaggagtttg ccttgtacgt ggtccatacg agtggtgaga aacagaagct    900

gaaggccacc gattacccgc tgattgcccg aatcctccag ggcccatgtg agcagatctc    960

caaagtgttc ctaatggaga aggaccaggt ggaggaagtc acctacgacg tggcccagta   1020

tataaagttc gagatgccgg tacttaaaag cttcattcag aagctccagg aggaagaaga   1080

tcgggaagta aagaagctga tgcgcaagta caccgtgctc cggctaatga ttcgacagag   1140

gctggaggag atagccgaga ccccagcaac aatctgagcc atgagaacga ggggatctgg   1200

gcaccccagg aaccgccatt gcccataaga cccccaggaa gctaggcact ttctttccat   1260

ggaaacattt agacacaaac ctccccagct ccggccaagc catcatttgc tacctggagc   1320

tggatgtaga agtcagcaga cagctcccta tccctggacc cctgccctcc ttttttctgc   1380

tcacaaggac ttttgatttt agttataagg aggacccaaa atgtgtgtgt gtacattgtg   1440

tgtgcacaca tggtacgtgt ccatgtgcct acctgatact ttcacatgta attaaattcc   1500

aggcaaccag cacaagagcc gtgagcttgg cacatgtgct gctcgtgagc aggaaaatca   1560

gaggagccac tgatctgagt ggtatttagg ttgaaggaaa gatttctcct ctcaagtgcc   1620

agggagcagc cacacgtctg tctgtgttta gagagggaag agggttctcc aggttcacca   1680

tttgggttgt ttatatgttg gtagaaattc tccctgtatg cctagaagga tcagtgaatg   1740

taagagcctt ggaaattaac aaaataacag ccacataacc ttgcggcaag tctgatggaa   1800
```

-continued agaaaaagat aaaccatccg tggggtagat gcaataagcc cacgtatttt tacactggaa 1860
acgttgattg ttttaaatga caaagacata tgtgatgttc tatgtggaaa cctgtgaaga 1920
gtggattctg cctccatctc tgcctccatg gctaccttta ggagacagag aagatcctgt 1980
gtgtttctct gtacccagct gacagcctgt ctctatggcg cttccttgag tggaaggaaa 2040
tgtctcaaga aacaaagatc tcgctggtgc gtacacagtg ctgaccagct agtatggcca 2100
gggcctggtg gcctggtggc caggaagttt caggttgaag ggaaatgtcg aggctacctg 2160
cagatatgac aggtgccttg aacgcagccc atcttcatgt catcaaaggt cttcctgcac 2220
ttgaagctgg ggcgatgttt gcagtcaaga ccattctttc caacctctgg gttcttgcaa 2280
gttgccctca ccttgtgtgt ggagatgcat tccaagaatg aagcctcatc ttgctactga 2340
gtgtggggtt cagggaagct ctttaggcca cctggtgaag gtgcatgggg aggatggagc 2400
ttctcctcag ctcctctgag cagccaccta tgtgatcttt aaatccaacc ccaatgggag 2460
aaaagggcaa gaacagtctg tgccctggga ctcctatcag gaagcttgac aggcagctgg 2520
gcatcagtgc agctgatatc gtttgaggag ggagacagat gcttggacct gggtgcctgg 2580
ctatggagat tgaccaagca agatcaggag ctcctgatag caggcgtctt tgagcctagc 2640
tggggtagag gcactgccca tctcttctcc accttctctc cacagaatgt ttgcagagct 2700
gggcagttga ggaaaggaca gcccctggtt ggtgcctcca aaggaaggtg gacttttttg 2760
gtggagacgt ttctgccctg ggcaccctcc tgcccccgat tcatacctat ggcttcttga 2820
gaaggctcac agctgtggtc ttaacgtaga ctgcagaaag atggcatgcg gcccctggca 2880
tttcgccaag ggttttatag caagtctcct tcctccatag ggacagcagc accagccctg 2940
tggggcatgg agtggaagcc cagaagggct tctgcaagct gcacagaact ggggtaagaa 3000
gacaaagagt agccaccggg agaggcttcc tttgttacag ctgggaaaga acagttctgt 3060
gaatgcaaac acctcctgag ttttgcaatt gagaaaatga tttggagaac ttctcttctg 3120
gtaattttta ttttgaatgt tcagggcctt agttggcccc agtaattctc cttggaggac 3180
ttgggagaag aatttccaca aagcaaacta ctaaccacta gctcttattg gacagcgatt 3240
tctggcttat aagagttctc tttgatttgc actagcacta cgatagtgtt agatggggaa 3300
atactgcaac atgtccagtt ggccagatca ctttccaagg gagcgatact aaggcagact 3360
gagcttttta aagatgggag gtcaggaggt ggaagcgaga ggagatccca tctcacacaa 3420
cacacttcca cgtaatgcag accacacttt tccattttgt cctgccctct tgagaggtca 3480
tttctcacgt cctaagaacc tgatcagaaa ttttggaagg gttctttgaa atagcagcag 3540
ttgaaacaga gacactttgc cacagtgtgg agcagatttt ctcactggta tcacatggtc 3600
ttgcagtttt gaactcttcg accgatttgt gggagtttat gtaattgcgt gcaatgaacc 3660
tgaaattgtg taaaggacaa aagaccagtt tatagggttg ggttttttttt ccaacttgtg 3720
aaaagcagtt tagctgcatc tgtctcccca ccaccccccac cccgggaggg gcttatgtta 3780
caaggtgatc aagtgaagga aaaacctgag cctatctggc tgggatggtg gaattaagca 3840
caaggtcaca ttctctgtga tcacatgaga gggaaggtga tgacttaaat ggcagggggt 3900
ggggattatc ttggggagag gctgaaaagc acaaaagata gtcttccctg tacgtattgg 3960
tgaagaacgt gcacaaggct ggatggactt caacttggag ttgagttgag gcaagaggat 4020
ttctggatat tagtcaccca tctgcaagaa aaatgctgag gcctcgggtc aagattttga 4080
tctgagacat gctgatgctt caaggagaaa tattttcaca atcctctctt ccctcaccag 4140
aagagaacag tactctctcc tagaaacctc taggtaaaca cattttatcc taatatcggt 4200

-continued

```
agcatataat gcccccccc aaaatatctg ttttccatgc aaaaaagtct caacaagaag   4260
tctgtggagt tgagtggtta cttcaaagtg tcaggagagt gaagaaattg gccacagaag   4320
agcaagaagc tctcttaaga aaagggaatt ctctttaaag aaaccaccac caacaacaaa   4380
acaaccaaaa accatgtttt atgtcaaagc tctgtagcac agagaatgtg gtgtcacaga   4440
tacatcgccg agagaggnnn nnnnnnnnnn nnnnnnnnnn nnnnnnnnnn nnnnnnnnnn   4500
nnnnnnnnnn nnnnnnnnnn nnnnnnnnnn nnnnnnnnnn nnnnnnnnnn nnnnnnnnnn   4560
nnnnnnnnnn nnnnnnnnnn nnnnnnnnnn nnnnnnnnnn nnnnnnnnnn nnnnnnnnnn   4620
nnnnnnnnnn nnnnnnnnnn nnnnnnnnnn nnnnnnnnnn nnnnnnnnnn nnnnnnnnnn   4680
nnnnnnnnnn nnnnnnnnnn nnnnnnnnnn nnnnnnnnnn nnnnnnnnnn nnnnnnnnnn   4740
nnnnnnnnnn nnnnnnnnnn nnnnnnnnna agagaaattt ctacatgaac aaggcaattt   4800
cagtgtctta cagcggccaa accatgacgt gaagaatgag ataggagaca ggagatcacc   4860
ataagcgtcc ctgatatagc agcacacatt ttcacgtttc cacttaaatc gttttgcaca   4920
aagtcttgct tcgctcagat gagatgagat atgatttcct agagatgtaa aaataagaat   4980
gaatgtggcg ccccccttctt ccagatgtaa tagaaagctc tgccctatca caagggggggt   5040
gttgaagcgc cccttgtgtt ttaactgtat ttaactgagc acaagatgca caagctgtgg   5100
tgggaaaccc tcagtttacc tttggagtct tccctgcaga tcgcagacct gtttccaggc   5160
tgatgtttct ggtgtgtaat tgctagcgtt tctgaagggt tttcccaatt gttttagcct   5220
tgtgaagtat tcttaattat aacttgcctt tcagcgatgg tacatgactt gattcaacgt   5280
ttggttctga acttacacac tgatgcgttt actcatctaa cataatctga cagggcctca   5340
gcaagggagc catacatttt tgtaacattt tgatatgttt taatgcatct gacttagatc   5400
ttactgaaat aaagcacttt tcaaagaaaa aaacaccaaa aagg                    5444
```

```
<210> SEQ ID NO 115
<211> LENGTH: 4092
<212> TYPE: DNA
<213> ORGANISM: Homo sapiens
<220> FEATURE:
<221> NAME/KEY: misc_feature
<223> OTHER INFORMATION: Incyte ID No: 480076.9

<400> SEQUENCE: 115
```

```
ggcgacaggg gcggctcttt cctgtggtgg ggtttgtgaa gtcgtggccc gttagcagga     60
agcctaacag tcgccccgac gctagtgcag ggacccaatc tgagtccccg gccagccgaa    120
tccaagccgt gtgtactgcg tgctcagcac tggcccgaca gtcctagcta aacttcgcca    180
actccgctgc ctttgccgcc accatgccca aaacgatcag tgtgcgtgtg accaccatgg    240
atgcagagct ggagtttgcc atccagccca acaccaccgg gaagcagcta tttgaccagg    300
tggtgaaaac tattggcttg agggaagttt ggttctttgg tctgcagtac caggacacta    360
aaggtttctc cacctggctg aaactcaata agaaggtgac tgcccaggat gtgcggaagg    420
aaagcccccct gctctttaag ttccgtgcca agttctaccc tgaggatgtg tccgaggaat    480
tgattcagga catcactcag cgcctgttct ttctgcaagt gaaagagggc attctcaatg    540
atgatattta ctgcccgcct gagaccgctg tgctgctggc ctcgtatgct gtccagtcta    600
agtatggcga cttcaataag gaagtgcata agtctggcta cctggccgga gacaagttgc    660
tcccgcagag agtcctggaa cagcacaaac tcaacaagga ccagtgggag gagcggatcc    720
aggtgtggca tgaggaacac cgtggcatgc tcagggagga tgctgtcctg gaatatctga    780
```

-continued

```
agattgctca agatctggag atgtatggtg tgaactactt cagcatcaag aacaagaaag    840
gctcagagct gtggctgggg gtggatgccc tgggtctcaa catctatgag cagaatgaca    900
gactaactcc caagataggc ttcccctgga gtgaaatcag gaacatctct ttcaatgata    960
agaaatttgt catcaagccc attgacaaaa aagccccgga cttcgtcttc tatgctcccc   1020
ggctgcggat taacaagcgg atcttggcct tgtgcatggg gaaccatgaa ctatacatgc   1080
gccgtcgcaa gcctgatacc attgaggtgc agcagatgaa ggcacaggcc cgggaggaga   1140
agcaccagaa gcagatggag cgtgctatgc tggaaaatga gaagaagaag cgtgaaatgg   1200
cagagaagga gaaagagaag attgaacggg agaaggagga gctgatggag aggctgaagc   1260
agatcgagga acagactaag aaggctcagc aagaactgga agaacagacc cgtagggctc   1320
tggaacttga gcaggaacgg aagcgtgccc agagcgaggc tgaaaagctg gccaaggagc   1380
gtcaagaagc tgaagaggcc aaggaggcct tgctgcaggc ctcccgggac cagaaaaaga   1440
ctcaggaaca gctggccttg gaaatggcag agctgacagc tcgaatctcc cagctggaga   1500
tggcccgaca gaagaaggag agtgaggctg tggagtggca gcagaaggcc cagatggtac   1560
aggaagactt ggagaagacc cgtgctgagc tgaagactgc catgagtaca cctcatgtgg   1620
cagagcctgc tgagaatgag caggatgagc aggatgagaa tggggcagag gctagtgctg   1680
acctacgggc tgatgctatg gccaaggacc gcagtgagga ggaacgtacc actgaggcag   1740
agaagaatga gcgtgtgcag aagcacctga aggccctcac ttcggagctg gccaatgcca   1800
gagatgagtc caagaagact gccaatgaca tgatccatgc tgagaacatg cgactgggcc   1860
gagacaaata caagaccctg cgccagatcc ggcagggcaa caccaagcag cgcattgacg   1920
aatttgagtc tatgtaatgg gcacccagcc tctagggacc cctcctccct ttttccttgt   1980
ccccacactc ctacacctaa ctcacctaac tcatactgtg ctggagccac taactagagc   2040
agccctggag tcatgccaag catttaatgt agccatggga ccaaacctag ccccttagcc   2100
cccacccact tccctgggca aatgaatggc tcactatggt gccaatggaa cctcctttct   2160
cttctctgtt ccattgaatc tgtatggcta gaatatccta cttctccagc ctagaggtac   2220
tttccacttg attttgcaaa tgcccttaca cttactgttg tcctatggga gtcaagtgtg   2280
gagtaggttg gaagctagct cccctcctct cccctaccac tgtcttcttc agggtcctga   2340
gatttacacg gttggagtgt tatgcggtct agggaatgag acaggaccta ggatatcttc   2400
tccaggatgt caactgacct aaaatttgcc ctcccatccc gtttagagtt atttaggctt   2460
tgtaacgatt gggggataaa aagatgttca gtcatttttg tttctacctc ccagatcgga   2520
tctgttgcaa actcagcctc aataagcctt gtcgttgact ttagggactc aatttctccc   2580
cagggtggat gggggaaatg gtgccttcaa gaccttcacc aaacatacta gaagggcatt   2640
ggccattcta ttgtggcaag gctgagtaga agatcctacc ccaattcctt gtaggagtat   2700
aggccggtct aaagtgagct ctatgggcag atctacccct tacttattat tccagatctg   2760
cagtcacttc gtgggatctg cccctccctg cttcaatacc caaatcctct ccagctataa   2820
cagtagggat gagtacccaa aagctcagcc agccccatca ggactcttgt gaaaagagag   2880
gatatgttca cacctagcgt cagtattttc cctgctaggg gttttaggtc tcttcccctc   2940
tcagagctac ttgggccata gctcctgctc cacagccatc ccagccttgg catctagagc   3000
ttgatgccag taggctcaac tagggagtga gtgcaaaaag ctgagtatgg tgagagaagc   3060
ctgtgccctg atccaagttt actcaaccct ctcaggtgac caaaatcccc ttctcatcac   3120
```

-continued

```
tcccctccaa agaggtgact gggccctgcc tctgtttgac aaacctctaa cccaggtctt   3180

gacaccagct gttctgtccc ttggagctgt aaaccagaga gctgctgggg attctggcct   3240

agtcccttcc acaccccac ccttgctct caacccagga gcatccacct ccttctctgt   3300

ctcatgtgtg ctcttcttct ttctacagta ttatgtactc tactgatatc taaatattga   3360

tttctgcctt ccttgctaat gcaccattag aagatattag tcttggggca ggatgatttt   3420

ggcctcatta ctttaccacc cccacacctg gaaagcatat actatattac aaaatgacat   3480

tttgccaaaa ttattaatat aagaagcttt cagtattagt gatgtcatct gtcactatag   3540

gtcatacaat ccattcttaa agtacttgtt atttgttttt attattactg tttgtcttct   3600

ccccagggtt cagtcctcaa ggggccatcc tgtcccacca tgcagtgccc ctagcttaga   3660

gcctccctca attcccctg gccaccaccc cccactctgt gcctgacctt gaggagtctt   3720

gtgtgcattg ctgtgaatta gctcacttgg tgatatgtcc tatattggct aaattgaaac   3780

ctggaattgt ggggcaatct attaatagct gccttaaagt cagtaactta cccttaggga   3840

ggctgggga aaaggttaga ttttgtattc aggggttttt tgtgtacttt ttgggttttt   3900

taaaaattgt ttttggaggg gtttatgctc aatccatgtt ctatttcagt gccaataaaa   3960

tttaggctcg agccgaatat ttttctttta caagagcaca acaggaacca aagtaacaga   4020

gtaatagata cagcactcag gataaatcat atctttaaaa taataataaa aaaatttaca   4080

ccttgtccta ta                                                       4092
```

<210> SEQ ID NO 116
<211> LENGTH: 4852
<212> TYPE: DNA
<213> ORGANISM: Homo sapiens
<220> FEATURE:
<221> NAME/KEY: misc_feature
<223> OTHER INFORMATION: Incyte ID No: 197687.11
<221> NAME/KEY: unsure
<222> LOCATION: 1756-1757, 1760-1761, 1764
<223> OTHER INFORMATION: a, t, c, g, or other

<400> SEQUENCE: 116

```
gatcttaaga aagagagcaa ggaggaagag cccggtgggg agcaggtcct tctcccccac     60

ccccctaccc ccaactccca ctggagccgc attgagactg tacggcacca ccgggcgccg    120

aatggctgtt ttctaactgg gatcctcggt gacgtatggc tgcctgcccc ttggcagctg    180

tctttatgga ccagtaggca gagcgaaatt gacgctgaca agacttttgc atcttggaag    240

ggactgtaat ctactgtagt gaagaacaga gcctctcaat cagacgggtg taaataagag    300

acggagggga gtccagaaga aaaggaagag gaggaaaaac aagtgtgtgt tggggggaac    360

agggggaaaa gcatttttgg tggatggtat gaagccagcc atggaaactg cagccgagga    420

aaatactgaa caaagccaag agagaaaagg ctgctttgaa tgctgcatca agtgtctggg    480

aggagtcccc tacgcctccc tggtggccac catcctctgc ttctccgggg tggccttatt    540

ctgcggctgt gggcatgtgg ctctcgcagg caccgtggcg attcttgagc aacacttctc    600

caccaacgcc agtgaccatg ccttgctgag cgaggtgata caactgatgc agtatgtcat    660

ctatggaatt gcgtcctttt tcttcttgta tgggatcatt ctgttggcag aaggctttta    720

caccacaagt gcagtgaaag aactgcacgg tgagtttaaa acaaccgctt gtggccgatg    780

catcagtgga atgttcgttt tcctcaccta tgtgcttgga gtggcctggc tgggtgtgtt    840

tggtttctca gcggtgcccg tgtttatgtt ctacaacata tggtcaactt gtgaagtcat    900

caagtcaccg cagaccaacg ggaccacggg tgtggagcag atctgtgtgg atatccgaca    960
```

-continued

```
atacggtatc attccttgga atgctttccc cggaaaaata tgtggctctg ccctggagaa   1020
catctgcaac acaaacgagt tctacatgtc ctatcacctg ttcattgtgg cctgtgcagg   1080
agctggtgcc accgtcattg ccctgctgat ctacatgatg gctactacat ataactatgc   1140
ggttttgaag tttaagagtc gggaagattg ctgcactaaa ttctaaattg cataaggagt   1200
tttagagagc tatgctctgt agcatgaaat atcactgaca ctccagacta aagcagagtc   1260
taggtttctg caattttgtt acagtaattt gtaaatagct ttagtaaact caccttgcat   1320
ggtagattaa taagatgact tactgtacat gaattacaca ataatgagat ctggtggcta   1380
tttccacatt ttgaaaagga ttcagttatt tactgacagt ggtgagcatc ctttttaaaa   1440
taatgttctc atacttaaac attagagagc agtatcttta aatgaattat taacactttg   1500
gaatacttac attttctgtt atttttgatt gcctgataac cagtttcaat gatgaaaatg   1560
aaaacaagtg ctgaagatga aatggaagag aaccgtttta atctggattt tgttttgtca   1620
cacctggaaa atactttgca aatatgttct aaattgaaaa caattttttt atgatcacat   1680
ggttcactac caaatgaccc tcaaataagc cagatgaaaa tttgaagaaa aaggtcaccc   1740
agttctctgg aaaaannaan naanaaaaaa aaaaaaagga tttatatgtg ggtagttttt   1800
tttttggtac aacacaatca ttctgttaga gcccacaaaa ttggtaacct taaattgtgt   1860
gttttggtaa gtaataacta actgtttcct catagctagt tctcaagctg catgtaagat   1920
tttaacggga agagaaaata ggcctggacc tgaaggtctc aaatatgttg agaagaaagt   1980
atgaactata aggaacttga gatgtagatt tattttgcag gaaatacgag gaaaatagga   2040
aagaagtgtt tgccgcatca agtgtaaaga atgatactga ggatttttac attttatgaa   2100
atgaaataat ggcatttaca aaatgaaaaa tgtagtttca caactaagtt ttgttaacag   2160
agactgcatg ctttgcttat agttcttaat tttggttttg acattcattt aattttttcc   2220
atgttaaata tgtagtttaa ttatttactc aaaataaaca ttgttcatgc ttttaggcct   2280
ttgggggaat tgatttttat ccacaggtag aaaatggtct ttgcacacac tacacttatt   2340
tcaaatatac aatgtgctcc cgaactttcg cattagtctt taaaattact ctcaaaatgg   2400
tattaaaaaa aaaaaaaaaa gcaccctctc gtatttcatt tttgcttttt cttaacaata   2460
cctttggcca ttttttttcca gttcactatg tttgtatact aacttttctt cagcctttta   2520
atgcgaagcc aactagtaga gcatgctttc aggatctgac agctctgcta gtagagcgag   2580
tatttattaa tacagaatta accttcgccc ctttaaagtc aagtctgtct aatctaacta   2640
gcgcctcgct ttgccttctc acaatgctca ctagccatca tgctcaccct tctcttccag   2700
atccacttcc tcatgatact gtcttctaac tgggcttact taaaggatgc gagcaaaatg   2760
caggcttacc aggatatcaa agcaaaggaa gaacaggaac tgcaagatat ccagtctcgg   2820
tcaaaagaac aactcaattc ttacacataa atgtttgcca gagtgtttcg gccgacgtat   2880
ttacagctct gacaaatcat cagacagctg ctctgcagta cagatgtgta tcccaccaaa   2940
ctaatgtaga tgtacaaaca cttcactgtc tgtctcaagc tgctgggatg tatctctagg   3000
aaaaccttcc agtgggtaaa tctttttctt tagaacaaat attggaggtt tcatgttagc   3060
cattttaaaa ggcaacactt tgacaaaatg atcgttcata ctttgggaat ttgtggcatg   3120
ttcacattta ttgctagggc aattctacca agacactcaa tggaatatgt cacactcctt   3180
aatagggacc tgtgactcct taataaggac ctgtgacatg cccagcatca agggataaga   3240
ccgtaaattc acatatatgc catctgtcct caagtgttat ctacatagga aataaaatgg   3300
```

-continued aattgatgta aagttccatt tctgacagct gacatttatt aaactttgga tcaaagataa 3360
tgtgattctt atgattgatt tctcaaacta gcttttccct cccaagtcca ggacccatta 3420
atttcctgag ccaatcagaa atatattttt caataatgct aaaattagct acaattctgc 3480
tgaccctact attaaagaat ctggatgctg gactcactga caagctttcc agaagcaatt 3540
ttataacaga tttcatttta acaaaatact gatccaattt tcattattct tgagaaatgt 3600
cagctttgcc ttaatgagta tttgctttaa atttctaaga atttatatca taactagaga 3660
cccaaatatc tttcacagaa ttttgttcca taaatgtttt tcttaattat taagaagtgt 3720
taccttatta aaatgaccac cattctaaac catttttcag tggtctggat acgaagttta 3780
cagtttcata ccaactatct aaaacctaat tgcaaattga ccacagacct ctaacctcct 3840
acttttatag acttgaatac ttaagtaatt taaattaggg ttggtatttc attttttttct 3900 tatctaaatc ttagtttcct ggaataataa agtttgatgt tcagcaagag aactgcttga 3960
gtttaagcca ttttcaaaag aaacttgcct tttacattat tgtgttccag aacattaagt 4020
gactgtaggt actgggtatt agtgatggta aactttgtgt tgctctttat gaaatgatcc 4080
atataactgt tgggtgcatc agtgcttttc aaaggggctg cttactatag ggttaactat 4140
gtatattcat tgttaagagt taacttgtgg tttggctgtt tcctggattt tataacatac 4200
atgtgcagaa atgtattcaa atgaaaggaa gcataccttt atcaagatgc tattaaaatt 4260
gaacatcaag tataatattt catttggatt ctcttttttg gttaatgcct aaaaatgcct 4320
atttgggatt tttttttctt tttaaattaa gagaagctct cttctgtgta gaacagttgt 4380
tccaaaatag cttagtgttt tgttttcctg ttgcatgaca gatttaacta ttctttccag 4440
cagtggaggt gctgtcagag tccagtgttc tagaagaggc agtgtctaaa gcctaatttt 4500
acttttctaa ttctggtagc tattaccagg aatttttgaa agttttgttt aagtagtcta 4560
atatttttta tgtaaagagc attaaatttt gctatgtata aatttttgta acctaacagt 4620
gaatcaatat tttctatcag tgccaagggc ttcctgtagt tctattcaag tgttacaata 4680
aatatttgta gataatagtc aatacttgtg tatgcttatt ttaaagatct atttaggtgg 4740
aaatagttgt ggatgtacta agagtaatga aataaaatta tagcttcatt cacttgcctt 4800
tttaccatac ataaatccta tctttctttg ttctcagtat ggtttcactt tt 4852

<210> SEQ ID NO 117
<211> LENGTH: 1303
<212> TYPE: DNA
<213> ORGANISM: Homo sapiens
<220> FEATURE:
<221> NAME/KEY: misc_feature
<223> OTHER INFORMATION: Incyte ID No: 202234.2

<400> SEQUENCE: 117
ctccgcgcca cgtgactccg cggccgggcc gggacgcgac gggacgcgct gggaccggcg 60
tcgggggtcg cggggaccat gcagcggagg tgggtcttcg tgctgctcga cgtgctgtgc 120
ttactggtcg cctccctgcc cttcgctatc ctgacgctgg tgaacgcccc gtacaagcga 180
ggattttact gcggggatga ctccatccgg tacccctacc gtccagatac catcacccac 240
gggctcatgg ctggggtcac catcacggcc accgtcatcc ttgtctcggc cggggaagcc 300
tacctggtgt acacagaccg gctctattct cgctcggact tcaacaacta cgtggctgct 360
gtatacaagg tgctggggac cttcctgttt ggggctgccg tgagccagtc tctgacagac 420
ctggccaagt acatgattgg gcgtctgagg cccaacttcc tagccgtctg cgaccccgac 480

-continued

```
tggagccggg tcaactgctc ggtctatgtg cagctggaga aggtgtgcag gggaaaccct    540
gctgatgtca ccgaggccag gttgtctttc tactcgggac actcttcctt tgggatgtac    600
tgcatggtgt tcttggtgct gtatgtgcag gcacgactct gttggaagtg ggcacggctg    660
ctgcgaccca cagtccagtt cttcctggtg gcctttgccc tctacgtggg ctacacccgc    720
gtgtctgatt acaaacacca ctggagcgat gtccttgttg gcctcctgca gggggcactg    780
gtggctgccc tcactgtctg ctacatctca gacttcttca aagcccgacc cccacagcac    840
tgtctgaagg aggaggagct ggaacggaag cccagcctgt cactgacgtt gaccctgggc    900
gaggctgacc acaaccacta tggatacccg cactcctcct cctgaggccg gaccccgccc    960
aggcagggag ctactgtgag tccagctgag gcccacccag gtggtccctc cagccctggt   1020
taggcactga gggctctgga cgggctccag gaaccctggg ctgatgggag cagtgagcgg   1080
gctccgctgc cccctgccct gcactggacc aggagtctgg agatgcctgg gtagccctca   1140
gcatttggag gggaacctgt tcccgtcggt ccccaaatat ccccttcttt ttatggggtt   1200
aaggaaggga ccgagagatc agatagttgc tgttttgtaa aatgtaatgt atatgtggtt   1260
tttagtaaaa tagggcacct gtttcacaaa aaaaaaaaaa agg                     1303
```

```
<210> SEQ ID NO 118
<211> LENGTH: 5702
<212> TYPE: DNA
<213> ORGANISM: Homo sapiens
<220> FEATURE:
<221> NAME/KEY: misc_feature
<223> OTHER INFORMATION: Incyte ID No: 025595.15

<400> SEQUENCE: 118
```

```
ctttgctcaa agtcgctgga ctctaagctg tcggagggac cgctggacag acctgggaac     60
tgacagaggg cctggaggga aacaggccaa agacccacag gcagagttga cacggaaccc    120
caaagcaagg aggagggctc gggcccgaga ccgttcacct ccccttatcc ctgttcccct    180
cttcaggatg gagctgacct caagggaaag agggagggga cagcctctgc cctgggaact    240
tcgactgggc ctactgctaa gcgtgctggc tgccacactg gcacaggccc ctgccccgga    300
tgtgcctggc tgttccaggg gaagctgcta ccccgccacg ggcgacctgc tggtgggccg    360
agctgacaga ctgactgcct catccacttg tggcctgaat ggcccccagc cctactgcat    420
cgtcagtcac ctgcaggacg aaaagaagtg cttcctttgt gactcccggc gccccttctc    480
tgctagagac aacccacaca gccatcgcat ccagaatgta gtcaccagct ttgcaccaca    540
gcggcgggca gcctggtggc agtcagagaa tggtatccct gcggtcacca tccagctgga    600
cctggaggct gagtttcatt tcacacacct cattatgacc ttcaagacat ttcgccctgc    660
tgccatgctg gtggaacgct cagcagactt tggccgcacc tggcatgtgt accgatattt    720
ctcctatgac tgtggggctg acttcccagg agtcccacta gcacccccac ggcactggga    780
tgatgtagtc tgtgagtccc gctactcaga gattgagcca tccactgaag gcgaggtcat    840
ctatcgtgtg ctggaccctg ccatccctat cccagacccc tacagctcac ggattcagaa    900
cctgttgaag atcaccaacc tacgggtgaa cctgactcgt ctacacacgt tgggagacaa    960
cctactcgac ccacggaggg agatccgaga gaagtactac tatgccctct atgagctggt   1020
tgtacgtggc aactgcttct gctacggaca cgcctcagag tgtgcacccg ccccagggggc  1080
accagcccat gctgagggca tggtgcacgg agcttgcatc tgcaaacaca acacacgtgg   1140
cctcaactgc gagcagtgtc aggatttcta tcgtgacctg ccctggcgtc cggctgagga   1200
```

-continued

```
cggccatagt catgcctgta ggaagtgtga gtgccatggg cacacccaca gctgccactt   1260
cgacatggcc gtatacctgg catctggcaa tgtgagtgga ggtgtgtgtg atggatgtca   1320
gcataacaca gctgggcgcc actgtgagct ctgtcggccc ttcttctacc gtgacccaac   1380
caaggacctg cgggatccgg ctgtgtgccg ctcctgtgat tgtgacccca tgggttctca   1440
agacggtggt cgctgtgatt cccatgatga ccctgcactg ggactggtct ccggccagtg   1500
tcgctgcaaa gaacatgtgg tgggcactcg ctgccagcaa tgccgtgatg gcttctttgg   1560
gctcagcatc agtgaccgtc tgggctgccg gcgatgtcaa tgtaatgcac ggggcacagt   1620
gcctgggagc actccttgtg accccaacag tggatcctgt tactgcaaac gtctagtgac   1680
tggacgtgga tgtgaccgct gcctgcctgg ccactggggc ctgagccacg acctgctcgg   1740
ctgccgcccc tgtgactgcg acgtgggtgg tgctttggat ccccagtgtg atgagggcac   1800
aggtcaatgc cactgccgcc agcacatggt tgggcgacgc tgtgagcagg tgcaacctgg   1860
ctacttccgg cccttcctgg accacctaat ttgggaggct gaggacaccc gagggcaggt   1920
gctcgatgtg gtggagcgcc tggtgacccc cggggaaact ccatcctgga ctggctcagg   1980
cttcgtgcgg ctacaggaag gtcagaccct ggagttcctg gtggcctctg tgccgaaggc   2040
tatggactat gacctgctgc tgcgcttaga gccccaggtc cctgagcaat gggcagagtt   2100
ggaactgatt gtgcagcgtc cagggcctgt gcctgcccac agcctgtgtg ggcatttggt   2160
gcccaaggat gatcgcatcc aagggactct gcaaccacat gccaggtact tgatatttcc   2220
taatcctgtc tgccttgagc ctggtatctc ctacaagctg catctgaagc tggtacggac   2280
agggggaagt gcccagcctg agactcccta ctctggacct ggcctgctca ttgactcgct   2340
ggtgctgctg ccccgtgtcc tggtgctaga gatgtttagt gggggtgatg ctgctgccct   2400
ggagcgccag gccacctttg aacgctacca atgccatgag gagggtctgg tgcccagcaa   2460
gacttctccc tctgaggcct gcgcacccct cctcatcagc ctgtccaccc tcatctacaa   2520
tggtgccctg ccatgtcagt gcaaccctca aggttcactg agttctgagt gcaaccctca   2580
tggtggtcag tgcctgtgca agcctggagt ggttgggcgc cgctgtgacc tctgtgcccc   2640
tggctactat ggctttggcc ccacaggctg tcaagcctgc cagtgcagcc acgagggggc   2700
actcagcagt ctctgtgaaa agaccagtgg gcaatgtctc tgtcgaactg gtgcctttgg   2760
gcttcgctgt gaccgctgcc agcgtggcca gtggggattc cctagctgcc ggccatgtgt   2820
ctgcaatggg catgcagatg agtgcaacac ccacacaggc gcttgcctgg gctgccgtga   2880
tcacacaggg ggtgagcact gtgaaaggtg cattgctggt ttccacgggg acccacggct   2940
gccatatggg ggccagtgcc ggccctgtcc ctgtcctgaa ggccctggga gccaacggca   3000
ctttgctact tcttgccacc aggatgaata ttcccagcag attgtgtgcc actgccgggc   3060
aggctatacg gggctgcgat gtgaagcttg tgcccctggg cactttgggg acccatcaag   3120
gccaggtggc cggtgccaac tgtgtgagtg cagtgggaac attgacccaa tggatcctga   3180
tgcctgtgac ccccacacgg ggcaatgcct gcgctgttta caccacacag agggtccaca   3240
ctgtgcccac tgcaagcctg gcttccatgg gcaggctgcc cgacagagct gtcaccgctg   3300
cacatgcaac ctgctgggca caaatccgca gcagtgccca tctcctgacc agtgccactg   3360
tgatccaagc agtgggcagt gcccatgcct ccccaatgtc cagggcccta gctgtgaccg   3420
ctgtgccccc aacttctgga acctcaccag tggccatggt tgccagcctt gtgcctgcca   3480
cccaagccgg gccagaggcc ccacctgcaa cgagttcaca gggcagtgcc actgccgtgc   3540
cggctttgga gggcggactt gttctgagtg ccaagagctc cactggggag accctgggtt   3600
```

-continued

```
gcagtgccat gcctgtgatt gtgactctcg tggaatagat acacctcagt gtcaccgctt   3660
cacaggtcac tgcagctgcc gcccaggggt gtctggtgtg cgctgtgacc agtgtgcccg   3720
tggcttctca ggaatctttc ctgcctgcca tccctgccat gcatgcttcg gggattggga   3780
ccgagtggtg caggacttgg cagcccgtac acagcgccta gagcagcggg cgcaggagtt   3840
gcaacagacg ggtgtgctgg gtgcctttga gagcagcttc tggcacatgc aggagaagct   3900
gggcattgtg cagggcatcg taggtgcccg caacacctca gccgcctcca ctgcacagct   3960
tgtggaggcc acagaggagc tgcggcgtga aattggggag gccactgagc acctgactca   4020
gctcgaggca gacctgacag atgtgcaaga tgagaacttc aatgccaacc atgcactaag   4080
tggtctggag cgagataggc ttgcacttaa tctcacactg cggcagctcg accagcatct   4140
tgacttgctc aaacattcaa acttcctggg tgcctatgac agcatccggc atgcccatag   4200
ccagtctgca gaggcagaac gtcgtgccaa tacctcagcc ctggcagtac ctagccctgt   4260
gagcaactcg gcaagtgctc ggcatcggac agaggcactg atggatgctc agaaggagga   4320
cttcaacagc aaacacatgg ccaaccagcg ggcacttggc aagctctctg cccataccca   4380
caccctgagc ctgacagaca taaatgagct ggtgtgtggg gcaccagggg atgcaccctg   4440
tgctacaagc ccttgtgggg gtgccggctg tcgagatgag gatgggcagc cgcgctgtgg   4500
gggcctcagc tgcaatgggg cagcggctac agcagaccta gcactgggcc gggcccggca   4560
cacacaggca gagctgcagc gggcactggc agaaggtggt agcatcctca gcagagtggc   4620
tgagactcgt cggcaggcaa gcgaggcaca gcagcgggcc caggcagccc tggacaaggc   4680
taatgcttcc aggggacagg tggaacaggc caaccaggaa cttcaagaac ttatccagag   4740
tgtgaaggac ttcctcaacc aggaggggc tgatcctgat agcattgaaa tggtggccac   4800
acgggtgcta gagctctcca tcccagcttc agctgagcag atccagcacc tggcgggtgc   4860
gattgcagag cgagtccgga gcctggcaga tgtggatgcg atcctggcac gtactgtagg   4920
agatgtgcgt cgtgccgagc agctactgca ggatgcacgg cgggcaagga gctgggctga   4980
ggatgagaaa cagaaggcag agacagtaca ggcagcactg gaggaggccc agcgggcaca   5040
gggtattgcc cagggtgcca tccgggggc agtggctgac acacgggaca cagagcagac   5100
cctgtaccag gtacaggaga ggatggcagg tgcagagcgg gcactgagct ctgcaggtga   5160
aagggctcgg cagttggatg ctctcctgga ggctctgaaa ttgaaacggg caggaaatag   5220
tctggcagcc tctacagcag aagaaacggc aggcagtgcc cagggtcgtg cccaggaggc   5280
tgagcagctg ctacgcggtc ctctgggtga tcagtaccag acggtgaagg ccctagctga   5340
gcgcaaggcc caaggtgtgc tggctgcaca ggcaagggca gaacaactgc gggatgaggc   5400
tcgggacctg ttgcaagccg ctcaggacaa gctgcagcgg ctacaggaat tggaaggcac   5460
ctatgaggaa aatgagcggg cactggagag taaggcagcc cagttggacg ggttggaggc   5520
caggatgcgc agcgtgcttc aagccatcaa cttgcaggtg cagatctaca acacctgcca   5580
gtgacccctg cccaaggcct accccagttc ctagcactgc cccacatgca tgtctgccta   5640
tgcactgaag agctcttggc ccggcagggc ccccaataaa ccagtgtgaa cccccaaaaa   5700
aa                                                                  5702
```

<210> SEQ ID NO 119
<211> LENGTH: 1081
<212> TYPE: DNA
<213> ORGANISM: Homo sapiens
<220> FEATURE:

-continued

<221> NAME/KEY: misc_feature
<223> OTHER INFORMATION: Incyte ID No: 021192.8

<400> SEQUENCE: 119
cttcctcagc ccatgtgcaa tcctggctcc cagcaagtcc ccggggctgc ttggtcaatg 60
cagccctgtg tgcaggcctg gcagccctgc cacccccgcc ctcggctccc attgggctgc 120
cacggcctgc agtgggctgc accagggttc atccatcctc cctgggcaga gggaataaga 180
ggctgcctct gcccaccagt cctgccgccc aggacccgca gcagagacga cgcctgcagc 240
aaggagacca ggaaggggtg agacaaggaa gagatgagaa ggcaactttc ctttgcgagc 300
ccctaggatg tctgagctgg agaaggccat ggtggccctc atcgacgttt tccaccaata 360
ttctggaagg gagggagaca agcacaagct gaagaaatcc gaactgaagg agctcatcaa 420
caatgagctt tcccatttct tagaggaaat caaagagcag gaggttgtgg acaaagtcat 480
ggaaacactg gacaatgatg gagacggcga atgtgacttc caggaattca tggcctttgt 540
tgccatggtt actactgcct gccacgagtt ctttgaacat gagtgagatt agaaagcagc 600
caaacctttc ctgtaacaga gacggtcatg caagaaagca gacagcaagg gcttgcagcc 660
tagtaggagc tgagctttcc agccgtgttg tagctaatta ggaagcttga tttgctttgt 720
gattgaaaaa ttgaaaacct ctttccaaag gctgttttaa cggcctgcat cattctttct 780
gctatattag gcctgtgtgt aagctgactg gccccaggga ctcttgttaa cagtaactta 840
ggagtcaggt ctcagtgata aagcgtgcac cgtgcagccc gccatggccg tgtagaccct 900
aacccggagg gaaccctgac tacagaaatt accccggggc acccttaaaa cttccactac 960
ctttaaaaaa caaagcctta tccagcatta tttgaaaaca ctgctgttct ttaaatgcgt 1020
tcctcatcca tgcagataac agctggttgg ccggtgtggc cctgcaaggc gtggtggctt 1080
c 1081

<210> SEQ ID NO 120
<211> LENGTH: 3835
<212> TYPE: DNA
<213> ORGANISM: Homo sapiens
<220> FEATURE:
<221> NAME/KEY: misc_feature
<223> OTHER INFORMATION: Incyte ID No: 196545.7
<221> NAME/KEY: unsure
<222> LOCATION: 3743-3768
<223> OTHER INFORMATION: a, t, c, g, or other

<400> SEQUENCE: 120
tatcgtgact ctgaaggtgc cacggaactg tatttactgt gattgttttc attcagtccc 60
agcaacctct agaggatctt gatgctcaat tgagaagaac acttagtcca gagatgatca 120
cagtgacttc tgcggttggt cctgtgtcca tggcggctcc aacagcaatc acagaagcag 180
gaacacagcc tcagaagggt gtttctcaag tcaaagaagg ccctgtccta gcaactagtt 240
caggagctgg tgtttttaag atgggacgat ttcaggtttc tgttgcagca gacggtgccc 300
agaaagaggg taaaaataag tcagaagatg caaagtctgt tcattttgaa tccagcacct 360
cagagtcctc agtgctatca agtagtagtc cagagagtac cttggtgaaa ccagagccga 420
atggcataac catccctggt atctcttcag atgtgccaga gagtgcccac aaaactactg 480
cctcagaggc aaagtcagac actgggcagc ctaccaaggt tggacgtttt caggtgacaa 540
ctacagcaaa caaagtgggt cgtttctctg tatcaaaaac tgaggacaag atcactgaca 600
caaagaaaga aggaccagtg gcatctcctc cttttatgga tttggaacaa gctgttcttc 660

-continued

```
ctgctgtgat accaaagaaa gagaagcctg aactgtcaga gccttcacat ctaaatgggc    720
cgtcttctga cccggaggcc gctttttttaa gtagggatgt ggatgatggt tccggtagtc    780
cacactcgcc ccatcagctg agctcaaaga gccttcctag ccagaatcta agtcaaagcc    840
ttagtaattc atttaactcc tcttacatga gtagcgacaa tgagtcagat atcgaagatg    900
aagacttaaa gttagagctg cgacgactac gagataaaca tctcaaagag attcaggacc    960
tgcagagtcg ccagaagcat gaaattgaat ctttgtatac caaactgggc aaggtgcccc   1020
ctgctgttat tattccccca gctgctcccc tttcagggag aagacgacga cccactaaaa   1080
gcaaaggcag caaatctagt cgaagcagtt ccttggggaa taaaagcccc cagctttcag   1140
gtaacctgtc tggtcagagt gcagcttcag tcttgcaccc ccagcagacc ctccaccctc   1200
ctggcaacat cccagagtcc gggcagaatc agctgttaca gccccttaag ccatctccct   1260
ccagtgacaa cctctattca gccttcacca gtgatggtgc catttcagta ccaagccttt   1320
ctgctccagg tcaaggaacc agcagcacaa acactgttgg ggcaacagtg aacagccaag   1380
ccgcccaagc tcagcctcct gccatgacgt ccagcaggaa gggcacattc acagatgact   1440
tgcacaagtt ggtagacaat tggcccgag atgccatgaa tctctcaggc aggagaggaa   1500
gcaaagggca catgaattat gagggccctg gaatggcaag gaagttctct gcacctgggc   1560
aactgtgcat ctccatgacc tcgaacctgg gtggctctgc ccccatctct gcagcatcag   1620
ctacctctct aggtcacttc accaagtcta tgtgcccccc acagcagtat ggctttccag   1680
ctaccccatt tggcgctcaa tggagtggga cgggtggccc agcaccacag ccacttggcc   1740
agttccaacc tgtgggaact gcctccttgc agaatttcaa catcagcaat ttgcagaaat   1800
ccatcagcaa ccccccaggc tccaacctgc ggaccactta gacctagaga cattaactga   1860
atagatctgg gggcaggaga tggaatgctg aggggtggg tgggggtggg aagtagccta   1920
tatactaact actagtgctg catttaactg gttatttctt gccagagggg aatgtttta   1980
atactgcatt gagccctcag aatggagagt ctcccccgct ccagttattg gaatgggaga   2040
ggaaggaaag aacagctttt ttgtcaaggg gcagcttcag accatgcttt cctgtttatc   2100
tatactcagt aatgaggatg agggctagga aagtcttgtt cataaggaag ctggagaact   2160
caatgtaaaa tcaaacccat ctgtaatttc gagtgggtgg agctcttgct tttggtacat   2220
gccctgaatc cctcactccc tcaagaatcc gaaccacagg acaaaaacca cctactgggc   2280
tctctcctac cctgccctcc tcccttttt ttaccccctct cttttttatt ttttctttgc   2340
tctttagaac ccagtgaaaa ataccagggt actggggtgc aactctttct tatgataggt   2400
cattagtgct ttaagcaaaa gatattagca gctttgactg cagcattagc aattaggaaa   2460
aaaaaaaaat taagttccct gcggacatgt aactttgcca tcagttttga tgtggaaaca   2520
ctgtgatata taaaatgttg ttggacaaca gtagttttaa gagtaaaata tgaaacgttt   2580
aaaaagttcc aaaaaaagct agctctgtcc tttacttatt gagacacttt aactttttcc   2640
tttgtatttc cattgtatta gataaataaa tgtgaatgta aaattgtata aattactgta   2700
cttgaatact tctgtttccc agtgttgctt gctggacatt ttagtgcctt ggacttctat   2760
tgcttctgcc attagcatca acttaccaga ccccagatca ataaagggca tgtggaagga   2820
aatcgtaggt ccatgtgacc ccagcagtcc agcagtggtt atgccaaagg gaaattgaaa   2880
aagtattttt ttaagtcatt caacaacttt gtctagagca ggtgtaagat gagtagggtg   2940
ggaagttagg ttggcatcag tggttaaaaa cagaaagttc tgtttcggga atagtgagga   3000
gggggtgttg taacaaaatt ggacaactta aaagaatggt gtgtgctggg tgaaagacaa   3060
```

-continued

```
agactaaaga atgaggaaac aaacgtgatg cctggccagt gactgtcata taaacctttc   3120

ttatttgagc taggcttgaa cagacgtgac ctagaagaaa ctgaacataa agagaagggg   3180

gtggggggct agttttcaag ttggggaacc tgatagtgaa aagtcacaga tggagaaaat   3240

tgctctcaga aaaactgttt ggattgcttt cctcttgttg cacatgtacc atgcatttct   3300

cagcttgggg tactacattt tgtggaaagt taatctatct atctttccac atctgaatta   3360

atcattctag gaaagaatac ttattcctac tcatttcctt tatgatgtcc aaatggttgc   3420

aggatcataa tctattgtgc cacctttatt tctagaagta caactaatat gttcacattt   3480

tcaaataaat aatactcccc gtaagtaata actgcaacca atcagtgtta ttcagtgcta   3540

tgcctccttg taatgggtag ttattaatta ttttcagagc tttccggaaa tactgtccta   3600

actggctatg tttaggatct ttgttatctc tgaagacaaa gaaagaagct aggactctta   3660

attttggggt gcttcttgac tcttagttgg gaaactgaaa atatttccaa ccttttaccc   3720

acgtcaatgg catattctgg gannnnnnnn nnnnnnnnnn nnnnnnnnag aaagaggctg   3780

gaggctcctg taccctgttc atccttaagg gccctgcttc ccttaataag taagt        3835
```

```
<210> SEQ ID NO 121
<211> LENGTH: 3092
<212> TYPE: DNA
<213> ORGANISM: Homo sapiens
<220> FEATURE:
<221> NAME/KEY: misc_feature
<223> OTHER INFORMATION: Incyte ID No: 481242.1

<400> SEQUENCE: 121
```

```
tacaaaaaag cttttacgag gtatcagcac ttttctttca ttagggggaa ggcgtgagga     60

aagtaccaaa cagcagcgga gttttaaact ttaaatagac aggtctgagt gcctgaactt    120

gccttttcat tttacttcat cctccaagga gttcaatcac ttggcgtgac ttcactactt    180

ttaagcaaaa gagtggtgcc caggcaacat gggtgactgg agcgccttag gcaaactcct    240

tgacaaggtt caagcctact caactgctgg agggaaggtg tggctgtcag tacttttcat    300

tttccgaatc ctgctgctgg ggacagcggt tgagtcagcc tggggagatg agcagtctgc    360

ctttcgttgt aacactcagc aacctggttg tgaaaatgtc tgctatgaca agtctttccc    420

aatctctcat gtgcgcttct gggtcctgca gatcatattt gtgtctgtac ccacactctt    480

gtacctggct catgtgttct atgtgatgcg aaaggaagag aaactgaaca agaaagagga    540

agaactcaag gttgcccaaa ctgatggtgt caatgtggac atgcacttga agcagattga    600

gataaagaag ttcaagtacg gtattgaaga gcatggtaag gtgaaaatgc gagggggggtt   660

gctgcgaacc tacatcatca gtatcctctt caagtctatc tttgaggtgg ccttcttgct    720

gatccagtgg tacatctatg gattcagctt gagtgctgtt tacacttgca aaagagatcc    780

ctgcccacat caggtggact gtttcctctc tcgccccacg gagaaaacca tcttcatcat    840

cttcatgctg gtggtgtcct tggtgtccct ggccttgaat atcattgaac tcttctatgt    900

ttcttcaag ggcgttaagg atcgggttaa gggaaagagc gacccttacc atgcgaccag    960

tggtgcgctg agccctgcca aagactgtgg gtctcaaaaa tatgcttatt tcaatggctg   1020

ctcctcacca accgctcccc tctcgcctat gtctcctcct gggtacaagc tggttactgg   1080

cgacagaaac aattcttctt gccgcaatta caacaagcaa gcaagtgagc aaaactgggc   1140

taattacagt gcagaacaaa atcgaatggg gcaggcggga agcaccatct ctaactccca   1200

tgcacagcct tttgatttcc ccgatgataa ccagaattct aaaaaactag ctgctggaca   1260
```

-continued

```
tgaattacag ccactagcca ttgtggacca gcgaccttca agcagagcca gcagtcgtgc   1320
cagcagcaga cctcggcctg atgacctgga gatctagata caggcttgaa agcatcaaga   1380
ttccactcaa ttgtggagaa gaaaaaaggt gctgtagaaa gtgcaccagg tgttaatttt   1440
gatccggtgg aggtggtact caacagcctt attcatgagg cttagaaaac acaaagacat   1500
tagaatacct aggttcactg ggggtgtatg gggtagatgg gtggagaggg aggggataag   1560
agaggtgcat gttggtattt aaagtagtgg attcaaagaa cttagattat aaataagagt   1620
tccattaggt gatacataga taagggcttt ttctccccgc aaacacccct aagaatggtt   1680
ctgtgtatgt gaatgagcgg gtggtaattg tggctaaata tttttgtttt accaagaaac   1740
tgaaataatt ctggccagga ataaatactt cctgaacatc ttaggtcttt tcaacaagaa   1800
aaagacagag gattgtcctt aagtccctgc taaaacattc cattgttaaa atttgcactt   1860
tgaaggtaag ctttctaggc ctgaccctcc aggtgtcaat ggacttgtgc tactatattt   1920
ttttattctt ggtatcagtt taaaattcag acaaggccca cagaataaga ttttccatgg   1980
catttgcaaa tacgtatatt ctttttccat ccacttgcac aatatcatta ccatcacttt   2040
ttcatcattc ctcagctact actcacattc atttaatggt ttctgtaaac atttttaaga   2100
cagttgggat gtcacttaac attttttttt tgagctaaag tcagggaatc aagccatgct   2160
taatatttaa caatcactta tatgtgtgtc gaagagtttg ttttgtttgt catgtattgg   2220
tacaagcaga tacagtataa actcacaaac acagatttga aaataatgca catatggtgt   2280
tcaaatttga acctttctca tggatttttg tggtgtgggc caatatggtg tttacattat   2340
ataattcctg ctgtggcaag taaagcacac tttttttttc tcctaaaatg tttttccctg   2400
tgtatcctat tatggatact ggttttgtta attatgattc tttattttct ctcctttttt   2460
taggatatag cagtaatgct attactgaaa tgaatttcct ttttctgaaa tgtaatcatt   2520
gatgcttgaa tgatagaatt ttagtactgt aaacaggctt tagtcattaa tgtgagagac   2580
ttagaaaaaa tgcttagagt ggactattaa atgtgcctaa atgaattttg cagtaactgg   2640
tattcttggg ttttcctact taatacacag taattcagaa cttgtattct attatgagtt   2700
tagcagtctt ttggagtgac cagcaacttt gatgtttgca ctaagatttt atttggaatg   2760
caagagaggt tgaaagagga ttcagtagta cacatacaac taatttattt gaactatatg   2820
ttgaagacat ctaccagttt ctccaaatgc cttttttaaa actcatcaca gaagattggt   2880
gaaaatgctg agtatgacac ttttcttctt gcatgcatgt cagctacata aacagttttg   2940
tacaatgaaa attactaatt tgtttgacat tccatgttaa actacggtca tgttcagctt   3000
cattgcatgt aatgtagacc tagtccatca gatcatgtgt tctggagagt gttctttatt   3060
caataaagtt ttaatttagt ataaacataa aa                                  3092
```

<210> SEQ ID NO 122
<211> LENGTH: 1192
<212> TYPE: DNA
<213> ORGANISM: Homo sapiens
<220> FEATURE:
<221> NAME/KEY: misc_feature
<223> OTHER INFORMATION: Incyte ID No: 1090667.2
<221> NAME/KEY: unsure
<222> LOCATION: 394, 635, 914, 1085
<223> OTHER INFORMATION: a, t, c, g, or other

<400> SEQUENCE: 122

```
gggtggaggg ggatcatagt tctccctgag tgagacttgc ctgctcctct ggcccctggt     60
```

-continued

```
cctgtcctgt tctccagcat ggtgtgtctg aagctccctg gaggttccta catggcagtg    120

ctgacagtga cactgatggt gctgagctcc ccactggctt tggctgggga cacccgacca    180

tgtttcttgc agcaggataa gtatgagtgt catttcttca acgggacgga gcgggtgcgg    240

ttcctgcaca gaggcatcta taaccaagag gaggactgcg cttcgacagc gacgtggggg    300

agtaccgggc ggtgacggag ctggggcggc ctgatgccga gtactggaac agccagaagg    360

acctcctgga gcagaggcgg gccgcggtgg acanctactg cagacacaac tacggggttg    420

tggagagctt cacagtgcag cggcgagtct atcctaaggt gactgtgtat cctgcaaaga    480

cccagaccct gcagcaccac aacctcctgg tctgctctgt gaatggtttc tatccaggca    540

gcattgaagt caggtggttc cggaacggcc aggaagagaa gactggggtg gtgtccacag    600

gcctgatcca gaatggagac tggaccttcc agacnctggt gatgctggaa acagttcctc    660

ggagtggaga ggtttacacc tgccaagtgg agcacccaag cctgacgagc cctctcacag    720

tggaatggag agcacggtct gaatctgcac agagcaagat gctgagtgga gtcgggggct    780

tcgtgctggg cctgctcttc cttggggccg ggctgttcat ctacttcagg aatcagaaag    840

gacactctgg acttcagcca acaggattcc tgagctgaag tgaagatgac cacattcaag    900

gaagaacctt ctgncccagc tttgcaggat gaaacacttc cccgcttggc tctcattctt    960

ccacaagaga gacctttctc cggacctggt tgctactggt tcagcagctc tgcagaaaat   1020

gtcctccctt gtggctgcct cagctcgtac ctttggcctg aagtcccagc attaatggca   1080

gcccntcatc ttccaagttt tgtgctcccc tttacctaat gcttcctgcc tcccatgcat   1140

ctgtactcct gctgtgccac aaacacatta cattattaaa tgtttctcaa ac           1192
```

<210> SEQ ID NO 123
<211> LENGTH: 1946
<212> TYPE: DNA
<213> ORGANISM: Homo sapiens
<220> FEATURE:
<221> NAME/KEY: misc_feature
<223> OTHER INFORMATION: Incyte ID No: 1088652.1

<400> SEQUENCE: 123

```
caggggactt agacctggtt gttggcatgg agtggaggat gaagaggtat cttctgagca     60

gagcattttt gtagtaggag tgtcagaggt caggactctc atggcagagc tggagtctca    120

cccatgtgac atatgtggcc caatattgaa agataccttta cacctggcta aataccatgg    180

gggaaaagcc aggcagaaac catacttgtg tggggcatgt ggaaagcaat tctggttcag    240

tacagacttt gaccagcacc agaaccagcc caatggaggg aaacttttcc caaggaagga    300

gggcagagac tctgtgaaaa gctgcagagt ccatgtgcca gagaagaccc tcacatgtgg    360

gaaaggtagg agagactttt cagccacatc tggccttctt cagcatcagg cctctctcag    420

cagcatgaag ccccacaaga gcactaagct tgtgagtggc tttctcatgg gacagaggta    480

tcacaggtgt ggtgaatgtg ggaaagcctt cacccgcaaa gacacacttg ctcggcatca    540

gagaatccac actggagaaa ggccttatga gtgtaacgaa tgtgggaaat tcttcagcca    600

aagctatgac ctctttaaac accagacagt tcacactgga gaaaggccat acgagtgcag    660

cgaatgtggg aaattcttta gacaaatctc cggcctgatt gagcacaggc gagttcacac    720

gggtgaaaga ctctatcagt gtggcaaatg tgggaaattt tttagcagta agtctaatct    780

cattcgacac caggaagttc acacaggagc caggccttat gtatgcagcg aatgtgggaa    840

agagttcagt cggaaacaca cacttgttct gcaccaacga actcacactg gagaaaggcc    900
```

-continued

```
ttatgagtgc agtgaatgtg ggaaggcctt tagccaaagc tcccacctta atgtacactg    960

gagaattcac agcagtgatt atgagtgtag cagatgtggt aaagctttca gctgcatctc   1020

caaactcatt cagcaccaga aagttcactc tggagaaaag ccttatgagt gcagcaagtg   1080

cgggaaagcc ttcactcaaa gacccaacct catcaggcac tggaaagtcc acactgggga   1140

aaggccttat gtgtgtagtg agtgcgggag agaattcatc cggaaacaga cacttgttct   1200

gcaccagagg gttcatgctg gagaaaagct ttaagagtgt agcaaatgtg ggggaaagtc   1260

ttaggccaat gcccccgact tactatatgg tggggaacta gcagtagtta atgagtgcag   1320

cagatgcagg aaagccttcc cctggaggct gaaccttacc cgccattggg aatttcacac   1380

cggacacagg ccttagcagt ctaagcaatg tgctgtctct gttcagccca acagctcacc   1440

ctagagtgga actctgggag cagccattgg gagggaacca tcagtaagaa gtgaaacttc   1500

atagatatgg acattcccac tgggggagat tccctgtgag tgtcaagtat gtgagatgct   1560

ttcagcagct gtgttgcact ttttaaatgg ctattggcct ttgctggggc aggagccatc   1620

tgctcctacc atctggcaga atcatactgc gtttaccatt taccccagca tgcttgtgac   1680

gggcagacct ctcttctctc cccagtccct aaaaggtgtt gtgagtggtc tcacagccca   1740

ctaggggtct taatttcctc tcttttgatg taaatggcat ggaaataatc agctttgttc   1800

aagaggacac agaaggattc tgcaaatagc ctgcagagac ttacctgtgt tgattgattt   1860

catatgatgc tcgttatgga tatatccaat atccaagtca cccagctctg gaactgcctg   1920

cttcacattg ctcatgataa taaagg                                         1946
```

<210> SEQ ID NO 124
<211> LENGTH: 1755
<212> TYPE: DNA
<213> ORGANISM: Homo sapiens
<220> FEATURE:
<221> NAME/KEY: misc_feature
<223> OTHER INFORMATION: Incyte ID No: 248306.1
<221> NAME/KEY: unsure
<222> LOCATION: 1751-1752
<223> OTHER INFORMATION: a, t, c, g, or other

<400> SEQUENCE: 124

```
cacactgacg aggccatgat tgaatttagg tgacctatag acgcgctgta actacgctcg     60

gaattcggct cgaggtcacc tcctcccctt gtcgcctagg tccacccgag ccccctcccc    120

cgggccgccc acgagcacga agttggcggg agcctataaa agctggtgcc ggcgcgaccc    180

gcggacacac agtgcaggcg cccaagccgc cgccgccaga tcggtgccga ttcctgccct    240

gccccgaccg ccagcgcgac catgtcccat cactgggggt acggcaaaca caacggacct    300

gagcactggc ataaggactt ccccattgcc aagggagagc gccagtcccc tgttgacatc    360

gacactcata cagccaagta tgacccttcc ctgaagcccc tgtctgtttc ctatgatcaa    420

gcaacttccc tgaggatcct caacaatggt catgctttca acgtggagtt tgatgactct    480

caggacaaag cagtgctcaa gggaggaccc ctggatggca cttacagatt gattcagttt    540

cactttcact ggggttcact tgatggacaa ggttcagagc atactgtgga taaaaagaaa    600

tatgctgcag aacttcactt ggttcactgg aacaccaaat atggggattt tgggaaagct    660

gtgcagcaac ctgatggact ggccgttcta ggtatttttt tgaaggttgg cagcgctaaa    720

ccgggccttc agaaagttgt tgatgtgctg gattccatta aaacaaaggg caagagtgct    780

gacttcacta acttcgatcc tcgtggcctc cttcctgaat ccctggatta ctggacctac    840

ccaggctcac tgaccacccc tcctcttctg gaatgtgtga cctggattgt gctcaaggaa    900
```

-continued

```
cccatcagcg tcagcagcga gcaggtgttg aaattccgta aacttaactt caatggggag     960

ggtgaacccg aagaactgat ggtggacaac tggcgcccag ctcagccact gaagaacagg    1020

caaatcaaag cttccttcaa ataagatggt cccatagtct gtatccaaat aatgaatctt    1080

cgggtgtttc cctttagcta agcacagatc taccttggtg atttggaccc tggttgcttt    1140

gtgtctagtt ttctagaccc ttcatctctt acttgataga cttactaata aaatgtgaag    1200

actagaccaa ttgtcatgct tgacacaact gctgtggctg gttggtgctt tgtttatggt    1260

agtagttttt ctgtaacaca gaatatagga taagaaataa gaataaagta ccttgacttt    1320

gttcacagca tgtagggtga tgagcactca caattgttga ctaaaatgct gcttttaaaa    1380

cataggaaag tagaatggtt gagtgcaaat ccatagcaca agataaattg agctagttaa    1440

ggcaaatcag gtaaaatagt catgattcta tgtaatgtaa accagaaaaa ataaatgttc    1500

atgatttcaa gatgttatat taaagaaaaa ctttaaaaat tattatatat ttatagcaaa    1560

gttatcttaa atatgaattc tgttgtaatt taatgacttt tgaattacag agatataaat    1620

gaagtattat ctgtaaaaat tgttataatt agagttgtga tacagagtat atttccattc    1680

agacaatata tcataactta ataaatattg tattttagat atattctcta ataaaattca    1740

gaattctaaa nngga                                                     1755
```

<210> SEQ ID NO 125
<211> LENGTH: 2494
<212> TYPE: DNA
<213> ORGANISM: Homo sapiens
<220> FEATURE:
<221> NAME/KEY: misc_feature
<223> OTHER INFORMATION: Incyte ID No: 431588.3
<221> NAME/KEY: unsure
<222> LOCATION: 2018-2291, 2487
<223> OTHER INFORMATION: a, t, c, g, or other

<400> SEQUENCE: 125

```
gagtctctga agccacagat ctcttaagaa ctttctgtct ccaaaccgtg gctgctcgat      60

aaatcagaca gaacagttaa tcctcaattt aagcctgatc taacccctag aaacagatat     120

agaacaatgg aagtgacaac aagattgaca tggaatgatg aaaatcatct gcgcaagtgc     180

ttggaaatgt ttctttgagt cttctctata agtctagtgt tcatggaggt agcattgaag     240

atatggttga aagatgcagc cgtcagggat gtactataac aatggcttac attgattaca     300

atatgattgt agcctttatg cttggaaatt atattaattt acgtgaaagt tctacagagc     360

caaatgattc cctatggttt tcacttcaaa agaaaaatga caccactgaa atagaaactt     420

tactcttaaa tacagcacca aaaattattg atgagcaact ggtgtgtcgt ttatcgaaaa     480

cggatatttt cattatatgt cgagataata aaatttatct agataaaatg ataacaagaa     540

acttgaaact aaggttttat ggccaccgtc agtatttgga atgtgaagtt tttcgagttg     600

aaggaattaa ggataaccta gacgacataa agaggataat taaagccaga gagcacagaa     660

ataggcttct agcagacatc agagactata ggccctatgc agacttggtt tcagaaattc     720

gtattctttt ggtgggtcca gttgggtctg gaaagtccag ttttttcaat tcagtcaagt     780

ctatttttca tggccatgtg actggccaag ccgtagtggg gtctgatatc accagcataa     840

ccgagcggta taggatatat tctgttaaag atggaaaaaa tggaaaatct ctgccattta     900

tgttgtgtga cactatgggg ctagatgggg cagaaggagc aggactgtgc atggatgaca     960

ttccccacat cttaaaaggt tgtatgccag acagatatca gtttaattcc cgtaaaccaa    1020
```

-continued

```
ttacacctga gcattctact tttatcacct ctccatctct gaaggacagg attcactgtg   1080

tggcttatgt cttagacatc aactctattg acaatctcta ctctaaaatg ttggcaaaag   1140

tgaagcaagt tcacaaagaa gtattaaact gtggtatagc atatgtggcc ttgcttacta   1200

aagtggatga ttgcagtgag gttcttcaag acaacttttt aaacatgagt agatctatga   1260

cttctcaaag ccgggtcatg aatgtccata aaatgctagg cattcctatt tccaatattt   1320

tgatggttgg aaattatgct tcagatttgg aactggaccc catgaaggat attctcatcc   1380

tctctgcact gaggcagatg ctgcgggctg cagatgattt tttagaagat ttgcctcttg   1440

aggaaactgg tgcaattgag agagcgttac agccctgcat ttgagataag ttgccttgat   1500

tctgacattt ggcccagcct gtactggtgt gccgcaatga gagtcaatct ctattgacag   1560

cctgcttcag attttgcttt tgttcgtttt gccttctgtc cttggaacag tcatatctca   1620

agttcaaagg ccaaaacctg agaagcggtg ggctaagata ggtcctactg caaaccaccc   1680

ctccatattt ccgtaccatt tacaattcag tttctgtgac atctttttaa accactggag   1740

gaaaaatgag atattctcta atttattctt ctataacact ctatatagag ctatgtgagt   1800

actaatcaca ttgaataata gttataaaat tattgtatag acatctgctt cttaaacaga   1860

ttgtgagttc tttgagaaac agcgtggatt ttacttatct gtgtattcac agagcttagc   1920

acagtgcctg gtaatgagca agcatacttg ccattacttt tccttcccac tctctccaac   1980

atcacattca ctttaaattt ttctgtatat agaaaggnnn nnnnnnnnnn nnnnnnnnnn   2040

nnnnnnnnnn nnnnnnnnnn nnnnnnnnnn nnnnnnnnnn nnnnnnnnnn nnnnnnnnnn   2100

nnnnnnnnnn nnnnnnnnnn nnnnnnnnnn nnnnnnnnnn nnnnnnnnnn nnnnnnnnnn   2160

nnnnnnnnnn nnnnnnnnnn nnnnnnnnnn nnnnnnnnnn nnnnnnnnnn nnnnnnnnnn   2220

nnnnnnnnnn nnnnnnnnnn nnnnnnnnnn nnnnnnnnnn nnnnnnnnnn nnnnnnnnnn   2280

nnnnnnnnnn ngactgaaag agaatgaaaa gctggggaga ggaaataaaa ataaagaagg   2340

aagagtgttt catttatatc tgaatgaaaa tatgaatgac tctaagtaat tgaattaatt   2400

aaaatgagcc aacttttttt ttaacaattt acattttatt tctatgggaa aaaataaata   2460

ttcctcttct aacaaaaaag gaaaagntct aaac                               2494
```

```
<210> SEQ ID NO 126
<211> LENGTH: 3711
<212> TYPE: DNA
<213> ORGANISM: Homo sapiens
<220> FEATURE:
<221> NAME/KEY: misc_feature
<223> OTHER INFORMATION: Incyte ID No: 252234.3

<400> SEQUENCE: 126

gtgcgagata ttttgaaaaa tatacttgat tgattataac atctccccag acccagaaaa     60

acagaaagct ccacagaaat taaatgttga agagaaactc tcaaaggaag ttacagaaga    120

aactatctct ttcccagtaa gttcagtgga aagtgcacta gaacatgaat atgacttggt    180

gaaattagat gaaagttttt atggaccaga aaagggccac aacatattat ctcatccaga    240

gacccaaagc caaaactcag ctgacaggaa tgtttcaaag gacacaaaga gagatgtgga    300

ctcaaagtca ccggggatgc ctttatttga agcagaggaa ggagttctat cacgaaccca    360

gatatttcct accactatta aagtcattga tccagaattt ctggaggagc cacctgcact    420

tgcatttttta tataaggatc tgtatgaaga agcagttgga gagaaaaaga aggaagagga    480

gacagcttct gaaggtgaca gtgtgaattc tgaggcatca tttcccagca gaaattctga    540
```

-continued

```
cactgatgat ggaacaggaa tatattttga gaagtacata ctcaaagatg acattctcca    600
tgacacatct ctaactcaaa aggaccaggg ccaaggtctg gaagaaaaac gagttggtaa    660
ggatgattca taccaaccga tagctgcaga aggggaaatt tggggaaagt ttggaactat    720
ttgcaggaga agagtctgga agaacagaaa ggtgtttatg gggaaggaga atcagtagac    780
catgtggaga ccgttggtaa cgtagcgatg cagaagaaag ctcccatcac agaggacgtc    840
agagtggcta cccagaaaat aagttatgcg gttccatttg aagacaccca tcatgttctg    900
gagcgtgcag atgaagcagg cagtcacggt aatgaagtcg gaaatgcaag tccagaggtc    960
aatctgaatg tcccagtaca agtgtccttc ccggaggaag aatttgcatc tggtgcaact   1020
catgttcaag aaacatcact agaagaacct aaaatcctgg tcccacctga gccaagtgaa   1080
gagaggctcc gtaatagccc tgttcaggat gagtatgaat ttacagaatc cctgcataat   1140
gaagtggttc ctcaagacat attatcagaa gaactgtctt cagaatccac acctgaagat   1200
gtcttatctc aaggaaagga atcctttgag cacatcagtg aaaatgaatt tgcgagtgag   1260
gcagaacaaa gtacacctgc tgaacaaaaa gagttgggca gcgagaggaa agaagaagac   1320
caattatcat ctgaggtagt aactgaaaag gcacaaaaag agctgaaaaa gtcccagatt   1380
gacacatact gttacacctg caaatgtcca atttctgcca ctgacaaggt gtttggcacc   1440
cacaaagacc atgaagtttc aacgcttgac acagctataa gtgctgtaaa ggttcaatta   1500
gcagaatttc tagaaaattt acaagaaaag tccttgagga ttgaagcctt tgttagtgag   1560
atagaatcct tttttaatac cattgaggaa aactgtagta aaaatgagaa aaggctagaa   1620
gaacagaatg aggaaatgat gaagaaggtt ttagcacagt atgatgagaa agcccagagc   1680
tttgaggaag tgaagaagaa gaagatggag ttcctgcatg agcagatggt ccactttctg   1740
cagagcatgg acactgccaa agacaccctg gagaccatcg tgagagaagc agaggagctt   1800
gatgaggccg tcttcctgac ttcgtttgag gaaatcaatg aaaggttgct ttctgcaatg   1860
gagagcactg cttctttaga gaaaatgcct gctgcgtttt ccctttttcga acattatgat   1920
gacagctcgg caagaagtga ccagatgtta aaacaagtgg ctgttccaca gcctcctaga   1980
ttagaacctc aggaaccaaa ttctgccacc agcacaacaa ttgcagttta ctggagcatg   2040
aacaaggaag atgtcattga ttcatttcag gtttactgca tggaggagcc acaagatgat   2100
caagaagtaa atgagttggt agaagaatac agactgacag tgaaagaaag ctactgcatt   2160
tttgaagatc tggaacctga ccgatgctat caagtgtggg tgatggctgt gaacttcact   2220
ggatgtagcc tgcccagtga aagggccatc tttaggacag caccctccac ccctgtgatc   2280
cgcgctgagg actgtactgt gtgttggaac acagccacta tccgatggcg gcccaccacc   2340
ccagaggcca cggagaccta cactctggag tactgcagac agcactctcc tgagggagag   2400
ggcctcagat ctttctctgg aatcaaagga ctccagctga aagttaacct ccaacccaat   2460
gataactact ttttctatgt gagggccatc aatgcatttg ggacaagtga acagagtgaa   2520
gctgctctca tctccaccag aggaaccaga tttctcttgt tgagagaaac agctcatcct   2580
gctctacaca tttcctcaag tgggacagtg atcagctttg gtgagaggag acggctgacg   2640
gaaatcccgt cagtgctggg tgaggagctg ccttcctgtg gccagcatta ctgggaaacc   2700
acagtcacag actgcccagc atatcgactc ggcatctgct ccagctcggc tgtgcaggca   2760
ggtgccctag gacaagggga gacctcatgg tacatgcact gctctgagcc acagagatac   2820
acatttttct acagtggtat tgtgagtgat gttcatgtga ctgagcgtcc agccagagtg   2880
ggcatcctgc tggactacaa caaccagaga cttatcttca tcaacgcaga gagcgagcag   2940
```

```
ttgctcttca tcatcaggca caggtttaat gagggtgtcc accctgcctt tgccctggag   3000

aaacctggaa aatgtacttt gcacctgggg atagagcccc cggattctgt aaggcacaag   3060

tgatccttgg ctttcagaat ttgcaagaac agcgatttga attttggggg ggtctgctgt   3120

tcattccttt aggtgctata cattattcaa aaagtctccc gcgcatttgc actaatgatg   3180

gctgcatgca tagcaatcag catgtgagca aaatcgacaa gaaaaccttg actttacaga   3240

gcagtgtgtg agtaaacaga atgaaaacaa caacctccac tctttagttt atataagttt   3300

gagttctttc ctaaattaaa agatctacac ttgagttggg aaccgaaaga gaaaaatgga   3360

cttccatctg ttttactggt aaaggaaatc ctctgatgga caggtcagag tgaaggaagg   3420

ttgtgctggt aagacatctc tgacgaagag ccatggatgc tttccacaaa atgtcacctc   3480

gctgcactaa aggatgatga atcctaatca ttaaaggaat tgtttcagct gatttaaatt   3540

tataatgaac tcttttgtaa taatgtatac tgtagaacat gagtctctcc tccctaaaat   3600

tttaaatgta gaaaagtgct atatattaga aatttccatt ttgttaaata aatggttaga   3660

gtctataaag ccagtcatgt tatgtgaact tactccatgt aacttactgg c            3711
```

```
<210> SEQ ID NO 127
<211> LENGTH: 825
<212> TYPE: DNA
<213> ORGANISM: Homo sapiens
<220> FEATURE:
<221> NAME/KEY: misc_feature
<223> OTHER INFORMATION: Incyte ID No: 349084.63

<400> SEQUENCE: 127

tagctgggac ctggatttgc ttcctttatc gtcgcaccat gcaggccgac ctcgggggct     60

acttcgccgc agcccgagga atatggagcc cgcaatgcct gctggccaaa actacagacc    120

gtcgagccaa ggaccaggtt gaatctgtca ctttccctgc catcgtttta ggagcggctc    180

cgggcacttg cgagtgctca gaagcagctc cgctttctct tcctgctctc catcatggcg    240

caggatcaag gtgaaaagga gaaccccatg cgggaacttc gcatccgcaa actctgtctc    300

aacatctgtg ttggggagag tggagacaga ctgacgcgag cagccaaggt gttggagcag    360

ctcacagggc agacccctgt gttttccaaa gctagataca ctgtcagatc ctttggcatc    420

cggagaaatg aaaagattgc tgtccactgc acagttcgag ggccaaggc agaagaaatc    480

ttggagaagg gtctaaaggt gcgggagtat gagttaagaa aaaacaactt ctcagatact    540

ggaaactttg gttttgggat ccaggaacac atcgatctgg gtatcaaata tgacccaagc    600

attggtatct acggcctgga cttctatgtg gtgctgggta ggccaggttt cagcatcgca    660

gacaagaagc gcaggacagg ctgcattggg gccaaacaca gaatcagcaa agaggaggcc    720

atgcgctggt tccagcagaa gtatgatggg atcatccttc ctggcaaata aattcccgtt    780

tctatccaaa agagcaataa aaagttttca gtgaaatgtg caaaa                    825
```

```
<210> SEQ ID NO 128
<211> LENGTH: 1631
<212> TYPE: DNA
<213> ORGANISM: Homo sapiens
<220> FEATURE:
<221> NAME/KEY: misc_feature
<223> OTHER INFORMATION: Incyte ID No: 348829.1

<400> SEQUENCE: 128

ctgggcctct caaagtctga gccccgctcc gctgatgcct gtctgcagaa tccgcaccaa     60
```

-continued ccagcaccat gcccatgact ctggggtact gggacatccg tgggctggcc cacgccatcc 120
gcttgctcct ggaatacaca gactcaagct atgtggaaaa gaagtacacg ctgggggacg 180
ctcctgacta tgacagaagc cagtggctga atgaaaaatt caagctgggc ctggactttc 240
ccaatctgcc ctacttgatt gatggggctc acaagatcac ccagagcaat gccatcctgc 300
gctacattgc ccgcaagcac aacctgtgtg gggagacaga agaggagaag attcgtgtgg 360
acattttgga gaaccaggtt atggataacc acatggagct ggtcagactg tgctatgacc 420
cagattttga gaaactgaag ccaaaatact tggaggaact ccctgaaaag ctaaagctct 480
actcagagtt tctggggaag cggccatggt ttgcaggaga caagatcacc tttgtggatt 540
tccttgccta tgatgtcctt gacatgaagc gtatatttga gcccaagtgc ttggacgcct 600
tcctaaactt gaaggacttc atctcccgct ttgagggttt gaagaagatc tctgcctaca 660
tgaagtccag ccaattcctc cgaggtcttt tgtttggaaa gtcagctaca tggaacagca 720
aatagggccc agtgatgcca gaagatggga gggaggagcc aaccttgctg cctgcgaccc 780
tggaggacag cctgactccc tggacctgcc ttcttccttt ttccttcttt ctactctctt 840
ctcttcccca aggcctcatt ggcttccttt cttctaacat catccctccc cgcatcgagg 900
ctctttaaag cttcagctcc ccactgtcct ccatcaaagt ccccctccta acgtcttcct 960
ttccctgcac taacgccaac ctgactgctt ttcctgtcag tgcttttctc ttctttgaga 1020
agccagactg atctctgagc tccctagcac tgtcctcaaa gaccatctgt atgccctgct 1080
ccctttgctg ggtccctacc ccagctccgt gtgatgccca gtaaagcctg aaccatgcct 1140
gccatgtctt gtcttattcc ctgaggctcc cttgactcag gactgtgctc gaattgtggg 1200 tggtttttg tcttctgttg tccacagcca gagcttagtg gatgggtgtg tgtgtgtgtg 1260 tgttggggt ggtgatcagg caggttcata aatttccttg gtcatttctg ccctctagcc 1320
acatccctct gttcctcact gtggggatta ctacagaaag gtgctctgtg ccaagttcct 1380
cactcattcg cgctcctgta ggccgtctag aactggcacg gttcaaagag gggctaggct 1440
gatggggaag gggctgagc agctcccagg cagactgcct tctttcaccc tgtcctgata 1500
gacttccctg atctagatat ccttcgtcat gacacttctc aataaaacgt atcccaccgt 1560
attgtaatca tggtacttgt ttttcaccca aactcaatca taaatttatt gaagagaaaa 1620
aaaaaaaaaa a 1631

<210> SEQ ID NO 129
<211> LENGTH: 1850
<212> TYPE: DNA
<213> ORGANISM: Homo sapiens
<220> FEATURE:
<221> NAME/KEY: misc_feature
<223> OTHER INFORMATION: Incyte ID No: 1095628.1

<400> SEQUENCE: 129
caaaacggcg cgcaggccgg gcgcacccag ccgccacttc cgagagcgcc tgccgcccct 60
gcgccgccga ggccagctgc cagaatgccc gaactgggga ggaggcaaga aatgtggggt 120
gtgtcagaag acggtttact ttgccgaaga ggttcagtgc gaaggcaaca gcttccataa 180
atcctgcttc ctgtgcatgg tctgcaagaa gaatctggac agtaccactg tggccgtgca 240
tggtgaggag atttactgca agtcctgcta cggcaagaag tatgggccca aaggctatgg 300
ctacgggcag ggcgcaggca ccctcagcac tgacaagggg gagtcgctgg gtatcaagca 360
cgaggaagcc cctgggccac aggcccacca ccaaccccaa tgcatccaaa tttgcccaga 420

-continued

```
agattggtgg ctccgagcgc tgcccccgat gcagccaggc agtctatgct gcggagaagg    480

tgattggtgc tgggaagtcc tggcataagg cctgctttcg atgtgccaag tgtggcaaag    540

gccttgagtc aaccaccctg gcagacaagg atggcgagat ttactgcaaa ggatgttatg    600

ctaaaaactt cgggcccaag ggctttggtt ttgggcaagg agctggggcc ttggtccact    660

ctgagtgagg ccaccatcac ccaccacacc ctgcccactc ctgcgctttt catcgccatt    720

ccattcccag cagctttgga gacctccagg attatttctc tgtcagccct gccacatatc    780

actaatgact tgaacttggg catctggctc cctttggttt gggggtctgc ctgaggtccc    840

accccactaa agggctcccc aggcctggga tctgacacca tcaccagtag gagacctcag    900

tgttttgggt ctaggtgaga gcaggcccct ctccccacac ctcgccccac agagctctgt    960

tcttagcctc ctgtgctgcg tgtccatcat cagctgacca agacacctga ggacacatct   1020

tggcacccag aggagcagca gcaacaggct ggagggagag ggaagcaaga ccaagatgag   1080

gagggggaa ggctgggttt tttggatctc agagattctc ctctgtggga aagaggttga   1140

gcttcctggt gtccctcaga gtaagcctga ggagtcccag cttagggagt cactattgga   1200

ggcagagagg catgcaggcg gggtcctagg agcccctgct tctccaggcc tcttgccttt   1260

gagtctttgt ggaatggata gcctcccact aggactggga ggagaataac ccaggtctta   1320

aggaccccaa agtcaggatg ttgtttgatc ttctcaaaca tctagttccc tgcttgatgg   1380

gaggatccta atgaaatacc tgaaacatat attggcattt atcaatggct caaatcttca   1440

tttatctctg gccttaaccc tggctcctga ggctgcggcc agcagagccc aggccagggc   1500

tctgttcttg ccacacctgc ttgatcctca gatgtggagg gaggtaggca ctgcctcagt   1560

cttcatccaa acacctttcc ctttgccctg agacctcaga atcttccctt taacccaaga   1620

ccctgcctct tccactccac ccttctccag ggacccttag atcacatcac tccacccctg   1680

ccaggcccca ggttaggaat agtggtggga ggaaggggaa agggctgggc ctcaccgctc   1740

ccagcaactg aaaggacaac actatctgga gccacccact gaaagggctg caggcatggg   1800

ctgtacccaa gctgatttct catctggtca ataaagctgt ttagaccaga              1850


<210> SEQ ID NO 130
<211> LENGTH: 1521
<212> TYPE: DNA
<213> ORGANISM: Homo sapiens
<220> FEATURE:
<221> NAME/KEY: misc_feature
<223> OTHER INFORMATION: Incyte ID No: 1040429.6

<400> SEQUENCE: 130

agatgctggt catggcgccc cgaaccgtcc tcctgctgct ctcgggcggc cctggccctg     60

accgagacct gggccggctc ccacttccat gaggtatttc gacaccgcca tgtcccggcc    120

cggccgcggg gagccccgct tcatctcagt gggctacgtg gacgacacgc agttcgtgag    180

gttcgacagc gacgccgcga gtccgagaga ggagccgcgg gcgccgtgga tagagcagga    240

ggggccggag tattgggacc ggaacacaca gatcttcaag accaacacac agactgaccg    300

agagagcctg cggaacctgc gcggctacta caaccagagc gaggccgggt ctcacaccct    360

ccagagcatg tacggctgcg acgtggggcc ggacgggcgc ctcctccgcg ggcataacca    420

gtacgcctac gacggcaagg attacatcgc cctgaacgag gacctgcgct cctggaccgc    480

ggcggacacc gcggctcaga tcacccagcg caagtgggag gcggcccgtg tggcggagca    540

ggacagagcc tacctggagg gcacgtgcgt ggagtggctc cgcagatacc tggagaacgg    600
```

-continued

```
gaaggacacg ctggagcgcg cggacccccc aaagacacac gtgacccacc accccatctc    660

tgaccatgag gccaccctga ggtgctgggc cctgggcttc taccctgcgg agatcacact    720

gacctggcag cgggatggcg aggaccaaac tcaggacact gagcttgtgg agaccagacc    780

agcaggagat agaaccttcc agaagtgggc agctgtggtg gtgccttctg gagaagagca    840

gagatacaca tgccatgtac agcatgaggg gctgccgaag cccctgcacc ctgagatggg    900

agccgtcttc ccagtccacc gtccccatcg tgggcattgt tgctggcctg gctgtcctag    960

cagttgtggt catcggagct gtggtcgctg ctgtgatgtg taggaggaag agctcaggtg   1020

gaaaaggagg gagctactct caggctgcgt gcagcgacag tgcccagggc tctgatgtgt   1080

ctctcacagc ttgaaaagcc tgagacagct gtcttgtgag ggactgagat gcaggatttc   1140

ttcacgcctc ccctttgtga cttcaagagc ctctggcatc tctttctgca aaggcacctg   1200

aatgtgtctg cgtccctgtt agcataatgt gaggaggtgg agagacagcc cacccttgtg   1260

tccactgtga cccctgttcc catgctgacc tgtgtttcct ccccagtcat ctttcttgtt   1320

ccagagaggt ggggctggat gtctccatct ctgtctcaac tttacgtgca ctgagctgca   1380

acttcttact tccctactga aaataagaat ctgaatataa atttgttttc tcaaatattt   1440

gctatgagag gttgatggat taattaaata agtcaattcc tggaatttga aagagcaaat   1500

aaagacctga gaaccttcca g                                             1521
```

<210> SEQ ID NO 131
<211> LENGTH: 1325
<212> TYPE: DNA
<213> ORGANISM: Homo sapiens
<220> FEATURE:
<221> NAME/KEY: misc_feature
<223> OTHER INFORMATION: Incyte ID No: 977410.12

<400> SEQUENCE: 131

```
aggactatcc caacactact tttttctttt gctcttgtcc cagatttgag aaaaagaatc     60

aagcagaggg acaaaggata cgttcacttc ctgatgctga agtggtaaca ctttttatca    120

ttccccagaa acctgatgtt ttgttatgca cttcccctt ctggaacatt gttctccgtg    180

ccattgccat cctgttcttt ttgcttatga tcatatccat ggtttgcagc agtcgccgtt    240

ccagggctag aatatccgtg tcagtcacat tcctgaggaa gtaagacatg taagtgtatg    300

ggcagttgac agcaccaaat ccagaaagag tcccgcgggt ctgtctcttg cttcaacagt    360

gtttggacgg aacagatccg gggactctct tccagcctcc gaccgccctc cgatttcctc    420

tccgcttgca acctccggga ccatcttctc ggccatctcc tgcttctggg acctgccagc    480

accgtttttg tggttagctc cttcttgcca accaaccatg agctcccaga ttcgtcagaa    540

ttattccacc gacgtggagg cagccgtcaa cagcctggtc aatttgtacc tgcaggcctc    600

ctacacctac ctctctctgg gcttctattt cgaccgcgat gatgtggctc tggaaggcgt    660

gagccacttc ttccgcgaat tggccgagga gaagcgcgag ggctacgagc gtctcctgaa    720

gatgcaaaac cagcgtggcg gccgcgctct cttccaggac atcaagaagc cagctgaaga    780

tgagtggggt aaaaccccag acgccatgaa agctgccatg gccctggaga aaaagctgaa    840

ccaggccctt ttggatcttc atgccctggg ttctgcccgc acggaccccc atctctgtga    900

cttcctggag actcacttcc tagatgagga agtgaagctt atcaagaaga tgggtgacca    960

cctgaccaac ctccacaggc tgggtggccc ggaggctggg ctgggcgagt atctcttcga   1020

aaggctcact ctcaagcacg actaagagcc ttctgagccc agcgacttct gaagggcccc   1080
```

-continued

```
ttgcaaagta atagggcttc tgcctaagcc tctccctcca gccaataggc agctttctta   1140

actatcctaa caagccttgg accaaatgga aataaagctt tctgtttctt ggtgatctgt   1200

tcaaaatttc atcctcctct gctttaggtt ttctgtcttc ctcctcttga ctgacagtgc   1260

caccatcttc ttcagcatca cttttctgtg tctcttcaag tgtctcttct ccttcctcct   1320

cctca                                                                1325
```

<210> SEQ ID NO 132
<211> LENGTH: 1513
<212> TYPE: DNA
<213> ORGANISM: Homo sapiens
<220> FEATURE:
<221> NAME/KEY: misc_feature
<223> OTHER INFORMATION: Incyte ID No: 207667.8

<400> SEQUENCE: 132

```
cgactcggct cgagcggctc gaggagcttg cagggccgct cccctcaccc gccccccttcg     60

agtccccggg cttcgcccca cccggcccgt gggggagtat ctgtcctgcc gccttcgccc    120

acgccctgca ctccggggac cgtccctgcg cgctctgggg cgcaccatgg gcccgcgggg    180

ctggcgctgg gcgctgctgc tcttcggcct gctgggtgtt ctggtcgccg ccccggatgg    240

tggtttcgat ttatccgatg cccttcctga caatgaaaac aagaaaccca ctgcaatccc    300

caagaaaccc agtgctgggg atgactttga cttaggagat gctgttgttg atggagaaaa    360

tgacgaccca cgaccaccga acccacccaa accgatgcca aatccaaacc ccaaccaccc    420

tagttcctcc ggtagctttt cagatgctga ccttgcggat ggcgtttcag gtggagaagg    480

aaaaggaggc agtgatggtg gaggcagcca caggaaagaa ggggaagagg ccgacgcccc    540

aggcgtgatc cccgggattg tgggggctgt cgtggtcgcc gtggctggag ccatctctag    600

cttcattgct taccagaaaa agaagctatg cttcaaagaa aatgacgacc cacgaccacc    660

gaacccaccc aaaccgatgc caaatccaaa ccccaaccac cctagttcct ccggtagctg    720

ttcagatgct gaccttgcgg atggcgtttc aggtggagaa ggaaaaggag gcagagatgg    780

tggaggcagc cacaggaaag aaggggaaga ggccgacgcc ccaggcgtga tccccgggat    840

tgtgggggct gtcgtggtcg ccgtggctgg agccatctct agcttcattg cttaccagaa    900

aaagaagcta tgcttcaaag aaaatgcaga acaaggggag gtggacatgg agagccaccg    960

gaatgccaac gcagagccag ctgttcagcg tactctttta gagaaataga agattgtcgg   1020

cagaaacagc ccaggcgttg gcagcagggt tagaacagct gcctgaggct cctccctgaa   1080

ggacacctgc ctgagagcag agatggaggc cttctgttca cggcggattc tttgttttaa   1140

tcttgcgatg tgctttgctt gttgctgggc ggatgatgtt tactaacgat gaattttaca   1200

tccaaagggg gaataggcac ttggaccccc attctccaag gcccgggggg gcggtttccc   1260

atgggatgtg aaaggctggc cattattaag tccctgtaac tcaaatgtca accccaccga   1320

ggcacccccc cgtcccccag aatcttggct gtttacaaat cacgtgtcca tcgagcacgt   1380

ctgaaacccc tggtagcccc gacttctttt taattaaaat aaggtaagcc cttcaatttg   1440

tttcttcaat atttctttca tttgtaggga tatttgtttt tcatatcaga ctaataaaaa   1500

gaaattagaa acc                                                       1513
```

<210> SEQ ID NO 133
<211> LENGTH: 8734
<212> TYPE: DNA
<213> ORGANISM: Homo sapiens
<220> FEATURE:

-continued

<221> NAME/KEY: misc_feature
<223> OTHER INFORMATION: Incyte ID No: 256009.4
<221> NAME/KEY: unsure
<222> LOCATION: 500
<223> OTHER INFORMATION: a, t, c, g, or other

<400> SEQUENCE: 133

```
ggtgagtgga agggacccca agtctcctct gctctcaact tggacacatc taagtttgct     60
gggggccttc atttctcagg accaaaggtg gaaggaggtg tgaaaggagg tcagattgga    120
ctccaggctc ctgggctgag tgtgtctggg cctcaaggtc acttggaaag tggatctgga    180
aaagtaacat tccctaaaat gaagatcccc aaatttacct tctctggccg tgagctggtt    240
ggcagagaaa tgggggtgga tgtcacttcc ctaaagcaga ggccagcatc caagctggtg    300
ctggagacgg cgagtgggaa gagtctgaag tcaaactgaa aaagtccaag tttaaaatgc    360
ctttcctgag tatttcatct cccaaagttt ctatgcctga cgtggagcta aatttgaaag    420
gtcccaaatt caagatgcct gacatgaata tcaaagctcc caagatctcc atgcctgata    480
ttgacttaaa cttgaaaggn cccaaagtga agggcgatgt ggatgtttct ctgcccaaaa    540
tggaaggtga cctcaagggc ccagaagctg acatcaaggg ccccaaagtg gacattaatg    600
ctccagatgt tgatgttcaa ggcccagact ggcacctgaa gatgcccaag gtgaaaatgc    660
ccaagttcag catgcctggc ttcaaaggag agggcccaga tgtggatgtg aacctgccca    720
aggctgacct tgatgtctca ggacccaagg tggacattga tgttccagat gtgaatatcg    780
aaggcccaga gggaaagttg aaaggtccca aattcaagat gcctgagatg aacatcaaag    840
cccccaagat ctccatgcct gacattgatc ttaacctgaa aggacccaaa gtgaagggtg    900
atatggatgt gtctctgcca aaagtggaag gtgacatgca agttcctgac ttggatatta    960
aaggccccaa agtggatatt aatgccccag atgtggatgt tcgaggccca gactggcacc   1020
tgaagatgcc taagataaaa atgcccaaga tcagcatgcc tggcttcaaa ggagaaggtc   1080
cagaagtgga tgtgaacctg cccaaggctg accttgacgt ctcaggaccc aaggtggacg   1140
ttgatgttcc agatgtgaat attgaaggtc cagatgcgaa actgaagggc cctaaattca   1200
agatgccaga gatgaacatc aaagccccca agatctccat gcctgacttt gatttgcatc   1260
tgaaaggccc taaggtgaaa ggagatgtgg atgtttctct gcctaagatg gaaggtgatc   1320
taaaggcccc tgaagttgac atcaagggcc ccaaagtgga cattgatgcc ccagatgtgg   1380
atgttcatgg cccagactgg cacctgaaga tgcccaaggt gaaaatgccc aaattcagca   1440
tgccaggatt taaaggagag ggcccagaag tggatgttaa tttgcccaaa gctgacattg   1500
atgtctcagg acccaaagtg gacattgaca ctcctgatat tgatattcat ggtccagaag   1560
ggaaactgaa gggccccaaa tttaaaatgc ctgacctgca cctcaaggca ccgaagatct   1620
ctatgcctga agttgacctg aatctgaaag gtccaaagat gaagggcgac gtggacgttt   1680
ctctgcccaa agtggaaggc gacctcaagg gccctgaagt tgacatcaag ggccccaaag   1740
tggacattga tgtcccagat gtggacgttc aaggcccaga ctggcactta aaaatgccca   1800
aagtgaaaat gcccaagttc agcatgcctg gcttcaaagg agagggccca gatgtggatg   1860
tgaacctgcc caaggctgac cttgacgtct caggacccaa ggtggacatt gatgttcctg   1920
atgtgaatat cgaaggtcca gatgcgaaac taaagggccc taaattcaag atgcctgaga   1980
tgaacatcaa agcccccaag atctccatgc ctgactttga tttgcatctg aaaggtccca   2040
aggtgaaggg tgatgtggat gtttcccttc ctaaagtgga aggtgacctc aagggcccag   2100
aagttgacat caagggcccc aaagtggaca tcgatgcccc tgatgtagat gttcatggcc   2160
```

-continued cagactggca cctgaagatg cccaaggtga aaatgcccaa attcagcatg ccaggattca 2220
aaggagaggg cccagatgtg gatgttaccc ttcctaaggc tgacattgag atttctggcc 2280
ccaaagtgga cattgatgcc cctgatgtca gtatcgaagg tccagatgca aaactcaagg 2340
gtccaaagtt caagatgcca gagatgaaca tcaaggcccc caaaatctcc atgcctgaca 2400
ttgactttaa cttgaagggt cccaaagtga aaggtgatgt ggatgtctct ctgcccaaag 2460
tggaaggtga tctcaagggc cctgaaattg acataaaagg ccccagtttg gacattgaca 2520
cacctgatgt caatattgaa ggtccggaag gaaaattgaa ggggcccaaa tttaagatgc 2580
ctgagatgaa catcaaagct cccaaaatct ctatgcctga ctttgatttg cacctgaaag 2640
gtcccaaggt gaagggtgat gtggatgttt cactacctaa ggtggaaagt gatctgaaag 2700
ggccagaggt agacattgaa ggtcctgaag ggaagctcaa aggtcccaag tttaagatgc 2760
ctgatgtaca tttcaaaagc ccacaaatct ccatgagtga cattgatttg aatttgaaag 2820
gacctaagat aaaaggagat atggacattt ccgttcctaa actggaggga gatctgaaag 2880
gtcccaaagt ggatgtcaaa ggccctaaag tgggcattga cactcctgat attgacattc 2940
atggtccaga agggaaactg aagggcccca aatttaaaat gcctgactta cacctcaagg 3000
caccgaagat ctctatgcct gaagttgacc tgaatctgaa aggtccaaag gtgaagggcg 3060
acatggacat ttctctgccc aaagtggaag gcgacctcaa gggccccgaa gttgacatca 3120
gggaccccaa agtggacatt gatgtcccag atgtggacgt tcaaggccca gactggcacc 3180
taaaaatgcc caaagtgaaa atgcccaagt tcagcatgcc tggcttcaaa ggagagggcc 3240
cagatgtgga tgtgaacctg cccaaggctg acattgatgt ctcaggaccc aaagtggacg 3300
ttgatgttcc tgatgtgaat atcgaaggtc cagatgcgaa actaaagggc cccaagttca 3360
agatgcctga gatgagcatc aaagccccca agatctccat gcctgatatt gacttaaacc 3420
tgaaaggacc caaagtgaag ggcgatgtgg atgttacct tcctaaagtg gaaggtgacc 3480
tcaagggccc agaagctgac atcaagggcc caaaagtgga catcaacacc cctgatgtgg 3540
atgttcatgg cccagactgg cacctgaaga tgcccaaggt gaaaatgccc aaattcagca 3600
tgcctggctt caaaggagag ggcccagatg tggatgtgaa cctgcccaag gctgacattg 3660
atgtctcagg acccaaagtg gacgttgatg ttcctgatgt gaatatcgaa ggtccagatg 3720
cgaaactaaa gggccccaag ttcaagatgc ctgagatgag catcaaagcc cccaagatct 3780
ccatgcctga tattgactta aacctgaaag gacccaaagt gaagggcgat gtggatgtta 3840
cccttcctaa agtggaaggt gacctcaagg gcccagaagc tgacatcaag ggcccaaaag 3900
tggacatcaa cacccctgat gtggatgttc atggcccaga ctggcacctg aagatgccca 3960
aggtgaaaat gcccaaattc agcatgcctg gcttcaaagg agaaggtcca gatgtggatg 4020
tgagcctgcc caaggccgac atcgatgtct cgggacccaa ggtggacgtt gatattccag 4080
atgtgaatat cgaaggtcca gacgcaaaac tgaagggccc caagttcaag atgcctgaaa 4140
taaatatcaa agctcccaag atctccatac ctgatgttga cctggatttg aaaggaccca 4200
aagtaaaagg agattttgat gtgtctgtcc ctaaggttga agggactttg aaaggcccag 4260
aagtagatct taaaggtcca cgtctggatt tcgaaggccc tgatgccaaa ctcagtggcc 4320
catctttgaa gatgccatcg ctggagatat ctgctcctaa agtaactgct cctgatgttg 4380
atttgcatct caaggcacca aaaattggat tttcaggtcc gaagttagaa ggtggtgaag 4440
tggacctcaa gggacccaaa gttgaagctc caagcttaga tgtacacatg gacagcccag 4500

-continued atattaacat cgaagggcca gatgttaaaa tccccaaatt taagaaaccc aagtttggat 4560
ttggggcaaa aagccccaaa gctgacatca agtcaccttc actggatgtc actgttcctg 4620
aggcagagct gaaccttgag actcctgaaa ttagtgttgg tggcaagggc aagaaaagta 4680
agtttaaaat gcctaaaatt catatgagtg gtcctaagat taaggccaaa aaacagggat 4740
ttgacctgaa tgttcctggg ggtgaaattg atgccagcct caaggctccg gatgtagatg 4800
tcaacatcgc agggccggat gctgcactca aagtcgacgt gaaatcgccc aaaaccaaga 4860
aaacgatgtt tggaaaaatg tacttcccag atgtagagtt tgacattaaa tcacctaaat 4920
ttaaagctga ggcccctctc cctagcccca aactggaggg tgaactccag gcacctgatc 4980
tggaactttc tttgccagcg attcacgtcg aaggtcttga catcaaggcg aaggctccca 5040
aggtcaagat gccagatgtg gacatctcag tgccaaaaat agagggtgac ctgaaaggcc 5100
ccaaagtgca ggcaaacttg ggtgcacctg acatcaacat cgaaggccta gatgctaaag 5160
tcaaaacacc gtccttcggc atttctgccc ctcaagtctc catccctgat gtgaatgtaa 5220
acttgaaagg accaaagata aagggtgatg tccccagcgt gggactggaa ggaccagatg 5280
tagatctgca aggtccagaa gcaaaaatta agttccccaa gttttccatg cccaagatcg 5340
gcatcccagg tgtgaaaatg gagggtgggg gagccgaggt ccatgcccag ctaccctctc 5400
ttgaaggaga cttgagagga ccagatgtta agctcgaagg gcccgatgtt tctctaaagg 5460
ggccaggagt agacttgcct tcagtgaacc tctctatgcc aaaagtctct gggcctgacc 5520
ttgatctgaa cttgaaagga ccaagtttga agggagacct ggatgcatct gttcccagca 5580
tgaaggtgca tgctccaggg ctcaacctca gtggtgtcgg tggcaaaatg caggtgggag 5640
gagacggtgt gaaagtgcca gggatcgatg ccacaacaaa gcttaacgtt ggggcaccag 5700
atgtgacact gaggggacca agcctgcagg gagatctggc tgtctctggt gacatcaaat 5760
gccctaaagt atccgtagga gctcctgatc taagcttgga ggcatccgaa ggcagcatta 5820
aacttcccaa aatgaagctg ccccaatttg gcatctctac tccgggtcc gacttgcacg 5880
tcaatgccaa ggggccacag gtttctggcg aactgaaggg gccaggtgtg gatgtgaacc 5940
tgaaagggcc tcggatttca gcaccgaatg tggactttaa cttggaagga ccaaaagtga 6000
aagggagcct tggggccact ggtgagatca aaggccccac tgtcggagga ggtcttccag 6060
gcattggtgt tcaaggccta gaaggaaacc tccagatgcc tggaattaag tcctctggat 6120
gtgatgtgaa cctgccaggc gtgaatgtga aactcccaac tgggcagatt tctgggcctg 6180
aaatcaaagg tggtctgaaa ggttcagaag taggtttcca tggggctgct cctgatatca 6240
gtgtgaaggg gcctgccttt aatatggcat ctcctgagtc agattttggc atcaacttga 6300
agggcccaaa aatcaaagga ggtgcggatg tttcaggggg tgtcagtgcc ccagacatca 6360
gccttggtga agggcatttg agtgttaaag gttccggggg tgagtggaag ggaccccaag 6420
tctcctctgc tctcaacttg gacacatcta agtttgctgg gggccttcat ttctcaggac 6480
caaaggtgga aggaggtgtg aaaggaggtc agattggact ccaggctcct gggctgagtg 6540
tgtctgggcc tcaaggtcac ttggaaagtg gatctggaaa agtaacattc cctaaaatga 6600
agatccccaa atttaccttc tctggccgtg agctggttgg cagagaaatg ggggtggatg 6660
ttcacttccc taaagcagag gccagcatcc aagctggtgc tggagacggc gagtgggaag 6720
agtctgaagt caaactgaaa aagtccaaga tcaaaatgcc caagtttaat ttttccaaac 6780
ctaaagggaa aggtggtgtc actggctcac cagaagcatc aatttctggg tccaaaggtg 6840
acctgaaaag ttcaaaggcc agcctgggct ctctggaagg agaggcagag gccgaagcct 6900

-continued

```
cttcaccgaa aggcaaattc tccttattta aaagtaagaa gccacggcac cgctcaaatt   6960

cattcagtga tgaaagagag ttctctggac cttccacccc gacggggacg ctggagtttg   7020

aaggtgggga agtgtctctg gaaggtggga aagttaaagg gaaacacggg aagctgaaat   7080

tcggtacctt tggtggattg gggtcaaaga gcaaaggtca ttatgaggtg actgggagcg   7140

atgatgagac aggcaagtta caggggagtg gggtgtccct ggcctctaag aagtcccgac   7200

tgtcctcctc ttctagcaat gacagtggga ataaggttgg catccagctt cccgaggtgg   7260

agctgtcagt ttccacaaag aaagagtagc aggcctttgt atgtgtgtac atatatatat   7320

atataacaaa acatcagcct tgggtggtgt gttcctatat aaactccaaa gggaaacaca   7380

ccgactgcct cagcaatcat gcaaagacct tgcctggccc ggtggcaagc gctgaaaaac   7440

cgaccgcctg taggctcctg gaactataca gataggtaaa gagttccaag ttcgtccagc   7500

ccatgtgcaa agtcaacagt atttgcctta agatttcata tatatatatt tttttgcatt   7560

gactgctgag agctcctgtt tactaagcaa gcttttgtgt ttattatcct catttttact   7620

gaacattgtt agttttgggg taatggaaac ccactttttc attgtaatga ctttgggggc   7680

ttttgttagt aagggtgggt ggggtgatgg gttgcagacg gaggtcaggt cttcctcttt   7740

cctgagactg gatctgttca aacagcaaac gcccacagat ggcccagagg tggtggtagt   7800

cagggtgtgt gggtgttttt agggttcttt agtgttgttt ctttcaccca ggggtggtgg   7860

tcccagccag tttggtgctg acggtgagag gaaattagaa tctgtttgca aattgtccaa   7920

cccacccccct caacatgagg ggcttccatt ttctgtgttt tgtaagggaa ctgtttcctt   7980

catgccgcca tgttcctgat attagttctg atttcttttt aacaaatgtt atcatgatta   8040

agaaaatttc cagcacttta atggccaatt aactgagaat gtaagaaaat tgatgctgta   8100

caaggcaaat aaagctgttt attaaccttg tacagcatca attttcttac attttctgtg   8160

ttttgtaagg gaactgtttc cttcatgccg ccatgttcct gatattagtt ctgatttctt   8220

tttaacaaat gttatcatga ttaagaaaat ttccagcact ttaatggcct attggtactt   8280

tggggtgctg atacccaaaa cagatgcaat cttctctcca aggaagtcac acactgagag   8340

agttgatgta gcagcccgaa gcatgtaaaa ccataagtag ggaccccagg taagttttgt   8400

cggatcaaca gtaggcaaaa catctttctt ctccaggcca tcaacttcgt cttcatctgt   8460

gctatattct tccattgttt caccactaac aaagtggatg actctccttg ggactttctt   8520

ctttttttcct atgactccca gttctacatt ttcaaagcct ctttcgttac tcatctgcca   8580

tataacctga gcgcccgcgc ggccacgaca cgaggaattc gcccacgcag gaggcgcggc   8640

gctccggagg ccccagggtt atgagactat cactgctcag gacctactaa caacaaagat   8700

ttaattaaga tataagatgt aaattgatac aagt                               8734
```

<210> SEQ ID NO 134
<211> LENGTH: 4530
<212> TYPE: DNA
<213> ORGANISM: Homo sapiens
<220> FEATURE:
<221> NAME/KEY: misc_feature
<223> OTHER INFORMATION: Incyte ID No: 364726.12

<400> SEQUENCE: 134

```
cgggtcggca ccccggcggt tgggctgcgg gtcagagcac tgtccggtgg tgcccaggag     60

gagtaggagc aggagcagaa gcagaagcgg ggtccggagc tgcgcgccta cgcgggacct    120

gtgtccgaaa tgccggtgcg aggagaccgc gggtttccac cccggcggga gctgtcaggt    180
```

-continued

```
tggctccgcg ccccaggcat ggaagagctg atatgggaac agtacactgt gaccctacaa    240
aaggattcca aaagaggatt tggaattgca gtgtccggag gcagagacaa cccccacttt    300
gaaaatggag aaacgtcaat tgtcatttct gatgtgctcc cgggtgggcc tgctgatggg    360
ctgctccaag aaaatgacag agtggtcatg gtcaatggca cccccatgga ggatgtgctt    420
cattcgtttg cagttcagca gctcagaaaa agtgggaagg tcgctgctat tgtggtcaag    480
aggccccgga aggtccaggt ggccgcactt caggccagcc ctcccctgga tcaggatgac    540
cgggcttttg aggtgatgga cgagtttgat ggcagaagtt tccggagtgg ctacagcgag    600
aggagccggc tgaacagcca tgggggggcgc agccgcagct gggaggacag cccggaaagg    660
gggcgtcccc atgagcgggc ccggagccgg gagcgggacc tcagccggga ccggagccgt    720
ggccggagcc tggagcgggg cctggaccaa gaccatgcgc gcacccgaga ccgcagccgt    780
ggccggagcc tggagcgggg cctggaccac gactttgggc catcccggga ccgggaccgt    840
gaccgcagcc gcggccggag cattgaccag gactacgagc gagcctatca ccgggcctac    900
gacccagact acgagcgggc ctacagcccg gagtacaggc gcggggcccg ccacgatgcc    960
cgctctcggg gaccccgaag ccgcagccgc gagcacccgc actcacggag ccccagcccc   1020
gagcctaggg ggcggccggg gcccatcggg gtcctcctga tgaaaagcag agcgaacgaa   1080
gagtatggtc tccggcttgg gagtcagatc ttcgtaaagg aaatgacccg aacgggtctg   1140
gcaactaaag atggcaacct tcacgaagga gacataattc tcaagatcaa tgggactgta   1200
actgagaaca tgtctttaac ggatgctcga aaattgatag aaaagtcaag aggaaaacta   1260
cagctagtgg tgttgagaga cagccagcag accctcatca acatcccgtc attaaatgac   1320
agtgactcag aaatagaaga tatttcagaa atagagtcaa accgatcatt ttctccagag   1380
gagagacgtc atcagtattc tgattatgat tatcattcct caagtgagaa gctgaaggaa   1440
aggccaagtt ccagagagga cacgccgagc agattgtcca ggatgggtgc gacacccact   1500
ccctttaagt ccacagggga tattgcaggc acagttgtcc cagagaccaa caaggaaccc   1560
agataccaag aggacccccc agctcctcaa ccaaaagcag ccccgagaac ttttcttcgt   1620
cctagtcctg aagatgaagc aatatatggc cctaatacca aaatggtaag gttcaagaag   1680
ggagacagcg tgggcctccg gttggctggt ggcaatgatg tcgggatatt tgttgctggc   1740
attcaagaag ggacctcggc ggagcaggag ggccttcaag aaggagacca gattctgaag   1800
gtgaacacac aggatttcag aggattagtg cgggaggatg ccgttctcta cctgttagaa   1860
atccctaaag gtgaaatggt gaccatttta gctcagagcc gagccgatgt gtatagagac   1920
atcctggctt gtggcagagg ggattcgttt tttataagaa gccactttga atgtgagaag   1980
gaaactccac agagcctggc cttcaccaga ggggaggtct tccgagtggt agacacactg   2040
tatgacggca agctgggcaa ctggctggct gtgaggattg ggaacgagtt ggagaaaggc   2100
ttaatcccca acaagagcag agctgaacaa atggccagtg ttcaaaatgc ccagagagac   2160
aacgctgggg accgggcaga tttctggaga atgcgtggcc agaggtctgg ggtgaagaag   2220
aacctgagga aaagtcggga agacctcaca gctgttgtgt ctgtcagcac caagttccca   2280
gcttatgaga gggttttgct gcgagaagct ggtttcaaga gacctgtggt cttattcggc   2340
cccatagctg atatagcaat ggaaaaattg gctaatgagt tacctgactg gtttcaaact   2400
gctaaaacgg aaccaaaaga tgcaggatct gagaaatcca ctggagtggt ccggttaaat   2460
accgtgaggc aagttattga acaggataag catgcactac tggatgtgac tccgaaagct   2520
```

-continued

```
gtggacctgt tgaattacac ccagtggttc tcaattgtga tttctttcac gccagactcc   2580
agacaaggtg tcaacaccat gagacaaagg ttagacccaa cgtccaacaa aagttctcga   2640
aagttatttg atcaagccaa caagcttaaa aaaacgtgtg cacacctttt tacagctaca   2700
atcaacctaa attcagccaa tgatagctgg tttggcagct taaaggacac tattcagcat   2760
cagcaaggag aagcggtttg ggtctctgaa ggaaagatgg aagggatgga tgatgacccc   2820
gaagaccgca tgtcctactt aaccgccatg ggcgcggact atctgagttg cgacagccgc   2880
ctcatcagtg actttgaaga cacggacggt gaaggaggcg cctacactga caatgagctg   2940
gatgagccag ccgaggagcc gctggtgtcg tccatcaccc gctcctcgga gccggtgcag   3000
cacgaggaga gcataaggaa acccagccca gagccacgag ctcagatgag gagggctgct   3060
agcagcgatc aacttaggga caatagcccg cccccagcat tcaagccaga gccgcccaag   3120
gccaaaaccc agaacaaaga agaatcctat gacttctcca aatcctatga atataagtca   3180
aacccctctg ccgttgctgg taatgaaact cctggggcat ctaccaaagg ttatcctcct   3240
cctgttgcag caaaacctac ctttgggcgg tctatactga agccctccac tcccatccct   3300
cctcaagagg gtgaggaggt gggagagagc agtgaggagc aagataatgc tcccaaatca   3360
gtcctgggca aagtcaaaat atttgagaag atggatcaca aggccaggtt acagagaatg   3420
caggagctcc aggaagcaca gaatgcaagg atcgaaattg cccagaagca tcctgatatc   3480
tatgcagttc caatcaaaac gcacaagcca gaccctggca cgccccagca cacgagttcc   3540
agaccccctg agccacagaa agctccttcc agaccttatc aggataccag aggaagttat   3600
ggcagtgatg ccgaggagga ggagtaccgc cagcagctgt cagaacactc caagcgcggt   3660
tactatggcc agtctgcccg ataccgggac acagaattat agatgtctga gcacggactc   3720
tcccaggcct gcctgcatgg catcagacta gccactcctg ccaggccgcc gggatggttc   3780
ttctccagtt agaatgcacc atggagacgt ggtgggactc cagctcgtgt gtcctcatgg   3840
agaacccagg ggacagctgg tgcaaattca gaactgaggg ctctgtttgt gggactgggt   3900
tagaggagtc tgtggctttt tgttcagaat taagcagaac actgcagtca gatcctgtta   3960
cttgcttcag tggaccgaaa tctgtattct gtttgcgtac ttgtaatatg tatattaaga   4020
agcaataact atttttcctc attaatagct gccttcaagg actgtttcag tgtgagtcag   4080
aatgtgaaaa aggaataaaa aatactgttg ggctcaaact aaattcaaag aagtacttta   4140
ttgcaactct tttaagtgcc ttggatgaga agtgtcttaa attttcttcc tttgaagctt   4200
taggcagagc cataatggac taaaacattt tgactaagtt tttataccag cttaatagct   4260
gtagttttcc ctgcactgtg tcatcttttc aaggcatttg tctttgtaat attttccata   4320
aatttggact gtctatatca taactatact tgatagtttg gctataagtg ctcaatagct   4380
tgaagcccaa gaagttggta tcgaaatttg ttgtttgttt aaacccaagt gctgcacaaa   4440
agcagatact tgaggaaaac actatttcca aaagcacatg tattgacaac agttttataa   4500
tttaataaaa aggaatacat tgcaatccgt                                    4530
```

```
<210> SEQ ID NO 135
<211> LENGTH: 8044
<212> TYPE: DNA
<213> ORGANISM: Homo sapiens
<220> FEATURE:
<221> NAME/KEY: misc_feature
<223> OTHER INFORMATION: Incyte ID No: 427813.14

<400> SEQUENCE: 135
```

-continued

```
cggctcgagc cggctgtgct gcacaggggg aggagaggga accccaggcg cgagcgggaa     60
gaggggacct gcagccacaa cttctctggt cctctgcatc ccttctgtcc ctccacccgt    120
ccccttcccc accctctggc ccccaccttc ttggaggcga caaccccccgg gaggcattag   180
aagggatttt tcccgcaggt tgcgaaggga agcaaacttg gtggcaactt gcctcccggt    240
gcgggcgtct ctcccccacc gtctcaacat gcttaggggt ccggggcccg ggctgctgct    300
gctggccgtc ctgtgcctgg ggacagcggt gccctccacg ggagcctcga agagcaagag    360
gcaggctcag caaatggttc agccccagtc cccggtggct gtcagtcaaa gcaagcccgg    420
ttgttatgac aatggaaaac actatcagat aaatcaacag tgggagcgga cctacctagg    480
caatgcgttg gtttgtactt gttatggagg aagccgaggt tttaactgcg agagtaaacc    540
tgaagctgaa gagacttgct ttgacaagta cactgggaac acttaccgag tgggtgacac    600
ttatgagcgt cctaaagact ccatgatctg ggactgtacc tgcattgggg ctgggcgagg    660
gagaataagc tgtaccatcg caaaccgctg ccatgaaggg ggtcagtcct acaagattgg    720
tgacacctgg aggagaccac atgagactgg tggttacatg ttagagtgtg tgtgtcttgg    780
taatggaaaa ggagaatgga cctgcaagcc catagctgag aagtgttttg atcatgctgc    840
tgggacttcc tatgtggtcg gagaaacgtg ggagaagccc taccaaggct ggatgatggt    900
agattgtact tgcctgggag aaggcagcgg acgcatcact tgcacttcta gaaatagatg    960
caacgatcag gacacaagga catcctatag aattggagac acctggagca agaaggataa   1020
tcgaggaaac ctgctccagt gcatctgcac aggcaacggc cgaggagagt ggaagtgtga   1080
gaggcacacc tctgtgcaga ccacatcgag cggatctggc cccttcaccg atgttcgtgc   1140
agctgtttac caaccgcagc ctcacccccca gcctcctccc tatggccact gtgtcacaga  1200
cagtggtgtg gtctactctg tggggatgca gtggctgaag acacaaggaa ataagcaaat   1260
gctttgcacg tgcctgggca acggagtcag ctgccaagag acagctgtaa cccagactta   1320
cggtggcaac tcaaatggag agccatgtgt cttaccattc acctacaatg gcaggacgtt   1380
ctactcctgc accacagaag ggcgacagga cggacatctt tggtgcagca caacttcgaa   1440
ttatgagcag gaccagaaat actctttctg cacagaccac actgttttgg ttcagactcg   1500
aggaggaaat tccaatggtg ccttgtgcca cttccccttc ctatacaaca accacaatta   1560
cactgattgc acttctgagg gcagaagaga caacatgaag tggtgtggga ccacacagaa   1620
ctatgatgcc gaccagaagt ttgggttctg ccccatggct gcccacgagg aaatctgcac   1680
aaccaatgaa ggggtcatgt accgcattgg agatcagtgg gataagcagc atgacatggg   1740
tcacatgatg aggtgcacgt gtgttgggaa tggtcgtggg gaatggacat gcattgccta   1800
ctcgcagctt cgagatcagt gcattgttga tgacatcact tacaatgtga acgacacatt   1860
ccacaagcgt catgaagagg ggcacatgct gaactgtaca tgcttcggtc agggtcgggg   1920
caggtggaag tgtgatcccg tcgaccaatg ccaggattca gagactggga cgttttatca   1980
aattggagat tcatgggaga agtatgtgca tggtgtcaga taccagtgct actgctatgg   2040
ccgtggcatt ggggagtggc attgccaacc tttacagacc tatccaagct caagtggtcc   2100
tgtcgaagta tttatcactg agactccgag tcagcccaac tcccacccca tccagtggaa   2160
tgcaccacag ccatctcaca tttccaagta cattctcagg tggagaccta aaaattctgt   2220
aggccgttgg aaggaagcta ccataccagg ccacttaaac tcctacacca tcaaaggcct   2280
gaagcctggt gtggtatacg agggccagct catcagcatc cagcagtacg gccaccaaga   2340
agtgactcgc tttgacttca ccaccaccag caccagcaca cctgtgacca gcaacaccgt   2400
```

-continued

```
gacaggagag acgactccct tttctcctct tgtggccact tctgaatctg tgaccgaaat   2460
cacagccagt agctttgtgg tctcctgggt ctcagcttcc gacaccgtgt cgggattccg   2520
ggtggaatat gagctgagtg aggagggaga tgagccacag tacctggatc ttccaagcac   2580
agccacttct gtgaacatcc ctgacctgct tcctggccga aaatacattg taaatgtcta   2640
tcagatatct gaggatgggg agcagagttt gatcctgtct acttcacaaa caacagcgcc   2700
tgatgcccct cctgacccga ctgtggacca agttgatgac acctcaattg ttgttcgctg   2760
gagcagaccc caggctccca tcacagggta cagaatagtc tattcgccat cagtagaagg   2820
tagcagcaca gaactcaacc ttcctgaaac tgcaaactcc gtcaccctca gtgacttgca   2880
acctggtgtt cagtataaca tcactatcta tgctgtggaa gaaaatcaag aaagtacacc   2940
tgttgtcatt caacaagaaa ccactggcac cccacgctca gatacagtgc cctctcccag   3000
ggacctgcag tttgtggaag tgacagacgt gaaggtcacc atcatgtgga caccgcctga   3060
gagtgcagtg accggctacc gtgtggatgt gatccccgtc aacctgcctg gcgagcacgg   3120
gcagaggctg cccatcagca ggaacacctt tgcagaagtc accgggctgt cccctggggt   3180
cacctattac ttcaaagtct ttgcagtgag ccatgggagg gagagcaagc ctctgactgc   3240
tcaacagaca accaaactgg atgctcccac taacctccag tttgtcaatg aaactgattc   3300
tactgtcctg gtgagatgga ctccacctcg ggcccagata acaggatacc gactgaccgt   3360
gggccttacc cgaagaggcc agcccaggca gtacaatgtg ggtccctctg tctccaagta   3420
ccccctgagg aatctgcagc ctgcatctga gtacaccgta tccctcgtgg ccataaaggg   3480
caaccaagag agccccaaag ccactggagt ctttaccaca ctgcagcctg ggagctctat   3540
tccaccttac aacaccgagg tgactgagac caccattgtg atcacatgga cgcctgctcc   3600
aagaattggt tttaagctgg gtgtacgacc aagccaggga ggagaggcac cacgagaagt   3660
gacttcagac tcaggaagca tcgttgtgtc cggcttgact ccaggagtag aatacgtcta   3720
caccatccaa gtcctgagag atggacagga aagagatgcg ccaattgtaa acaaagtggt   3780
gacaccattg tctccaccaa caaacttgca tctggaggca aaccctgaca ctggagtgct   3840
cacagtctcc tgggagagga gcaccacccc agacattact ggttatagaa ttaccacaac   3900
ccctacaaac ggccagcagg gaaattcttt ggaagaagtg gtccatgctg atcagagctc   3960
ctgcactttt gataacctga gtcccggcct ggagtacaat gtcagtgttt acactgtcaa   4020
ggatgacaag gaaagtgtcc ctatctctga taccatcatc ccagctgttc ctcctcccac   4080
tgacctgcga ttcaccaaca ttggtccaga caccatgcgt gtcacctggg ctccaccccc   4140
atccattgat ttaaccaact tcctggtgcg ttactcacct gtgaaaaatg aggaagatgt   4200
tgcagagttg tcaatttctc cttcagacaa tgcagtggtc ttaacaaatc tcctgcctgg   4260
tacagaatat gtagtgagtg tctccagtgt ctacgaacaa catgagagca cacctcttag   4320
aggaagacag aaaacaggtc ttgattcccc aactggcatt gacttttctg atattactgc   4380
caactctttt actgtgcact ggattgctcc tcgagccacc atcactggct acaggatccg   4440
ccatcatccc gagcacttca gtgggagacc tcgagaagat cgggtgcccc actctcggaa   4500
ttccatcacc ctcaccaacc tcactccagg cacagagtat gtggtcagca tcgttgctct   4560
taatggcaga gaggaaagtc ccttattgat tggccaacaa tcaacagttt ctgatgttcc   4620
gagggacctg gaagttgttg ctgcgacccc caccagccta ctgatcagct gggatgctcc   4680
tgctgtcaca gtgagatatt acaggatcac ttacggagaa acaggaggaa atagccctgt   4740
```

-continued

```
ccaggagttc actgtgcctg ggagcaagtc tacagctacc atcagcggcc ttaaacctgg   4800
agttgattat accatcactg tgtatgctgt cactggccgt ggagacagcc ccgcaagcag   4860
caagccaatt tccattaatt accgaacaga aattgacaaa ccatcccaga tgcaagtgac   4920
cgatgttcag gacaacagca ttagtgtcaa gtggctgcct tcaagttccc ctgttactgg   4980
ttacagagta accaccactc ccaaaaatgg accaggacca acaaaaacta aaactgcagg   5040
tccagatcaa acagaaatga ctattgaagg cttgcagccc acagtggagt atgtggttag   5100
tgtctatgct cagaatccaa gcggagagag tcagcctctg gttcagactg cagtaaccaa   5160
cattgatcgc cctaaaggac tggcattcac tgatgtggat gtcgattcca tcaaaattgc   5220
ttgggaaagc ccacaggggc aagtttccag gtacagggtg acctactcga gccctgagga   5280
tggaatccat gagctattcc ctgcacctga tggtgaagaa gacactgcag agctgcaagg   5340
cctcagaccg ggttctgagt acacagtcag tgtggttgcc ttgcacgatg atatggagag   5400
ccagcccctg attggaaccc agtccacagc tattcctgca ccaactgacc tgaagttcac   5460
tcaggtcaca cccacaagcc tgagcgccca gtggacacca cccaatgttc agctcactgg   5520
atatcgagtg cgggtgaccc ccaaggagaa gaccggacca atgaaagaaa tcaaccttgc   5580
tcctgacagc tcatccgtgg ttgtatcagg acttatggtg gccaccaaat atgaagtgag   5640
tgtctatgct cttaaggaca ctttgacaag cagaccagct cagggtgttg tcaccactct   5700
ggagaatgtc agcccaccaa gaagggctcg tgtgacagat gctactgaga ccaccatcac   5760
cattagctgg agaaccaaga ctgagacgat cactggcttc caagttgatg ccgttccagc   5820
caatggccag actccaatcc agagaaccat caagccagat gtcagaagct acaccatcac   5880
aggtttacaa ccaggcactg actacaagat ctacctgtac accttgaatg acaatgctcg   5940
gagctcccct gtggtcatcg acgcctccac tgccattgat gcaccatcca acctgcgttt   6000
cctggccacc acacccaatt ccttgctggt atcatggcag ccgccacgtg ccaggattac   6060
cggctacatc atcaagtatg agaagcctgg gtctcctccc agagaagtgg tccctcggcc   6120
ccgccctggt gtcacagagg ctactattac tggcctggaa ccgggaaccg aatatacaat   6180
ttatgtcatt gccctgaaga ataatcagaa gagcgagccc ctgattggaa ggaaaaagac   6240
agacgagctt ccccaactgg taacccttcc acaccccaat cttcatggac cagagatctt   6300
ggatgttcct tccacagttc aaaagacccc tttcgtcacc caccctgggt atgacactgg   6360
aaatggtatt cagcttcctg gcacttctgg tcagcaaccc agtgttgggc aacaaatgat   6420
ctttgaggaa catggtttta ggcggaccac accgcccaca acggccaccc ccataaggca   6480
taggccaaga ccatacccgc cgaatgtagg acaagaagct ctctctcaga caaccatctc   6540
atgggcccca ttccaggaca cttctgagta catcatttca tgtcatcctg ttggcactga   6600
tgaagaaccc ttacagttca gggttcctgg aacttctacc agtgccactc tgacaggcct   6660
caccagaggt gccacctaca acatcatagt ggaggcactg aaagaccagc agaggcataa   6720
ggttcgggaa gaggttgtta ccgtgggcaa ctctgtcaac gaaggcttga accaacctac   6780
ggatgactcg tgctttgacc cctacacagt ttcccattat gccgttggag atgagtggga   6840
acgaatgtct gaatcaggct ttaaactgtt gtgccagtgc ttaggctttg gaagtggtca   6900
tttcagatgt gattcatcta gatggtgcca tgacaatggt gtgaactaca agattggaga   6960
gaagtgggac cgtcagggag aaaatggcca gatgatgagc tgcacatgtc ttgggaacgg   7020
aaaaggagaa ttcaagtgtg accctcatga ggcaacgtgt tacgatgatg ggaagacata   7080
ccacgtagga gaacagtggc agaaggaata tctcggtgcc atttgctcct gcacatgctt   7140
```

-continued tggaggccag cggggctggc gctgtgacaa ctgccgcaga cctgggggtg aacccagtcc 7200
cgaaggcact actggccagt cctacaacca gtattctcag agataccatc agagaacaaa 7260
cactaatgtt aattgcccaa ttgagtgctt catgccttta gatgtacagg ctgacagaga 7320
agattcccga gagtaaatca tctttccaat ccagaggaac aagcatgtct ctctgccaag 7380
atccatctaa actggagtga tgttagcaga cccagcttag agttcttctt tctttcttaa 7440
gccctttgct ctggaggaag ttctccagct tcagctcaac tcacagcttc tccaagcatc 7500
accctgggag tttcctgagg gttttctcat aaatgagggc tgcacattgc ctgttctgct 7560
tcgaagtatt caataccgct cagtatttta aatgaagtga ttctaagatt tggtttggga 7620
tcaataggaa agcatatgca gccaaccaag atgcaaatgt tttgaaatga tatgaccaaa 7680
attttaagta ggaaagtcac ccaaacactt ctgctttcac ttaagtgtct ggcccgcaat 7740
actgtaggaa caagcatgat cttgttactg tgatatttta aatatccaca gtactcactt 7800
tttccaaatg atcctagtaa ttgcctagaa atatctttct cttacctgtt atttatcaat 7860
ttttcccagt atttttatac ggaaaaaatt gtattgaaaa cacttagtat gcagttgata 7920
agaggaattt ggtataatta tggtgggtga ttattttta tactgtatgt gccaaagctt 7980
tactactgtg gaaagacaac tgttttaata aaagatttac attccacaaa aaaaaaaaaa 8040
aggg 8044

<210> SEQ ID NO 136
<211> LENGTH: 841
<212> TYPE: DNA
<213> ORGANISM: Homo sapiens
<220> FEATURE:
<221> NAME/KEY: misc_feature
<223> OTHER INFORMATION: Incyte ID No: 993585.1
<221> NAME/KEY: unsure
<222> LOCATION: 610-611
<223> OTHER INFORMATION: a, t, c, g, or other

<400> SEQUENCE: 136
ccacgcgtcc gcgctgccaa catggtgagt cttactgttg cgggctccgg ggccgtcgac 60
catgccgctc gacctccacc tccgctggga agctgaggcg ccgaacggct cccagagggt 120
cccgggaagc gcatggtgtt caggcgcttc gtggaggttg gccgggtggc ctatgtctcc 180
tttggacctc atgccggaaa attggtcgcg attgtagatg ttattgatca gaacagggct 240
ttggtcgatg gaccttgcac tcaagtgagg agacaggcca tgcctttcaa gtgcatgcag 300
ctcactgatt tcatcctcaa gtttccgcac agtgcccacc agaagtatgt ccgacaagcc 360
tggcagaagg cagacatcaa tacaaaatgg gcagccacac gatgggccaa gaagattgaa 420
gccagagaaa ggaaagccaa gatgacagat tttgatcgtt ttaaagttat gaaggcaaag 480
aaaatgagga acagaataat caagaatgaa gttaagaagc ttcaaaaggc agctctcctg 540
aaagcttctc ccaaaaaagc acctggtact aagggtactg ctgctgctgc tgctgctgct 600
gctgcttctn ntgctaaagt tccagcaaaa aagatcaccg ccgcgagtaa aaaggctcca 660
gcccagaagg ttcctgccca gaaagccaca ggccagaaag cagcgcctgc tccaaaagct 720
cagaagggtc aaaaagctcc agcccagaaa gcacctgctc caaaggcatc tggcaagaaa 780
gcataagtgg caatcataaa aagtaataaa ggttcttttt gacctgttga caaatgtaaa 840
a 841

<210> SEQ ID NO 137

-continued

<211> LENGTH: 878
<212> TYPE: DNA
<213> ORGANISM: Homo sapiens
<220> FEATURE:
<221> NAME/KEY: misc_feature
<223> OTHER INFORMATION: Incyte ID No: 242984.17

<400> SEQUENCE: 137

```
gttgggctgg actcagggac cgactcttcc cgtctcatga ctgtgtttac tgggctggat     60

tttgggaagg ggccagattg catcagacag ggcctgatgg gctggagcca gactgtggtc    120

tgaggaggag acacagcctt ataagctgag ggagtggaga ggcccggggc caggaaagca    180

gagacagaca aagcgttagg agaagaagag aggcagggaa gacaagccag gcacgatggc    240

caccttccca ccagcaacca gcgcccccca gcagccccca ggcccggagg acgaggactc    300

cagcctggat gaatctgacc tctatagcct ggcccattcc tacctcgggc ctctcatcat    360

gcctatgcct acttcacctc tgactcctgc cttggttaca ggaggtggag gccggaaagg    420

tcgcaccaag agagaagctg ctgccaacac caaccgcccc agccctggcg ggcacgagag    480

gaaactggtg accaagctgc agaattcaga gaggaagaag cgaggggcac ggcgctgaga    540

cagagctgga gatgaggcca gaccatggac actacaccca gcaatagaga cgggactgcg    600

gaggaaggag gacccaggac aggatccagg ccggcttgcc acacccccca cccctaggac    660

ttattcccgc tgactgagtc tctgaggggc taccaggaaa gcgcctccaa ccctagcaaa    720

agtgcaagat ggggagtgag aggctgggaa tggaggggca gagccaggaa gatcccccag    780

aaaagaaagc tacagaagaa actggggctc ctccagggtg gcagcaacaa taaatagaca    840

cgcacggcag ccacagcttg ggtgtgtgtt catccttg                            878
```

<210> SEQ ID NO 138
<211> LENGTH: 1002
<212> TYPE: DNA
<213> ORGANISM: Homo sapiens
<220> FEATURE:
<221> NAME/KEY: misc_feature
<223> OTHER INFORMATION: Incyte ID No: 444820.12
<221> NAME/KEY: unsure
<222> LOCATION: 220-243
<223> OTHER INFORMATION: a, t, c, g, or other

<400> SEQUENCE: 138

```
caaatcggct gattctgcat ctggaaactg ccttcatctt gaaagaaaag tttaccagga     60

agtaacccgg gcaaattcac ctcgttggta cgaagagagt gtcagcagag gtcgcctcca    120

gaggaggtgc tgtggagact gagcgcatag cacccttaaa atcctgggac cagggcttct    180

ccacggctcc aggtcccttc tccagccacc cagccccaan nnnnnnnnnn nnnnnnnnnn    240

nnnttccgca ctggctggcc tcttcggtgc ggcagaggga caagcatttc atcttgggaa    300

gtgccccaat cctccggtgc aggagaattt tgacgtgaat aagtatctcg gaagatggta    360

cgaaattgag aagatcccaa caacctttga gaatggacgc tgcatccagg ccaactactc    420

actaatggga aaacggaaag atcaaagtgt taaaccagga gttgagagct gatggaactg    480

tgaatcaaat cgaaggtgaa gccaccccag ttaacctcac agagcctgcc aagctggaag    540

ttaagttttc ctggtttatg ccatcggcac cgtactggat cctggccacc gactatgaga    600

actatgccct cgtgtattcc tgtacctgca tcatccaact ttttcacgtg gattttgctt    660

ggatcttggc aagaaaccct aatctccctc cagaaacagt ggactctcta aaaaatatcc    720

tgacttctaa taacattgat gtcaagaaaa tgacggtcac agaccaggtg aactgcccca    780
```

```
                                              -continued

agctctcgta accaggttct acagggaggc tgcacccact ccatgttact tctgcttcgc    840

tttcccctac cccacccccc ccccataaag acaaaccaat caaccacgac aaaggaagtt    900

gacctgaaca tgtaaccatg ccctaccctg ttaccttgct agctgcaaaa taaacttgtt    960

gctgacctgc tgtgctcgca gtagattcca aaaaaaaaaa aa                     1002
```

GENES EXPRESSED IN ALZHEIMER'S DISEASE

FIELD OF THE INVENTION

Figure 1:
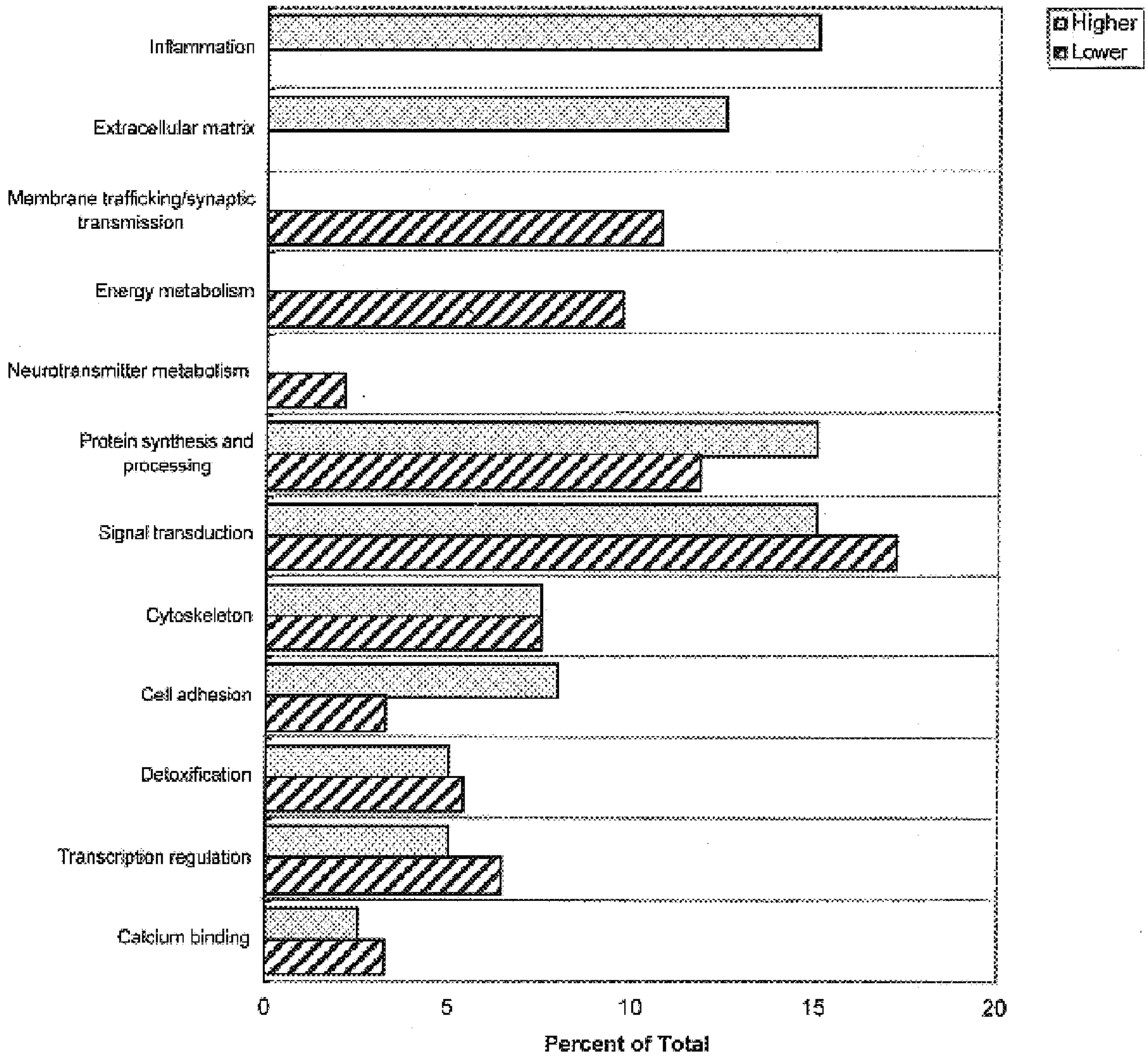

The present invention relates to a composition comprising a plurality of cDNAs which are differentially expressed in Alzheimer's disease and which may be used entirely or in part to diagnose, to stage, to treat, or to monitor the treatment of a subject with a brain disorder.

BACKGROUND OF THE INVENTION

Array technology can provide a simple way to explore the expression of a single polymorphic gene or the expression profile of a large number of related or unrelated genes. When the expression of a single gene is examined, arrays are employed to detect the expression of a specific gene or its variants. When an expression profile is examined, arrays provide a platform for examining which genes are tissue specific, carrying out housekeeping functions, parts of a signaling cascade, or specifically related to a particular genetic predisposition, condition, disease, or disorder.

The potential application of gene expression profiling is particularly relevant to improving diagnosis, prognosis, and treatment of disease. For example, both the levels and sequences expressed in tissues from subjects with Alzheimer's disease may be compared with the levels and sequences expressed in normal brain tissue.

Alzheimer's disease is a progressive neurodegenerative disorder that is characterized by the formation of senile plaques and neurofibrillary tangles containing amyloid beta peptide. These plaques are found in limbic and association cortices of the brain. The hippocampus is part of the limbic system and plays an important role in learning and memory. In subjects with Alzheimer's disease, accumulating plaques damage the neuronal architecture in limbic areas and eventually cripple the memory process.

Approximately twenty million people worldwide suffer with dementia that results from Alzheimer's disease. The disease can be early onset affecting individuals as young as 30 years of age, or it can be familial or sporadic. Familial Alzheimer's disease was once thought to be inherited strictly as an autosomal dominant trait; however, this view is changing as more genetic determinants are isolated. For example, some normal allelic variants of apolipoprotein E (ApoE), which is found in senile plaques, can either protect against or increase the risk of developing the disease (Strittmatter et al. (1993) Proc Natl Acad Sci 90:1977–1981).

Mutations in four genes are known to predispose an individual to Alzheimer's disease: ApoE, amyloid precursor protein (APP), presenilin-1, and presenilin-2 (Selkoe (1999) Nature 399:A23–A31). The e4 allele of the ApoE gene confers increased risk for late onset Alzheimer's disease. β-amyloid protein (Aβ) is the major component of senile plaques, and it is normally formed when β- and γ-secretases cleave APP. In Alzheimer's disease patients, large quantities of Aβ are generated and accumulate extracellularly in these neuropathological plaques. Efforts to understand the mechanism underlying Aβ deposition have recently focused on the APP-cleaving secretases. In fact, two yeast aspartyl proteases have been shown to process APP in vitro (Zhang et al. (1997) Biochim Biophys Acta 1359:110–122). Evidence using peptidomimetic probes further confirms that the secretases are intramembrane-cleaving aspartyl proteases (Wolfe et al. (1999) Biochemistry 38:4720–4727). The presenilin-1 gene is a candidate for the γ-secretase that cleaves the APP carboxyl terminus. Several lines of evidence support the involvement of presenilins in the disease process. Presenilin can be coimmunoprecipitated with APP, and mutations in the presenilin genes increase production of the 42-amino acid peptide form of Aβ. These missense point mutations result in a particularly aggressive, early onset form of the disease (Haas and DeStrooper (1999) Science 286:916–919).

The proteases, BACE1 and BACE2 (β-site APP cleaving enzymes 1 and 2) which appear to be β-secretases, are potential therapeutic targets because of their ability to cleave APP. Vasser et al. (1999; Science 286:735–741) have found that BACE1 is an aspartyl protease with β-secretase activity which cleaves APP to produce Aβ peptide in vitro. It is expressed at moderate levels across all brain regions and is concentrated in neurons but not in glia. BACE2, which has 52% amino acid identity with BACE1, has been described by Saunders et al. (1999; Science 286:1255a). Whereas BACE1 maps to the long arm of chromosome 11, BACE2 maps to the Down syndrome region of chromosome 21 (Acquati et al. (2000) 468: 59–64; Saunders et al. supra). This location is significant because middle-aged Down syndrome patients have enhanced β-amyloid deposits. Other members of the BACE family may also participate in this APP cleavage: the amino terminals of Aβ peptides appear to be cleaved heterogeneously indicating that there may be several β-secretases involved in APP processing (Vasser (1999) Science 286:735–741).

Associations between Alzheimer's disease and many other genes and proteins have been reported. Fetal Alzheimer antigen (FALZ) and synuclein a (SNCA) are found in brain plaques and tangles. Inheritance of some gene polymorphisms is also linked to increased risk of developing the disease. For example, a polymorphism in the gene encoding β2-macroglobulin, a protein that can act as a protease inhibitor, is associated with increased risk for developing a late-onset form of Alzheimer's disease.

The present invention provides for a composition comprising a plurality of cDNAs for use in detecting changes in expression of genes encoding proteins that are associated with Alzheimer's disease. Such a composition can be employed for the diagnosis, prognosis or treatment of Alzheimer's disease and possibly other forms of dementia correlated with differential gene expression. Differential gene expression may also reflect inflammation, proliferation, and glial cell activation which occur secondary to the disease process. The present invention satisfies a need in the art in that it provides a set of differentially expressed genes which may be used entirely or in part to diagnose, to stage, to treat, or to monitor the progression or treatment of a subject with a brain disorder such as Alzheimer's disease.

SUMMARY

The present invention provides a composition comprising a plurality of cDNAs and their complements which are differentially expressed in brain tissues and which are selected from SEQ ID NOs:1–138 as presented in the Sequence Listing. In one embodiment, each cDNA is downregulated at least two-fold, SEQ ID NOs: 1–95; in another embodiment, each cDNA is upregulated at least two-fold, SEQ ID NOs:96–138. In one aspect, the composition is useful to diagnose a brain disorder selected from akathesia, Alzheimer's disease, amnesia, amyotrophic lateral sclerosis, ataxias, bipolar disorder, catatonia, cerebral palsy, cerebrovascular disease Creutzfeldt-Jakob disease, dementia, depression, Down's syndrome, tardive dyskinesia, dystonias, epilepsy, Huntington's disease, multiple sclerosis, muscular dystrophy, neuralgias, rneurofibromatosis, neuropathies, Parkinson's disease, Pick's disease, retinitis pigmentosa, schizophrenia, seasonal affective disorder, senile dementia, stroke, Tourette's syndrome and cancers including adenocarcinomas, melanomas, and teratocarcinomas, particularly of the brain. In another aspect, the composition is immobilized on a substrate.

The invention also provides a high throughput method to detect differential expression of one or more of the cDNAs of the composition. The method comprises hybridizing the substrate comprising the composition with the nucleic acids of a sample, thereby forming one or more hybridization complexes, detecting the hybridization complexes, and comparing the hybridization complexes with those of a standard, wherein differences in the size and signal intensity of each hybridization complex indicates differential expression of nucleic acids in the sample. In one aspect, the sample is from a subject with a brain disorder and differential expression determines an early, mid, and late stage of that disorder.

The invention further provides a high throughput method of screening a library of molecules or compounds to identify a ligand. The method comprises combining the substrate comprising the composition with a library of molecules or compounds under conditions to allow specific binding and detecting specific binding, thereby identifying a ligand. Libraries of molecules or compounds are selected from DNA molecules, RNA molecules, mimetics, peptides, transcription factors and other regulatory proteins.

The invention still further provides an isolated cDNA selected from SEQ ID NOs:16, 34, 59, 86, and 126 as presented in the Sequence Listing. The invention also provides an expression vector comprising the cDNA, a host cell comprising the expression vector, and a method for producing a protein comprising culturing the host cell under conditions for the expression of a protein and recovering the protein from the host cell culture. The invention additionally provides a method for purifying a ligand, the method comprising combining a cDNA of the invention with a sample under conditions which allow specific binding, recovering the bound cDNA, and separating the cDNA from the ligand, thereby obtaining purified ligand.

The present invention provides a purified protein encoded and produced by a cDNA of the invention. The invention also provides a high-throughput method for using a protein to screen a library of molecules or compounds to identify a ligand. The method comprises combining the protein or a portion thereof with the library of molecules or compounds under conditions to allow specific binding and detecting specific binding, thereby identifying a ligand which specifically binds the protein. Libraries of molecules or compounds are selected from DNA molecules, RNA molecules, PNAs, mimetics, peptides, proteins, agonists, antagonists, antibodies or their fragments, immunoglobulins, inhibitors, drug compounds, and pharmaceutical agents. The invention further provides for using a protein to purify a ligand. The method comprises combining the protein or a portion thereof with a sample under conditions to allow specific binding, recovering the bound protein, and separating the protein from the ligand, thereby obtaining purified ligand. The invention still further provides a pharmaceutical composition comprising the protein. The invention yet still further provides a method for using the protein to produce an antibody. The method comprises immunizing an animal with the protein or an antigenically-effective portion thereof under conditions to elicit an antibody response, isolating animal antibodies, and screening the isolated antibodies with the protein to identify an antibody which specifically binds the protein.

DESCRIPTION OF THE SEQUENCE LISTING AND TABLES

A portion of the disclosure of this patent document contains material that is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

The Sequence Listing is a compilation of cDNAs obtained by sequencing and extension of clone inserts. Each sequence is identified by a sequence identification number (SEQ ID NO) and by the clone number (Clone ID) from which it was obtained.

Table 1 lists the cDNAs which are differentially expressed, downregulated at least two-fold, by their SEQ ID NO, Accession number, Clone ID, and by the description associated with at least a fragment of a cDNA found in GenBank. The descriptions were obtained using the sequences of the Sequence Listing and BLAST analysis.

Table 2 lists the cDNAs which are differentially expressed, upregulated at least two-fold, by their SEQ ID NO, Accession number, Clone ID, and by the description associated with at least a fragment of a cDNA found in GenBank. The descriptions were obtained using the sequences of the Sequence Listing and BLAST analysis.

Table 3 lists the source of the RNAs used to produce cDNAs for hybridization to the UNIGEM V microarray (Incyte Pharmaceuticals, Palo Alto Calif.). The columns present the Tissue, Gender, and medical conditions as known for each donor, Person 1 and Person 2.

FIG. 1 is a bar graph that shows changes in gene expression for different groups of functionally related genes. The relative percent of genes on the array with higher levels of expression in Alzheimer's samples vs. controls is indicated with a grey bar, and the relative percent with lower levels of expression is indicated with a hatched bar.

DESCRIPTION OF THE INVENTION

Definitions

"Array" refers to an ordered arrangement of cDNAs. The cDNAs are arranged on a substrate so that there are a "plurality" of cDNAs, preferably at least 10 cDNAs, more preferably at least 100 cDNAs, even more preferably from about 500 to about 1000 cDNAs, and most preferably at least 10,000 cDNAs. Furthermore, the arrangement of the cDNAs on the substrate assures that the size and signal intensity of each hybridization complex formed between a CDNA and a sample nucleic acid is individually distinguishable.

"cDNA" refers to a chain of nucleotides, an isolated polynucleotide, nucleotide, nucleic acid molecule, or any fragment or complement thereof. It may have originated recombinantly or synthetically and be double-stranded or single-stranded, coding and/or noncoding, an exon or an intron of a genomic DNA molecule, or combined with carbohydrate, lipids, protein or inorganic elements or substances. Preferably, the chain is from about 15 to about 10,000 nucleotides, more preferably from about 60 to about 6,000 nucleotides and most preferably from about 4000 to about 5000 nucleotides.

The phrase "cDNA encoding a protein" refers to a nucleic acid sequence that closely aligns with sequences which encode conserved protein motifs or domains that were identified by employing analyses well known in the art. These analyses include Hidden Markov Models (HMMs) such as PFAM (Krogh (1994) J Mol Biol 235:1501–1531; Sonnhamer et al. (1988) Nucl Acids Res 26:320–322), BLAST (Basic Local Alignment Search Tool; Altschul (1993) J Mol Evol 36: 290–300; and Altschul et al. (1990) J Mol Biol 215:403–410), or other analytical tools such as BLIMPS (Henikoff et al. (1998) Nucl Acids Res 26:309–12). Additionally, the phrase may be associated with specific human metabolic processes, conditions, disorders, or diseases.

"Derivative" refers to a cDNA or a protein that has been subjected to a chemical modification such as the replacement of a hydrogen by, for example, an acetyl, acyl, alkyl, amino, formyl, or morpholino group. Derivative cDNAs may encode proteins that retain the essential biological characteristics of naturally occurring proteins.

"Disorder" refers to conditions, diseases or syndromes of the brain and nervous system and includes akathesia, Alzheimer's disease, amnesia, amyotrophic lateral sclerosis, ataxias, bipolar disorder, catatonia, cerebral palsy, cerebrovascular disease Creutzfeldt-Jakob disease, dementia, depression, Down's syndrome, tardive dyskinesia, dystonias, epilepsy, Huntington's disease, multiple sclerosis, muscular dystrophy, neuralgias, neurofibromatosis, neuropathies, Parkinson's disease, Pick's disease, retinitis pigmentosa, schizophrenia, seasonal affective disorder, senile dementia, stroke, Tourette's syndrome and cancers including adenocarcinomas, melanomas, and teratocarcinomas, particularly of the brain.

"Fragment" refers to a chain of at least 18 consecutive nucleotides from any part of a cDNA. Fragments may be used in PCR or hybridization technologies to identify related nucleic acid molecules and to screen for or to purify a ligand. Nucleic acids and their ligands identified in this manner are useful as therapeutics to regulate replication, transcription or translation.

A "hybridization complex" is formed between a cDNA and a nucleic acid of a sample when the purines of one molecule hydrogen bond with the pyrimidines of the complementary molecule. In most cases, the molecules will be completely complementary, e.g., 5'-A-G-T-C-3' base pairs with 3'-T-C-A-G-5'.

"Ligand" refers to any agent, molecule, or compound which will bind specifically to a complementary site on a cDNA molecule, polynucleotide, or protein. Such ligands stabilize or modulate the activity of cDNA molecules, cDNAs or proteins and may be composed of at least one of the following: inorganic and organic substances including nucleic acids, proteins, carbohydrates, fats, and lipids.

"Oligonucleotide" or "oligomer" refers to a nucleotide sequence of at least about 15 nucleotides to as many as about 60 nucleotides, preferably about 18 to 30 nucleotides, and most preferably about 20 to 25 nucleotides that are used as a "primer" or "amplimer" in the polymerase chain reaction (PCR) or as an array element.

"Portion" refers to any part of a protein used for any purpose; but especially, to an epitope for the screening or purification of ligands or for the production of antibodies.

"Post-translational modification" of a protein may involve lipidation, glycosylation, phosphorylation, acetylation, racemization, proteolytic cleavage, and the like. These processes may occur synthetically or biochemically. Biochemical modifications will vary by cellular location, cell type, pH, enzymatic milieu, and the like.

"Probe" refers to a cDNA or a fragment thereof that hybridizes to at least one nucleic acid molecule in a sample or on a substrate. Where the molecular targets are double stranded, the probes may be either sense or antisense strands. Where targets are single stranded, probes are complementary single strands. Probes can be operably linked to reporter molecules for use in hybridization reactions including Southern, northern, in situ, dot blot, array, and like technologies or in screening or purification assays.

"Protein" refers to a polypeptide or any portion thereof. A portion of a protein generally retains biological or immunogenic characteristics of a native protein. An "oligopeptide" is an amino acid sequence of at least about 5 residues, more preferably 10 residues and most preferably about 15 residues that is used as part of a fusion protein to produce an antibody.

"Purified" refers to any molecule or compound that is separated from its natural environment and is at least about 60% free, preferably about 75% free, and most preferably about 90% free, from other components with which it is naturally associated.

"Sample" is used in its broadest sense. A sample containing nucleic acids, proteins, antibodies, and the like may comprise a bodily fluid; a soluble fraction of a cell preparation or media in which cells were grown; a chromosome, an organelle, or membrane isolated or extracted from a cell; genomic DNA, RNA, or cDNA in solution or bound to a substrate; a cell; a tissue; a tissue print; a fingerprint, skin or hair; and the like.

"Specific binding" refers to a special and precise interaction between two molecules which is dependent upon their structure, particularly their molecular side groups. For example, the intercalation of a regulatory protein into the major groove of a DNA molecule, the hydrogen bonding between two single stranded nucleic acids, or the binding between an epitope of a protein and an agonist, antagonist, or antibody.

"Substrate" refers to any rigid or semi-rigid support to which cDNAs or proteins are bound and includes membranes, filters, chips, slides, wafers, fibers, magnetic or nonmagnetic beads, gels, capillaries or other tubing, plates, polymers, and microparticles with a variety of surface forms including wells, trenches, pins, channels and pores.

"Variant" refers to molecules that are recognized variations of a cDNA or a protein encoded by the cDNA. Splice variants may be determined by BLAST score, wherein the score is at least 100, and most preferably at least 400. Allelic variants have a high percent identity to the cDNAs and may differ, for example, by about three bases per hundred bases. "Single nucleotide polymorphism" (SNP) refers to a change in a single base as a result of a substitution, insertion or deletion. The change may be conservative (purine for purine) or non-conservative (purine to pyrimidine) and may or may not result in a change in an encoded amino acid. Such changes may predispose an individual to a specific disease or condition.

The Invention

The present invention provides for a composition comprising a plurality of cDNAs or their complements, SEQ ID NOs:1–138 which may be used on a substrate to diagnose, to stage, to treat or to monitor the progression or treatment of a brain disorder. These cDNAs represent known and novel genes differentially expressed in the cells or tissues of brains from subjects with Alzheimer's disease. The composition may be used in its entirety or in part, as subsets of downregulated cDNAs, SEQ ID NOs:1–95, or of upregulated cDNAs, SEQ ID NOs:96–138. SEQ ID NOs:16, 34, 59, 86, and 126 represent novel cDNAs associated with Alzheimer's disease.

Table 1 shows those genes on the array having lower expression (2× or greater decrease) in Alzheimer's brain samples. Column 1 shows the SEQ ID NO, column 2 shows the Accession number, and column 3 shows a description associated with at least a fragment of a cDNA found in GenBank. Table 2 shows those genes on the array that had higher expression (2× or greater increase) in Alzheimer's brain samples. Column 1 shows the SEQ ID NO, column 2 shows the Accession number, and column 3 shows the description associated with at least a fragment of a cDNA found in GenBank. Table 3 contains information about the origin of tissue samples used to prepare nucleic acids for hybridization with the arrays. Column 1 shows the type of tissue used, column 2 shows the gender, columns 3 and 4 show information about the control used, and the severity of the disease state for each donor, respectively.

FIG. 1 shows functional differences in gene expression that are associated with Alzheimer's disease. Genes were categorized by their likely function in the brain by surveying Genbank accession number and name for both nucleotide and amino acid sequences, as well as surveying the scientific literature on each gene. The percentage of genes in each functional category is shown in the graph.

SEQ ID NOs: 16, 34 and 59 are variants of SEQ ID NOs; 15, 34, and 58, genes downregulated in Alzheimer's brain tissue. SEQ ID NO:16 is 3159 nucleic acids in length and has about 98% match from about nucleic acid 443 to about nucleic acid 3159 with ZAKI-4 (g1435039). ZAKI-4 encodes a thyroid hormone responsive protein and is a member of a gene family that includes the Down syndrome candidate region 1 (DSCR-1, g2612866) gene and the Down syndrome candidate region 1-like 2 (DSCR1-like 2, g6017919) gene. SEQ ID NO:16 differs from ZAKI-4 in the 5' untranslated region and only has 25% amino acid identity with the first 28 amino acids of the ZAKI-4 translated region. This 28 amino acid region of SEQ ID NO:16 has 64% identity with the analogous region of the DSCR1-like 2 protein.

SEQ ID NO:34 is 2677 nucleic acids in length and has about 100% nucleic acid sequence identity from nucleic acid 447 to nucleic acid 1987 with the JNK3 α2 kinase (g1463124). The JNK3 kinases are required for stress-induced neuronal apoptosis SEQ ID NO:34 also has about 99.9% nucleic acid sequence identity from nucleic acid 398 to nucleic acid 2677 to a gene encoding p493F12 MAP kinase (g468150). P493F12 is highly expressed in hippocampus and neocortex and immunoreactive neurons closely match those that are targeted in Alzheimer's brains. SEQ ID NO:34 differs from both JNK α3 and p493F12 MAP kinases at its 5' end, having a 27 nucleotide insertion at nucleic acid 581 which changes the start site of the encoded protein. The encoded protein is likely to start 38 amino acids downstream of the P493F12/JNK3 α2 start sites. An identical insertion is seen in g2002940, a 420 nucleotide EST from human fetal brain (g2002940) which is 100% identical to p493F12 and JNK3 α2 genes over 243 nucleotides of its 5' end. However, the EST sequence diverges following the insertion region. At he amino acid level, SEQ ID NO:34 is more similar to JNK α2 at its 3' end due to a 5 nucleotide deletion at nucleic acid 1793 which is absent in the p493F12 gene.

SEQ ID NO:59 is a variant of SEQ ID NO:58, which has 98% identity from nucleotide 543 to nucleotide 2627 to the TR3 orphan receptor (g292833), an immediate early gene expressed in brain. The variant has identical amino acid sequence to SEQ ID NO:58 over the 3' most 42 amino acids. 5' to this region, the sequences diverge significantly. Whereas SEQ ID NO:58 encodes a protein 240 amino acids in length, the SEQ ID NO:59 variant likely encodes a shorter protein of 84 amino acids.

SEQ ID NOs:86 is a novel sequence downregulated in association with Alzheimer's disease. SEQ ID NO: 86 is 887 nucleotides in length, and has 97% identity from nucleic acid 6 to 73 with g219587, a member of the DnaJ heat shock protein family. SEQ ID NO:126 is a novel sequence upregulated in association with Alzheimer's disease. SEQ ID NO:126 is 1237 amino acids in length and has about 20% sequence identity from about residue, 185 to about residue 746 with a rat ring finger protein Fxy (g5919217; Perry and Ashworth (1999) Curr Biol 9:987–989).

The cDNAs of the invention define a differential expression pattern against which to compare the expression pattern of biopsied and/or in vitro treated neurological tissues. Experimentally, differential expression of the cDNAs can be evaluated by methods including, but not limited to, differential display by spatial immobilization or by gel electrophoresis, genome mismatch scanning, representational discriminant analysis, clustering, transcript imaging and array technologies. These methods may be used alone or in combination.

The composition may be arranged on a substrate and hybridized with tissues from subjects with diagnosed nervous system disorders to identify those sequences which are differentially expressed in both Alzheimer's disease and other nervous system disorders. This allows identification of those sequences of highest diagnostic and potential therapeutic value. In a third aspect, the composition is arranged on a substrate with an additional set of cDNAs, such as cDNAs encoding signaling molecules. Such combinations may be useful in the elucidation of pathways which are affected in a particular brain disorder or to identify new, coexpressed, candidate, therapeutic molecules.

In a fourth aspect, the composition can be used for large scale genetic or gene expression analysis of a large number of novel, nucleic acid molecules. These samples are prepared by methods well known in the art and are from mammalian cells or tissues which are in a certain stage of development; have been treated with a known molecule or compound, such as a cytokine, growth factor, a drug, and the like; or have been extracted or biopsied from a mammal with a known or unknown condition, disorder, or disease before or after treatment. The sample nucleic acid molecules are hybridized to the composition for the purpose of defining a novel gene profile associated with that developmental stage, treatment, or disorder.

cDNAs and Their Use

CDNAs can be prepared by a variety of synthetic or enzymatic methods well known in the art. CDNAs can be synthesized, in whole or in part, using chemical methods well known in the art (Caruthers et al. (1980) Nucleic Acids Symp. Ser. (7)215–233). Alternatively, cDNAs can be produced enzymatically or recombinantly, by in vitro or in vivo transcription.

Nucleotide analogs can be incorporated into cDNAs by methods well known in the art. The only requirement is that the incorporated analog must base pair with native purines or pyrimidines. For example, 2,6-diaminopurine can substitute for adenine and form stronger bonds with thymidine than those between adenine and thymidine. A weaker pair is formed when hypoxanthine is substituted for guanine and base pairs with cytosine. Additionally, cDNAs can include nucleotides that have been derivatized chemically or enzymatically.

CDNAs can be synthesized on a substrate. Synthesis on the surface of a substrate may be accomplished using a chemical coupling procedure and a piezoelectric printing apparatus as described by Baldeschweiler et al. (PCT publication WO95/251116). Alternatively, the cDNAs can be synthesized on a substrate surface using a self-addressable electronic device that controls when reagents are added as described by Heller et al. (U.S. Pat. No. 5,605,662). cDNAs can be synthesized directly on a substrate by sequentially dispensing reagents for their synthesis on the substrate surface or by dispensing preformed DNA fragments to the substrate surface. Typical dispensers include a micropipette delivering solution to the substrate with a robotic system to control the position of the micropipette with respect to the substrate. There can be a multiplicity of dispensers so that reagents can be delivered to the reaction regions efficiently.

cDNAs can be immobilized on a substrate by covalent means such as by chemical bonding procedures or UV irradiation. In one method, a cDNA is bound to a glass surface which has been modified to contain epoxide or aldehyde groups. In another method, a cDNA is placed on a polylysine coated surface and UV cross-linked to it as described by Shalon et al. (WO95/35505). In yet another method, a cDNA is actively transported from a solution to a given position on a substrate by electrical means (Heller, supra). cDNAs do not have to be directly bound to the substrate, but rather can be bound to the substrate through a linker group. The linker groups are typically about 6 to 50 atoms long to provide exposure of the attached cDNA. Preferred linker groups include ethylene glycol oligomers, diamines, diacids and the like. Reactive groups on the substrate surface react with a terminal group of the linker to bind the linker to the substrate. The other terminus of the linker is then bound to the cDNA. Alternatively, polynucleotides, plasmids or cells can be arranged on a filter. In the latter case, cells are lysed, proteins and cellular components degraded, and the DNA is coupled to the filter by UV cross-linking.

The cDNAs may be used for a variety of purposes. For example, the composition of the invention may be used on a microarray. The microarray, in turn, can be used in high-throughput methods for detecting a related polynucleotide in a sample, screening libraries of molecules or compounds to identify a ligand, diagnosing a particular brain disorder, or inhibiting or inactivating a therapeutically relevant gene related to the cDNA.

When the cDNAs of the invention are employed on a microarray, the cDNAs are organized in an ordered fashion so that each cDNA is present at a specified location on the substrate. Because the cDNAs are at specified locations on the substrate, the hybridization patterns and intensities, which together create a unique expression profile, can be interpreted in terms of expression levels of particular genes and can be correlated with a particular metabolic process, condition, disorder, disease, stage of disease, or treatment.

Hybridization

The cDNAs or fragments or complements thereof may be used in various hybridization technologies. The cDNAs may labeled using a variety of reporter molecules by either PCR, recombinant, or enzymatic techniques. For example, a commercially available vector containing the cDNA is transcribed in the presence of an appropriate polymerase, such as T7 or SP6 polymerase, and at least one labeled nucleotide. Commercial kits are available for labeling and cleanup of such cDNAs. Radioactive (Amersham Pharmacia Biotech (APB), Piscataway N.J.), fluorescent (Operon Technologies, Alameda Calif.), and chemiluminescent labeling (Promega, Madison Wis.), are well known in the art.

A cDNA may represent the complete coding region of an mRNA or be designed or derived from unique regions of the mRNA or genomic molecule, an intron, a 3' untranslated region, or from a conserved motif. The cDNA is at least 18 contiguous nucleotides in length and is usually single stranded. Such a cDNA may be used under hybridization conditions that allow binding only to an identical sequence, a naturally occurring molecule encoding the same protein, or an allelic variant. Discovery of related human and mammalian sequences may also be accomplished using a pool of degenerate cDNAs and appropriate hybridization conditions. Generally, a cDNA for use in Southern or northern hybridizations may be from about 400 to about 5000 nucleotides long. Such cDNAs have high binding specificity in solution-based or substrate-based hybridizations. An oligonucleotide, a fragment the cDNA, may be used to detect a polynucleotide in a sample using PCR.

The stringency of hybridization is determined by G+C content of the cDNA, salt concentration, and temperature. In particular, stringency is increased by reducing the concentration of salt or raising the hybridization temperature. In solutions used for some membrane based hybridizations, addition of an organic solvent such as formamide allows the reaction to occur at a lower temperature. Hybridization may be performed with buffers, such as 5× saline sodium citrate (SSC) with 1% sodium dodecyl sulfate (SDS) at 60° C., that permits the formation of a hybridization complex between nucleic acid sequences that contain some mismatches. Subsequent washes are performed with buffers such as 0.2×SSC with 0.1% SDS at either 45° C. (medium stringency) or 65°–68° C. (high stringency). At high stringency, hybridization complexes will remain stable only where the nucleic acid molecules are completely complementary. In some membrane-based hybridizations, preferably 35% or most preferably 50%, formamide may be added to the hybridization solution to reduce the temperature at which hybridization is performed. Background signals may be reduced by the use of detergents such as Sarkosyl or Triton X-100 (Sigma Aldrich, St. Louis Mo.) and a blocking agent such as denatured salmon sperm DNA. Selection of components and conditions for hybridization are well known to those skilled in the art and are reviewed in Ausubel (supra, pp. 6.11–6.19, 14.11–14.36, and A1–43).

Dot-blot, slot-blot, low density and high density arrays are prepared and analyzed using methods known in the art. cDNAs from about 18 consecutive nucleotides to about 5000 consecutive nucleotides in length are contemplated by the invention and used in array technologies. The preferred number of cDNAs on an array is at least about 100,000, a more preferred number is at least about 40,000, an even more preferred number is at least about 10,000, and a most preferred number is at least about 600 to about 800. The array may be used to monitor the expression level of large numbers of genes simultaneously and to identify genetic variants, mutations, and SNPs. Such information may be used to determine gene function; to understand the genetic basis of a disorder; to diagnose a disorder; and to develop and monitor the activities of therapeutic agents being used to control or cure a disorder. (See, e.g., U.S. Pat. No. 5,474,796; WO95/11995; WO95/35505; U.S. Pat. Nos. 5,605,662; and 5,958,342.)

Screening and Purification Assays

A cDNA may be used to screen a library or a plurality of molecules or compounds for a ligand which specifically binds the cDNA. Ligands may be DNA molecules, RNA molecules, PNAs, peptides, proteins such as transcription factors, promoters, enhancers, repressors, and other proteins that regulate replication, transcription, or translation of the polynucleotide in the biological system. The assay involves combining the cDNA or a fragment thereof with the molecules or compounds under conditions that allow specific binding and detecting the bound cDNA to identify at least one ligand that specifically binds the cDNA.

In one embodiment, the cDNA may be incubated with a library of isolated and purified molecules or compounds and binding activity determined by methods such as a gel-retardation assay (U.S. Pat. No. 6,010,849) or a reticulocyte lysate transcriptional assay. In another embodiment, the cDNA may be incubated with nuclear extracts from biopsied and/or cultured cells and tissues. Specific binding between the cDNA and a molecule or compound in the nuclear extract is initially determined by gel shift assay. Protein binding may be confirmed by raising antibodies against the protein and adding the antibodies to the gel-retardation assay where specific binding will cause a supershift in the assay.

In another embodiment, the cDNA may be used to purify a molecule or compound using affinity chromatography methods well known in the art. In one embodiment, the cDNA is chemically reacted with cyanogen bromide groups on a polymeric resin or gel. Then a sample is passed over and reacts with or binds to the cDNA. The molecule or compound which is bound to the cDNA may be released from the cDNA by increasing the salt concentration of the flow-through medium and collected.

The cDNA may be used to purify a ligand from a sample. A method for using a cDNA to purify a ligand would involve combining the cDNA or a fragment thereof with a sample under conditions to allow specific binding, recovering the bound cDNA, and using an appropriate agent to separate the cDNA from the purified ligand.

Protein Production and Uses

The full length cDNAs or fragment thereof may be used to produce purified proteins using recombinant DNA technologies described herein and taught in Ausubel (supra; pp. 16.1–16.62). One of the advantages of producing proteins by these procedures is the ability to obtain highly-enriched sources of the proteins thereby simplifying purification procedures.

The proteins may contain amino acid substitutions, deletions or insertions made on the basis of similarity in polarity, charge, solubility, hydrophobicity, hydrophilicity, and/or the amphipathic nature of the residues involved. Such substitutions may be conservative in nature when the substituted residue has structural or chemical properties similar to the original residue (e.g., replacement of leucine with isoleucine or valine) or they may be nonconservative when the replacement residue is radically different (e.g., a glycine replaced by a tryptophan). Computer programs included in LASERGENE software (DNASTAR, Madison Wis.), MACVECTOR software (Genetics Computer Group, Madison Wis.) and RasMol software (www.umass.edu/microbio/rasmol) may be used to help determine which and how many amino acid residues in a particular portion of the protein may be substituted, inserted, or deleted without abolishing biological or immunological activity.

Expression of Encoded Proteins

Expression of a particular cDNA may be accomplished by cloning the cDNA into a vector and transforming this vector into a host cell. The cloning vector used for the construction of cDNA libraries in the LIFESEQ databases may also be used for expression. Such vectors usually contain a promoter and a polylinker useful for cloning, priming, and transcription. An exemplary vector may also contain the promoter for β-galactosidase, an amino-terminal methionine and the subsequent seven amino acid residues of β-galactosidase. The vector may be transformed into competent *E. coli* cells. Induction of the isolated bacterial strain with isopropylthiogalactoside (IPTG) using standard methods will produce a fusion protein that contains an N terminal methionine, the first seven residues of β-galactosidase, about 15 residues of linker, and the protein encoded by the cDNA.

The cDNA may be shuttled into other vectors known to be useful for expression of protein in specific hosts. Oligonucleotides containing cloning sites and fragments of DNA sufficient to hybridize to stretches at both ends of the cDNA may be chemically synthesized by standard methods. These primers may then be used to amplify the desired fragments by PCR. The fragments may be digested with appropriate restriction enzymes under standard conditions and isolated using gel electrophoresis. Alternatively, similar fragments are produced by digestion of the cDNA with appropriate restriction enzymes and filled in with chemically synthesized oligonucleotides. Fragments of the coding sequence from more than one gene may be ligated together and expressed.

Signal sequences that dictate secretion of soluble proteins are particularly desirable as component parts of a recombinant sequence. For example, a chimeric protein may be expressed that includes one or more additional purification-facilitating domains. Such domains include, but are not limited to, metal-chelating domains that allow purification on immobilized metals, protein A domains. that allow purification on immobilized immunoglobulin, and the domain utilized in the FLAGS extension/affinity purification system (Immunex, Seattle Wash.). The inclusion of a cleavable-linker sequence such as ENTEROKINASEMAX (Invitrogen, San Diego Calif.) between the protein and the purification domain may also be used to recover the protein.

Suitable host cells may include, but are not limited to, mammalian cells such as Chinese Hamster Ovary (CHO) and human 293 cells, insect cells such as Sf9 cells, plant cells such as *Nicotiana tabacum*, yeast cells such as *Saccharomyces cerevisiae*, and bacteria such as *E. coli*. For each of these cell systems, a useful expression vector may also include an origin of replication and one or two selectable markers to allow selection in bacteria as well as in a transformed eukaryotic host. Vectors for use in eukaryotic expression hosts may require the addition of 3' poly(A) tail if the cDNA lacks poly(A).

Additionally, the vector may contain promoters or enhancers that increase gene expression. Many promoters are known and used in the art. Most promoters are host specific and exemplary promoters includes SV40 promoters for CHO cells; T7 promoters for bacterial hosts; viral promoters and enhancers for plant cells; and PGH promoters for yeast. Adenoviral vectors with the rous sarcoma virus enhancer or retroviral vectors with long terminal repeat promoters may be used to drive protein expression in mammalian cell lines. Once homogeneous cultures of recombinant cells are obtained, large quantities of secreted soluble protein may be recovered from the conditioned medium and analyzed using chromatographic methods well known in the art. An alternative method for the production of large amounts of secreted protein involves the transformation of mammalian embryos and the recovery of the recombinant protein from milk produced by transgenic cows, goats, sheep, and the like.

In addition to recombinant production, proteins or portions thereof may be produced manually, using solid-phase techniques (Stewart et al. (1969) *Solid-Phase Peptide Synthesis*, WH Freeman, San Francisco Calif.; Merrifield (1963) J Am Chem Soc 5:2149–2154), or using machines such as the ABI 431A peptide synthesizer (PE Biosystems, Norwalk Conn.). Proteins produced by any of the above methods may be used as pharmaceutical compositions to treat disorders associated with null or inadequate expression of the genomic sequence.

Screening and Purification Assays

A protein or a portion thereof encoded by the cDNA may be used to screen libraries or a plurality of molecules or compounds for a ligand with specific binding affinity or to purify a molecule or compound from a sample. The protein or portion thereof employed in such screening may be free in solution, affixed to an abiotic or biotic substrate, or located intracellularly. For example, viable or fixed prokaryotic host cells that are stably transformed with recombinant nucleic acids that have expressed and positioned a protein on their cell surface can be used in screening assays. The cells are screened against libraries or a plurality of ligands and the specificity of binding or formation of complexes between the expressed protein and the ligand may be measured. The ligands may be DNA, RNA, or PNA molecules, agonists, antagonists, antibodies, immunoglobulins, inhibitors, peptides, pharmaceutical agents, proteins, drugs, or any other test molecule or compound that specifically binds the protein. An exemplary assay involves combining the mammalian protein or a portion thereof with the molecules or compounds under conditions that allow specific binding and detecting the bound protein to identify at least one ligand that specifically binds the protein.

This invention also contemplates the use of competitive drug screening assays in which neutralizing antibodies capable of binding the protein specifically compete with a test compound capable of binding to the protein or oligopeptide or fragment thereof. One method for high throughput screening using very small assay volumes and very small amounts of test compound is described in U.S. Pat. No. 5,876,946. Molecules or compounds identified by screening may be used in a model system to evaluate their toxicity, diagnostic, or therapeutic potential.

The protein may be used to purify a ligand from a sample. A method for using a protein to purify a ligand would involve combining the protein or a portion thereof with a sample under conditions to allow specific binding, recovering the bound protein, and using an appropriate chaotropic agent to separate the protein from the purified ligand.

Production of Antibodies

A protein encoded by a cDNA of the invention may be used to produce specific antibodies. Antibodies may be produced using an oligopeptide or a portion of the protein with inherent immunological activity. Methods for producing antibodies include: 1) injecting an animal, usually goats, rabbits, or mice, with the protein, or an antigenically effective portion or an oligopeptide thereof, to induce an immune response; 2) engineering hybridomas to produce monoclonal antibodies; 3) inducing in vivo production in the lymphocyte population; or 4) screening libraries of recombinant immunoglobulins. Recombinant immunoglobulins may be produced as taught in U.S. Pat. No. 4,816,567.

Antibodies produced using the proteins of the invention are useful for the diagnosis of prepathologic disorders as well as the diagnosis of chronic or acute discases characterized by abnormalities in the expression, amount, or distribution of the protein. A variety of protocols for competitive binding or immunoradiometric assays using either polyclonal or monoclonal antibodies specific for proteins are well known in the art. Immunoassays typically involve the formation of complexes between a protein and its specific binding molecule or compound and the measurement of complex formation.

Immunoassay procedures may be used to quantify expression of the protein in cell cultures, in subjects with a particular disorder or in model animal systems under various conditions. Increased or decreased production of proteins as monitored by immunoassay may contribute to knowledge of the cellular activities associated with developmental pathways, engineered conditions or diseases, or treatment efficacy. The quantity of a given protein in a given tissue may be determined by performing immunoassays on freeze-thawed detergent extracts of biological samples and comparing the slope of the binding curves to binding curves generated by purified protein.

Labeling of Molecules for Assay

A wide variety of reporter molecules and conjugation techniques are known by those skilled in the art and may be used in various cDNA, polynucleotide, protein, peptide or antibody assays. Synthesis of labeled molecules may be achieved using commercial kits for incorporation of a labeled nucleotide such as $^{32}$P-dCTP, Cy3-dCTP or Cy5-dCTP or amino acid such as $^{35}$S-methionine. Polynucleotides, cDNAs, proteins, or antibodies may be directly labeled with a reporter molecule by chemical conjugation to amines, thiols and other groups present in the molecules using reagents such as BIODIPY or FITC (Molecular Probes, Eugene Oreg.).

The proteins and antibodies may be labeled for purposes of assay by joining them, either covalently or noncovalently, with a reporter molecule that provides for a detectable signal. A wide variety of labels and conjugation techniques are known and have been reported in the scientific and patent literature including, but not limited to U.S. Pat. Nos. 3,817,837; 3,850,752; 3,939,350; 3,996,345; 4,277,437; 4,275,149; and 4,366,241.

Diagnostics

The cDNAs, or fragments thereof, may be used to detect and quantify altered gene expression; absence, presence, or excess expression of mRNAs; or to monitor mRNA levels during therapeutic intervention. Disorders associated with altered expression include akathesia, Alzheimer's disease, amnesia, amyotrophic lateral sclerosis, ataxias, bipolar disorder, catatonia, cerebral palsy, cerebrovascular disease Creutzfeldt-Jakob disease, dementia, depression, Down's syndrome, tardive dyskinesia, dystonias, epilepsy, Huntington's disease, multiple sclerosis, muscular dystrophy, neuralgias, neurofibromatosis, neuropathies, Parkinson's disease, Pick's disease, retinitis pigmentosa, schizophrenia, seasonal affective disorder, senile dementia, stroke, Tourette's syndrome and cancers including adenocarcinomas, melanomas, and teratocarcinomas, particularly of the brain. These cDNAs can also be utilized as markers of treatment efficacy against the diseases noted above and other brain disorders, conditions, and diseases over a period ranging from several days to months. The diagnostic assay may use hybridization or amplification technology to compare gene expression in a biological sample from a patient to standard samples in order to detect altered gene expression. Qualitative or quantitative methods for this comparison are well known in the art.

For example, the cDNA may be labeled by standard methods and added to a biological sample from a patient under conditions for the formation of hybridization complexes. After an incubation period, the sample is washed and the amount of label (or signal) associated with hybridization complexes, is quantified and compared with a standard value. If the amount of label in the patient sample is significantly altered in comparison to the standard value, then the presence of the associated condition, disease or disorder is indicated.

In order to provide a basis for the diagnosis of a condition, disease or disorder associated with gene expression, a normal or standard expression profile is established. This may be accomplished by combining a biological sample taken from normal subjects, either animal or human, with a probe under conditions for hybridization or amplification. Standard hybridization may be quantified by comparing the values obtained using normal subjects with values from an experiment in which a known amount of a substantially purified target sequence is used. Standard values obtained in this manner may be compared with values obtained from samples from patients who are symptomatic for a particular condition, disease, or disorder. Deviation from standard values toward those associated with a particular condition is used to diagnose that condition.

Such assays may also be used to evaluate the efficacy of a particular therapeutic treatment regimen in animal studies and in clinical trial or to monitor the treatment of an individual patient. Once the presence of a condition is established and a treatment protocol is initiated, diagnostic assays may be repeated on a regular basis to determine if the level of expression in the patient begins to approximate that which is observed in a normal subject. The results obtained from successive assays may be used to show the efficacy of treatment over a period ranging from several days to months.

Gene Expression Profiles

A gene expression profile comprises a plurality of cDNAs and a plurality of detectable hybridization complexes, wherein each complex is formed by hybridization of one or more probes to one or more complementary sequences in a sample. The cDNA composition of the invention is used as elements on a microarray to analyze gene expression profiles. In one embodiment, the microarray is used to monitor the progression of disease. Researchers can assess and catalog the differences in gene expression between healthy and diseased tissues or cells. By analyzing changes in patterns of gene expression, disease can be diagnosed at earlier stages before the patient is symptomatic. The invention can be used to formulate a prognosis and to design a treatment regimen. The invention can also be used to monitor the efficacy of treatment. For treatments with known side effects, the microarray is employed to improve the treatment regimen. A dosage is established that causes a change in genetic expression patterns indicative of successful treatment. Expression patterns associated with the onset of undesirable side effects are avoided. This approach may be more sensitive and rapid than waiting for the patient to show inadequate improvement, or to manifest side effects, before altering the course of treatment.

In another embodiment, animal models which mimic a human disease can be used to characterize expression profiles associated with a particular condition, disorder or disease or treatment of the condition, disorder or disease. Novel treatment regimens may be tested in these animal models using microarrays to establish and then follow expression profiles over time. In addition, microarrays may be used with cell cultures or tissues removed from animal models to rapidly screen large numbers of candidate drug molecules, looking for ones that produce an expression profile similar to those of known therapeutic drugs, with the expectation that molecules with the same expression profile will likely have similar therapeutic effects. Thus, the invention provides the means to rapidly determine the molecular mode of action of a drug.

Assays Using Antibodies

Antibodies directed against epitopes on a protein encoded by a cDNA of the invention may be used in assays to quantify the amount of protein found in a particular human cell. Such assays include methods utilizing the antibody and a label to detect expression level under normal or disease conditions. The antibodies may be used with or without modification, and labeled by joining them, either covalently or noncovalently, with a labeling moiety.

Protocols for detecting and measuring protein expression using either polyclonal or monoclonal antibodies are well known in the art. Examples include ELISA, RIA, and fluorescent activated cell sorting (FACS). Such immunoassays typically involve the formation of complexes between the protein and its specific antibody and the measurement of such complexes. These and other assays are described in Pound (supra). The method may employ a two-site, monoclonal-based immunoassay utilizing monoclonal antibodies reactive to two non-interfering epitopes, or a competitive binding assay. (See, e.g., Coligan et al. (1997) *Current Protocols in Immunology*, Wiley-Interscience, New York N.Y.; Pound, supra)

Therapeutics

The cDNAs and fragments thereof can be used in gene therapy. cDNAs can be delivered ex vivo to target cells, such as cells of bone marrow. Once stable integration and transcription and or translation are confirmed, the bone marrow may be reintroduced into the subject. Expression of the protein encoded by the cDNA may correct a disease state associated with mutation of a normal sequence, reduction or loss of an endogenous target protein, or overepression of an endogenous or mutant protein. Alternatively, cDNAs may be delivered in vivo using vectors such as retrovirus, adenovirus, adeno-associated virus, herpes simplex virus, and bacterial plasmids. Non-viral methods of gene delivery include cationic liposomes, polylysine conjugates, artificial viral envelopes, and direct injection of DNA (Anderson (1998) Nature 392:25–30; Dachs et al. (1997) Oncol Res 9:313–325; Chu et al. (1998) J Mol Med 76(3–4):184–192; Weiss et al. (1999) Cell Mol Life Sci 55(3):334–358; Agrawal (1996) *Antisense Therapeutics*, Humana Press, Totowa N.J.; and August et al. (1997) *Gene Therapy (Advances in Pharmacology*, Vol. 40), Academic Press, San Diego Calif.).

In addition, expression of a particular protein can be modulated through the specific binding of a fragment of a cDNA to a genomic sequence or an mRNA which encodes the protein or directs its transcription or translation. The cDNA can be modified or derivatized to any RNA-like or DNA-like material including peptide nucleic acids, branched nucleic acids, and the like. These sequences can be produced biologically by transforming an appropriate host cell with an expression vector containing the sequence of interest.

Molecules which modulate the activity of the cDNA or encoded protein are useful as therapeutics for brain disorders. Such molecules include agonists which increase the expression or activity of the polynucleotide or encoded protein, respectively; or antagonists which decrease expression or activity of the polynucleotide or encoded protein, respectively. In one aspect, an antibody which specifically binds the protein may be used directly as an antagonist or indirectly as a delivery mechanism for bringing a pharmaceutical agent to cells or tissues which express the protein.

Additionally, any of the proteins, or their ligands, or complementary nucleic acid sequences may be administered in combination with other appropriate therapeutic agents. Selection of the appropriate agents for use in combination therapy may be made by one of ordinary skill in the art, according to conventional pharmaceutical principles. The combination of therapeutic agents may act synergistically to affect the treatment or prevention of the conditions and disorders associated with an immune response. Using this approach, one may be able to achieve therapeutic efficacy with lower dosages of each agent, thus reducing the potential for adverse side effects. Further, the therapeutic agents may be combined with pharmaceutically-acceptable carriers including excipients and auxiliaries which facilitate processing of the active compounds into preparations which can be used pharmaceutically. Further details on techniques for formulation and administration may be found in the latest edition of *Remington's Pharmaceutical Sciences* (Maack Publishing, Easton Pa.).

Model Systems

Animal models may be used as bioassays where they exhibit a phenotypic response similar to that of humans and where exposure conditions are relevant to human exposures. Mammals are the most common models, and most infectious agent, cancer, drug, and toxicity studies are performed on rodents such as rats or mice because of low cost, availability, lifespan, reproductive potential, and abundant reference literature. Inbred and outbred rodent strains provide a convenient model for investigation of the physiological consequences of underexpression or overexpression of genes of interest and for the development of methods for diagnosis and treatment of diseases. A mammal inbred to overexpress a particular gene (for example, secreted in milk) may also serve as a convenient source of the protein expressed by that gene.

Transgenic Animal Models

Transgenic rodents that overexpress or underexpress a gene of interest may be inbred and used to model human diseases or to test therapeutic or toxic agents. (See, e.g., U.S. Pat. Nos. 5,175,383 and 5,767,337.) In some cases, the introduced gene may be activated at a specific time in a specific tissue type during fetal or postnatal development. Expression of the transgene is monitored by analysis of phenotype, of tissue-specific mRNA expression, or of serum and tissue protein levels in transgenic animals before, during, and after challenge with experimental drug therapies.

Embryonic Stem Cells

Embryonic (ES) stem cells isolated from rodent embryos retain the potential to form embryonic tissues. When ES cells such as the mouse 129/SvJ cell line are placed in a blastocyst from the C57BL/6 mouse strain, they resume normal development and contribute to tissues of the live-born animal. ES cells are preferred for use in the creation of experimental knockout and knockin animals. The method for this process is well known in the art and the steps are: the cDNA is introduced into a vector, the vector is transformed into ES cells, transformed cells are identified and microinjected into mouse cell blastocysts, blastocysts are surgically transferred to pseudopregnant dams. The resulting chimeric progeny are genotyped and bred to produce heterozygous or homozygous strains.

Knockout Analysis

In gene knockout analysis, a region of a gene is enzymatically modified to include a non-natural intervening sequence such as the neomycin phosphotransferase gene (neo; Capecchi (1989) Science 244:1288–1292). The modified gene is transformed into cultured ES cells and integrates into the endogenous genome by homologous recombination. The inserted sequence disrupts transcription and translation of the endogenous gene.

Knockin Analysis

ES cells can be used to create knockin humanized animals or transgenic animal models of human diseases. With knockin technology, a region of a human gene is injected into animal ES cells, and the human sequence integrates into the animal cell genome. Transgenic progeny or inbred lines are studied and treated with potential pharmaceutical agents to obtain information on the progression and treatment of the analogous human condition.

As described herein, the uses of the cDNAs, provided in the Sequence Listing of this application, and their encoded proteins are exemplary of known techniques and are not intended to reflect any limitation on their use in any technique that would be known to the person of average skill in the art. Furthermore, the cDNAs provided in this application may be used in molecular biology techniques that have not yet been developed, provided the new techniques rely on properties of nucleotide sequences that are currently known to the person of ordinary skill in the art, e.g., the triplet genetic code, specific base pair interactions, and the like. Likewise, reference to a method may include combining more than one method for obtaining or assembling full length cDNA sequences that will be known to those skilled in the art. It is also to be understood that this invention is not limited to the particular methodology, protocols, and reagents described, as these may vary. It is also understood that the terminology used herein is for the purpose of describing particular embodiments only, and is not intended to limit the scope of the present invention which will be limited only by the appended claims. The examples below are provided to illustrate the subject invention and are not included for the purpose of limiting the invention.

EXAMPLES

I Construction of cDNA Libraries

RNA was purchased from Clontech Laboratories (Palo Alto Calif.) or isolated from various tissues. Some tissues were homogenized and lysed in guanidinium isothiocyanate, while others were homogenized and lysed in phenol or in a suitable mixture of denaturants, such as TRIZOL reagent (Life Technologies, Rockville Md.). The resulting lysates were centrifuged over CsCl cushions or extracted with chloroform. RNA was precipitated with either isopropanol or ethanol and sodium acetate, or by other routine methods.

Phenol extraction and precipitation of RNA were repeated as necessary to increase RNA purity. In most cases, RNA was treated with DNase. For most libraries, poly(A) RNA was isolated using oligo d(T)-coupled paramagnetic particles (Promega), OLIGOTEX latex particles (Qiagen, Valencia Calif.), or an OLIGOTEX mRNA purification kit (Qiagen). Alternatively, poly(A) RNA was isolated directly from tissue lysates using other kits, including the POLY(A) PURE mRNA purification kit (Ambion, Austin Tex.).

In some cases, Stratagene (La Jolla Calif.) was provided with RNA and constructed the corresponding cDNA libraries. Otherwise, cDNA was synthesized and cDNA libraries were constructed with the UNIZAP vector system (Stratagene) or SUPERSCRIPT plasmid system (Life Technologies) using the recommended procedures or similar methods known in the art. (See Ausubel, supra, Units 5.1 through 6.6.) Reverse transcription was initiated using oligo d(T) or random primers. Synthetic oligonucleotide adapters were ligated to double stranded cDNA, and the cDNA was digested with the appropriate restriction enzyme or enzymes. For most libraries, the cDNA was size-selected (300–1000 bp) using SEPHACRYL S1000, SEPHAROSE CL2B, or SEPHAROSE CL4B column chromatography (APB) or preparative agarose gel electrophoresis. cDNAs. were ligated into compatible restriction enzyme sites of the polylinker of the PBLUESCRIPT phagemid (Stratagene), PSPORT1 plasmid (Life Technologies), or PINCY plasmid (Incyte Pharmaceuticals). Recombinant plasmids were transformed into XL1-BLUE, XL1-BLUEMRF, or SOLR competent *E. coli* cells (Stratagene) or DH5α, DH10B, or ELECTROMAX DH10B competent *E. coli* cells (Life Technologies).

In some cases, libraries were superinfected with a 5× excess of the helper phage, M13K07, according to the method of Vieira et al. (1987, Methods Enzymol. 153:3–11) and normalized or subtracted using a methodology adapted from Soares (1994, Proc Natl Acad Sci 91:9228–9232), Swaroop et al. (1991, Nucl Acids Res 19:1954), and Bonaldo et al. (1996, Genome Research 6:791–806). The modified Soares normalization procedure was utilized to reduce the repetitive cloning of highly expressed high abundance cDNAs while maintaining the overall sequence complexity of the library. Modification included significantly longer hybridization times which allowed for increased gene discovery rates by biasing the normalized libraries toward those infrequently expressed low-abundance cDNAs which are poorly represented in a standard transcript image (Soares et al., supra).

II Isolation and Sequencing of cDNA Clones

Plasmids were recovered from host cells by in vivo excision using the UNIZAP vector system (Stratagene) or by cell lysis. Plasmids were purified using one of the following: the Magic or WIZARD MINIPREPS DNA purification system (Promega); the AGTC MINIPREP purification kit (Edge BioSystems, Gaithersburg Md.); the QIAWELL 8, QIAWELL 8 Plus, or QIAWELL 8 Ultra plasmid purification systems, or the REAL PREP 96 plasmid purification kit (QIAGEN). Following precipitation, plasmids were resuspended in 0.1 ml of distilled water and stored, with or without lyophilization, at 4° C.

Alternatively, plasmid DNA was amplified from host cell lysates using direct link PCR in a high-throughput format (Rao (1994) Anal Biochem 216:1–14). Host cell lysis and thermal cycling steps were carried out in a single reaction mixture. Samples were processed and stored in 384-well plates, and the concentration of amplified plasmid DNA was quantified fluorometrically using PICOGREEN dye (Molecular Probes) and a FLUOROSKAN II fluorescence scanner (Labsystems Oy, Helsinki, Finland).

cDNA sequencing reactions were processed using standard methods or high-throughput instrumentation such as the ABI CATALYST 800 thermal cycler (PE Biosystems) or the DNA ENGINE thermal cycler (MJ Research, Watertown Mass.) in conjunction with the HYDRA microdispenser (Robbins Scientific, Sunnyvale Calif.) or the MICROLAB 2200 system (Hamilton, Reno Nev.). cDNA sequencing reactions were prepared using reagents provided by APB or supplied in ABI sequencing kits such as the ABI PRISM BIGDYE cycle sequencing kit (PE Biosystems). Electrophoretic separation of cDNA sequencing reactions and detection of labeled cDNAs were carried out using the MEGABACE 1000 DNA sequencing system (APB); the ABI PRISM 373 or 377 sequencing systems (PE Biosystems) in conjunction with standard ABI protocols and base calling software; or other sequence analysis systems known in the art. Reading frames within the cDNA sequences were identified using standard methods (reviewed in Ausubel, supra, Unit 7.7).

III Extension of cDNA Sequences

Nucleic acid sequences were extended using the cDNA clones and oligonucleotide primers. One primer was synthesized to initiate 5' extension of the known fragment, and the other, to initiate 3' extension of the known fragment. The initial primers were designed using OLIGO 4.06 software (National Biosciences), or another appropriate program, to be about 22 to 30 nucleotides in length, to have a GC content of about 50% or more, and to anneal to the target sequence at temperatures of about 68° C. to about 72° C. Any stretch of nucleotides which would result in hairpin structures and primer-primer dimerizations was avoided.

Selected human cDNA libraries were used to extend the sequence. If more than one extension was necessary or desired, additional or nested sets of primers were designed. Preferred libraries are ones that have been size-selected to include larger cDNAs. Also, random primed libraries are preferred because they will contain more sequences with the 5' and upstream regions of genes. A randomly primed library is particularly useful if an oligo d(T) library does not yield a full-length cDNA.

High fidelity amplification was obtained by PCR using methods well known in the art. PCR was performed in 96-well plates using the DNA ENGINE thermal cycler (MJ Research). The reaction mix contained DNA template, 200 nmol of each primer, reaction buffer containing $Mg^{2+}$, $(NH_4)_2SO_4$, and β-mercaptoethanol, Taq DNA polymerase (APB), ELONGASE enzyme (Life Technologies), and Pfu DNA polymerase (Stratagene), with the following parameters for primer pair PCI A and PCI B (Incyte Pharmaceuticals): Step 1: 94° C., 3 min; Step 2: 94° C., 15 sec; Step 3: 60° C., 1 min; Step 4: 68° C., 2 min; Step 5: Steps 2, 3, and 4 repeated 20 times; Step 6: 68° C., 5 min; Step 7: storage at 4° C., 2 min; alternative, the parameters for primer pair T7 and SK+(Stratagene) were as follows: Step 1: 94° C., 3 min; Step 2: 94° C., 15 sec; Step 3: 57° C., 1 min; Step 4: 68° C., 2 min; Step 5: Steps 2, 3, and 4 repeated 20 times; Step 6: 68° C., 5 min; Step 7: storage at 4° C.

The concentration of DNA in each well was determined by dispensing 100 μl PICOGREEN reagent (0.25% reagent in 1×TE, v/v; Molecular Probes) and 0.5 μl of undiluted PCR product into each well of an opaque fluorimeter plate (Coming Costar, Acton Mass.) and allowing the DNA to bind to the reagent. The plate was scanned in a FLUOROSKAN II (Labsystems Oy) to measure the fluorescence of the sample and to quantify the concentration of DNA. A 5 μl to 10 μl aliquot of the reaction mixture was analyzed by electrophoresis on a 1% agarose mini-gel to determine which reactions were successful in extending the sequence.

The extended nucleic acids were desalted and concentrated, transferred to 384-well plates, digested with CviJI cholera virus endonuclease (Molecular Biology Research, Madison Wis.), and sonicated or sheared prior to religation into pUC 18 vector (APB). For shotgun sequencing, the digested nucleic acids were separated on low concentration (0.6 to 0.8%) agarose gels, fragments were excised, and agar digested with AGARACE enzyme (Promega). Extended clones were religated using T4 DNA ligase (New England Biolabs, Beverly Mass.) into pUC18 vector (APB), treated with Pfu DNA polymerase (Stratagene) to fill-in restriction site overhangs, and transformed into competent *E. coli* cells. Transformed cells were selected on antibiotic-containing media, and individual colonies were picked and cultured overnight at 37° C. in 384-well plates in LB/2×carbenicillin liquid media.

The cells were lysed, and DNA was amplified by PCR using Taq DNA polymerase (APB) and Pfu DNA polymerase (Stratagene) with the following parameters: Step 1: 94° C., 3 min; Step 2: 94° C., 15 sec; Step 3: 60° C., 1 min; Step 4: 72° C., 2 min; Step 5: steps 2, 3, and 4 repeated 29 times; Step 6: 72° C., 5 min; Step 7: storage at 4° C. DNA was quantified using PICOGREEN reagent (Molecular Probes) as described above. Samples with low DNA recoveries were reamplified using the same conditions described above. Samples were diluted with 20% dimethylsulfoxide (DMSO; 1:2, v/v), and sequenced using DYENAMIC energy transfer sequencing primers and the DYENAMIC DIRECT cycle sequencing kit (APB) or the ABI PRISM BIGDYE terminator cycle sequencing kit (PE Biosystems).

IV Assembly and Analysis of Sequences

Component nucleotide sequences from chromatograms were subjected to PHRED analysis (Phil Green, University of Washington, Seattle Wash.) and assigned a quality score. The sequences having at least a required quality score were subject to various pre-processing algorithms to eliminate low quality 3' ends, vector and linker sequences, polyA tails, Alu repeats, mitochondrial and ribosomal sequences, bacterial contamination sequences, and sequences smaller than 50 base pairs. Sequences were screened using the BLOCK 2 program (Incyte Pharmaceuticals), a motif analysis program based on sequence information contained in the SWISS-PROT and PROSITE databases (Bairoch et al. (1997) Nucleic Acids Res 25:217–221; Attwood et al. (1997) J Chem Inf Comput Sci 37:417–424).

Processed sequences were subjected to assembly procedures in which the sequences were assigned to bins, one sequence per bin. Sequences in each bin were assembled to produce consensus sequences, templates. Subsequent new sequences were added to existing bins using BLAST (Altschul (supra); Altschul et al. (supra); Karlin et al. (1988) Proc Natl Acad Sci 85:841–845), BLASTn (vers.1.4, WashU), and CROSSMATCH software (Phil Green, supra). Candidate pairs were identified as all BLAST hits having a quality score greater than or equal to 150. Alignments of at least 82% local identity were accepted into the bin. The component sequences from each bin were assembled using PHRAP (Phil Green, supra). Bins with several overlapping component sequences were assembled using DEEP PHRAP (Phil Green, supra).

Bins were compared against each other, and those having local similarity of at least 82% were combined and reassembled. Reassembled bins having templates of insufficient overlap (less than 95% local identity) were re-split. Assembled templates were also subjected to analysis by STITCHER/EXON MAPPER algorithms which analyzed the probabilities of the presence of splice variants, alternatively spliced exons, splice junctions, differential expression of alternative spliced genes across tissue types, disease states, and the like. These resulting bins were subjected to several rounds of the above assembly procedures to generate the template sequences found in the LWFESEQ GOLD database (Incyte Pharmaceuticals).

The assembled templates were annotated using the following procedure. Template sequences were analyzed using BLASTn (vers. 2.0, NCBI) versus GBpri (GenBank vers. 116). "Hits" were defined as an exact match having from 95% local identity over 200 base pairs through 100% local identity over 100 base pairs, or a homolog match having an E-value equal to or greater than $1\times10^{-8}$. (The "E-value" quantifies the statistical probability that a match between two sequences occurred by chance). The hits were subjected to frameshift FASTx versus GENPEPT (GenBank version 109). In this analysis, a homolog match was defined as having an E-value of $1\times10^{-8}$. The assembly method used above was described in U.S. Ser. No. 09/276,534, filed Mar. 25, 1999, and the LWFESEQ GOLD user manual (Incyte Pharmaceuticals).

Following assembly, template sequences were subjected to motif, BLAST, Hidden Markov Model (HMM; Pearson and Lipman (1988) Proc Natl Acad Sci 85:2444–2448; Smith and Waterman (1981) J Mol Biol 147:195–197), and functional analyses, and categorized in protein hierarchies using methods described in U.S. Ser. No. 08/812,290, filed Mar. 6, 1997; U.S. Ser. No. 08/947,845, filed Oct. 9, 1997; U.S. Pat. No. 5,953,727; and U.S. Ser. No. 09/034,807, filed Mar. 4, 1998. Template sequences may be further, queried against public databases such as the GenBank rodent, mammalian, vertebrate, eukaryote, prokaryote, and human EST databases.

V Selection of Sequences, Microarray Preparation and Use

Incyte clones were mapped to non-redundant Unigene clusters (Unigene database (build 46), NCBI; Shuler (1997) J Mol Med 75:694–698), and the 5' clone with the strongest BLAST alignment (at least 90% identity and 100 bp overlap) was chosen, verified, and used in the construction of the microarray. The UNIGEM V microarray (Incyte Pharmaceuticals) contains 7075 array elements which represent 4610 annotated genes and 2,184 unannotated clusters. Tables 1 and 2 show the GenBank annotations for SEQ ID NOs:1–138 of this invention as produced by BLAST analysis.

Purified cDNAs were immobilized on polymer-coated glass slides. Glass microscope slides (Corning, Corning N.Y.) were cleaned by ultrasound in 0.1% SDS and acetone, with extensive distilled water washes between and after treatments. Glass slides were etched in 4% hydrofluoric acid (VWR Scientific Products, West Chester Pa.), washed extensively in distilled water, and coated with 0.05% aminopropyl silane (Sigma Aldrich) in 95% ethanol. Coated slides were cured in a 110° C. oven. cDNAs were applied to the coated glass substrate using a procedure described in U.S. Pat. No. 5,807,522. One microliter of the cDNA at an average concentration of 100 ng/ul was loaded into the open capillary printing element by a high-speed robotic apparatus which then deposited about 5 nl of cDNA per slide.

Microarrays were UV-crosslinked using a STRATALINKER UV-crosslinker (Stratagene), and then washed at room temperature once in 0.2% SDS and three times in distilled water. Non-specific binding sites were blocked by incubation of microarrays in 0.2% casein in phosphate buffered saline (Tropix, Bedford Mass.) for 30 minutes at 60° C. followed by washes in 0.2% SDS and distilled water as before.

Twenty-two UNIGEM V arrays were used to evaluate differential expression across the patient and control tissue samples.

VI Preparation of Samples

The tissues used to prepare nucleic acids to be hybridized with the array are described in Table 3 and were obtained from Dr. John Lee; Department of Pathology Loyola University School of Medicine, Maywood Ill. Total RNA was extracted using the RNA STAT-60 kit (Tel-Test, Friendswood Tex.). Poly(A) RNA was purified using the POLYATRACT mRNA isolation system (Promega). Each poly(A) RNA sample was reverse transcribed using MMLV reverse-transcriptase, 0.05 pg/$\mu$l oligo-d(T) primer (21 mer), 1× first strand buffer, 0.03 units/ul RNase inhibitor, 500 uM dATP, 500 uM dGTP, 500 uM dTTP, 40 uM dCTP, and 40 uM either dCTP-Cy3 or dCTP-Cy5 (APB). The reverse transcription reaction was performed in a 25 ml volume containing 200 ng poly(A) RNA using the GEMBRIGHT kit (Incyte Pharmaceuticals). Specific control poly(A) RNAs (YCFR06, YCFR45, YCFR67, YCFR85, YCFR43, YCFR22, YCFR23, YCFR25, YCFR44, YCFR26) were synthesized by in vitro transcription from non-coding yeast genomic DNA (W. Lei, unpublished). As quantitative controls, control mRNAs (YCFR06, YCFR45, YCFR67, and YCFR85) at 0.002 ng, 0.02 ng, 0.2 ng, and 2 ng were diluted into reverse transcription reaction at ratios of 1:100,000, 1:10,000, 1:1000, 1:100 (w/w) to sample mRNA, respectively. To sample differential expression patterns, control mRNAs (YCFR43, YCFR22, YCFR23, YCFR25, YCFR44, YCFR26) were diluted into reverse transcription reaction at ratios of 1:3, 3:1, 1:10, 10:1, 1:25, 25:1 (w/w) to sample mRNA. Reactions were incubated at 37° C. for 2 hr, treated with 2.5 ml of 0.5M sodium hydroxide, and incubated for 20 minutes at 85° C. to the stop the reaction and degrade the RNA.

cDNAs were purified using two successive CHROMA SPIN 30 gel filtration spin columns (Clontech). Cy3- and Cy5-labeled reaction samples were combined as described below and ethanol precipitated using 1 ml of glycogen (1 mg/ml), 60 ml sodium acetate, and 300 ml of 100% ethanol. The cDNAs were then dried to completion using a SpeedVAC system (Savant Instruments, Holbrook N.Y.) and resuspended in 14 $\mu$l 5×SSC/0.2% SDS.

VII Hybridization and Detection

Hybridization reactions contained 9 $\mu$l of sample mixture containing 0.2 $\mu$g each of Cy3 and Cy5 labeled cDNA synthesis products in 5×SSC, 0.2% SDS hybridization buffer. The mixture was heated to 65° C. for 5 minutes and was aliquoted onto the microarray surface and covered with an 1.8 $cm^2$ coverslip. The microarrays were transferred to a waterproof chamber having a cavity just slightly larger than a microscope slide. The chamber was kept at 100% humidity internally by the addition of 140 $\mu$l of 5×SSC in a corner of the chamber. The chamber containing the microarrays was incubated for about 6.5 hours at 60° C. The microarrays were washed for 10 min at 45° C. in low stringency wash buffer (1×SSC, 0.1% SDS), three times for 10 minutes each at 45° C. in high stringency wash buffer (0.1×SSC), and dried.

Reporter-labeled hybridization complexes were detected with a microscope equipped with an Innova 70 mixed gas 10 W laser (Coherent, Santa Clara Calif.) capable of generating spectral lines at 488 nm for excitation of Cy3 and at 632 nm for excitation of Cy5. The excitation laser light was focused on the microarray using a 20× microscope objective (Nikon, Melville N.Y.). The slide containing the microarray was placed on a computer-controlled X-Y stage on the microscope and raster-scanned past the objective. The 1.8 cm×1.8 cm microarray used in the present example was scanned with a resolution of 20 micrometers.

In two separate scans, the mixed gas multiline laser excited the two fluorophores sequentially. Emitted light was split, based on wavelength, into two photomultiplier tube detectors (PMT R1477; Hamamatsu Photonics Systems, Bridgewater N.J.) corresponding to the two fluorophores. Appropriate filters positioned between the microarray and the photomultiplier tubes were used to filter the signals. The emission maxima of the fluorophores used were 565 nm for Cy3 and 650 nm for Cy5. Each microarray was typically scanned twice, one scan per fluorophore using the appropriate filters at the laser source, although the apparatus was capable of recording the spectra from both fluorophores simultaneously.

The sensitivity of the scans was calibrated using the signal intensity generated by a cDNA control species. Samples of the calibrating cDNA were separately labeled with the two fluorophores and identical amounts of each were added to the hybridization mixture. A specific location on the microarray contained a complementary DNA sequence, allowing the intensity of the signal at that location to be correlated with a weight ratio of hybridizing species of 1:100,000.

The output of the photomultiplier tube was digitized using a 12-bit RTI-835H analog-to-digital (A/D) conversion board (Analog Devices, Norwood, Mass.) installed in an IBM-compatible PC computer. The digitized data were displayed as an image where the signal intensity was mapped using a linear 20-color transformation to a pseudocolor scale ranging from blue (low signal) to red (high signal). The data was also analyzed quantitatively. Where two different fluorophores were excited and measured simultaneously, the data were first corrected for optical crosstalk (due to overlapping emission spectra) between the fluorophores using each fluorophore's emission spectrum.

A grid was superimposed over the fluorescence signal image such that the signal from each spot was centered in each element of the grid. The fluorescence signal within each element was then integrated to obtain a numerical value corresponding to the average intensity of the signal. The software used for signal analysis was the GEMTOOLS gene expression analysis program (Incyte Pharmaceuticals). Significance was defined as signal to background ratio exceeding 2× and area hybridization exceeding 40%.

VIII Other Hybridization Technologies and Analyses

Other hybridization technologies utilize a variety of substrates such as nylon membranes, capillary tubes, etc. Arranging cDNAs on polymer coated slides is described in Example V; sample cDNA preparation and hybridization and analysis using polymer coated slides is described in examples VI and VII, respectively.

The cDNAs are applied to a membrane substrate by one of the following methods. A mixture of cDNAs is fractionated by gel electrophoresis and transferred to a nylon membrane by capillary transfer. Alternatively, the cDNAs are individually ligated to a vector and inserted into bacterial host cells to form a library. The cDNAs are then arranged on a substrate by one of the following methods. In the first method, bacterial cells containing individual clones are robotically picked and arranged on a nylon membrane. The membrane is placed on LB agar containing selective agent (carbenicillin, kanamycin, ampicillin, or chloramphenicol depending on the vector used) and incubated at 37° C. for 16 hr. The membrane is removed from the agar and consecutively placed colony side up in 10% SDS, denaturing solution (1.5 M NaCl, 0.5 M NaOH ), neutralizing solution (1.5 M NaCl, 1 M Tris, pH 8.0), and twice in 2×SSC for 10 min each. The membrane is then UV irradiated in a STRATALINKER UV-crosslinker (Stratagene).

In the second method, cDNAs are amplified from bacterial vectors by thirty cycles of PCR using primers complementary to vector sequences flanking the insert. PCR amplification increases a starting concentration of 1–2 ng nucleic acid to a final quantity greater than 5 $\mu$g. Amplified nucleic acids from about 400 bp to about 5000 bp in length are purified using SEPHACRYL-400 beads (APB). Purified nucleic acids are arranged on a nylon membrane manually or using a dot/slot blotting manifold and suction device and are immobilized by denaturation, neutralization, and UV irradiation as described above.

Hybridization probes derived from cDNAs of the Sequence Listing are employed for screening cDNAs, mRNAs, or genomic DNA in membrane-based hybridizations. Probes are prepared by diluting the cDNAs to a concentration of 40–50 ng in 45 $\mu$l TE buffer, denaturing by heating to 100° C. for five min, and briefly centrifuging. The denatured cDNA is then added to a REDIPRIME tube (APB), gently mixed until blue color is evenly distributed, and briefly centrifuged. Five microliters of [$^{32}$P]dCTP is added to the tube, and the contents are incubated at 37° C.

for 10 min. The labeling reaction is stopped by adding 5 μl of 0.2M EDTA, and probe is purified from unincorporated nucleotides using a PROBEQUANT G-50 microcolumn (APB). The purified probe is heated to 100° C. for five min, snap cooled for two min on ice.

Membranes are pre-hybridized in hybridization solution containing 1% Sarkosyl and 1× high phosphate buffer (0.5 M NaCl, 0.1 M $Na_2HPO_4$, 5 mM EDTA, pH 7) at 55° C. for two hr. The probe, diluted in 15 ml fresh hybridization solution, is then added to the membrane. The membrane is hybridized with the probe at 55° C. for 16 hr. Following hybridization, the membrane is washed for 15 min at 25° C. in 1 mM Tris (pH 8.0), 1% Sarkosyl, and four times for 15 min each at 25° C. in 1 mM Tris (pH 8.0). To detect hybridization complexes, XOMAT-AR film (Eastman Kodak, Rochester N.Y.) is exposed to the membrane overnight at −70° C., developed, and examined.

IX Further Characterization of Differentially Expressed CDNAs and Proteins

Clones were blasted against the LIFESEQ Gold 5.1 database (Incyte Pharmaceuticals) and an Incyte template and its sequence variants were chosen for each clone. The template and variant sequences were blasted against the GenBank database to acquire annotation. The nucleotide sequences were translated into amino acid sequence which was blasted against the GenPept and other protein databases to acquire annotation and characterization, i.e., structural motifs.

Percent sequence identity can also be determined electronically for two or more amino acid or nucleic acid sequences using the MEGALIGN program (DNASTAR). The percent similarity between two amino acid sequences is calculated by dividing the length of sequence A, minus the number of gap residues in sequence A, minus the number of gap residues in sequence B, into the sum of the residue matches between sequence A and sequence B, times one hundred. Gaps of low or of no homology between the two amino acid sequences are not included in determining percentage similarity.

Sequences with conserved protein motifs may be searched using the BLOCKS search program. This program analyses sequence information contained in the Swiss-Prot and PROSITE databases and is useful for determining the classification of uncharacterized proteins translated from genomic or cDNA sequences (Bairoch et al.(supra); Attwood et al. (supra). PROSITE database is a useful source for identifying functional or structural domains that are not detected using motifs due to extreme sequence divergence. Using weight matrices, these domains are calibrated against the SWISS-PROT database to obtain a measure of the chance distribution of the matches.

The PRINTS database can be searched using the BLIMPS search program to obtain protein family "fingerprints". The PRINTS database complements the PROSITE database by exploiting groups of conserved motifs within sequence alignments to build characteristic signatures of different protein families. For both BLOCKS and PRINTS analyses, the cutoff scores for local similarity were: >1300=strong, 1000–1300=suggestive; for global similarity were: p<exp−3; and for strength (degree of correlation) were: >1300=strong, 1000–1300=weak.

X Expression of the Encoded Protein

Expression and purification of a protein encoded by a cDNA of the invention is achieved using bacterial or virus-based expression systems. For expression in bacteria, cDNA is subcloned into a vector containing an antibiotic resistance gene and an inducible promoter that directs high levels of cDNA transcription. Examples of such promoters include, but are not limited to, the trp-lac (tac) hybrid promoter and the T5 or T7 bacteriophage promoter in conjunction with the lac operator regulatory element. Recombinant vectors are transformed into bacterial hosts, such as BL21(DE3). Antibiotic resistant bacteria express the protein upon induction with IPTG. Expression in eukaryotic cells is achieved by infecting *Spodoptera fruginerda* (Sf9) insect cells with recombinant baculovirus, *Autographica californica* nuclear polyhedrosis virus. The polyhedrin gene of baculovirus is replaced with the cDNA by either homologous recombination or bacterial-mediated transposition involving transfer plasmid intermediates. Viral infectivity is maintained and the strong polyhedrin promoter drives high levels of transcription.

For ease of purification, the protein is synthesized as a fusion protein with glutathione-S-transferase (GST; APB) or a similar alternative such as FLAG. The fusion protein is purified on immobilized glutathione under conditions that maintain protein activity and antigenicity. After purification, the GST moiety is proteolytically cleaved from the protein with thrombin. A fusion protein with FLAG, an 8-amino acid peptide, is purified using commercially available monoclonal and polyclonal anti-FLAG antibodies (Eastman Kodak, Rochester N.Y.).

XI Production of Specific Antibodies

A denatured protein from a reverse phase HPLC separation is obtained in quantities up to 75 mg. This denatured protein is used to immunize mice or rabbits following standard protocols. About 100 μg is used to immunize a mouse, while up to 1 mg is used to immunize a rabbit. The denatured protein is radioiodinated and incubated with murine B-cell hybridomas to screen for monoclonal antibodies. About 20 mg of protein is sufficient for labeling and screening several thousand clones.

In another approach, the amino acid sequence translated from a cDNA of the invention is analyzed using PROTEAN software (DNASTAR) to determine regions of high immunogenicity, antigenically-effective portions of the protein. The optimal sequences for immunization are usually at the C-terminus, the N-terminus, and those intervening, hydrophilic regions of the protein that are likely to be exposed to the external environment when the protein is in its natural conformation. Typically, oligopeptides about 15 residues in length are synthesized using an ABI 431 Peptide synthesizer (PE Biosystems) using Fmoc-chemistry and then coupled to keyhole limpet hemocyanin (KLH; Sigma Aldrich) by reaction with M-maleimidobenzoyl-N-hydroxysuccinimide ester. If necessary, a cysteine may be introduced at the N-terminus of the peptide to permit coupling to KLH. Rabbits are immunized with the oligopeptide-KLH complex in complete Freund's adjuvant. The resulting antisera are tested for antipeptide activity by binding the peptide to plastic, blocking with 1% BSA, reacting with rabbit antisera, washing, and reacting with radioiodinated goat anti-rabbit IgG.

Hybridomas are prepared and screened using standard techniques. Hybridomas of interest are detected by screening with radioiodinated protein to identify those fusions producing a monoclonal antibody specific for the protein. In a typical protocol, wells of 96 well plates (FAST, Becton-Dickinson, Palo Alto Calif.) are coated with affinity-purified, specific rabbit-anti-mouse (or suitable anti-species Ig) antibodies at 10 mg/ml. The coated wells are blocked with 1% BSA and washed and exposed to supernatants from hybridomas. After incubation, the wells are exposed to radiolabeled protein at 1 mg/ml. Clones producing antibodies bind a quantity of labeled protein that is detectable above background.

Such clones are expanded and subjected to 2 cycles of cloning at 1 cell/3 wells. Cloned hybridomas are injected into pristane-treated mice to produce ascites, and monoclonal antibody is purified from the ascitic fluid by affinity chromatography on protein A (APB). Monoclonal antibodies with affinities of at least $10^8$ $M^{-1}$, preferably $10^9$ to $10^{10}$ $M^{-1}$ or stronger, are made by procedures well known in the art.

XII Purification of Naturally Occurring Protein Using Specific Antibodies

Naturally occurring or recombinant protein is substantially purified by immunoaffinity chromatography using antibodies specific for the protein. An immunoaffinity column is constructed by covalently coupling the antibody to CNBr-activated SEPHAROSE resin (APB). Media containing the protein is passed over the immunoaffinity column, and the column is washed using high ionic strength buffers in the presence of detergent to allow preferential absorbance of the protein. After coupling, the protein is eluted from the column using a buffer of pH 2–3 or a high concentration of urea or thiocyanate ion to disrupt antibody/protein binding, and the protein is collected.

XIII Screening Molecules for Specific Binding with the CDNA or Protein

The cDNA or fragments thereof and the protein or portions thereof are labeled with $^{32}$P-dCTP, Cy3-dCTP, Cy5-dCTP (APB), or BIODIPY or FITC (Molecular Probes), respectively. Candidate molecules or compounds previously arranged on a substrate are incubated in the presence of labeled nucleic or amino acid. After incubation under conditions for either a cDNA or a protein, the substrate is washed, and any position on the substrate retaining label, which indicates specific binding or complex formation, is assayed. The binding molecule is identified by its arrayed position on the substrate. Data obtained using different concentrations of the nucleic acid or protein are used to calculate affinity between the labeled nucleic acid or protein and the bound molecule. High throughput screening using very small assay volumes and very small amounts of test compound is fully described in Burbaum et al. U.S. Pat. No. 5,876,946.

All patents and publications mentioned in the specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the field of molecular biology or related fields are intended to be within the scope of the following claims.

TABLE 1

LOWER EXPRESSION LEVELS IN PATHOLOGICALLY AFFECTED REGIONS OF AD BRAIN

| SEQ ID NO | ACCESSION | CLONE ID | DESCRIPTION |
|---|---|---|---|
| 1 | AF005889 | 30131 | Cytochrome c oxidase subunit IV |
| 2 | U40369 | 63038 | Spermidine/spermine N1-acetyltransferase |
| 3 | AF052578 | 552654 | *Homo sapiens* androgen receptor associated protein 24 (ARA24) |
| 4 | U06681 | 608148 | Human clone CCA12 mRNA containing CCA trinucleotide repeat |
| 5 | L18983 | 750899 | *Home sapiens* tyrosine phosphatase (IA-2/PTP) mRNA, complete cds |
| 6 | AF055026 | 927476 | *Homo sapiens* RaP2 interacting protein 8 (RPIP8) mRNA, complete cds |
| 7 | M28209 | 997034 | RAS-RELATED PROTEIN RAB-1A |
| 8 | AB007898 | 1000729 | *Homo sapiens* KIAA0438 mRNA, complete cds |
| 9 | U28389 | 1001356 | Erythrocyte membrane protein band 4.9 (dematin) |
| 10 | X78669 | 1251819 | *H. sapiens* ERC-55 mRNA |
| 11 | AB003791 | 1287093 | *Homo sapiens* chondroitin-6-sulfotransferase mRNA, complete cds |
| 12 | U85245 | 1315666 | Human phosphatidylinositol-4-phosphate 5-kinase type II beta mRNA |
| 13 | L13616 | 1361963 | Human focal adhesion kinase (FAK) mRNA, complete cds |
| 14 | U24576 | 1375107 | Human breast tumor autoantigen mRNA, complete sequence |
| 15 | D83407 | 1375877 | ZAKI-4 mRNA in human skin fibroblast, complete cds |
| 16 | D83407 | 1375877 | ZAKI-4 mRNA in human skin fibroblast, complete cds |
| 17 | AA191662 | 1412749 | ESTs, Weakly similar to BRAIN NEURON CYTOPLASMIC PROTEIN 1 [*H. sapiens*] |
| 18 | D44466 | 1441333 | Human mRNA for proteasome subunit p112, complete cds |
| 19 | AF100759 | 1444525 | Human transmembrane 4 superfamily protein mRNA, complete cds |
| 20 | AB007884 | 1479612 | *Homo sapiens* KIAA0424 mRNA, partial cds |
| 21 | AB002367 | 1506978 | Human mRNA for KIAA0369 gene, complete cds |
| 22 | L12563 | 1512070 | Human alternatively spliced microtubule-associated protein 2 (MAP2) mRNA |
| 23 | AF022152 | 1522953 | Human neuron-spec vesicle coat prot and cerebellar degeneration antigen (beta-NAP), |
| 24 | L40027 | 1555993 | *Homo sapiens* glycogen synthase kinase 3 mRNA, complete cds |
| 25 | AF055004 | 1560143 | *Homo sapiens* close 24640 mRNA sequence |
| 26 | U57342 | 1570330 | Human myelodysplasia/myeloid leukemia factor 2 (MLF2) mRNA, complete cds |
| 27 | X57398 | 1578951 | Human mRNA for pM5 protein |
| 28 | X70649 | 1601687 | *Homo sapiens* DDX1 gene, complete CDS |
| 29 | U36341 | 1623318 | *Homo sapiens* creatine transporter mRNA, complete cds |
| 30 | X69141 | 1624459 | FARNESYL-DIPHOSPHATE FARNESYLTRANSFERASE |
| 31 | U18914 | 1629861 | Human 19.8 kDa protein mRNA, complete cds |
| 32 | L06237 | 1649906 | MICROTUBULE-ASSOCIATED PROTEIN 1B |
| 33 | U07620 | 1665264 | Human MAP kinase mRNA, complete cds |
| 34 | U07620 | 1665264 | Human MAP kinase mRNA, complete cds |
| 35 | AF043324 | 1671251 | GLYCYLPEPTIDE N-TETRADECANOYL TRANSFERASE |
| 36 | U62961 | 1685342 | Human succinyl CoA:3-oxoacid CoA transferase precursor (OXCT) mRNA, |
| 37 | D16227 | 1692164 | Hippocalcin-like 1 |
| 38 | X56832 | 1719955 | Enolase 3, (beta, muscle) |
| 39 | AF038535 | 1726196 | *Homo sapiens* synaptotagmin VII mRNA, partial cds |
| 40 | S78296 | 1739904 | Neurofilament-66 [human, fetal brain, mRNA, 3197 nt] |

TABLE 1-continued

LOWER EXPRESSION LEVELS IN PATHOLOGICALLY AFFECTED REGIONS OF AD BRAIN

| SEQ ID NO | ACCESSION | CLONE ID | DESCRIPTION |
|---|---|---|---|
| 41 | U14747 | 1741701 | Visinin-like 1 |
| 42 | Y07759 | 1752531 | Myosin VA (heavy polypeptide 12, myoxin) |
| 43 | U95740 | 1817611 | Human chromosome 16p13.1 BAC clone CIT987SK-362G6 complete sequence |
| 44 | AF035315 | 1818261 | *Homo sapiens* clone 23664 and 23905 mRNA sequence |
| 45 | D26070 | 1818834 | Human mRNA for type 1 inositol 1,4,5-trisphosphate receptor, complete cds |
| 46 | AF035287 | 1818969 | *Homo sapiens* clone 23742 mRNA, partial cds |
| 47 | Y12711 | 1846226 | *H. sapiens* mRNA for putative progesterone binding protein |
| 48 | M88279 | 1846781 | FK506-binding protein 4 (59kD) |
| 49 | M60483 | 1858308 | Protein phosphatase 2 (formerly 2A), catalytic subunit, alpha isoform |
| 50 | AC004472 | 1871335 | *Homo sapiens* chromosome 9, P1 clone 11659 |
| 51 | U50733 | 1873115 | Human dynamitin mRNA, complete cds |
| 52 | Z15108 | 1888731 | Protein kinase C, zeta |
| 53 | AF004563 | 1889867 | *Homo sapiens* hUNC18a alternatively-spliced mRNA, complete cds |
| 54 | AB007877 | 1890791 | *Homo sapiens* KIAA0417 mRNA, complete cds |
| 55 | X98801 | 1910968 | *H. sapiens* mRNA for dynactin |
| 56 | M37400 | 1922596 | Glutamic-oxaloacetic transaminase 1, soluble (aspartate aminotransferase 1) |
| 57 | AB002336 | 1938953 | Human mRNA for KIAA0338 gene, partial cds |
| 58 | D49728 | 1958560 | Hormone receptor (growth factor-inducible nuclear protein N10) |
| 59 | D49728 | 1958560 | Hormone receptor (growth factor-inducible nuclear protein N10) |
| 60 | J04973 | 1964449 | Ubiquinol-cytochrome c reductase core protein II |
| 61 | U33429 | 1970073 | Human K+ channel beta 2 subunit mRNA, complete cds |
| 62 | X52882 | 1976788 | T-COMPLEX PROTEIN 1, ALPHA SUBUNIT |
| 63 | D32050 | 1985161 | Alanyl-tRNA synthetase |
| 64 | J03746 | 1995380 | GLUTATHIONE S-TRANSFERASE, MICROSOMAL |
| 65 | D87457 | 1996449 | Human mRNA for KIAA0281 gene, complete cds |
| 66 | J02966 | 1997963 | ADP, ATP CARRIER PROTEIN, HEART/SKELETAL MUSCLE ISOFORM T1 |
| 67 | M13485 | 2048551 | Human metallothionein I-B gene |
| 68 | D83004 | 2070593 | Human epidermoid carcinoma mRNA for UCE E2 sim to Drosophiia bendless, |
| 69 | AL009266 | 2081502 | *Homo sapiens* cDNA similar to RNA binding protein *C. elegans*, complete |
| 70 | W05585 | 2100538 | ESTs, Weakly similar to PROTEIN Q300 [*Mus musculus*] |
| 71 | U51205 | 2114020 | Human COP9 homoiog (HCOP9) mRNA, complete cds |
| 72 | X51757 | 2123516 | Heat shock 70kD protein 6 (HSP70B') |
| 73 | D38293 | 2135517 | Human mRNA for clathrin-like protein, complete cds |
| 74 | AJ002309 | 2150020 | *Homo sapiens* mRNA for synaptogyrin 3 |
| 75 | AF002246 | 2154406 | *Homo sapiens* neural cell adhesion molecule (CALL) mRNA, complete cds |
| 76 | Z50781 | 2307314 | *H. sapiens* mRNA for leucine zipper protein |
| 77 | AJ000334 | 2346704 | Human clone 23693 mRNA sequence |
| 78 | AF047434 | 2503003 | *H sapiens* NADH:ubiquinone oxidoreductase 15 kDa IP su mRNA, nuclear |
| 79 | AF038186 | 2588820 | *Homo sapiens* clone 23914 mRNA sequence |
| 80 | U60061 | 2623268 | Human FEZ2 mRNA, partial cds |
| 81 | M34181 | 2675641 | Protein kinase, cAMP-dependent, catalytic, beta |
| 82 | Z81326 | 2716511 | *H. sapiens* mRNA for protease inhibitor 12 (PI12; neuroserpin) |
| 83 | Z71460 | 2732710 | *H. sapiens* mRNA for vacuolar-type H(+)-ATPase 115 kDa subunit |
| 84 | L11284 | 2749295 | DUAL SPECIFICITY MITOGEN-ACTIVATED PROTEIN KINASE KINASE 1 |
| 85 | X99906 | 2785292 | Human mRNA for alpha endosulfine |
| 86 | D13388 | 2786429 | Human mRNA for DnaJ protein homolog, complete cds |
| 87 | U47924 | 2832214 | Triosephosphate isomerase 1 |
| 88 | M26252 | 2832314 | Pyruvate kinase, muscle |
| 89 | AB023166.1 | 2839995 | Human mRNA for KIAA0949 protein, partial cds |
| 90 | X87949 | 2884613 | 78 KD GLUCOSE REGULATED PROTEIN PRECURSOR |
| 91 | X57346 | 2930621 | Tyrosine 3/5-monooxygenase activation protein, beta polypeptide |
| 92 | M22382 | 3132987 | Heat shock 60 kD protein 1 (chaperonin) |
| 93 | U09813 | 3223710 | Human mitoch ATP synthase su 9, P3 gene, mRNA, nuclear |
| 94 | Y11072 | 3246379 | *Homo sapiens* mRNA for synaptopodin |
| 95 | AB011085 | 3519862 | *Homo sapiens* clone 24440 mRNA sequence |

TABLE 2

HIGHER EXPRESSION LEVELS IN PATHOLOGICALLY AFFECTED REGIONS OF AD BRAIN

| SEQ ID NO | ACCESSION | CLONE ID | DESCRIPTION |
|---|---|---|---|
| 96 | Z49148 | 452536 | *H. sapiens* mRNA for ribosomal protein L29 |
| 97 | L05424 | 549196 | CD44 antigen (cell adhesion molecule) |
| 98 | J02611 | 551403 | Human apolipoprotein D mRNA, complete cds |
| 99 | X53777 | 747335 | 60S RIBOSOMAL PROTEIN L23 |
| 100 | AF006484 | 902381 | *Homo sapiens* putative oral tumor suppressor protein (doc-1) mRNA, complete cds |
| 101 | AF006043 | 998612 | *Homo sapiens* 3-phosphoglycerate dehydrogenase mRNA, complete cds |
| 102 | M13560 | 1001730 | HLA CLASS II HISTOCOMPATIBILITY ANTIGEN, GAMMA CHAIN |
| 103 | U37230 | 1214494 | 60S RIBOSOMAL PROTEIN L23A |
| 104 | U14973 | 1306814 | Ribosomal protein S29 |
| 105 | U97502 | 1405036 | Human butyrophilin protein (BT3.3) mRNA, partial cds |

TABLE 2-continued

HIGHER EXPRESSION LEVELS IN PATHOLOGICALLY AFFECTED REGIONS OF AD BRAIN

| SEQ ID NO | ACCESSION | CLONE ID | DESCRIPTION |
|---|---|---|---|
| 106 | D67031 | 1481225 | Adducin 3 (gamma) |
| 107 | K02765 | 1513989 | COMPLEMENT C3 PRECURSOR |
| 108 | Z19554 | 1522716 | Vimentin |
| 109 | M11313 | 1600726 | ALPHA-2-MACROGLOBULIN PRECURSOR |
| 110 | D38305 | 1603605 | Human mRNA for Tob, complete cds |
| 111 | AB008109 | 1624543 | *Homo sapiens* mRNA for RGS5, complete cds |
| 112 | AB002379 | 1653064 | Human mRNA tor KIAA0381 gene, partial cds |
| 113 | L27560 | 1686585 | Human insulin-like growth factor binding protein 5 (IGFBP5) mRNA |
| 114 | D79990 | 1702752 | Human mRNA for KIAA0168 gene, complete cds |
| 115 | M69066 | 1733490 | Moesin |
| 116 | U45955 | 1740547 | Human neuronal membrane glycoprotein M6b mRNA, partial cds |
| 117 | AF035959 | 1820522 | *Homo sapiens* type-2 phosphatidic acid phosphatase-gamma (PAP2-g) mRNA, complete cds |
| 118 | X79683 | 1962971 | Laminin, beta 2 (laminin S) |
| 119 | M59488 | 1963081 | S-100 PROTEIN, BETA CHAIN |
| 120 | U00946 | 1987975 | Human clone A9A2BRB5 (CAC)n/(GTG)n repeat-containing mRNA |
| 121 | X52947 | 1997703 | Cardiac gap junction protein |
| 122 | M32578 | 2105963 | Major histocompatibility complex, class II, DR beta 5 |
| 123 | AAC24610.1 | 2105963 | ZNF134 |
| 124 | J03037 | 2474163 | Carbonic anhydrase II |
| 125 | AB000115 | 2537863 | *Homo sapiens* mRNA expressed in osteoblast, complete cds |
| 126 | AA258550 | 2739522 | Incyte Unique EST |
| 127 | X79234 | 2739522 | Human mRNA for ribosomal protein L11 |
| 128 | L02321 | 2815711 | Glutathione S-transferase M5 |
| 129 | M33146 | 2852042 | CYSTEINE-RICH PROTEIN |
| 130 | M80469 | 2859033 | Human MHC class I HLA-J gene, exons 1–8 and complete cds |
| 131 | M11147 | 2868138 | Ferritin, light polypeptide |
| 132 | M16279 | 3031028 | Antigen identified by monoclonal antibodies 12E7, F21 and O13 |
| 133 | M80899 | 3068454 | AHNAK nucleoprotein (desmoyokin) |
| 134 | L27476 | 3494714 | Human X104 mRNA, complete cds |
| 135 | X02761 | 3553729 | Fibronectin 1 |
| 136 | D87735 | 3721812 | *Homo sapiens* CAG-isl 7 mRNA, complete cds ED: SAME AS RIBOSOMAL PROTEIN L14 |
| 137 | AC002425 | 3721987 | *Homo sapiens* P8 protein mRNA, complete cds |
| 138 | J02611 | 3948420 | Apolipoprotein D |

TABLE 3

TISSUE SOURCE

| Tissue | Gender | Person 1 | Person 2 |
|---|---|---|---|
| Amygdala | Female | Control-age matche | AD severe |
| Amygdala | Female/Male | female | male |
| Cerebellum | Female | Control-age matche | AD moderate |
| Cerebellum | Female | Control-age matche | AD severe |
| Cerebellum | Female | Control-age matche | AD severe |
| Cerebellum | Female | Control-age matche | AD moderate |
| Cerebellum | Male | Control-age matche | AD severe |
| Cerebellum | Male | Control-age matche | AD severe |
| Cingulate Corte | Female | Control-age matche | AD moderate |
| Cingulate Corte | Female | Control-age matche | AD severe |
| Cingulate Corte | Female | Control-age matche | AD severe |
| Cingulate Corte | Female/Male | female | male |
| Cingulate Corte | Male | Control-age matche | AD moderate |
| Cingulate Corte | Male | Control-age matche | AD severe |

TABLE 3-continued

TISSUE SOURCE

| Tissue | Gender | Person 1 | Person 2 |
|---|---|---|---|
| Cingulate Corte | Male | Control-age matche | AD severe |
| Striatum | Female | Control-age matche | AD moderate |
| Striatum | Female | Control-age matche | AD severe |
| Striatum | Female | Control-age matche | AD severe |
| Striatum | Female/Male | female | male |
| Striatum | Male | Control-age matche | AD moderate |
| Striatum | Male | Control-age matche | AD severe |
| Striatum | Male | Control-age matche | AD severe |

What is claimed is:

1. A composition comprising a nucleic acid sequence of SEQ ID NO:59 and a plurality of cDNAs that are differentially repressed in brain disorders and selected from SEQ ID NOs:1–138 and a complete complement SEQ ID NOs:1–138.

2. The composition of claim 1, wherein expression of each of the cDNAs is downregulated at least two-fold and is selected from SEQ ID NOs:1–95 and a complete complement of SEQ ID NOs:1–95.

3. The composition of claim 1, wherein the brain disorder is Alzheimer's disease.

4. The composition of claim 2, wherein the expression of cDNAs are downregulated in brain of subjects with Alzheimer's disease.

5. The composition of claim 1, wherein the cDNAs are immobilized on a substrate.

6. A high throughput method for detecting differential expression of one or more cDNAs in a sample containing nucleic acids, the method comprising:
   (a) hydridizing the substrate of claim 5 with nucleic acids of the sample, thereby forming one or more hybridization complexes;
   (b) detecting the hybridization complexes; and
   (c) comparing the hybridization complexes with those of a standard, wherein differences in the size and intensity of each hybridization complex indicates differential expression of cDNAs in the sample.

7. The method of claim 6, wherein the sample is from brain.

8. A high throughput method of screening a library of molecules or compounds to identify a ligand which specifically binds a cDNA, the method comprising:
   a) combining the composition of claim 1 with the library of molecules or compounds under conditions to allow specific binding; and
   b) detecting specific binding between each cDNA and at least one molecule or compound, thereby identifying a ligand that specifically binds to each cDNA.

9. The method of claim 6 wherein the nucleic acids are amplified prior to hybridization.

10. The method of claim 8 wherein the library is selected from DNA molecules, RNA molecules, mimetics, peptides, peptide nucleic acids, proteins, and transcription factors.

11. The composition of claim 2, wherein the cDNAs are immobilized on a substrate.

12. A high throughput method for detecting differential expression of one or more cDNAs in a sample containing nucleic acids, the method comprising:
   a) hybridizing the composition of claim 11 with nucleic acids of the sample, thereby forming one or more hybridization complexes;
   b) detecting the hybridization complexes; and
   c) comparing the hybridization complexes with those of a standard, wherein differences in the size and intensity of each hybridization complex indicates differential expression of cDNAs in the sample.

13. The method of claim 12 wherein the nucleic acids are amplified prior to hybridization.

14. The method of claim 12, wherein the sample is from brain.

15. A high throughput method of screening a library of molecules or compounds to identify a ligand which specifically binds a cDNA, the method comprising:
   a) combining the composition of claim 2 with the library of molecules or compounds under conditions to allow specific binding; and
   b) detecting specific binding between each cDNA and at least one molecule or compound, thereby identifying a ligand that specifically binds to each cDNA.

16. The method of claim 15 wherein the library is selected from DNA molecules, RNA molecules, mimetics, peptides, peptide nucleic acids, proteins, and transcription factors.

* * * * *

UNITED STATES PATENT AND TRADEMARK OFFICE

CERTIFICATE OF CORRECTION

PATENT NO. : 6,682,888 B1
DATED : January 27, 2004
INVENTOR(S) : Loring et al.

It is certified that error appears in the above-identified patent and that said Letters Patent is hereby corrected as shown below:

Column 441,
Line 3, replace "repressed" with -- expressed --

Signed and Sealed this

Eighth Day of June, 2004

JON W. DUDAS
*Acting Director of the United States Patent and Trademark Office*